(12) United States Patent
Jones et al.

(10) Patent No.: US 11,214,548 B2
(45) Date of Patent: *Jan. 4, 2022

(54) CANNABINOID RECEPTOR MODULATORS

(71) Applicant: Arena Pharmaceuticals, Inc., San Diego, CA (US)

(72) Inventors: Robert M. Jones, San Diego, CA (US); Sangdon Han, San Diego, CA (US); Lars Thoresen, San Diego, CA (US); Jae-Kyu Jung, San Diego, CA (US); Sonja Strah-Pleynet, Newton, MA (US); Xiuwen Zhu, San Diego, CA (US); Yifeng Xiong, San Diego, CA (US); Dawei Yue, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 16/580,697

(22) Filed: Sep. 24, 2019

(65) Prior Publication Data

US 2020/0017448 A1  Jan. 16, 2020

Related U.S. Application Data

(60) Continuation of application No. 15/912,700, filed on Mar. 6, 2018, now abandoned, which is a division of application No. 13/616,918, filed on Sep. 14, 2012, now Pat. No. 9,944,606, which is a division of application No. 13/392,074, filed as application No. PCT/US2010/002360 on Aug. 27, 2010, now Pat. No. 8,778,950.

(60) Provisional application No. 61/400,146, filed on Jul. 22, 2010, provisional application No. 61/396,588, filed on May 28, 2010, provisional application No. 61/275,506, filed on Aug. 28, 2009.

(51) Int. Cl.

| | |
|---|---|
| *C07D 231/24* | (2006.01) |
| *C07D 401/04* | (2006.01) |
| *C07D 401/14* | (2006.01) |
| *C07D 403/04* | (2006.01) |
| *C07D 405/14* | (2006.01) |
| *C07F 9/6558* | (2006.01) |
| *C07D 401/12* | (2006.01) |
| *C07D 403/12* | (2006.01) |
| *C07D 413/12* | (2006.01) |
| *C07D 413/14* | (2006.01) |
| *C07D 231/54* | (2006.01) |

(52) U.S. Cl.
CPC ......... *C07D 231/54* (2013.01); *C07D 401/04* (2013.01); *C07D 401/12* (2013.01); *C07D 401/14* (2013.01); *C07D 403/04* (2013.01); *C07D 403/12* (2013.01); *C07D 405/14* (2013.01); *C07D 413/12* (2013.01); *C07D 413/14* (2013.01); *C07F 9/65583* (2013.01)

(58) Field of Classification Search
CPC ................ C07D 231/54; C07D 401/04; C07D 401/12; C07D 401/14; C07D 403/04; C07D 403/12; C07D 405/14; C07D 413/12; C07D 413/14; C07F 9/65583
See application file for complete search history.

(56) References Cited

U.S. PATENT DOCUMENTS

| | | | |
|---|---|---|---|
| 5,977,108 | A | 11/1999 | Kikuchi et al. |
| 6,329,402 | B1 | 12/2001 | Kikuchi et al. |
| 6,541,474 | B2 | 4/2003 | Kikuchi et al. |
| 6,630,463 | B2 | 10/2003 | Kikuchi et al. |

(Continued)

FOREIGN PATENT DOCUMENTS

| | | |
|---|---|---|
| DE | 102004054666 | 5/2006 |
| EP | 0838453 | 4/2005 |

(Continued)

OTHER PUBLICATIONS

Zaragoza, "Side Reactions in Organic Synthesis: A Guide to Successful Synthesis Design," Weinheim: WILEY-VCH Verlag GmbH & Co. KGaA, 2005, Preface.
Jordan, Nature Reviews: Drug Discovery, 2003, 2:205-213.
"PI3K / Akt Cell Signaling" (2010) www.cellsignal.com.
Alexander et al., "Cannabinoids in the treatment of cancer," Cancer Letters, 2009, 285:6-12.
Anand et al., "Cannabinoid Receptor CB2 localisation and Agonist-Mediated Inhibition of Capsaicin Responses in Human Sensory Neurons," Pain, 2008, 138(3):667-680, doi:10.1016/j.pain.2008.06.007.

(Continued)

*Primary Examiner* — Kortney L. Klinkel
*Assistant Examiner* — William Y Lee
(74) *Attorney, Agent, or Firm* — Fish & Richardson P.C.

(57) ABSTRACT

The present invention relates to certain compounds of Formula Ia and pharmaceutical compositions thereof that modulate the activity of the cannabinoid CB2 receptor. The present invention further relates to certain compounds of Formula Ia and pharmaceutical compositions thereof that modulate the activities of both the CB1 receptor and the CB2 receptor. Compounds of the present invention and pharmaceutical compositions thereof are directed to methods useful in the treatment of: pain, for example bone and joint pain, muscle pain, dental pain, migraine and other headache pain, inflammatory pain, neuropathic pain, pain that occurs as an adverse effect of therapeutics and pain associated with osteoarthritis; hyperalgesia; allodynia; inflammatory hyperalgesia; neuropathic hyperalgesia; acute nociception; osteoporosis; multiple sclerosis-associated spasticity; autoimmune disorders; allergic reactions; CNS inflammation; atherosclerosis; undesired immune cell activity and inflammation; age-related macular degeneration; cough; leukemia; lymphoma; CNS tumors; prostate cancer; Alzheimer's disease; stroke-induced damage; dementia; amyotrophic lateral sclerosis, and Parkinson's disease.

8 Claims, 18 Drawing Sheets

(56) References Cited

U.S. PATENT DOCUMENTS

| | | | |
|---|---|---|---|
| 6,884,808 B2 | 4/2005 | Kikuchi et al. | |
| 8,778,950 B2 | 7/2014 | Jones | |
| 9,458,136 B2 | 10/2016 | Blackburn | |
| 9,492,447 B2 * | 11/2016 | Thatte | C07D 231/54 |
| 9,597,340 B2 * | 3/2017 | Thatte | A61K 31/416 |
| 9,867,822 B2 | 1/2018 | Thatte | |
| 9,944,606 B2 | 4/2018 | Jones et al. | |
| 10,183,930 B2 | 1/2019 | Blackburn | |
| 2004/0259936 A1 | 12/2004 | Nagarkatti et al. | |
| 2010/0160288 A1 | 6/2010 | Astles et al. | |
| 2013/0165412 A1 | 6/2013 | Jones et al. | |
| 2018/0354907 A1 | 12/2018 | Jones et al. | |
| 2021/0188781 A1 | 6/2021 | Jones et al. | |

FOREIGN PATENT DOCUMENTS

| | | |
|---|---|---|
| EP | 1177187 | 7/2007 |
| WO | WO1997/02244 | 1/1997 |
| WO | WO2000/064888 | 11/2000 |
| WO | WO2004/060882 | 7/2004 |
| WO | WO2006/025069 | 3/2006 |
| WO | WO2006/030124 | 3/2006 |
| WO | WO2006/069242 | 6/2006 |
| WO | WO2006/129178 | 12/2006 |
| WO | WO2008/003665 | 1/2008 |
| WO | WO2008/039645 | 4/2008 |
| WO | WO2008/048914 | 4/2008 |
| WO | WO2008/053341 | 5/2008 |
| WO | WO2008/063781 | 5/2008 |
| WO | WO2008/064054 | 5/2008 |
| WO | WO2008/079316 | 7/2008 |
| WO | WO2008/085302 | 7/2008 |
| WO | WO2008/109007 | 9/2008 |
| WO | WO2008/119694 | 10/2008 |
| WO | WO2008/157500 | 12/2008 |
| WO | WO2008/157751 | 12/2008 |
| WO | WO2009/009550 | 1/2009 |
| WO | WO2009/015169 | 1/2009 |
| WO | WO2009/025785 | 2/2009 |
| WO | WO2010/088050 | 8/2010 |

OTHER PUBLICATIONS

Belvisi et al., (2008) "Inhibitory Activity Of The Novel CB2 Receptor Agonist, GW833972A, On Guinea-Pig And Human Sensory Nerve Function In The Airways," British Journal of Pharmacology, 1-11.

Bingham et al., (2007) "Species-specific In Vitro Pharmacological Effects Of The Cannabinoid Receptor 2 (CB2) Selective Ligand AM1241 And Its Resolved Enantiomers," British Journal of Pharmacology 151:1061-1070.

Bouaboula et al., (1996) "Signaling Pathway Associated With Stimulation Of CB2 Peripheral Cannabinoid Receptor," Eur. J. Biochem. 237:704-711.

Caffarel et al., (2010) "Cannabinoids Reduce ErbB2-Driven Breast Cancer Progression Through Akt Inhibition," Molecular Cancer 2010, 9:196 and Supplement.

Carracedo et al., (2006) "Cannabinoids Induce Apoptosis of Pancreatic Tumor Cells via Endoplasmic Reticulum Stress-Related Genes," Cancer Res 66:6748-6755.

Casanova et al., (2003) "Inhibition Of Skin Tumor Growth And Angiogenesis In Vivo By Activation Of Cannabinoid Receptors," J. Clin, Invest. 111:43-50, doi:10.1172/JC1200316116.

Cheng et al., (2008) "Discovery and Optimization of a Novel Series of N-Arylamide Oxadiazoles as Potent, Highly Selective and Orally Bioavailable Cannabinoid Receptor 2 (CB2) Agonists," J. Med. Chem. 51:5019-5034.

Compton et al., (1992) "Aminoalkylindole Analogs: Cannabimimetic Activity of a Class of Compounds Structurally Distinct from L19-Tetrahydrocannabinols," JPET 263:1118-1126.

Di Marzo et al., (2006) "Plant, Synthetic, And Endogenous Cannabinoids In Medicine," Annu. Rev. Med. 57:553-74.

Diaz et al., (2008) "Design and Synthesis of a Novel Series of N-Alkyl Isatin Acylhydrazone Derivatives that Act as Selective Cannabinoid Receptor 2 Agonists for the Treatment of Neuropathic Pain," J. Med. Chem. 51(16):4932-4947.

DiMauro et al., (2008) "Structural Modifications Of N-arylamide Oxadiazoles: Identification Of N-Arylpiperidine Oxadiazoles As Potent And Selective Agonists Of CB2," Bioorganic & Medicinal Chemistiy Letters 18:4267-4274.

Ermann et al., (2008) "Arylsulfonamide CB2 receptor agonists: SAR and Optimization of CB2 Selectivity," Bioorganic & Medicinal Chemistry Letters 18:1725-1729.

Galiegue et al., (1995) "Expression Of Central And Peripheral Cannabinoid Receptors In Human Immune Tissues And Leukocyte Subpopulations," Eur. J. Biochem. 232:54-61.

Giblin et al., (2007) "Discovery of 2-[(2,4-Dichlorophenyl)amino]-N-[(tetrahydro-2H-pyran-4-yl)methyl]-4-(trifluoromethyl)-5-pyrimidinecarboxamide, a Selective CB2 Receptor Agonist for the Treatment of Inflammatoiy Pain," J. Med. Chem. 50:2597-2600.

Goodman et al., (2009) "CB2 selective Sulfamoyl Benzamides: Optimization Of The Amide Functionality," Bioorganic & Medicinal Chemistry Letters 19:309-313.

Graham et al., (2009) "Cannabinoid Receptors: A Brief History And 'What's Hot,'" Frontiers in Bioscience 14:944-957.

Hanus et al., (1999) "HU-308: A Specific Agonist For CB2, A Peripheral Cannabinoid Receptor," PNAS, 96:14228-14233.

Hosohata et al., (1997) "AM630 Antagonism Of Cannabinoid-Stimulated [35S]GTPγS Binding In The Mouse Brain," European Journal of Pharmacology 321(1):R1-R3.

Kikuchi et al., (2008) "Pharmacological Evaluation of a Novel Cannabinoid 2 (CB2) Ligand, PF-03550096, In Vitro and In Vivo by Using a Rat Model of Visceral Hypersensitivity," J. Pharmacol. Sci. 106:219-224.

Lozano-Ondoua et al., (2010) "A Cannabinoid 2 Receptor Agonist Attenuates Bone Cancer-Induced Pain And Bone Loss," Life Sciences 86:646-653.

Maresz et al., (2007) "Direct Suppression Of CNS Autoimmune Inflammation Via The Cannabinoid Receptor CB1 On Neurons And CB2 On Autoreactive T Cells," Nature Medicine 13:492-497.

Markt et al., (2009) "Discovery of Novel CB2 Receptor Ligands by a Pharmacophore-Based Virtual Screening Workflow," J. Med. Chem. 52:369-378.

Marx et al., (2009) "Discovery Of α-Amidosulfones As Potent And Selective Agonists Of CB2: Synthesis, SAR, And Pharmacokinetic Properties," Bioorganic & Medicinal Chemistry Letters 19:31-35.

McKallip et al., (2002) "Targeting CB2 Cannabinoid Receptors As A Novel Therapy To Treat Malignant Lymphoblastic Disease," Blood 100:627-634.

Michalski et al., (2008) "Cannabinoids In Pancreatic Cancer: Correlation With Survival And Pain," Int J Cancer. 122:742-750.

Mitchell et al., (2009) "Pyridine-3-carboxamides As Novel CB2 Agonists For Analgesia," Bioorganic & Medicinal Chemistry Letters 19:259-263.

Munro et al., (1993) "Molecular Characterization Of A Peripheral Receptor For Cannabinoids," Nature, 365:61-65.

Naguib et al., (2008) "MDA7: A Novel Selective Agonist For CB2 Receptors That Prevents Allodynia In Rat Neuropathic Pain Models," British Journal of Pharmacology 155(7):1-13.

Narayanan et al., (2006) "GRC 10622: A Novel Orally Active CB2 Receptor Agonist With Potential Anti-Hyperalgesic Effects," poster submitted at Society for Neuroscience, Oct. 14-18, 2006, Atlanta, Georgia, USA.

Nunez et al., (2004) "Cannabinoid CB2 Receptors Are Expressed by Perivascular Microglial Cells in the Human Brain: An Immunohistochemical Study," Synapse 53:208-213.

Ofek et al., (2006) "Peripheral Cannabinoid Receptor, CB2, Regulates Bone Mass," PNAS 103:696-701.

Ohta et al., (2007) "N-Alkylidenearylcarboxamides As New Potent And Selective CB2 Cannabinoid Receptor Agonists With Good Oral Bioavailability," Bioorganic & Medicinal Chemistry Letters 17:6299-6304.

(56) References Cited

OTHER PUBLICATIONS

Ohta et al., (2008) "Imine Derivatives As New Potent And Selective CB2 Cannabinoid Receptor Agonists With An Analgesic Action," Bioorganic & Medicinal Chemistiy 16:1111-1124.
Olea-Herrero et al., (2009) "Inhibition Of Human Tumour Prostate PC-3 cell growth by Cannabinoids R(+)-Methanandamide and JWH-015: Involvement of CB2," British Journal of Cancer 101:940-950.
Omura et al., (2008) "The SAR Studies of Novel CB2 Selective Agonists, Benzimidazolone Derivatives," Bioorganic & Medicinal Chemistry Letters 18(11):3310-3314, doi: 10.1016/j.bmcl.2008.04.032.
Page et al., (2007) "New 1,2,3,4-Tetrahydropyrrolo[3,4-b]indole Derivatives As Selective CB2 Receptor Agonists," Bioorganic & Medicinal Chemistiy Letters 17:6183-6187.
Page et al., (2008) "Novel Benzimidazole Derivatives As Selective CB2 Agonists," Bioorganic & Medicinal Chemistiy Letters 18:3695-3700.
Palazuelos et al., (2008) "The CB2 Cannabinoid Receptor Controls Myeloid Progenitor Trafficking," J Biol. Chem. 283(19):13320-13329, http://www.jbc.org/cgi/doi/10.1074/jbc.M707960200.
Pasquini et al., (2008) "Investigations on the 4-Quinolone-3-carboxylic Acid Motif. 2. Synthesis and Structure-Activity Relationship of Potent and Selective Cannabinoid-2 Receptor Agonists Endowed with Analgesic Activity in Vivo," J. Med. Chem. 51:5075-5084.
Pisanti et al., (2009) "Use Of Cannabinoid Receptor Agonists In Cancer Therapy As Palliative And Curative Agents," Best Practice & Research Clinical Endocrinology & Metabolism 23:117-131.
Preet et al., (2010) "Cannabinoid Receptors, CB1 and CB2, as Novel Targets for Inhibition of Non-Small Cell Lung Cancer Growth and Metastasis," Published OnlineFirst on Nov. 19, 2010 as 10,1158/1940-6207,CAPR-10-0181.
Rinaldi-Carmona et al., (1998) "SR 144528, the First Potent and Selective Antagonist of the CB2 Cannabinoid Receptor," JPET 284:644-650.
Sanchez et al., (2001) "Inhibition of Glioma Growth in Vivo by Selective Activation of the CB2 Cannabinoid Receptor," Cancer Research 61:5784-5789.
Sharma et al., (2010) "Cell Line-Based Platforms To Evaluate The Therapeutic Efficacy Of Candidate Anticancer Agents," Nature Reviews I Cancer 10:241-253.
Shi et al., (2008) "Cannabinoid 2 Receptor Induction By IL-12 And Its Potential As A Therapeutic Target For The Treatment Of Anaplastic Thyroid Carcinoma," Cancer Gene Therapy 15:101-107.
Slipetz et al., (1995) "Activation of the Human Peripheral Cannabinoid Receptor Results in Inhibition of Adenylyl Cyclase," Molecular Pharmacology, 48:352-361.
Stansfield et al., (2007) "Development Of Carboxylic Acid Replacements In Indole-N-acetamide Inhibitors Of Hepatitis C Virus NS5B Polymerase," Bioorganic & Medicinal Chemistry Letters 17:5143-5149.
Valenzano et al., (2003) "Pharmacological And Pharmacokinetic Characterization Of The Cannabinoid Receptor 2 Agonist, GW405833, Utilizing Rodent Models Of Acute And Chronic Pain, Anxiety, Ataxia And Catalepsy," Neuropharmacology, 48:658-672.
Van Sickle et al., (2005) "Identification and Functional Characterization of Brainstem Cannabinoid CB2 Receptors," Science, 310:329.
Verbist et al., (2008) "5-Sulfonyl-benzimidazoles As Selective CB2 Agonists," Bioorganic & Medicinal Chemistiy Letters, 18:2574-2579.
Whiteside et al., (2007) "The Role of the Cannabinoid CB2 Receptor in Pain Transmission and Therapeutic Potential of Small Molecule CB2 Receptor Agonists," Current Medicinal Chemistry, 14:917-936.
Worm et al., (2008) "Sulfamoyl Benzamides As Novel CB2 Cannabinoid Receptor Ligands," Bioorganic & Medicinal Chemistry Letters, 18:2830-2835.
Wotherspoon et al., (2005) "Peripheral Nerve Injury Induces Cannabinoid Receptor 2 Protein Expression In Rat Sensory Neurons," Neuroscience 135:235-245.
Yao et al., (2008) "Characterization of a Cannabinoid CB2 Receptor Selective Agonist, A-836339, in In Vitro Pharmacological assays and In Vivo Pain Models," JPET Fast Forward, published on Oct. 17, 2008 as DOI: 10.1124/jpet.1 08.145011.
Yao et al., (2008) "In Vitro And In Vivo Characterization Of A-796260: A Selective Cannabinoid CB2 Receptor Agonist Exhibiting Analgesic Activity In Rodent Pain Models," British Journal of Pharmacology, 153:390-401.
Zindell et al., (2009) "Morpholine Containing CB2 Selective Agonists," Bioorganic & Medicinal Chemistiy Letters 19(6):1604-1609, doi: 10.1016/j.bmcl.2009.02.033.
Agarwal et al., "Cannabinoids mediate analgesia largely via peripheral type 1 cannabinoid receptors in nociceptors," Nat. Neurosci., 2007, 10(7):870-879.
Ashton et al., "The cannabinoid CB2 receptor as a target for inflammation-dependent neurodegeneration," Curr. Neuropharmacol., 2007, 5(2):73-80.
Berge et al., "Pharmaceutical salts," J. Pharm. Sci., 1997, 66:1-19.
Calignano et al., "Bidirectional control of airway responsiveness by endogenous cannabinoids," Nature, 2000, 408:96-101.
Calignano et al., "Control of pain initiation by endogenous cannabinoids," Nature, 1998, 394:277-281.
Chaplan et al., "Quantitative assessment of tactile allodynia in the rat paw," J. Neuroscience Methods, 1994, 53(1):55-63.
Collier et al., "Radiosynthesis and in-vivo evaluation of the psuedopeptide δ-opioid antagonist [125I]-1TIPP(Ψ)," J. Labelled Compd. Radiopharm., 1999, 42:S264-S266.
Dvorak et al., "Histamine induced responses are attenuated by a cannabinoid receptor agonist in human skin," Inflamm. Res., 2003, 52:238-245.
Furuse et al., "Reduction of bone cancer pain by activation of spinal cannabinoid receptor 1 and its expression in the superficial dorsal horn of the spinal cord in a murine model of bone cancer pain," Anesthesiology, 2009, 111(1):173-186.
Gabriel et al., "High throughput screening technologies for direct cyclic AMP measurement," ASSAY and Drug Development Technologies, 2003, 1:291-303.
Goncalves et al., "A diacylglycerol lipase-CB2 cannabinoid pathway regulates adult subventricular zone neurogenesis in an age-dependent manner," Mol. Cell Neurosci., 2008, 38(4):526-36.
Guindon et al., "Cannabinoid CB2 receptors: a therapeutic target for the treatment of inflammatory and neuropathic pain," Br. J. Pharmacol., 2008, 153:319-334.
Hu et al., "Depression-like behaviour in rats with mononeuropathy is reduced by the CB2-selective agonist GW405833," Pain, 2009, 143:206-212.
Ibrahim et al., "Activation of CB2 cannabinoid receptors by AM1241 inhibits experimental neuropathic pain: pain inhibition by receptors not present in the CNS," Proc. Natl. Aca. Sci., 2003, 100(18):10529-10533.
Karsak et al., "Attenuation of allergic contact dermatitis through the endocannabinoid system," Science, 2007, 316(5830), 1494-1497.
Le Bas et al., "Radioiodinated Analogs of EP 00652218 for the Exploration of the Tachykinin NK1 Receptor by SPECT," J. Labelled Compd. Radiopharm., 2001, S280-S282.
Malan et al., "CB2 cannabinoid receptor-mediated peripheral antinociception," Pain, 2001, 93:239-245.
Manzanares et al., "Role of the cannabinoid system in pain control and therapeutic implications for the management of acute and chronic pain episodes," Current Neuropharmacology, 2006, 4:239-57.
Matsuda et al., "Molecular cloning of a human cannabinoid receptor which is also expressed in testis," Nature, 1990, 346:561-564.
Mbvundula et al., "Arthritis and cannabinoids: HU-210 and Win-55,212-2 prevent IL-1 alpha-induced matrix degradation in bovine articular chondrocytes in-vitro," J. Pharm. And Pharmacol., 2006, 58:351-358.
Morita et al., "Antitussive effect of WIN 55212-2, a cannabinoid receptor agonist," Eur. J. Pharmacol., 2003, 474:269-272.

(56) References Cited

OTHER PUBLICATIONS

Pacher et al., "The endocannabinoid system as an emerging target of pharmacotherapy," Pharmacol. Rev. 1993, 58(3):389-462.

Patel et al., "Inhibition of guinea-pig and human sensory nerve activity and the cough reflex in guinea-pigs by cannabinoid (CB2) receptor activation," British J. Pharm., 2003, 140:261-8.

Pryce et al., "Cannabinoids inhibit neurodegeneration in models of multiple sclerosis," Brain, 2003, 126:2191-2202.

Richardson et al., "Antihyperalgesic effects of spinal cannabinoids," Eur. J. Pharmacol., 1997, 345:145-153.

Rukwied et al., "Cannabinoid agonists attenuate capsaicin-induced responses in human skin," Pain, 2003, 102:283-288.

Stahly, "Diversity in Single- and Multiple-Component Crystals. The Search for and Prevalence of Polymorphs and Cocrystals," Crystal Growth & Design, 2007, 7(6):1007-1026.

Steffans et al., "Low dose oral cannabinoid therapy reduces progression of atherosclerosis in mice," Nature, 2005, 434:782-786.

Walker et al., "Cannabinoid analgesia," Pharmacol. Ther., 2002, 95:127-135.

Wei et al., "Presence and regulation of cannabinoid receptors in human retinal pigment epithelial cells," Mol. Vis., 2009, 15:1243-51.

Widmer, "High concentrations of cannabinoids activate apoptosis in human U373MG glioma cells," J. Neurosci. Res., 2008, 86(14):3212-20.

Yan et al., "Cell-based high-throughput screening assay system for monitoring G protein-coupled receptor activation using beta-galactosidase enzyme complementation technology," J. Biomol. Screen, 2002, 7:451-459.

Zhang et al., "Cannabinoid CB(2) receptor activation decreases cerebral infarction in a mouse focal ischemia/reperfusion model," J. Cereb. Blood Flow Metab., 2007, 27:1387-96.

Zhu et al., "Synthesis and mode of action of (125)I- and (3)H-labeled thieno[2,3-c]pyridine antagonists of cell adhesion molecule expression," J. Org. Chem., 2002, 67:943-948.

\* cited by examiner

Effects of Compound 455 on Body Temperature and Locomotor Activity in Rats

CANNABINOID RECEPTOR MODULATORS

CROSS-REFERENCE TO RELATED APPLICATIONS

This application is a continuation of U.S. patent application Ser. No. 15/912,700, filed Mar. 6, 2018, which is a continuation of U.S. patent application Ser. No. 13/616,918, filed Sep. 14, 2012, now issued U.S. Pat. No. 9,944,606, which is a divisional of U.S. patent application Ser. No. 13/392,074, filed May 7, 2012, now issued U.S. Pat. No. 8,778,950, which is a National Stage Entry of International Patent Application No. PCT/US2010/002360, filed Aug. 27, 2010, and claims the benefit of U.S. Provisional Patent Application Nos. 61/400,146, filed Jul. 22, 2010; 61/396,588, filed May 28, 2010; and 61/275,506, filed Aug. 28, 2009, each of which is incorporated by reference in its entirety.

FIELD OF THE INVENTION

The present invention relates to certain compounds of Formula Ia and pharmaceutical compositions thereof that modulate the activity of the cannabinoid $CB_2$ receptor. The present invention further relates to certain compounds of Formula Ia and pharmaceutical compositions thereof that modulate the activities of both the $CB_1$ receptor and the $CB_2$ receptor. Compounds of the present invention and pharmaceutical compositions thereof are directed to methods useful in the treatment of: pain, for example bone and joint pain, muscle pain, dental pain, migraine and other headache pain, inflammatory pain, neuropathic pain, pain that occurs as an adverse effect of therapeutics, and pain associated with a disorder selected from: osteoarthritis, cancer, multiple sclerosis, allergic reactions, nephritic syndrome, scleroderma, thyroiditis, diabetic neuropathy, fibromyalgia, HIV related-neuropathy, sciatica, and autoimmune conditions; hyperalgesia; allodynia; inflammatory hyperalgesia; neuropathic hyperalgesia; acute nociception; osteoporosis; multiple sclerosis-associated spasticity; autoimmune disorders, for example an autoimmune disorder selected from the group consisting of: multiple sclerosis, Guillan-Barré syndrome, polyradiculoneuropathy, chronic inflammatory demyelination, rheumatoid arthritis, psoriatic arthritis, ankylosing spondylarthritis, and reactive arthritis; allergic reactions, for example, an allergic reaction associated with a disorder selected from: atopic dermatitis, pruritis, urticaria, asthma, conjunctivitis, allergic rhinitis, and anaphylaxis; CNS inflammation for example, CNS inflammation associated with a disorder selected from: Alzheimer's disease, stroke, dementia, amyotrophic lateral sclerosis, and human immunodeficiency virus; atherosclerosis; undesired immune cell activity, and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus; age-related macular degeneration; cough; leukemia; lymphoma; CNS tumors; prostate cancer; Alzheimer's disease; stroke-induced damage; dementia; amyotrophic lateral sclerosis, and Parkinson's disease.

BACKGROUND OF THE INVENTION

Cannabinoids are a group of extracellular signaling molecules that are found in both plants and animals. Signals from these molecules are mediated in animals by two G-protein coupled receptors, Cannabinoid Receptor 1 ($CB_1$) and Cannabinoid Receptor 2 ($CB_2$). $CB_1$ is expressed most abundantly in the neurons of the CNS but is also present at lower concentrations in a variety of peripheral tissues and cells (Matsuda, L. A. et al. (1990) Nature 346:561-564). In contrast, $CB_2$ is expressed predominantly, although not exclusively, in non-neural tissues, e.g. in hematopoietic cells, endothelial cells, osteoblasts, osteoclasts, the endocrine pancreas, and cancerous cell lines (Munro, S. et al. (1993) Nature 365:61-65; and as reviewed in Pacher, P. et al. (2006) Pharmacol. Rev. 58(3): 389-462). As such, $CB_1$ is believed to be primarily responsible for mediating the psychotropic effects of cannabinoids on the body, whereas $CB_2$ is believed to be primarily responsible for most of their non-neural effects.

The texts of the references cited in this disclosure are herein incorporated by reference in their entireties. In the event that a definition of a term as incorporated by reference differs from the meaning defined herein, then the meaning provided herein is intended.

SUMMARY OF THE INVENTION

One aspect of the present invention encompasses certain pyrazole derivatives selected from compounds of Formula Ia and pharmaceutically acceptable salts, solvates, hydrates, and N-oxides thereof:

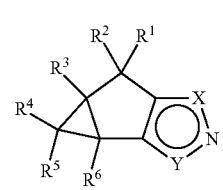

wherein:

$R^1$, $R^2$, $R^3$, $R^4$, $R^5$, and $R^6$ are each independently selected from: H and $C_1$-$C_6$ alkyl;

X is $NR^7$ and Y is $CC(O)N(R^8)R^9$; or

X is $CC(O)N(R^8)R^9$ and Y is $NR^7$;

$R^7$ is —$R^{10}$—$R^{11}$—$R^{12}$—$R^{13}$; wherein:

$R^{10}$ is selected from: $C_1$-$C_6$ alkylene, heteroarylene, and heterocyclylene; or $R^{10}$ is absent;

$R^{11}$ is selected from: —C(O)NH— and $C_1$-$C_6$ alkylene; or $R^{11}$ is absent;

$R^{12}$ is $C_1$-$C_6$ alkylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;

$R^8$ is —$R^{14}$—$R^{15}$—$R^{16}$—$R^{17}$; wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;

$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;

$R^{16}$ is $C_1$-$C_6$ alkylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

One aspect of the present invention encompasses certain pyrazole derivatives selected from compounds of Formula Ia and pharmaceutically acceptable salts, solvates, and hydrates thereof:

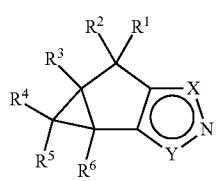

Ia wherein:

$R^1$, $R^2$, $R^3$, $R^4$, $R^5$, and $R^6$ are each independently selected from: H and $C_1$-$C_6$ alkyl;

X is $NR^7$ and Y is $CC(O)N(R^8)R^9$; or

X is $CC(O)N(R^8)R^9$ and Y is $NR^7$;

$R^7$ is —$R^{10}$—$R^{11}$—$R^{12}$—$R^{13}$; wherein:

$R^{10}$ is selected from: $C_1$-$C_6$ alkylene, heteroarylene, and heterocyclylene; or $R^{10}$ is absent;

$R^{11}$ is selected from: —C(O)NH— and $C_1$-$C_6$ alkylene; or $R^{11}$ is absent;

$R^{12}$ is $C_1$-$C_6$ alkylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;

$R^8$ is —$R^{14}$—$R^{15}$—$R^{16}$—$R^{17}$; wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;

$R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;

$R^{16}$ is $C_1$-$C_6$ alkylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

One aspect of the present invention relates to processes for preparing pharmaceutical compositions comprising admixing a compound of the present invention and a pharmaceutically acceptable carrier.

One aspect of the present invention relates to pharmaceutical compositions comprising a compound of the present invention and a pharmaceutically acceptable carrier.

One aspect of the present invention relates to method for the treatment of a cannabinoid receptor-mediated disorder in an individual, comprising administering to said individual in need thereof, a therapeutically effective amount of a compound of the present invention.

One aspect of the present invention relates to a method for the treatment of a $CB_2$ receptor-mediated disorder in an individual, comprising administering to said individual in need thereof, a therapeutically effective amount of a compound of the present invention.

One aspect of the present invention relates to a method for the treatment of a $CB_1$/$CB_2$ receptor-mediated disorder in an individual, comprising administering to said individual in need thereof, a therapeutically effective amount of a compound of the present invention.

One aspect of the present invention relates to a method for the treatment of pain in an individual, comprising administering to said individual in need thereof, a therapeutically effective amount of a compound of the present invention.

One aspect of the present invention relates to a method for the treatment of bone and joint pain in an individual, comprising administering to said individual in need thereof, a therapeutically effective amount of a compound of the present invention.

One aspect of the present invention relates to a method for the treatment of bone pain in an individual, comprising administering to said individual in need thereof, a therapeutically effective amount of a compound of the present invention.

One aspect of the present invention relates to a method for the treatment of joint pain in an individual, comprising administering to said individual in need thereof, a therapeutically effective amount of a compound of the present invention.

One aspect of the present invention relates to a method for the treatment of pain associated with osteoarthritis in an individual, comprising administering to said individual in need thereof, a therapeutically effective amount of a compound of the present invention.

One aspect of the present invention relates to a method for the treatment of osteoarthritis in an individual, comprising administering to said individual in need thereof, a therapeutically effective amount of a compound of the present invention.

One aspect of the present invention relates to a method for the treatment of osteoporosis in an individual, comprising administering to said individual in need thereof, a therapeutically effective amount of a compound of the present invention.

One aspect of the present invention relates to a method for the treatment of hyperalgesia in an individual, comprising administering to said individual in need thereof, a therapeutically effective amount of a compound of the present invention.

One aspect of the present invention relates to a method for the treatment of allodynia in an individual, comprising administering to said individual in need thereof, a therapeutically effective amount of a compound of the present invention.

One aspect of the present invention relates to a method for the treatment of inflammatory pain in an individual, comprising administering to said individual in need thereof, a therapeutically effective amount of a compound of the present invention.

One aspect of the present invention relates to a method for the treatment of inflammatory hyperalgesia in an individual, comprising administering to said individual in need thereof, a therapeutically effective amount of a compound of the present invention.

One aspect of the present invention relates to a method for the treatment of neuropathic pain in an individual, comprising administering to said individual in need thereof, a therapeutically effective amount of a compound of the present invention.

One aspect of the present invention relates to a method for the treatment of neuropathic hyperalgesia in an individual, comprising administering to said individual in need thereof, a therapeutically effective amount of a compound of the present invention.

One aspect of the present invention relates to a method for the treatment of acute nociception in an individual, comprising administering to said individual in need thereof, a therapeutically effective amount of a compound of the present invention.

One aspect of the present invention relates to a method for the treatment of muscle pain in an individual, comprising administering to said individual in need thereof, a therapeutically effective amount of a compound of the present invention.

One aspect of the present invention relates to a method for the treatment of dental pain in an individual, comprising administering to said individual in need thereof, a therapeutically effective amount of a compound of the present invention.

One aspect of the present invention relates to a method for the treatment of migraine and other headache pain in an individual, comprising administering to said individual in need thereof, a therapeutically effective amount of a compound of the present invention.

One aspect of the present invention relates to a method for the treatment of pain that occurs as an adverse effect of therapeutics in an individual, comprising administering to said individual in need thereof, a therapeutically effective amount of a compound of the present invention.

One aspect of the present invention relates to a method for the treatment of pain associated with a disorder selected from: cancer, multiple sclerosis, allergic reactions, nephritic syndrome, scleroderma, thyroiditis, diabetic neuropathy, fibromyalgia, HIV related-neuropathy, sciatica, and autoimmune conditions, in an individual, comprising administering to said individual in need thereof, a therapeutically effective amount of a compound of the present invention.

One aspect of the present invention relates to a method for the treatment of multiple sclerosis-associated spasticity in an individual, comprising administering to said individual in need thereof, a therapeutically effective amount of a compound of the present invention.

One aspect of the present invention relates to a method for the treatment of autoimmune disorders in an individual, comprising administering to said individual in need thereof, a therapeutically effective amount of a compound of the present invention.

One aspect of the present invention relates to a method for the treatment of an autoimmune disorder selected from the group consisting of: multiple sclerosis, Guillan-Barré syndrome, polyradiculoneuropathy, chronic inflammatory demyelination, rheumatoid arthritis, psoriatic arthritis, ankylosing spondylarthritis, and reactive arthritis, in an individual, comprising administering to said individual in need thereof, a therapeutically effective amount of a compound of the present invention.

One aspect of the present invention relates to a method for the treatment of allergic reactions in an individual, comprising administering to said individual in need thereof, a therapeutically effective amount of a compound of the present invention.

One aspect of the present invention relates to a method for the treatment of an allergic reaction associated with a disorder selected from: atopic dermatitis, pruritis, urticaria, asthma, conjunctivitis, allergic rhinitis, and anaphylaxis in an individual, comprising administering to said individual in need thereof, a therapeutically effective amount of a compound of the present invention.

One aspect of the present invention relates to a method for the treatment of CNS inflammation in an individual, comprising administering to said individual in need thereof, a therapeutically effective amount of a compound of the present invention.

One aspect of the present invention relates to a method for the treatment of CNS inflammation associated with a disorder selected from: Alzheimer's disease, stroke, dementia, amyotrophic lateral sclerosis, and human immunodeficiency virus, in an individual, comprising administering to said individual in need thereof, a therapeutically effective amount of a compound of the present invention.

One aspect of the present invention relates to a method for the treatment of atherosclerosis in an individual, comprising administering to said individual in need thereof, a therapeutically effective amount of a compound of the present invention.

One aspect of the present invention relates to a method for the treatment of undesired immune cell activity and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus, in an individual, comprising administering to said individual in need thereof, a therapeutically effective amount of a compound of the present invention.

One aspect of the present invention relates to a method for the treatment of age-related macular degeneration in an individual, comprising administering to said individual in need thereof, a therapeutically effective amount of a compound of the present invention.

One aspect of the present invention relates to a method for the treatment of cough in an individual, comprising administering to said individual in need thereof, a therapeutically effective amount of a compound of the present invention.

One aspect of the present invention relates to a method for the treatment of leukemia in an individual, comprising administering to said individual in need thereof, a therapeutically effective amount of a compound of the present invention.

One aspect of the present invention relates to a method for the treatment of lymphoma in an individual, comprising administering to said individual in need thereof, a therapeutically effective amount of a compound of the present invention.

One aspect of the present invention relates to a method for the treatment of CNS tumors in an individual, comprising administering to said individual in need thereof, a therapeutically effective amount of a compound of the present invention.

One aspect of the present invention relates to a method for the treatment of prostate cancer in an individual, comprising administering to said individual in need thereof, a therapeutically effective amount of a compound of the present invention.

One aspect of the present invention relates to a method for the treatment of Alzheimer's disease in an individual, comprising administering to said individual in need thereof, a therapeutically effective amount of a compound of the present invention.

One aspect of the present invention relates to a method for the treatment of stroke-induced damage in an individual, comprising administering to said individual in need thereof, a therapeutically effective amount of a compound of the present invention.

One aspect of the present invention relates to a method for the treatment of dementia in an individual, comprising administering to said individual in need thereof, a therapeutically effective amount of a compound of the present invention.

One aspect of the present invention relates to a method for the treatment of amyotrophic lateral sclerosis in an individual, comprising administering to said individual in need thereof, a therapeutically effective amount of a compound of the present invention.

A method for the treatment of Parkinson's disease in an individual, comprising administering to said individual in need thereof, a therapeutically effective amount of a compound of the present invention.

One aspect of the present invention relates to the use of a compound of the present invention in the manufacture of a medicament for the treatment of a cannabinoid receptor-mediated disorder.

One aspect of the present invention relates to the use of a compound of the present invention in the manufacture of a medicament for the treatment of a $CB_2$ receptor-mediated disorder.

One aspect of the present invention relates to the use of a compound of the present invention in the manufacture of a medicament for the treatment of a $CB_1/CB_2$ receptor-mediated disorder.

One aspect of the present invention relates to the use of a compound of the present invention in the manufacture of a medicament for the treatment of pain.

One aspect of the present invention relates to the use of a compound of the present invention in the manufacture of a medicament for the treatment of bone and joint pain.

One aspect of the present invention relates to the use of a compound of the present invention in the manufacture of a medicament for the treatment of bone pain.

One aspect of the present invention relates to the use of a compound of the present invention in the manufacture of a medicament for the treatment of joint pain.

One aspect of the present invention relates to the use of a compound of the present invention in the manufacture of a medicament for the treatment of pain associated with osteoarthritis.

One aspect of the present invention relates to the use of a compound of the present invention in the manufacture of a medicament for the treatment of osteoarthritis.

One aspect of the present invention relates to the use of a compound of the present invention in the manufacture of a medicament for the treatment of osteoporosis.

One aspect of the present invention relates to the use of a compound of the present invention in the manufacture of a medicament for the treatment of hyperalgesia.

One aspect of the present invention relates to the use of a compound of the present invention in the manufacture of a medicament for the treatment of allodynia.

One aspect of the present invention relates to the use of a compound of the present invention in the manufacture of a medicament for the treatment of inflammatory pain.

One aspect of the present invention relates to the use of a compound of the present invention in the manufacture of a medicament for the treatment of inflammatory hyperalgesia.

One aspect of the present invention relates to the use of a compound of the present invention in the manufacture of a medicament for the treatment of neuropathic pain.

One aspect of the present invention relates to the use of a compound of the present invention in the manufacture of a medicament for the treatment of neuropathic hyperalgesia.

One aspect of the present invention relates to the use of a compound of the present invention in the manufacture of a medicament for the treatment of acute nociception.

One aspect of the present invention relates to the use of a compound of the present invention in the manufacture of a medicament for the treatment of muscle pain.

One aspect of the present invention relates to the use of a compound of the present invention in the manufacture of a medicament for the treatment of dental pain.

One aspect of the present invention relates to the use of a compound of the present invention in the manufacture of a medicament for the treatment of migraine and other headache pain.

One aspect of the present invention relates to the use of a compound of the present invention in the manufacture of a medicament for the treatment of pain that occurs as an adverse effect of therapeutics.

One aspect of the present invention relates to the use of a compound of the present invention in the manufacture of a medicament for the treatment of pain associated with a disorder selected from: cancer, multiple sclerosis, allergic reactions, nephritic syndrome, scleroderma, thyroiditis, diabetic neuropathy, fibromyalgia, HIV related-neuropathy, sciatica, and autoimmune conditions.

One aspect of the present invention relates to the use of a compound of the present invention in the manufacture of a medicament for the treatment of multiple sclerosis-associated spasticity.

One aspect of the present invention relates to the use of a compound of the present invention in the manufacture of a medicament for the treatment of autoimmune disorders.

One aspect of the present invention relates to the use of a compound of the present invention in the manufacture of a medicament for the treatment of an autoimmune disorder selected from the group consisting of: multiple sclerosis, Guillan-Barré syndrome, polyradiculoneuropathy, chronic inflammatory demyelination, rheumatoid arthritis, psoriatic arthritis, ankylosing spondylarthritis, and reactive arthritis.

One aspect of the present invention relates to the use of a compound of the present invention in the manufacture of a medicament for the treatment of allergic reactions.

One aspect of the present invention relates to the use of a compound of the present invention in the manufacture of a medicament for the treatment of an allergic reaction associated with a disorder selected from: atopic dermatitis, pruritis, urticaria, asthma, conjunctivitis, allergic rhinitis, and anaphylaxis.

One aspect of the present invention relates to the use of a compound of the present invention in the manufacture of a medicament for the treatment of CNS inflammation.

One aspect of the present invention relates to the use of a compound of the present invention in the manufacture of a medicament for the treatment of CNS inflammation associated with a disorder selected from: Alzheimer's disease, stroke, dementia, amyotrophic lateral sclerosis, and human immunodeficiency virus.

One aspect of the present invention relates to the use of a compound of the present invention in the manufacture of a medicament for the treatment of atherosclerosis.

One aspect of the present invention relates to the use of a compound of the present invention in the manufacture of a medicament for the treatment of undesired immune cell activity and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus.

One aspect of the present invention relates to the use of a compound of the present invention in the manufacture of a medicament for the treatment of age-related macular degeneration.

One aspect of the present invention relates to the use of a compound of the present invention in the manufacture of a medicament for the treatment of cough.

One aspect of the present invention relates to the use of a compound of the present invention in the manufacture of a medicament for the treatment of leukemia.

One aspect of the present invention relates to the use of a compound of the present invention in the manufacture of a medicament for the treatment of lymphoma.

One aspect of the present invention relates to the use of a compound of the present invention in the manufacture of a medicament for the treatment of CNS tumors.

One aspect of the present invention relates to the use of a compound of the present invention in the manufacture of a medicament for the treatment of prostate cancer.

One aspect of the present invention relates to the use of a compound of the present invention in the manufacture of a medicament for the treatment of Alzheimer's disease.

One aspect of the present invention relates to the use of a compound of the present invention in the manufacture of a medicament for the treatment of stroke-induced damage.

One aspect of the present invention relates to the use of a compound of the present invention in the manufacture of a medicament for the treatment of dementia.

One aspect of the present invention relates to the use of a compound of the present invention in the manufacture of a medicament for the treatment of amyotrophic lateral sclerosis.

One aspect of the present invention relates to the use of a compound of the present invention in the manufacture of a medicament for the treatment of Parkinson's disease.

One aspect of the present invention relates to compounds of the present invention for use in a method of treatment of a cannabinoid receptor-mediated disorder.

One aspect of the present invention relates to compounds of the present invention for use in a method of treatment of the human or animal body by therapy.

One aspect of the present invention relates to compounds of the present invention for use in a method of treatment of a $CB_2$ receptor-mediated disorder.

One aspect of the present invention relates to compounds of the present invention for use in a method of treatment of a $CB_1/CB_2$ receptor-mediated disorder.

One aspect of the present invention relates to compounds of the present invention for use in a method of treatment of pain.

One aspect of the present invention relates to compounds of the present invention for use in a method of treatment of bone and joint pain.

One aspect of the present invention relates to compounds of the present invention for use in a method of treatment of bone pain.

One aspect of the present invention relates to compounds of the present invention for use in a method of treatment of joint pain.

One aspect of the present invention relates to compounds of the present invention for use in a method of treatment of pain associated with osteoarthritis.

One aspect of the present invention relates to compounds of the present invention for use in a method of treatment of osteoarthritis.

One aspect of the present invention relates to compounds of the present invention for use in a method of treatment of osteoporosis.

One aspect of the present invention relates to compounds of the present invention for use in a method of treatment of hyperalgesia.

One aspect of the present invention relates to compounds of the present invention for use in a method of treatment of allodynia.

One aspect of the present invention relates to compounds of the present invention for use in a method of treatment of inflammatory pain.

One aspect of the present invention relates to compounds of the present invention for use in a method of treatment of inflammatory hyperalgesia.

One aspect of the present invention relates to compounds of the present invention for use in a method of treatment of neuropathic pain.

One aspect of the present invention relates to compounds of the present invention for use in a method of treatment of neuropathic hyperalgesia.

One aspect of the present invention relates to compounds of the present invention for use in a method of treatment of acute nociception.

One aspect of the present invention relates to compounds of the present invention for use in a method of treatment of muscle pain.

One aspect of the present invention relates to compounds of the present invention for use in a method of treatment of dental pain.

One aspect of the present invention relates to compounds of the present invention for use in a method of treatment of migraine and other headache pain.

One aspect of the present invention relates to compounds of the present invention for use in a method of treatment of pain that occurs as an adverse effect of therapeutics.

One aspect of the present invention relates to compounds of the present invention for use in a method of treatment of pain associated with a disorder selected from: cancer, multiple sclerosis, allergic reactions, nephritic syndrome, scleroderma, thyroiditis, diabetic neuropathy, fibromyalgia, HIV related-neuropathy, sciatica, and autoimmune conditions.

One aspect of the present invention relates to compounds of the present invention for use in a method of treatment of multiple sclerosis-associated spasticity.

One aspect of the present invention relates to compounds of the present invention for use in a method of treatment of autoimmune disorders.

One aspect of the present invention relates to compounds of the present invention for use in a method of treatment of an autoimmune disorder selected from the group consisting of: multiple sclerosis, Guillan-Barré syndrome, polyradiculoneuropathy, chronic inflammatory demyelination, rheumatoid arthritis, psoriatic arthritis, ankylosing spondylarthritis, and reactive arthritis.

One aspect of the present invention relates to compounds of the present invention for use in a method of treatment of allergic reactions.

One aspect of the present invention relates to compounds of the present invention for use in a method of treatment of an allergic reaction associated with a disorder selected from: atopic dermatitis, pruritis, urticaria, asthma, conjunctivitis, allergic rhinitis, and anaphylaxis.

One aspect of the present invention relates to compounds of the present invention for use in a method of treatment of CNS inflammation.

One aspect of the present invention relates to compounds of the present invention for use in a method of treatment of CNS inflammation associated with a disorder selected from: Alzheimer's disease, stroke, dementia, amyotrophic lateral sclerosis, and human immunodeficiency virus.

One aspect of the present invention relates to compounds of the present invention for use in a method of treatment of atherosclerosis.

One aspect of the present invention relates to compounds of the present invention for use in a method of treatment of undesired immune cell activity and inflammation associated with a disorder selected from: osteoarthritis, anaphylaxis, Behcet's disease, graft rejection, vasculitis, gout, spondylitis, viral disease, bacterial disease, lupus, inflammatory bowel disease, autoimmune hepatitis, and type 1 diabetes mellitus.

One aspect of the present invention relates to compounds of the present invention for use in a method of treatment of age-related macular degeneration.

One aspect of the present invention relates to compounds of the present invention for use in a method of treatment of cough.

One aspect of the present invention relates to compounds of the present invention for use in a method of treatment of leukemia.

One aspect of the present invention relates to compounds of the present invention for use in a method of treatment of lymphoma.

One aspect of the present invention relates to compounds of the present invention for use in a method of treatment of CNS tumors.

One aspect of the present invention relates to the use of a compound of the present invention in the manufacture of a medicament for the treatment of prostate cancer.

One aspect of the present invention relates to compounds of the present invention for use in a method of treatment of Alzheimer's disease.

One aspect of the present invention relates to compounds of the present invention for use in a method of treatment of stroke-induced damage.

One aspect of the present invention relates to compounds of the present invention for use in a method of treatment of dementia.

One aspect of the present invention relates to compounds of the present invention for use in a method of treatment of amyotrophic lateral sclerosis.

One aspect of the present invention relates to compounds of the present invention for use in a method of treatment of Parkinson's disease.

These and other aspects of the invention disclosed herein will be set forth in greater detail as the patent disclosure proceeds.

DETAILED DESCRIPTION OF THE INVENTION

Definitions

Figure 1:
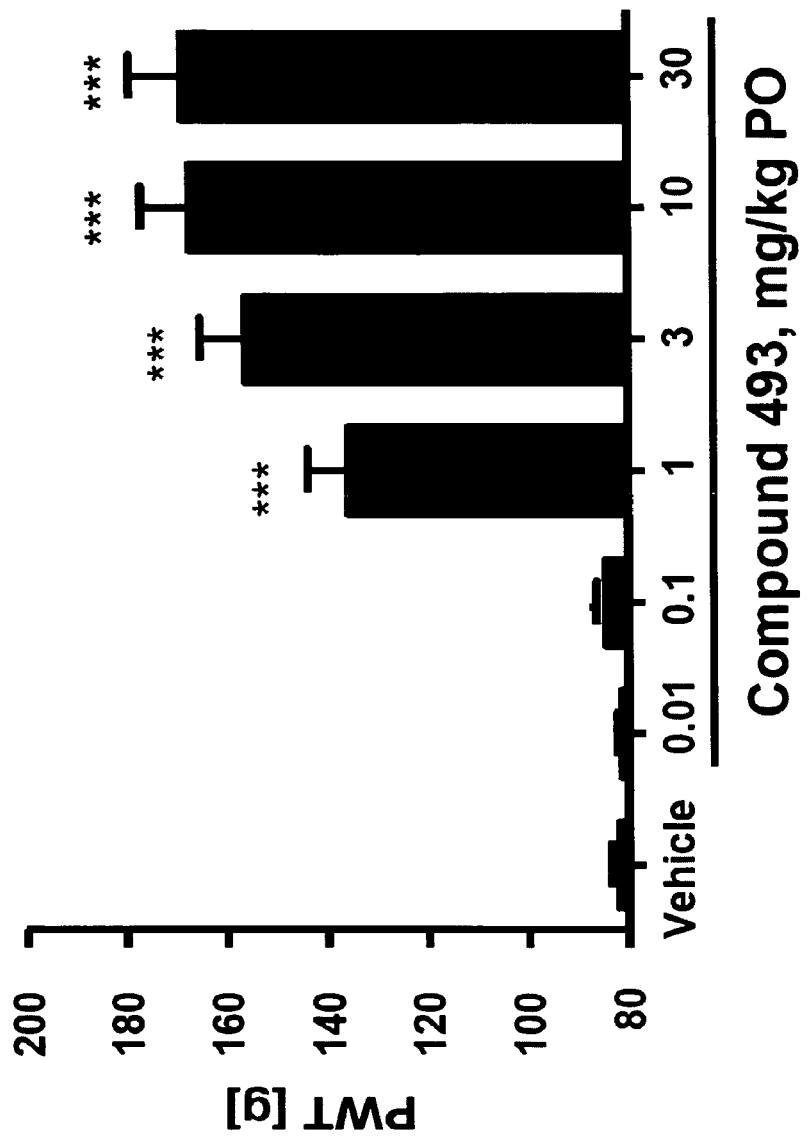
FIG. 1 shows the effect of Compound 493 in the FCA-induced hyperalgesia model of inflammatory pain in rats at 1 h post dosing. See Example 7.

For clarity and consistency, the following definitions will be used throughout this patent document.

The term "agonist" is intended to mean a moiety that interacts with and activates a G-protein-coupled receptor, for instance a cannabinoid receptor, and can thereby initiate a physiological or pharmacological response characteristic of that receptor. For example, an agonist may activate an intracellular response upon binding to a receptor, or enhance GTP binding to a membrane.

The term "antagonist" is intended to mean a moiety that competitively binds to the receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist.

The term "hydrate" as used herein means a compound of the invention or a salt thereof, that further includes a stoichiometric or non-stoichiometric amount of water bound by non-covalent intermolecular forces.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates, and most preferably humans.

The term "inverse agonist" is intended to mean a moiety that binds to the endogenous form of the receptor or to the constitutively activated form of the receptor and which inhibits the baseline intracellular response initiated by the active form of the receptor below the normal base level of activity which is observed in the absence of an agonist or partial agonist, or decreases GTP binding to a membrane. Preferably, the baseline intracellular response is inhibited in the presence of the inverse agonist by at least 30%, more preferably by at least 50% and most preferably by at least 75%, as compared with the baseline response in the absence of the inverse agonist.

The term "modulate or modulating" is intended to mean an increase or decrease in the amount, quality, response or effect of a particular activity, function or molecule.

The term "pharmaceutical composition" is intended to mean a composition comprising at least one active ingredient; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician or caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

Chemical Group, Moiety or Radical

The term "$C_1$-$C_4$ acyl" is intended to mean a radical comprising a $C_1$-$C_4$ alkyl group attached to the carbon of a carbonyl group, wherein $C_1$-$C_4$ alkyl has the same definition as found herein. Examples include, but are not limited to acetyl, propionyl, butyryl, isobutyryl, pivaloyl, and the like.

The term "amino" is intended to mean the group —$NH_2$.

The term "aryl" is intended to mean a ring system containing 6 to 10 carbon atoms, that may contain a single ring or two fused rings, and wherein at least one ring is aromatic. Examples include phenyl, indanyl, and naphthyl.

The term "arylamino" is intended to mean a radical comprising an aryl group, attached to a nitrogen, wherein aryl has the same definition as found herein. Examples include, but are not limited to, phenylamino and naphthylamino.

The term "arylcarbonyl" is intended to mean a radical comprising an aryl group, attached to the carbon atom of a carbonyl group, wherein aryl has the same definition as found herein. Examples include, but are not limited to, benzoyl and naphthylcarbonyl.

The term "aryloxy" is intended to mean a radical comprising an aryl group, attached to an oxygen, wherein aryl has the same definition as found herein. Examples include, but are not limited to, phenoxy and naphthyloxy.

The term "$C_1$-$C_6$ alkoxy" is intended to mean a radical comprising a $C_1$-$C_6$ alkyl group attached directly to an oxygen atom, wherein $C_1$-$C_6$ alkyl has the same definition as found herein. Some embodiments contain 1 to 5 carbons. Some embodiments contain 1 to 4 carbons. Some embodiments contain 1 to 3 carbons. Some embodiments contain 1 or 2 carbons. Examples include, but are not limited to methoxy, ethoxy, n-propoxy, isopropoxy, n-butoxy, t-butoxy, isobutoxy, s-butoxy, and the like.

The term "$C_1$-$C_6$ alkoxycarbonyl" is intended to mean a radical comprising a single $C_1$-$C_6$ alkoxy group attached to the carbon of a carbonyl group, wherein $C_1$-$C_6$ alkoxy has the same definition as found herein. The alkoxycarbonyl group may be represented by the following:

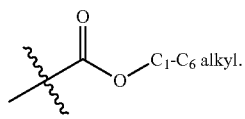

The term "$C_1$-$C_6$ alkyl" is intended to mean a straight or branched carbon radical containing 1 to 6 carbons. Some embodiments contain 1 to 5 carbons. Some embodiments contain 1 to 4 carbons. Some embodiments contain 1 to 3 carbons. Some embodiments contain 1 or 2 carbons. Examples of an alkyl group include, but are not limited to, methyl, ethyl, n-propyl, isopropyl, n-butyl, s-butyl, isobutyl, t-butyl, pentyl, isopentyl, t-pentyl, neopentyl, 1-methylbutyl [i.e., —$CH(CH_3)CH_2CH_2CH_3$], 2-methylbutyl [i.e., —$CH_2CH(CH_3)CH_2CH_3$], n-hexyl, and the like.

The term "$C_1$-$C_4$ alkyl" is intended to mean a straight or branched carbon radical containing 1 to 4 carbons. Some embodiments contain 1 to 3 carbons. Some embodiments contain 1 or 2 carbons. Examples of an alkyl group include, but are not limited to, methyl, ethyl, n-propyl, isopropyl, n-butyl, s-butyl, isobutyl, t-butyl, and the like.

The term "$C_1$-$C_6$ alkylamino" is intended to mean a radical comprising one $C_1$-$C_6$ alkyl group attached to an NH group, wherein $C_1$-$C_6$ alkyl has the same meaning as described herein. Some examples include, but are not limited to, methylamino, ethylamino, n-propylamino, isopropylamino, n-butylamino, s-butylamino, isobutylamino, t-butylamino, and the like. Some embodiments are "$C_1$-$C_2$ alkylamino."

The term "$C_1$-$C_6$ alkylcarboxamide" is intended to mean a single $C_1$-$C_6$ alkyl group attached to either the carbon or the nitrogen of an amide group, wherein $C_1$-$C_6$ alkyl has the same definition as found herein. The $C_1$-$C_6$ alkylcarboxamido group may be represented by the following:

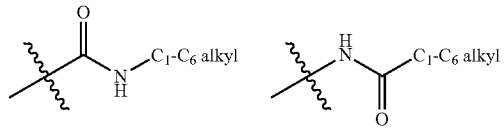

Examples include, but are not limited to, N-methylcarboxamide, N-ethylcarboxamide, N-n-propylcarboxamide, N-isopropylcarboxamide, N-n-butylcarboxamide, N-s-butylcarboxamide, N-isobutylcarboxamide, N-t-butylcarboxamide, and the like.

The term "$C_1$-$C_6$ alkylene" is intended to mean a straight or branched, saturated aliphatic, divalent radical having 1 to 6 carbon atoms. Some embodiments contain 1 to 5 carbons. Some embodiments contain 1 to 4 carbons. Some embodiments contain 1 to 3 carbons. Some embodiments contain 1 or 2 carbons. Examples include, but are not limited to, methylene, ethylene, n-propylene, isopropylene, n-butylene, s-butylene, isobutylene, t-butylene, pentylene, isopentylene, t-pentylene, neopentylene, 1-methylbutylene [i.e., —$CH(CH_3)CH_2CH_2CH_3$], 2-methylbutylene [i.e., —$CH_2CH(CH_3)CH_2CH_3$], n-hexylene, and the like.

The term "$C_1$-$C_6$ alkylsulfonyl" is intended to mean a radical comprising a $C_1$-$C_6$ alkyl group attached to the sulfur of a sulfonyl group, wherein the $C_1$-$C_6$ alkyl radical has the same definition as described herein. Examples include, but are not limited to, methylsulfonyl, ethylsulfonyl, n-propylsulfonyl, isopropylsulfonyl, n-butylsulfonyl, s-butylsulfonyl, isobutylsulfonyl, t-butylsulfonyl, and the like.

The term "$C_5$-$C_{11}$ bicycloalkyl" is intended to mean a radical comprising two fused or bridged, saturated rings containing 5 to 11 ring carbon atoms. Examples of a bicycloalkyl group include, but are not limited to, bicyclo[3.1.1]heptyl, bicyclo[2.2.1]heptyl, and the like.

The term "$C_3$-$C_7$ cycloalkenylene" is intended to mean is intended to mean a mono unsaturated ring di-radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropenediyl, cyclobutenediyl, cyclopentenediyl, cyclohexenediyl, cycloheptenediyl, and the like.

The term "$C_3$-$C_7$ cycloalkyl" is intended to mean a saturated ring radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropyl, cyclobutyl, cyclopentyl, cyclohexyl, cycloheptyl, and the like.

The term "$C_3$-$C_7$ cycloalkylamino" is intended to mean a radical comprising a $C_3$-$C_7$ cycloalkyl attached the nitrogen of an amino group, wherein $C_3$-$C_7$ cycloalkyl has the same definition as found herein. Examples include, but are not limited to, cyclopropylamino, cyclobutylamino, cyclopentylamino, cyclohexylamino, and the like.

The term "$C_3$-$C_7$ cycloalkylene" is intended to mean a saturated ring di-radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropanediyl, cyclobutanediyl, cyclopentanediyl, cyclohexanediyl, cycloheptanediyl, and the like. In some embodiments $C_3$-$C_7$ cycloalkylene is selected from: 1,1-cyclopropanediyl, 1,1-cyclobutanediyl, 1,1-cyclopentanediyl, 1,1-cyclohexanediyl, 1,1-cycloheptanediyl, and the like. In some embodiments $C_3$-$C_7$ cycloalkylene is selected from: 1,2-cyclopropanediyl, 1,2-cyclobutanediyl, 1,2-cyclopentanediyl, 1,2-cyclohexanediyl, 1,2-cycloheptanediyl, and the like.

The term "carbo-$C_1$-$C_6$-alkoxy" is intended to mean a $C_1$-$C_6$ alkyl ester of a carboxylic acid, wherein $C_1$-$C_6$ alkyl has the same definition as found herein. Examples include, but are not limited to, carbomethoxy [—C(O)OCH$_3$], carboethoxy, carbo-n-propoxy, carboisopropoxy, carbo-n-butoxy, carbo-s-butoxy, carbo-isobutoxy, carbo-t-butoxy, carbo-n-pentoxy, carbo-isopentoxy, carbo-t-pentoxy, carboneopentoxy, carbo-n-hexyloxy, and the like.

The term "carboxamide" is intended to mean the group —CONH$_2$.

The term "carboxy" is intended to mean the group —CO$_2$H; also referred to as a carboxylic acid group.

The term "cyano" is intended to mean the group —CN.

The term "$C_2$-$C_8$ dialkylamino" is intended to mean a radical comprising an amino group substituted with two of the same or different $C_1$-$C_4$ alkyl groups, wherein $C_1$-$C_4$ alkyl has the same definition as found herein. Some examples include, but are not limited to, dimethylamino, methylethylamino, diethylamino, methylpropylamino, methylisopropylamino, ethylpropylamino, ethylisopropylamino, dipropylamino, propylisopropylamino, and the like. Some embodiments are $C_2$-$C_4$ dialkylamino.

The term "$C_2$-$C_8$ dialkylsulfonamide" is intended to mean is intended to mean one of the following groups shown below:

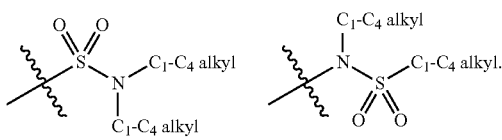

wherein $C_1$-$C_4$ alkyl has the same definition as found herein.

The term "$C_1$-$C_6$ haloalkoxy" is intended to mean a radical comprising a $C_1$-$C_6$ haloalkyl group directly attached to an oxygen atom, wherein $C_1$-$C_6$ haloalkyl has the same definition as found herein. Examples include, but are not limited to, difluoromethoxy, trifluoromethoxy, 2,2,2-trifluoroethoxy, pentafluoroethoxy, and the like.

The term "$C_1$-$C_6$ haloalkyl" is intended to mean a radical comprising a $C_1$-$C_6$ alkyl group substituted with one or more halogens, wherein $C_1$-$C_6$ alkyl has the same definition as found herein. The $C_1$-$C_6$ haloalkyl may be fully substituted in which case it can be represented by the formula $C_nL_{2n+1}$, wherein L is a halogen and "n" is 1, 2, 3, 4, 5 or 6. When more than one halogen is present then they may be the same or different and selected from: fluorine, chlorine, bromine, and iodine. In some embodiments, haloalkyl contains 1 to 5 carbons. In some embodiments, haloalkyl contains 1 to 4 carbons. In some embodiments, haloalkyl contains 1 to 3 carbons. In some embodiments, haloalkyl contains 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl, and the like.

The term "halogen" is intended to mean to a fluoro, chloro, bromo or iodo group.

The term "heteroaryl" is intended to mean a ring system containing 5 to 14 ring atoms, that may contain a single ring, two fused rings or three fused rings, and wherein at least one ring is aromatic and at least one ring atom is a heteroatom selected from, for example: O, S and N, wherein N is optionally substituted with H, $C_1$-$C_4$ acyl, $C_1$-$C_4$ alkyl, or oxide (i.e., together with an aromatic ring nitrogen form an N-oxide). Some embodiments contain 5 to 6 ring atoms for example furanyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, triazinyl, and the like. Some embodiments contain 8 to 14 ring atoms for example quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran, 2,3-dihydrobenzofuranyl, 4H-benzo[1,3]dioxinyl, 3,4-dihydro-1H-isoquinolinyl, 1,4,6,7-tetrahydroimidazo[4,5-c]pyridinyl, 7,8-dihydro-5H-[1,6]naphthyridinyl, 5,6-dihydro-8H-[1,2,4]triazolo[4,3-a]pyrazinyl, benzo[1,3]dioxolyl, pyrazolo[1,5-a]pyrimidinyl, 1,2,3,4-tetrahydroquinolinyl, and the like.

The term "heteroarylene" is intended to mean is intended to mean an aromatic ring di-radical containing 5 to 14 ring atoms that may be a single ring, two fused rings or three fused rings, wherein at least one aromatic ring atom is a heteroatom selected from, for example: 0, S, and N, wherein N is optionally substituted with H, $C_1$-$C_4$ acyl, $C_1$-$C_4$ alkyl, or oxide (i.e., together with an aromatic ring nitrogen form an N-oxide). Some embodiments contain 5 to 6 ring atoms for example furandiyl, thiophenediyl, pyrrolediyl, imidazolediyl, oxazolediyl, thiazolediyl, isoxazolediyl, pyrazolediyl, isothiazolediyl, oxadiazolediyl, triazolediyl, thiadiazolediyl, pyridinediyl, pyrazinediyl, pyrimidinediyl, pyridazinediyl, triazinediyl, and the like. Some embodiments contain 8 to 14 ring atoms for example quinolizinediyl, quinolinediyl, isoquinolinediyl, cinnolinediyl, phthalazinediyl, quinazolinediyl, quinoxalinediyl, triazinediyl, indolediyl, isoindolediyl, indazolediyl, indolizinediyl, purinediyl, naphthyridinediyl, pteridinediyl, carbazolediyl, acridinediyl. phenazinediyl, phenothiazinediyl, phenoxazinediyl, benzoxazolediyl, benzothiazolediyl, 1H-benzimidazolediyl, imidazopyridinediyl, benzothienediyl, benzofurandiyl, isobenzofurandiyl, and the like.

The term "heteroaryloxy" is intended to mean a radical comprising a heteroaryl group, attached to an oxygen, wherein heteroaryl has the same definition as found herein. The term "heterobicyclyl" is intended to mean a radical comprising two fused or bridged, non-aromatic rings containing 5 to 11 ring atoms wherein one, two, three or four ring atoms are heteroatoms selected from, for example: O, S, and N, wherein N is substituted with H, $C_1$-$C_4$ acyl or $C_1$-$C_4$ alkyl, and S is optionally substituted with one or two oxygens. Examples of a heterobicyclyl group include, but are not limited to, octahydropyrrolo[1,2-a]pyrazinyl, 1-azabicyclo[2.2.2]octyl, 9-aza-bicyclo[3.3.1]nonyl, and the like.

The term "heterocyclyl" is intended to mean a non-aromatic ring radical containing 3 to 8 ring atoms, wherein one, two or three ring atoms are heteroatoms selected from, for example: O, S, and N, wherein N is substituted with H, $C_1$-$C_4$ acyl or $C_1$-$C_4$ alkyl, and S is optionally substituted with one or two oxygens. Examples of a heterocyclyl group include, but are not limited to, aziridinyl, azetidinyl, piperidinyl, morpholinyl, piperazinyl, pyrrolidinyl, [1,3]-dioxolanyl, thiomorpholinyl, [1,4]oxazepanyl, 1,1-dioxothiomorpholinyl, azepanyl, tetrahydrofuranyl, tetrahydropyranyl, tetrahydrothiopyranyl, 1-oxo-hexahydro-1$\lambda^4$-thiopyranyl, 1,1-dioxo-hexahydro-1$\lambda^6$-thiopyranyl, and the like.

The term "heterocyclylene" is intended to mean a non-aromatic ring di-radical containing 3 to 8 ring atoms, wherein one, two or three ring atoms are heteroatoms selected from, for example: O, S, and N, wherein N is substituted with H, $C_1$-$C_4$ acyl or $C_1$-$C_4$ alkyl, and S is optionally substituted with one or two oxygens. Examples of a heterocyclylene group include, but are not limited to, aziridinediyl, azetidinediyl, piperidinediyl, morpholinediyl, piperazinediyl, pyrrolidinediyl, [1,3]-dioxolanediyl, thiomorpholinediyl, [1,4]oxazepanediyl, 1,1-dioxothiomorpholinediyl, azepanediyl, tetrahydrofurandiyl, and the like.

The term "hydroxyl" is intended to mean the group —OH.
The term "phosphonooxy" is intended to mean the group —OP(O)(OH)$_2$.
The term "ureyl" is intended to mean the group —NH$_2$C(O)NH$_2$.

Compounds of the Invention

One aspect of the present invention pertains to certain compounds as shown in Formula Ia and pharmaceutically acceptable salts, solvates, and hydrates thereof:

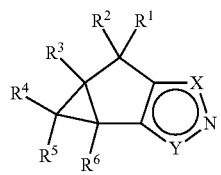

Ia wherein $R^1$, $R^2$, $R^3$, $R^4$, $R^5$, $R^6$, X, and Y have the same definitions as described herein, supra and infra.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, X, and Y) contained within the generic chemical formulae described herein, for example, Ia, Ic, Id, and Ie, etc., are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents, and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

The present disclosure includes all isotopes of atoms occurring in the present compounds, salts and crystalline forms thereof. Compounds of the invention can also include all isotopes of atoms occurring in the intermediates and/or final compounds. Isotopes include those atoms having the same atomic number but different mass numbers. By way of general example, and without limitation, isotopes of hydrogen include $^2$H (deuterium) and $^3$H (tritium). Isotopes of carbon include $^{13}$C and $^{14}$C.

It is understood and appreciated that compounds of Formula Ia and formulae related thereto may have one or more chiral centers and therefore can exist as enantiomers and/or diastereoisomers. The invention is understood to extend to and embrace all such enantiomers, diastereoisomers and mixtures thereof, including but not limited to racemates. It is understood that compounds of Formula Ia and formulae used throughout this disclosure are intended to represent all individual enantiomers and mixtures thereof, unless stated or shown otherwise.

The Group $R^1$:
In some embodiments, $R^1$ is selected from: H and $C_1$-$C_6$ alkyl.
In some embodiments, $R^1$ is H.
In some embodiments, $R^1$ is $C_1$-$C_6$ alkyl.

In some embodiments, $R^1$ is methyl.
In some embodiments, $R^1$ is isopropyl.
The Group $R^2$:
In some embodiments, $R^2$ is selected from: H and $C_1$-$C_6$ alkyl.
In some embodiments, $R^2$ is H.
In some embodiments, $R^2$ is $C_1$-$C_6$ alkyl.
In some embodiments, $R^2$ is methyl.
In some embodiments, $R^2$ is isopropyl.
The Group $R^3$:
In some embodiments, $R^3$ is selected from: H and $C_1$-$C_6$ alkyl.
In some embodiments, $R^3$ is H.
In some embodiments, $R^3$ is $C_1$-$C_6$ alkyl.
In some embodiments, $R^3$ is methyl.
In some embodiments, $R^3$ is isopropyl.
The Group $R^4$:
In some embodiments, $R^4$ is selected from: H and $C_1$-$C_6$ alkyl.
In some embodiments, $R^4$ is H.
In some embodiments, $R^4$ is $C_1$-$C_6$ alkyl.
In some embodiments, $R^4$ is methyl.
In some embodiments, $R^4$ is isopropyl.
The Group $R^5$:
In some embodiments, $R^5$ is selected from: H and $C_1$-$C_6$ alkyl.
In some embodiments, $R^5$ is H.
In some embodiments, $R^5$ is $C_1$-$C_6$ alkyl.
In some embodiments, $R^5$ is methyl.
In some embodiments, $R^5$ is isopropyl.
The Group $R^6$:
In some embodiments, $R^6$ is selected from: H and $C_1$-$C_6$ alkyl.
In some embodiments, $R^6$ is H.
In some embodiments, $R^6$ is $C_1$-$C_6$ alkyl.
In some embodiments, $R^6$ is methyl.
In some embodiments, $R^6$ is isopropyl.
The Group X:
In some embodiments, X is $NR^7$; wherein $R^7$ is —$R^{10}$—$R^{11}$—$R^{12}$—$R^{13}$
In some embodiments, X is $CCONR^8R^9$.
In some embodiments, X is $CC(O)NHR^8$.
The Group Y:
In some embodiments, Y is $NR^7$; wherein $R^7$ is —$R^{10}$—$R^{11}$—$R^{12}$—$R^{13}$
In some embodiments, Y is $CCONR^8R^9$.
In some embodiments, Y is $CC(O)NHR^8$.
The Group $R^7$:
In some embodiments, $R^7$ is —$R^{10}$—$R^{11}$—$R^{12}$—$R^{13}$, or an N-oxide thereof.
In some embodiments, $R^7$ is —$R^{10}$—$R^{11}$—$R^{12}$—$R^{13}$.
In some embodiments, $R^7$ is selected from: aryl and heteroaryl; wherein said aryl and heteroaryl are each optionally substituted with one or two substituents selected from: cyano and halogen.
In some embodiments, $R^7$ is selected from: aryl and heteroaryl; wherein said aryl and heteroaryl are each optionally substituted with one or two substituents selected from: fluoro, chloro, and cyano.
In some embodiments, $R^7$ is selected from: 2,4-difluoro-phenyl, 2,4-dichloro-phenyl, 5-chloro-pyridin-2-yl, 5-cyano-pyrazin-2-yl, pyrazin-2-yl, 5-fluoro-pyridin-2-yl, 4-chloro-pyridin-2-yl, 4-fluoro-pyridin-2-yl, 4-cyano-pyridin-2-yl, and 4-oxy-pyrazin-2-yl.
In some embodiments, $R^7$ is selected from: 2,4-difluoro-phenyl, 2,4-dichloro-phenyl, 5-chloro-pyridin-2-yl, 5-cyano-pyrazin-2-yl, pyrazin-2-yl, 5-fluoro-pyridin-2-yl, 4-chloro-pyridin-2-yl, 4-fluoro-pyridin-2-yl, 4-cyano-pyridin-2-yl, and 4-oxy-pyrazin-2-yl.
In some embodiments, $R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3']bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, piperidin-4-yl, tetrahydro-pyran-4-yl, 3-methyl-1,1-dioxo-tetrahydro-1$\lambda^6$-thiophen-3-yl, 5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 3-hydroxy-3-methyl-butyl, 4-iodo-pyridin-2-yl, 1-oxy-pyridin-3-yl, 4-tert-butylcarbamoyl-pyridin-2-yl, and 4-hydroxy-pyridin-2-yl.
In some embodiments, $R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3']bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, and piperidin-4-yl.

In some embodiments, $R^7$ is 2,4-difluoro-phenyl. In some embodiments, $R^7$ is 5-bromo-pyridin-2-yl. In some embodiments, $R^7$ is 4-cyano-phenyl. In some embodiments, $R^7$ is pyridin-3-yl. In some embodiments, $R^7$ is pyridin-2-yl. In some embodiments, $R^7$ is 5-thiazol-2-yl-pyridin-2-yl. In some embodiments, $R^7$ is 5-trifluoromethyl-pyridin-2-yl. In some embodiments, $R^7$ is 5-o-tolyl-pyridin-2-yl. In some embodiments, $R^7$ is 5-dimethylamino-pyrazin-2-yl. In some embodiments, $R^7$ is 2,4-dichloro-phenyl. In some embodiments, $R^7$ is 5-isopropyl-pyridin-2-yl. In some embodiments, $R^7$ is 5-methyl-pyridin-2-yl. In some embodiments, $R^7$ is 5-(4-methoxy-phenyl)-pyridin-2-yl. In some embodiments, $R^7$ is 2-fluoro-4-methanesulfonyl-phenyl. In some embodiments, $R^7$ is 2-fluoro-phenyl. In some embodiments, $R^7$ is 5-chloro-pyridin-2-yl. In some embodiments, $R^7$ is 5-bromo-pyridin-3-yl. In some embodiments, $R^7$ is tert-butyl. In some embodiments, $R^7$ is 2-methoxy-pyridin-4-yl. In some embodiments, $R^7$ is 2,2-dimethyl-propyl. In some embodiments, $R^7$ is tetrahydro-pyran-4-ylmethyl. In some embodiments, $R^7$ is phenyl. In some embodiments, $R^7$ is 4-trifluoromethyl-pyridin-2-yl. In some embodiments, $R^7$ is 6-chloro-pyrazin-2-yl. In some embodiments, $R^7$ is 1-oxo-hexahydro-1$\lambda^4$-thiopyran-4-yl. In some embodiments, $R^7$ is 5-morpholin-4-yl-pyridin-2-yl. In some embodiments, $R^7$ is 6-bromo-pyridin-3-yl. In some embodiments, $R^7$ is 5-methoxy-pyridin-2-yl. In some embodiments, $R^7$ is 5,6-difluoro-pyridin-3-yl. In some embodiments, $R^7$ is 6-methoxy-pyridazin-3-yl. In some embodiments, $R^7$ is 2-chloro-pyridin-4-yl. In some embodiments, $R^7$ is 5-cyclopropyl-pyrazin-2-yl. In some embodiments, $R^7$ is 1,1-dioxo-tetrahydro-1$\lambda^6$-thiophen-3-yl. In some embodiments, $R^7$ is 1-benzyl-piperidin-4-yl. In some embodiments, $R^7$ is 6-cyano-pyrazin-2-yl. In some embodiments, $R^7$ is 2-hydroxy-2-methyl-propyl. In some embodiments, $R^7$ is 4-fluoro-phenyl. In some embodiments, $R^7$ is 5-ethyl-pyridin-2-yl. In some embodiments, $R^7$ is isopropyl. In some embodiments, $R^7$ is 5-phenyl-pyridin-2-yl. In some embodiments, $R^7$ is pyridin-4-yl. In some embodiments, $R^7$ is 2,5-difluoro-phenyl. In some embodiments, $R^7$ is 3-fluoro-phenyl. In some embodiments, $R^7$ is pyrimidin-4-yl. In some embodiments, $R^7$ is 2-(tetrahydro-pyran-4-yl)-ethyl. In some embodiments, $R^7$ is 3,5-difluoro-pyridin-2-yl. In some embodiments, $R^7$ is pyrazin-2-yl. In some embodiments, $R^7$ is tetrahydro-thiopyran-4-yl. In some embodiments, $R^7$ is 5-p-tolyl-pyridin-2-yl. In some embodiments, $R^7$ is 4-methoxy-phenyl. In some embodiments, $R^7$ is 2-morpholin-4-yl-ethyl. In some embodiments, $R^7$ is 5-cyano-pyridin-2-yl. In some embodiments, $R^7$ is 5-cyano-pyrazin-2-yl. In some embodiments, $R^7$ is 6'-methyl-[3,3']bipyridinyl-6-yl. In some embodiments, $R^7$ is 6-chloro-pyridazin-3-yl. In some embodiments, $R^7$ is 5-fluoro-pyridin-2-yl. In some embodiments, $R^7$ is 5-ethyl-pyrazin-2-yl. In some embodiments, $R^7$ is 6-methoxy-pyrazin-2-yl. In some embodiments, $R^7$ is 5-dimethylamino-pyridin-2-yl. In some embodiments, $R^7$ is 1-(4-fluoro-phenyl)-1-methyl-ethyl. In some embodiments, $R^7$ is 5-pyrimidin-5-yl-pyridin-2-yl. In some embodiments, $R^7$ is 4-methyl-pyridin-2-yl. In some embodiments, $R^7$ is 5-methoxy-pyrazin-2-yl. In some embodiments, $R^7$ is 5-propyl-pyridin-2-yl. In some embodiments, $R^7$ is 5-m-tolyl-pyridin-2-yl. In some embodiments, $R^7$ is 5-hydroxy-pyrazin-2-yl. In some embodiments, $R^7$ is cyclopropyl-pyridin-2-yl. In some embodiments, $R^7$ is 2,6-difluoro-phenyl. In some embodiments, $R^7$ is 3-fluoro-pyridin-4-yl. In some embodiments, $R^7$ is 5-isopropyl-pyrazin-2-yl. In some embodiments, $R^7$ is 5-bromo-pyrazin-2-yl. In some embodiments, $R^7$ is 5-cyclopentyl-pyridin-2-yl. In some embodiments, $R^7$ is o-tolyl. In some embodiments, $R^7$ is 4-fluoro-benzyl. In some embodiments, $R^7$ is 3-methyl-pyridin-2-yl. In some embodiments, $R^7$ is 6-methyl-4-trifluoromethyl-pyridin-2-yl. In some embodiments, $R^7$ is 6-dimethylamino-pyrazin-2-yl. In some embodiments, $R^7$ is 1,1-dioxo-hexahydro-1$\lambda^6$-thiopyran-4-yl. In some embodiments, $R^7$ is 5-(4-fluoro-phenyl)-pyridin-2-yl. In some embodiments, $R^7$ is 5-cyclopropyl-pyridin-2-yl. In some embodiments, $R^7$ is 6-ethyl-pyrazin-2-yl. In some embodiments, $R^7$ is 5-methylamino-pyrazin-2-yl. In some embodiments, $R^7$ is dichloro-phenyl. In some embodiments, $R^7$ is 3-fluoro-pyridin-2-yl. In some embodiments, $R^7$ is 5-cyclobutyl-pyrazin-2-yl. In some embodiments, $R^7$ is 5-ethoxy-pyrazin-2-yl. In some embodiments, $R^7$ is 5-trifluoromethyl-pyrazin-2-yl. In some embodiments, $R^7$ is 5-cyano-pyridin-3-yl. In some embodiments, $R^7$ is 5-cyclopropylmethyl-pyrazin-2-yl. In some embodiments, $R^7$ is 5-pentafluoroethyl-pyrazin-2-yl. In some embodiments, $R^7$ is 5-heptafluoropropyl-pyrazin-2-yl. In some embodiments, $R^7$ is 5-chloro-4-methyl-pyridin-2-yl. In some embodiments, $R^7$ is 5-chloro-4-trifluoromethyl-pyridin-2-yl. In some embodiments, $R^7$ is 4-bromo-pyridin-2-yl. In some embodiments, $R^7$ is 4-chloro-pyridin-2-yl. In some embodiments, $R^7$ is 4-fluoro-pyridin-2-yl. In some embodiments, $R^7$ is 4-oxy-pyrazin-2-yl. In some embodiments, $R^7$ is 4-cyclopropyl-pyridin-2-yl. In some embodiments, $R^7$ is 4-cyano-pyridin-2-yl. In some embodiments, $R^7$ is 4-methanesulfonyl-pyridin-2-yl. In some embodiments, $R^7$ is 4-methoxy-pyridin-2-yl. In some embodiments, $R^7$ is piperidin-4-yl. In some embodiments, $R^7$ is tetrahydro-pyran-4-yl. In some embodiments, $R^7$ is 3-methyl-1,1-dioxo-tetrahydro-1$\lambda^6$-thiophen-3-yl. In some embodiments, $R^7$ is 5-chloro-3-fluoro-pyridin-2-yl. In some embodiments, $R^7$ is 3-fluoro-5-methoxy-pyridin-2-yl. In some embodiments, $R^7$ is 2-chloro-4-fluoro-phenyl. In some embodiments, $R^7$ is 6-fluoro-pyridin-3-yl. In some embodiments, $R^7$ is 6-cyano-pyridin-3-yl. In some embodiments, $R^7$ is 3-hydroxy-3-methyl-butyl. In some embodiments, $R^7$ is 4-iodo-pyridin-2-yl. In some embodiments, $R^7$ is 1-oxy-pyridin-3-yl. In some embodiments, $R^7$ is 4-tert-butylcarbamoyl-pyridin-2-yl. In some embodiments, $R^7$ is 4-hydroxy-pyridin-2-yl.

The Group $R^8$:

In some embodiments, $R^8$ is —$R^{14}$—$R^{15}$—$R^{16}$—$R^{17}$.

In some embodiments, $R^8$ is selected from: 1-hydroxymethyl-2,2-dimethyl-propyl, 2-hydroxy-1,1-dimethyl-ethyl, 1-hydroxymethyl-cyclopropyl, 2-hydroxy-indan-1-yl, 1-hydroxymethyl-cyclobutyl, tert-butyl, 2-hydroxy-1-phenyl-ethyl, 2-hydroxy-1-hydroxymethyl-1-methyl-ethyl, tert-butylamino, 2,2,2-trifluoro-1,1-dimethyl-ethyl, 2-methyl-1-(phosphonooxy)propan-2-yl, 1-methyl-cyclobutyl, 1-hydroxymethyl-2-methyl-propyl, cyano-dimethyl-methyl, 2,2-dimethyl-1-(methylcarbamoyl)-propyl, 3,3-dimethyl-1-(phosphonooxy)butan-2-yl, 2-hydroxy-1-tetrahydro-pyran-4-yl-ethyl, 1,2-dimethyl-propyl, 1-pyridin-2-yl-cyclobutyl, 2-(methylamino)-2-oxo-1-phenylethyl, 2,2-dimethyl-1-pyridin-2-yl-propyl, 1-methoxy-3,3-dimethyl-1-oxobutan-2-yl, 1-(2-amino-3-methylbutanoyloxy)-3-methylbutan-2-yl, 1-(4-carboxybutanoyloxy)-3-methylbutan-2-yl, 3,3,3-trifluoro-1-hydroxymethyl-propyl, 2-fluoro-1,1-dimethyl-ethyl, 2-fluoro-1-fluoromethyl-1-hydroxymethyl-ethyl, 1-fluoromethyl-2,2-dimethyl-propyl, 1-fluoromethyl-cyclobutyl, 1-trifluoromethyl-cyclopropyl, and 1-trifluoromethyl-cyclobutyl.

In some embodiments, $R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluoro-phenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclobutyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)piperidin-3-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluoro-phenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1$\lambda^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1$\lambda^{4+}$thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, indan-1-ylamide, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydro-furan-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1$\lambda^6$-thiophen-3-ylmethyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chloro-phenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxy-benzyl, 4-hydroxy-1-methyl-piperidin-4-ylmethyl, 1-(2,5-dimethylpyrrolidine-1-carbonyl)cyclopentyl, 2-methoxy-benzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoropropyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1$\lambda^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1$\lambda^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methylamino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoro-ethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino)ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, 2,2-dimethyl-1-pyridin-2-yl-propyl, (1,1-dioxo-tetrahydro-1$\lambda^6$-thiophen-3-yl)amino, 1-hydroxycarbamoyl-2,2-dimethyl-propyl, 1-hydroxymethyl-2-methyl-butyl, 1-(2-hydroxy-ethylcarbamoyl)-2,2-dimethyl-propyl, 1,1-bis-hydroxymethyl-propyl, 1-(5-fluoro-pyridin-2-yl)-2,2-dimethyl-propyl, 4-hydroxymethyl-tetrahydro-2H-pyran-4-yl, 1-(2-(tert-butoxycarbonylamino)-3-methylbutanoyloxy)-2-methylpropan-2-yl, 1-(2-amino-3-methylbutanoyloxy)-3-methylbutan-2-yl, 1-(2-amino-3-methylbutanoyloxy)-2-methylpropan-2-yl, 2-hydroxy-1-(tetrahydro-2H-pyran-4-yl)-ethyl, 1-(4-carboxybutanoyloxy)-2-methylpropan-2-yl, 1-(4-carboxybutanoyloxy)-3-methylbutan-2-yl, 1-(4-carboxybutanoyloxy)-3,3-dimethylbutan-2-yl, 1-(2-amino-3-methylbutanoyloxy)-3,3-dimethylbutan-2-yl, 2-(2-amino-3-methylbutanoyloxy)-1-(tetrahydro-2H-pyran-4-yl)ethyl, 3,3,3-trifluoro-1-hydroxymethyl-propyl, 3-fluoro-1-methoxy-3-methyl-1-oxobutan-2-yl, 1-ethoxy-4,4,4-trifluoro-1-oxo-3-(trifluoromethyl)butan-2-yl, 2-fluoro-1-hydroxymethyl-2-methyl-propyl, 1-(2-(tert-butoxycarbonylamino)-3-methylbutanoyloxy)-3,3-dimethylbutan-2-yl, 4,4,4-trifluoro-1-methoxy-1-oxobutan-2-yl, 2-fluoro-1,1-dimethyl-ethyl, 3-fluoro-2-(fluoromethyl)-1-methoxy-1-oxopropan-2-yl, 2-fluoro-1-fluoromethyl-1-hydroxymethyl-ethyl, 3-hydroxy-1-methoxy-2-methyl-1-oxopropan-2-yl, 2-carboxy-1-hydroxypropan-2-yl, 2,2,2-trifluoroethylamino, 1-fluoromethyl-2-methyl-propyl, 1-fluoromethyl-2,2-dimethyl-propyl, 3-methyl-oxetan-3-yl, 1-fluoromethyl-cyclobutyl, 1,1-bis-hydroxymethyl-2-methyl-propyl, 1-trifluoromethyl-cyclopropyl, 1-methyl-cyclopropyl, and 1-trifluoromethyl-cyclobutyl.

In some embodiments, $R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenylethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluoro-phenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclobutyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-methoxy-phenyl)-ethyl, 2-methoxy-pyridin-4-yl, 1-pyridin-2-yl-cyclopropyl, 1-(tert-butoxycarbonyl)piperidin-4-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluorophenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1$\lambda^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1$\lambda^4$-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydro-furan-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1$\lambda^6$-thiophen-3-ylmethyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chloro-phenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxy-benzyl, 4-hydroxy-1-methyl-piperidin-4-ylmethyl, 1-(2,5-dimethylpyrrolidine-1-carbonyl)cyclopentyl, 2-methoxy-benzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoropropyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1$\lambda^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1$\lambda^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methylamino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoro-ethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino) ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, and 2,2-dimethyl-1-pyridin-2-yl-propyl.

In some embodiments, $R^8$ is H. In some embodiments, $R^8$ is 2-methyl-2-morpholin-4-yl-propyl. In some embodiments, $R^8$ is 1-hydroxymethyl-2,2-dimethyl-propyl. In some embodiments, $R^8$ is 2-(tert-butoxycarbonylamino)cyclohexyl. In some embodiments, $R^8$ is 1-phenyl-cyclopropyl. In some embodiments, $R^8$ is 5-trifluoromethyl-pyridin-2-yl. In some embodiments, $R^8$ is 1-methyl-1-phenyl-ethyl. In some embodiments, $R^8$ is 1-(2-methoxy-ethyl)-pyrrolidin-3-ylmethyl. In some embodiments, $R^8$ is 1-(methoxycarbonyl)cyclopropyl. In some embodiments, $R^8$ is tetrahydro-pyran-4-ylmethyl. In some embodiments, $R^8$ is 1-(tert-butoxycarbonyl)piperidin-4-yl. In some embodiments, $R^8$ is 1-(4-fluoro-phenyl)-cyclopropyl. In some embodiments, $R^8$ is 6-methyl-pyridin-3-ylmethyl. In some embodiments, $R^8$ is 2-hydroxy-1-phenyl-ethyl. In some embodiments, $R^8$ is 1,3,3-trimethyl-bicyclo[2.2.1]hept-2-yl. In some embodiments, $R^8$ is 2-hydroxy-1,1-dimethyl-ethyl. In some embodiments, $R^8$ is 2-(5-hydroxy-1H-indol-3-yl)-ethyl. In some embodiments, $R^8$ is 1-hydroxymethyl-cyclopropyl. In some embodiments, $R^8$ is 3-chloro-5-methyl-pyridin-2-yl. In some embodiments, $R^8$ is 6-fluoro-pyridin-3-yl. In some embodiments, $R^8$ is 1-(3-fluoro-phenyl)-cyclobutyl. In some embodiments, $R^8$ is 2-methyl-pyridin-3-yl. In some embodiments, $R^8$ is 2-hydroxy-1-(tetrahydro-furan-3-yl)-ethyl. In some embodiments, $R^8$ is 2-(pyridin-3-yloxy)-propyl. In some embodiments, $R^8$ is carbamoyl-phenyl-methyl. In some embodiments, $R^8$ is 5-fluoro-2-methoxy-phenyl. In some embodiments, $R^8$ is 2-methoxy-ethyl. In some embodiments, $R^8$ is 2,3-dihydroxy-propyl. In some embodiments, $R^8$ is 1-(tert-butoxycarbonyl)pyrrolidin-3-yl. In some embodiments, $R^8$ is 2-oxo-2-phenyl-ethyl. In some embodiments, $R^8$ is 1-(3,3,3-trifluoro-propyl)-azetidin-3-yl. In some embodiments, $R^8$ is 2-hydroxy-1-pyridin-2-yl-ethyl. In some embodiments, $R^8$ is 3-hydroxy-pyridin-4-yl. In some embodiments, $R^8$ is 1-methyl-1-pyridin-4-yl-ethyl. In some embodiments, $R^8$ is 1-hydroxymethyl-2-3H-imidazol-4-yl-ethyl. In some embodiments, $R^8$ is 4-hydroxy-3-methoxy-benzyl. In some embodiments, $R^8$ is 5-fluoro-2-oxo-2,3-dihydro-pyrimidin-4-yl. In some embodiments, $R^8$ is 1-(4-fluoro-phenyl)-3-hydroxy-propyl. In some embodiments, $R^8$ is 1-pyridin-4-yl-cyclopropyl. In some embodiments, In some embodiments, $R^8$ is 2-hydroxy-1-pyridin-3-yl-ethyl. In some embodiments, $R^8$ is 1,1-dimethyl-2-(4-methyl-piperidin-1-yl)-ethyl. In some embodiments, $R^8$ is 6-cyano-pyridin-3-yl. In some embodiments, $R^8$ is 5-fluoro-pyridin-2-yl. In some embodiments, $R^8$ is 2,5-dimethyl-benzyl. In some embodiments, $R^8$ is 1-isopropyl-piperidin-4-yl. In some embodiments, $R^8$ is 2-methoxy-1-methoxymethyl-ethyl. In some embodiments, $R^8$ is 2,3-dimethyl-benzyl. In some embodiments, $R^8$ is 1-pyridin-2-yl-ethyl. In some embodiments, $R^8$ is 6-chloro-pyridin-3-ylmethyl. In some embodiments, $R^8$ is 3-methyl-pyridin-2-yl. In some embodiments, $R^8$ is 2-hydroxy-indan-1-yl. In some embodiments, $R^8$ is (1S,2S)-2-hydroxy-indan-1-yl. In some embodiments, $R^8$ is (1S,2R)-2-hydroxy-indan-1-yl. In some embodiments, $R^8$ is (1R,2R)-2-hydroxy-indan-1-yl. In some embodiments, $R^8$ is (1R,2S)-2-hydroxy-indan-1-yl. In some embodiments, $R^8$ is 1-hydroxymethyl-cyclobutyl. In some embodiments, $R^8$ is 2-(4-chloro-phenyl)-1,1-dimethyl-ethyl. In some embodiments, $R^8$ is 3-hydroxy-pyridin-2-ylmethyl. In some embodiments, $R^8$ is 3-methyl-pyridin-4-yl. In some embodiments, $R^8$ is 5-tert-butyl-isoxazol-3-yl. In some embodiments, $R^8$ is 1-(6-methoxy-pyridin-3-yl)-1-methyl-ethyl. In some embodiments, $R^8$ is 1H-benzoimidazol-2-yl. In some embodiments, $R^8$ is tert-butyl. In some embodiments, $R^8$ is 4-phenyl-thiazol-2-yl. In some embodiments, $R^8$ is 1-(2-fluoro-phenyl)-cyclobutyl. In some embodiments, $R^8$ is 2,4-dimethoxy-benzyl. In some embodiments, $R^8$ is 5-bromo-3-methyl-pyridin-2-yl. In some embodiments, $R^8$ is 4-benzyl-morpholin-2-ylmethyl. In some embodiments, $R^8$ is 6-trifluoromethyl-pyridin-3-ylmethyl. In some embodiments, $R^8$ is tetrahydro-furan-3-yl. In some embodiments, $R^8$ is pyridin-3-ylmethyl. In some embodiments, $R^8$ is pyrazin-2-yl. In some embodiments, $R^8$ is piperidin-4-yl. In some embodiments, $R^8$ is 1-(6-hydroxy-pyridin-3-yl)-1- methyl-ethyl. In some embodiments, $R^8$ is 1-methyl-1-pyridin-2-yl-ethyl. In some embodiments, $R^8$ is 1-hydroxymethyl-cyclopentyl. In some embodiments, $R^8$ is 1-azabicyclo[2.2.2]oct-3-yl. In some embodiments, $R^8$ is 2-hydroxy-cyclopentyl. In some embodiments, $R^8$ is 2-hydroxy-1-(hydroxymethyl)-propyl. In some embodiments, $R^8$ is 1-(tert-butoxycarbonyl)piperidin-4-yl)methyl. In some embodiments, $R^8$ is 3,5-dimethoxy-phenyl. In some embodiments, $R^8$ is 6-fluoro-4H-benzo[1,3]dioxin-8-ylmethyl. In some embodiments, $R^8$ is 4,6-dimethyl-pyridin-2-yl. In some embodiments, $R^8$ is 1,1-dimethyl-2-morpholin-4-yl-ethyl. In some embodiments, $R^8$ is 2-hydroxy-cyclohexyl-methyl. In some embodiments, $R^8$ is 1-(4-methoxy-phenyl)-cyclopropyl. In some embodiments, $R^8$ is 1-ethyl-pyrrolidin-2-ylmethyl. In some embodiments, $R^8$ is indan-1-yl. In some embodiments, $R^8$ is pyrimidin-4-yl. In some embodiments, $R^8$ is 2-fluoro-4-methanesulfonyl-phenyl. In some embodiments, $R^8$ is 6-hydroxy-pyridin-2-yl. In some embodiments, $R^8$ is cyclobutyl. In some embodiments, $R^8$ is 1-(3-methoxy-phenyl)-cyclopropyl. In some embodiments, $R^8$ is 1-(3,3,3-trifluoro-propyl)-pyrrolidin-3-yl. In some embodiments, $R^8$ is 2-hydroxy-pyridin-3-yl. In some embodiments, $R^8$ is 4-difluoromethoxy-benzyl. In some embodiments, $R^8$ is 1-piperidin-1-yl-cyclopentylmethyl. In some embodiments, $R^8$ is 3-hydroxy-3-methyl-butyl. In some embodiments, $R^8$ is 1-(4-fluoro-phenyl)-cyclobutyl. In some embodiments, $R^8$ is 4-methoxy-benzyl. In some embodiments, $R^8$ is pyridin-2-yl. In some embodiments, $R^8$ is 2-hydroxy-2-phenyl-ethyl. In some embodiments, $R^8$ is 2-hydroxymethyl-2,3-dihydro-indol-1-yl. In some embodiments, $R^8$ is 3-hydroxy-pyridin-2-yl. In some embodiments, $R^8$ is 4-dimethylamino-tetrahydro-pyran-4-ylmethyl. In some embodiments, $R^8$ is 2-(4-fluoro-phenyl)-ethyl. In some embodiments, $R^8$ is 1-(2-methoxy-ethyl)-piperidin-4-ylmethyl. In some embodiments, $R^8$ is 2-morpholin-4-yl-ethyl. In some embodiments, $R^8$ is 1-(tert-butoxycarbonyl)-4-carboxypiperidin-4-yl. In some embodiments, $R^8$ is quinolin-3-yl. In some embodiments, $R^8$ is 1-morpholin-4-ylmethyl-cyclopentyl. In some embodiments, $R^8$ is 1,4-dimethyl-1H-pyrrol-2-ylmethyl. In some embodiments, $R^8$ is 2-hydroxy-2-pyridin-2-yl-ethyl. In some embodiments, $R^8$ is pyridin-3-yl. In some embodiments, $R^8$ is 2-dimethylamino-benzyl. In some embodiments, $R^8$ is tetrahydro-thiopyran-4-yl. In some embodiments, $R^8$ is 1-m-tolyl-cyclopropyl. In some embodiments, $R^8$ is 1-(2-methoxy-ethyl)-piperidin-3-yl. In some embodiments, $R^8$ is 5-methoxy-pyridin-2-ylmethyl. In some embodiments, $R^8$ is 2-hydroxy-1-pyridin-4-yl-ethyl. In some embodiments, $R^8$ is 4-methyl-pyridin-2-yl. In some embodiments, $R^8$ is 4-carboxy-2-fluorophenyl. In some embodiments, $R^8$ is 6-methanesulfonyl-pyridin-3-yl. In some embodiments, $R^8$ is 1-o-tolyl-cyclobutyl. In some embodiments, $R^8$ is 1,1-dimethyl-2-pyrrolidin-1-yl-ethyl. In some embodiments, $R^8$ is 2,6-dimethoxy-pyridin-3-yl. In some embodiments, $R^8$ is pyridin-2-yl. In some embodiments, $R^8$ is 4-hydroxymethyl-tetrahydro-pyran-4-yl. In some embodiments, $R^8$ is 2-(1H-imidazol-4-yl)-ethyl. In some embodiments, $R^8$ is 3-fluoro-pyridin-4-yl. In some embodiments, $R^8$ is 1-carbamoyl-2-phenyl-ethyl. In some embodiments, $R^8$ is oxazol-4-ylmethyl. In some embodiments, $R^8$ is 6-methoxy-pyrimidin-4-yl. In some embodiments, $R^8$ is 1,1-dioxo-hexahydro-1$\lambda^6$-thiopyran-4-yl. In some embodiments, $R^8$ is 1-methoxy-1-oxo-3-phenylpropan-2-yl. In some embodiments, $R^8$ is 1-(2-methoxy-ethyl)-pyrrolidin-3-yl. In some embodiments, $R^8$ is 1-(6-methyl-pyridin-2-yl)-ethyl. In some embodiments, $R^8$ is 2-hydroxy-1-(4-hydroxy-phenyl)-ethyl. In some embodiments, $R^8$ is 2-methoxy-pyridin-4-yl. In some embodiments, $R^8$ is 1-pyridin-2-yl-cyclopropyl. In some embodiments, $R^8$ is 1-(tert-butoxycarbonyl)piperidin-3-yl. In some embodiments, $R^8$ is 3-methyl-pyridin-2-ylmethyl. In some embodiments, $R^8$ is 3-fluoro-pyridin-2-yl. In some embodiments, $R^8$ is 1-pyridin-4-yl-cyclobutyl. In some embodiments, $R^8$ is 2-carboxy-1-(pyridin-3-yl)ethyl. In some embodiments, $R^8$ is 2-hydroxy-1-methyl-ethyl. In some embodiments, $R^8$ is 1-(methoxycarbonyl)cyclohexyl. In some embodiments, $R^8$ is 3-hydroxymethyl-pyridin-4-yl. In some embodiments, $R^8$ is 2-hydroxy-1-phenyl-ethyl. In some embodiments, $R^8$ is 3-dimethylamino-tetrahydro-thiophen-3-ylmethyl. In some embodiments, $R^8$ is tetrahydro-pyran-4-yl. In some embodiments, $R^8$ is 5-chloro-pyridin-2-yl. In some embodiments, $R^8$ is 1-carbamoyl-cyclobutyl. In some embodiments, $R^8$ is 5-fluoro-2-methyl-benzyl. In some embodiments, $R^8$ is 2-morpholin-4-yl-2-pyridin-3-yl-ethyl. In some embodiments, $R^8$ is 1-(3-methoxy-phenyl)-cyclobutyl. In some embodiments, $R^8$ is 5-methyl-pyridin-2-yl. In some embodiments, $R^8$ is 1-(tetrahydro-furan-2-yl)methyl. In some embodiments, $R^8$ is 1-dimethylaminomethyl-cyclopentyl. In some embodiments, $R^8$ is 2-(4-fluoro-phenyl)-1-methyl-ethyl. In some embodiments, $R^8$ is benzothiazol-2-yl. In some embodiments, $R^8$ is 1-(2-fluoro-phenyl)-cyclopropyl. In some embodiments, $R^8$ is 1-(2-methoxy-ethyl)-piperidin-4-yl. In some embodiments, $R^8$ is 2-hydroxy-1-pyridin-4-yl-ethyl. In some embodiments, $R^8$ is 1-(3,3,3-trifluoro-propyl)-azetidin-3-ylmethyl. In some embodiments, $R^8$ is 6-pyrrolidin-1-yl-pyridin-2-ylmethyl. In some embodiments, $R^8$ is 1,1-dioxo-tetrahydro-1$\lambda^6$-thiophen-3-yl. In some embodiments, $R^8$ is 2,3-dimethoxy-benzyl. In some embodiments, $R^8$ is 3-cyano-5-methyl-pyridin-2-yl. In some embodiments, $R^8$ is 2,3-dihydro-benzofuran-3-yl. In some embodiments, $R^8$ is 1-hydroxymethyl-cyclohexyl. In some embodiments, $R^8$ is 2,5-difluoro-benzyl. In some embodiments, $R^8$ is 4-dimethylamino-benzyl. In some embodiments, $R^8$ is 4-hydroxy-1,1-dioxo-tetrahydro-1$\lambda^6$-thiophen-3-yl. In some embodiments, $R^8$ is 4-trifluoromethyl-pyridin-2-yl. In some embodiments, $R^8$ is 5-methyl-thiazol-2-yl. In some embodiments, $R^8$ is 6-trifluoromethyl-pyridin-3-yl. In some embodiments, $R^8$ is 5-hydroxy-1H-pyrazol-3-yl. In some embodiments, $R^8$ is 2-thiomorpholin-4-yl-ethyl. In some embodiments, $R^8$ is benzo[1,3]dioxol-5-ylmethyl. In some embodiments, $R^8$ is 2-amino-cyclohexyl. In some embodiments, $R^8$ is 3-dimethylamino-1-oxo-tetrahydro-1$\lambda^4$-thiophen-3-ylmethyl. In some embodiments, $R^8$ is 4-methyl-morpholin-2-ylmethyl. In some embodiments, $R^8$ is 1-(2-methoxy-phenyl)-cyclopropyl. In some embodiments, $R^8$ is 2-carboxy-1-(4-fluorophenyl)propan-2-yl. In some embodiments, $R^8$ is pyridin-2-ylmethyl. In some embodiments, $R^8$ is pyridazin-3-yl. In some embodiments, $R^8$ is 4-pyridin-2-yl-thiazol-2-yl. In some embodiments, $R^8$ is 1-(3,3,3-trifluoro-propyl)-piperidin-4-ylmethyl. In some embodiments, $R^8$ is 6-chloro-2-methyl-pyridin-3-yl. In some embodiments, $R^8$ is 6-hydroxy-pyridin-3-yl. In some embodiments, $R^8$ is 3-trifluoromethoxy-benzyl. In some embodiments, $R^8$ is 1-morpholin-4-yl-cyclopentylmethyl. In some embodiments, $R^8$ is 1-pyridin-2-yl-cyclobutylmethyl. In some embodiments, $R^8$ is 2-hydroxy-1-hydroxymethyl-1-methyl-ethyl. In some embodiments, $R^8$ is 5-hydroxymethyl-pyridin-2-yl. In some embodiments, $R^8$ is 5-fluoro-1-oxy-pyridin-2-yl. In some embodiments, $R^8$ is 6-methoxy-pyridin-2-yl. In some embodiments, $R^8$ is 1-methyl-1-pyridin-3-yl-ethyl. In some embodiments, $R^8$ is 6-methyl-pyridin-3-yl. In some embodiments, $R^8$ is 2-hydroxy-1-hydroxymethyl-propyl. In some embodiments, $R^8$ is 2-chloro-pyridin-3-yl. In some embodiments, $R^8$ is 3-methyl-3H-imidazol-4-ylmethyl. In some embodiments, $R^8$ is 6-fluoro-pyridin-2-yl. In some embodiments, $R^8$ is 3-dimethylamino-benzyl. In some embodiments, $R^8$ is 6-morpholin-4-yl-pyridin-3-yl. In some embodiments, $R^8$ is 1-o-tolyl-cyclopropyl. In some embodiments, $R^8$ is 1-(3,3,3-trifluoro-propyl)-piperidin-3-yl. In some embodiments, $R^8$ is 6-methanesulfonyl-4-methyl-pyridin-3-yl. In some embodiments, $R^8$ is 2-methyl-quinolin-4-yl. In some embodiments, $R^8$ is 1-(3,3,3-trifluoro-propyl)-pyrrolidin-3-ylmethyl. In some embodiments, $R^8$ is benzooxazol-2-yl. In some embodiments, $R^8$ is 1-methyl-piperidin-4-ylmethyl. In some embodiments, $R^8$ is 2-(2,6-dimethyl-morpholin-4-yl)-2-methyl-propyl. In some embodiments, $R^8$ is 1-methyl-piperidin-2-ylmethyl. In some embodiments, $R^8$ is pyridin-4-ylmethyl. In some embodiments, $R^8$ is 4-hydroxymethyl-pyridin-2-yl. In some embodiments, $R^8$ is 5,7-dimethyl-pyrazolo[1,5-a]pyrimidin-2-yl. In some embodiments, $R^8$ is 6,6-dimethyl-bicyclo[3.1.1]hept-2-ylmethyl. In some embodiments, $R^8$ is 1-(5-methyl-pyridin-2-yl)-ethyl. In some embodiments, $R^8$ is 2-fluoro-pyridin-3-yl. In some embodiments, $R^8$ is morpholin-4-yl. In some embodiments, $R^8$ is 2-hydroxy-2-pyridin-4-yl-ethyl. In some embodiments, $R^8$ is pyridin-4-yl. In some embodiments, $R^8$ is 4-hydroxy-pyridin-2-yl. In some embodiments, $R^8$ is 3-methoxy-benzyl. In some embodiments, $R^8$ is 1-oxy-pyridin-2-yl. In some embodiments, $R^8$ is 1-ethyl-propyl. In some embodiments, $R^8$ is 6-carboxypyridin-2-yl. In some embodiments, $R^8$ is 1,2,2,6,6-pentamethyl-piperidin-4-yl. In some embodiments, $R^8$ is 6-methoxy-pyridin-3-yl. In some embodiments, $R^8$ is cyclopentyl. In some embodiments, $R^8$ is morpholin-2-ylmethyl. In some embodiments, $R^8$ is 1-(tert-butoxycarbonyl)azetidin-3-yl)methyl. In some embodiments, $R^8$ is 2-dimethylamino-2-pyridin-3-yl-ethyl. In some embodiments, $R^8$ is 1-(4-methoxy-phenyl)-cyclobutyl. In some embodiments, $R^8$ is 3-hydroxy-benzyl. In some embodiments, $R^8$ is tetrahydro-furan-2-ylmethyl. In some embodiments, $R^8$ is 4-(tert-butoxycarbonyl)morpholin-2-ylmethyl. In some embodiments, $R^8$ is 1-(3-fluoro-phenyl)-cyclopropyl. In some embodiments, $R^8$ is 2-o-tolyl-ethyl. In some embodiments, $R^8$ is 3-hydroxymethyl-1-isobutyl-pyrrolidin-3-yl. In some embodiments, $R^8$ is 1-(2-methoxy-ethyl)-azetidin-3-yl. In some embodiments, $R^8$ is 6-morpholin-4-yl-pyridin-2-ylmethyl. In some embodiments, $R^8$ is 1,1-dioxo-tetrahydro-1$\lambda^6$-thiophen-3-ylmethyl. In some embodiments, $R^8$ is 2-(4-fluoro-phenoxy)-ethyl. In some embodiments, $R^8$ is 2,6-dimethyl-pyrimidin-4-yl. In some embodiments, $R^8$ is 1-hydroxymethyl-2-(3H-imidazol-4-yl)-ethyl. In some embodiments, $R^8$ is 4-methanesulfonyl-benzyl. In some embodiments, $R^8$ is 1-pyridin-3-yl-cyclopropyl. In some embodiments, $R^8$ is 9-methyl-9-aza-bicyclo[3.3.1]non-1-yl. In some embodiments, $R^8$ is 2,6-dimethyl-pyridin-3-yl. In some embodiments, $R^8$ is 4-hydroxy-benzyl. In some embodiments, $R^8$ is 2-oxo-2-phenyl-ethyl). In some embodiments, $R^8$ is 1-methyl-1H-pyrazol-3-ylmethyl. In some embodiments, $R^8$ is pyrimidin-2-yl. In some embodiments, $R^8$ is 5-methyl-pyrazin-2-yl. In some embodiments, $R^8$ is 1-(2-methoxy-pyridin-3-yl)-1-methyl-ethyl. In some embodiments, $R^8$ is 6-methanesulfonyl-2-methyl-pyridin-3-yl. In some embodiments, $R^8$ is 2-hydroxy-benzyl. In some embodiments, $R^8$ is 6-bromo-2-methyl-pyridin-3-yl. In some embodiments, $R^8$ is 2-methoxy-pyridin-3-yl. In some embodiments, $R^8$ is 1-(4-chloro-phenyl)-cyclobutyl. In some embodiments, $R^8$ is 2-(pyridine-2-sulfonyl)-ethyl. In some embodiments, $R^8$ is 1-pyridin-2-yl-cyclopropylmethyl. In some embodiments, $R^8$ is 1-methyl-1,2,3,4-tetrahydro-quinolin-7-yl. In some embodiments, $R^8$ is benzyl. In some embodiments, $R^8$ is 3,5-dimethyl-pyrazin-2-yl. In some embodiments, $R^8$ is 1-(2-hydroxy-pyridin-3-yl)-1-methyl-ethyl. In some embodiments, $R^8$ is 1-(ethoxycarbonyl)cyclobutyl. In some embodiments, $R^8$ is 1-(tert-butoxycarbonyl)pyrrolidin-3-ylmethyl. In some embodiments, $R^8$ is quinolin-4-ylmethyl. In some embodiments, $R^8$ is 2-(4-fluoro-phenyl)-1-(2-hydroxy-ethylcarbamoyl)-1-methyl-ethyl. In some embodiments, $R^8$ is 2-morpholin-4-yl-pyridin-3-yl. In some embodiments, $R^8$ is 6-methyl-pyridin-2-yl. In some embodiments, $R^8$ is 3-difluoromethoxy-benzyl. In some embodiments, $R^8$ is 4-hydroxy-1-methyl-piperidin-4-ylmethyl. In some embodiments, $R^8$ is 1-(2,5-dimethylpyrrolidine-1-carbonyl)cyclopentyl. In some embodiments, $R^8$ is 2-methoxy-benzyl. In some embodiments, $R^8$ is 6-methyl-pyridin-2-ylmethyl. In some embodiments, $R^8$ is 3-chloro-pyridin-4-yl. In some embodiments, $R^8$ is 2-carboxypropan-2-yl. In some embodiments, $R^8$ is 6-chloro-pyridin-3-yl. In some embodiments, $R^8$ is 2-hydroxy-2-pyridin-3-yl-ethyl. In some embodiments, $R^8$ is 1-p-tolyl-cyclopropyl. In some embodiments, $R^8$ is 1-(3,3,3-trifluoro-propyl)-piperidin-4-yl. In some embodiments, $R^8$ is 4-methoxy-pyridin-2-yl. In some embodiments, $R^8$ is 3-azepan-1-yl-2,2-dimethyl-propyl. In some embodiments, $R^8$ is 1-(tert-butoxycarbonyl)azetidin-3-yl. In some embodiments, $R^8$ is 5-methyl-pyrazin-2-ylmethyl. In some embodiments, $R^8$ is 1-oxo-hexahydro-1$\lambda^4$-thiopyran-4-yl. In some embodiments, $R^8$ is 2-(2-chloro-phenyl)-ethyl. In some embodiments, $R^8$ is 3-chloro-5-trifluoromethyl-pyridin-2-ylmethyl. In some embodiments, $R^8$ is 2-hydroxy-1-hydroxymethyl-ethyl. In some embodiments, $R^8$ is (1-methyl-pyrrolidin-2-yl)-pyridin-2-yl. In some embodiments, $R^8$ is 5-fluoro-2-hydroxyphenyl. In some embodiments, $R^8$ is methyl. In some embodiments, $R^8$ is 4-(methoxycarbonyl)-1-methylpiperidin-4-yl. In some embodiments, $R^8$ is 4-hydroxymethyl-1-methyl-piperidin-4-yl. In some embodiments, $R^8$ is 2-(2-hydroxymethyl-pyrrolidin-1-yl)-ethyl. In some embodiments, $R^8$ is 1-phenyl-cyclohexyl. In some embodiments, $R^8$ is 3-methyl-1,1-dioxo-tetrahydro-1$\lambda^6$-thiophen-3-yl. In some embodiments, $R^8$ is 1-cyano-cyclohexyl. In some embodiments, $R^8$ is 1-(5-methyl-[1,2,4]oxadiazol-3-yl)-cyclohexyl. In some embodiments, $R^8$ is 2-cyanopropan-2-yl. In some embodiments, $R^8$ is 3-methyl-1-phenylureido. In some embodiments, $R^8$ is 1-carbamoyl-2,2-dimethyl-propyl. In some embodiments, $R^8$ is tert-butylamino. In some embodiments, $R^8$ is 2,2,2-trifluoro-1,1-dimethyl-ethyl. In some embodiments, $R^8$ is 2,2-dimethyl-1-methylcarbamoyl-propyl. In some embodiments, $R^8$ is 1-cyclopropyl-ethyl. In some embodiments, $R^8$ is amino. In some embodiments, $R^8$ is N-tert-butylmethylsulfonamido. In some embodiments, $R^8$ is 1,1-dimethyl-prop-2-ynyl. In some embodiments, $R^8$ is 2-methyl-1-(phosphonooxy)propan-2-yl. In some embodiments, $R^8$ is 1-tert-butyl-3-methylureido. In some embodiments, $R^8$ is 4-cyano-tetrahydro-pyran-4-yl. In some embodiments, $R^8$ is 1-methyl-cyclobutyl. In some embodiments, $R^8$ is 1-hydroxymethyl-2-methyl-propyl. In some embodiments, $R^8$ is cyclobutylamino. In some embodiments, $R^8$ is 1-cyano-cyclopentyl. In some embodiments, $R^8$ is cyano-dimethyl-methyl. In some embodiments, $R^8$ is 2,2-dimethyl-1-(methylcarbamoyl)-propyl. In some embodiments, $R^8$ is phenylamino. In some embodiments, $R^8$ is 1-hydroxymethyl-propyl. In some embodiments, $R^8$ is 1-methyl-1-(1H-tetrazol-5-yl)-ethyl. In some embodiments, $R^8$ is 3,3-dimethyl-1-(phosphonooxy)butan-2-yl). In some embodiments, $R^8$ is 2-hydroxy-1-tetrahydro-pyran-4-yl-ethyl. In some embodiments, $R^8$ is 1,2-dimethyl-propyl. In some embodiments, $R^8$ is 1-pyridin-2-yl-cyclobutyl. In some embodiments, $R^8$ is 1-hydroxymethyl-2-phenyl-ethyl. In some embodiments, $R^8$ is 4-methylcarbamoyl-tetrahydropyran-4-yl. In some embodiments, $R^8$ is 1-methyl-1-methylcarbamoyl-ethyl. In some embodiments, $R^8$ is 2,2-dimethyl-1-morpholin-4-ylmethyl-propyl. In some embodiments, $R^8$ is 1-methylcarbamoyl-cyclopent-3-enyl. In some embodiments, $R^8$ is 2-methoxy-2-oxo-1-(pyridin-2-yl)ethyl. In some embodiments, $R^8$ is methylcarbamoyl-pyridin-2-yl-methyl. In some embodiments, $R^8$ is 1-methylcarbamoyl-cyclopentyl. In some embodiments, $R^8$ is 1-(tert-butylcarbamoyl)-2,2-dimethyl-propyl. In some embodiments, $R^8$ is 2,2-dimethyl-1-(pyridin-2-ylcarbamoyl)-propyl. In some embodiments, $R^8$ is 1-(pyridin-2-ylcarbamoyl)-cyclobutyl. In some embodiments, $R^8$ is 1-methylcarbamoyl-cyclobutyl. In some embodiments, $R^8$ is 2-(methylamino)-2-oxo-1-phenylethyl. In some embodiments, $R^8$ is pyrrolidin-1-yl. In some embodiments, $R^8$ is piperidin-1-yl. In some embodiments, $R^8$ is 2,6-dimethyl-piperidin-1-yl. In some embodiments, $R^8$ is 1-cyclopropylcarbamoyl-2,2-dimethyl-propyl. In some embodiments, $R^8$ is 2,2-dimethyl-1-(2,2,2-trifluoro-ethylcarbamoyl)-propyl. In some embodiments, $R^8$ is 1-ethylcarbamoyl-2,2-dimethyl-propyl. In some embodiments, $R^8$ is 2-hydroxy-1-(tetrahydro-pyran-4-yl)-ethyl. In some embodiments, $R^8$ is N-cyclobutylmethylsulfonamido. In some embodiments, $R^8$ is N-phenylmethylsulfonamido. In some embodiments, $R^8$ is 1-cyclopropyl-2-hydroxy-ethyl. In some embodiments, $R^8$ is 1,2,2-trimethyl-propyl. In some embodiments, $R^8$ is 2-oxo-1-(pyridin-2-yl)-2-(2,2,2-trifluoroethylamino)ethyl. In some embodiments, $R^8$ is 2,2-dimethyl-1-pyridin-2-yl-propyl. In some embodiments, $R^8$ is 1-methoxy-3,3-dimethyl-1-oxobutan-2-yl. In some embodiments, $R^8$ is 1-carboxy-2,2-dimethylpropyl. In some embodiments, $R^8$ is 1-(hydroxymethyl-carbamoyl)-2,2-dimethyl-propyl. In some embodiments, $R^8$ is 1-dimethylcarbamoyl-2,2-dimethyl-propyl. In some embodiments, $R^8$ is 1-(azetidine-1-carbonyl)-2,2-dimethyl-propyl. In some embodiments, $R^8$ is 1-methoxycarbamoyl-2,2-dimethyl-propyl. In some embodiments, $R^8$ is 1-(methoxy-methyl-carbamoyl)-2,2-dimethyl-propyl. In some embodiments, $R^8$ is 1-tert-butoxycarbamoyl-2,2-dimethyl-propyl. In some embodiments, $R^8$ is 2,2-dimethyl-1-pyridin-2-yl-propyl. In some embodiments, $R^8$ is fluoromethyl. In some embodiments, $R^8$ is 2,2,2-trifluoroethylamino. In some embodiments, $R^8$ is (1,1-dioxo-tetrahydro-1$\lambda^6$-thiophen-3-yl)amino. In some embodiments, $R^8$ is 1-hydroxycarbamoyl-2,2-dimethyl-propyl. In some embodiments, $R^8$ is 1-hydroxymethyl-2-methyl-butyl. In some embodiments, $R^8$ is 1-(2-hydroxyethylcarbamoyl)-2,2-dimethyl-propyl. In some embodiments, $R^8$ is 1,1-bis-hydroxymethyl-propyl. In some embodiments, $R^8$ is 1-(5-fluoro-pyridin-2-yl)-2,2-dimethyl-propyl. In some embodiments, $R^8$ is 4-hydroxymethyl-tetrahydro-2H-pyran-4-yl. In some embodiments, $R^8$ is 1-(2-(tert-butoxycarbonylamino)-3-methylbutanoyloxy)-2-methylpropan-2-yl. In some embodiments, $R^8$ is 1-(2-amino-3-methylbutanoyloxy)-3-methylbutan-2-yl. In some embodiments, $R^8$ is 1-(2-amino-3-methylbutanoyloxy)-2-methylpropan-2-yl. In some embodiments, $R^8$ is 2-hydroxy-1-(tetrahydro-2H-pyran-4-yl)-ethyl. In some embodiments, $R^8$ is 1-(4-carboxybutanoyloxy)-2-methylpropan-2-yl. In some embodiments, $R^8$ is 1-(4-carboxybutanoyloxy)-3-methylbutan-2-yl. In some embodiments, $R^8$ is 1-(4-carboxybutanoyloxy)-3,3-dimethylbutan-2-yl. In some embodiments, $R^8$ is 1-(2-amino-3-methylbutanoyloxy)-3,3-dimethylbutan-2-yl. In some embodiments, $R^8$ is 2-(2-amino-3-methylbutanoyloxy)-1-(tetrahydro-2H-pyran-4-yl)ethyl. In some embodiments, $R^8$ is 3,3,3-trifluoro-1-hydroxymethyl-propyl. In some embodiments, $R^8$ is 3-fluoro-1-methoxy-3-methyl-1-oxobutan-2-yl. In some embodiments, $R^8$ is 1-ethoxy-4,4,4-trifluoro-1-oxo-3-(trifluoromethyl)butan-2-yl. In some embodiments, $R^8$ is 2-fluoro-1-hydroxymethyl-2-methyl-propyl. In some embodiments, $R^8$ is 1-(2-(tert-butoxycarbonylamino)-3-methylbutanoyloxy)-3,3-dimethylbutan-2-yl. In some embodiments, $R^8$ is 4,4,4-trifluoro-1-methoxy-1-oxobutan-2-yl. In some embodiments, $R^8$ is 2-fluoro-1,1-dimethyl-ethyl. In some embodiments, $R^8$ is 3-fluoro-2-(fluoromethyl)-1-methoxy-1-oxopropan-2-yl. In some embodiments, $R^8$ is 2-fluoro-1-fluoromethyl-1-hydroxymethyl-ethyl. In some embodiments, $R^8$ is 3-hydroxy-1-methoxy-2-methyl-1-oxopropan-2-yl. In some embodiments, $R^8$ is 2-carboxy-1-hydroxypropan-2-yl. In some embodiments, $R^8$ is 2,2,2-trifluoroethylamino. In some embodiments, $R^8$ is 1-fluoromethyl-2-methyl-propyl. In some embodiments, $R^8$ is 1-fluoromethyl-2,2-dimethyl-propyl. In some embodiments, $R^8$ is 3-methyl-oxetan-3-yl. In some embodiments, $R^8$ is 1-fluoromethyl-cyclobutyl. In some embodiments, $R^8$ is 1,1-bis-hydroxymethyl-2-methyl-propyl. In some embodiments, $R^8$ is 1-trifluoromethyl-cyclopropyl. In some embodiments, $R^8$ is 1-methyl-cyclopropyl. In some embodiments, $R^8$ is 1-trifluoromethyl-cyclobutyl.

The Group $R^9$:

In some embodiments, $R^9$ is selected from H, $C_1$-$C_6$ alkyl, and $C_3$-$C_7$ cycloalkyl.

In some embodiments, $R^9$ is $C_1$-$C_6$ alkyl.

In some embodiments, $R^9$ is $C_3$-$C_7$ cycloalkyl.

In some embodiments, $R^9$ is selected from H, methyl, tert-butyl, and cyclobutyl.

In some embodiments, $R^9$ is H.

In some embodiments, $R^9$ is methyl.

In some embodiments, $R^9$ is tert-butyl.

In some embodiments, $R^9$ is cyclobutyl.

The Group $R^{10}$:

In some embodiments, $R^{10}$ is selected from: $C_1$-$C_6$ alkylene, heteroarylene, and heterocyclylene.

In some embodiments, $R^{10}$ is selected from: 1,1-dimethylethylene, 1,1-dimethylmethylene, ethylene, methylene, 1,4-piperidinylene, 2,5-pyrazinylene, and 2,4-pyridinylene.

In some embodiments, $R^{10}$ is $C_1$-$C_6$ alkylene.

In some embodiments, $R^{10}$ is selected from: 1,1-dimethylethylene, 1,1-dimethylmethylene, ethylene, and methylene.

In some embodiments, $R^{10}$ is 1,1-dimethylethylene.

In some embodiments, $R^{10}$ is 1,1-dimethylmethylene.

In some embodiments, $R^{10}$ is ethylene.

In some embodiments, $R^{10}$ is methylene.

In some embodiments, $R^{10}$ is heteroarylene.

In some embodiments, $R^{10}$ is selected from: 2,5-pyrazinylene, and 2,4-pyridinylene.

In some embodiments, $R^{10}$ is heterocyclylene.

In some embodiments, $R^{10}$ is 1,4-piperidinylene.

In some embodiments, $R^{10}$ is absent.

The Group $R^{11}$:

In some embodiments, $R^{11}$ is selected from: —C(O)NH— and $C_1$-$C_6$ alkylene.

In some embodiments, $R^{11}$ is selected from: —C(O)NH— and methylene.

In some embodiments, $R^{11}$ is —C(O)NH—.

In some embodiments, $R^{11}$ is $C_1$-$C_6$ alkylene.

In some embodiments, $R^{11}$ is methylene.

In some embodiments, $R^{11}$ is absent.

The Group $R^{12}$:

In some embodiments, $R^{12}$ is $C_1$-$C_6$ alkylene.

In some embodiments, $R^{12}$ is methylene.

In some embodiments, $R^{12}$ is 1,1-dimethyl-methylene.

In some embodiments, $R^{12}$ is absent.

The Group $R^{13}$:

In some embodiments, $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl.

In some embodiments, $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, iodo, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl.

In some embodiments, $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl.

In some embodiments, $R^{13}$ is selected from: 2,4-difluoro-phenyl, 2,4-dichloro-phenyl, 2-fluoro-4-methanesulfonyl-phenyl, 2,6-difluoro-phenyl, 2,5-difluoro-phenyl, 4-methoxy-phenyl, 4-cyano-phenyl, 4-fluoro-phenyl, phenyl, 2-fluoro-phenyl, 3-fluoro-phenyl, o-tolyl, tert-butyl, isopropyl, 2,2-dimethylpropyl, hydroxyl, 2-hydroxy-2-methylpropyl, 1-oxo-hexahydro-1$\lambda^4$-thiopyran-4-yl, 1,1-dioxo-hexahydro-1$\lambda^6$-thiopyran-4-yl, tetrahydrothiopyran-4-yl, morpholin-4-yl, tetrahydro-pyran-4-yl, 1,1-dioxo-tetrahydro-1$\lambda^6$-thiophen-3-yl, pyrazin-2-yl, 5-ethyl-pyrazin-2-yl, 5-hydroxy-pyrazin-2-yl, 5-isopropyl-pyrazin-2-yl, 5-heptafluoropropyl-pyrazin-2-yl, 5-cyclobutyl-pyrazin-2-yl, 5-methyl-pyrazin-2-yl, 6-ethyl-pyrazin-2-yl, 5-trifluoromethyl-pyrazin-2-yl, cyclopropyl, 5-cyclopropyl-pyrazin-2-yl, 6-chloro-pyrazin-2-yl, 5-dimethylamino-pyrazin-2-yl, 4-cyano-phenyl, 6-methoxy-pyridazin-3-yl, 6-chloro-pyridazin-3-yl, pyrimidin-5-yl, 6-dimethylamino-pyrazin-2-yl, 6-methoxy-pyrazin-2-yl, 2-pyrimidin-4-yl, 5-bromo-pyrazin-2-yl, 5-hydroxy-pyrazin-2-yl, 5-methoxy-pyrazin-2-yl, 5-ethoxypyrazin-2-yl, 5-methylamino-pyrazin-2-yl, 5-bromo-pyridin-2-yl, pyridin-3-yl, 5-trifluoromethyl-pyridin-2-yl, 5-isopropyl-pyridin-2-yl, 5-isopropyl-pyridin-2-yl, 5-methyl-pyridin-2-yl, 5-ethyl-pyridin-2-yl, 5-methoxy-pyridin-2-yl, 4-trifluoromethyl-pyridin-2-yl, 5-cyano-pyridin-2-yl, 5-dimethylamino-pyridin-2-yl, 4-methyl-pyridin-2-yl, 5-chloro-4-methyl-pyridin-2-yl, 5-chloro-4-trifluoromethyl-pyridin-2-yl, 4-trifluoromethyl-pyridin-2-yl, 3-fluoro-pyridin-2-yl, 6-methyl-4-trifluoromethyl-pyridin-2-yl, 3-methyl-pyridin-2-yl, 5-propyl-pyridin-2-yl, 5-cyclopropyl-pyridin-2-yl, 5-fluoro-pyridin-2-yl, 3,5-difluoro-pyridin-2-yl, 6-bromo-pyridin-3-yl, 5-bromo-pyridin-3-yl, 5,6-difluoro-pyridin-3-yl, 6-chloro-pyridin-3-yl, 3-fluoro-pyridin-4-yl, 5-cyano-pyridin-3-yl, pyridin-4-yl, 2-chloro-pyridin-4-yl, 2-methoxy-pyridin-4-yl, 6-methyl-pyridin-3-yl, m-tolyl, thiazol-2-yl, cyclopentyl, 4-amino-pyridin-2-yl, 4-methoxy-pyridin-2-yl, 4-choro-pyridin-2-yl, 4-fluoro-pyridin-2-yl, 4-cyclopropyl-pyridin-2-yl, 4-bromo-pyridin-2-yl, 4-methanesulfonyl-pyridin-2-yl, 4-cyano-pyridin-2-yl, hydroxymethyl, 4-oxy-pyrazin-2-yl, 3-methyl-1,1-dioxo-tetrahydro-1$\lambda^6$-thiophen-3-yl, 5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 4-iodo-pyridin-2-yl, 1-oxy-pyridin-3-yl, and 4-hydroxy-pyridin-2-yl.

In some embodiments, $R^{13}$ is selected from: 2,4-difluoro-phenyl, 2,4-dichloro-phenyl, 2-fluoro-4-methanesulfonyl-phenyl, 2,6-difluoro-phenyl, 2,5-difluoro-phenyl, 4-methoxy-phenyl, 4-cyano-phenyl, 4-fluoro-phenyl, phenyl, 2-fluoro-phenyl, 3-fluoro-phenyl, o-tolyl, tert-butyl, isopropyl, 2,2-dimethylpropyl, hydroxyl, 2-hydroxy-2-methylpropyl, 1-oxo-hexahydro-1$\lambda^4$-thiopyran-4-yl, 1,1-dioxo-hexahydro-1$\lambda^6$-thiopyran-4-yl, tetrahydrothiopyran-4-yl, morpholin-4-yl, tetrahydro-pyran-4-yl, 1,1-dioxo-tetrahydro-1$\lambda^6$-thiophen-3-yl, pyrazin-2-yl, 5-ethyl-pyrazin-2-yl, 5-hydroxy-pyrazin-2-yl, 5-isopropyl-pyrazin-2-yl, 5-heptafluoropropyl-pyrazin-2-yl, 5-cyclobutyl-pyrazin-2-yl, 5-methyl-pyrazin-2-yl, 6-ethyl-pyrazin-2-yl, 5-trifluoromethyl-pyrazin-2-yl, cyclopropyl, 5-cyclopropyl-pyrazin-2-yl, 6-chloro-pyrazin-2-yl, 5-dimethylamino-pyrazin-2-yl, 4-cyano-phenyl, 6-methoxy-pyridazin-3-yl, 6-chloro-pyridazin-3-yl, pyrimidin-5-yl, 6-dimethylamino-pyrazin-2-yl, 6-methoxy-pyrazin-2-yl, 2-pyrimidin-4-yl, 5-bromo-pyrazin-2-yl, 5-hydroxy-pyrazin-2-yl, 5-methoxy-pyrazin-2-yl, 5-ethoxypyrazin-2-yl, 5-methylamino-pyrazin-2-yl, 5-bromo-pyridin-2-yl, pyridin-3-yl, 5-trifluoromethyl-pyridin-2-yl, 5-isopropyl-pyridin-2-yl, 5-isopropyl-pyridin-2-yl, 5-methyl-pyridin-2-yl, 5-ethyl-pyridin-2-yl, 5-methoxy-pyridin-2-yl, 4-trifluoromethyl-pyridin-2-yl, 5-cyano-pyridin-2-yl, 5-dimethylamino-pyridin-2-yl, 4-methyl-pyridin-2-yl, 5-chloro-4-methyl-pyridin-2-yl, 5-chloro-4-trifluoromethyl-pyridin-2-yl, 4-trifluoromethyl-pyridin-2-yl, 3-fluoro-pyridin-2-yl, 6-methyl-4-trifluoromethyl-pyridin-2-yl, 3-methyl-pyridin-2-yl, 5-propyl-pyridin-2-yl, 5-cyclopropyl-pyridin-2-yl, 5-fluoro-pyridin-2-yl, 3,5-difluoro-pyridin-2-yl, 6-bromo-pyridin-3-yl, 5-bromo-pyridin-3-yl, 5,6-difluoro-pyridin-3-yl, 6-chloro-pyridin-3-yl, 3-fluoro-pyridin-4-yl, 5-cyano-pyridin-3-yl, pyridin-4-yl, 2-chloro-pyridin-4-yl, 2-methoxy-pyridin-4-yl, 6-methyl-pyridin-3-yl, m-tolyl, thiazol-2-yl, cyclopentyl, 4-methoxy-pyridin-2-yl, 4-choro-pyridin-2-yl, 4-fluoro-pyridin-2-yl, 4-cyclopropyl-pyridin-2-yl, 4-bromo-pyridin-2-yl, 4-methanesulfonyl-pyridin-2-yl, 4-cyano-pyridin-2-yl, hydroxymethyl, and 4-oxy-pyrazin-2-yl.

In some embodiments, $R^{13}$ is 2,4-difluoro-phenyl. In some embodiments, $R^{13}$ is 2,4-dichloro-phenyl. In some embodiments, $R^{13}$ is 2-fluoro-4-methanesulfonyl-phenyl. In some embodiments, $R^{13}$ is 2,6-difluoro-phenyl. In some embodiments, $R^{13}$ is 2,5-difluoro-phenyl. In some embodiments, $R^{13}$ is 4-methoxy-phenyl. In some embodiments, $R^{13}$ is 4-cyano-phenyl. In some embodiments, $R^{13}$ is 4-fluoro-phenyl. In some embodiments, $R^{13}$ is phenyl. In some embodiments, $R^{13}$ is 2-fluoro-phenyl. In some embodiments, $R^{13}$ is 3-fluoro-phenyl. In some embodiments, $R^{13}$ is o-tolyl. In some embodiments, $R^{13}$ is tert-butyl. In some embodiments, $R^{13}$ is isopropyl. In some embodiments, $R^{13}$ is 2,2-dimethylpropyl. In some embodiments, $R^{13}$ is hydroxyl. In some embodiments, $R^{13}$ is 2-hydroxy-2-methylpropyl. In some embodiments, $R^{13}$ is 1-oxo-hexahydro-1$\lambda^4$-thiopyran-4-yl. In some embodiments, $R^{13}$ is 1,1-dioxo-hexahydro-1$\lambda^6$-thiopyran-4-yl. In some embodiments, $R^{13}$ is tetrahydrothiopyran-4-yl. In some embodiments, $R^{13}$ is morpholin-4-yl. In some embodiments, $R^{13}$ is tetrahydro-pyran-4-yl. In some embodiments, $R^{13}$ is 1,1-dioxo-tetrahydro-1$\lambda^6$-thiophen-3-yl. In some embodiments, $R^{13}$ is pyrazin-2-yl. In some embodiments, $R^{13}$ is 5-ethyl-pyrazin-2-yl. In some embodiments, $R^{13}$ is 5-hydroxy-pyrazin-2-yl. In some embodiments, $R^{13}$ is 5-isopropyl-pyrazin-2-yl. In some embodiments, $R^{13}$ is 5-heptafluoropropyl-pyrazin-2-yl. In some embodiments, $R^{13}$ is 5-cyclobutyl-pyrazin-2-yl. In some embodiments, $R^{13}$ is 5-methyl-pyrazin-2-yl. In some embodiments, $R^{13}$ is 6-ethyl-pyrazin-2-yl. In some embodiments, $R^{13}$ is 5-trifluoromethyl-pyrazin-2-yl. In some embodiments, $R^{13}$ is cyclopropyl. In some embodiments, $R^{13}$ is 5-cyclopropyl-pyrazin-2-yl. In some embodiments, $R^{13}$ is 6-chloro-pyrazin-2-yl. In some embodiments, $R^{13}$ is 5-dimethylamino-pyrazin-2-yl. In some embodiments, $R^{13}$ is 4-cyano-phenyl. In some embodiments, $R^{13}$ is 6-methoxy-pyridazin-3-yl. In some embodiments, $R^{13}$ is 6-chloro-pyridazin-3-yl. In some embodiments, $R^{13}$ is pyrimidin-5-yl. In some embodiments, $R^{13}$ is 6-dimethylamino-pyrazin-2-yl. In some embodiments, $R^{13}$ is 6-methoxy-pyrazin-2-yl. In some embodiments, $R^{13}$ is 2-pyrimidin-4-yl. In some embodiments, $R^{13}$ is 5-bromo-pyrazin-2-yl. In some embodiments, $R^{13}$ is 5-hydroxy-pyrazin-2-yl. In some embodiments, $R^{13}$ is 5-methoxy-pyrazin-2-yl. In some embodiments, $R^{13}$ is 5-ethoxypyrazin-2-yl. In some embodiments, $R^{13}$ is 5-methylamino-pyrazin-2-yl. In some embodiments, $R^{13}$ is 5-bromo-pyridin-2-yl. In some embodiments, $R^{13}$ is pyridin-3-yl. In some embodiments, $R^{13}$ is 5-trifluoromethyl-pyridin-2-yl. In some embodiments, $R^{13}$ is 5-isopropyl-pyridin-2-yl. In some embodiments, $R^{13}$ is 5-isopropyl-pyridin-2-yl. In some embodiments, $R^{13}$ is 5-methyl-pyridin-2-yl. In some embodiments, $R^{13}$ is 5-ethyl-pyridin-2-yl. In some embodiments, $R^{13}$ is 5-methoxy-pyridin-2-yl. In some embodiments, $R^{13}$ is 4-trifluoromethyl-pyridin-2-yl. In some embodiments, $R^{13}$ is 5-cyano-pyridin-2-yl. In some embodiments, $R^{13}$ is 5-dimethylamino-pyridin-2-yl. In some embodiments, $R^{13}$ is 4-methyl-pyridin-2-yl. In some embodiments, $R^{13}$ is 5-chloro-4-methyl-pyridin-2-yl. In some embodiments, $R^{13}$ is 5-chloro-4-trifluoromethyl-pyridin-2-yl. In some embodiments, $R^{13}$ is 4-trifluoromethyl-pyridin-2-yl. In some embodiments, $R^{13}$ is 3-fluoro-pyridin-2-yl. In some embodiments, $R^{13}$ is 6-methyl-4-trifluoromethyl-pyridin-2-yl. In some embodiments, $R^{13}$ is 3-methyl-pyridin-2-yl. In some embodiments, $R^{13}$ is 5-propyl-pyridin-2-yl. In some embodiments, $R^{13}$ is 5-cyclopropyl-pyridin-2-yl. In some embodiments, $R^{13}$ is 5-fluoro-pyridin-2-yl. In some embodiments, $R^{13}$ is 3,5-difluoro-pyridin-2-yl. In some embodiments, $R^{13}$ is 6-bromo-pyridin-3-yl. In some embodiments, $R^{13}$ is 5-bromo-pyridin-3-yl. In some embodiments, $R^{13}$ is 5,6-difluoro-pyridin-3-yl. In some embodiments, $R^{13}$ is 6-chloro-pyridin-3-yl. In some embodiments, $R^{13}$ is 3-fluoro-pyridin-4-yl. In some embodiments, $R^{13}$ is 5-cyano-pyridin-3-yl. In some embodiments, $R^{13}$ is pyridin-4-yl. In some embodiments, $R^{13}$ is 2-chloro-pyridin-4-yl. In some embodiments, $R^{13}$ is 2-methoxy-pyridin-4-yl. In some embodiments, $R^{13}$ is 6-methyl-pyridin-3-yl. In some embodiments, $R^{13}$ is m-tolyl. In some embodiments, $R^{13}$ is thiazol-2-yl. In some embodiments, $R^{13}$ is cyclopentyl. In some embodiments, $R^{13}$ is 4-amino-pyridin-2-yl. In some embodiments, $R^{13}$ is 4-methoxy-pyridin-2-yl. In some embodiments, $R^{13}$ is 4-choro-pyridin-2-yl. In some embodiments, $R^{13}$ is 4-fluoro-pyridin-2-yl. In some embodiments, $R^{13}$ is 4-cyclopropyl-pyridin-2-yl. In some embodiments, $R^{13}$ is 4-bromo-pyridin-2-yl. In some embodiments, $R^{13}$ is 4-methanesulfonyl-pyridin-2-yl. In some embodiments, $R^3$ is 4-cyano-pyridin-2-yl. In some embodiments, $R^{13}$ is hydroxymethyl. In some embodiments, $R^{13}$ is 4-oxy-pyrazin-2-yl. In some embodiments, $R^{13}$ is 3-methyl-1,1-dioxo-tetrahydro-1$\lambda^6$-thiophen-3-yl. In some embodiments, $R^{13}$ is 5-chloro-3-fluoro-pyridin-2-yl. In some embodiments, $R^{13}$ is 3-fluoro-5-methoxy-pyridin-2-yl. In some embodiments, $R^{13}$ is 2-chloro-4-fluoro-phenyl. In some embodiments, $R^{13}$ is 6-fluoro-pyridin-3-yl. In some embodiments, $R^{13}$ is 6-cyano-pyridin-3-yl. In some embodiments, $R^{13}$ is 4-iodo-pyridin-2-yl. In some embodiments, $R^{13}$ is 1-oxy-pyridin-3-yl. In some embodiments, $R^{13}$ is 4-hydroxy-pyridin-2-yl.

The Group $R^{14}$:

In some embodiments, $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl.

In some embodiments, $R^{14}$ is selected from: $C_1$-$C_6$ alkylene and $C_3$-$C_7$ cycloalkylene; wherein said $C_1$-$C_6$ alkylene is optionally substituted with one or more substituents selected from: $C_1$-$C_6$ alkyl, aryl, heterocyclyl, and hydroxyl; wherein said $C_1$-$C_6$ alkyl is optionally substituted with one substituent selected from: halogen, and hydroxyl.

In some embodiments, $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydrofuranyl, 3H-imidazolylmethyl, hydroxyl, pyrrolidinyl, cyclopropyl, sec-butyl, 2,2,2-trifluoroethyl, 2-fluoropropan-2-yl, 1,1,1,3,3,3-hexafluoropropan-2-yl, and fluoromethyl.

In some embodiments, $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydrofuranyl, 3H-imidazolylmethyl, hydroxyl, pyrrolidinyl, and cyclopropyl.

In some embodiments, $R^{14}$ is selected from: $C_1$-$C_6$ alkylene and $C_3$-$C_7$ cycloalkylene; wherein said $C_1$-$C_6$ alkylene is optionally substituted with one or more substituents selected from: tetrahydro-2H-pyranyl, hydroxyl, 2,2,2-trifluoroethyl, and fluoromethyl.

In some embodiments, $R^{14}$ is selected from: methylene, ethylene, cyclopropylene, cyclobutylene, piperidinylene, pyridinylene, tetrahydropyranylene, thiazolylene, cyclohexylene, cyclopentylene, cyclopentenylene, dioxohexahydrothiopyranylene, pyrrolidinylene, tetrahydrothiophenylene, propylene, 3,3-oxetanylene, and —$SO_2$—; wherein said ethylene, methylene, piperidinylene, propylene, and pyrrolidinylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydro-furanyl, 3H-imidazolylmethyl, hydroxyl, pyrrolidinyl, cyclopropyl, sec-butyl, 2,2,2-trifluoroethyl, 2-fluoropropan-2-yl, 1,1,1,3,3,3-hexafluoropropan-2-yl, and fluoromethyl.

In some embodiments, $R^{14}$ is selected from: methylene, ethylene, cyclopropylene, cyclobutylene, piperidinylene, pyridinylene, tetrahydropyranylene, thiazolylene, cyclohexylene, cyclopentylene, cyclopentenylene, dioxohexahydrothiopyranylene, pyrrolidinylene, tetrahydrothiophenylene, propylene, and —$SO_2$—; wherein said ethylene, methylene, piperidinylene, propylene, and pyrrolidinylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydro-furanyl, 3H-imidazolylmethyl, hydroxyl, pyrrolidinyl, and cyclopropyl.

In some embodiments, $R^{14}$ is selected from: methylene, ethylene, 1,1-cyclopropylene, 1,1-dimethyl-methylene, 1,1-cyclobutylene, tert-butyl-methylene, 1-methyl-4,4-piperidinylene, 4,4-tetrahydro-2H-pyranylene, methyl-methylene, 1,1-cyclohexylene, 1,2-cyclohexylene, 1,1-dimethyl-ethylene, 1-tert-butyl-ethylene, 1-ethyl-ethylene, 1-methyl-ethylene, 1-(tetrahydro-2H-pyran-4-yl)-ethylene, isopropylmethylene, 1,1-cyclopentylene, benzyl-methylene, 4,4-cyclopent-1-enylene, 1,1-dioxo-hexahydro-1$\lambda^6$-4,4-thiopyranylene, 1-tert-butoxycarbonyl-4,4-piperidinylene, 1-(pyridin-4-yl)-ethylene, 1-(pyridin-3-yl)-ethylene, 1-(pyridin-2-yl)-ethylene, 1-(4-fluoro-phenyl)-ethylene, 1-hydroxymethyl-1-methyl-ethylene, 1-carboxy-1-methyl-ethylene, 1-methoxymethyl-ethylene, 1-hydroxymethyl-ethylene, 1-(1-hydroxyethyl)-ethylene, 1,1-dimethyl-ethylene, 1-(tetrahydro-furan-3-yl)-ethylene, phenyl-methylene, 1-(3H-imidazol-4-ylmethyl)-ethylene, 1-(4-hydroxy-phenyl)-ethylene, benzyl-ethylene, (1-hydroxymethyl-2-methyl)-ethylene, 1-isopropyl-ethylene, pyridin-2-yl-methylene, 1,1-dimethyl-propylene, 2-hydroxy-propylene, (1-isobutyl-pyrrolidin-3-yl)-methylene, 1,3-azetidinylene, 1,3-pyrrolidinylene, 1,3-piperidinylene, 1,4-piperidinylene, 2,4-thiazolylene, 3,4-pyridinylene, 2,4-pyridinylene, 2,5-pyridinylene, —SO$_2$—, 2,5-pyridinylene, 1-cyclopropyl-ethylene, 1-(sec-butyl)-ethylene, 1-hydroxymethyl-1-ethyl-ethylene, 1-isopropyl-ethylene, 1-(2,2,2-trifluoroethyl)-ethylene, (2-fluoropropan-2-yl)-methylene, (1,1,1,3,3,3-hexafluoropropan-2-yl)-methylene, 1-(2-fluoropropan-2-yl)-ethylene, (2,2,2-trifluoroethyl)-methylene, 1,1-di(fluoromethyl)-ethylene, (hydroxymethyl)(methyl)methylene, (hydroxymethyl)(methyl)methylene, 3,3-oxetanylene, and 1-hydroxymethyl-1-isopropyl-ethylene.

In some embodiments, $R^{14}$ is selected from: methylene, ethylene, 1,1-cyclopropylene, 1,1-dimethyl-methylene, 1,1-cyclobutylene, tert-butyl-methylene, 1-methyl-4,4-piperidinylene, 4,4-tetrahydro-2H-pyranylene, methyl-methylene, 1,1-cyclohexylene, 1,2-cyclohexylene, 1,1-dimethyl-ethylene, 1-tert-butyl-ethylene, 1-ethyl-ethylene, 1-methyl-ethylene, 1-(tetrahydro-2H-pyran-4-yl)-ethylene, isopropylmethylene, 1,1-cyclopentylene, benzyl-methylene, 4,4-cyclopent-1-enylene, 1,1-dioxo-hexahydro-1$\lambda^6$-4,4-thiopyranylene, 1-tert-butoxycarbonyl-4,4-piperidinylene, 1-(pyridin-4-yl)-ethylene, 1-(pyridin-3-yl)-ethylene, 1-(pyridin-2-yl)-ethylene, 1-(4-fluoro-phenyl)-ethylene, 1-hydroxymethyl-1-methyl-ethylene, 1-carboxy-1-methyl-ethylene, 1-methoxymethyl-ethylene, 1-hydroxymethyl-ethylene, 1-(1-hydroxyethyl)-ethylene, 1,1-dimethyl-ethylene, 1-(tetrahydro-furan-3-yl)-ethylene, phenyl-methylene, 1-(3H-imidazol-4-ylmethyl)-ethylene, 1-(4-hydroxy-phenyl)-ethylene, benzyl-ethylene, (1-hydroxymethyl-2-methyl)-ethylene, 1-isopropyl-ethylene, pyridin-2-yl-methylene, 1,1-dimethyl-propylene, 2-hydroxy-propylene, (1-isobutyl-pyrrolidin-3-yl)-methylene, 1,3-azetidinylene, 1,3-pyrrolidinylene, 1,3-piperidinylene, 1,4-piperidinylene, 2,4-thiazolylene, 3,4-pyridinylene, 2,4-pyridinylene, 2,5-pyridinylene, —SO$_2$—, 2,5-pyridinylene, and 1-cyclopropyl-ethylene.

In some embodiments, $R^{14}$ is selected from: 1,1-cyclopropylene, 1,1-dimethyl-methylene, 1,1-cyclobutylene, tert-butyl-methylene, 1,1-dimethyl-ethylene, 1-tert-butyl-ethylene, 1-(tetrahydro-2H-pyran-4-yl)-ethylene, isopropylmethylene, 1-hydroxymethyl-1-methyl-ethylene, phenylmethylene, 1-isopropyl-ethylene, 1-(2,2,2-trifluoroethyl)-ethylene, and 1,1-di(fluoromethyl)-ethylene.

In some embodiments, $R^{14}$ is methylene. In some embodiments, $R^{14}$ is ethylene. In some embodiments, $R^{14}$ is 1,1-cyclopropylene. In some embodiments, $R^{14}$ is 1,1-dimethyl-methylene. In some embodiments, $R^{14}$ is 1,1-cyclobutylene. In some embodiments, $R^{14}$ is tert-butyl-methylene. In some embodiments, $R^{14}$ is 1-methyl-4,4-piperidinylene. In some embodiments, $R^{14}$ is 4,4-tetrahydro-2H-pyranylene. In some embodiments, $R^{14}$ is methyl-methylene. In some embodiments, $R^{14}$ is 1,1-cyclohexylene. In some embodiments, $R^{14}$ is 1,2-cyclohexylene. In some embodiments, $R^{14}$ is 1,1-dimethyl-ethylene. In some embodiments, $R^{14}$ is 1-tert-butyl-ethylene. In some embodiments, $R^{14}$ is 1-ethyl-ethylene. In some embodiments, $R^{14}$ is 1-methyl-ethylene. In some embodiments, $R^{14}$ is 1-(tetrahydro-2H-pyran-4-yl)-ethylene. In some embodiments, $R^{14}$ is isopropyl-methylene. In some embodiments, $R^{14}$ is 1,1-cyclopentylene. In some embodiments, $R^{14}$ is benzyl-methylene. In some embodiments, $R^{14}$ is 4,4-cyclopent-1-enylene. In some embodiments, $R^{14}$ is 1,1-dioxo-hexahydro-1$\lambda^6$-4,4-thiopyranylene. In some embodiments, $R^{14}$ is 1-tert-butoxycarbonyl-4,4-piperidinylene. In some embodiments, $R^{14}$ is 1-(pyridin-4-yl)-ethylene. In some embodiments, $R^{14}$ is 1-(pyridin-3-yl)-ethylene. In some embodiments, $R^{14}$ is 1-(pyridin-2-yl)-ethylene. In some embodiments, $R^{14}$ is 1-(4-fluoro-phenyl)-ethylene. In some embodiments, $R^{14}$ is 1-hydroxymethyl-1-methyl-ethylene. In some embodiments, $R^{14}$ is 1-carboxy-1-methyl-ethylene. In some embodiments, $R^{14}$ is 1-methoxymethyl-ethylene. In some embodiments, $R^{14}$ is 1-hydroxymethyl-ethylene. In some embodiments, $R^{14}$ is 1-(1-hydroxyethyl)-ethylene. In some embodiments, $R^{14}$ is 1,1-dimethyl-ethylene. In some embodiments, $R^{14}$ is 1-(tetrahydro-furan-3-yl)-ethylene. In some embodiments, $R^{14}$ is phenyl-methylene. In some embodiments, $R^{14}$ is 1-(3H-imidazol-4-ylmethyl)-ethylene. In some embodiments, $R^{14}$ is 1-(4-hydroxy-phenyl)-ethylene. In some embodiments, $R^{14}$ is benzyl-ethylene. In some embodiments, $R^{14}$ is (1-hydroxymethyl-2-methyl)-ethylene. In some embodiments, $R^{14}$ is 1-isopropyl-ethylene. In some embodiments, $R^{14}$ is pyridin-2-yl-methylene. In some embodiments, $R^{14}$ is 1,1-dimethyl-propylene. In some embodiments, $R^{14}$ is 2-hydroxy-propylene. In some embodiments, $R^{14}$ is (1-isobutyl-pyrrolidin-3-yl)-methylene. In some embodiments, $R^{14}$ is 1,3-azetidinylene. In some embodiments, $R^{14}$ is 1,3-pyrrolidinylene. In some embodiments, $R^{14}$ is 1,3-piperidinylene. In some embodiments, $R^{14}$ is 1,4-piperidinylene. In some embodiments, $R^{14}$ is 2,4-thiazolylene. In some embodiments, $R^{14}$ is 3,4-pyridinylene. In some embodiments, $R^{14}$ is 2,4-pyridinylene. In some embodiments, $R^{14}$ is 2,5-pyridinylene. In some embodiments, $R^{14}$ is —SO$_2$—. In some embodiments, $R^{14}$ is 2,5-pyridinylene. In some embodiments, $R^{14}$ is 1-cyclopropyl-ethylene. In some embodiments, $R^{14}$ is 1-(sec-butyl)-ethylene. In some embodiments, $R^{14}$ is 1-hydroxymethyl-1-ethyl-ethylene. In some embodiments, $R^{14}$ is 1-isopropyl-ethylene. In some embodiments, $R^{14}$ is 1-(2,2,2-trifluoroethyl)-ethylene. In some embodiments, $R^{14}$ is (2-fluoropropan-2-yl)-methylene. In some embodiments, $R^{14}$ is (1,1,1,3,3,3-hexafluoropropan-2-yl)-methylene. In some embodiments, $R^{14}$ is 1-(2-fluoropropan-2-yl)-ethylene. In some embodiments, $R^{14}$ is (2,2,2-trifluoroethyl)-methylene. In some embodiments, $R^{14}$ is 1,1-di(fluoromethyl)-ethylene. In some embodiments, $R^{14}$ is (hydroxymethyl)(methyl)methylene. In some embodiments, $R^{14}$ is (hydroxymethyl)(methyl)methylene. In some embodiments, $R^{14}$ is 3,3-oxetanylene. In some embodiments, $R^{14}$ is 1-hydroxymethyl-1-isopropyl-ethylene.

In some embodiments, $R^{14}$ is absent.

The Group $R^{15}$:

In some embodiments, $R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl.

In some embodiments, $R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl.

In some embodiments, $R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with methyl.

In some embodiments, $R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with methyl.

In some embodiments, $R^{15}$ is selected from: pyrrolidinylene, piperidinylene, pyridinylene, azetidinylene, —C(O)NH—, —C(O)—, —C(O)O—, morpholinylene, methylene, ethylene, cyclopropylene, tetrahydropyranylene, cyclopentylene, tetrahydrothiophenylene, oxotetrahydrothiophenylene; wherein said piperidinylene is optionally substituted with methyl.

In some embodiments, $R^{15}$ is selected from: pyrrolidinylene, piperidinylene, pyridinylene, azetidinylene, —C(O)NH—, —C(O)—, morpholinylene, methylene, ethylene, cyclopropylene, tetrahydropyranylene, cyclopentylene, tetrahydrothiophenylene, oxotetrahydrothiophenylene; wherein said piperidinylene is optionally substituted with methyl.

In some embodiments, $R^{15}$ is selected from: 1,3-pyrrolidinylene, 1,4-piperidinylene, 2,6-pyridinylene, 1,3-azetidinylene, —C(O)NH—, —C(O)—, —C(O)O—, 1,2-pyrrolidinylene, 2,4-morpholinylene, ethylene, methylene, 1,1-cyclopentylene, 4,4-tetrahydro-2H-pyranylene, 3,3-tetrahydro-thiophenylene, 1,1-cyclopropylene, 1-methyl-4,4-piperidinylene, and 1-oxo-tetrahydro-1$\lambda^4$-3,3-thiophenylene.

In some embodiments, $R^{15}$ is selected from: 1,3-pyrrolidinylene, 1,4-piperidinylene, 2,6-pyridinylene, 1,3-azetidinylene, —C(O)NH—, —C(O)—, 1,2-pyrrolidinylene, 2,4-morpholinylene, ethylene, methylene, 1,1-cyclopentylene, 4,4-tetrahydro-2H-pyranylene, 3,3-tetrahydro-thiophenylene, 1,1-cyclopropylene, 1-methyl-4,4-piperidinylene, and 1-oxo-tetrahydro-1$\lambda^4$-3,3-thiophenylene.

In some embodiments, $R^{15}$ is selected from: —C(O)NH— and —C(O)O—.

In some embodiments, $R^{15}$ is 1,3-pyrrolidinylene. In some embodiments, $R^{15}$ is 1,4-piperidinylene. In some embodiments, $R^{15}$ is 2,6-pyridinylene. In some embodiments, $R^{15}$ is 1,3-azetidinylene. In some embodiments, $R^{15}$ is —C(O)NH—. In some embodiments, $R^5$ is —C(O)—. In some embodiments, $R^{15}$ is 1,2-pyrrolidinylene. In some embodiments, $R^{15}$ is 2,4-morpholinylene. In some embodiments, $R^{15}$ is ethylene. In some embodiments, $R^{15}$ is methylene. In some embodiments, $R^{15}$ is 1,1-cyclopentylene. In some embodiments, $R^{15}$ is 4,4-tetrahydro-2H-pyranylene. In some embodiments, $R^{15}$ is 3,3-tetrahydro-thiophenylene. In some embodiments, $R^{15}$ is 1,1-cyclopropylene. In some embodiments, $R^{15}$ is 1-methyl-4,4-piperidinylene. In some embodiments, $R^{15}$ is 1-oxo-tetrahydro-1$\lambda^4$-3,3-thiophenylene.

In some embodiments, $R^{15}$ is absent.

The Group $R^{16}$:

In some embodiments, $R^{16}$ is $C_1$-$C_6$ alkylene.

In some embodiments, $R^{16}$ is selected from: ethylene, methylene, isopropyl-methylene, and propylene.

In some embodiments, $R^{16}$ is selected from: methylene, isopropyl-methylene, and propylene.

In some embodiments, $R^{16}$ is selected from: ethylene, and methylene.

In some embodiments, $R^{16}$ is ethylene.

In some embodiments, $R^{16}$ is methylene.

In some embodiments, $R^{16}$ is absent.

The Group $R^{17}$:

In some embodiments, $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_3$-$C_7$ cycloalkylamino, $C_2$-$C_8$ dialkylamino, $C_1$-$C_6$ haloalkoxy, $C_1$-$C_6$ haloalkyl, halogen, heteroaryl, heterocyclyl, and hydroxyl.

In some embodiments, $R^{17}$ is selected from: H, $C_1$-$C_6$ alkyl, $C_1$-$C_6$ alkylamino, amino, aryl, carboxy, cyano, $C_1$-$C_6$ haloalkyl, heteroaryl, hydroxyl, and phosphonooxy; wherein said aryl is optionally substituted with one hydroxyl group.

In some embodiments, $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, tert-butoxycarbonylamino, methyl, tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, 1-methyl-pyrrolidinyl, 2,2,2-trifluoroethyl, and 1,1-dioxo-tetrahydro-1$\lambda^6$-thiophen-3-yl.

In some embodiments, $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, 1-tert-butoxycarbonylamino, methyl, 1-tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, and 1-methyl-pyrrolidinyl.

In some embodiments, $R^{17}$ is selected from: H, $C_1$-$C_6$ alkyl, $C_1$-$C_6$ alkylamino, amino, aryl, carboxy, cyano, $C_3$-$C_7$ cycloalkyl, $C_1$-$C_6$ haloalkyl, heteroaryl, heterocyclyl, hydroxyl, and phosphonooxy; wherein said aryl and $C_3$-$C_7$ cycloalkyl are each optionally substituted with one or more substituents selected from: hydroxyl and trifluoromethyl.

In some embodiments, $R^{17}$ is selected from: H, amino, 1-tert-butoxycarbonylamino, morpholin-4-yl, 4-methyl-piperidin-1-yl, piperidin-4-yl, 1-tert-butoxycarbonyl-piperidin-3-yl, tetrahydro-thiopyran-4-yl, 1-oxo-hexahydro-1$\lambda^4$-thiopyran-4-yl, tetrahydro-pyran-4-yl, pyrrolidin-1-yl, 1-tert-butoxycarbonyl-azetidin-3-yl, 2,6-dimethyl-morpholin-4-yl, piperidin-1-yl, 1-tert-butoxycarbonyl-piperidin-4-yl, 1,1-dioxo-hexahydro-1$\lambda^6$-thiopyran-4-yl, tetrahydro-furan-2-yl, 1-ethyl-pyrrolidin-2-yl, 1-methyl-pyrrolidin-2-yl, morpholin-2-yl, 1-methyl-piperidin-2-yl, 1-methyl-piperidin-4-yl, 4-hydroxy-1-methyl-piperidin-4-yl, thiomorpholin-4-yl, tetrahydro-furan-3-yl, 1-tert-butoxycarbonyl-pyrrolidin-4-yl, 1,2,2,6,6-pentamethyl-piperidin-4-yl, 1,1-dioxo-tetrahydro-1$\lambda^6$-thiophen-3-yl, 4-methyl-morpholin-2-yl, 4-tert-butoxycarbonyl-morpholin-2-yl, 1-isopropyl-piperidin-4-yl, 4-hydroxy-1,1-dioxo-tetrahydro-1$\lambda^6$-thiophen-3-yl, 3-methyl-1,1-dioxo-tetrahydro-1$\lambda^6$-thiophen-3-yl, phenyl, 2-hydroxy-indan-1-yl, indan-1-yl, cyclopentyl, 2-hydroxy-cyclopentyl, cyclobutyl, 2-hydroxy-cyclohexyl, 1,3,3-trimethyl-bicyclo[2.2.1]hept-2-yl, 6,6-dimethyl-bicyclo[3.1.1]hept-2-yl, 1-aza-bicyclo[2.2.2]oct-3-yl, 9-methyl-9-aza-bicyclo[3.3.1]non-1-yl, 3-azepan-1-yl, 2-fluoro-phenyl, 2-chloro-phenyl, 4-fluoro-phenyl, 4-chloro-phenyl, 3-fluoro-phenyl, 5-fluoro-2-methoxy-phenyl, 2-fluoro-4-methanesulfonyl-phenyl, 4-carboxy-2-fluoro-phenyl, 2,5-difluoro-phenyl, m-tolyl, o-tolyl, 2,5-dimethyl-phenyl, 2,3-dimethyl-phenyl, 4-hydroxy-3-methoxy-phenyl, 2,4-dimethoxy-phenyl, 2,3-dimethoxy-phenyl, 3,5-dimethoxy-phenyl, 4-methoxy-phenyl, 3-methoxy-phenyl, 2-methoxy-phenyl, 3-hydroxy-phenyl, 4-hydroxy-phenyl, 2-hydroxy-phenyl, 5-fluoro-2-hydroxy-phenyl, 3-trifluoromethoxy-phenyl, 4-difluoromethoxy-phenyl, 3-difluoromethoxy-phenyl, 4-fluoro-phenoxy, 2-dimethylamino-phenyl, 4-dimethylamino-phenyl, 6-fluoro-4H-benzo[1,3]dioxin-8-yl, benzo[1,3]dioxol-5-yl, pyrimidin-2-yl, pyrimidin-4-yl, 2,6-dimethyl-pyrimidin-4-yl, pyridazin-3-yl, 5-methyl-pyrazin-2-yl, 6-methoxy-pyrimidin-4-yl, pyrazin-2-yl, 3,5-dimethyl-pyrazin-2-yl, 5-fluoro-2-oxo-2,3-dihydro-pyrimidin-4-yl, hydroxyl, methoxycarbonyl, ethoxycarbonyl, carboxy, 1-piperidin-1-yl, carboxamide, methoxy, trifluoromethyl, methyl, tert-butyl, diethylamino, dimethylamino, cyano, tert-butylamino, cyclopropyl, pyridin-3-yloxy, 1H-tetrazol-5-yl, 5-methyl-[1,2,4]oxadiazol-3-yl, phosphonooxy, cyclobutylamino, phenylamino, 1-tert-butyl-3-methylureido, 3-methyl-1-phenylureido, N-tert-butylmethylsulfonamido, 1-cyclobutyl-3-methylureido, methylcarbamoyl, 5-hydroxy-1H-indol-3-yl, 1H-benzoimidazol-2-yl, 5,7-dimethyl-pyrazolo[1,5-a]pyrimidin-2-yl, 1H-benzoimidazol-2-yl, 2-(tert-butoxycarbonyl)-3,4-dihydro-1H-isoquinoline-2-yl, quinolin-3-yl, quinolin-4-yl, 2-methyl-quinolin-4-yl, benzooxazol-2-yl, 1-methyl-1,2,3,4-tetrahydro-quinolin-7-yl, 2,3-dihydro-benzofuran-3-yl, benzothiazol-2-yl, 1,4-dimethyl-1H-pyrrol-2-yl, 3-methyl-3H-imidazol-4-yl, 1H-imidazol-4-yl, 5-hydroxy-1H-pyrazol-3-yl, 1-methyl-1H-pyrazol-3-yl, 4-pyridin-2-yl-thiazol-2-yl, 5-methyl-thiazol-2-yl, oxazol-4-yl, 4-phenyl-thiazol-2-yl, 5-tert-butyl-isoxazol-3-yl, pyridin-2-yl, pyridin-3-yl, pyridin-4-yl, 3-hydroxy-pyridin-2-yl, 6-hydroxy-pyridin-3-yl, 3-hydroxy-pyridin-4-yl, 4-hydroxy-pyridin-2-yl, 6-hydroxy-pyridin-2-yl, 2-hydroxy-pyridin-3-yl, 2-methoxy-pyridin-3-yl, 5-methoxy-pyridin-2-yl, 4-methoxy-pyridin-2-yl, 2-methoxy-pyridin-4-yl, 6-methoxy-pyridin-2-yl, 6-methoxy-pyridin-3-yl, 3-fluoro-pyridin-2-yl, 2-fluoro-pyridin-3-yl, 6-fluoro-pyridin-2-yl, 5-fluoro-pyridin-2-yl, 6-fluoro-pyridin-3-yl, 3-fluoro-pyridin-4-yl, 3-methyl-pyridin-2-yl, 3-methyl-pyridin-4-yl, 6-methyl-pyridin-2-yl, 4-methyl-pyridin-2-yl, 6-methyl-pyridin-3-yl, 2-methyl-pyridin-3-yl, 5-trifluoromethyl-pyridin-2-yl, 6-trifluoromethyl-pyridin-3-yl, 4-trifluoromethyl-pyridin-2-yl, 3-chloro-5-trifluoromethyl-pyridin-2-yl, 4,6-dimethyl-pyridin-2-yl, 4,6-dimethyl-pyridin-2-yl, 3-chloro-5-methyl-pyridin-2-yl, 6-cyano-pyridin-3-yl, 3-cyano-5-methyl-pyridin-2-yl, 3-cyano-5-methyl-pyridin-2-yl, 3-chloro-5-methyl-pyridin-2-yl, 2-chloro-pyridin-3-yl, 5-chloro-pyridin-2-yl, 6-chloro-2-methyl-pyridin-3-yl, 6-chloro-pyridin-3-yl, 3-chloro-pyridin-4-yl, 6-bromo-2-methyl-pyridin-3-yl, 5-bromo-3-methyl-pyridin-2-yl, 6-carboxypyridin-2-yl, 6-methanesulfonyl-4-methyl-pyridin-3-yl, 6-methanesulfonyl-4-methyl-pyridin-3-yl, 6-methanesulfonyl-2-methyl-pyridin-3-yl, 6-methanesulfonyl-pyridin-3-yl, 2,6-dimethoxy-pyridin-3-yl, 5-fluoro-1-oxy-pyridin-2-yl, 1-oxy-pyridin-2-yl, 6-pyrrolidin-1-yl-pyridin-2-ylmethyl, 5-(1-methyl-pyrrolidin-2-yl)-pyridin-2-yl, 6-morpholin-4-yl-pyridin-2-yl, 6-morpholin-4-yl-pyridin-3-yl, ethynyl, tert-butyl(methyl)amino, 2,2,2-trifluoroethyl, N-cyclobutylmethylsulfonamido, N-phenylmethylsulfonamido, hydroxy(methyl)amino, methoxy(methyl)amino, azetidin-1-yl, tert-butoxy, fluoromethyl, 2,2,2-trifluoroethylamino, and (1,1-dioxo-tetrahydro-1$\lambda^6$-thiophen-3-yl)amino.

In some embodiments, $R^{17}$ is selected from: H, amino, 1-tert-butoxycarbonylamino, morpholin-4-yl, 4-methyl-piperidin-1-yl, piperidin-4-yl, 1-tert-butoxycarbonyl-piperidin-3-yl, tetrahydro-thiopyran-4-yl, 1-oxo-hexahydro-1$\lambda^4$-thiopyran-4-yl, tetrahydro-pyran-4-yl, pyrrolidin-1-yl, 1-tert-butoxycarbonyl-azetidin-3-yl, 2,6-dimethyl-morpholin-4-yl, piperidin-1-yl, 1-tert-butoxycarbonyl-piperidin-4-yl, 1,1-dioxo-hexahydro-1$\lambda^6$-thiopyran-4-yl, tetrahydro-furan-2-yl, 1-ethyl-pyrrolidin-2-yl, 1-methyl-pyrrolidin-2-yl, morpholin-2-yl, 1-methyl-piperidin-2-yl, 1-methyl-piperidin-4-yl, 4-hydroxy-1-methyl-piperidin-4-yl, thiomorpholin-4-yl, tetrahydro-furan-3-yl, 1-tert-butoxycarbonyl-pyrrolidin-4-yl, 1,2,2,6,6-pentamethyl-piperidin-4-yl, 1,1-dioxo-tetrahydro-1$\lambda^6$-thiophen-3-yl, 4-methyl-morpholin-2-yl, 4-tert-butoxycarbonyl-morpholin-2-yl, 1-isopropyl-piperidin-4-yl, 4-hydroxy-1,1-dioxo-tetrahydro-1$\lambda^6$-thiophen-3-yl, 3-methyl-1,1-dioxo-tetrahydro-1$\lambda^6$-thiophen-3-yl, phenyl, 2-hydroxy-indan-1-yl, indan-1-yl, cyclopentyl, 2-hydroxy-cyclopentyl, cyclobutyl, 2-hydroxy-cyclohexyl, 1,3,3-trimethyl-bicyclo[2.2.1]hept-2-yl, 6,6-dimethyl-bicyclo[3.1.1]hept-2-yl, 1-aza-bicyclo[2.2.2]oct-3-yl, 9-methyl-9-aza-bicyclo[3.3.1]non-1-yl, 3-azepan-1-yl, 2-fluoro-phenyl, 2-chloro-phenyl, 4-fluoro-phenyl, 4-chloro-phenyl, 3-fluoro-phenyl, 5-fluoro-2-methoxy-phenyl, 2-fluoro-4-methanesulfonyl-phenyl, 4-carboxy-2-fluoro-phenyl, 2,5-difluoro-phenyl, m-tolyl, o-tolyl, 2,5-dimethyl-phenyl, 2,3-dimethyl-phenyl, 4-hydroxy-3-methoxy-phenyl, 2,4-dimethoxy-phenyl, 2,3-dimethoxy-phenyl, 3,5-dimethoxy-phenyl, 4-methoxy-phenyl, 3-methoxy-phenyl, 2-methoxy-phenyl, 3-hydroxy-phenyl, 4-hydroxy-phenyl, 2-hydroxy-phenyl, 5-fluoro-2-hydroxy-phenyl, 3-trifluoromethoxy-phenyl, 4-difluoromethoxy-phenyl, 3-difluoromethoxy-phenyl, 4-fluoro-phenoxy, 2-dimethylamino-phenyl, 4-dimethylamino-phenyl, 6-fluoro-4H- benzo[1,3]dioxin-8-yl, benzo[1,3]dioxol-5-yl, pyrimidin-2-yl, pyrimidin-4-yl, 2,6-dimethyl-pyrimidin-4-yl, pyridazin-3-yl, 5-methyl-pyrazin-2-yl, 6-methoxy-pyrimidin-4-yl, pyrazin-2-yl, 3,5-dimethyl-pyrazin-2-yl, 5-fluoro-2-oxo-2,3-dihydro-pyrimidin-4-yl, hydroxyl, methoxycarbonyl, ethoxycarbonyl, carboxy, 1-piperidin-1-yl, carboxamide, methoxy, trifluoromethyl, methyl, tert-butyl, diethylamino, dimethylamino, cyano, tert-butylamino, cyclopropyl, pyridin-3-yloxy, 1H-tetrazol-5-yl, 5-methyl-[1,2,4]oxadiazol-3-yl, phosphonooxy, cyclobutylamino, phenylamino, 1-tert-butyl-3-methylureido, 3-methyl-1-phenylureido, N-tert-butylmethylsulfonamido, 1-cyclobutyl-3-methylureido, methylcarbamoyl, 5-hydroxy-1H-indol-3-yl, 1H-benzoimidazol-2-yl, 5,7-dimethyl-pyrazolo[1,5-a]pyrimidin-2-yl, 1H-benzoimidazol-2-yl, 2-(tert-butoxycarbonyl)-3,4-dihydro-1H-isoquinoline-2-yl, quinolin-3-yl, quinolin-4-yl, 2-methyl-quinolin-4-yl, benzooxazol-2-yl, 1-methyl-1,2,3,4-tetrahydro-quinolin-7-yl, 2,3-dihydro-benzofuran-3-yl, benzothiazol-2-yl, 1,4-dimethyl-1H-pyrrol-2-yl, 3-methyl-3H-imidazol-4-yl, 1H-imidazol-4-yl, 5-hydroxy-1H-pyrazol-3-yl, 1-methyl-1H-pyrazol-3-yl, 4-pyridin-2-yl-thiazol-2-yl, 5-methyl-thiazol-2-yl, oxazol-4-yl, 4-phenyl-thiazol-2-yl, 5-tert-butyl-isoxazol-3-yl, pyridin-2-yl, pyridin-3-yl, pyridin-4-yl, 3-hydroxy-pyridin-2-yl, 6-hydroxy-pyridin-3-yl, 3-hydroxy-pyridin-4-yl, 4-hydroxy-pyridin-2-yl, 6-hydroxy-pyridin-2-yl, 2-hydroxy-pyridin-3-yl, 2-methoxy-pyridin-3-yl, 5-methoxy-pyridin-2-yl, 4-methoxy-pyridin-2-yl, 2-methoxy-pyridin-4-yl, 6-methoxy-pyridin-2-yl, 6-methoxy-pyridin-3-yl, 3-fluoro-pyridin-2-yl, 2-fluoro-pyridin-3-yl, 6-fluoro-pyridin-2-yl, 5-fluoro-pyridin-2-yl, 6-fluoro-pyridin-3-yl, 3-fluoro-pyridin-4-yl, 3-methyl-pyridin-2-yl, 3-methyl-pyridin-4-yl, 6-methyl-pyridin-2-yl, 4-methyl-pyridin-2-yl, 6-methyl-pyridin-3-yl, 2-methyl-pyridin-3-yl, 5-trifluoromethyl-pyridin-2-yl, 6-trifluoromethyl-pyridin-3-yl, 4-trifluoromethyl-pyridin-2-yl, 3-chloro-5-trifluoromethyl-pyridin-2-yl, 4,6-dimethyl-pyridin-2-yl, 4,6-dimethyl-pyridin-2-yl, 3-chloro-5-methyl-pyridin-2-yl, 6-cyano-pyridin-3-yl, 3-cyano-5-methyl-pyridin-2-yl, 3-cyano-5-methyl-pyridin-2-yl, 3-chloro-5-methyl-pyridin-2-yl, 2-chloro-pyridin-3-yl, 5-chloro-pyridin-2-yl, 6-chloro-2-methyl-pyridin-3-yl, 6-chloro-pyridin-3-yl, 3-chloro-pyridin-4-yl, 6-bromo-2-methyl-pyridin-3-yl, 5-bromo-3-methyl-pyridin-2-yl, 6-carboxypyridin-2-yl, 6-methanesulfonyl-4-methyl-pyridin-3-yl, 6-methanesulfonyl-4-methyl-pyridin-3-yl, 6-methanesulfonyl-2-methyl-pyridin-3-yl, 6-methanesulfonyl-pyridin-3-yl, 2,6-dimethoxy-pyridin-3-yl, 5-fluoro-1-oxy-pyridin-2-yl, 1-oxy-pyridin-2-yl, 6-pyrrolidin-1-yl-pyridin-2-ylmethyl, 5-(1-methyl-pyrrolidin-2-yl)-pyridin-2-yl, 6-morpholin-4-yl-pyridin-2-yl, 6-morpholin-4-yl-pyridin-3-yl, ethynyl, tert-butyl(methyl)amino, 2,2,2-trifluoroethyl, N-cyclobutylmethylsulfonamido, N-phenylmethylsulfonamido, hydroxy(methyl)amino, methoxy(methyl)amino, azetidin-1-yl, and tert-butoxy.

In some embodiments, $R^{17}$ is selected from: is selected from: amino, 2-hydroxy-indan-1-yl, hydroxyl, carboxy, trifluoromethyl, methyl, tert-butyl, cyano, tert-butylamino, phosphonooxy, pyridin-2-yl, and fluoromethyl.

In some embodiments, $R^7$ is H. In some embodiments, $R^{17}$ is amino. In some embodiments, $R^{17}$ is 1-tert-butoxycarbonylamino. In some embodiments, $R^{17}$ is morpholin-4-yl. In some embodiments, $R^{17}$ is 4-methyl-piperidin-1-yl. In some embodiments, $R^{17}$ is piperidin-4-yl. In some embodiments, $R^{17}$ is 1-tert-butoxycarbonyl-piperidin-3-yl. In some embodiments, $R^{17}$ is tetrahydro-thiopyran-4-yl. In some embodiments, $R^{17}$ is 1-oxo-hexahydro-$1\lambda^4$-thiopyran-4-yl. In some embodiments, $R^{17}$ is tetrahydro-pyran-4-yl. In some embodiments, $R^{17}$ is pyrrolidin-1-yl. In some embodiments, $R^{17}$ is 1-tert-butoxycarbonyl-azetidin-3-yl. In some embodiments, $R^{17}$ is 2,6-dimethyl-morpholin-4-yl. In some embodiments, $R^{17}$ is piperidin-1-yl. In some embodiments, $R^{17}$ is 1-tert-butoxycarbonyl-piperidin-4-yl. In some embodiments, $R^{17}$ is 1,1-dioxo-hexahydro-$1\lambda^6$-thiopyran-4-yl. In some embodiments, $R^{17}$ is tetrahydro-furan-2-yl. In some embodiments, $R^{17}$ is 1-ethyl-pyrrolidin-2-yl. In some embodiments, $R^{17}$ is 1-methyl-pyrrolidin-2-yl. In some embodiments, $R^{17}$ is morpholin-2-yl. In some embodiments, $R^{17}$ is 1-methyl-piperidin-2-yl. In some embodiments, $R^7$ is 1-methyl-piperidin-4-yl. In some embodiments, $R^{17}$ is 4-hydroxy-1-methyl-piperidin-4-yl. In some embodiments, $R^{17}$ is thiomorpholin-4-yl. In some embodiments, $R^{17}$ is tetrahydro-furan-3-yl. In some embodiments, $R^{17}$ is 1-tert-butoxycarbonyl-pyrrolidin-4-yl. In some embodiments, $R^{17}$ is 1,2,2,6,6-pentamethyl-piperidin-4-yl. In some embodiments, $R^{17}$ is 1,1-dioxo-tetrahydro-$1\lambda^6$-thiophen-3-yl. In some embodiments, $R^{17}$ is 4-methyl-morpholin-2-yl. In some embodiments, $R^{17}$ is 4-tert-butoxycarbonyl-morpholin-2-yl. In some embodiments, $R^{17}$ is 1-isopropyl-piperidin-4-yl. In some embodiments, $R^{17}$ is 4-hydroxy-1,1-dioxo-tetrahydro-$1\lambda^6$-thiophen-3-yl. In some embodiments, $R^{17}$ is 3-methyl-1,1-dioxo-tetrahydro-$1\lambda^6$-thiophen-3-yl. In some embodiments, $R^{17}$ is phenyl. In some embodiments, $R^{17}$ is 2-hydroxy-indan-1-yl. In some embodiments, $R^{17}$ is indan-1-yl. In some embodiments, $R^{17}$ is cyclopentyl. In some embodiments, $R^{17}$ is 2-hydroxy-cyclopentyl. In some embodiments, $R^{17}$ is cyclobutyl. In some embodiments, $R^{17}$ is 2-hydroxy-cyclohexyl. In some embodiments, $R^7$ is 1,3,3-trimethyl-bicyclo[2.2.1]hept-2-yl. In some embodiments, $R^{17}$ is 6,6-dimethyl-bicyclo[3.1.1]hept-2-yl. In some embodiments, $R^{17}$ is 1-aza-bicyclo[2.2.2]oct-3-yl. In some embodiments, $R^{17}$ is 9-methyl-9-aza-bicyclo[3.3.1]non-1-yl. In some embodiments, $R^{17}$ is 3-azepan-1-yl. In some embodiments, $R^{17}$ is 2-fluoro-phenyl. In some embodiments, $R^{17}$ is 2-chloro-phenyl. In some embodiments, $R^{17}$ is 4-fluoro-phenyl. In some embodiments, $R^{17}$ is 4-chloro-phenyl. In some embodiments, $R^{17}$ is 3-fluoro-phenyl. In some embodiments, $R^{17}$ is 5-fluoro-2-methoxy-phenyl. In some embodiments, $R^{17}$ is 2-fluoro-4-methanesulfonyl-phenyl. In some embodiments, $R^{17}$ is 4-carboxy-2-fluoro-phenyl. In some embodiments, $R^{17}$ is 2,5-difluoro-phenyl. In some embodiments, $R^{17}$ is m-tolyl. In some embodiments, $R^{17}$ is o-tolyl. In some embodiments, $R^{17}$ is 2,5-dimethyl-phenyl. In some embodiments, $R^{17}$ is 2,3-dimethyl-phenyl. In some embodiments, $R^{17}$ is 4-hydroxy-3-methoxy-phenyl. In some embodiments, $R^{17}$ is 2,4-dimethoxy-phenyl. In some embodiments, $R^{17}$ is 2,3-dimethoxy-phenyl. In some embodiments, $R^{17}$ is 3,5-dimethoxy-phenyl. In some embodiments, $R^{17}$ is 4-methoxy-phenyl. In some embodiments, $R^{17}$ is 3-methoxy-phenyl. In some embodiments, $R^{17}$ is 2-methoxy-phenyl. In some embodiments, $R^{17}$ is 3-hydroxy-phenyl. In some embodiments, $R^{17}$ is 4-hydroxy-phenyl. In some embodiments, $R^{17}$ is 2-hydroxy-phenyl. In some embodiments, $R^{17}$ is 5-fluoro-2-hydroxy-phenyl. In some embodiments, $R^{17}$ is 3-trifluoromethoxy-phenyl. In some embodiments, $R^{17}$ is 4-difluoromethoxy-phenyl. In some embodiments, $R^{17}$ is 3-difluoromethoxy-phenyl. In some embodiments, $R^{17}$ is 4-fluoro-phenoxy. In some embodiments, $R^{17}$ is 2-dimethylamino-phenyl. In some embodiments, $R^{17}$ is 4-dimethylamino-phenyl. In some embodiments, $R^{17}$ is 6-fluoro-4H-benzo[1,3]dioxin-8-yl. In some embodiments, $R^{17}$ is benzo[1,3]dioxol-5-yl. In some embodiments, $R^{17}$ is pyrimidin-2-yl. In some embodiments, $R^{17}$ is pyrimidin-4-yl. In some embodiments, $R^{17}$ is 2,6-dimethyl-pyrimidin-4-yl. In some embodiments, $R^{17}$ is pyridazin-3-yl. In some embodiments, $R^{17}$ is 5-methyl-pyrazin-2-yl. In some embodiments, $R^{17}$ is 6-methoxy-pyrimidin-4-yl. In some embodiments, $R^{17}$ is pyrazin-2-yl. In some embodiments, $R^{17}$ is 3,5-dimethyl-pyrazin-2-yl. In some embodiments, $R^{17}$ is 5-fluoro-2-oxo-2,3-dihydro-pyrimidin-4-yl. In some embodiments, $R^{17}$ is hydroxyl. In some embodiments, $R^{17}$ is methoxycarbonyl. In some embodiments, $R^{17}$ is ethoxycarbonyl. In some embodiments, $R^{17}$ is carboxy. In some embodiments, $R^{17}$ is 1-piperidin-1-yl. In some embodiments, $R^{17}$ is carboxamide. In some embodiments, $R^{17}$ is methoxy. In some embodiments, $R^{17}$ is trifluoromethyl. In some embodiments, $R^{17}$ is methyl. In some embodiments, $R^{17}$ is tert-butyl. In some embodiments, $R^{17}$ is diethylamino. In some embodiments, $R^{17}$ is dimethylamino. In some embodiments, $R^{17}$ is cyano. In some embodiments, $R^{17}$ is tert-butylamino. In some embodiments, $R^{17}$ is cyclopropyl. In some embodiments, $R^{17}$ is pyridin-3-yloxy. In some embodiments, $R^{17}$ is 1H-tetrazol-5-yl. In some embodiments, $R^{17}$ is 5-methyl-[1,2,4]oxadiazol-3-yl. In some embodiments, $R^{17}$ is phosphonooxy. In some embodiments, $R^{17}$ is cyclobutylamino. In some embodiments, $R^{17}$ is phenylamino. In some embodiments, $R^{17}$ is 1-tert-butyl-3-methylureido. In some embodiments, $R^{17}$ is 3-methyl-1-phenylureido. In some embodiments, $R^{17}$ is N-tert-butylmethylsulfonamido. In some embodiments, $R^{17}$ is 1-cyclobutyl-3-methylureido. In some embodiments, $R^{17}$ is methylcarbamoyl. In some embodiments, $R^{17}$ is 5-hydroxy-1H-indol-3-yl. In some embodiments, $R^{17}$ is 1H-benzoimidazol-2-yl. In some embodiments, $R^{17}$ is 5,7-dimethyl-pyrazolo[1,5-a]pyrimidin-2-yl. In some embodiments, $R^{17}$ is 1H-benzoimidazol-2-yl. In some embodiments, $R^{17}$ is 2-(tert-butoxycarbonyl)-3,4-dihydro-1H-isoquinoline-2-yl. In some embodiments, $R^{17}$ is quinolin-3-yl. In some embodiments, $R^{17}$ is quinolin-4-yl. In some embodiments, $R^{17}$ is 2-methyl-quinolin-4-yl. In some embodiments, $R^{17}$ is benzooxazol-2-yl. In some embodiments, $R^{17}$ is 1-methyl-1,2,3,4-tetrahydro-quinolin-7-yl. In some embodiments, $R^{17}$ is 2,3-dihydro-benzofuran-3-yl. In some embodiments, $R^{17}$ is benzothiazol-2-yl. In some embodiments, $R^{17}$ is 1,4-dimethyl-1H-pyrrol-2-yl. In some embodiments, $R^{17}$ is 3-methyl-3H-imidazol-4-yl. In some embodiments, $R^{17}$ is 1H-imidazol-4-yl. In some embodiments, $R^{17}$ is 5-hydroxy-1H-pyrazol-3-yl. In some embodiments, $R^{17}$ is 1-methyl-1H-pyrazol-3-yl. In some embodiments, $R^{17}$ is 4-pyridin-2-yl-thiazol-2-yl. In some embodiments, $R^{17}$ is 5-methyl-thiazol-2-yl. In some embodiments, $R^{17}$ is oxazol-4-yl. In some embodiments, $R^{17}$ is 4-phenyl-thiazol-2-yl. In some embodiments, $R^{17}$ is 5-tert-butyl-isoxazol-3-yl. In some embodiments, $R^{17}$ is pyridin-2-yl. In some embodiments, $R^{17}$ is pyridin-3-yl. In some embodiments, $R^{17}$ is pyridin-4-yl. In some embodiments, $R^{17}$ is 3-hydroxy-pyridin-2-yl. In some embodiments, $R^{17}$ is 6-hydroxy-pyridin-3-yl. In some embodiments, $R^{17}$ is 3-hydroxy-pyridin-4-yl. In some embodiments, $R^{17}$ is 4-hydroxy-pyridin-2-yl. In some embodiments, $R^{17}$ is 6-hydroxy-pyridin-2-yl. In some embodiments, $R^{17}$ is 2-hydroxy-pyridin-3-yl. In some embodiments, $R^{17}$ is 2-methoxy-pyridin-3-yl. In some embodiments, $R^{17}$ is 5-methoxy-pyridin-2-yl. In some embodiments, $R^{17}$ is 4-methoxy-pyridin-2-yl. In some embodiments, $R^{17}$ is 2-methoxy-pyridin-4-yl. In some embodiments, $R^{17}$ is 6-methoxy-pyridin-2-yl. In some embodiments, $R^{17}$ is 6-methoxy-pyridin-3-yl. In some embodiments, $R^{17}$ is 3-fluoro-pyridin-2-yl. In some embodiments, $R^{17}$ is 2-fluoro-pyridin-3-yl. In some embodiments, $R^{17}$ is 6-fluoro-pyridin-2-yl. In some embodiments, $R^{17}$ is 5-fluoro-pyridin-2-yl. In some embodiments, $R^{17}$ is 6-fluoro-pyridin-3-yl. In some embodiments, $R^{17}$ is 3-fluoro-pyridin-4-yl. In some embodiments, $R^{17}$ is 3-methyl-pyridin-2-yl. In some embodiments, $R^{17}$ is 3-methyl-pyridin-4-yl. In some embodiments, $R^{17}$ is 6-methyl-pyridin-2-yl. In some embodiments, $R^{17}$ is 4-methyl-pyridin-2-yl. In some embodiments, $R^{17}$ is 6-methyl-pyridin-3-yl. In some embodiments, $R^{17}$ is 2-methyl-pyridin-3-yl. In some embodiments, $R^{17}$ is 5-trifluoromethyl-pyridin-2-yl. In some embodiments, $R^{17}$ is 6-trifluoromethyl-pyridin-3-yl. In some embodiments, $R^{17}$ is 4-trifluoromethyl-pyridin-2-yl. In some embodiments, $R^{17}$ is 3-chloro-5-trifluoromethyl-pyridin-2-yl. In some embodiments, $R^{17}$ is 4,6-dimethyl-pyridin-2-yl. In some embodiments, $R^{17}$ is 4,6-dimethyl-pyridin-2-yl. In some embodiments, $R^{17}$ is 3-chloro-5-methyl-pyridin-2-yl. In some embodiments, $R^{17}$ is 6-cyano-pyridin-3-yl. In some embodiments, $R^{17}$ is 3-cyano-5-methyl-pyridin-2-yl. In some embodiments, $R^{17}$ is 3-cyano-5-methyl-pyridin-2-yl. In some embodiments, $R^{17}$ is 3-chloro-5-methyl-pyridin-2-yl. In some embodiments, $R^{17}$ is 2-chloro-pyridin-3-yl. In some embodiments, $R^{17}$ is 5-chloro-pyridin-2-yl. In some embodiments, $R^{17}$ is 6-chloro-2-methyl-pyridin-3-yl. In some embodiments, $R^{17}$ is 6-chloro-pyridin-3-yl. In some embodiments, $R^{17}$ is 3-chloro-pyridin-4-yl. In some embodiments, $R^{17}$ is 6-bromo-2-methyl-pyridin-3-yl. In some embodiments, $R^{17}$ is 5-bromo-3-methyl-pyridin-2-yl. In some embodiments, $R^{17}$ is 6-carboxypyridin-2-yl. In some embodiments, $R^{17}$ is 6-methanesulfonyl-4-methyl-pyridin-3-yl. In some embodiments, $R^{17}$ is 6-methanesulfonyl-4-methyl-pyridin-3-yl. In some embodiments, $R^{17}$ is 6-methanesulfonyl-2-methyl-pyridin-3-yl. In some embodiments, $R^{17}$ is 6-methanesulfonyl-pyridin-3-yl. In some embodiments, $R^{17}$ is 2,6-dimethoxy-pyridin-3-yl. In some embodiments, $R^{17}$ is 5-fluoro-1-oxy-pyridin-2-yl. In some embodiments, $R^{17}$ is 1-oxy-pyridin-2-yl. In some embodiments, $R^{17}$ is 6-pyrrolidin-1-yl-pyridin-2-ylmethyl. In some embodiments, $R^{17}$ is 5-(1-methyl-pyrrolidin-2-yl)-pyridin-2-yl. In some embodiments, $R^{17}$ is 6-morpholin-4-yl-pyridin-2-yl. In some embodiments, $R^{17}$ is 6-morpholin-4-yl-pyridin-3-yl. In some embodiments, $R^{17}$ is ethynyl. In some embodiments, $R^{17}$ is tert-butyl(methyl)amino. In some embodiments, $R^{17}$ is 2,2,2-trifluoroethyl. In some embodiments, $R^{17}$ is N-cyclobutylmethylsulfonamido. In some embodiments, $R^{17}$ is N-phenylmethylsulfonamido. In some embodiments, $R^{17}$ is hydroxy(methyl)amino. In some embodiments, $R^{17}$ is methoxy(methyl)amino. In some embodiments, $R^{17}$ is azetidin-1-yl. In some embodiments, $R^{17}$ is tert-butoxy. In some embodiments, $R^{17}$ is fluoromethyl. In some embodiments, $R^{17}$ is 2,2,2-trifluoroethylamino. In some embodiments, $R^{17}$ is (1,1-dioxo-tetrahydro-1$\lambda^6$-thiophen-3-yl)amino.

Certain $R^{15}$ and $R^{17}$ Combinations:

In some embodiments, $R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl.

Certain Combinations:

In some embodiments, $R^1$, $R^2$, $R^3$, $R^4$, $R^5$, and $R^6$ are each independently selected from: H and $C_1$-$C_6$ alkyl.

In some embodiments, $R^1$ and $R^6$ are each independently selected from: H, and $C_1$-$C_6$ alkyl; and $R^2$, $R^3$, $R^4$, and $R^5$ are each H.

In some embodiments, $R^1$, $R^2$, $R^3$, $R^4$, $R^5$, and $R^6$ are each independently selected from: H, methyl, and isopropyl.

In some embodiments, $R^1$ is selected from: H and methyl; $R^2$, $R^3$, $R^4$, and $R^5$ are each H; and $R^6$ is selected from: H and is isopropyl.

In some embodiments, $R^1$ is methyl; $R^2$, $R^3$, $R^4$, and $R^5$ are each H; and $R^6$ is isopropyl.

In some embodiments, $R^1$, $R^2$, $R^3$, $R^4$, $R^5$, and $R^6$ are each H.

In some embodiments, $R^8$ and $R^9$ together with the nitrogen atom to which they are both bonded form group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

In some embodiments, $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl or pyrazin-2-yl.

In some embodiments, $R^8$ and $R^9$ together with the nitrogen atom to which they are both bonded form 4-cyclohexylmethyl-piperazin-1-yl. In some embodiments, $R^8$ and $R^9$ together with the nitrogen atom to which they are both bonded form hexahydro-pyrrolo[1,2-a]pyrazin-2-yl. In some embodiments, $R^8$ and $R^9$ together with the nitrogen atom to which they are both bonded form 5,7-dihydro-pyrrolo[3,4-b]pyridin-6-yl. In some embodiments, $R^8$ and $R^9$ together with the nitrogen atom to which they are both bonded form 4-methoxy-2,3-dihydro-indol-1-yl. In some embodiments, $R^8$ and $R^9$ together with the nitrogen atom to which they are both bonded form 2-phenyl-pyrrolidin-1-yl. In some embodiments, $R^8$ and $R^9$ together with the nitrogen atom to which they are both bonded form 2-pyridin-2-yl-thiomorpholin-4-yl. In some embodiments, $R^8$ and $R^9$ together with the nitrogen atom to which they are both bonded form 2-hydroxymethyl-2,3-dihydro-indol-1-yl. In some embodiments, $R^8$ and $R^9$ together with the nitrogen atom to which they are both bonded form 4-hydroxy-piperidin-1-yl. In some embodiments, $R^8$ and $R^9$ together with the nitrogen atom to which they are both bonded form hexahydro-pyrrolo[1,2-a]pyrazin-2-yl. In some embodiments, $R^8$ and $R^9$ together with the nitrogen atom to which they are both bonded form 7-(methoxycarbonyl)-3,4-dihydro-1H-isoquinolin-2-yl. In some embodiments, $R^8$ and $R^9$ together with the nitrogen atom to which they are both bonded form 7-methoxy-3,4-dihydro-1H-isoquinolin-2-yl. In some embodiments, $R^8$ and $R^9$ together with the nitrogen atom to which they are both bonded form 1,4,6,7-tetrahydro-imidazo[4,5-c]pyridin-5-yl. In some embodiments, $R^8$ and $R^9$ together with the nitrogen atom to which they are both bonded form 5-fluoro-1,3-dihydro-isoindol-2-yl. In some embodiments, $R^8$ and $R^9$ together with the nitrogen atom to which they are both bonded form 3-hydroxy-7,8-dihydro-5H-[1,6]naphthyridin-6-yl. In some embodiments, $R^8$ and $R^9$ together with the nitrogen atom to which they are both bonded form 4-(tert-butoxycarbonyl)-2-(hydroxymethyl)piperazin-1-yl. In some embodiments, $R^8$ and $R^9$ together with the nitrogen atom to which they are both bonded form 1,3-dihydro-isoindol-2-yl. In some embodiments, $R^8$ and $R^9$ together with the nitrogen atom to which they are both bonded form 3-trifluoromethyl-5,6-dihydro-8H-[1,2,4]triazolo[4,3-a]pyrazin-7-yl. In some embodiments, $R^8$ and $R^9$ together with the nitrogen atom to which they are both bonded form 4-morpholin-4-yl-piperidin-1-yl. In some embodiments, $R^8$ and $R^9$ together with the nitrogen atom to which they are both bonded form 3,4-dihydro-1H-isoquinolin-2-yl. In some embodiments, $R^8$ and $R^9$ together with the nitrogen atom to which they are both bonded form 4-(3-methoxy-pyridin-2-yl)-piperazin-1-yl. In some embodiments, $R^8$ and $R^9$ together with the nitrogen atom to which they are both bonded form 3-hydroxy-piperidin-1-yl. In some embodiments, $R^8$ and $R^9$ together with the nitrogen atom to which they are both bonded form 4-(3-chloro-phenyl)-piperazin-1-yl. In some embodiments, $R^8$ and $R^9$ together with the nitrogen atom to which they are both bonded form 6-methoxy-3,4-dihydro-1H-isoquinolin-2-yl. In some embodiments, $R^8$ and $R^9$ together with the nitrogen atom to which they are both bonded form morpholin-4-yl. In some embodiments, $R^8$ and $R^9$ together with the nitrogen atom to which they are both bonded form 2-hydroxymethyl-pyrrolidin-1-yl. In some embodiments, $R^8$ and $R^9$ together with the nitrogen atom to which they are both bonded form 1,3-dihydro-pyrrolo[3,4-c]pyridin-2-yl. In some embodiments, $R^8$ and $R^9$ together with the nitrogen atom to which they are both bonded form 3-pyridin-4-yl-pyrrolidin-1-yl. In some embodiments, $R^8$ and $R^9$ together with the nitrogen atom to which they are both bonded form 4-(pyridin-2-yloxy)-piperidin-1-yl. In some embodiments, $R^8$ and $R^9$ together with the nitrogen atom to which they are both bonded form 3-pyridin-2-yl-pyrrolidin-1-yl. In some embodiments, $R^8$ and $R^9$ together with the nitrogen atom to which they are both bonded form 7-methyl-3,4-dihydro-2H-[1,8]naphthyridin-1-yl. In some embodiments, $R^8$ and $R^9$ together with the nitrogen atom to which they are both bonded form 3-pyridin-3-yl-pyrrolidin-1-yl. In some embodiments, $R^8$ and $R^9$ together with the nitrogen atom to which they are both bonded form 3-hydroxy-pyrrolidin-1-yl. In some embodiments, $R^8$ and $R^9$ together with the nitrogen atom to which they are both bonded form 4-(4,6-dimethyl-pyrimidin-2-yl)-piperazin-1-yl. In some embodiments, $R^8$ and $R^9$ together with the nitrogen atom to which they are both bonded form 2-methyl-3,4-dihydro-2H-quinolin-1-yl. In some embodiments, $R^8$ and $R^9$ together with the nitrogen atom to which they are both bonded form 2-phenyl-morpholin-4-yl or pyrazin-2-yl.

Some embodiments of the present invention pertain to compounds of Formula Ic and pharmaceutically acceptable salts, solvates, hydrates, and N-oxides thereof:

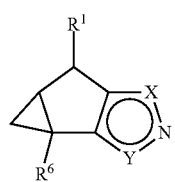

Ic wherein:
$R^1$ and $R^6$ are each independently selected from: H, and $C_1$-$C_6$ alkyl;
X is $NR^7$ and Y is $CC(O)N(R^8)R^9$; or
X is $CC(O)N(R^8)R^9$ and Y is $NR^7$.
$R^7$ is —$R^{10}$—$R^{11}$—$R^{12}$—$R^{13}$; wherein:
$R^{10}$ is selected from: $C_1$-$C_6$ alkylene, heteroarylene, and heterocyclylene; or $R^{10}$ is absent;
$R^{11}$ is selected from: —C(O)NH— and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is —$R^{14}$—$R^{15}$—$R^{16}$—$R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
$R^9$ is selected from H, $C_1$-$C_6$ alkyl, and $C_3$-$C_7$ cycloalkyl; or
$R^8$ and $R^9$ together with the nitrogen atom to which they are both bonded form a group selected from: heterocyclyl and heterobicyclyl, each optionally substituted with one or more substituents selected from: $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

Some embodiments of the present invention pertain to compounds of Formula Ic and pharmaceutically acceptable salts, solvates, hydrates, and N-oxides thereof:

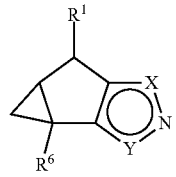

Ic wherein:
$R^1$ and $R^6$ are each independently selected from: H, and $C_1$-$C_6$ alkyl;
X is $NR^7$ and Y is $CC(O)N(R^8)R^9$; or
X is $CC(O)N(R^8)R^9$ and Y is $NR^7$;
$R^7$ is —$R^{10}$—$R^{11}$—$R^{12}$—$R^{13}$; wherein:
$R^{10}$ is selected from: $C_1$-$C_6$ alkylene, heteroarylene, and heterocyclylene; or $R^{10}$ is absent;
$R^{11}$ is selected from: —C(O)NH— and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is —$R^{14}$—$R^{15}$—$R^{16}$—$R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

Some embodiments of the present invention pertain to compounds of Formula Ic and pharmaceutically acceptable salts, solvates, hydrates, and N-oxides thereof:

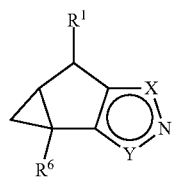

Ic wherein:
$R^1$ and $R^6$ are each independently selected from: H, and $C_1$-$C_6$ alkyl;
X is $NR^7$ and Y is $CC(O)N(R^8)R^9$; or
X is $CC(O)N(R^8)R^9$ and Y is $NR^7$;
$R^7$ is —$R^{10}$—$R^{11}$—$R^{12}$—$R^{13}$; wherein:
$R^{11}$ is selected from: 1,1-dimethylethylene, 1,1-dimethylmethylene, ethylene, methylene, 1,4-piperidinylene, 2,5-pyrazinylene, and 2,4-pyridinylene; or $R^{10}$ is absent;
$R^{11}$ is selected from: —C(O)NH— and methylene; or $R^{11}$ is absent;
$R^{12}$ is methylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, iodo, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl;
$R^8$ is —$R^{14}$—$R^{15}$—$R^{16}$—$R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluorophenyl, tert-butoxycarbonyl, carboxy, methoxymethyl, hydroxyethyl, tetrahydro-furanyl, 3H-imidazolylmethyl, hydroxyl, pyrrolidinyl, cyclopropyl, sec-butyl, 2,2,2-trifluoroethyl, 2-fluoropropan-2-yl, 1,1,1,3,3,3-hexafluoropropan-2-yl, and fluoromethyl; or $R^{14}$ is absent;

$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with methyl; or $R^{15}$ is absent;

$R^{16}$ is selected from: ethylene, methylene, isopropylmethylene, and propylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, tert-butoxycarbonylamino, methyl, tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, 1-methyl-pyrrolidinyl, 2,2,2-trifluoroethyl, and 1,1-dioxo-tetrahydro-1$\lambda^6$-thiophen-3-yl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

Some embodiments of the present invention pertain to compounds of Formula Ic and pharmaceutically acceptable salts, solvates, hydrates, and N-oxides thereof:

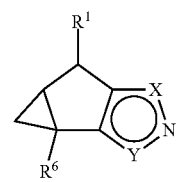

Ic wherein:
$R^1$ and $R^6$ are each independently selected from: H, and $C_1$-$C_6$ alkyl;
X is $NR^7$ and Y is $CC(O)N(R^8)R^9$; or
X is $CC(O)N(R^8)R^9$ and Y is $NR^7$,
$R^7$ is —$R^{10}$—$R^{11}$—$R^{12}$—$R^{13}$; wherein:
$R^{10}$ is selected from: 1,1-dimethylethylene, 1,1-dimethylmethylene, ethylene, methylene, 1,4-piperidinylene, 2,5-pyrazinylene, and 2,4-pyridinylene; or $R^{10}$ is absent;
$R^{11}$ is selected from: —C(O)NH— and methylene; or $R^{11}$ is absent;
$R^{12}$ is methylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl;

$R^8$ is —$R^{14}$—$R^{15}$—$R^{16}$—$R^{17}$; wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluorophenyl, tert-butoxycarbonyl, carboxy, methoxymethyl, hydroxyethyl, tetrahydro-furanyl, 3H-imidazolylmethyl, hydroxyl, pyrrolidinyl, and cyclopropyl; or $R^{14}$ is absent;

$R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with methyl; or $R^{15}$ is absent;

$R^{16}$ is selected from: ethylene and methylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, 1-tert-butoxycarbonylamino, methyl, 1-tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, and 1-methyl-pyrrolidinyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

Some embodiments of the present invention pertain to compounds of Formula Ic and pharmaceutically acceptable salts, solvates, hydrates, and N-oxides thereof:

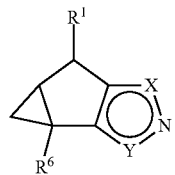

Ic wherein:

$R^1$ is selected from: H and methyl;
$R^6$ is selected from: H and isopropyl;
X is $NR^7$ and Y is $CC(O)N(R^8)R^9$; or
X is $CC(O)N(R^8)R^9$ and Y is $NR^7$;
$R^7$ is —$R^{10}$—$R^{11}$—$R^{12}$—$R^{13}$; wherein:

$R^{10}$ is selected from: 1,1-dimethylethylene, 1,1-dimethylmethylene, ethylene, methylene, 1,4-piperidinylene, 2,5-pyrazinylene, and 2,4-pyridinylene; or $R^{10}$ is absent;

$R^{11}$ is selected from: —C(O)NH— and methylene; or $R^{11}$ is absent;

$R^{12}$ is 1,1-dimethyl-methylene; or $R^{12}$ is absent; and $R^{13}$ is selected from: 2,4-difluoro-phenyl, 2,4-dichloro-phenyl, 2-fluoro-4-methanesulfonyl-phenyl, 2,6-difluoro-phenyl, 2,5-difluoro-phenyl, 4-methoxy-phenyl, 4-cyano-phenyl, 4-fluoro-phenyl, phenyl, 2-fluoro-phenyl, 3-fluoro-phenyl, o-tolyl, tert-butyl, isopropyl, 2,2-dimethylpropyl, hydroxyl, 2-hydroxy-2-methylpropyl, 1-oxo-hexahydro-1$\lambda^4$-thiopyran-4-yl, 1,1-dioxo-hexahydro-1$\lambda^6$-thiopyran-4-yl, tetrahydrothiopyran-4-yl, morpholin-4-yl, tetrahydro-pyran-4-yl, 1,1-dioxo-tetrahydro-1$\lambda^6$-thiophen-3-yl, pyrazin-2-yl, 5-ethyl-pyrazin-2-yl, 5-hydroxy-pyrazin-2-yl, 5-isopropyl-pyrazin-2-yl, 5-heptafluoropropyl-pyrazin-2-yl, 5-cyclobutyl-pyrazin-2-yl, 5-methyl-pyrazin-2-yl, 6-ethyl-pyrazin-2-yl, 5-trifluoromethyl-pyrazin-2-yl, cyclopropyl, 5-cyclopropyl-pyrazin-2-yl, 6-chloro-pyrazin-2-yl, 5-dimethylamino-pyrazin-2-yl, 4-cyano-phenyl, 6-methoxy-pyridazin-3-yl, 6-chloro-pyridazin-3-yl, pyrimidin-5-yl, 6-dimethylamino-pyrazin-2-yl, 6-methoxy-pyrazin-2-yl, 2-pyrimidin-4-yl, 5-bromo-pyrazin-2-yl, 5-hydroxy-pyrazin-2-yl, 5-methoxy-pyrazin-2-yl, 5-ethoxypyrazin-2-yl, 5-methylamino-pyrazin-2-yl, 5-bromo-pyridin-2-yl, pyridin-3-yl, 5-trifluoromethyl-pyridin-2-yl, 5-isopropyl-pyridin-2-yl, 5-isopropyl-pyridin-2-yl, 5-methyl-pyridin-2-yl, 5-ethyl-pyridin-2-yl, 5-methoxy-pyridin-2-yl, 4-trifluoromethyl-pyridin-2-yl, 5-cyano-pyridin-2-yl, 5-dimethylamino-pyridin-2-yl, 4-methyl-pyridin-2-yl, 5-chloro-4-methyl-pyridin-2-yl, 5-chloro-4-trifluoromethyl-pyridin-2-yl, 4-trifluoromethyl-pyridin-2-yl, 3-fluoro-pyridin-2-yl, 6-methyl-4-trifluoromethyl-pyridin-2-yl, 3-methyl-pyridin-2-yl, 5-propyl-pyridin-2-yl, 5-cyclopropyl-pyridin-2-yl, 5-fluoro-pyridin-2-yl, 3,5-difluoro-pyridin-2-yl, 6-bromo-pyridin-3-yl, 5-bromo-pyridin-3-yl, 5,6-difluoro-pyridin-3-yl, 6-chloro-pyridin-3-yl, 3-fluoro-pyridin-4-yl, 5-cyano-pyridin-3-yl, pyridin-4-yl, 2-chloro-pyridin-4-yl, 2-methoxy-pyridin-4-yl, 6-methyl-pyridin-3-yl, m-tolyl, thiazol-2-yl, cyclopentyl, 4-amino-pyridin-2-yl, 4-methoxy-pyridin-2-yl, 4-choro-pyridin-2-yl, 4-fluoro-pyridin-2-yl, 4-cyclopropyl-pyridin-2-yl, 4-bromo-pyridin-2-yl, 4-methanesulfonyl-pyridin-2-yl, 4-cyano-pyridin-2-yl, hydroxymethyl, 4-oxy-pyrazin-2-yl, 3-methyl-1,1-dioxo-tetrahydro-1$\lambda^6$-thiophen-3-yl, 5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 4-iodo-pyridin-2-yl, 1-oxy-pyridin-3-yl, and 4-hydroxy-pyridin-2-yl;

$R^8$ is —$R^{14}$—$R^{15}$—$R^{16}$—$R^{17}$; wherein:

$R^{14}$ is selected from: methylene, ethylene, 1,1-cyclopropylene, 1,1-dimethyl-methylene, 1,1-cyclobutylene, tert-butyl-methylene, 1-methyl-4,4-piperidinylene, 4,4-tetrahydro-2H-pyranylene, methyl-methylene, 1,1-cyclohexylene, 1,2-cyclohexylene, 1,1-dimethyl-ethylene, 1-tert-butyl-ethylene, 1-ethyl-ethylene, 1-methyl-ethylene, 1-(tetrahydro-2H-pyran-4-yl)-ethylene, isopropyl-methylene, 1,1-cyclopentylene, benzyl-methylene, 4,4-cyclopent-1-enylene, 1,1-dioxo-hexahydro-1$\lambda^6$-4,4-thiopyranylene, 1-tert-butoxycarbonyl-4,4-piperidinylene, 1-(pyridin-4-yl)-ethylene, 1-(pyridin-3-yl)-ethylene, 1-(pyridin-2-yl)-ethylene, 1-(4-fluoro-phenyl)-ethylene, 1-hydroxymethyl-1-methyl-ethylene, 1-carboxy-1-methyl-ethylene, 1-methoxymethyl-ethylene, 1-hydroxymethyl-ethylene, 1-(1-hydroxyethyl)-ethylene, 1,1-dimethyl-ethylene, 1-(tetrahydro-furan-3-yl)-ethylene, phenyl-methylene, 1-(3H-imidazol-4-ylmethyl)-ethylene, 1-(4-hydroxy-phenyl)-ethylene, benzyl-ethylene, (1-hydroxymethyl-2-methyl)-ethylene, 1-isopropyl-ethylene, pyridin-2-yl-methylene, 1,1-dimethyl-propylene, 2-hydroxy-propylene, (1-isobutyl-pyrrolidin-3-yl)-methylene, 1,3-azetidinylene, 1,3-pyrrolidinylene, 1,3-piperidinylene, 1,4-piperidinylene, 2,4-thiazolylene, 3,4-pyridinylene, 2,4-pyridinylene, 2,5-pyridinylene, —SO$_2$—, 2,5-pyridinylene, 1-cyclopropyl-ethylene, 1-(sec-butyl)-ethylene, 1-hydroxymethyl-1-ethyl-ethylene, 1-isopropyl-ethylene, 1-(2,2,2-trifluoroethyl)-ethylene, (2-fluoropropan-2-yl)-methylene, (1,1,1,3,3,3-hexafluoropropan-2-yl)-methylene, 1-(2-fluoropropan-2-yl)-ethylene, (2,2,2-trifluoroethyl)-methylene, 1,1-di(fluoromethyl)-ethylene, (hydroxymethyl)(methyl)methylene, (hydroxymethyl)(methyl)methylene, 3,3-oxetanylene, and 1-hydroxymethyl-1-isopropyl-ethylene; or $R^{14}$ is absent;

$R^{15}$ is selected from: 1,3-pyrrolidinylene, 1,4-piperidinylene, 2,6-pyridinylene, 1,3-azetidinylene, —C(O)NH—, —C(O)—, —C(O)O—, 1,2-pyrrolidinylene, 2,4-morpholinylene, ethylene, methylene, 1,1-cyclopentylene, 4,4-tetrahydro-2H-pyranylene, 3,3-tetrahydro-thiophenylene, 1,1-cyclopropylene, 1-methyl-4,4-piperidinylene, and 1-oxo-tetrahydro-1$\lambda^4$-3,3-thiophenylene; or $R^{15}$ is absent;

$R^{16}$ is selected from: ethylene and methylene; or $R^{16}$ is absent; and $R^{17}$ is selected from: is selected from: H, amino, 1-tert-butoxycarbonylamino, morpholin-4-yl, 4-methyl-piperidin-1-yl, piperidin-4-yl, 1-tert-butoxycarbonyl-piperidin-3-yl, tetrahydro-thiopyran-4-yl, 1-oxo-hexahydro-1$\lambda^4$-thiopyran-4-yl, tetrahydro-pyran-4-yl, pyrrolidin-1-yl, 1-tert-butoxycarbonyl-azetidin-3-yl, 2,6-dimethyl-morpholin-4-yl, piperidin-1-yl, 1-tert-butoxycarbonyl-piperidin-4-yl, 1,1-dioxo-hexahydro-1$\lambda^6$-thiopyran-4-yl, tetrahydro-furan-2-yl, 1-ethyl-pyrrolidin-2-yl, 1-methyl-pyrrolidin-2-yl, morpholin-2-yl, 1-methyl-piperidin-2-yl, 1-methyl-piperidin-4-yl, 4-hydroxy-1-methyl-piperidin-4-yl, thiomorpholin-4-yl, tetrahydro-furan-3-yl, 1-tert-butoxycarbonyl-pyrrolidin-4-yl, 1,2,2,6,6-pentamethyl-piperidin-4-yl, 1,1-dioxo-tetrahydro-1$\lambda^6$-thiophen-3-yl, 4-methyl-morpholin-2-yl, 4-tert-butoxycarbonyl-morpholin-2-yl, 1-isopropyl-piperidin-4-yl, 4-hydroxy-1,1-dioxo-tetrahydro-1$\lambda^6$-thiophen-3-yl, 3-methyl-1,1-dioxo-tetrahydro-1$\lambda^6$-thiophen-3-yl, phenyl, 2-hydroxy-indan-1-yl, indan-1-yl, cyclopentyl, 2-hydroxy-cyclopentyl, cyclobutyl, 2-hydroxy-cyclohexyl, 1,3,3-trimethyl-bicyclo[2.2.1]hept-2-yl, 6,6-dimethyl-bicyclo[3.1.1]hept-2-yl, 1-aza-bicyclo[2.2.2]oct-3-yl, 9-methyl-9-aza-bicyclo[3.3.1]non-1-yl, 3-azepan-1-yl, 2-fluoro-phenyl, 2-chloro-phenyl, 4-fluoro-phenyl, 4-chloro-phenyl, 3-fluoro-phenyl, 5-fluoro-2-methoxy-phenyl, 2-fluoro-4-methanesulfonyl-phenyl, 4-carboxy-2-fluoro-phenyl, 2,5-difluoro-phenyl, m-tolyl, o-tolyl, 2,5-dimethyl-phenyl, 2,3-dimethyl-phenyl, 4-hydroxy-3-methoxy-phenyl, 2,4-dimethoxy-phenyl, 2,3-dimethoxy-phenyl, 3,5-dimethoxy-phenyl, 4-methoxy-phenyl, 3-methoxy-phenyl, 2-methoxy-phenyl, 3-hydroxy-phenyl, 4-hydroxy-phenyl, 2-hydroxy-phenyl, 5-fluoro-2-hydroxy-phenyl, 3-trifluoromethoxy-phenyl, 4-difluoromethoxy-phenyl, 3-difluoromethoxy-phenyl, 4-fluoro-phenoxy, 2-dimethylamino-phenyl, 4-dimethylamino-phenyl, 6-fluoro-4H-benzo[1,3]dioxin-8-yl, benzo[1,3]dioxol-5-yl, pyrimidin-2-yl, pyrimidin-4-yl, 2,6-dimethyl-pyrimidin-4-yl, pyridazin-3-yl, 5-methyl-pyrazin-2-yl, 6-methoxy-pyrimidin-4-yl, pyrazin-2-yl, 3,5-dimethyl-pyrazin-2-yl, 5-fluoro-2-oxo-2,3-dihydro-pyrimidin-4-yl, hydroxyl, methoxycarbonyl, ethoxycarbonyl, carboxy, 1-piperidin-1-yl, carboxamide, methoxy, trifluoromethyl, methyl, tert-butyl, diethylamino, dimethylamino, cyano, tert-butylamino, cyclopropyl, pyridin-3-yloxy, 1H-tetrazol-5-yl, 5-methyl-[1,2,4]oxadiazol-3-yl, phosphonooxy, cyclobutylamino, phenylamino, 1-tert-butyl-3-methylureido, 3-methyl-1-phenylureido, N-tert-butylmethylsulfonamido, 1-cyclobutyl-3-methylureido, methylcarbamoyl, 5-hydroxy-1H-indol-3-yl, 1H-benzoimidazol-2-yl, 5,7-dimethyl-pyrazolo[1,5-a]pyrimidin-2-yl, 1H-benzoimidazol-2-yl, 2-(tert-butoxycarbonyl)-3,4-dihydro-1H-isoquinoline-2-yl, quinolin-3-yl, quinolin-4-yl, 2-methyl-quinolin-4-yl, benzooxazol-2-yl, 1-methyl-1,2,3,4-tetrahydro-quinolin-7-yl, 2,3-dihydro-benzofuran-3-yl, benzothiazol-2-yl, 1,4-dimethyl-1H-pyrrol-2-yl, 3-methyl-3H-imidazol-4-yl, 1H-imidazol-4-yl, 5-hydroxy-1H-pyrazol-3-yl, 1-methyl-1H-pyrazol-3-yl, 4-pyridin-2-yl-thiazol-2-yl, 5-methyl-thiazol-2-yl, oxazol-4-yl, 4-phenyl-thiazol-2-yl, 5-tert-butyl-isoxazol-3-yl, pyridin-2-yl, pyridin-3-yl, pyridin-4-yl, 3-hydroxy-pyridin-2-yl, 6-hydroxy-pyridin-3-yl, 3-hydroxy-pyridin-4-yl, 4-hydroxy-pyridin-2-yl, 6-hydroxy-pyridin-2-yl, 2-hydroxy-pyridin-3-yl, 2-methoxy-pyridin-3-yl, 5-methoxy-pyridin-2-yl, 4-methoxy-pyridin-2-yl, 2-methoxy-pyridin-4-yl, 6-methoxy-pyridin-2-yl, 6-methoxy-pyridin-3-yl, 3-fluoro-pyridin-2-yl, 2-fluoro-pyridin-3-yl, 6-fluoro-pyridin-2-yl, 5-fluoro-pyridin-2-yl, 6-fluoro-pyridin-3-yl, 3-fluoro-pyridin-4-yl, 3-methyl-pyridin-2-yl, 3-methyl-pyridin-4-yl, 6-methyl-pyridin-2-yl, 4-methyl-pyridin-2-yl, 6-methyl-pyridin-3-yl, 2-methyl-pyridin-3-yl, 5-trifluoromethyl-pyridin-2-yl, 6-trifluoromethyl-pyridin-3-yl, 4-trifluoromethyl-pyridin-2-yl, 3-chloro-5-trifluoromethyl-pyridin-2-yl, 4,6-dimethyl-pyridin-2-yl, 4,6-dimethyl-pyridin-2-yl, 3-chloro-5-methyl-pyridin-2-yl, 6-cyano-pyridin-3-yl, 3-cyano-5-methyl-pyridin-2-yl, 3-cyano-5-methyl-pyridin-2-yl, 3-chloro-5-methyl-pyridin-2-yl, 2-chloro-pyridin-3-yl, 5-chloro-pyridin-2-yl, 6-chloro-2-methyl-pyridin-3-yl, 6-chloro-pyridin-3-yl, 3-chloro-pyridin-4-yl, 6-bromo-2-methyl-pyridin-3-yl, 5-bromo-3-methyl-pyridin-2-yl, 6-carboxypyridin-2-yl, 6-methanesulfonyl-4-methyl-pyridin-3-yl, 6-methanesulfonyl-4-methyl-pyridin-3-yl, 6-methanesulfonyl-2-methyl-pyridin-3-yl, 6-methanesulfonyl-pyridin-3-yl, 2,6-dimethoxy-pyridin-3-yl, 5-fluoro-1-oxy-pyridin-2-yl, 1-oxy-pyridin-2-yl, 6-pyrrolidin-1-yl-pyridin-2-ylmethyl, 5-(1-methyl-pyrrolidin-2-yl)-pyridin-2-yl, 6-morpholin-4-yl-pyridin-2-yl, 6-morpholin-4-yl-pyridin-3-yl, ethynyl, tert-butyl(methyl)amino, 2,2,2-trifluoroethyl, N-cyclobutylmethylsulfonamido, N-phenylmethylsulfonamido, hydroxy(methyl)amino, methoxy(methyl)amino, azetidin-1-yl, tert-butoxy, fluoromethyl, 2,2,2-trifluoroethylamino, and (1,1-dioxo-tetrahydro-1$\lambda^6$-thiophen-3-yl)amino; and $R^9$ is selected from H, methyl, tert-butyl, and cyclobutyl; or $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydroisoindol-2-yl, 3-hydroxy-7,8-dihydro-5H-[1,6]naphthyridin-6-yl, 4-(tert-butoxycarbonyl)-2-(hydroxymethyl)

piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Ic and pharmaceutically acceptable salts, solvates, hydrates, and N-oxides thereof:

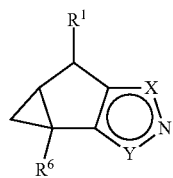

Ic wherein:
$R^1$ is selected from: H and methyl;
$R^6$ is selected from: H and isopropyl;
X is $NR^7$ and Y is $CC(O)N(R^8)R^9$; or
X is $CC(O)N(R^8)R^9$ and Y is $NR^7$.
$R^7$ is $—R^{10}—R^{11}—R^{12}—R^{13}$; wherein:
$R^{10}$ is selected from: 1,1-dimethylethylene, 1,1-dimethylmethylene, ethylene, methylene, 1,4-piperidinylene, 2,5-pyrazinylene, and 2,4-pyridinylene; or $R^{10}$ is absent;
$R^{11}$ is selected from: —C(O)NH— and methylene; or $R^{11}$ is absent;
$R^{12}$ is 1,1-dimethyl-methylene; or $R^{12}$ is absent; and
$R^{13}$ is selected from: 2,4-difluoro-phenyl, 2,4-dichloro-phenyl, 2-fluoro-4-methanesulfonyl-phenyl, 2,6-difluoro-phenyl, 2,5-difluoro-phenyl, 4-methoxy-phenyl, 4-cyano-phenyl, 4-fluoro-phenyl, phenyl, 2-fluoro-phenyl, 3-fluoro-phenyl, o-tolyl, tert-butyl, isopropyl, 2,2-dimethylpropyl, hydroxyl, 2-hydroxy-2-methylpropyl, 1-oxo-hexahydro-$1\lambda^4$-thiopyran-4-yl, 1,1-dioxo-hexahydro-$1\lambda^6$-thiopyran-4-yl, tetrahydrothiopyran-4-yl, morpholin-4-yl, tetrahydropyran-4-yl, 1,1-dioxo-tetrahydro-$1\lambda^6$-thiophen-3-yl, pyrazin-2-yl, 5-ethyl-pyrazin-2-yl, 5-hydroxy-pyrazin-2-yl, 5-isopropyl-pyrazin-2-yl, 5-heptafluoropropyl-pyrazin-2-yl, 5-cyclobutyl-pyrazin-2-yl, 5-methyl-pyrazin-2-yl, 6-ethyl-pyrazin-2-yl, 5-trifluoromethyl-pyrazin-2-yl, cyclopropyl, 5-cyclopropyl-pyrazin-2-yl, 6-chloro-pyrazin-2-yl, 5-dimethylamino-pyrazin-2-yl, 4-cyano-phenyl, 6-methoxy-pyridazin-3-yl, 6-chloro-pyridazin-3-yl, pyrimidin-5-yl, 6-dimethylamino-pyrazin-2-yl, 6-methoxy-pyrazin-2-yl, 2-pyrimidin-4-yl, 5-bromo-pyrazin-2-yl, 5-hydroxy-pyrazin-2-yl, 5-methoxy-pyrazin-2-yl, 5-ethoxypyrazin-2-yl, 5-methylamino-pyrazin-2-yl, 5-bromo-pyridin-2-yl, pyridin-3-yl, 5-trifluoromethyl-pyridin-2-yl, 5-isopropyl-pyridin-2-yl, 5-isopropyl-pyridin-2-yl, 5-methyl-pyridin-2-yl, 5-ethyl-pyridin-2-yl, 5-methoxy-pyridin-2-yl, 4-trifluoromethyl-pyridin-2-yl, 5-cyano-pyridin-2-yl, 5-dimethylamino-pyridin-2-yl, 4-methyl-pyridin-2-yl, 5-chloro-4-methyl-pyridin-2-yl, 5-chloro-4-trifluoromethyl-pyridin-2-yl, 4-trifluoromethyl-pyridin-2-yl, 3-fluoro-pyridin-2-yl, 6-methyl-4-trifluoromethyl-pyridin-2-yl, 3-methyl-pyridin-2-yl, 5-propyl-pyridin-2-yl, 5-cyclopropyl-pyridin-2-yl, 5-fluoro-pyridin-2-yl, 3,5-difluoro-pyridin-2-yl, 6-bromo-pyridin-3-yl, 5-bromo-pyridin-3-yl, 5,6-difluoro-pyridin-3-yl, 6-chloro-pyridin-3-yl, 3-fluoro-pyridin-4-yl, 5-cyano-pyridin-3-yl, pyridin-4-yl, 2-chloro-pyridin-4-yl, 2-methoxy-pyridin-4-yl, 6-methyl-pyridin-3-yl, m-tolyl, thiazol-2-yl, cyclopentyl, 4-amino-pyridin-2-yl, 4-methoxy-pyridin-2-yl, 4-choro-pyridin-2-yl, 4-fluoro-pyridin-2-yl, 4-cyclopropyl-pyridin-2-yl, 4-bromo-pyridin-2-yl, 4-methanesulfonyl-pyridin-2-yl, 4-cyano-pyridin-2-yl, hydroxymethyl, and 4-oxy-pyrazin-2-yl;

$R^8$ is $—R^{14}—R^{15}—R^{16}—R^{17}$; wherein:
$R^{14}$ is selected from: methylene, ethylene, 1,1-cyclopropylene, 1,1-dimethyl-methylene, 1,1-cyclobutylene, tert-butyl-methylene, 1-methyl-4,4-piperidinylene, 4,4-tetrahydro-2H-pyranylene, methyl-methylene, 1,1-cyclohexylene, 1,2-cyclohexylene, 1,1-dimethyl-ethylene, 1-tert-butyl-ethylene, 1-ethyl-ethylene, 1-methyl-ethylene, 1-(tetrahydro-2H-pyran-4-yl)-ethylene, isopropyl-methylene, 1,1-cyclopentylene, benzyl-methylene, 4,4-cyclopent-1-enylene, 1,1-dioxo-hexahydro-$1\lambda^6$-4,4-thiopyranylene, 1-tert-butoxycarbonyl-4,4-piperidinylene, 1-(pyridin-4-yl)-ethylene, 1-(pyridin-3-yl)-ethylene, 1-(pyridin-2-yl)-ethylene, 1-(4-fluoro-phenyl)-ethylene, 1-hydroxymethyl-1-methyl-ethylene, 1-carboxy-1-methyl-ethylene, 1-methoxymethyl-ethylene, 1-hydroxymethyl-ethylene, 1-(1-hydroxyethyl)-ethylene, 1,1-dimethyl-ethylene, 1-(tetrahydro-furan-3-yl)-ethylene, phenyl-methylene, 1-(3H-imidazol-4-ylmethyl)-ethylene, 1-(4-hydroxy-phenyl)-ethylene, benzyl-ethylene, (1-hydroxymethyl-2-methyl)-ethylene, 1-isopropyl-ethylene, pyridin-2-yl-methylene, 1,1-dimethyl-propylene, 2-hydroxy-propylene, (1-isobutyl-pyrrolidin-3-yl)-methylene, 1,3-azetidinylene, 1,3-pyrrolidinylene, 1,3-piperidinylene, 1,4-piperidinylene, 2,4-thiazolylene, 3,4-pyridinylene, 2,4-pyridinylene, 2,5-pyridinylene, —SO$_2$—, 2,5-pyridinylene, and 1-cyclopropyl-ethylene; or $R^{14}$ is absent;
$R^{15}$ is selected from: 1,3-pyrrolidinylene, 1,4-piperidinylene, 2,6-pyridinylene, 1,3-azetidinylene, —C(O)NH—, —C(O)—, 1,2-pyrrolidinylene, 2,4-morpholinylene, ethylene, methylene, 1,1-cyclopentylene, 4,4-tetrahydro-2H-pyranylene, 3,3-tetrahydro-thiophenylene, 1,1-cyclopropylene, 1-methyl-4,4-piperidinylene, and 1-oxo-tetrahydro-$1\lambda^4$-3,3-thiophenylene; or $R^{15}$ is absent;
$R^{16}$ is selected from: ethylene and methylene; or $R^{16}$ is absent; and
$R^{17}$ is selected from: H, amino, 1-tert-butoxycarbonylamino, morpholin-4-yl, 4-methyl-piperidin-1-yl, piperidin-4-yl, 1-tert-butoxycarbonyl-piperidin-3-yl, tetrahydrothiopyran-4-yl, 1-oxo-hexahydro-$1\lambda^4$-thiopyran-4-yl, tetrahydro-pyran-4-yl, pyrrolidin-1-yl, 1-tert-butoxycarbonyl-azetidin-3-yl, 2,6-dimethyl-morpholin-4-yl, piperidin-1-yl, 1-tert-butoxycarbonyl-piperidin-4-yl, 1,1-dioxo-hexahydro-$1\lambda^6$-thiopyran-4-yl, tetrahydro-furan-2-yl, 1-ethyl-pyrrolidin-2-yl, 1-methyl-pyrrolidin-2-yl, morpholin-2-yl, 1-methyl-piperidin-2-yl, 1-methyl-piperidin-4-yl, 4-hydroxy-1-methyl-piperidin-4-yl, thiomorpholin-4-yl, tetrahydro-furan-3-yl, 1-tert-butoxycarbonyl-pyrrolidin-4-yl, 1,2,2,6,6-pentamethyl-piperidin-4-yl, 1,1-dioxo-tetrahydro-$1\lambda^6$-thiophen-3-yl, 4-methyl-morpholin-2-yl, 4-tert-butoxycarbonyl-morpholin-2-yl, 1-isopropyl-piperidin-4-yl, 4-hydroxy-1,1-dioxo-tetrahydro-$1\lambda^6$-thiophen-3-yl, 3-methyl-1,1-dioxo-tetrahydro-$1\lambda^6$-thiophen-3-yl, phenyl, 2-hydroxy-indan-1-yl, indan-1-yl, cyclopentyl, 2-hydroxy-cyclopentyl, cyclobutyl, 2-hydroxy-cyclohexyl, 1,3,3-trimethyl-bicyclo[2.2.1]hept-2-yl, 6,6-dimethyl-bicyclo[3.1.1]hept-2-yl, 1-aza-bicyclo[2.2.2]oct-3-yl, 9-methyl-9-aza-bicyclo[3.3.1]non-1-yl, 3-azepan-1-yl, 2-fluoro-phenyl, 2-chloro-phenyl, 4-fluoro-phenyl, 4-chloro-phenyl, 3-fluoro-phenyl, 5-fluoro-2-methoxy-phenyl, 2-fluoro-4-methanesulfonyl-phenyl, 4-carboxy-2-fluoro-phenyl, 2,5-difluoro-phenyl, m-tolyl, o-tolyl, 2,5-dimethyl-phenyl, 2,3-dimethyl-phenyl, 4-hydroxy-3-methoxy-phenyl, 2,4-dimethoxy-phenyl, 2,3-dimethoxy-phenyl, 3,5-dimethoxy-phenyl, 4-methoxy-phenyl, 3-methoxy-phenyl, 2-methoxy-phenyl, 3-hydroxy-phenyl, 4-hydroxy-phenyl, 2-hydroxy-phenyl, 5-fluoro-2-hydroxy-phenyl, 3-trifluoromethoxy-phenyl, 4-difluoromethoxy-phenyl, 3-difluoromethoxy-phenyl, 4-fluoro-phenoxy, 2-dimethylamino-phenyl, 4-dimethylamino-phenyl, 6-fluoro-4H-benzo[1,3]dioxin-8-yl, benzo[1,3]dioxol-5-yl, pyrimidin-2-yl, pyrimidin-4-yl, 2,6-dimethyl-pyrimidin-4-yl, pyridazin-3-yl, 5-methyl-pyrazin-2-yl, 6-methoxy-pyrimidin-4-yl, pyrazin-2-yl, 3,5-dimethyl-pyrazin-2-yl, 5-fluoro-2-oxo-2,3-dihydro-pyrimidin-4-yl, hydroxyl, methoxycarbonyl, ethoxycarbonyl, carboxy, 1-piperidin-1-yl, carboxamide, methoxy, trifluoromethyl, methyl, tert-butyl, diethylamino, dimethylamino, cyano, tert-butylamino, cyclopropyl, pyridin-3-yloxy, 1H-tetrazol-5-yl, 5-methyl-[1,2,4]oxadiazol-3-yl, phosphonooxy, cyclobutylamino, phenylamino, 1-tert-butyl-3-methylureido, 3-methyl-1-phenylureido, N-tert-butylmethylsulfonamido, 1-cyclobutyl-3-methylureido, methylcarbamoyl, 5-hydroxy-1H-indol-3-yl, 1H-benzoimidazol-2-yl, 5,7-dimethyl-pyrazolo[1,5-a]pyrimidin-2-yl, 1H-benzoimidazol-2-yl, 2-(tert-butoxycarbonyl)-3,4-dihydro-1H-isoquinoline-2-yl, quinolin-3-yl, quinolin-4-yl, 2-methyl-quinolin-4-yl, benzooxazol-2-yl, 1-methyl-1,2,3,4-tetrahydro-quinolin-7-yl, 2,3-dihydro-benzofuran-3-yl, benzothiazol-2-yl, 1,4-dimethyl-1H-pyrrol-2-yl, 3-methyl-3H-imidazol-4-yl, 1H-imidazol-4-yl, 5-hydroxy-1H-pyrazol-3-yl, 1-methyl-1H-pyrazol-3-yl, 4-pyridin-2-yl-thiazol-2-yl, 5-methyl-thiazol-2-yl, oxazol-4-yl, 4-phenyl-thiazol-2-yl, 5-tert-butyl-isoxazol-3-yl, pyridin-2-yl, pyridin-3-yl, pyridin-4-yl, 3-hydroxy-pyridin-2-yl, 6-hydroxy-pyridin-3-yl, 3-hydroxy-pyridin-4-yl, 4-hydroxy-pyridin-2-yl, 6-hydroxy-pyridin-2-yl, 2-hydroxy-pyridin-3-yl, 2-methoxy-pyridin-3-yl, 5-methoxy-pyridin-2-yl, 4-methoxy-pyridin-2-yl, 2-methoxy-pyridin-4-yl, 6-methoxy-pyridin-2-yl, 6-methoxy-pyridin-3-yl, 3-fluoro-pyridin-2-yl, 2-fluoro-pyridin-3-yl, 6-fluoro-pyridin-2-yl, 5-fluoro-pyridin-2-yl, 6-fluoro-pyridin-3-yl, 3-fluoro-pyridin-4-yl, 3-methyl-pyridin-2-yl, 3-methyl-pyridin-4-yl, 6-methyl-pyridin-2-yl, 4-methyl-pyridin-2-yl, 6-methyl-pyridin-3-yl, 2-methyl-pyridin-3-yl, 5-trifluoromethyl-pyridin-2-yl, 6-trifluoromethyl-pyridin-3-yl, 4-trifluoromethyl-pyridin-2-yl, 3-chloro-5-trifluoromethyl-pyridin-2-yl, 4,6-dimethyl-pyridin-2-yl, 4,6-dimethyl-pyridin-2-yl, 3-chloro-5-methyl-pyridin-2-yl, 6-cyano-pyridin-3-yl, 3-cyano-5-methyl-pyridin-2-yl, 3-cyano-5-methyl-pyridin-2-yl, 3-chloro-5-methyl-pyridin-2-yl, 2-chloro-pyridin-3-yl, 5-chloro-pyridin-2-yl, 6-chloro-2-methyl-pyridin-3-yl, 6-chloro-pyridin-3-yl, 3-chloro-pyridin-4-yl, 6-bromo-2-methyl-pyridin-3-yl, 5-bromo-3-methyl-pyridin-2-yl, 6-carboxypyridin-2-yl, 6-methanesulfonyl-4-methyl-pyridin-3-yl, 6-methanesulfonyl-4-methyl-pyridin-3-yl, 6-methanesulfonyl-2-methyl-pyridin-3-yl, 6-methanesulfonyl-pyridin-3-yl, 2,6-dimethoxy-pyridin-3-yl, 5-fluoro-1-oxy-pyridin-2-yl, 1-oxy-pyridin-2-yl, 6-pyrrolidin-1-yl-pyridin-2-ylmethyl, 5-(1-methyl-pyrrolidin-2-yl)-pyridin-2-yl, 6-morpholin-4-yl-pyridin-2-yl, 6-morpholin-4-yl-pyridin-3-yl, ethynyl, tert-butyl(methyl)amino, 2,2,2-trifluoroethyl, N-cyclobutylmethylsulfonamido, N-phenylmethylsulfonamido, hydroxy(methyl)amino, methoxy(methyl)amino, azetidin-1-yl, and tert-butoxy; and $R^9$ is selected from H, methyl, tert-butyl, and cyclobutyl; or $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Ic and pharmaceutically acceptable salts, solvates, hydrates, and N-oxides thereof:

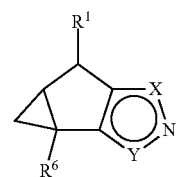

Ic wherein:
$R^1$ is selected from: H and methyl;
$R^6$ is selected from: H and isopropyl;
X is $NR^7$ and Y is $CC(O)N(R^8)R^9$; or
X is $CC(O)N(R^8)R^9$ and Y is $NR^7$;
$R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1λ⁴-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1λ⁶-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3']bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, piperidin-4-yl, tetrahydro-pyran-4-yl, 3-methyl-1,1-dioxo-tetrahydro-1$\lambda^6$-thiophen-3-yl, 5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 3-hydroxy-3-methyl-butyl, 4-iodo-pyridin-2-yl, 1-oxy-pyridin-3-yl, 4-tert-butylcarbamoyl-pyridin-2-yl, and 4-hydroxy-pyridin-2-yl;

$R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluoro-phenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclopropyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)piperidin-3-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluoro-phenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1$\lambda^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1$\lambda^4$-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, indan-1-ylamide, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydro-furan-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1$\lambda^6$-thiophen-3-ylmethyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chloro-phenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxy-benzyl, 4-hydroxy-1-methyl-piperidin-4-ylmethyl, 1-(2,5-dimethylpyrrolidine-1-carbonyl)cyclopentyl, 2-methoxy-benzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoro-propyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1$\lambda^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1$\lambda^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methylamino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoroethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino)ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, 2,2-dimethyl-1-pyridin-2-yl-propyl, (1,1-dioxo-tetrahydro-1$\lambda^6$-thiophen-3-yl)amino, 1-hydroxycarbamoyl-2,2-dimethyl-propyl, 1-hydroxymethyl-2-methyl-butyl, 1-(2-hydroxy-ethylcarbamoyl)-2,2-dimethyl-propyl, 1,1-bis-hydroxymethyl-propyl, 1-(5-fluoro-pyridin-2-yl)-2,2-dimethyl-propyl, 4-hydroxymethyl-tetrahydro-2H-pyran-4-yl, 1-(2-(tert-butoxycarbonylamino)-3-methylbutanoyloxy)-2-methylpropan-2-yl, 1-(2-amino-3-methylbutanoyloxy)-3-methylbutan-2-yl, 1-(2-amino-3-methylbutanoyloxy)-2-methylpropan-2-yl, 2-hydroxy-1-(tetrahydro-2H-pyran-4-yl)-ethyl, 1-(4-carboxybutanoyloxy)-2-methylpropan-2-yl, 1-(4-carboxybutanoyloxy)-3-methylbutan-2-yl, 1-(4-carboxybutanoyloxy)-3,3-dimethylbutan-2-yl, 1-(2-amino-3-methylbutanoyloxy)-3,3-dimethylbutan-2-yl, 2-(2-amino-3-methylbutanoyloxy)-1-(tetrahydro-2H-pyran-4-yl)ethyl, 3,3,3-trifluoro-1-hydroxymethyl-propyl, 3-fluoro-1-methoxy-3-methyl-1-oxobutan-2-yl, 1-ethoxy-4,4,4-trifluoro-1-oxo-3-(trifluoromethyl)butan-2-yl, 2-fluoro-1-hydroxymethyl-2-methyl-propyl, 1-(2-(tert-butoxycarbonylamino)-3-methylbutanoyloxy)-3,3-dimethylbutan-2-yl, 4,4,4-trifluoro-1-methoxy-1-oxobutan-2-yl, 2-fluoro-1,1-dimethyl-ethyl, 3-fluoro-2-(fluoromethyl)-1-methoxy-1-oxopropan-2-yl, 2-fluoro-1-fluoromethyl-1-hydroxymethyl-ethyl, 3-hydroxy-1-methoxy-2-methyl-1-oxopropan-2-yl, 2-carboxy-1-hydroxypropan-2-yl, 2,2,2-trifluoroethylamino, 1-fluoromethyl-2-methyl-propyl, 1-fluoromethyl-2,2-dimethyl-propyl, 3-methyl-oxetan-3-yl, 1-fluoromethyl-cyclobutyl, 1,1-bis-hydroxymethyl-2-methyl-propyl, 1-trifluoromethyl-cyclopropyl, 1-methyl-cyclopropyl, and 1-trifluoromethyl-cyclobutyl; and $R^9$ is selected from H, methyl, tert-butyl, and cyclobutyl; or $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo

[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Ic and pharmaceutically acceptable salts, solvates, hydrates, and N-oxides thereof:

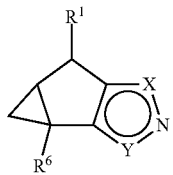

Ic wherein:
$R^1$ is selected from: H and methyl;
$R^6$ is selected from: H and isopropyl;
X is $NR^7$ and Y is $CC(O)N(R^8)R^9$; or
X is $CC(O)N(R^8)R^9$ and Y is $NR^7$;
$R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3']bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethyl-amino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, and piperidin-4-yl;

$R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluoro-phenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclobutyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, cyclobutanecarboxylic acid ethyl ester, pyridin-3-ylmethyl, pyrazin-2-ylmethyl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)piperidin-3-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluoro-phenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1$\lambda^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1$\lambda^4$-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydro-furan-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1$\lambda^6$-thiophen-3-ylmethyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chloro-phenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxy-benzyl, 4-hydroxy-1-methyl-piperidin-4-ylmethyl, 1-(2,5-dimethylpyrrolidine-1-carbonyl)cyclopentyl, 2-methoxy-benzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoro-propyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1$\lambda^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1$\lambda^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4- ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methylamino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoroethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino) ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, and 2,2-dimethyl-1-pyridin-2-yl-propyl; and $R^9$ is selected from H, methyl, tert-butyl, and cyclobutyl; or $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Ic and pharmaceutically acceptable salts, solvates, hydrates, and N-oxides thereof:

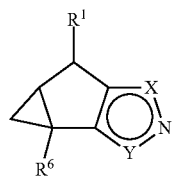

Ic wherein:
$R^1$ is H;
$R^6$ is H;

X is $NR^7$ and Y is $CC(O)N(R^8)R^9$; or
X is $CC(O)N(R^8)R^9$ and Y is $NR^7$;

$R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3']bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, piperidin-4-yl, tetrahydro-pyran-4-yl, 3-methyl-1,1-dioxo-tetrahydro-1$\lambda^6$-thiophen-3-yl, 5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 3-hydroxy-3-methyl-butyl, 4-iodo-pyridin-2-yl, 1-oxy-pyridin-3-yl, 4-tert-butylcarbamoyl-pyridin-2-yl, and 4-hydroxy-pyridin-2-yl;

$R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluoro-phenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclobutyl, 2-methyl-pyridin-3-yl, 2-hydroxy-1-

(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)piperidin-3-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluorophenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1$\lambda^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1$\lambda^4$-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, indan-1-ylamide, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydro-furan-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1$\lambda^6$-thiophen-3-ylmethyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chlorophenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxybenzyl, 4-hydroxy-1-methyl-piperidin-4-ylmethyl, 1-(2,5-dimethylpyrrolidine-1-carbonyl)cyclopentyl, 2-methoxybenzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoro-propyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1$\lambda^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1$\lambda^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methylamino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoroethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino)ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, 2,2-dimethyl-1-pyridin-2-yl-propyl, (1,1-dioxo-tetrahydro-1$\lambda^6$-thiophen-3-yl)amino, 1-hydroxycarbamoyl-2,2-dimethyl-propyl, 1-hydroxymethyl-2-methyl-butyl, 1-(2-hydroxyethylcarbamoyl)-2,2-dimethyl-propyl, 1,1-bis-hydroxymethyl-propyl, 1-(5-fluoro-pyridin-2-yl)-2,2-dimethyl-propyl, 4-hydroxymethyl-tetrahydro-2H-pyran-4-yl, 1-(2-(tert-butoxycarbonylamino)-3-methylbutanoyloxy)-2-methylpropan-2-yl, 1-(2-amino-3-methylbutanoyloxy)-3-methylbutan-2-yl, 1-(2-amino-3-methylbutanoyloxy)-2-methylpropan-2-yl, 2-hydroxy-1-(tetrahydro-2H-pyran-4-yl)-ethyl, 1-(4-carboxybutanoyloxy)-2-methylpropan-2-yl, 1-(4-carboxybutanoyloxy)-3-methylbutan-2-yl, 1-(4-carboxybutanoyloxy)-3,3-dimethylbutan-2-yl, 1-(2-amino-3-methylbutanoyloxy)-3,3-dimethylbutan-2-yl, 2-(2-amino-3-methylbutanoyloxy)-1-(tetrahydro-2H-pyran-4-yl)ethyl, 3,3,3-trifluoro-1-hydroxymethyl-propyl, 3-fluoro-1-methoxy-3-methyl-1-oxobutan-2-yl, 1-ethoxy-4,4,4-trifluoro-1-oxo-3-(trifluoromethyl)butan-2-yl, 2-fluoro-1-hydroxymethyl-2-methyl-propyl, 1-(2-(tert-butoxycarbonylamino)-3-methylbutanoyloxy)-3,3-dimethylbutan-2-yl, 4,4,4-trifluoro-1-methoxy-1-oxobutan-2-yl, 2-fluoro-1,1-dimethyl-ethyl, 3-fluoro-2-(fluoromethyl)-1-methoxy-1-oxopropan-2-yl, 2-fluoro-1-fluoromethyl-1-hydroxymethyl-ethyl, 3-hydroxy-1-methoxy-2-methyl-1-oxopropan-2-yl, 2-carboxy-1-hydroxypropan-2-yl, 2,2,2-trifluoroethylamino, 1-fluoromethyl-2-methyl-propyl, 1-fluoromethyl-2,2-dimethyl-propyl, 3-methyl-oxetan-3-yl, 1-fluoromethyl-cyclobutyl, 1,1-bis-hydroxymethyl-2-methyl-propyl, 1-trifluoromethyl-cyclopropyl, 1-methyl-cyclopropyl, and 1-trifluoromethyl-cyclobutyl; and $R^9$ is selected from H, methyl, tert-butyl, and cyclobutyl; or $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperazin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Ic and pharmaceutically acceptable salts, solvates, hydrates, and N-oxides thereof:

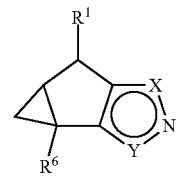

wherein:
$R^1$ is H;
$R^6$ is H;
X is $NR^7$ and Y is $CC(O)N(R^8)R^9$; or
X is $CC(O)N(R^8)R^9$ and Y is $NR^7$;
$R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o- tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3']bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoro-ethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, and piperidin-4-yl;

$R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluoro-phenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclobutyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, cyclobutanecarboxylic acid ethyl ester, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)piperidin-3-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluoro-phenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1λ⁶-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1λ⁴-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydro-furan-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1λ⁶-thiophen-3-ylmethyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chloro-phenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxy-benzyl, 4-hydroxy-1-methyl-piperidin-4-ylmethyl, 1-(2,5-dimethylpyrrolidine-1-carbonyl)cyclopentyl, 2-methoxy-benzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoro-propyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1λ⁴-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1λ⁶-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methylamino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoroethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino)ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, and 2,2-dimethyl-1-pyridin-2-yl-propyl; and $R^9$ is selected from H, methyl, tert-butyl, and cyclobutyl; or $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Id and pharmaceutically acceptable salts, solvates, hydrates, and N-oxides thereof:

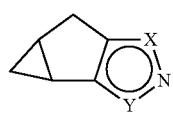

Id wherein:
X is $NR^7$ and Y is $CC(O)NHR^8$; or
X is $CC(O)NHR^8$ and Y is $NR^7$;
$R^7$ is selected from: aryl and heteroaryl; wherein said aryl and heteroaryl are each optionally substituted with one or two substituents selected from: cyano and halogen;
$R^8$ is $-R^{14}-R^{15}-R^{16}-R^{17}$; wherein:
$R^{14}$ is selected from: $C_1-C_6$ alkylene and $C_3-C_7$ cycloalkylene; wherein said $C_1-C_6$ alkylene is optionally substituted with one or more substituents selected from: $C_1-C_6$ alkyl, aryl, heterocyclyl, and hydroxyl; wherein said $C_1-C_6$ alkyl is optionally substituted with one substituent selected from: halogen, and hydroxyl; or $R^{14}$ is absent;
$R^{15}$ is selected from: $-C(O)NH-$ and $-C(O)O-$; or $R^5$ is absent;
$R^{16}$ is $C_1-C_6$ alkylene; or $R^{16}$ is absent; and
$R^{17}$ is selected from: H, $C_1-C_6$ alkyl, $C_1-C_6$ alkylamino, amino, aryl, carboxy, cyano, $C_1-C_6$ haloalkyl, heteroaryl, hydroxyl, and phosphonooxy; wherein said aryl is optionally substituted with one hydroxyl group.

Some embodiments of the present invention pertain to compounds of Formula Id and pharmaceutically acceptable salts, solvates, hydrates, and N-oxides thereof:

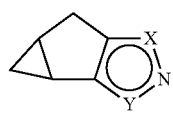

Id wherein:
X is $NR^7$ and Y is $CC(O)NHR^8$; or
X is $CC(O)NHR^8$ and Y is $NR^7$;
$R^7$ is selected from: aryl and heteroaryl; wherein said aryl and heteroaryl are each optionally substituted with one or two substituents selected from: fluoro, chloro, and cyano;
$R^8$ is $-R^{14}-R^{15}-R^{16}-R^{17}$; wherein:
$R^{14}$ is selected from: $C_1-C_6$ alkylene and $C_3-C_7$ cycloalkylene; wherein said $C_1-C_6$ alkylene is optionally substituted with one or more substituents selected from: tetrahydro-2H-pyranyl, hydroxyl, 2,2,2-trifluoroethyl, and fluoromethyl; or $R^{14}$ is absent;
$R^{15}$ is selected from: $-C(O)NH-$ and $-C(O)O-$; or $R^{15}$ is absent;
$R^{16}$ is selected from: methylene, isopropyl-methylene, and propylene; or $R^{16}$ is absent; and
$R^{17}$ is selected from: H, $C_1-C_6$ alkyl, $C_1-C_6$ alkylamino, amino, aryl, carboxy, cyano, $C_3-C_7$ cycloalkyl, $C_1-C_6$ haloalkyl, heteroaryl, heterocyclyl, hydroxyl, and phosphonooxy; wherein said aryl and $C_3-C_7$ cycloalkyl are each optionally substituted with one or more substituents selected from: hydroxyl and trifluoromethyl.

Some embodiments of the present invention pertain to compounds of Formula Id and pharmaceutically acceptable salts, solvates, hydrates, and N-oxides thereof:

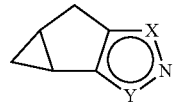

Id wherein:
X is $NR^7$ and Y is $CC(O)NHR^8$; or
X is $CC(O)NHR^8$ and Y is $NR^7$;
$R^7$ is selected from: 2,4-difluoro-phenyl, 2,4-dichlorophenyl, 5-chloro-pyridin-2-yl, 5-cyano-pyrazin-2-yl, pyrazin-2-yl, 5-fluoro-pyridin-2-yl, 4-chloro-pyridin-2-yl, 4-fluoro-pyridin-2-yl, 4-cyano-pyridin-2-yl, and 4-oxy-pyrazin-2-yl;
$R^8$ is $-R^{14}-R^{15}-R^{16}-R^{17}$; wherein:
$R^{14}$ is selected from: 1,1-cyclopropylene, 1,1-dimethyl-methylene, 1,1-cyclobutylene, tert-butyl-methylene, 1,1-dimethyl-ethylene, 1-tert-butyl-ethylene, 1-(tetrahydro-2H-pyran-4-yl)-ethylene, isopropyl-methylene, 1-hydroxymethyl-1-methyl-ethylene, phenyl-methylene, 1-isopropyl-ethylene, 1-(2,2,2-trifluoroethyl)-ethylene, and 1,1-di(fluoromethyl)-ethylene; or $R^{14}$ is absent;
$R^{15}$ is selected from: $-C(O)NH-$ and $-C(O)O-$; or $R^{15}$ is absent;
$R^{16}$ is selected from: methylene, isopropyl-methylene, and propylene; or $R^{16}$ is absent; and
$R^{17}$ is selected from: is selected from: amino, 2-hydroxy-indan-1-yl, hydroxyl, carboxy, trifluoromethyl, methyl, tert-butyl, cyano, tert-butylamino, phosphonooxy, pyridin-2-yl, and fluoromethyl.

Some embodiments of the present invention pertain to compounds of Formula Id and pharmaceutically acceptable salts, solvates, hydrates, and N-oxides thereof:

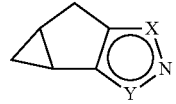

Id wherein:
X is $NR^7$ and Y is $CC(O)NHR^8$; or
X is $CC(O)NHR^8$ and Y is $NR^7$;
$R^7$ is selected from: 2,4-difluoro-phenyl, 2,4-dichlorophenyl, 5-chloro-pyridin-2-yl, 5-cyano-pyrazin-2-yl, pyrazin-2-yl, 5-fluoro-pyridin-2-yl, 4-chloro-pyridin-2-yl, 4-fluoro-pyridin-2-yl, 4-cyano-pyridin-2-yl, and 4-oxy-pyrazin-2-yl; and
$R^8$ is selected from: 1-hydroxymethyl-2,2-dimethyl-propyl, 2-hydroxy-1,1-dimethyl-ethyl, 1-hydroxymethyl-cyclopropyl, 2-hydroxy-indan-1-yl, 1-hydroxymethyl-cyclobutyl, tert-butyl, 2-hydroxy-1-phenyl-ethyl, 2-hydroxy-1-hydroxymethyl-1-methyl-ethyl, tert-butylamino, 2,2,2-trifluoro-1,1-dimethyl-ethyl, 2-methyl-1-(phosphonooxy)propan-2-yl, 1-methyl-cyclobutyl, 1-hydroxymethyl-2-methyl-propyl, cyano-dimethyl-methyl, 2,2-dimethyl-1-(methylcarbamoyl)-propyl, 3,3-dimethyl-1-(phosphonooxy)

butan-2-yl, 2-hydroxy-1-tetrahydro-pyran-4-yl-ethyl, 1,2-dimethyl-propyl, 1-pyridin-2-yl-cyclobutyl, 2-(methylamino)-2-oxo-1-phenylethyl, 2,2-dimethyl-1-pyridin-2-yl-propyl, 1-methoxy-3,3-dimethyl-1-oxobutan-2-yl, 1-(2-amino-3-methylbutanoyloxy)-3-methylbutan-2-yl, 1-(4-carboxybutanoyloxy)-3-methylbutan-2-yl, 3,3,3-trifluoro-1-hydroxymethyl-propyl, 2-fluoro-1,1-dimethyl-ethyl, 2-fluoro-1-fluoromethyl-1-hydroxymethyl-ethyl, 1-fluoromethyl-2,2-dimethyl-propyl, 1-fluoromethyl-cyclobutyl, 1-trifluoromethyl-cyclopropyl, and 1-trifluoromethyl-cyclobutyl.

Some embodiments of the present invention pertain to compounds of Formula Ie and pharmaceutically acceptable salts, solvates, hydrates, and N-oxides thereof:

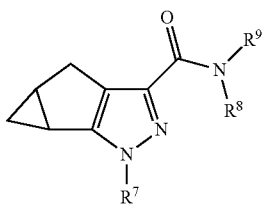

Ie wherein:

$R^7$ is —$R^{10}$—$R^{11}$—$R^{12}$—$R^{13}$; wherein:

$R^{10}$ is selected from: $C_1$-$C_6$ alkylene, heteroarylene, and heterocyclylene; or $R^{10}$ is absent;

$R^{11}$ is selected from: —C(O)NH— and $C_1$-$C_6$ alkylene; or $R^{11}$ is absent;

$R^{12}$ is $C_1$-$C_6$ alkylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;

$R^8$ is —$R^{14}$—$R^{15}$—$R^{16}$—$R^{17}$; wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;

$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;

$R^{16}$ is $C_1$-$C_6$ alkylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_3$-$C_7$ cycloalkylamino, $C_2$-$C_8$ dialkylamino, $C_1$-$C_6$ haloalkoxy, $C_1$-$C_6$ haloalkyl, halogen, heteroaryl, heterocyclyl, and hydroxyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

Some embodiments of the present invention pertain to compounds of Formula Ie and pharmaceutically acceptable salts, solvates, hydrates, and N-oxides thereof:

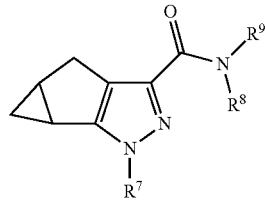

Ie wherein:

$R^7$ is —$R^{10}$—$R^{11}$—$R^{12}$—$R^{13}$; wherein:

$R^{11}$ is selected from: $C_1$-$C_6$ alkylene, heteroarylene, and heterocyclylene; or $R^{10}$ is absent;

$R^{11}$ is selected from: —C(O)NH— and $C_1$-$C_6$ alkylene; or $R^{11}$ is absent;

$R^{12}$ is $C_1$-$C_6$ alkylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;

$R^8$ is —$R^{14}$—$R^{15}$—$R^{16}$—$R^{17}$; wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;

$R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;

$R^{16}$ is $C_1$-$C_6$ alkylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_3$-$C_7$ cycloalkylamino, $C_2$-$C_8$ dialkylamino, $C_1$-$C_6$ haloalkoxy, $C_1$-$C_6$ haloalkyl, halogen, heteroaryl, heterocyclyl, and hydroxyl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

Some embodiments of the present invention pertain to compounds of Formula Ie and pharmaceutically acceptable salts, solvates, hydrates, and N-oxides thereof:

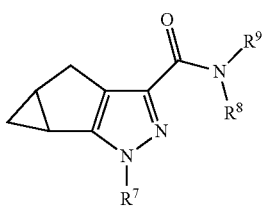

Ie wherein:

$R^7$ is —$R^{10}$—$R^{11}$—$R^{12}$—$R^{13}$; wherein:

$R^{10}$ is selected from: 1,1-dimethylethylene, 1,1-dimethylmethylene, ethylene, methylene, 1,4-piperidinylene, 2,5-pyrazinylene, and 2,4-pyridinylene; or $R^{10}$ is absent;

$R^{11}$ is selected from: —C(O)NH— and methylene; or $R^{11}$ is absent;

$R^{12}$ is methylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, iodo, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl;

$R^8$ is —$R^{14}$—$R^{15}$—$R^{16}$—$R^{17}$; wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluorophenyl, tert-butoxycarbonyl, carboxy, methoxymethyl, hydroxyethyl, tetrahydro-furanyl, 3H-imidazolylmethyl, hydroxyl, pyrrolidinyl, cyclopropyl, sec-butyl, 2,2,2-trifluoroethyl, 2-fluoropropan-2-yl, 1,1,1,3,3,3-hexafluoropropan-2-yl, and fluoromethyl; or $R^{14}$ is absent;

$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;

$R^{16}$ is selected from: ethylene and methylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, tert-butoxycarbonylamino, methyl, tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, 1-methyl-pyrrolidinyl, 2,2,2-trifluoroethyl, and 1,1-dioxo-tetrahydro-1$\lambda^6$-thiophen-3-yl; and $R^9$ is selected from H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

Some embodiments of the present invention pertain to compounds of Formula Ie and pharmaceutically acceptable salts, solvates, hydrates, and N-oxides thereof:

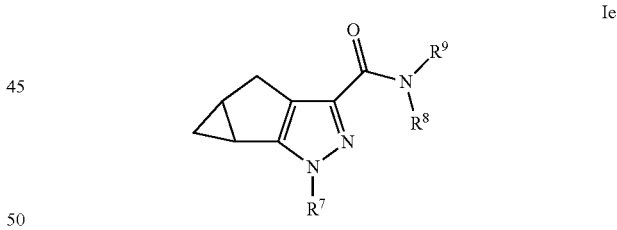

Ie wherein:

$R^7$ is —$R^{10}$—$R^{11}$—$R^{12}$—$R^{13}$; wherein:

$R^{10}$ is selected from: 1,1-dimethylethylene, 1,1-dimethylmethylene, ethylene, methylene, 1,4-piperidinylene, 2,5-pyrazinylene, and 2,4-pyridinylene; or $R^{10}$ is absent;

$R^{11}$ is selected from: —C(O)NH— and methylene; or $R^{11}$ is absent;

$R^{12}$ is methylene; or $R^{12}$ is absent; and $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl;

R[8] is —R[14]—R[15]—R[16]—R[17]; wherein:

R[14] is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydro-furanyl, 3H-imidazolylmethyl, hydroxyl, pyrrolidinyl, and cyclopropyl; or R[14] is absent;

R[15] is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with methyl; or R[15] is absent;

R[16] is selected from: ethylene and methylene; or R[16] is absent; and

R[17] is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, 1-tert-butoxycarbonylamino, methyl, 1-tert-butoxycarbonyl, ethyl, hydroxyl, isopropyl, tert-butyl, fluoro, chloro, methoxy, methanesulfonyl, carboxy, trifluoromethoxy, difluoromethoxy, dimethylamino, methoxycarbonyl, ethoxycarbonyl, carboxy, carboxamide, trifluoromethyl, diethylamino, cyano, tert-butylamino, cyclopropyl, cyclobutyl, phenyl, bromo, and 1-methyl-pyrrolidinyl; and R[9] is selected from H, $C_1$-$C_6$ alkyl, and $C_3$-$C_7$ cycloalkyl; or R[8] and R[9] together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

Some embodiments of the present invention pertain to compounds of Formula Ie and pharmaceutically acceptable salts, solvates, and hydrates thereof:

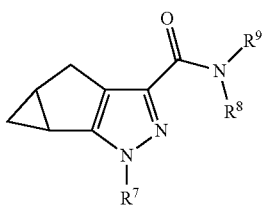

Ie wherein:

R[7] is —R[10]—R[11]—R[12]—R[13]; wherein:

R[10] is selected from: 1,1-dimethylethylene, 1,1-dimethylmethylene, ethylene, methylene, 1,4-piperidinylene, 2,5-pyrazinylene, and 2,4-pyridinylene; or R[10] is absent;

R[11] is selected from: —C(O)NH— and methylene; or R[11] is absent;

R[12] is 1,1-dimethyl-methylene; or R[12] is absent; and

R[13] is selected from: 2,4-difluoro-phenyl, 2,4-dichloro-phenyl, 2-fluoro-4-methanesulfonyl-phenyl, 2,6-difluoro-phenyl, 2,5-difluoro-phenyl, 4-methoxy-phenyl, 4-cyano-phenyl, 4-fluoro-phenyl, phenyl, 2-fluoro-phenyl, 3-fluoro-phenyl, o-tolyl, tert-butyl, isopropyl, 2,2-dimethylpropyl, hydroxyl, 2-hydroxy-2-methylpropyl, 1-oxo-hexahydro-1λ[4]-thiopyran-4-yl, 1,1-dioxo-hexahydro-1λ[6]-thiopyran-4-yl, tetrahydrothiopyran-4-yl, morpholin-4-yl, tetrahydro-pyran-4-yl, 1,1-dioxo-tetrahydro-1λ[6]-thiophen-3-yl, pyrazin-2-yl, 5-ethyl-pyrazin-2-yl, 5-hydroxy-pyrazin-2-yl, 5-isopropyl-pyrazin-2-yl, 5-heptafluoropropyl-pyrazin-2-yl, 5-cyclobutyl-pyrazin-2-yl, 5-methyl-pyrazin-2-yl, 6-ethyl-pyrazin-2-yl, 5-trifluoromethyl-pyrazin-2-yl, cyclopropyl, 5-cyclopropyl-pyrazin-2-yl, 6-chloro-pyrazin-2-yl, 5-dimethylamino-pyrazin-2-yl, 4-cyano-phenyl, 6-methoxy-pyridazin-3-yl, 6-chloro-pyridazin-3-yl, pyrimidin-5-yl, 6-dimethylamino-pyrazin-2-yl, 6-methoxy-pyrazin-2-yl, 2-pyrimidin-4-yl, 5-bromo-pyrazin-2-yl, 5-hydroxy-pyrazin-2-yl, 5-methoxy-pyrazin-2-yl, 5-ethoxypyrazin-2-yl, 5-methylamino-pyrazin-2-yl, 5-bromo-pyridin-2-yl, pyridin-3-yl, 5-trifluoromethyl-pyridin-2-yl, 5-isopropyl-pyridin-2-yl, 5-isopropyl-pyridin-2-yl, 5-methyl-pyridin-2-yl, 5-ethyl-pyridin-2-yl, 5-methoxy-pyridin-2-yl, 4-trifluoromethyl-pyridin-2-yl, 5-cyano-pyridin-2-yl, 5-dimethylamino-pyridin-2-yl, 4-methyl-pyridin-2-yl, 5-chloro-4-methyl-pyridin-2-yl, 5-chloro-4-trifluoromethyl-pyridin-2-yl, 4-trifluoromethyl-pyridin-2-yl, 3-fluoro-pyridin-2-yl, 6-methyl-4-trifluoromethyl-pyridin-2-yl, 3-methyl-pyridin-2-yl, 5-propyl-pyridin-2-yl, 5-cyclopropyl-pyridin-2-yl, 5-fluoro-pyridin-2-yl, 3,5-difluoro-pyridin-2-yl, 6-bromo-pyridin-3-yl, 5-bromo-pyridin-3-yl, 5,6-difluoro-pyridin-3-yl, 6-chloro-pyridin-3-yl, 3-fluoro-pyridin-4-yl, 5-cyano-pyridin-3-yl, pyridin-4-yl, 2-chloro-pyridin-4-yl, 2-methoxy-pyridin-4-yl, 6-methyl-pyridin-3-yl, m-tolyl, thiazol-2-yl, cyclopentyl, 4-amino-pyridin-2-yl, 4-methoxy-pyridin-2-yl, 4-choro-pyridin-2-yl, 4-fluoro-pyridin-2-yl, 4-cyclopropyl-pyridin-2-yl, 4-bromo-pyridin-2-yl, 4-methanesulfonyl-pyridin-2-yl, 4-cyano-pyridin-2-yl, hydroxymethyl, 4-oxy-pyrazin-2-yl, 3-methyl-1,1-dioxo-tetrahydro-1λ[6]-thiophen-3-yl, 5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 4-iodo-pyridin-2-yl, 1-oxy-pyridin-3-yl, and 4-hydroxy-pyridin-2-yl;

R[8] is —R[14]—R[15]—R[16]—R[17]; wherein:

R[14] is selected from: methylene, ethylene, 1,1-cyclopropylene, 1,1-dimethyl-methylene, 1,1-cyclobutylene, tert-butyl-methylene, 1-methyl-4,4-piperidinylene, 4,4-tetrahydro-2H-pyranylene, methyl-methylene, 1,1-cyclohexylene, 1,2-cyclohexylene, 1,1-dimethyl-ethylene, 1-tert-butyl-ethylene, 1-ethyl-ethylene, 1-methyl-ethylene, 1-(tetrahydro-2H-pyran-4-yl)-ethylene, isopropyl-methylene, 1,1-cyclopentylene, benzyl-methylene, 4,4-cyclopent-1-enylene, 1,1-dioxo-hexahydro-1λ[6]-4,4-thiopyranylene, 1-tert-butoxycarbonyl-4,4-piperidinylene, 1-(pyridin-4-yl)-ethylene, 1-(pyridin-3-yl)-ethylene, 1-(pyridin-2-yl)-ethylene, 1-(4-fluoro-phenyl)-ethylene, 1-hydroxymethyl-1-methyl-ethylene, 1-carboxy-1-methyl-ethylene, 1-methoxymethyl-ethylene, 1-hydroxymethyl-ethylene, 1-(1-hydroxyethyl)-ethylene, 1,1-dimethyl-ethylene, 1-(tetrahydro-furan-3-yl)-ethylene, phenyl-methylene, 1-(3H-imidazol-4-ylmethyl)-ethylene, 1-(4-hydroxy-phenyl)-ethylene, benzyl-ethylene, (1-hydroxymethyl-2-methyl)-ethylene, 1-isopropyl-ethylene, pyridin-2-yl-methylene, 1,1-dimethyl-propylene, 2-hydroxy-propylene, (1-isobutyl-pyrrolidin-3-yl)-methylene, 1,3-azetidinylene, 1,3- pyrrolidinylene, 1,3-piperidinylene, 1,4-piperidinylene, 2,4-thiazolylene, 3,4-pyridinylene, 2,4-pyridinylene, 2,5-pyridinylene, —SO$_2$—, 2,5-pyridinylene, 1-cyclopropyl-ethylene, 1-(sec-butyl)-ethylene, 1-hydroxymethyl-1-ethyl-ethylene, 1-isopropyl-ethylene, 1-(2,2,2-trifluoroethyl)-ethylene, (2-fluoropropan-2-yl)-methylene, (1,1,1,3,3,3-hexafluoropropan-2-yl)-methylene, 1-(2-fluoropropan-2-yl)-ethylene, (2,2,2-trifluoroethyl)-methylene, 1,1-di(fluoromethyl)-ethylene, (hydroxymethyl)(methyl)methylene, (hydroxymethyl)(methyl)methylene, 3,3-oxetanylene, and 1-hydroxymethyl-1-isopropyl-ethylene; or R$^{14}$ is absent;

R$^{15}$ is selected from: 1,3-pyrrolidinylene, 1,4-piperidinylene, 2,6-pyridinylene, 1,3-azetidinylene, —C(O)NH—, —C(O)—, —C(O)O—, 1,2-pyrrolidinylene, 2,4-morpholinylene, ethylene, methylene, 1,1-cyclopentylene, 4,4-tetrahydro-2H-pyranylene, 3,3-tetrahydro-thiophenylene, 1,1-cyclopropylene, 1-methyl-4,4-piperidinylene, and 1-oxo-tetrahydro-1λ$^4$-3,3-thiophenylene; or R$^{15}$ is absent;

R$^{16}$ is selected from: ethylene and methylene; or R$^{16}$ is absent; and

R$^{17}$ is selected from: H, amino, 1-tert-butoxycarbonylamino, morpholin-4-yl, 4-methyl-piperidin-1-yl, piperidin-4-yl, 1-tert-butoxycarbonyl-piperidin-3-yl, tetrahydro-thiopyran-4-yl, 1-oxo-hexahydro-1λ$^4$-thiopyran-4-yl, tetrahydro-pyran-4-yl, pyrrolidin-1-yl, 1-tert-butoxycarbonyl-azetidin-3-yl, 2,6-dimethyl-morpholin-4-yl, piperidin-1-yl, 1-tert-butoxycarbonyl-piperidin-4-yl, 1,1-dioxo-hexahydro-1λ$^6$-thiopyran-4-yl, tetrahydro-furan-2-yl, 1-ethyl-pyrrolidin-2-yl, 1-methyl-pyrrolidin-2-yl, morpholin-2-yl, 1-methyl-piperidin-2-yl, 1-methyl-piperidin-4-yl, 4-hydroxy-1-methyl-piperidin-4-yl, thiomorpholin-4-yl, tetrahydro-furan-3-yl, 1-tert-butoxycarbonyl-pyrrolidin-4-yl, 1,2,2,6,6-pentamethyl-piperidin-4-yl, 1,1-dioxo-tetrahydro-1λ$^6$-thiophen-3-yl, 4-methyl-morpholin-2-yl, 4-tert-butoxycarbonyl-morpholin-2-yl, 1-isopropyl-piperidin-4-yl, 4-hydroxy-1,1-dioxo-tetrahydro-1λ$^6$-thiophen-3-yl, 3-methyl-1,1-dioxo-tetrahydro-1λ$^6$-thiophen-3-yl, phenyl, 2-hydroxy-indan-1-yl, indan-1-yl, cyclopentyl, 2-hydroxy-cyclopentyl, cyclobutyl, 2-hydroxy-cyclohexyl, 1,3,3-trimethyl-bicyclo[2.2.1]hept-2-yl, 6,6-dimethyl-bicyclo[3.1.1]hept-2-yl, 1-aza-bicyclo[2.2.2]oct-3-yl, 9-methyl-9-aza-bicyclo[3.3.1]non-1-yl, 3-azepan-1-yl, 2-fluoro-phenyl, 2-chloro-phenyl, 4-fluoro-phenyl, 4-chloro-phenyl, 3-fluoro-phenyl, 5-fluoro-2-methoxy-phenyl, 2-fluoro-4-methanesulfonyl-phenyl, 4-carboxy-2-fluoro-phenyl, 2,5-difluoro-phenyl, m-tolyl, o-tolyl, 2,5-dimethyl-phenyl, 2,3-dimethyl-phenyl, 4-hydroxy-3-methoxy-phenyl, 2,4-dimethoxy-phenyl, 2,3-dimethoxy-phenyl, 3,5-dimethoxy-phenyl, 4-methoxy-phenyl, 3-methoxy-phenyl, 2-methoxy-phenyl, 3-hydroxy-phenyl, 4-hydroxy-phenyl, 2-hydroxy-phenyl, 5-fluoro-2-hydroxy-phenyl, 3-trifluoromethoxy-phenyl, 4-difluoromethoxy-phenyl, 3-difluoromethoxy-phenyl, 4-fluoro-phenoxy, 2-dimethylamino-phenyl, 4-dimethylamino-phenyl, 6-fluoro-4H-benzo[1,3]dioxin-8-yl, benzo[1,3]dioxol-5-yl, pyrimidin-2-yl, pyrimidin-4-yl, 2,6-dimethyl-pyrimidin-4-yl, pyridazin-3-yl, 5-methyl-pyrazin-2-yl, 6-methoxy-pyrimidin-4-yl, pyrazin-2-yl, 3,5-dimethyl-pyrazin-2-yl, 5-fluoro-2-oxo-2,3-dihydro-pyrimidin-4-yl, hydroxyl, methoxycarbonyl, ethoxycarbonyl, carboxy, 1-piperidin-1-yl, carboxamide, methoxy, trifluoromethyl, methyl, tert-butyl, diethylamino, dimethylamino, cyano, tert-butylamino, cyclopropyl, pyridin-3-yloxy, 1H-tetrazol-5-yl, 5-methyl-[1,2,4]oxadiazol-3-yl, phosphonooxy, cyclobutylamino, phenylamino, 1-tert-butyl-3-methylureido, 3-methyl-1-phenylureido, N-tert-butylmethylsulfonamido, 1-cyclobutyl-3-methylureido, methylcarbamoyl, 5-hydroxy-1H-indol-3-yl, 1H-benzoimidazol-2-yl, 5,7-dimethyl-pyrazolo[1,5-a]pyrimidin-2-yl, 1H-benzoimidazol-2-yl, 2-(tert-butoxycarbonyl)-3,4-dihydro-1H-isoquinoline-2-yl, quinolin-3-yl, quinolin-4-yl, 2-methyl-quinolin-4-yl, benzooxazol-2-yl, 1-methyl-1,2,3,4-tetrahydro-quinolin-7-yl, 2,3-dihydro-benzofuran-3-yl, benzothiazol-2-yl, 1,4-dimethyl-1H-pyrrol-2-yl, 3-methyl-3H-imidazol-4-yl, 1H-imidazol-4-yl, 5-hydroxy-1H-pyrazol-3-yl, 1-methyl-1H-pyrazol-3-yl, 4-pyridin-2-yl-thiazol-2-yl, 5-methyl-thiazol-2-yl, oxazol-4-yl, 4-phenyl-thiazol-2-yl, 5-tert-butyl-isoxazol-3-yl, pyridin-2-yl, pyridin-3-yl, pyridin-4-yl, 3-hydroxy-pyridin-2-yl, 6-hydroxy-pyridin-3-yl, 3-hydroxy-pyridin-4-yl, 4-hydroxy-pyridin-2-yl, 6-hydroxy-pyridin-2-yl, 2-hydroxy-pyridin-3-yl, 2-methoxy-pyridin-3-yl, 5-methoxy-pyridin-2-yl, 4-methoxy-pyridin-2-yl, 2-methoxy-pyridin-4-yl, 6-methoxy-pyridin-2-yl, 6-methoxy-pyridin-3-yl, 3-fluoro-pyridin-2-yl, 2-fluoro-pyridin-3-yl, 6-fluoro-pyridin-2-yl, 5-fluoro-pyridin-2-yl, 6-fluoro-pyridin-3-yl, 3-fluoro-pyridin-4-yl, 3-methyl-pyridin-2-yl, 3-methyl-pyridin-4-yl, 6-methyl-pyridin-2-yl, 4-methyl-pyridin-2-yl, 6-methyl-pyridin-3-yl, 2-methyl-pyridin-3-yl, 5-trifluoromethyl-pyridin-2-yl, 6-trifluoromethyl-pyridin-3-yl, 4-trifluoromethyl-pyridin-2-yl, 3-chloro-5-trifluoromethyl-pyridin-2-yl, 4,6-dimethyl-pyridin-2-yl, 4,6-dimethyl-pyridin-2-yl, 3-chloro-5-methyl-pyridin-2-yl, 6-cyano-pyridin-3-yl, 3-cyano-5-methyl-pyridin-2-yl, 3-cyano-5-methyl-pyridin-2-yl, 3-chloro-5-methyl-pyridin-2-yl, 2-chloro-pyridin-3-yl, 5-chloro-pyridin-2-yl, 6-chloro-2-methyl-pyridin-3-yl, 6-chloro-pyridin-3-yl, 3-chloro-pyridin-4-yl, 6-bromo-2-methyl-pyridin-3-yl, 5-bromo-3-methyl-pyridin-2-yl, 6-carboxypyridin-2-yl, 6-methanesulfonyl-4-methyl-pyridin-3-yl, 6-methanesulfonyl-4-methyl-pyridin-3-yl, 6-methanesulfonyl-2-methyl-pyridin-3-yl, 6-methanesulfonyl-pyridin-3-yl, 2,6-dimethoxy-pyridin-3-yl, 5-fluoro-1-oxy-pyridin-2-yl, 1-oxy-pyridin-2-yl, 6-pyrrolidin-1-yl-pyridin-2-ylmethyl, 5-(1-methyl-pyrrolidin-2-yl)-pyridin-2-yl, 6-morpholin-4-yl-pyridin-2-yl, 6-morpholin-4-yl-pyridin-3-yl, ethynyl, tert-butyl(methyl)amino, 2,2,2-trifluoroethyl, N-cyclobutylmethylsulfonamido, N-phenylmethylsulfonamido, hydroxy(methyl)amino, methoxy(methyl)amino, azetidin-1-yl, tert-butoxy, fluoromethyl, 2,2,2-trifluoroethylamino, and (1,1-dioxo-tetrahydro-1λ$^6$-thiophen-3-yl)amino; and R$^9$ is selected from H, methyl, tert-butyl, and cyclobutyl; or R$^8$ and R$^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1, 8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Ie and pharmaceutically acceptable salts, solvates, hydrates, and N-oxides thereof:

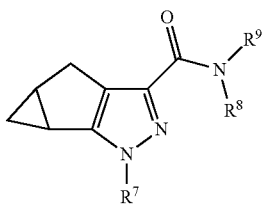

Ie wherein:
R$^7$ is —R$^{10}$—R$^{11}$—R$^{12}$—R$^{13}$; wherein:
R$^{10}$ is selected from: 1,1-dimethylethylene, 1,1-dimethylmethylene, ethylene, methylene, 1,4-piperidinylene, 2,5-pyrazinylene, and 2,4-pyridinylene; or R$^{10}$ is absent;
R$^{11}$ is selected from: —C(O)NH— and methylene; or R$^{11}$ is absent;
R$^{12}$ is 1,1-dimethyl-methylene; or R$^{12}$ is absent; and
R$^{13}$ is selected from: 2,4-difluoro-phenyl, 2,4-dichloro-phenyl, 2-fluoro-4-methanesulfonyl-phenyl, 2,6-difluoro-phenyl, 2,5-difluoro-phenyl, 4-methoxy-phenyl, 4-cyano-phenyl, 4-fluoro-phenyl, phenyl, 2-fluoro-phenyl, 3-fluoro-phenyl, o-tolyl, tert-butyl, isopropyl, 2,2-dimethylpropyl, hydroxyl, 2-hydroxy-2-methylpropyl, 1-oxo-hexahydro-1λ$^4$-thiopyran-4-yl, 1,1-dioxo-hexahydro-1λ$^6$-thiopyran-4-yl, tetrahydrothiopyran-4-yl, morpholin-4-yl, tetrahydro-pyran-4-yl, 1,1-dioxo-tetrahydro-1λ$^6$-thiophen-3-yl, pyrazin-2-yl, 5-ethyl-pyrazin-2-yl, 5-hydroxy-pyrazin-2-yl, 5-isopropyl-pyrazin-2-yl, 5-heptafluoropropyl-pyrazin-2-yl, 5-cyclobutyl-pyrazin-2-yl, 5-methyl-pyrazin-2-yl, 6-ethyl-pyrazin-2-yl, 5-trifluoromethyl-pyrazin-2-yl, cyclopropyl, 5-cyclopropyl-pyrazin-2-yl, 6-chloro-pyrazin-2-yl, 5-dimethylamino-pyrazin-2-yl, 4-cyano-phenyl, 6-methoxy-pyridazin-3-yl, 6-chloro-pyridazin-3-yl, pyrimidin-5-yl, 6-dimethylamino-pyrazin-2-yl, 6-methoxy-pyrazin-2-yl, 2-pyrimidin-4-yl, 5-bromo-pyrazin-2-yl, 5-hydroxy-pyrazin-2-yl, 5-methoxy-pyrazin-2-yl, 5-ethoxypyrazin-2-yl, 5-methylamino-pyrazin-2-yl, 5-bromo-pyridin-2-yl, pyridin-3-yl, 5-trifluoromethyl-pyridin-2-yl, 5-isopropyl-pyridin-2-yl, 5-isopropyl-pyridin-2-yl, 5-methyl-pyridin-2-yl, 5-ethyl-pyridin-2-yl, 5-methoxy-pyridin-2-yl, 4-trifluoromethyl-pyridin-2-yl, 5-cyano-pyridin-2-yl, 5-dimethylamino-pyridin-2-yl, 4-methyl-pyridin-2-yl, 5-chloro-4-methyl-pyridin-2-yl, 5-chloro-4-trifluoromethyl-pyridin-2-yl, 4-trifluoromethyl-pyridin-2-yl, 3-fluoro-pyridin-2-yl, 6-methyl-4-trifluoromethyl-pyridin-2-yl, 3-methyl-pyridin-2-yl, 5-propyl-pyridin-2-yl, 5-cyclopropyl-pyridin-2-yl, 5-fluoro-pyridin-2-yl, 3,5-difluoro-pyridin-2-yl, 6-bromo-pyridin-3-yl, 5-bromo-pyridin-3-yl, 5,6-difluoro-pyridin-3-yl, 6-chloro-pyridin-3-yl, 3-fluoro-pyridin-4-yl, 5-cyano-pyridin-3-yl, pyridin-4-yl, 2-chloro-pyridin-4-yl, 2-methoxy-pyridin-4-yl, 6-methyl-pyridin-3-yl, m-tolyl, thiazol-2-yl, cyclopentyl, 4-amino-pyridin-2-yl, 4-methoxy-pyridin-2-yl, 4-choro-pyridin-2-yl, 4-fluoro-pyridin-2-yl, 4-cyclopropyl-pyridin-2-yl, 4-bromo-pyridin-2-yl, 4-methanesulfonyl-pyridin-2-yl, 4-cyano-pyridin-2-yl, hydroxymethyl, and 4-oxy-pyrazin-2-yl;

R$^8$ is —R$^{14}$—R$^{15}$—R$^{16}$—R$^{17}$; wherein:
R$^{14}$ is selected from: methylene, ethylene, 1,1-cyclopropylene, 1,1-dimethyl-methylene, 1,1-cyclobutylene, tert-butyl-methylene, 1-methyl-4,4-piperidinylene, 4,4-tetrahydro-2H-pyranylene, methyl-methylene, 1,1-cyclohexylene, 1,2-cyclohexylene, 1,1-dimethyl-ethylene, 1-tert-butyl-ethylene, 1-ethyl-ethylene, 1-methyl-ethylene, 1-(tetrahydro-2H-pyran-4-yl)-ethylene, isopropyl-methylene, 1,1-cyclopentylene, benzyl-methylene, 4,4-cyclopent-1-enylene, 1,1-dioxo-hexahydro-1λ$^6$-4,4-thiopyranylene, 1-tert-butoxycarbonyl-4,4-piperidinylene, 1-(pyridin-4-yl)-ethylene, 1-(pyridin-3-yl)-ethylene, 1-(pyridin-2-yl)-ethylene, 1-(4-fluoro-phenyl)-ethylene, 1-hydroxymethyl-1-methyl-ethylene, 1-carboxy-1-methyl-ethylene, 1-methoxymethyl-ethylene, 1-hydroxymethyl-ethylene, 1-(1-hydroxyethyl)-ethylene, 1,1-dimethyl-ethylene, 1-(tetrahydro-furan-3-yl)-ethylene, phenyl-methylene, 1-(3H-imidazol-4-ylmethyl)-ethylene, 1-(4-hydroxy-phenyl)-ethylene, benzyl-ethylene, (1-hydroxymethyl-2-methyl)-ethylene, 1-isopropyl-ethylene, pyridin-2-yl-methylene, 1,1-dimethyl-propylene, 2-hydroxy-propylene, (1-isobutyl-pyrrolidin-3-yl)-methylene, 1,3-azetidinylene, 1,3-pyrrolidinylene, 1,3-piperidinylene, 1,4-piperidinylene, 2,4-thiazolylene, 3,4-pyridinylene, 2,4-pyridinylene, 2,5-pyridinylene, —SO$_2$—, 2,5-pyridinylene, and 1-cyclopropyl-ethylene; or R$^{14}$ is absent;
R$^{15}$ is selected from: 1,3-pyrrolidinylene, 1,4-piperidinylene, 2,6-pyridinylene, 1,3-azetidinylene, —C(O)NH—, —C(O)—, 1,2-pyrrolidinylene, 2,4-morpholinylene, ethylene, methylene, 1,1-cyclopentylene, 4,4-tetrahydro-2H-pyranylene, 3,3-tetrahydro-thiophenylene, 1,1-cyclopropylene, 1-methyl-4,4-piperidinylene, and 1-oxo-tetrahydro-1λ$^4$-3,3-thiophenylene; or R$^{15}$ is absent;
R$^{16}$ is selected from: ethylene and methylene; or R$^{16}$ is absent; and
R$^{17}$ is selected from: H, amino, 1-tert-butoxycarbonylamino, morpholin-4-yl, 4-methyl-piperidin-1-yl, piperidin-4-yl, 1-tert-butoxycarbonyl-piperidin-3-yl, tetrahydrothiopyran-4-yl, 1-oxo-hexahydro-1λ$^4$-thiopyran-4-yl, tetrahydro-pyran-4-yl, pyrrolidin-1-yl, 1-tert-butoxycarbonyl-azetidin-3-yl, 2,6-dimethyl-morpholin-4-yl, piperidin-1-yl, 1-tert-butoxycarbonyl-piperidin-4-yl, 1,1-dioxo-hexahydro-1λ$^6$-thiopyran-4-yl, tetrahydro-furan-2-yl, 1-ethyl-pyrrolidin-2-yl, 1-methyl-pyrrolidin-2-yl, morpholin-2-yl, 1-methyl-piperidin-2-yl, 1-methyl-piperidin-4-yl, 4-hydroxy-1-methyl-piperidin-4-yl, thiomorpholin-4-yl, tetrahydro-furan-3-yl, 1-tert-butoxycarbonyl-pyrrolidin-4-yl, 1,2,2,6,6-pentamethyl-piperidin-4-yl, 1,1-dioxo-tetrahydro-1λ$^6$-thiophen-3-yl, 4-methyl-morpholin-2-yl, 4-tert-butoxycarbonyl-morpholin-2-yl, 1-isopropyl-piperidin-4-yl, 4-hydroxy-1,1-dioxo-tetrahydro-1λ$^6$-thiophen-3-yl, 3-methyl-1,1-dioxo-tetrahydro-1λ$^6$-thiophen-3-yl, phenyl, 2-hydroxy-indan-1-yl, indan-1-yl, cyclopentyl, 2-hydroxy-cyclopentyl, cyclobutyl, 2-hydroxy-cyclohexyl, 1,3,3-trimethyl-bicyclo[2.2.1]hept-2-yl, 6,6-dimethyl-bicyclo[3.1.1]hept-2-yl, 1-aza-bicyclo[2.2.2]oct-3-yl, 9-methyl-9-aza-bicyclo[3.3.1]non-1-yl, 3-azepan-1-yl, 2-fluoro-phenyl, 2-chloro-phenyl, 4-fluoro-phenyl, 4-chloro-phenyl, 3-fluoro-phenyl, 5-fluoro-2-methoxy-phenyl, 2-fluoro-4-methanesulfonyl-phenyl, 4-carboxy-2-fluoro-phenyl, 2,5-difluoro-phenyl, m-tolyl, o-tolyl, 2,5-dimethyl-phenyl, 2,3-dimethyl-phenyl, 4-hydroxy-3-methoxy-phenyl, 2,4-dimethoxy-phenyl, 2,3-dimethoxy-phenyl, 3,5-dimethoxy-phenyl, 4-methoxy-phenyl, 3-methoxy-phenyl, 2-methoxy-phenyl, 3-hydroxy-phenyl, 4-hydroxy-phenyl, 2-hydroxy-phenyl, 5-fluoro-2-hydroxy-phenyl, 3-trifluoromethoxy-phenyl, 4-difluoromethoxy-phenyl, 3-difluoromethoxy-phenyl, 4-fluoro-phenoxy, 2-dimethylamino-phenyl, 4-dimethylamino-phenyl, 6-fluoro-4H- benzo[1,3]dioxin-8-yl, benzo[1,3]dioxol-5-yl, pyrimidin-2-yl, pyrimidin-4-yl, 2,6-dimethyl-pyrimidin-4-yl, pyridazin-3-yl, 5-methyl-pyrazin-2-yl, 6-methoxy-pyrimidin-4-yl, pyrazin-2-yl, 3,5-dimethyl-pyrazin-2-yl, 5-fluoro-2-oxo-2,3-dihydro-pyrimidin-4-yl, hydroxyl, methoxycarbonyl, ethoxycarbonyl, carboxy, 1-piperidin-1-yl, carboxamide, methoxy, trifluoromethyl, methyl, tert-butyl, diethylamino, dimethylamino, cyano, tert-butylamino, cyclopropyl, pyridin-3-yloxy, 1H-tetrazol-5-yl, 5-methyl-[1,2,4]oxadiazol-3-yl, phosphonooxy, cyclobutylamino, phenylamino, 1-tert-butyl-3-methylureido, 3-methyl-1-phenylureido, N-tert-butylmethylsulfonamido, 1-cyclobutyl-3-methylureido, methylcarbamoyl, 5-hydroxy-1H-indol-3-yl, 1H-benzoimidazol-2-yl, 5,7-dimethyl-pyrazolo[1,5-a]pyrimidin-2-yl, 1H-benzoimidazol-2-yl, 2-(tert-butoxycarbonyl)-3,4-dihydro-1H-isoquinoline-2-yl, quinolin-3-yl, quinolin-4-yl, 2-methyl-quinolin-4-yl, benzooxazol-2-yl, 1-methyl-1,2,3,4-tetrahydro-quinolin-7-yl, 2,3-dihydro-benzofuran-3-yl, benzothiazol-2-yl, 1,4-dimethyl-1H-pyrrol-2-yl, 3-methyl-3H-imidazol-4-yl, 1H-imidazol-4-yl, 5-hydroxy-1H-pyrazol-3-yl, 1-methyl-1H-pyrazol-3-yl, 4-pyridin-2-yl-thiazol-2-yl, 5-methyl-thiazol-2-yl, oxazol-4-yl, 4-phenyl-thiazol-2-yl, 5-tert-butyl-isoxazol-3-yl, pyridin-2-yl, pyridin-3-yl, pyridin-4-yl, 3-hydroxy-pyridin-2-yl, 6-hydroxy-pyridin-3-yl, 3-hydroxy-pyridin-4-yl, 4-hydroxy-pyridin-2-yl, 6-hydroxy-pyridin-2-yl, 2-hydroxy-pyridin-3-yl, 2-methoxy-pyridin-3-yl, 5-methoxy-pyridin-2-yl, 4-methoxy-pyridin-2-yl, 2-methoxy-pyridin-4-yl, 6-methoxy-pyridin-2-yl, 6-methoxy-pyridin-3-yl, 3-fluoro-pyridin-2-yl, 2-fluoro-pyridin-3-yl, 6-fluoro-pyridin-2-yl, 5-fluoro-pyridin-2-yl, 6-fluoro-pyridin-3-yl, 3-fluoro-pyridin-4-yl, 3-methyl-pyridin-2-yl, 3-methyl-pyridin-4-yl, 6-methyl-pyridin-2-yl, 4-methyl-pyridin-2-yl, 6-methyl-pyridin-3-yl, 2-methyl-pyridin-3-yl, 5-trifluoromethyl-pyridin-2-yl, 6-trifluoromethyl-pyridin-3-yl, 4-trifluoromethyl-pyridin-2-yl, 3-chloro-5-trifluoromethyl-pyridin-2-yl, 4,6-dimethyl-pyridin-2-yl, 4,6-dimethyl-pyridin-3-yl, 3-chloro-5-methyl-pyridin-2-yl, 6-cyano-pyridin-3-yl, 3-cyano-5-methyl-pyridin-2-yl, 3-cyano-5-methyl-pyridin-2-yl, 3-chloro-5-methyl-pyridin-2-yl, 2-chloro-pyridin-3-yl, 5-chloro-pyridin-2-yl, 6-chloro-2-methyl-pyridin-3-yl, 6-chloro-pyridin-3-yl, 3-chloro-pyridin-4-yl, 6-bromo-2-methyl-pyridin-3-yl, 5-bromo-3-methyl-pyridin-2-yl, 6-carboxypyridin-2-yl, 6-methanesulfonyl-4-methyl-pyridin-3-yl, 6-methanesulfonyl-4-methyl-pyridin-3-yl, 6-methanesulfonyl-2-methyl-pyridin-3-yl, 6-methanesulfonyl-pyridin-3-yl, 2,6-dimethoxy-pyridin-3-yl, 5-fluoro-1-oxy-pyridin-2-yl, 1-oxy-pyridin-2-yl, 6-pyrrolidin-1-yl-pyridin-2-ylmethyl, 5-(1-methyl-pyrrolidin-2-yl)-pyridin-2-yl, 6-morpholin-4-yl-pyridin-2-yl, 6-morpholin-4-yl-pyridin-3-yl, ethynyl, tert-butyl(methyl)amino, 2,2,2-trifluoroethyl, N-cyclobutylmethylsulfonamido, N-phenylmethylsulfonamido, hydroxy(methyl)amino, methoxy(methyl)amino, azetidin-1-yl, and tert-butoxy; and $R^9$ is selected from H, methyl, tert-butyl, and cyclobutyl; or $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Ie and pharmaceutically acceptable salts, solvates, hydrates, and N-oxides thereof:

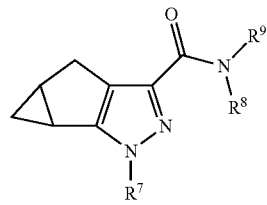

Ie wherein:

$R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3']bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, piperidin-4-yl, tetrahydro-pyran-4-yl, 3-methyl-1,1-dioxo-tetrahydro-1$\lambda^6$-thiophen-3-yl, 5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 3-hydroxy-3-methyl-butyl, 4-iodo-pyridin-2-yl, 1-oxy-pyridin-3-yl, 4-tert-butylcarbamoyl-pyridin-2-yl, and 4-hydroxy-pyridin-2-yl;

$R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluorophenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluorophenyl)-cyclobutyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)piperidin-3-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluoro-phenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1$\lambda^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1$\lambda^4$-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, indan-1-ylamide, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydrofuran-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1λ$^6$-thiophen-3-ylmethyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chloro-phenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxy-benzyl, 4-hydroxy-1-methyl-piperidin-4-ylmethyl, 1-(2,5-dimethylpyrrolidine-1-carbonyl)cyclopentyl, 2-methoxy-benzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoropropyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1λ$^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1λ$^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methyl-amino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoro-ethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino)ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, 2,2-dimethyl-1-pyridin-2-yl-propyl, (1,1-dioxo-tetrahydro-1λ$^6$-thiophen-3-yl)amino, 1-hydroxycarbamoyl-2,2-dimethyl-propyl, 1-hydroxymethyl-2-methyl-butyl, 1-(2-hydroxy-ethylcarbamoyl)-2,2-dimethyl-propyl, 1,1-bis-hydroxymethyl-propyl, 1-(5-fluoro-pyridin-2-yl)-2,2-dimethyl-propyl, 4-hydroxymethyl-tetrahydro-2H-pyran-4-yl, 1-(2-(tert-butoxycarbonylamino)-3-methylbutanoyloxy)-2-methylpropan-2-yl, 1-(2-amino-3-methylbutanoyloxy)-3-methylbutan-2-yl, 1-(2-amino-3-methylbutanoyloxy)-2-methylpropan-2-yl, 2-hydroxy-1-(tetrahydro-2H-pyran-4-yl)-ethyl, 1-(4-carboxybutanoyloxy)-2-methylpropan-2-yl, 1-(4-carboxybutanoyloxy)-3-methylbutan-2-yl, 1-(4-carboxybutanoyloxy)-3,3-dimethylbutan-2-yl, 1-(2-amino-3-methylbutanoyloxy)-3,3-dimethylbutan-2-yl, 2-(2-amino-3-methylbutanoyloxy)-1-(tetrahydro-2H-pyran-4-yl)ethyl, 3,3,3-trifluoro-1-hydroxymethyl-propyl, 3-fluoro-1-methoxy-3-methyl-1-oxobutan-2-yl, 1-ethoxy-4,4,4-trifluoro-1-oxo-3-(trifluoromethyl)butan-2-yl, 2-fluoro-1-hydroxymethyl-2-methyl-propyl, 1-(2-(tert-butoxycarbonylamino)-3-methylbutanoyloxy)-3,3-dimethylbutan-2-yl, 4,4,4-trifluoro-1-methoxy-1-oxobutan-2-yl, 2-fluoro-1,1-dimethyl-ethyl, 3-fluoro-2-(fluoromethyl)-1-methoxy-1-oxopropan-2-yl, 2-fluoro-1-fluoromethyl-1-hydroxymethyl-ethyl, 3-hydroxy-1-methoxy-2-methyl-1-oxopropan-2-yl, 2-carboxy-1-hydroxypropan-2-yl, 2,2,2-trifluoroethylamino, 1-fluoromethyl-2-methyl-propyl, 1-fluoromethyl-2,2-dimethyl-propyl, 3-methyl-oxetan-3-yl, 1-fluoromethyl-cyclobutyl, 1,1-bis-hydroxymethyl-2-methyl-propyl, 1-trifluoromethyl-cyclopropyl, 1-methyl-cyclopropyl, and 1-trifluoromethyl-cyclobutyl; and R$^9$ is selected from H, methyl, tert-butyl, and cyclobutyl; or R$^8$ and R$^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3- dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention pertain to compounds of Formula Ie and pharmaceutically acceptable salts, solvates, hydrates, and N-oxides thereof:

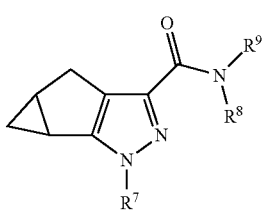

Ie wherein:

$R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3']bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, and piperidin-4-yl;

$R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluoro-phenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclobutyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, cyclobutanecarboxylic acid ethyl ester, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)piperidin-3-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluoro-phenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1$\lambda^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1$\lambda^4$-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxybenzyl, 1-morpholin-4-yl-cyclopentylmethyl, 1-pyridin-2-yl-cyclobutylmethyl, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydrofuran-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1$\lambda^6$-thiophen-3-ylmethyl, 2-(4-fluorophenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chlorophenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxybenzyl, 4-hydroxy-1-methyl-piperidin-4-ylmethyl, 1-(2,5-dimethylpyrrolidine-1-carbonyl)cyclopentyl, 2-methoxybenzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoropropyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1$\lambda^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1$\lambda^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethylpropyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methylamino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoroethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino) ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, and 2,2-dimethyl-1-pyridin-2-yl-propyl; and $R^9$ is selected from H, methyl, tert-butyl, and cyclobutyl; or $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl, and pyrazin-2-yl.

Some embodiments of the present invention include every combination of one or more compounds selected from the following group, wherein the Compound Number in bold directly preceding the chemical name is used elsewhere in this disclosure:

Compound 1: (1aR,5aR)-2-(2,4-Difluoro-phenyl)-1a,2,5,5a-tetrahydro-1H-2,3-diaza-cyclopropa[a]pentalene-4-carboxylic acid (2-methyl-2-morpholin-4-yl-propyl)-amide; Compound 2: (1aS,5aS)-2-(2,4-Difluoro-phenyl)-1a,2,5,5a-tetrahydro-1H-2,3-diaza-cyclopropa[a]pentalene-4-carboxylic acid ((R)-1-hydroxymethyl-2,2-dimethyl-propyl)-amide; Compound 3: ((2S,5S)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclohexyl)-carbamic acid tert-butyl ester; Compound 4: (1aR,5aR)-2-(5-Bromo-pyridin-2-yl)-1a,2,5,5a-tetrahydro-1H-2,3-diaza-cyclopropa[a]pentalene-4-carboxylic acid (1-phenyl-cyclopropyl)-amide; Compound 5: (1aR,5aR)-2-(2,4-Difluoro-phenyl)-1a,2,5,5a-tetrahydro-1H-2,3-diaza-cyclopropa[a]pentalene-4-carboxylic acid (5-trifluoromethyl-pyridin-2-yl)-amide; Compound 6: (1aR,5aR)-2-(4-Cyano-phenyl)-1a,2,5,5a-tetrahydro-1H-2,3-diaza-cyclopropa[a]pentalene-4-carboxylic acid (1-methyl-1-phenyl-ethyl)-amide; Compound 7: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-ethyl)-pyrrolidin-3-ylmethyl]-amide; Compound 8: 1-{[(1aS,5aS)-2-(2,4-Difluoro-phenyl)-1a,2,5,5a-tetrahydro-1H-2,3-diaza-cyclopropa[a]pentalene-4-carbonyl]-amino}-cyclopropanecarboxylic acid methyl ester; Compound 9: (4-Cyclohexylmethyl-piperazin-1-yl)-[(1aR,5aR)-2-(2,4-difluoro-phenyl)-1a,2,5,5a-tetrahydro-1H-2,3-diaza-cyclopropa[a]pentalen-4-yl]-methanone; Compound 10: (1aR,5aR)-2-Pyridin-3-yl-1a,2,5,5a-tetrahydro-1H-2,3-diaza-cyclopropa[a]pentalene-4-carboxylic acid (tetrahydro-pyran-4-ylmethyl)-amide; Compound 11: 4-{([(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1-carboxylic acid tert-butyl ester; Compound 12: (1aR,5aR)-2-Pyridin-2-yl-1a,2,5,5a-tetrahydro-1H-2,3-diaza-cyclopropa[a]pentalene-4-carboxylic acid [1-(4-fluoro-phenyl)-cyclopropyl]-amide; Compound 13: (1aR,5aR)-2-(2,4-Difluoro-phenyl)-1a,2,5,5a-tetrahydro-1H-2,3-diaza-cyclopropa[a]pentalene-4-carboxylic acid (6-methyl-pyridin-3-ylmethyl)-amide; Compound 14: 1-(2,4-Difluoro-phenyl)-3b,4,4a,5-tetrahydro-1H-cyclopropa[3,4]cyclopenta[1,2-c]pyrazole-3-carboxylic acid ((S)-2-hydroxy-1-phenyl-ethyl)-amide; Compound 15: (1aR,5aR)-2-(2,4-Difluoro-phenyl)-1a,2,5,5a-tetrahydro-1H-2,3-diaza-cyclopropa[a]pentalene-4-carboxylic acid ((1S,2S,4R)-1,3,3-trimethyl-bicyclo[2.2.1]hept-2-yl)-amide; Compound 16: (1aR,5aR)-2-(2,4-Difluoro-phenyl)-1a,2,5,5a-tetrahydro-1H-2,3-diaza-cyclopropa[a]pentalene-4-carboxylic acid (1-phenyl-cyclopropyl)-amide; Compound 17: (1aS,5aS)-2-(5-Thiazol-2-yl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 18: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-phenyl-ethyl)-amide; Compound 19: (1aR,5aR)-2-(2,4-Difluoro-phenyl)-1a,2,5,5a-tetrahydro-1H-2,3-diaza-cyclopropa[a]pentalene-4-carboxylic acid [2-(5-hydroxy-1H-indol-3-yl)-ethyl]-amide; Compound 20: (1aR,5aR)-2-(5-Trifluoromethyl-pyridin-2-yl)-1a,2,5,5a-tetrahydro-H-2,3-diaza-cyclopropa[a]pentalene-4-carboxylic acid (1-hydroxymethyl-cyclopropyl)-amide; Compound 21: [(1aR,5aR)-2-(2,4-Difluoro-phenyl)-1a,2,5,5a-tetrahydro-1H-2,3-diaza-cyclopropa[a]pentalen-4-yl]-(S)-hexahydro-pyrrolo[1,2-a]pyrazin-2-yl-methanone; Compound 22: (1aS,5aS)-2-(2,4-Difluoro-phenyl)-1a,2,5,5a-tetrahydro-1H-2,3-diaza-cyclopropa[a]pentalene-4-carboxylic acid (3-chloro-5-methyl-pyridin-2-yl)-amide; Compound 23: (1aS,5aS)-2-(5-o-Tolyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 24: (1aR,5aR)-2-(2,4-Difluoro-phenyl)-1a,2,5,5a-tetrahydro-1H-2,3-diaza-cyclopropa[a]pentalene-4-carboxylic acid (6-fluoro-pyridin-3-yl)-amide; Compound 25: (1aR,5aR)-2-(2,4-Difluoro-phenyl)-1a,2,5,5a-tetrahydro-1H-2,3-diaza-cyclopropa[a]pentalene-4-carboxylic acid [1-(3-fluoro-phenyl)-cyclobutyl]-amide; Compound 26: (1aR,5aR)-2-(2,4-Difluoro-phenyl)-1a,2,5,5a-tetrahydro-1H-2,3-diaza-cyclopropa[a]pentalene-4-carboxylic acid (2-methyl-pyridin-3-yl)-amide; Compound 27: (1aS,5aS)-2-(2,4-Difluoro-phenyl)-1a,2,5,5a-tetrahydro-1H-2,3-diaza-cyclopropa[a]pentalene-4-carboxylic acid [2-hydroxy-1-(tetrahydro-furan-3-yl)-ethyl]-amide; Compound 28: (1aR,5aR)-2-(2,4-Difluoro-phenyl)-1a,2,5,5a-tetrahydro-1H-2,3-diaza-cyclopropa[a]pentalene-4-carboxylic acid [2-(pyridin-3-yloxy)-propyl]-amide; Compound 29: (1aR,5aR)-2-(2,4-Difluoro-phenyl)-1a,2,5,5a-tetrahydro-1H-2,3-diaza-cyclopropa[a]pentalene-4-carboxylic acid ((S)-carbamoyl-phenyl-methyl)-amide; Compound 30: (1aS,5aS)-2-(2,4-Difluoro-phenyl)-1a,2,5,5a-tetrahydro-1H-2,3-diaza-cyclopropa[a]pentalene-4-carboxylic acid (5-fluoro-2-methoxy-phenyl)-amide; Compound 31: (1aR,5aR)-2-(2,4-Difluoro-phenyl)-1a,2,5,5a-tetrahydro-1H-2,3-diaza-cyclopropa[a]pentalene-4-carboxylic acid (2-methoxy-ethyl)-amide; Compound 32: [(1aR,5aR)-2-(2,4-Difluoro-phenyl)-1a,2,5,5a-tetrahydro-1H-2,3-diaza-cyclopropa[a]pentalen-4-yl]-(5,7-dihydro-pyrrolo[3,4-b]pyridin-6-yl)-methanone; Compound 33: (1aS,5aS)-2-(2,4-Difluoro-phenyl)-1a,2,5,5a-tetrahydro-1H-2,3-diaza-cyclopropa[a]

pentalene-4-carboxylic acid ((S)-2,3-dihydroxy-propyl)-amide; Compound 34: (S)-3-{[(1aR,5aR)-2-(2,4-Difluoro-phenyl)-1a,2,5,5a-tetrahydro-1H-2,3-diaza-cyclopropa[a]pentalene-4-carbonyl]-amino}-pyrrolidine-1-carboxylic acid tert-butyl ester; Compound 35: (1aS,5aS)-2-(2,4-Difluoro-phenyl)-1a,2,5,5a-tetrahydro-1H-2,3-diaza-cyclopropa[a]pentalene-4-carboxylic acid (2-oxo-2-phenyl-ethyl)-amide; Compound 36: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-azetidin-3-yl]-amide; Compound 37: (1aR,5aR)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-2-yl-ethyl)-amide; Compound 38: [(1aR,5aR)-2-(2,4-Difluoro-phenyl)-1a,2,5,5a-tetrahydro-1H-2,3-diaza-cyclopropa[a]pentalen-4-yl]-(4-methoxy-2,3-dihydro-indol-1-yl)-methanone; Compound 39: (1aS,5aS)-2-(2,4-Difluoro-phenyl)-1a,2,5,5a-tetrahydro-1H-2,3-diaza-cyclopropa[a]pentalene-4-carboxylic acid (3-hydroxy-pyridin-4-yl)-amide; Compound 40: (1aR,5aR)-2-(5-Dimethylamino-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 41: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-pyridin-4-yl-ethyl)-amide; Compound 42: (1aR,5aR)-2-(2,4-Difluoro-phenyl)-1a,2,5,5a-tetrahydro-1H-2,3-diaza-cyclopropa[a]pentalene-4-carboxylic acid ((R)-1-hydroxymethyl-2-3H-imidazol-4-yl-ethyl)-amide; Compound 43: (1aR,5aR)-2-(2,4-Dichloro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 44: (1aR,5aR)-2-(2,4-Difluoro-phenyl)-1a,2,5,5a-tetrahydro-1H-2,3-diaza-cyclopropa[a]pentalene-4-carboxylic acid 4-hydroxy-3-methoxy-benzylamide; Compound 45: (1aR,5aR)-2-(2,4-Difluoro-phenyl)-1a,2,5,5a-tetrahydro-1H-2,3-diaza-cyclopropa[a]pentalene-4-carboxylic acid (5-fluoro-2-oxo-2,3-dihydro-pyrimidin-4-yl)-amide; Compound 46: (1aS,5aS)-2-(2,4-Difluoro-phenyl)-1a,2,5,5a-tetrahydro-1H-2,3-diaza-cyclopropa[a]pentalene-4-carboxylic acid [(R)-1-(4-fluoro-phenyl)-3-hydroxy-propyl]-amide; Compound 47: (1aS,5aS)-2-(2,4-Difluoro-phenyl)-1a,2,5,5a-tetrahydro-1H-2,3-diaza-cyclopropa[a]pentalene-4-carboxylic acid (1-pyridin-4-yl-cyclopropyl)-amide; Compound 48: (1aR,5aR)-2-(5-Isopropyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 49: [(1aR,5aR)-2-(2,4-Difluoro-phenyl)-1a,2,5,5a-tetrahydro-1H-2,3-diaza-cyclopropa[a]pentalen-4-yl]-((S)-2-phenyl-pyrrolidin-1-yl)-methanone; Compound 50: (1aR,5aR)-2-(2,4-Difluoro-phenyl)-1a,2,5,5a-tetrahydro-H-2,3-diaza-cyclopropa[a]pentalene-4-carboxylic acid (2-hydroxy-1-pyridin-3-yl-ethyl)-amide; Compound 51: [(1aR,5aR)-2-(2,4-Difluoro-phenyl)-1a,2,5,5a-tetrahydro-1H-2,3-diaza-cyclopropa[a]pentalen-4-yl]-(2-pyridin-2-yl-thiomorpholin-4-yl)-methanone; Compound 52: (1aR,5aR)-2-(5-Methyl-pyridin-2-yl)-1a,2,5,5a-tetrahydro-1H-2,3-diaza-cyclopropa[a]pentalene-4-carboxylic acid (tetrahydro-pyran-4-ylmethyl)-amide; Compound 53: (1aS,5aS)-2-[5-(4-Methoxy-phenyl)-pyridin-2-yl]-1a,2,5,5a-tetrahydro-1H-2,3-diaza-cyclopropa[a]pentalene-4-carboxylic acid (2-hydroxy-1,1-dimethyl-ethyl)-amide; Compound 54: (1aR,5aR)-2-(2,4-Difluoro-phenyl)-1a,2,5,5a-tetrahydro-1H-2,3-diaza-cyclopropa[a]pentalene-4-carboxylic acid [1,1-dimethyl-2-(4-methyl-piperidin-1-yl)-ethyl]-amide; Compound 55: (1aR,5aR)-2-(2,4-Difluoro-phenyl)-1a,2,5,5a-tetrahydro-1H-2,3-diaza-cyclopropa[a]pentalene-4-carboxylic acid (6-cyano-pyridin-3-yl)-amide; Compound 56: (1aR,5aR)-2-(2-Fluoro-4-methanesulfonyl-phenyl)-1a,2,5,5a-tetrahydro-1H-2,3-diaza-cyclopropa[a]pentalene-4-carboxylic acid (5-fluoro-pyridin-2-yl)-amide; Compound 57: (1aR,5aR)-2-(2-Fluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 58: (1aR,5aR)-2-(2,4-Difluoro-phenyl)-1a,2,5,5a-tetrahydro-1H-2,3-diaza-cyclopropa[a]pentalene-4-carboxylic acid 2,5-dimethyl-benzylamide; Compound 59: (1aR,5aR)-2-(2,4-Difluoro-phenyl)-1a,2,5,5a-tetrahydro-1H-2,3-diaza-cyclopropa[a]pentalene-4-carboxylic acid (1-isopropyl-piperidin-4-yl)-amide; Compound 60: (1aR,5aR)-2-(2,4-Difluoro-phenyl)-1a,2,5,5a-tetrahydro-1H-2,3-diaza-cyclopropa[a]pentalene-4-carboxylic acid (2-methoxy-1-methoxymethyl-ethyl)-amide; Compound 61: (1aS,5aS)-2-(2,4-Difluoro-phenyl)-1a,2,5,5a-tetrahydro-1H-2,3-diaza-cyclopropa[a]pentalene-4-carboxylic acid (1-hydroxymethyl-cyclopropyl)-amide; Compound 62: (1aR,5aR)-2-(2,4-Difluoro-phenyl)-1a,2,5,5a-tetrahydro-1H-2,3-diaza-cyclopropa[a]pentalene-4-carboxylic acid 2,3-dimethyl-benzylamide; Compound 63: (1aR,5aR)-2-(2,4-Difluoro-phenyl)-1a,2,5,5a-tetrahydro-1H-2,3-diaza-cyclopropa[a]pentalene-4-carboxylic acid ((R)-1-pyridin-2-yl-ethyl)-amide; Compound 64: (1aS,5aS)-2-(2,4-Difluoro-phenyl)-1a,2,5,5a-tetrahydro-1H-2,3-diaza-cyclopropa[a]pentalene-4-carboxylic acid (1-phenyl-cyclopropyl)-amide; Compound 65: (1aR,5aR)-2-(5-Chloro-pyridin-2-yl)-1a,2,5,5a-tetrahydro-1H-2,3-diaza-cyclopropa[a]pentalene-4-carboxylic acid ((S)-2-hydroxy-1-phenyl-ethyl)-amide; Compound 66: (1aR,5aR)-2-(2,4-Difluoro-phenyl)-1a,2,5,5a-tetrahydro-1H-2,3-diaza-cyclopropa[a]pentalene-4-carboxylic acid (6-chloro-pyridin-3-ylmethyl)-amide; Compound 67: (1aS,5aS)-2-(2,4-Difluoro-phenyl)-1a,2,5,5a-tetrahydro-1H-2,3-diaza-cyclopropa[a]pentalene-4-carboxylic acid (3-methyl-pyridin-2-yl)-amide; Compound 68: (1aS,5aS)-2-(2,4-Difluoro-phenyl)-1a,2,5,5a-tetrahydro-1H-2,3-diaza-cyclopropa[a]pentalene-4-carboxylic acid ((1S,2R)-2-hydroxy-indan-1-yl)-amide; Compound 69: (1aS,5aS)-2-(2,4-Difluoro-phenyl)-1a,2,5,5a-tetrahydro-1H-2,3-diaza-cyclopropa[a]pentalene-4-carboxylic acid (1-hydroxymethyl-cyclobutyl)-amide; Compound 70: (1aR,5aR)-2-(5-Bromo-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 71: (1aR,5aR)-2-tert-Butyl-1a,2,5,5a-tetrahydro-1H-2,3-diaza-cyclopropa[a]pentalene-4-carboxylic acid [2-(4-chloro-phenyl)-1,1-dimethyl-ethyl]-amide; Compound 72: (1aR,5aR)-2-(2,4-Difluoro-phenyl)-1a,2,5,5a-tetrahydro-1H-2,3-diaza-cyclopropa[a]pentalene-4-carboxylic acid (3-hydroxy-pyridin-2-ylmethyl)-amide; Compound 73: (1aR,5aR)-2-(2,4-Difluoro-phenyl)-1a,2,5,5a-tetrahydro-1H-2,3-diaza-cyclopropa[a]pentalene-4-carboxylic acid (3-methyl-pyridin-4-yl)-amide; Compound 74: (1aR,5aR)-2-(2,4-Difluoro-phenyl)-1a,2,5,5a-tetrahydro-1H-2,3-diaza-cyclopropa[a]pentalene-4-carboxylic acid (5-tert-butyl-isoxazol-3-yl)-amide; Compound 75: (1aR,5aR)-2-(2-Methoxy-pyridin-4-yl)-1a,2,5,5a-tetrahydro-H-2,3-diaza-cyclopropa[a]pentalene-4-carboxylic acid (2-hydroxy-1,1-dimethyl-ethyl)-amide; Compound 76: (1aR,5aR)-2-(2,2-Dimethyl-propyl)-1a,2,5,5a-tetrahydro-1H-2,3-diaza-cyclopropa[a]pentalene-4-carboxylic acid (1-methyl-1-phenyl-ethyl)-amide; Compound 77: (1aR,5aR)-2-(2,4-Difluoro-phenyl)-1a,2,5,5a-tetrahydro-1H-2,3-diaza-cyclopropa[a]pentalene-4-carboxylic acid [1-(6-methoxy-pyridin-3-yl)-1-methyl-ethyl]-amide; Compound 78: (1aR,5aR)-2-(2,4-Difluoro-phenyl)-1a,2,5,5a-tetrahydro-1H-2,3- diaza-cyclopropa[a]pentalene-4-carboxylic acid (1H-benzoimidazol-2-yl)-amide; Compound 79: (1aR,5aR)-2-(Tetrahydro-pyran-4-ylmethyl)-1a,2,5,5a-tetrahydro-H-2,3-diaza-cyclopropa[a]pentalene-4-carboxylic acid tert-butylamide; Compound 80: (1aR,5aR)-2-Phenyl-1a,2,5,5a-tetrahydro-1H-2,3-diaza-cyclopropa[a]pentalene-4-carboxylic acid (2-hydroxy-1,1-dimethyl-ethyl)-amide; Compound 81: (1aR,5aR)-2-(2,4-Difluoro-phenyl)-1a,2,5,5a-tetrahydro-1H-2,3-diaza-cyclopropa[a]pentalene-4-carboxylic acid (4-phenyl-thiazol-2-yl)-amide; Compound 82: (1aR,5aR)-2-(Tetrahydro-pyran-4-ylmethyl)-1a,2,5,5a-tetrahydro-1H-2,3-diaza-cyclopropa[a]pentalene-4-carboxylic acid (1-phenyl-cyclopropyl)-amide; Compound 83: (1aR,5aR)-2-(2,4-Difluoro-phenyl)-1a,2,5,5a-tetrahydro-1H-2,3-diaza-cyclopropa[a]pentalene-4-carboxylic acid [1-(2-fluoro-phenyl)-cyclobutyl]-amide; Compound 84: (1aR,5aR)-2-(2,4-Difluoro-phenyl)-1a,2,5,5a-tetrahydro-1H-2,3-diaza-cyclopropa[a]pentalene-4-carboxylic acid 2,4-dimethoxy-benzylamide; Compound 85: (1aR,5aR)-2-(2,4-Difluoro-phenyl)-1a,2,5,5a-tetrahydro-H-2,3-diaza-cyclopropa[a]pentalene-4-carboxylic acid (5-bromo-3-methyl-pyridin-2-yl)-amide; Compound 86: (1aR,5aR)-2-(2,4-Difluoro-phenyl)-1a,2,5,5a-tetrahydro-H-2,3-diaza-cyclopropa[a]pentalene-4-carboxylic acid (4-benzyl-morpholin-2-ylmethyl)-amide; Compound 87: (1aR,5aR)-2-(2,4-Difluoro-phenyl)-1a,2,5,5a-tetrahydro-1H-2,3-diaza-cyclopropa[a]pentalene-4-carboxylic acid (1-hydroxymethyl-cyclobutyl)-amide; Compound 88: (1aR,5aR)-2-(4-Trifluoromethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 89: (1aR,5aR)-2-(2,4-Difluoro-phenyl)-1a,2,5,5a-tetrahydro-1H-2,3-diaza-cyclopropa[a]pentalene-4-carboxylic acid (6-trifluoromethyl-pyridin-3-ylmethyl)-amide; Compound 90: 6-{[(1aR,5aR)-2-(2,4-Difluoro-phenyl)-1a,2,5,5a-tetrahydro-1H-2,3-diaza-cyclopropa[a]pentalene-4-carbonyl]-amino}-3,4-dihydro-1H-isoquinoline-2-carboxylic acid tert-butyl ester; Compound 91: (1aR,5aR)-2-(2,4-Difluoro-phenyl)-1a,2,5,5a-tetrahydro-1H-2,3-diaza-cyclopropa[a]pentalene-4-carboxylic acid (3R)-(tetrahydro-furan-3-yl)-amide; Compound 92: 1-{[(1aS,5aS)-2-(2,4-Difluoro-phenyl)-1a,2,5,5a-tetrahydro-1H-2,3-diaza-cyclopropa[a]pentalene-4-carbonyl]-amino}-cyclobutanecarboxylic acid ethyl ester; Compound 93: (1aR,5aR)-2-(6-Chloro-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 94: (1aR,5aR)-2-(2,4-Difluoro-phenyl)-1a,2,5,5a-tetrahydro-1H-2,3-diaza-cyclopropa[a]pentalene-4-carboxylic acid (pyridin-3-ylmethyl)-amide; Compound 95: (1aS,5aS)-2-(2,4-Difluoro-phenyl)-1a,2,5,5a-tetrahydro-1H-2,3-diaza-cyclopropa[a]pentalene-4-carboxylic acid pyrazin-2-ylamide; Compound 96: (1aS,5aS)-2-(2,4-Difluoro-phenyl)-1a,2,5,5a-tetrahydro-1H-2,3-diaza-cyclopropa[a]pentalene-4-carboxylic acid ((1R,2S)-2-hydroxy-indan-1-yl)-amide; Compound 97: (1aR,5aR)-2-(5-Trifluoromethyl-pyridin-2-yl)-1a,2,5,5a-tetrahydro-1H-2,3-diaza-cyclopropa[a]pentalene-4-carboxylic acid (1-phenyl-cyclopropyl)-amide; Compound 98: (1aR,5aR)-2-(1-Oxo-hexahydro-1λ⁴-thiopyran-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 99: (1aR,5aR)-2-(2,4-Difluoro-phenyl)-1a,2,5,5a-tetrahydro-1H-2,3-diaza-cyclopropa[a]pentalene-4-carboxylic acid piperidin-4-ylamide; Compound 100: (1aR,5aR)-2-(2,4-Difluoro-phenyl)-1a,2,5,5a-tetrahydro-1H-2,3-diaza-cyclopropa[a]pentalene-4-carboxylic acid [1-(6-hydroxy-pyridin-3-yl)-1-methyl-ethyl]-amide; Compound 101: (1aS,5aS)-2-(2,4-Difluoro-phenyl)-1a,2,5,5a-tetrahydro-1H-2,3-diaza-cyclopropa[a]pentalene-4-carboxylic acid (1-methyl-1-pyridin-2-yl-ethyl)-amide; Compound 102: (1aR,5aR)-2-(2,4-Difluoro-phenyl)-1a,2,5,5a-tetrahydro-1H-2,3-diaza-cyclopropa[a]pentalene-4-carboxylic acid (1-hydroxymethyl-cyclopentyl)-amide; Compound 103: (1aS,5aS)-2-(5-Morpholin-4-yl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 104: (1aR,5aR)-2-(2,4-Difluoro-phenyl)-1a,2,5,5a-tetrahydro-1H-2,3-diaza-cyclopropa[a]pentalene-4-carboxylic acid (3S)-(1-aza-bicyclo[2.2.2]oct-3-yl)-amide; Compound 105: (1aS,5aS)-2-(2,4-Difluoro-phenyl)-1a,2,5,5a-tetrahydro-1H-2,3-diaza-cyclopropa[a]pentalene-4-carboxylic acid ((R)-2-hydroxy-1-phenyl-ethyl)-amide; Compound 106: (1aS,5aS)-2-(2,4-Difluoro-phenyl)-1a,2,5,5a-tetrahydro-1H-2,3-diaza-cyclopropa[a]pentalene-4-carboxylic acid ((1S,2S)-2-hydroxy-cyclopentyl)-amide; Compound 107: (1aR,5aR)-2-(2,4-Difluoro-phenyl)-1a,2,5,5a-tetrahydro-H-2,3-diaza-cyclopropa[a]pentalene-4-carboxylic acid [(R)-2-hydroxy-1-((S)-hydroxymethyl)-propyl]-amide; Compound 108: 4-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-piperidine-1-carboxylic acid tert-butyl ester; Compound 109: (1aR,5aR)-2-(2,4-Difluoro-phenyl)-1a,2,5,5a-tetrahydro-1H-2,3-diaza-cyclopropa[a]pentalene-4-carboxylic acid (3,5-dimethoxy-phenyl)-amide; Compound 110: (1aS,5aS)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 111: (1aR,5aR)-2-(5-Trifluoromethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 112: (1aR,5aR)-2-(2,4-Difluoro-phenyl)-1a,2,5,5a-tetrahydro-1H-2,3-diaza-cyclopropa[a]pentalene-4-carboxylic acid (6-fluoro-4H-benzo[1,3]dioxin-8-ylmethyl)-amide; Compound 113: (1aS,5aS)-2-(2,4-Difluoro-phenyl)-1a,2,5,5a-tetrahydro-1H-2,3-diaza-cyclopropa[a]pentalene-4-carboxylic acid (4,6-dimethyl-pyridin-2-yl)-amide; Compound 114: 1-(2,4-Difluoro-phenyl)-3b,4,4a,5-tetrahydro-1H-cyclopropa[3,4]cyclopenta[1,2-c]pyrazole-3-carboxylic acid (1,1-dimethyl-2-morpholin-4-yl-ethyl)-amide; Compound 115: (1aR,5aR)-2-(6-Bromo-pyridin-3-yl)-1a,2,5,5a-tetrahydro-1H-2,3-diaza-cyclopropa[a]pentalene-4-carboxylic acid (1-phenyl-cyclopropyl)-amide; Compound 116: (1aS,5aS)-2-(2,4-Difluoro-phenyl)-1a,2,5,5a-tetrahydro-1H-2,3-diaza-cyclopropa[a]pentalene-4-carboxylic acid (1-methyl-1-phenyl-ethyl)-amide; Compound 117: (1aR,5aR)-2-(2,4-Difluoro-phenyl)-1a,2,5,5a-tetrahydro-1H-2,3-diaza-cyclopropa[a]pentalene-4-carboxylic acid ((1R,2R)-2-hydroxy-cyclohexylmethyl)-amide; Compound 118: (1aR,5aR)-2-(2,4-Difluoro-phenyl)-1a,2,5,5a-tetrahydro-1H-2,3-diaza-cyclopropa[a]pentalene-4-carboxylic acid [1-(4-methoxy-phenyl)-cyclopropyl]-amide; Compound 119: (1aS,5aS)-2-(2,4-Difluoro-phenyl)-1a,2,5,5a-tetrahydro-1H-2,3-diaza-cyclopropa[a]pentalene-4-carboxylic acid ((S)-1-ethyl-pyrrolidin-2-ylmethyl)-amide; Compound 120: (1aR,5aR)-2-tert-Butyl-1a,2,5,5a-tetrahydro-1H-2,3-diaza-cyclopropa[a]pentalene-4-carboxylic acid (S)-indan-1-ylamide; Compound 121: (1aR,5aR)-2-(2,4-Difluoro-phenyl)-1a,2,5,5a-tetrahydro-1H-2,3-diaza-cyclopropa[a]pentalene-4-carboxylic acid pyrimidin-4-ylamide; Compound 122: (1aR,5aR)-2-(2,4-Difluoro-phenyl)-1a,2,5,5a-tetrahydro-1H-2,3-diaza-cyclopropa[a]pentalene-4-carboxylic acid (2-fluoro-4-methanesulfonyl-phenyl)-amide; Compound 123: (1aR,5aR)-2-(5-Methyl-pyridin-2-yl)-1a,2,5,5a-tetrahydro-1H-2,3-diaza-cyclopropa[a]

pentalene-4-carboxylic acid (1-phenyl-cyclopropyl)-amide; Compound 124: (1aR,5aR)-2-(5-Methoxy-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 125: (1aR,5aR)-2-(5,6-Difluoro-pyridin-3-yl)-1a,2,5,5a-tetrahydro-1H-2,3-diaza-cyclopropa[a]pentalene-4-carboxylic acid (1-methyl-1-phenyl-ethyl)-amide; Compound 126: (1aR,5aR)-2-(2,4-Difluoro-phenyl)-1a,2,5,5a-tetrahydro-1H-2,3-diaza-cyclopropa[a]pentalene-4-carboxylic acid (6-hydroxy-pyridin-2-yl)-amide; Compound 127: (1aR,5aR)-2-(2,4-Difluoro-phenyl)-1a,2,5,5a-tetrahydro-1H-2,3-diaza-cyclopropa[a]pentalene-4-carboxylic acid cyclobutylamide; Compound 128: (1aS,5aS)-2-(2,4-Difluoro-phenyl)-1a,2,5,5a-tetrahydro-1H-2,3-diaza-cyclopropa[a]pentalene-4-carboxylic acid [1-(3-methoxy-phenyl)-cyclopropyl]-amide; Compound 129: (1aR,5aR)-2-(6-Methoxy-pyridazin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 130: (1aR,5aR)-2-(2,4-Difluoro-phenyl)-1a,2,5,5a-tetrahydro-1H-2,3-diaza-cyclopropa[a]pentalene-4-carboxylic acid [(S)-1-(3,3,3-trifluoro-propyl)-pyrrolidin-3-yl]-amide; Compound 131: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-pyridin-3-yl)-amide; Compound 132: (1aR,5aR)-2-(2-Chloro-pyridin-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 133: (1aR,5aR)-2-(2,4-Difluoro-phenyl)-1a,2,5,5a-tetrahydro-1H-2,3-diaza-cyclopropa[a]pentalene-4-carboxylic acid 4-difluoromethoxy-benzylamide; Compound 134: (1aR,5aR)-2-(2,4-Difluoro-phenyl)-1a,2,5,5a-tetrahydro-1H-2,3-diaza-cyclopropa[a]pentalene-4-carboxylic acid (1-piperidin-1-yl-cyclopentylmethyl)-amide; Compound 135: (1aS,5aS)-2-(2,4-Difluoro-phenyl)-1a,2,5,5a-tetrahydro-1H-2,3-diaza-cyclopropa[a]pentalene-4-carboxylic acid (3-hydroxy-3-methyl-butyl)-amide; Compound 136: (1aR,5aR)-2-(2,4-Difluoro-phenyl)-1a,2,5,5a-tetrahydro-1H-2,3-diaza-cyclopropa[a]pentalene-4-carboxylic acid [1-(4-fluoro-phenyl)-cyclobutyl]-amide; Compound 137: (1aR,5aR)-2-(5-Cyclopropyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 138: (1aR,5aR)-2-(2,4-Difluoro-phenyl)-1a,2,5,5a-tetrahydro-1H-2,3-diaza-cyclopropa[a]pentalene-4-carboxylic acid 4-methoxy-benzylamide; Compound 139: (1aR,5aR)-2-(2,4-Difluoro-phenyl)-1a,2,5,5a-tetrahydro-1H-2,3-diaza-cyclopropa[a]pentalene-4-carboxylic acid methyl-pyridin-2-yl-amide; Compound 140: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-2-phenyl-ethyl)-amide; Compound 141: (1aR,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid tert-butylamide; Compound 142: (1aR,5aR)-2-(1-Benzyl-piperidin-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 143: [(1aR,5aR)-2-(2,4-Difluoro-phenyl)-1a,2,5,5a-tetrahydro-1H-2,3-diaza-cyclopropa[a]pentalen-4-yl]-((R)-2-hydroxymethyl-2,3-dihydro-indol-1-yl)-methanone; Compound 144: (1aS,5aS)-2-(2,4-Difluoro-phenyl)-1a,2,5,5a-tetrahydro-1H-2,3-diaza-cyclopropa[a]pentalene-4-carboxylic acid (3-hydroxy-pyridin-2-yl)-amide; Compound 145: (1aS,5aS)-2-(2,4-Difluoro-phenyl)-1a,2,5,5a-tetrahydro-1H-2,3-diaza-cyclopropa[a]pentalene-4-carboxylic acid (4-dimethylamino-tetrahydro-pyran-4-ylmethyl)-amide; Compound 146: (1aR,5aR)-2-(4-Cyano-phenyl)-1a,2,5,5a-tetrahydro-1H-2,3-diaza-cyclopropa[a]pentalene-4-carboxylic acid (1-phenyl-cyclopropyl)-amide; Compound 147: (1aR,5aR)-2-(6-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 148: (1aR,5aR)-2-tert-Butyl-1a,2,5,5a-tetrahydro-1H-2,3-diaza-cyclopropa[a]pentalene-4-carboxylic acid [2-(4-fluoro-phenyl)-ethyl]-amide; Compound 149: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-ethyl)-piperidin-4-ylmethyl]-amide; Compound 150: (1aS,5aS)-2-(2,4-Difluoro-phenyl)-1a,2,5,5a-tetrahydro-1H-2,3-diaza-cyclopropa[a]pentalene-4-carboxylic acid (6-hydroxy-pyridin-2-yl)-amide; Compound 151: (1aR,5aR)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 152: (1aS,5aS)-2-Pyridin-2-yl-1a,2,5,5a-tetrahydro-1H-2,3-diaza-cyclopropa[a]pentalene-4-carboxylic acid (1-phenyl-cyclopropyl)-amide; Compound 153: [(1aR,5aR)-2-(2,4-Difluoro-phenyl)-1a,2,5,5a-tetrahydro-1H-2,3-diaza-cyclopropa[a]pentalen-4-yl]-(4-hydroxy-piperidin-1-yl)-methanone; Compound 154: (1aR,5aR)-2-(2,4-Difluoro-phenyl)-1a,2,5,5a-tetrahydro-1H-2,3-diaza-cyclopropa[a]pentalene-4-carboxylic acid (2-morpholin-4-yl-ethyl)-amide; Compound 155: (1aR,5aR)-2-Pyridin-2-yl-1a,2,5,5a-tetrahydro-1H-2,3-diaza-cyclopropa[a]pentalene-4-carboxylic acid (tetrahydro-pyran-4-ylmethyl)-amide; Compound 156: 4-{[(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1,4-dicarboxylic acid mono-tert-butyl ester; Compound 157: (1aR,5aR)-2-(2,4-Difluoro-phenyl)-1a,2,5,5a-tetrahydro-1H-2,3-diaza-cyclopropa[a]pentalene-4-carboxylic acid (3-hydroxy-pyridin-2-yl)-amide; Compound 158: (1aR,5aR)-2-(2,4-Difluoro-phenyl)-1a,2,5,5a-tetrahydro-1H-2,3-diaza-cyclopropa[a]pentalene-4-carboxylic acid quinolin-3-ylamide; Compound 159: (1aR,5aR)-2-(2-Hydroxy-2-methyl-propyl)-1a,2,5,5a-tetrahydro-1H-2,3-diaza-cyclopropa[a]pentalene-4-carboxylic acid (1-phenyl-cyclopropyl)-amide; Compound 160: (1aR,5aR)-2-(5-Chloro-pyridin-2-yl)-1a,2,5,5a-tetrahydro-1H-2,3-diaza-cyclopropa[a]pentalene-4-carboxylic acid (1-morpholin-4-ylmethyl-cyclopentyl)-amide; Compound 161: (1aR,5aR)-2-(2,4-Difluoro-phenyl)-1a,2,5,5a-tetrahydro-1H-2,3-diaza-cyclopropa[a]pentalene-4-carboxylic acid (1,4-dimethyl-1H-pyrrol-2-ylmethyl)-amide; Compound 162: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-2-pyridin-2-yl-ethyl)-amide; Compound 163: 1-(2,4-Difluoro-phenyl)-3b,4,4a,5-tetrahydro-1H-cyclopropa[3,4]cyclopenta[1,2-c]pyrazole-3-carboxylic acid (tetrahydro-pyran-4-ylmethyl)-amide; Compound 164: (1aR,5aR)-2-(4-Fluoro-phenyl)-1a,2,5,5a-tetrahydro-1H-2,3-diaza-cyclopropa[a]pentalene-4-carboxylic acid (1-phenyl-cyclopropyl)-amide; Compound 165: (1aR,5aR)-2-(2,4-Difluoro-phenyl)-1a,2,5,5a-tetrahydro-1H-2,3-diaza-cyclopropa[a]pentalene-4-carboxylic acid pyridin-3-ylamide; Compound 166: (1aR,5aR)-2-(2,4-Difluoro-phenyl)-1a,2,5,5a-tetrahydro-1H-2,3-diaza-cyclopropa[a]pentalene-4-carboxylic acid 2-dimethylamino-benzylamide; Compound 167: (1aR,5aR)-2-(2,4-Difluoro-phenyl)-1a,2,5,5a-tetrahydro-1H-2,3-diaza-cyclopropa[a]pentalene-4-carboxylic acid (tetrahydro-thiopyran-4-yl)-amide; Compound 168: (1aR,5aR)-2-(2,4-Difluoro-phenyl)-1a,2,5,5a-tetrahydro-H-2,3-diaza-cyclopropa[a]pentalene-4-carboxylic acid (1-m-tolyl-cyclopropyl)-amide; Compound 169: (1aS, 5aS)-2-(5-Ethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 170: (1aR,5aR)-2-Isopropyl-1a,2,5,5a-tetrahydro-1H-2,3-diaza-cyclopropa[a]pentalene-4-carboxylic acid (1-methyl-1-phenyl-ethyl)-amide; Compound 171: (1aR,5aR)-2-(2,4-Difluoro-phenyl)-1a,2,5,5a-tetrahydro-1H-2,3-diaza-cyclopropa[a]pentalene-4-carboxylic acid [(S)-1-(2-methoxy-ethyl)-piperidin-3-yl]-amide; Compound 172: (1aR,5aR)-2-(2,4-Difluoro-phenyl)-1a,2,5,5a-tetrahydro-1H-2,3-diaza-cyclopropa[a]pentalene-4-carboxylic acid (5-methoxy-pyridin-2-ylmethyl)-amide; Compound 173: (1aS,5aS)-2-(2,4-Difluoro-phenyl)-1a,2,5,5a-tetrahydro-1H-2,3-diaza-cyclopropa[a]pentalene-4-carboxylic acid ((R)-2-hydroxy-1-pyridin-4-yl-ethyl)-amide; Compound 174: (1aR,5aR)-2-(2,4-Dichloro-phenyl)-1a,2,5,5a-tetrahydro-1H-2,3-diaza-cyclopropa[a]pentalene-4-carboxylic acid (1-hydroxymethyl-cyclopropyl)-amide; Compound 175: [(1aR,5aR)-2-(2,4-Difluoro-phenyl)-1a,2,5,5a-tetrahydro-1H-2,3-diaza-cyclopropa[a]pentalen-4-yl]-(R)-hexahydro-pyrrolo[1,1,2-a]pyrazin-2-yl-methanone; Compound 176: (1aR,5aR)-2-(2,4-Difluoro-phenyl)-1a,2,5,5a-tetrahydro-1H-2,3-diaza-cyclopropa[a]pentalene-4-carboxylic acid (4-methyl-pyridin-2-yl)-amide; Compound 177: 4-{[(1aR,5aR)-2-(2,4-Difluoro-phenyl)-1a,2,5,5a-tetrahydro-1H-2,3-diaza-cyclopropa[a]pentalene-4-carbonyl]-amino}-3-fluoro-benzoic acid; Compound 178: (1aR,5aR)-2-Pyridin-2-yl-1a,2,5,5a-tetrahydro-H-2,3-diaza-cyclopropa[a]pentalene-4-carboxylic acid (2-hydroxy-1,1-dimethyl-ethyl)-amide; Compound 179: (1aS,5aS)-2-(5-Phenyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 180: 2-[(1aR,5aR)-2-(2,4-Difluoro-phenyl)-1a,2,5,5a-tetrahydro-1H-2,3-diaza-cyclopropa[a]pentalene-4-carbonyl]-1,2,3,4-tetrahydro-isoquinoline-7-carboxylic acid methyl ester; Compound 181: (1aR,5aR)-2-(2,4-Difluoro-phenyl)-1a,2,5,5a-tetrahydro-1H-2,3-diaza-cyclopropa[a]pentalene-4-carboxylic acid (6-methanesulfonyl-pyridin-3-yl)-amide; Compound 182: (1aR,5aR)-2-Pyridin-3-yl-1a,2,5,5a-tetrahydro-1H-2,3-diaza-cyclopropa[a]pentalene-4-carboxylic acid (1-phenyl-cyclopropyl)-amide; Compound 183: (1aR,5aR)-2-(2,4-Difluoro-phenyl)-1a,2,5,5a-tetrahydro-1H-2,3-diaza-cyclopropa[a]pentalene-4-carboxylic acid (1-o-tolyl-cyclobutyl)-amide; Compound 184: (1aR,5aR)-2-(2,4-Difluoro-phenyl)-1a,2,5,5a-tetrahydro-1H-2,3-diaza-cyclopropa[a]pentalene-4-carboxylic acid (1,1-dimethyl-2-pyrrolidin-1-yl-ethyl)-amide; Compound 185: (1aR,5aR)-2-(2,4-Difluoro-phenyl)-1a,2,5,5a-tetrahydro-1H-2,3-diaza-cyclopropa[a]pentalene-4-carboxylic acid (2,6-dimethoxy-pyridin-3-yl)-amide; Compound 186: (1aR,5aR)-2-Pyridin-4-yl-1a,2,5,5a-tetrahydro-1H-2,3-diaza-cyclopropa[a]pentalene-4-carboxylic acid pyridin-2-ylamide; Compound 187: (1aS,5aS)-2-(2,4-Difluoro-phenyl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 188: (1aR,5aR)-2-(2,5-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 189: (1aR,5aR)-2-(2,4-Difluoro-phenyl)-1a,2,5,5a-tetrahydro-1H-2,3-diaza-cyclopropa[a]pentalene-4-carboxylic acid [2-(1H-imidazol-4-yl)-ethyl]-amide; Compound 190: (1aR,5aR)-2-(2,4-Difluoro-phenyl)-1a,2,5,5a-tetrahydro-1H-2,3-diaza-cyclopropa[a]pentalene-4-carboxylic acid (3-fluoro-pyridin-4-yl)-amide; Compound 191: (1aR,5aR)-2-(2,4-Dichloro-phenyl)-1a,2,5,5a-tetrahydro-1H-2,3-diaza-cyclopropa[a]pentalene-4-carboxylic acid (1-methyl-1-phenyl-ethyl)-amide; Compound 192: (1aR,5aR)-2-(2,4-Difluoro-phenyl)-1a,2,5,5a-tetrahydro-1H-2,3-diaza-cyclopropa[a]pentalene-4-carboxylic acid ((S)-1-carbamoyl-2-phenyl-ethyl)-amide; Compound 193: (1aR,5aR)-2-(2,4-Difluoro-phenyl)-1a,2,5,5a-tetrahydro-1H-2,3-diaza-cyclopropa[a]pentalene-4-carboxylic acid (oxazol-4-ylmethyl)-amide; Compound 194: (1aR,5aR)-2-(2,4-Difluoro-phenyl)-1a,2,5,5a-tetrahydro-1H-2,3-diaza-cyclopropa[a]pentalene-4-carboxylic acid (6-methoxy-pyrimidin-4-yl)-amide; Compound 195: (1aR,5aR)-2-(2,4-Difluoro-phenyl)-1a,2,5,5a-tetrahydro-1H-2,3-diaza-cyclopropa[a]pentalene-4-carboxylic acid (1,1-dioxo-hexahydro-1$\lambda^6$-thiopyran-4-yl)-amide; Compound 196: (1aR,5aR)-2-(4-Cyano-phenyl)-1a,2,5,5a-tetrahydro-1H-2,3-diaza-cyclopropa[a]pentalene-4-carboxylic acid (tetrahydro-pyran-4-ylmethyl)-amide; Compound 197: (1aR,5aR)-2-(3-Fluoro-phenyl)-1a,2,5,5a-tetrahydro-H-2,3-diaza-cyclopropa[a]pentalene-4-carboxylic acid (2-hydroxy-1,1-dimethyl-ethyl)-amide; Compound 198: 2-[((1aR,5aR)-2-tert-Butyl-1a,2,5,5a-tetrahydro-1H-2,3-diaza-cyclopropa[a]pentalene-4-carbonyl)-amino]-3-phenyl-propionic acid methyl ester; Compound 199: (1aR,5aR)-2-(2,4-Difluoro-phenyl)-1a,2,5,5a-tetrahydro-1H-2,3-diaza-cyclopropa[a]pentalene-4-carboxylic acid [(R)-1-(2-methoxy-ethyl)-pyrrolidin-3-yl]-amide; Compound 200: (1aR,5aR)-2-(2,4-Difluoro-phenyl)-1a,2,5,5a-tetrahydro-1H-2,3-diaza-cyclopropa[a]pentalene-4-carboxylic acid [1-(6-methyl-pyridin-2-yl)-ethyl]-amide; Compound 201: (1aR,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (1-methyl-1-phenyl-ethyl)-amide; Compound 202: (1aR,5aR)-2-Pyrimidin-4-yl-1a,2,5,5a-tetrahydro-1H-2,3-diaza-cyclopropa[a]pentalene-4-carboxylic acid (2-hydroxy-1,1-dimethyl-ethyl)-amide; Compound 203: (1aR,5aR)-2-(2,4-Difluoro-phenyl)-1a,2,5,5a-tetrahydro-1H-2,3-diaza-cyclopropa[a]pentalene-4-carboxylic acid [(R)-2-hydroxy-1-(4-hydroxy-phenyl)-ethyl]-amide; Compound 204: (1aR,5aR)-2-(2,4-Difluoro-phenyl)-1a,2,5,5a-tetrahydro-1H-2,3-diaza-cyclopropa[a]pentalene-4-carboxylic acid (2-methoxy-pyridin-4-yl)-amide; Compound 205: (1aR,5aR)-2-(2,4-Difluoro-phenyl)-1a,2,55a-tetrahydro-1H-2,3-diaza-cyclopropa[a]pentalene-4-carboxylic acid (1-pyridin-2-yl-cyclopropyl)-amide; Compound 206: (1aR,5aR)-2-(2-Fluoro-phenyl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 207: (R)-3-{[(1aR,5aR)-2-(2,4-Difluoro-phenyl)-1a,2,5,5a-tetrahydro-H-2,3-diaza-cyclopropa[a]pentalene-4-carbonyl]-amino}-piperidine-1-carboxylic acid tert-butyl ester; Compound 208: (1aR,5aR)-2-(2,4-Difluoro-phenyl)-1a,2,5,5a-tetrahydro-1H-2,3-diaza-cyclopropa[a]pentalene-4-carboxylic acid (3-methyl-pyridin-2-ylmethyl)-amide; Compound 209: (1aR,5aR)-2-[2-(Tetrahydro-pyran-4-yl)-ethyl]-1a,2,5,5a-tetrahydro-1H-2,3-diaza-cyclopropa[a]pentalene-4-carboxylic acid (1-methyl-1-phenyl-ethyl)-amide; Compound 210: (1aR,5aR)-2-(3,5-Difluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 211: [(1aR,5aR)-2-(2,4-Difluoro-phenyl)-1a,2,5,5a-tetrahydro-1H-2,3-diaza-cyclopropa[a]pentalen-4-yl]-(7-methoxy-3,4-dihydro-1H-isoquinolin-2-yl)-methanone; Compound 212: (1aR,5aR)-2-(2,4-Difluoro-phenyl)-1a,2,5,5a-tetrahydro-1H-2,3-diaza-cyclopropa[a]pentalene-4-carboxylic acid (3-fluoro-pyridin-2-yl)-amide; Compound 213: 1-(2,4-Difluoro-phenyl)-3b,4,4a,5-tetrahydro-1H-cyclopropa[3,4]cyclopenta[1,2-c]pyrazole-3-carboxylic acid (1-phenyl-cyclopropyl)-amide; Compound 214: (1aR,5aR)-2-(2-Fluoro-phenyl)-1a,2,5,5a-tetrahydro-1H-2,3-diaza-cyclopropa[a]pentalene-4-carboxylic acid (1-pyridin-4-yl-cyclobutyl)-amide; Compound 215: [(1aR,5aR)-2-(2,4-Difluoro-phenyl)-1a,2,5,5a-tetrahydro-1H-2,3-diaza-cyclopropa[a]pentalen-4-yl]-(1,4,6,7-tetrahydro-imidazo[4,5-c]pyridin-5-yl)-methanone; Compound 216: (1aR,5aR)-2-(2,4-Difluoro-phenyl)-1a,2,5,5a-tetrahydro-1H-2,3-diaza-cyclopropa[a]pentalene-4-carboxylic acid (5-fluoro-pyridin-2-yl)-amide; Compound 217: 3-{[(1aS,5aS)-2-(2,4-Difluoro-phenyl)-1a,2,5,5a-tetrahydro-1H-2,3-diaza-cyclopropa[a]pentalene-4-carbonyl]-amino}-3-(R)-pyridin-3-yl-propionic acid; Compound 218: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-methyl-ethyl)-amide; Compound 219: (1aR,5aR)-2-Pyrazin-2-yl-a,2,5,5a-tetrahydro-1H-2,3-diaza-cyclopropa[a]pentalene-4-carboxylic acid (4-hydroxymethyl-tetrahydro-pyran-4-yl)-amide; Compound 220: (1aR,5aR)-2-(2,4-Difluoro-phenyl)-1a,2,5,5a-tetrahydro-1H-2,3-diaza-cyclopropa[a]pentalene-4-carboxylic acid ((R)-2-hydroxy-1-phenyl-ethyl)-amide; Compound 221: (1aS,5aS)-2-(2,4-Difluoro-phenyl)-1a,2,5,5a-tetrahydro-1H-2,3-diaza-cyclopropa[a]pentalene-4-carboxylic acid [(S)-1-(4-fluoro-phenyl)-3-hydroxy-propyl]-amide; Compound 222: 1-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclohexanecarboxylic acid methyl ester; Compound 223: (1aR,5aR)-2-(Tetrahydro-thiopyran-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 224: [(1aR,5aR)-2-(2,4-Difluoro-phenyl)-1a,2,5,5a-tetrahydro-1H-2,3-diaza-cyclopropa[a]pentalen-4-yl]-((R)-2-phenyl-pyrrolidin-1-yl)-methanone; Compound 225: ((1R,2R)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclohexyl)-carbamic acid tert-butyl ester; Compound 226: (1aS,5aS)-2-(2,4-Difluoro-phenyl)-1a,2,5,5a-tetrahydro-1H-2,3-diaza-cyclopropa[a]pentalene-4-carboxylic acid (5-bromo-3-methyl-pyridin-2-yl)-amide; Compound 227: (1aR,5aR)-2-(2,4-Difluoro-phenyl)-1a,2,5,5a-tetrahydro-1H-2,3-diaza-cyclopropa[a]pentalene-4-carboxylic acid amide; Compound 228: (1aS,5aS)-2-(5-p-Tolyl-pyridin-2-yl)-1a,2,5,5a-tetrahydro-H-2,3-diaza-cyclopropa[a]pentalene-4-carboxylic acid (2-hydroxy-1,1-dimethyl-ethyl)-amide; Compound 229: (1aR,5aR)-2-(2,4-Difluoro-phenyl)-1a,2,5,5a-tetrahydro-1H-2,3-diaza-cyclopropa[a]pentalene-4-carboxylic acid (S)-indan-1-ylamide; Compound 230: (1aR,5aR)-2-(2,4-Difluoro-phenyl)-1a,2,5,5a-tetrahydro-1H-2,3-diaza-cyclopropa[a]pentalene-4-carboxylic acid (3-hydroxymethyl-pyridin-4-yl)-amide; Compound 231: (1aR,5aR)-2-Pyridin-4-yl-1a,2,5,5a-tetrahydro-1H-2,3-diaza-cyclopropa[a]pentalene-4-carboxylic acid (1-phenyl-cyclopropyl)-amide; Compound 232: (1aR,5aR)-2-(4-Fluoro-phenyl)-1a,2,5,5a-tetrahydro-1H-2,3-diaza-cyclopropa[a]pentalene-4-carboxylic acid ((S)-2-hydroxy-1-phenyl-ethyl)-amide; Compound 233: (1aR,5aR)-2-(2,4-Difluoro-phenyl)-1a,2,5,5a-tetrahydro-1H-2,3-diaza-cyclopropa[a]pentalene-4-carboxylic acid (3-dimethylamino-tetrahydro-thiophen-3-ylmethyl)-amide; Compound 234: (1aR,5aR)-2-(2,4-Difluoro-phenyl)-1a,2,5,5a-tetrahydro-1H-2,3-diaza-cyclopropa[a]pentalene-4-carboxylic acid (tetrahydro-pyran-4-yl)-amide; Compound 235: (1aR,5aR)-2-(2,4-Difluoro-phenyl)-1a,2,5,5a-tetrahydro-1H-2,3-diaza-cyclopropa[a]pentalene-4-carboxylic acid (5-chloro-pyridin-2-yl)-amide; Compound 236: (1aS,5aS)-2-(2,4-Difluoro-phenyl)-1a,2,5,5a-tetrahydro-1H-2,3-diaza-cyclopropa[a]pentalene-4-carboxylic acid (1-carbamoyl-cyclobutyl)-amide; Compound 237: (1aR,5aR)-2-(2,4-Difluoro-phenyl)-1a,2,5,5a-tetrahydro-1H-2,3-diaza-cyclopropa[a]pentalene-4-carboxylic acid 5-fluoro-2-methyl-benzylamide; Compound 238: (1aR,5aR)-2-(2,4-Difluoro-phenyl)-1a,2,5,5a-tetrahydro-1H-2,3-diaza-cyclopropa[a]pentalene-4-carboxylic acid (2-morpholin-4-yl-2-pyridin-3-yl-ethyl)-amide; Compound 239: (1aR,5aR)-2-(4-Methoxy-phenyl)-1a,2,5,5a-tetrahydro-1H-2,3-diaza-cyclopropa[a]pentalene-4-carboxylic acid (1-methyl-1-phenyl-ethyl)-amide; Compound 240: (1aR,5aR)-2-(2,4-Difluoro-phenyl)-1a,2,5,5a-tetrahydro-1H-2,3-diaza-cyclopropa[a]pentalene-4-carboxylic acid [1-(3-methoxy-phenyl)-cyclobutyl]-amide; Compound 241: [(1aR,5aR)-2-(2,4-Difluoro-phenyl)-1a,2,5,5a-tetrahydro-1H-2,3-diaza-cyclopropa[a]pentalen-4-yl]-(5-fluoro-1,3-dihydro-isoindol-2-yl)-methanone; Compound 242: (1aS,5aS)-2-(2,4-Difluoro-phenyl)-1a,2,5,5a-tetrahydro-1H-2,3-diaza-cyclopropa[a]pentalene-4-carboxylic acid (5-methyl-pyridin-2-yl)-amide; Compound 243: (1aR,5aR)-2-(2,4-Difluoro-phenyl)-1a,2,5,5a-tetrahydro-1H-2,3-diaza-cyclopropa[a]pentalene-4-carboxylic acid [(S)-1-(tetrahydro-furan-2-yl)methyl]-amide; Compound 244: (1aS,5aS)-2-(2,4-Difluoro-phenyl)-1a,2,5,5a-tetrahydro-1H-2,3-diaza-cyclopropa[a]pentalene-4-carboxylic acid (1-hydroxymethyl-cyclopentyl)-amide; Compound 245: (1aR,5aR)-2-(2,4-Difluoro-phenyl)-1a,2,5,5a-tetrahydro-1H-2,3-diaza-cyclopropa[a]pentalene-4-carboxylic acid (1-dimethylaminomethyl-cyclopentyl)-amide; Compound 246: (1aR,5aR)-2-tert-Butyl-1a,2,5,5a-tetrahydro-1H-2,3-diaza-cyclopropa[a]pentalene-4-carboxylic acid [2-(4-fluoro-phenyl)-1-methyl-ethyl]-amide; Compound 247: [(1aR,5aR)-2-(2,4-Difluoro-phenyl)-1a,2,5,5a-tetrahydro-1H-2,3-diaza-cyclopropa[a]pentalen-4-yl]-(3-hydroxy-7,8-dihydro-5H-[1,6]naphthyridin-6-yl)-methanone; Compound 248: (1aR,5aR)-2-(2,4-Difluoro-phenyl)-1a,2,5,5a-tetrahydro-1H-2,3-diaza-cyclopropa[a]pentalene-4-carboxylic acid benzothiazol-2-ylamide; Compound 249: (1aR,5aR)-2-(2,4-Difluoro-phenyl)-1a,2,5,5a-tetrahydro-1H-2,3-diaza-cyclopropa[a]pentalene-4-carboxylic acid [1-(2-fluoro-phenyl)-cyclopropyl]-amide; Compound 250: (1aR,5aR)-2-(Tetrahydro-pyran-4-ylmethyl)-1a,2,5,5a-tetrahydro-1H-2,3-diaza-cyclopropa[a]pentalene-4-carboxylic acid (2-hydroxy-1,1-dimethyl-ethyl)-amide; Compound 251: (1aR,5aR)-2-(2-Morpholin-4-yl-ethyl)-1a,2,5,5a-tetrahydro-1H-2,3-diaza-cyclopropa[a]pentalene-4-carboxylic acid (1-methyl-1-phenyl-ethyl)-amide; Compound 252: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-ethyl)-piperidin-4-yl]-amide; Compound 253: 4-[(1aR,5aR)-2-(2,4-Difluoro-phenyl)-1a,2,5,5a-tetrahydro-1H-2,3-diaza-cyclopropa[a]pentalene-4-carbonyl]-3-hydroxymethyl-piperazine-1-carboxylic acid (S)-tert-butyl ester; Compound 254: (1aR,5aR)-2-(2,4-Difluoro-phenyl)-1a,2,5,5a-tetrahydro-1H-2,3-diaza-cyclopropa[a]pentalene-4-carboxylic acid ((R)-2-hydroxy-1-pyridin-4-yl-ethyl)-amide; Compound 255: (1aR,5aR)-2-(5-Cyano-pyridin-2-yl)-1a,2,5,5a-tetrahydro-H-2,3-diaza-cyclopropa[a]pentalene-4-carboxylic acid (1-hydroxymethyl-cyclopropyl)-amide; Compound 256: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-azetidin-3-ylmethyl]-amide; Compound 257: (1aR,5aR)-2-(2,4-Difluoro-phenyl)-1a,2,5,5a-tetrahydro-1H-2,3-diaza-cyclopropa[a]pentalene-4-carboxylic acid (6-pyrrolidin-1-yl-pyridin-2-ylmethyl)-amide; Compound 258: (1aR,5aR)-2-(Tetrahydro-pyran-4-ylmethyl)-1a,2,5,5a-tetrahydro-1H-2,3-diaza-cyclopropa[a]pentalene-4- carboxylic acid (5-fluoro-pyridin-2-yl)-amide; Compound 259: (1aR,5aR)-2-(2,4-Difluoro-phenyl)-1a,2,5,5a-tetrahydro-1H-2,3-diaza-cyclopropa[a]pentalene-4-carboxylic acid (1,1-dioxo-tetrahydro-1$\lambda^6$-thiophen-3-yl)-amide; Compound 260: (1aR,5aR)-2-(2,4-Difluoro-phenyl)-1a,2,5,5a-tetrahydro-1H-2,3-diaza-cyclopropa[a]pentalene-4-carboxylic acid 2,3-dimethoxy-benzylamide; Compound 261: (1aR,5aR)-2-(2,4-Difluoro-phenyl)-1a,2,5,5a-tetrahydro-1H-2,3-diaza-cyclopropa[a]pentalene-4-carboxylic acid (3-cyano-5-methyl-pyridin-2-yl)-amide; Compound 262: (1aR,5aR)-2-(2,4-Difluoro-phenyl)-1a,2,5,5a-tetrahydro-1H-2,3-diaza-cyclopropa[a]pentalene-4-carboxylic acid (2,3-dihydro-benzofuran-3-yl)-amide; Compound 263: (1aR,5aR)-2-(2,4-Difluoro-phenyl)-1a,2,5,5a-tetrahydro-1H-2,3-diaza-cyclopropa[a]pentalene-4-carboxylic acid (1-hydroxymethyl-cyclohexyl)-amide; Compound 264: (1aR,5aR)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 265: (1aR,5aR)-2-(2,4-Difluoro-phenyl)-1a,2,5,5a-tetrahydro-1H-2,3-diaza-cyclopropa[a]pentalene-4-carboxylic acid 2,5-difluoro-benzylamide; Compound 266: (1aS,5aS)-2-(2,4-Difluoro-phenyl)-1a,2,5,5a-tetrahydro-1H-2,3-diaza-cyclopropa[a]pentalene-4-carboxylic acid 4-dimethylamino-benzylamide; Compound 267: (1aS,5aS)-2-(2,4-Difluoro-phenyl)-1a,2,5,5a-tetrahydro-1H-2,3-diaza-cyclopropa[a]pentalene-4-carboxylic acid ((3R,4R)-4-hydroxy-1,1-dioxo-tetrahydro-1$\lambda^6$-thiophen-3-yl)-amide; Compound 268: (1aR,5aR)-2-(2,4-Difluoro-phenyl)-1a,2,5,5a-tetrahydro-1H-2,3-diaza-cyclopropa[a]pentalene-4-carboxylic acid [1-(3-methoxy-phenyl)-cyclopropyl]-amide; Compound 269: (1aR,5aR)-2-Pyridin-3-yl-1a,2,5,5a-tetrahydro-1H-2,3-diaza-cyclopropa[a]pentalene-4-carboxylic acid (2-hydroxy-1,1-dimethyl-ethyl)-amide; Compound 270: [(1aR,5aR)-2-(2,4-Difluoro-phenyl)-1a,2,5,5a-tetrahydro-1H-2,3-diaza-cyclopropa[a]pentalen-4-yl]-(1,3-dihydro-isoindol-2-yl)-methanone; Compound 271: (1aR,5aR)-2-(2,4-Difluoro-phenyl)-1a,2,5,5a-tetrahydro-1H-2,3-diaza-cyclopropa[a]pentalene-4-carboxylic acid (4-trifluoromethyl-pyridin-2-yl)-amide; Compound 272: (1aS,5aS)-2-(2,4-Difluoro-phenyl)-1a,2,5,5a-tetrahydro-1H-2,3-diaza-cyclopropa[a]pentalene-4-carboxylic acid ((1S,2S)-2-hydroxy-indan-1-yl)-amide; Compound 273: (1aS,5aS)-2-(2,4-Difluoro-phenyl)-1a,2,5,5a-tetrahydro-1H-2,3-diaza-cyclopropa[a]pentalene-4-carboxylic acid [1-(4-fluoro-phenyl)-cyclopropyl]-amide; Compound 274: (1aR,5aR)-2-(5-Ethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 275: [(1aR,5aR)-2-(2,4-Difluoro-phenyl)-1a,2,5,5a-tetrahydro-1H-2,3-diaza-cyclopropa[a]pentalen-4-yl]-(3-trifluoromethyl-5,6-dihydro-8H-[1,2,4]triazolo[4,3-a]pyrazin-7-yl)-methanone; Compound 276: (1aR,5aR)-2-(2,4-Difluoro-phenyl)-1a,2,5,5a-tetrahydro-1H-2,3-diaza-cyclopropa[a]pentalene-4-carboxylic acid (5-methyl-thiazol-2-yl)-amide; Compound 277: [(1aR,5aR)-2-(2,4-Difluoro-phenyl)-1a,2,5,5a-tetrahydro-1H-2,3-diaza-cyclopropa[a]pentalen-4-yl]-(4-morpholin-4-yl-piperidin-1-yl)-methanone; Compound 278: 1-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclopropanecarboxylic acid methyl ester; Compound 279: (1aS,5aS)-2-(6'-Methyl-[3,3']bipyridinyl-6-yl)-1a,2,5,5a-tetrahydro-1H-2,3-diaza-cyclopropa[a]pentalene-4-carboxylic acid (2-hydroxy-1,1-dimethyl-ethyl)-amide; Compound 280: (1aR,5aR)-2-(2,4-Difluoro-phenyl)-1a,2,5,5a-tetrahydro-1H-2,3-diaza-cyclopropa[a]pentalene-4-carboxylic acid (3R)-(1-aza-bicyclo[2.2.2]oct-3-yl)-amide; Compound 281: (1aR,5aR)-2-(2,4-Difluoro-phenyl)-1a,2,5,5a-tetrahydro-1H-2,3-diaza-cyclopropa[a]pentalene-4-carboxylic acid (6-trifluoromethyl-pyridin-3-yl)-amide; Compound 282: (1aR,5aR)-2-(2-Fluoro-4-methanesulfonyl-phenyl)-1a,2,5,5a-tetrahydro-1H-2,3-diaza-cyclopropa[a]pentalene-4-carboxylic acid (1-phenyl-cyclopropyl)-amide; Compound 283: (1aR,5aR)-2-(5-Methyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 284: (1aR,5aR)-2-(2,4-Difluoro-phenyl)-1a,2,5,5a-tetrahydro-1H-2,3-diaza-cyclopropa[a]pentalene-4-carboxylic acid (5-hydroxy-1H-pyrazol-3-yl)-amide; Compound 285: (1aR,5aR)-2-(2,4-Difluoro-phenyl)-1a,2,5,5a-tetrahydro-1H-2,3-diaza-cyclopropa[a]pentalene-4-carboxylic acid (2-thiomorpholin-4-yl-ethyl)-amide; Compound 286: (1aR,5aR)-2-(2,4-Dichloro-phenyl)-1a,2,5,5a-tetrahydro-1H-2,3-diaza-cyclopropa[a]pentalene-4-carboxylic acid (1-phenyl-cyclopropyl)-amide; Compound 287: (1aR,5aR)-2-(5-Bromo-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 288: (1aR,5aR)-2-(2,4-Difluoro-phenyl)-1a,2,5,5a-tetrahydro-1H-2,3-diaza-cyclopropa[a]pentalene-4-carboxylic acid (benzo[1,3]dioxol-5-ylmethyl)-amide; Compound 289: (1aR,5aR)-2-(2,4-Difluoro-phenyl)-1a,2,5,5a-tetrahydro-1H-2,3-diaza-cyclopropa[a]pentalene-4-carboxylic acid ((1S,2S)-2-amino-cyclohexyl)-amide; Compound 290: (1aS,5aS)-2-(2,4-Difluoro-phenyl)-1a,2,5,5a-tetrahydro-1H-2,3-diaza-cyclopropa[a]pentalene-4-carboxylic acid (3-dimethylamino-1-oxo-tetrahydro-1$\lambda^4$-thiophen-3-ylmethyl)-amide; Compound 291: (1aR,5aR)-2-(2,4-Difluoro-phenyl)-1a,2,5,5a-tetrahydro-1H-2,3-diaza-cyclopropa[a]pentalene-4-carboxylic acid (4-methyl-morpholin-2-ylmethyl)-amide; Compound 292: (1aR,5aR)-2-(2,4-Difluoro-phenyl)-1a,2,5,5a-tetrahydro-1H-2,3-diaza-cyclopropa[a]pentalene-4-carboxylic acid (3-methyl-pyridin-2-yl)-amide; Compound 293: (1aR,5aR)-2-(2,4-Difluoro-phenyl)-1a,2,5,5a-tetrahydro-1H-2,3-diaza-cyclopropa[a]pentalene-4-carboxylic acid ((1R,2S)-2-hydroxy-cyclohexylmethyl)-amide; Compound 294: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-phenyl)-cyclopropyl]-amide; Compound 295: (1aS,5aS)-2-(2,4-Difluoro-phenyl)-1a,2,5,5a-tetrahydro-1H-2,3-diaza-cyclopropa[a]pentalene-4-carboxylic acid ((R)-1-ethyl-pyrrolidin-2-ylmethyl)-amide; Compound 296: (R)-2-[((1aR,5aR)-2-tert-Butyl-1a,2,5,5a-tetrahydro-1H-2,3-diaza-cyclopropa[a]pentalene-4-carbonyl)-amino]-3-(4-fluoro-phenyl)-2-methyl-propionic acid; Compound 297: (1aR,5aR)-2-(2,4-Difluoro-phenyl)-1a,2,5,5a-tetrahydro-1H-2,3-diaza-cyclopropa[a]pentalene-4-carboxylic acid pyrazin-2-ylamide; Compound 298: (1aS,5aS)-2-(2,4-Difluoro-phenyl)-1a,2,5,5a-tetrahydro-1H-2,3-diaza-cyclopropa[a]pentalene-4-carboxylic acid (pyridin-2-ylmethyl)-amide; Compound 299: (1aR,5aR)-2-(5-Methyl-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 300: (1aR,5aR)-2-(5-Bromo-pyridin-2-yl)-1a,2,5,5a-tetrahydro-1H-2,3-diaza-cyclopropa[a]pentalene-4-carboxylic acid (1-hydroxymethyl-cyclopropyl)-amide; Compound 301: (1aR,5aR)-2-(3,5-Difluoro-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 302: (1aR,5aR)-2-(2,4-Difluoro-phenyl)-1a,2,5,5a-tetrahydro-1H-2,3-diaza-cyclopropa[a]pentalene-4-carboxylic acid pyridazin-3-ylamide; Compound 303: (1aR,5aR)-2-(2,4-Difluorophenyl)-1a,2,5,5a-tetrahydro-1H-2,3-diaza-cyclopropa[a]pentalene-4-carboxylic acid (4-pyridin-2-yl-thiazol-2-yl)-amide; Compound 304: (1aS,5aS)-2-(2,4-Difluoro-phenyl)-1a,2,5,5a-tetrahydro-1H-2,3-diaza-cyclopropa[a]pentalene-4-carboxylic acid [1-(2-methoxy-phenyl)-cyclopropyl]-amide; Compound 305: (1aR,5aR)-2-(6-Chloro-pyridazin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 306: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-piperidin-4-ylmethyl]-amide; Compound 307: (1aR,5aR)-2-(2,4-Difluoro-phenyl)-1a,2,5,5a-tetrahydro-1H-2,3-diaza-cyclopropa[a]pentalene-4-carboxylic acid (6-chloro-2-methyl-pyridin-3-yl)-amide; Compound 308: (1aR,5aR)-2-(2,4-Difluoro-phenyl)-1a,2,5,5a-tetrahydro-1H-2,3-diaza-cyclopropa[a]pentalene-4-carboxylic acid (6-hydroxy-pyridin-3-yl)-amide; Compound 309: (1aR,5aR)-2-(5-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 310: (1aR,5aR)-2-(2,4-Difluoro-phenyl)-1a,2,5,5a-tetrahydro-1H-2,3-diaza-cyclopropa[a]pentalene-4-carboxylic acid 3-trifluoromethoxy-benzylamide; Compound 311: (1aR,5aR)-2-(2,4-Difluoro-phenyl)-1a,2,5,5a-tetrahydro-1H-2,3-diaza-cyclopropa[a]pentalene-4-carboxylic acid (1-morpholin-4-yl-cyclopentylmethyl)-amide; Compound 312: (1aS,5aS)-2-(2,4-Difluoro-phenyl)-1a,2,5,5a-tetrahydro-1H-2,3-diaza-cyclopropa[a]pentalene-4-carboxylic acid (4-benzyl-morpholin-2-ylmethyl)-amide; Compound 313: (1aR,5aR)-2-(2,4-Difluoro-phenyl)-1a,2,5,5a-tetrahydro-1H-2,3-diaza-cyclopropa[a]pentalene-4-carboxylic acid (1-pyridin-2-yl-cyclobutylmethyl)-amide; Compound 314: (1aR,5aR)-2-(5-Ethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 315: (1aR,5aR)-2-(2,4-Difluoro-phenyl)-1a,2,5,5a-tetrahydro-1H-2,3-diaza-cyclopropa[a]pentalene-4-carboxylic acid (R)-indan-1-ylamide; Compound 316: (1aR,5aR)-2-(2,4-Difluoro-phenyl)-1a,2,5,5a-tetrahydro-1H-2,3-diaza-cyclopropa[a]pentalene-4-carboxylic acid ((S)-2-hydroxy-1-phenyl-ethyl)-amide; Compound 317: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 318: (1aR,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (1-phenyl-cyclopropyl)-amide; Compound 319: (1aR,5aR)-2-(6-Methoxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 320: [(1aR,5aR)-2-(2,4-Difluoro-phenyl)-1a,2,5,5a-tetrahydro-1H-2,3-diaza-cyclopropa[a]pentalen-4-yl]-(3,4-dihydro-1H-isoquinolin-2-yl)-methanone; Compound 321: (1aS,5aS)-2-(2,4-Difluoro-phenyl)-1a,2,5,5a-tetrahydro-1H-2,3-diaza-cyclopropa[a]pentalene-4-carboxylic acid (5-hydroxymethyl-pyridin-2-yl)-amide; Compound 322: (1aS,5aS)-2-(2,4-Difluoro-phenyl)-1a,2,5,5a-tetrahydro-1H-2,3-diaza-cyclopropa[a]pentalene-4-carboxylic acid (5-fluoro-1-oxy-pyridin-2-yl)-amide; Compound 323: (1aR,5aR)-2-(5-Trifluoromethyl-pyridin-2-yl)-1a,2,5,5a-tetrahydro-H-2,3-diaza-cyclopropa[a]pentalene-4-carboxylic acid (1-methyl-1-phenyl-ethyl)-amide; Compound 324: (1aR,5aR)-2-(5-Dimethylamino-pyridin-2-yl)-1a,2,5,5a-tetrahydro-H-2,3-diaza-cyclopropa[a]pentalene-4-carboxylic acid (2-hydroxy-1,1-dimethyl-ethyl)-amide; Compound 325: (1aR,5aR)-2-tert-Butyl-1a,2,5,5a-tetrahydro-1H-2,3-diaza-cyclopropa[a]pentalene-4-carboxylic acid (1-methyl-1-phenyl-ethyl)-amide; Compound 326: (1aR,5aR)-2-(2,4-Difluoro-phenyl)-1a,2,5,5a-tetrahydro-1H-2,3-diaza-cyclopropa[a]pentalene-4-carboxylic acid (6-methoxy-pyridin-2-yl)-amide; Compound 327: [(1aR,5aR)-2-(2,4-Difluoro-phenyl)-1a,2,5,5a-tetrahydro-1H-2,3-diaza-cyclopropa[a]pentalen-4-yl]-[4-(3-methoxy-pyridin-2-yl)-piperazin-1-yl]-methanone; Compound 328: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-pyridin-3-yl-ethyl)-amide; Compound 329: (1aR,5aR)-2-(5-Cyano-pyridin-2-yl)-1a,2,5,5a-tetrahydro-1H-2,3-diaza-cyclopropa[a]pentalene-4-carboxylic acid (1-phenyl-cyclopropyl)-amide; Compound 330: [(1aR,5aR)-2-(2,4-Difluoro-phenyl)-1a,2,5,5a-tetrahydro-1H-2,3-diaza-cyclopropa[a]pentalen-4-yl]-(3-hydroxy-piperidin-1-yl)-methanone; Compound 331: (1aR,5aR)-2-(2,4-Difluoro-phenyl)-1a,2,5,5a-tetrahydro-1H-2,3-diaza-cyclopropa[a]pentalene-4-carboxylic acid (6-methyl-pyridin-3-yl)-amide; Compound 332: (1aR,5aR)-2-(5-Chloro-pyridin-2-yl)-1a,2,5,5a-tetrahydro-1H-2,3-diaza-cyclopropa[a]pentalene-4-carboxylic acid (1-methyl-1-phenyl-ethyl)-amide; Compound 333: (1aR,5aR)-2-(2,4-Difluoro-phenyl)-1a,2,5,5a-tetrahydro-1H-2,3-diaza-cyclopropa[a]pentalene-4-carboxylic acid ((1R,2R)-2-hydroxy-1-hydroxymethyl-propyl)-amide; Compound 334: (1aR,5aR)-2-(2,4-Difluoro-phenyl)-1a,2,5,5a-tetrahydro-1H-2,3-diaza-cyclopropa[a]pentalene-4-carboxylic acid pyridin-2-ylamide; Compound 335: (1aR,5aR)-2-(2,4-Difluoro-phenyl)-1a,2,5,5a-tetrahydro-1H-2,3-diaza-cyclopropa[a]pentalene-4-carboxylic acid (2-chloro-pyridin-3-yl)-amide; Compound 336: (1aR,5aR)-2-(2-Hydroxy-2-methyl-propyl)-1a,2,5,5a-tetrahydro-1H-2,3-diaza-cyclopropa[a]pentalene-4-carboxylic acid (tetrahydro-pyran-4-ylmethyl)-amide; Compound 337: (1aR,5aR)-2-(5-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 338: (1aR,5aR)-2-(2,4-Difluoro-phenyl)-1a,2,5,5a-tetrahydro-1H-2,3-diaza-cyclopropa[a]pentalene-4-carboxylic acid (3-methyl-3H-imidazol-4-ylmethyl)-amide; Compound 339: (1aS,5aS)-2-(2,4-Difluoro-phenyl)-1a,2,5,5a-tetrahydro-1H-2,3-diaza-cyclopropa[a]pentalene-4-carboxylic acid (6-fluoro-pyridin-2-yl)-amide; Compound 340: 1-(2,4-Difluoro-phenyl)-3b,4,4a,5-tetrahydro-1H-cyclopropa[3,4]cyclopenta[1,2-c]pyrazole-3-carboxylic acid (1-methyl-1-pyridin-4-yl-ethyl)-amide; Compound 341: (1aR,5aR)-2-(6-Bromo-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 342: (1aR,5aR)-2-[1-(4-Fluoro-phenyl)-1-methyl-ethyl]-1a,2,5,5a-tetrahydro-1H-2,3-diaza-cyclopropa[a]pentalene-4-carboxylic acid (1-methyl-1-pyridin-4-yl-ethyl)-amide; Compound 343: (1aR,5aR)-2-(2,4-Difluoro-phenyl)-1a,2,5,5a-tetrahydro-1H-2,3-diaza-cyclopropa[a]pentalene-4-carboxylic acid 3-dimethylamino-benzylamide; Compound 344: (1aR,5aR)-2-(2,4-Difluoro-phenyl)-1a,2,5,5a-tetrahydro-1H-2,3-diaza-cyclopropa[a]pentalene-4-carboxylic acid (6-morpholin-4-yl-pyridin-3-yl)-amide; Compound 345: (1aR,5aR)-2-(2,4-Difluoro-phenyl)-1a,2,5,5a-tetrahydro-1H-2,3-diaza-cyclopropa[a]pentalene-4-carboxylic acid (1-o-tolyl-cyclopropyl)-amide; Compound 346: (1aS,5aS)-2-Phenyl-1a,2,5,5a-tetrahydro-H-2,3-diaza-cyclopropa[a]pentalene-4-carboxylic acid (2-hydroxy-1,1-dimethyl-ethyl)-amide; Compound 347: ((1aR,5aR)-2-tert-Butyl-1a,2,5,5a-tetrahydro-1H-2,3-diaza-cyclopropa[a]pentalen-4-yl)-[4-(3-chloro-phenyl)-piperazin-1-yl]-methanone; Compound 348: (1aR,5aR)-2-(2,4-Difluoro-phenyl)-1a,2,5,5a-tetrahydro- 1H-2,3-diaza-cyclopropa[a]pentalene-4-carboxylic acid [(R)-1-(3,3,3-trifluoro-propyl)-piperidin-3-yl]-amide; Compound 349: (1aR,5aR)-2-(2,4-Difluoro-phenyl)-1a,2,5,5a-tetrahydro-1H-2,3-diaza-cyclopropa[a]pentalene-4-carboxylic acid (6-methanesulfonyl-4-methyl-pyridin-3-yl)-amide; Compound 350: (1aR,5aR)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-4-yl-ethyl)-amide; Compound 351: (1aS,5aS)-2-(5-Bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 352: (1aR,5aR)-2-Pyridin-2-yl-1a,2,5,5a-tetrahydro-1H-2,3-diaza-cyclopropa[a]pentalene-4-carboxylic acid (1-methyl-1-phenyl-ethyl)-amide; Compound 353: (1aR,5aR)-2-(2,4-Difluoro-phenyl)-1a,2,5,5a-tetrahydro-1H-2,3-diaza-cyclopropa[a]pentalene-4-carboxylic acid (5-methyl-pyridin-2-yl)-amide; Compound 354: (1aR,5aR)-2-(2,4-Difluoro-phenyl)-1a,2,5,5a-tetrahydro-1H-2,3-diaza-cyclopropa[a]pentalene-4-carboxylic acid (2-methyl-quinolin-4-yl)-amide; Compound 355: (1aS,5aS)-2-(2,4-Difluoro-phenyl)-1a,2,5,5a-tetrahydro-1H-2,3-diaza-cyclopropa[a]pentalene-4-carboxylic acid (1-pyridin-4-yl-cyclobutyl)-amide; Compound 356: (1aS,5aS)-2-(5-Pyrimidin-5-yl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 357: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-pyrrolidin-3-ylmethyl]-amide; Compound 358: (1aR,5aR)-2-(2,4-Difluoro-phenyl)-1a,2,5,5a-tetrahydro-1H-2,3-diaza-cyclopropa[a]pentalene-4-carboxylic acid benzooxazol-2-ylamide; Compound 359: (1aR,5aR)-2-(2,4-Difluoro-phenyl)-1a,2,5,5a-tetrahydro-1H-2,3-diaza-cyclopropa[a]pentalene-4-carboxylic acid (1-pyridin-4-yl-cyclopropyl)-amide; Compound 360: (1aS,5aS)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 361: (1aR,5aR)-2-(2,4-Difluoro-phenyl)-1a,2,5,5a-tetrahydro-1H-2,3-diaza-cyclopropa[a]pentalene-4-carboxylic acid (1-methyl-piperidin-4-ylmethyl)-amide; Compound 362: (1aR,5aR)-2-(2,4-Difluoro-phenyl)-1a,2,5,5a-tetrahydro-1H-2,3-diaza-cyclopropa[a]pentalene-4-carboxylic acid (tetrahydro-pyran-4-ylmethyl)-amide; Compound 363: (1aR,5aR)-2-Pyridin-4-yl-1a,2,5,5a-tetrahydro-1H-2,3-diaza-cyclopropa[a]pentalene-4-carboxylic acid (5-fluoro-pyridin-2-yl)-amide; Compound 364: (1aS,5aS)-2-(2,4-Difluoro-phenyl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 365: (1aR,5aR)-2-(4-Methyl-pyridin-2-yl)-1a,2,5,5a-tetrahydro-H-2,3-diaza-cyclopropa[a]pentalene-4-carboxylic acid (2-hydroxy-1,1-dimethyl-ethyl)-amide; Compound 366: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-pyridin-2-yl-ethyl)-amide; Compound 367: (1aR,5aR)-2-(2,4-Difluoro-phenyl)-1a,2,5,5a-tetrahydro-1H-2,3-diaza-cyclopropa[a]pentalene-4-carboxylic acid [2-(2,6-dimethyl-morpholin-4-yl)-2-methyl-propyl]-amide; Compound 368: (3bS,4aR,5R)-1-(2,4-Difluoro-phenyl)-3b-isopropyl-5-methyl-3b,4,4a,5-tetrahydro-1H-cyclopropa[3,4]cyclopenta[1,2-c]pyrazole-3-carboxylic acid ((1S,2S)-2-hydroxy-indan-1-yl)-amide; Compound 369: (1aR,5aR)-2-(2,4-Difluoro-phenyl)-1a,2,5,5a-tetrahydro-1H-2,3-diaza-cyclopropa[a]pentalene-4-carboxylic acid (1-methyl-piperidin-2-ylmethyl)-amide; Compound 370: (1aR,5aR)-2-(2,4-Difluoro-phenyl)-1a,2,5,5a-tetrahydro-1H-2,3-diaza-cyclopropa[a]pentalene-4-carboxylic acid (pyridin-4-ylmethyl)-amide; Compound 371: (1aR,5aR)-2-(2,4-Difluoro-phenyl)-1a,2,5,5a-tetrahydro-1H-2,3-diaza-cyclopropa[a]pentalene-4-carboxylic acid (4-hydroxymethyl-pyridin-2-yl)-amide; Compound 372: (1aR,5aR)-2-(2,4-Difluoro-phenyl)-1a,2,5,5a-tetrahydro-1H-2,3-diaza-cyclopropa[a]pentalene-4-carboxylic acid (5,7-dimethyl-pyrazolo[1,5-a]pyrimidin-2-yl)-amide; Compound 373: (1aR,5aR)-2-(4-Cyano-phenyl)-1a,2,5,5a-tetrahydro-H-2,3-diaza-cyclopropa[a]pentalene-4-carboxylic acid tert-butylamide; Compound 374: (1aR,5aR)-2-(5-Methoxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 375: (1aR,5aR)-2-tert-Butyl-1a,2,5,5a-tetrahydro-1H-2,3-diaza-cyclopropa[a]pentalene-4-carboxylic acid ((1S,2S,5S)-6,6-dimethyl-bicyclo[3.1.1]hept-2-ylmethyl)-amide; Compound 376: (1aR,5aR)-2-(2,4-Difluoro-phenyl)-1a,2,5,5a-tetrahydro-1H-2,3-diaza-cyclopropa[a]pentalene-4-carboxylic acid [(S)-1-(2-methoxy-ethyl)-pyrrolidin-3-yl]-amide; Compound 377: (1aR,5aR)-2-(2,4-Difluoro-phenyl)-1a,2,5,5a-tetrahydro-1H-2,3-diaza-cyclopropa[a]pentalene-4-carboxylic acid [1-(5-methyl-pyridin-2-yl)-ethyl]-amide; Compound 378: (1aR,5aR)-2-(2,4-Difluoro-phenyl)-1a,2,5,5a-tetrahydro-1H-2,3-diaza-cyclopropa[a]pentalene-4-carboxylic acid [2-hydroxy-1-(tetrahydro-furan-3-yl)-ethyl]-amide; Compound 379: (1aS,5aS)-2-(5-Chloro-pyridin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 380: [(1aR,5aR)-2-(2,4-Difluoro-phenyl)-1a,2,5,5a-tetrahydro-1H-2,3-diaza-cyclopropa[a]pentalen-4-yl]-(6-methoxy-3,4-dihydro-1H-isoquinolin-2-yl)-methanone; Compound 381: [(1aR,5aR)-2-(2,4-Difluoro-phenyl)-1a,2,5,5a-tetrahydro-1H-2,3-diaza-cyclopropa[a]pentalen-4-yl]-morpholin-4-yl-methanone; Compound 382: (1aR,5aR)-2-(5-Chloro-pyridin-2-yl)-1a,2,5,5a-tetrahydro-1H-2,3-diaza-cyclopropa[a]pentalene-4-carboxylic acid (tetrahydro-pyran-4-ylmethyl)-amide; Compound 383: (1aR,5aR)-2-(4-Fluoro-phenyl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 384: (S)-3-{[(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1-carboxylic acid tert-butyl ester; Compound 385: (1aR,5aR)-2-(2,4-Difluoro-phenyl)-1a,2,5,5a-tetrahydro-1H-2,3-diaza-cyclopropa[a]pentalene-4-carboxylic acid (2-fluoro-pyridin-3-yl)-amide; Compound 386: (1aR,5aR)-2-(Tetrahydro-pyran-4-ylmethyl)-1a,2,5,5a-tetrahydro-1H-2,3-diaza-cyclopropa[a]pentalene-4-carboxylic acid (1-methyl-1-phenyl-ethyl)-amide; Compound 387: (1aR,5aR)-2-Pyrazin-2-yl-1a,2,5,5a-tetrahydro-1H-2,3-diaza-cyclopropa[a]pentalene-4-carboxylic acid (2-hydroxy-1,1-dimethyl-ethyl)-amide; Compound 388: (1aR,5aR)-2-(2,4-Difluoro-phenyl)-1a,2,5,5a-tetrahydro-1H-2,3-diaza-cyclopropa[a]pentalene-4-carboxylic acid morpholin-4-ylamide; Compound 389: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-2-pyridin-4-yl-ethyl)-amide; Compound 390: 1-(2,4-Difluoro-phenyl)-3b,4,4a,5-tetrahydro-1H-cyclopropa[3,4]cyclopenta[1,2-c]pyrazole-3-carboxylic acid ((1S,2S)-2-hydroxy-indan-1-yl)-amide; Compound 391: (1aR,5aR)-2-(2-Fluoro-phenyl)-1a,2,5,5a-tetrahydro-1H-2,3-diaza-cyclopropa[a]pentalene-4-carboxylic acid (1-phenyl-cyclopropyl)-amide; Compound 392: (1aR,5aR)-2-(2,4-Difluoro-phenyl)-1a,2,5,5a-tetrahydro-1H-2,3-diaza-cyclopropa[a]pentalene-4-carboxylic acid pyridin-4-ylamide; Compound 393: (1aR,5aR)-2-(2,4-Difluorophenyl)-1a,2,5,5a-tetrahydro-1H-2,3-diaza-cyclopropa[a]pentalene-4-carboxylic acid (4-hydroxy-pyridin-2-yl)-amide; Compound 394: (S)-3-{[(1aS,5aS)-2-(2,4-Difluoro-phenyl)-1a,2,5,5a-tetrahydro-H-2,3-diaza-cyclopropa[a]pentalene-4-carbonyl]-amino}-3-pyridin-3-yl-propionic acid; Compound 395: (1aR,5aR)-2-(5-Chloro-pyridin-2-yl)-1a,2,5,5a-tetrahydro-H-2,3-diaza-cyclopropa[a]pentalene-4-carboxylic acid [1-(4-fluoro-phenyl)-cyclopropyl]-amide; Compound 396: (1aS,5aS)-2-(5-Propyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 397: (1aR,5aR)-2-(2,4-Difluoro-phenyl)-1a,2,5,5a-tetrahydro-1H-2,3-diaza-cyclopropa[a]pentalene-4-carboxylic acid 3-methoxy-benzylamide; Compound 398: (1aS,5aS)-2-(2,4-Difluoro-phenyl)-1a,2,5,5a-tetrahydro-1H-2,3-diaza-cyclopropa[a]pentalene-4-carboxylic acid (5-fluoro-pyridin-2-yl)-amide; Compound 399: (1aS,5aS)-2-(2,4-Difluoro-phenyl)-1a,2,5,5a-tetrahydro-1H-2,3-diaza-cyclopropa[a]pentalene-4-carboxylic acid (1-oxy-pyridin-2-yl)-amide; Compound 400: (1aR,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (tetrahydro-pyran-4-ylmethyl)-amide; Compound 401: (1aR,5aR)-2-(6-Chloro-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 402: (1aR,5aR)-2-(2,4-Difluoro-phenyl)-1a,2,5,5a-tetrahydro-1H-2,3-diaza-cyclopropa[a]pentalene-4-carboxylic acid (1-ethyl-propyl)-amide; Compound 403: 6-{[(1aR,5aR)-2-(2,4-Difluoro-phenyl)-1a,2,5,5a-tetrahydro-1H-2,3-diaza-cyclopropa[a]pentalene-4-carbonyl]-amino}-pyridine-2-carboxylic acid; Compound 404: (1aS,5aS)-2-(2,4-Difluoro-phenyl)-1a,2,5,5a-tetrahydro-1H-2,3-diaza-cyclopropa[a]pentalene-4-carboxylic acid (3-cyano-5-methyl-pyridin-2-yl)-amide; Compound 405: [(1aR,5aR)-2-(2,4-Difluoro-phenyl)-1a,2,5,5a-tetrahydro-1H-2,3-diaza-cyclopropa[a]pentalen-4-yl]-((S)-2-hydroxymethyl-pyrrolidin-1-yl)-methanone; Compound 406: (1aS,5aS)-2-(5-m-Tolyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 407: (1aR,5aR)-2-(2,4-Difluoro-phenyl)-1a,2,5,5a-tetrahydro-1H-2,3-diaza-cyclopropa[a]pentalene-4-carboxylic acid (5-fluoro-2-methoxy-phenyl)-amide; Compound 408: (1aS,5aS)-2-(2,4-Difluoro-phenyl)-1a,2,5,5a-tetrahydro-1H-2,3-diaza-cyclopropa[a]pentalene-4-carboxylic acid (tetrahydro-pyran-4-ylmethyl)-amide; Compound 409: (1aR,5aR)-2-(4-Fluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 410: (1aR,5aR)-2-(2,4-Difluoro-phenyl)-1a,2,5,5a-tetrahydro-1H-2,3-diaza-cyclopropa[a]pentalene-4-carboxylic acid (1,2,2,6,6-pentamethyl-piperidin-4-yl)-amide; Compound 411: (1aR,5aR)-2-(2,4-Difluoro-phenyl)-1a,2,5,5a-tetrahydro-1H-2,3-diaza-cyclopropa[a]pentalene-4-carboxylic acid (6-methoxy-pyridin-3-yl)-amide; Compound 412: (1aR,5aR)-2-Pyridin-4-yl-1a,2,5,5a-tetrahydro-1H-2,3-diaza-cyclopropa[a]pentalene-4-carboxylic acid cyclopentyl-amide; Compound 413: (1aR,5aR)-2-(2,4-Difluoro-phenyl)-1a,2,5,5a-tetrahydro-1H-2,3-diaza-cyclopropa[a]pentalene-4-carboxylic acid (morpholin-2-ylmethyl)-amide; Compound 414: (1aR,5aR)-2-(5-Hydroxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 415: 3-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-azetidine-1-carboxylic acid tert-butyl ester; Compound 416: (1aR,5aR)-2-(2,4-Difluoro-phenyl)-1a,2,5,5a-tetrahydro-1H-2,3-diaza-cyclopropa[a]pentalene-4-carboxylic acid (2-dimethylamino-2-pyridin-3-yl-ethyl)-amide; Compound 417: (1aR,5aR)-2-(4-Methoxy-phenyl)-1a,2,5,5a-tetrahydro-1H-2,3-diaza-cyclopropa[a]pentalene-4-carboxylic acid (tetrahydro-pyran-4-ylmethyl)-amide; Compound 418: (1aR,5aR)-2-(2,4-Difluoro-phenyl)-1a,2,5,5a-tetrahydro-1H-2,3-diaza-cyclopropa[a]pentalene-4-carboxylic acid [1-(4-methoxy-phenyl)-cyclobutyl]-amide; Compound 419: (1aR,5aR)-2-(2,4-Difluoro-phenyl)-1a,2,5,5a-tetrahydro-1H-2,3-diaza-cyclopropa[a]pentalene-4-carboxylic acid 3-hydroxy-benzylamide; Compound 420: (1aS,5aS)-2-(2,4-Difluoro-phenyl)-1a,2,5,5a-tetrahydro-1H-2,3-diaza-cyclopropa[a]pentalene-4-carboxylic acid (6-methoxy-pyridin-2-yl)-amide; Compound 421: (1aR,5aR)-2-(2,4-Difluoro-phenyl)-1a,2,5,5a-tetrahydro-1H-2,3-diaza-cyclopropa[a]pentalene-4-carboxylic acid [(R)-1-(tetrahydro-furan-2-yl)methyl]-amide; Compound 422: 2-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-morpholine-4-carboxylic acid tert-butyl ester; Compound 423: (1aR,5aR)-2-(5-Cyclopropyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 424: (1aR,5aR)-2-tert-Butyl-1a,2,5,5a-tetrahydro-1H-2,3-diaza-cyclopropa[a]pentalene-4-carboxylic acid (1,1-dimethyl-2-morpholin-4-yl-ethyl)-amide; Compound 425: [(1aR,5aR)-2-(2,4-Difluoro-phenyl)-1a,2,5,5a-tetrahydro-1H-2,3-diaza-cyclopropa[a]pentalen-4-yl]-(1,3-dihydro-pyrrolo[3,4-c]pyridin-2-yl)-methanone; Compound 426: (R)-2-{[(1aR,5aR)-2-(2,4-Difluoro-phenyl)-1a,2,5,5a-tetrahydro-H-2,3-diaza-cyclopropa[a]pentalene-4-carbonyl]-amino}-3-phenyl-propionic acid methyl ester; Compound 427: (1aR,5aR)-2-(2,4-Difluoro-phenyl)-1a,2,5,5a-tetrahydro-1H-2,3-diaza-cyclopropa[a]pentalene-4-carboxylic acid [1-(3-fluoro-phenyl)-cyclopropyl]-amide; Compound 428: (1aR,5aR)-2-(2,6-Difluoro-phenyl)-1a,2,5,5a-tetrahydro-H-2,3-diaza-cyclopropa[a]pentalene-4-carboxylic acid (2-hydroxy-1,1-dimethyl-ethyl)-amide; Compound 429: (R)-3-{[(1aR,5aR)-2-(2,4-Difluoro-phenyl)-1a,2,5,5a-tetrahydro-1H-2,3-diaza-cyclopropa[a]pentalene-4-carbonyl]-amino}-pyrrolidine-1-carboxylic acid tert-butyl ester; Compound 430: (1aR,5aR)-2-(2,4-Difluoro-phenyl)-1a,2,5,5a-tetrahydro-1H-2,3-diaza-cyclopropa[a]pentalene-4-carboxylic acid (2-o-tolyl-ethyl)-amide; Compound 431: (1aS,5aS)-2-(2,4-Difluoro-phenyl)-1a,2,5,5a-tetrahydro-1H-2,3-diaza-cyclopropa[a]pentalene-4-carboxylic acid (3-hydroxymethyl-1-isobutyl-pyrrolidin-3-yl)-amide; Compound 432: (1aR,5aR)-2-(3-Fluoro-pyridin-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 433: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-ethyl)-azetidin-3-yl]-amide; Compound 434: (1aR,5aR)-2-(2,4-Difluoro-phenyl)-1a,2,5,5a-tetrahydro-1H-2,3-diaza-cyclopropa[a]pentalene-4-carboxylic acid (6-morpholin-4-yl-pyridin-2-ylmethyl)-amide; Compound 435: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-2-yl-ethyl)-amide; Compound 436: (1aR,5aR)-2-(2,4-Difluoro-phenyl)-1a,2,5,5a-tetrahydro-1H-2,3-diaza-cyclopropa[a]pentalene-4-carboxylic acid (1,1-dioxo-tetrahydro-1$\lambda^6$-thiophen-3-ylmethyl)-amide; Compound 437: (1aR,5aR)-2-(2,4-Difluoro-phenyl)-1a,2,5,a-tetrahydro-1H-2,3-diaza-cyclopropa[a]pentalene-4-carboxylic acid [2-(4-fluoro-phenoxy)-ethyl]-amide; Compound 438: (1aR,5aR)-2-(2,4-Difluoro-phenyl)-1a,2,5,5a-tetrahydro-1H-2,3-diaza-cyclopropa[a]pentalene- 4-carboxylic acid (3-chloro-5-methyl-pyridin-2-yl)-amide; Compound 439: (1aS,5aS)-2-(2,4-Difluoro-phenyl)-1a,2,5,5a-tetrahydro-1H-2,3-diaza-cyclopropa[a]pentalene-4-carboxylic acid (1,1-dimethyl-2-morpholin-4-yl-ethyl)-amide; Compound 440: (1aR,5aR)-2-(2,4-Difluoro-phenyl)-1a,2,5,5a-tetrahydro-1H-2,3-diaza-cyclopropa[a]pentalene-4-carboxylic acid (1-hydroxymethyl-cyclopropyl)-amide; Compound 441: (1aR,5aR)-2-(5-Isopropyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 442: (1aR,5aR)-2-(2,4-Difluoro-phenyl)-1a,2,5,5a-tetrahydro-1H-2,3-diaza-cyclopropa[a]pentalene-4-carboxylic acid (pyridin-2-ylmethyl)-amide; Compound 443: (1aR,5aR)-2-(2,4-Difluoro-phenyl)-1a,2,5,5a-tetrahydro-1H-2,3-diaza-cyclopropa[a]pentalene-4-carboxylic acid (2,6-dimethyl-pyrimidin-4-yl)-amide; Compound 444: (1aR,5aR)-2-(2,4-Difluoro-phenyl)-1a,2,5,5a-tetrahydro-1H-2,3-diaza-cyclopropa[a]pentalene-4-carboxylic acid [(S)-1-hydroxymethyl-2-(3H-imidazol-4-yl)-ethyl]-amide; Compound 445: (1aR,5aR)-2-(2,4-Difluoro-phenyl)-1a,2,5,5a-tetrahydro-1H-2,3-diaza-cyclopropa[a]pentalene-4-carboxylic acid ((R)-2-hydroxy-1-pyridin-3-yl-ethyl)-amide; Compound 446: (1aR,5aR)-2-(5-Bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 447: (1aR,5aR)-2-(2,4-Difluoro-phenyl)-1a,2,5,5a-tetrahydro-1H-2,3-diaza-cyclopropa[a]pentalene-4-carboxylic acid 4-methanesulfonyl-benzylamide; Compound 448: (1aR,5aR)-2-(2,4-Difluoro-phenyl)-1a,2,5,5a-tetrahydro-1H-2,3-diaza-cyclopropa[a]pentalene-4-carboxylic acid (6-fluoro-pyridin-2-yl)-amide; Compound 449: (1aS,5aS)-2-(2,4-Difluoro-phenyl)-1a,2,5,5a-tetrahydro-1H-2,3-diaza-cyclopropa[a]pentalene-4-carboxylic acid ((1R,2R)-2-hydroxy-indan-1-yl)-amide; Compound 450: (1aS,5aS)-2-(2,4-Difluoro-phenyl)-1a,2,5,5a-tetrahydro-1H-2,3-diaza-cyclopropa[a]pentalene-4-carboxylic acid (1-pyridin-3-yl-cyclopropyl)-amide; Compound 451: (1aR,5aR)-2-(5-Propyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 452: [(1aR,5aR)-2-(2,4-Difluoro-phenyl)-1a,2,5,5a-tetrahydro-1H-2,3-diaza-cyclopropa[a]pentalen-4-yl]-(3-pyridin-4-yl-pyrrolidin-1-yl)-methanone; Compound 453: (1aR,5aR)-2-(2,4-Difluoro-phenyl)-1a,2,5,5a-tetrahydro-1H-2,3-diaza-cyclopropa[a]pentalene-4-carboxylic acid (5-hydroxymethyl-pyridin-2-yl)-amide; Compound 454: [(1aR,5aR)-2-(2,4-Difluoro-phenyl)-1a,2,5,5a-tetrahydro-1H-2,3-diaza-cyclopropa[a]pentalen-4-yl]-[4-(pyridin-2-yloxy)-piperidin-1-yl]-methanone; Compound 455: (1aR,5aR)-2-(2,4-Difluoro-phenyl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 456: (1aS,5aS)-2-[5-(2,4-Difluoro-phenyl)-pyridin-2-yl]-1a,2,5,5a-tetrahydro-1H-2,3-diaza-cyclopropa[a]pentalene-4-carboxylic acid (2-hydroxy-1,1-dimethyl-ethyl)-amide; Compound 457: (1aR,5aR)-2-(2,4-Difluoro-phenyl)-1a,2,5,5a-tetrahydro-1H-2,3-diaza-cyclopropa[a]pentalene-4-carboxylic acid (9-methyl-9-aza-bicyclo[3.3.1]non-1-yl)-amide; Compound 458: (1aR,5aR)-2-(2,4-Difluoro-phenyl)-1a,2,5,5a-tetrahydro-1H-2,3-diaza-cyclopropa[a]pentalene-4-carboxylic acid (2,6-dimethyl-pyridin-3-yl)-amide; Compound 459: (1aR,5aR)-2-(2-Fluoro-4-methanesulfonyl-phenyl)-1a,2,5,5a-tetrahydro-1H-2,3-diaza-cyclopropa[a]pentalene-4-carboxylic acid (tetrahydro-pyran-4-ylmethyl)-amide; Compound 460: (1aR,5aR)-2-(2-Fluoro-phenyl)-a,2,55a-tetrahydro-1H-2,3-diaza-cyclopropa[a]pentalene-4-carboxylic acid ((S)-2-hydroxy-1-phenyl-ethyl)-amide; Compound 461: (1aR,5aR)-2-(2,4-Difluoro-phenyl)-1a,2,5,5a-tetrahydro-1H-2,3-diaza-cyclopropa[a]pentalene-4-carboxylic acid 4-hydroxy-benzylamide; Compound 462: (1aR,5aR)-2-(2,4-Difluoro-phenyl)-1a,2,5,5a-tetrahydro-1H-2,3-diaza-cyclopropa[a]pentalene-4-carboxylic acid (2-oxo-2-phenyl-ethyl)-amide; Compound 463: (1aR,5aR)-2-(2,4-Difluoro-phenyl)-1a,2,5,5a-tetrahydro-1H-2,3-diaza-cyclopropa[a]pentalene-4-carboxylic acid tert-butylamide; Compound 464: (1aR,5aR)-2-(5-Bromo-pyridin-2-yl)-1a,2,5,5a-tetrahydro-1H-2,3-diaza-cyclopropa[a]pentalene-4-carboxylic acid (tetrahydro-pyran-4-ylmethyl)-amide; Compound 465: (1aR,5aR)-2-(2,4-Difluoro-phenyl)-1a,2,5,5a-tetrahydro-1H-2,3-diaza-cyclopropa[a]pentalene-4-carboxylic acid (1-methyl-1H-pyrazol-3-ylmethyl)-amide; Compound 466: (1aR,5aR)-2-(2,4-Difluoro-phenyl)-1a,2,5,5a-tetrahydro-1H-2,3-diaza-cyclopropa[a]pentalene-4-carboxylic acid ((S)-1-pyridin-2-yl-ethyl)-amide; Compound 467: (1aR,5aR)-2-Pyridin-2-yl-1a,2,5,5a-tetrahydro-1H-2,3-diaza-cyclopropa[a]pentalene-4-carboxylic acid (1-phenyl-cyclopropyl)-amide; Compound 468: (1aR,5aR)-2-(6-Bromo-pyridin-3-yl)-1a,2,5,5a-tetrahydro-1H-2,3-diaza-cyclopropa[a]pentalene-4-carboxylic acid (1,1-dimethyl-2-morpholin-4-yl-ethyl)-amide; Compound 469: [(1aR,5aR)-2-(2,4-Difluoro-phenyl)-1a,2,5,5a-tetrahydro-1H-2,3-diaza-cyclopropa[a]pentalen-4-yl]-(3-pyridin-2-yl-pyrrolidin-1-yl)-methanone; Compound 470: (1aR,5aR)-2-(2,4-Difluoro-phenyl)-1a,2,5,5a-tetrahydro-1H-2,3-diaza-cyclopropa[a]pentalene-4-carboxylic acid ((1R,2R)-2-amino-cyclohexyl)-amide; Compound 471: (1aS,5aS)-2-(2,4-Difluoro-phenyl)-1a,2,5,5a-tetrahydro-1H-2,3-diaza-cyclopropa[a]pentalene-4-carboxylic acid ((R)-1-pyridin-2-yl-ethyl)-amide; Compound 472: (1aR,5aR)-2-Pyridin-2-yl-1a,2,5,5a-tetrahydro-1H-2,3-diaza-cyclopropa[a]pentalene-4-carboxylic acid (1-pyridin-2-yl-cyclopropyl)-amide; Compound 473: (1aS,5aS)-2-(5-Cyclopentyl-pyridin-2-yl)-1a,2,5,5a-tetrahydro-H-2,3-diaza-cyclopropa[a]pentalene-4-carboxylic acid (2-hydroxy-1,1-dimethyl-ethyl)-amide; Compound 474: (1aR,5aR)-2-(2,4-Difluoro-phenyl)-1a,2,5,5a-tetrahydro-1H-2,3-diaza-cyclopropa[a]pentalene-4-carboxylic acid pyrimidin-2-ylamide; Compound 475: (1aR,5aR)-2-(2,4-Difluoro-phenyl)-1a,2,55a-tetrahydro-1H-2,3-diaza-cyclopropa[a]pentalene-4-carboxylic acid (5-methyl-pyrazin-2-yl)-amide; Compound 476: (1aR,5aR)-2-o-Tolyl-1a,2,5,5a-tetrahydro-1H-2,3-diaza-cyclopropa[a]pentalene-4-carboxylic acid (2-hydroxy-1,1-dimethyl-ethyl)-amide; Compound 477: (1aR,5aR)-2-(4-Fluoro-benzyl)-1a,2,5,5a-tetrahydro-H-2,3-diaza-cyclopropa[a]pentalene-4-carboxylic acid (1-methyl-1-phenyl-ethyl)-amide; Compound 478: (1aR,5aR)-2-(2,4-Difluoro-phenyl)-1a,2,5,5a-tetrahydro-1H-2,3-diaza-cyclopropa[a]pentalene-4-carboxylic acid [1-(2-methoxy-pyridin-3-yl)-1-methyl-ethyl]-amide; Compound 479: (1aR,5aR)-2-(2,4-Difluoro-phenyl)-1a,2,5,5a-tetrahydro-1H-2,3-diaza-cyclopropa[a]pentalene-4-carboxylic acid (6-methanesulfonyl-2-methyl-pyridin-3-yl)-amide; Compound 480: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-methyl-ethyl)-amide; Compound 481: (1aR,5aR)-2-(3-Methyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 482: (1aR,5aR)-2-(2,4-Difluoro-phenyl)-1a,2,5,5a-tetrahydro-1H-2,3-diaza-cyclopropa[a]pentalene-4-carboxylic acid 2-hydroxy-benzylamide; Compound 483: (1aR,5aR)-2-(2,4-Difluoro-phenyl)-1a,2,5,5a-tetrahydro-1H-2,3-diaza-cyclopropa[a]pentalene-4-carboxylic acid (6-bromo-2-methyl-pyridin-3-yl)-amide; Compound 484: (1aR,5aR)-2-(2,4-Difluoro-phenyl)-1a,2,5,5a-tetrahydro-1H-2,3-diazacyclopropa[a]pentalene-4-carboxylic acid (2-methoxy-pyridin-3-yl)-amide; Compound 485: (1aR,5aR)-2-(2,4-Difluoro-phenyl)-1a,2,5,5a-tetrahydro-1H-2,3-diaza-cyclopropa[a]pentalene-4-carboxylic acid [1-(4-chloro-phenyl)-cyclobutyl]-amide; Compound 486: (1aR,5aR)-2-(2,4-Difluoro-phenyl)-1a,2,5,5a-tetrahydro-1H-2,3-diaza-cyclopropa[a]pentalene-4-carboxylic acid [2-(pyridine-2-sulfonyl)-ethyl]-amide; Compound 487: [(1aR,5aR)-2-(2,4-Difluoro-phenyl)-1a,2,5,5a-tetrahydro-1H-2,3-diaza-cyclopropa[a]pentalen-4-yl]-(7-methyl-3,4-dihydro-2H-[1,8]naphthyridin-1-yl)-methanone; Compound 488: (1aS,5aS)-2-(2,4-Difluoro-phenyl)-1a,2,5,5a-tetrahydro-1H-2,3-diaza-cyclopropa[a]pentalene-4-carboxylic acid (1-pyridin-2-yl-cyclopropyl)-amide; Compound 489: (1aR,5aR)-2-(2,4-Difluoro-phenyl)-1a,2,5,5a-tetrahydro-H-2,3-diaza-cyclopropa[a]pentalene-4-carboxylic acid (1-pyridin-2-yl-cyclopropylmethyl)-amide; Compound 490: (1aR,5aR)-2-(6-Methyl-4-trifluoromethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 491: (1aR,5aR)-2-(2,4-Difluoro-phenyl)-1a,2,5,5a-tetrahydro-1H-2,3-diaza-cyclopropa[a]pentalene-4-carboxylic acid (1,1-dimethyl-2-morpholin-4-yl-ethyl)-amide; Compound 492: (1aR,5aR)-2-(2,4-Difluoro-phenyl)-1a,2,5,5a-tetrahydro-1H-2,3-diaza-cyclopropa[a]pentalene-4-carboxylic acid (1-methyl-1,2,3,4-tetrahydro-quinolin-7-yl)-amide; Compound 493: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 494: 1-{[(1aS,5aS)-2-(2,4-Difluoro-phenyl)-1a,2,5,5a-tetrahydro-1H-2,3-diaza-cyclopropa[a]pentalene-4-carbonyl]-amino}-cyclohexanecarboxylic acid methyl ester; Compound 495: (1aR,5aR)-2-(6-Dimethylamino-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 496: (1aR,5aR)-2-(2,4-Difluoro-phenyl)-1a,2,5,5a-tetrahydro-1H-2,3-diaza-cyclopropa[a]pentalene-4-carboxylic acid benzylamide; Compound 497: (1aS,5aS)-2-(2,4-Difluoro-phenyl)-1a,2,5,5a-tetrahydro-1H-2,3-diaza-cyclopropa[a]pentalene-4-carboxylic acid (3,5-dimethyl-pyrazin-2-yl)-amide; Compound 498: (1aR,5aR)-2-(2,4-Difluoro-phenyl)-1a,2,5,5a-tetrahydro-1H-2,3-diaza-cyclopropa[a]pentalene-4-carboxylic acid (5-fluoro-1-oxy-pyridin-2-yl)-amide; Compound 499: (1aR,5aR)-2-(5-Trifluoromethyl-pyridin-2-yl)-1a,2,5,5a-tetrahydro-1H-2,3-diaza-cyclopropa[a]pentalene-4-carboxylic acid (tetrahydro-pyran-4-ylmethyl)-amide; Compound 500: (1aR,5aR)-2-(1,1-Dioxo-hexahydro-1λ$^6$-thiopyran-4-yl)-1a,2,5,5a-tetrahydro-1H-2,3-diaza-cyclopropa[a]pentalene-4-carboxylic acid (2-hydroxy-1,1-dimethyl-ethyl)-amide; Compound 501: [(1aR,5aR)-2-(2,4-Difluoro-phenyl)-1a,2,5,5a-tetrahydro-1H-2,3-diaza-cyclopropa[a]pentalen-4-yl]-(3-pyridin-3-yl-pyrrolidin-1-yl)-methanone; Compound 502: (1aR,5aR)-2-(2,4-Difluoro-phenyl)-1a,2,5,5a-tetrahydro-1H-2,3-diaza-cyclopropa[a]pentalene-4-carboxylic acid [1-(2-hydroxy-pyridin-3-yl)-1-methyl-ethyl]-amide; Compound 503: (1aS,5aS)-2-(2,4-Difluoro-phenyl)-1a,2,5,5a-tetrahydro-1H-2,3-diaza-cyclopropa[a]pentalene-4-carboxylic acid (2-fluoro-pyridin-3-yl)-amide; Compound 504: 1-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclobutanecarboxylic acid ethyl ester; Compound 505: (1aS,5aS)-2-(5-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 506: [(1aR,5aR)-2-(2,4-Difluoro-phenyl)-1a,2,5,5a-tetrahydro-1H-2,3-diaza-cyclopropa[a]pentalen-4-yl]-((S)-3-hydroxy-pyrrolidin-1-yl)-methanone; Compound 507: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-phenyl-ethyl)-amide; Compound 508: (1aR,5aR)-2-(2-Difluoro-phenyl)-1a,2,5,5a-tetrahydro-1H-2,3-diaza-cyclopropa[a]pentalene-4-carboxylic acid ((1R,2S)-2-hydroxy-1-hydroxymethyl-propyl)-amide; Compound 509: 3-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-pyrrolidine-1-carboxylic acid tert-butyl ester; Compound 510: (1aS,5aS)-2-(2,4-Difluoro-phenyl)-1a,2,5,5a-tetrahydro-1H-2,3-diaza-cyclopropa[a]pentalene-4-carboxylic acid (tetrahydro-pyran-4-yl)-amide; Compound 511: (1aR,5aR)-2-(2-Hydroxy-2-methyl-propyl)-1a,2,5,5a-tetrahydro-1H-2,3-diaza-cyclopropa[a]pentalene-4-carboxylic acid (5-fluoro-pyridin-2-yl)-amide; Compound 512: (1aR,5aR)-2-(5-Bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 513: (1aR,5aR)-2-(2,4-Difluoro-phenyl)-1a,2,5,5a-tetrahydro-1H-2,3-diaza-cyclopropa[a]pentalene-4-carboxylic acid (quinolin-4-ylmethyl)-amide; Compound 514: (1aS,5aS)-2-(2,4-Difluoro-phenyl)-1a,2,5,5a-tetrahydro-1H-2,3-diaza-cyclopropa[a]pentalene-4-carboxylic acid pyrimidin-4-ylamide; Compound 515: 1-(2,4-Difluoro-phenyl)-3b,4,4a,5-tetrahydro-1H-cyclopropa[3,4]cyclopenta[1,2-c]pyrazole-3-carboxylic acid (2-hydroxy-1,1-dimethyl-ethyl)-amide; Compound 516: 1-{[(1aR,5aR)-2-(6-Bromo-pyridin-3-yl)-1a,2,5,5a-tetrahydro-1H-2,3-diaza-cyclopropa[a]pentalene-4-carbonyl]-amino}-cyclohexanecarboxylic acid methyl ester; Compound 517: (1aR,5aR)-2-tert-Butyl-1a,2,5,5a-tetrahydro-1H-2,3-diaza-cyclopropa[a]pentalene-4-carboxylic acid [(R)-2-(4-fluoro-phenyl)-1-(2-hydroxy-ethylcarbamoyl)-1-methyl-ethyl]-amide; Compound 518: (1aS,5aS)-2-(2,4-Difluoro-phenyl)-1a,2,5,5a-tetrahydro-1H-2,3-diaza-cyclopropa[a]pentalene-4-carboxylic acid pyridin-2-ylamide; Compound 519: (1aS,5aS)-2-(2,4-Difluoro-phenyl)-1a,2,5,5a-tetrahydro-1H-2,3-diaza-cyclopropa[a]pentalene-4-carboxylic acid ((S)-1-pyridin-2-yl-ethyl)-amide; Compound 520: (1aR,5aR)-2-(2,4-Difluoro-phenyl)-1a,2,5,5a-tetrahydro-H-2,3-diaza-cyclopropa[a]pentalene-4-carboxylic acid (1-pyridin-4-yl-cyclobutyl)-amide; Compound 521: (1aS,5aS)-2-[5-(4-Fluoro-phenyl)-pyridin-2-yl]-1a,2,5,5a-tetrahydro-1H-2,3-diaza-cyclopropa[a]pentalene-4-carboxylic acid (2-hydroxy-1,1-dimethyl-ethyl)-amide; Compound 522: (1aR,5aR)-2-tert-Butyl-1a,2,5,5a-tetrahydro-1H-2,3-diaza-cyclopropa[a]pentalene-4-carboxylic acid (R)-indan-1-ylamide; Compound 523: (1aR,5aR)-2-(2,4-Difluoro-phenyl)-1a,2,5,5a-tetrahydro-1H-2,3-diaza-cyclopropa[a]pentalene-4-carboxylic acid [(S)-1-(3,3,3-trifluoro-propyl)-piperidin-3-yl]-amide; Compound 524: (1aR,5aR)-2-(2,4-Difluoro-phenyl)-1a,2,5,5a-tetrahydro-H-2,3-diaza-cyclopropa[a]pentalene-4-carboxylic acid (2-morpholin-4-yl-pyridin-3-yl)-amide; Compound 525: (1aR,5aR)-2-(5-Methyl-pyridin-2-yl)-1a,2,5,5a-tetrahydro-1H-2,3-diaza-cyclopropa[a]pentalene-4-carboxylic acid tert-butylamide; Compound 526: (1aR,5aR)-2-(1,1-Dioxo-tetrahydro-1λ$^6$-thiophen-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 527: (1aR,5aR)-2-Pyridin-3-yl-1a,2,5,5a-tetrahydro-1H-2,3-diaza-cyclopropa[a]pentalene-4-carboxylic acid (1-methyl-1-phenyl-ethyl)-amide; Compound 528: (1aR,5aR)-2-(2,4-Difluoro-phenyl)-1a,2,5,5a-tetrahydro-1H-2,3-diaza-cyclopropa[a]pentalene-4-carboxylic acid (6-methyl-pyridin-2-yl)-amide; Compound 529: (1aR,5aR)-2-(2,4-Difluoro-phenyl)-1a,2,5,5a-tetrahydro-1H-2,3-diazacyclopropa[a]pentalene-4-carboxylic acid (tetrahydro-furan-2-ylmethyl)-amide; Compound 530: (1aS,5aS)-2-(2,4-Difluoro-phenyl)-1a,2,5,5a-tetrahydro-1H-2,3-diaza-cyclopropa[a]pentalene-4-carboxylic acid [1-(4-methoxy-phenyl)-cyclopropyl]-amide; Compound 531: (1aS,5aS)-2-(5-Cyclopropyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 532: (1aR,5aR)-2-(2,4-Difluoro-phenyl)-1a,2,5,5a-tetrahydro-1H-2,3-diaza-cyclopropa[a]pentalene-4-carboxylic acid [(R)-1-(3,3,3-trifluoro-propyl)-pyrrolidin-3-yl]-amide; Compound 533: [(1aR,5aR)-2-(2,4-Difluoro-phenyl)-1a,2,5,5a-tetrahydro-1H-2,3-diaza-cyclopropa[a]pentalen-4-yl]-[4-(4,6-dimethyl-pyrimidin-2-yl)-piperazin-1-yl]-methanone; Compound 534: (1aR,5aR)-2-(2,4-Difluoro-phenyl)-1a,2,5,5a-tetrahydro-1H-2,3-diaza-cyclopropa[a]pentalene-4-carboxylic acid [1-(4-fluoro-phenyl)-cyclopropyl]-amide; Compound 535: (1aS,5aS)-2-Pyridin-2-yl-1a,2,5,5a-tetrahydro-1H-2,3-diaza-cyclopropa[a]pentalene-4-carboxylic acid (2-hydroxy-1,1-dimethyl-ethyl)-amide; Compound 536: (1aR,5aR)-2-(2,4-Difluoro-phenyl)-1a,2,5,5a-tetrahydro-1H-2,3-diaza-cyclopropa[a]pentalene-4-carboxylic acid 3-difluoromethoxy-benzylamide; Compound 537: (1aS,5aS)-2-(2,4-Difluoro-phenyl)-1a,2,5,5a-tetrahydro-1H-2,3-diaza-cyclopropa[a]pentalene-4-carboxylic acid (4-hydroxy-1-methyl-piperidin-4-ylmethyl)-amide; Compound 538: (1aR,5aR)-2-(2,4-Difluoro-phenyl)-1a,2,5,5a-tetrahydro-1H-2,3-diaza-cyclopropa[a]pentalene-4-carboxylic acid [1-((R)-2-(S)-methyl-5-methyl-pyrrolidine-1-carbonyl)-cyclopentyl]-amide; Compound 539: (1aR,5aR)-2-(2,4-Difluoro-phenyl)-1a,2,5,5a-tetrahydro-1H-2,3-diaza-cyclopropa[a]pentalene-4-carboxylic acid (1-methyl-1-pyridin-3-yl-ethyl)-amide; Compound 540: (1aR,5aR)-2-(4-Methoxy-phenyl)-1a,2,5,5a-tetrahydro-1H-2,3-diaza-cyclopropa[a]pentalene-4-carboxylic acid (1-phenyl-cyclopropyl)-amide; Compound 541: (1aR,5aR)-2-(2,4-Difluoro-phenyl)-1a,2,5,5a-tetrahydro-1H-2,3-diaza-cyclopropa[a]pentalene-4-carboxylic acid 2-methoxy-benzylamide; Compound 542: 2-({[(1aS,5aS)-2-(2,4-Difluoro-phenyl)-1a,2,5,5a-tetrahydro-1H-2,3-diaza-cyclopropa[a]pentalene-4-carbonyl]-amino}-methyl)-morpholine-4-carboxylic acid tert-butyl ester; Compound 543: (1aR,5aR)-2-(6-Ethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 544: (1aR,5aR)-2-tert-Butyl-1a,2,5,5a-tetrahydro-1H-2,3-diaza-cyclopropa[a]pentalene-4-carboxylic acid (tetrahydro-pyran-4-ylmethyl)-amide; Compound 545: (1aR,5aR)-2-(2,4-Difluoro-phenyl)-1a,2,5,5a-tetrahydro-1H-2,3-diaza-cyclopropa[a]pentalene-4-carboxylic acid (6-methyl-pyridin-2-ylmethyl)-amide; Compound 546: (1aS,5aS)-2-(5-Chloro-pyridin-2-yl)-1a,2,5,5a-tetrahydro-1H-2,3-diaza-cyclopropa[a]pentalene-4-carboxylic acid (1-phenyl-cyclopropyl)-amide; Compound 547: (1aR,5aR)-2-(2,4-Difluoro-phenyl)-1a,2,5,5a-tetrahydro-1H-2,3-diaza-cyclopropa[a]pentalene-4-carboxylic acid (3-chloro-pyridin-4-yl)-amide; Compound 548: 2-{[(1aR,5aR)-2-(2,4-Difluoro-phenyl)-1a,2,5,5a-tetrahydro-1H-2,3-diaza-cyclopropa[a]pentalene-4-carbonyl]-amino}-2-methyl-propionic acid; Compound 549: (1aR,5aR)-2-(2,4-Difluoro-phenyl)-1a,2,5,5a-tetrahydro-1H-2,3-diaza-cyclopropa[a]pentalene-4-carboxylic acid (6-chloro-pyridin-3-yl)-amide; Compound 550: (1aR,5aR)-2-(2,4-Difluoro-phenyl)-1a,2,5,5a-tetrahydro-1H-2,3-diaza-cyclopropa[a]pentalene-4-carboxylic acid (1-morpholin-4-ylmethyl-cyclopentyl)-amide; Compound 551: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-2-pyridin-3-yl-ethyl)-amide; Compound 552: (1aR,5aR)-2-(4-Fluoro-phenyl)-1a,2,5,5a-tetrahydro-1H-2,3-diaza-cyclopropa[a]pentalene-4-carboxylic acid (1-pyridin-4-yl-cyclobutyl)-amide; Compound 553: [(1aR,5aR)-2-(2,4-Difluoro-phenyl)-1a,2,5,5a-tetrahydro-1H-2,3-diaza-cyclopropa[a]pentalen-4-yl]-(2-methyl-3,4-dihydro-2H-quinolin-1-yl)-methanone; Compound 554: (1aR,5aR)-2-(2,4-Difluoro-phenyl)-1a,2,5,5a-tetrahydro-1H-2,3-diaza-cyclopropa[a]pentalene-4-carboxylic acid (1-p-tolyl-cyclopropyl)-amide; Compound 555: (1aR,5aR)-2-(2,4-Difluoro-phenyl)-1a,2,5,5a-tetrahydro-1H-2,3-diaza-cyclopropa[a]pentalene-4-carboxylic acid [(R)-1-(2-methoxy-ethyl)-piperidin-3-yl]-amide; Compound 556: (1aS,5aS)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-4-yl-ethyl)-amide; Compound 557: (1aR,5aR)-2-(2,4-Difluoro-phenyl)-1a,2,5,5a-tetrahydro-1H-2,3-diaza-cyclopropa[a]pentalene-4-carboxylic acid [1-(3,3,3-trifluoro-propyl)-piperidin-4-yl]-amide; Compound 558: [(1aR,5aR)-2-(2,4-Difluoro-phenyl)-1a,2,5,5a-tetrahydro-H-2,3-diaza-cyclopropa[a]pentalen-4-yl]-((R)-2-hydroxymethyl-pyrrolidin-1-yl)-methanone; Compound 559: (1aR,5aR)-2-(2,4-Difluoro-phenyl)-1a,2,5,5a-tetrahydro-1H-2,3-diaza-cyclopropa[a]pentalene-4-carboxylic acid (4-methoxy-pyridin-2-yl)-amide; Compound 560: (1aR,5aR)-2-(5-Chloro-pyridin-2-yl)-1a,2,5,5a-tetrahydro-1H-2,3-diaza-cyclopropa[a]pentalene-4-carboxylic acid (1-phenyl-cyclopropyl)-amide; Compound 561: (1aR,5aR)-2-(2,4-Difluoro-phenyl)-1a,2,5,5a-tetrahydro-H-2,3-diaza-cyclopropa[a]pentalene-4-carboxylic acid (3-azepan-1-yl-2,2-dimethyl-propyl)-amide; Compound 562: (1aR,5aR)-2-Pyridin-4-yl-1a,2,5,5a-tetrahydro-1H-2,3-diaza-cyclopropa[a]pentalene-4-carboxylic acid (tetrahydro-pyran-4-ylmethyl)-amide; Compound 563: (1aR,5aR)-2-(5-Methylamino-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 564: 3-{[(1aR,5aR)-2-(2,4-Difluoro-phenyl)-1a,2,5,5a-tetrahydro-1H-2,3-diaza-cyclopropa[a]pentalene-4-carbonyl]-amino}-azetidine-1-carboxylic acid tert-butyl ester; Compound 565: (1aR,5aR)-2-(2,4-Dichloro-phenyl)-1a,2,5,5a-tetrahydro-1H-2,3-diaza-cyclopropa[a]pentalene-4-carboxylic acid (tetrahydro-pyran-4-ylmethyl)-amide; Compound 566: (1aR,5aR)-2-(2,4-Difluoro-phenyl)-1a,2,5,5a-tetrahydro-1H-2,3-diaza-cyclopropa[a]pentalene-4-carboxylic acid (5-methyl-pyrazin-2-ylmethyl)-amide; Compound 567: (1aR,5aR)-2-(2,4-Difluoro-phenyl)-1a,2,5,5a-tetrahydro-1H-2,3-diaza-cyclopropa[a]pentalene-4-carboxylic acid (1-oxo-hexahydro-1$\lambda^4$-thiopyran-4-yl)-amide; Compound 568: (1aR,5aR)-2-(5-Methyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 569: ((1aR,5aR)-2-tert-Butyl-a,2,5,5a-tetrahydro-H-2,3-diaza-cyclopropa[a]pentalen-4-yl)-(2-phenyl-morpholin-4-yl)-methanone; Compound 570: (S)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-3-phenyl-propionic acid methyl ester; Compound 571: (1aS,5aS)-2-(5-Chloro-pyridin-2-yl)-1a,2,5,5a-tetrahydro-1H-2,3-diaza-cyclopropa[a]pentalene-4-carboxylic acid (1-hydroxymethyl-cyclopropyl)-amide; Compound 572: (1aR,5aR)-2-(2,4-Difluoro-phenyl)-1a,2,5,5a-tetrahydro-1H-2,3-diaza-cyclopropa[a]pentalene-4-carboxylic acid [2-(2-chloro-phenyl)-ethyl]-amide; Compound 573: (1aR,5aR)-2-(3-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 574:

(1aR,5aR)-2-(2,4-Difluoro-phenyl)-1a,2,5,5a-tetrahydro-1H-2,3-diaza-cyclopropa[a]pentalene-4-carboxylic acid (3-chloro-5-trifluoromethyl-pyridin-2-ylmethyl)-amide; Compound 575: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1-hydroxymethyl-ethyl)-amide; Compound 576: (1aR,5aR)-2-(2,4-Difluoro-phenyl)-1a,2,5,5a-tetrahydro-1H-2,3-diaza-cyclopropa[a]pentalene-4-carboxylic acid [5-((S)-1-methyl-pyrrolidin-2-yl)-pyridin-2-yl]-amide; Compound 577: (1aS,5aS)-2-(2,4-Difluoro-phenyl)-1a,2,5,5a-tetrahydro-1H-2,3-diaza-cyclopropa[a]pentalene-4-carboxylic acid (1-hydroxymethyl-cyclohexyl)-amide; Compound 578: (1aR,5aR)-2-(2,4-Difluoro-phenyl)-1a,2,5,5a-tetrahydro-1H-2,3-diaza-cyclopropa[a]pentalene-4-carboxylic acid (4,6-dimethyl-pyridin-2-yl)-amide; Compound 579: (1aR,5aR)-2-(2,4-Difluoro-phenyl)-1a,2,5,5a-tetrahydro-1H-2,3-diaza-cyclopropa[a]pentalene-4-carboxylic acid ((S)-2-hydroxy-1-pyridin-3-yl-ethyl)-amide; Compound 580: (1aR,5aR)-2-(2,4-Difluoro-phenyl)-1a,2,5,5a-tetrahydro-1H-2,3-diaza-cyclopropa[a]pentalene-4-carboxylic acid (5-fluoro-2-hydroxy-phenyl)-amide; Compound 581: (1aR,5aR)-2-(5-Cyclobutyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 582: (1aR,5aR)-2-(5-Ethoxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 583: (1aR,5aR)-2-(5-Trifluoromethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 584: (1aR,5aR)-2-(5-Trifluoromethyl-pyrazin-2-yl)-1a,2,5,5a-tetrahydro-1H-2,3-diaza-cyclopropa[a]pentalene-4-carboxylic acid dimethylamide; Compound 585: (1aR,5aR)-2-(5-Cyano-pyridin-3-yl)-1a,2,5,5a-tetrahydro-H-2,3-diaza-cyclopropa[a]pentalene-4-carboxylic acid (2-hydroxy-1,1-dimethyl-ethyl)-amide; Compound 586: (1aR,5aR)-2-(5-Cyclopropylmethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 587: (1aR,5aR)-2-(4-Trifluoromethyl-pyridin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 588: (1aR,5aR)-2-(5-Bromo-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 589: (1aR,5aR)-2-(4-Trifluoromethyl-pyridin-2-yl)-1a,2,5,5a-tetrahydro-1H-2,3-diaza-cyclopropa[a]pentalene-4-carboxylic acid (1-hydroxymethyl-cyclopropyl)-amide; Compound 590: (1aR,5aR)-2-(5-Cyclopropyl-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 591: (1aR,5aR)-2-(5-Trifluoromethyl-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 592: (1aR,5aR)-2-(5-Cyano-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 593: (1aR,5aR)-2-Pyrazin-2-yl-1a,2,5,5a-tetrahydro-1H-2,3-diaza-cyclopropa[a]pentalene-4-carboxylic acid tert-butylamide; Compound 594: (1aR,5aR)-2-Pyrazin-2-yl-1a,2,5,5a-tetrahydro-1H-2,3-diaza-cyclopropa[a]pentalene-4-carboxylic acid (1-pyridin-4-yl-cyclobutyl)-amide; Compound 595: (1aR,5aR)-2-(5-Bromo-pyrazin-2-yl)-1a,2,5,5a-tetrahydro-1H-2,3-diaza-cyclopropa[a]pentalene-4-carboxylic acid (1-hydroxymethyl-cyclopropyl)-amide; Compound 596: (1aR,5aR)-2-(5-Pentafluoroethyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 597: (1aR,5aR)-2-(5-Heptafluoropropyl-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 598: 4-{[(1aR,5aR)-2-(2,4-Difluoro-phenyl)-1a,2,5,5a-tetrahydro-1H-2,3-diaza-cyclopropa[a]pentalene-4-carbonyl]-amino}-1-methyl-piperidine-4-carboxylic acid methyl ester; Compound 599: (1aR,5aR)-2-(2,4-Difluoro-phenyl)-1a,2,5,5a-tetrahydro-1H-2,3-diaza-cyclopropa[a]pentalene-4-carboxylic acid (4-hydroxymethyl-1-methyl-piperidin-4-yl)-amide; Compound 600: (1aR,5aR)-2-(2,4-Difluoro-phenyl)-1a,2,5,5a-tetrahydro-1H-2,3-diaza-cyclopropa[a]pentalene-4-carboxylic acid [2-((R)-2-hydroxymethyl-pyrrolidin-1-yl)-ethyl]-amide; Compound 601: (1aR,5aR)-2-(2,4-Difluoro-phenyl)-1a,2,5,5a-tetrahydro-1H-2,3-diaza-cyclopropa[a]pentalene-4-carboxylic acid [2-((S)-2-hydroxymethyl-pyrrolidin-1-yl)-ethyl]-amide; Compound 602: (1aR,5aR)-2-(4-Trifluoromethyl-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 603: (1aS,5aS)-2-(4-Trifluoromethyl-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 604: (1aR,5aR)-2-Pyrazin-2-yl-1a,2,5,5a-tetrahydro-1H-2,3-diaza-cyclopropa[a]pentalene-4-carboxylic acid (1-phenyl-cyclohexyl)-amide; Compound 605: 1-[((1aR,5aR)-2-Pyrazin-2-yl-1a,2,5,5a-tetrahydro-1H-2,3-diaza-cyclopropa[a]pentalene-4-carbonyl)-amino]-cyclohexanecarboxylic acid methyl ester; Compound 606: (1aR,5aR)-2-(5-Chloro-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 607: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 608: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 609: (1aR,5aR)-2-Pyrazin-2-yl-1a,2,5,5a-tetrahydro-1H-2,3-diaza-cyclopropa[a]pentalene-4-carboxylic acid (1-hydroxymethyl-cyclohexyl)-amide; Compound 610: (1aS,5aS)-2-(5-Bromo-pyrazin-2-yl)-1a,2,5,5a-tetrahydro-H-2,3-diaza-cyclopropa[a]pentalene-4-carboxylic acid (4-hydroxymethyl-tetrahydro-pyran-4-yl)-amide; Compound 611: (1aR,5aR)-2-(5-Chloro-4-trifluoromethyl-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 612: (1aS,5aS)-2-(5-Bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 613: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 614: (1aR,5aR)-2-(5-Chloro-4-methyl-pyridin-2-yl)-1a,2,5,5a-tetrahydro-1H-2,3-diaza-cyclopropa[a]pentalene-4-carboxylic acid tert-butylamide; Compound 615: (1aS,5aS)-2-(2,4-Difluoro-phenyl)-1a,2,5,5a-tetrahydro-H-2,3-diaza-cyclopropa[a]pentalene-4-carboxylic acid tert-butylamide; Compound 616: (1aR,5aR)-2-Pyrazin-2-yl-1a,2,5,5a-tetrahydro-1H-2,3-diaza-cyclopropa[a]pentalene-4-carboxylic acid (3-methyl-1,1-dioxo-tetrahydro-1$\lambda^6$-thiophen-3-yl)-amide; Compound 617: (1aR,5aR)-2-(5-Chloro-4-trifluoromethyl-pyridin-2-yl)-1a,2,5,5a-tetrahydro-1H-2,3-diazacyclopropa[a]pentalene-4-carboxylic acid (1-pyridin-4-yl-cyclobutyl)-amide; Compound 618: (1aR,5aR)-2-Pyrazin-2-yl-1a,2,5,5a-tetrahydro-1H-2,3-diaza-cyclopropa[a]pentalene-4-carboxylic acid (1-cyano-cyclohexyl)-amide; Compound 619: (1aR,5aR)-2-Pyrazin-2-yl-1a,2,5,5a-tetrahydro-1H-2,3-diaza-cyclopropa[a]pentalene-4-carboxylic acid [1-(5-methyl-[1,2,4]oxadiazol-3-yl)-cyclohexyl]-amide; Compound 620: (1aS,5aS)-2-(4-Trifluoromethyl-pyridin-2-yl)-1a,2,5,5a-tetrahydro-1H-2,3-diaza-cyclopropa[a]pentalene-4-carboxylic acid tert-butylamide; Compound 621: (1aS,5aS)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 622: (1aR,5aR)-2-(4-Bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 623: (1aR,5aR)-2-(4-Trifluoromethyl-pyridin-2-yl)-1a,2,5,5a-tetrahydro-1H-2,3-diaza-cyclopropa[a]pentalene-4-carboxylic acid (cyano-dimethyl-methyl)-amide; Compound 624: (1aR,5aR)-2-(2,4-Difluoro-phenyl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 625: (1aR,5aR)-2-(4-Chloro-pyridin-2-yl)-1a,2,5,5a-tetrahydro-1H-2,3-diaza-cyclopropa[a]pentalene-4-carboxylic acid (cyano-dimethyl-methyl)-amide; Compound 626: (1aR,5aR)-2-Pyrazin-2-yl-1a,2,5,5a-tetrahydro-1H-2,3-diaza-cyclopropa[a]pentalene-4-carboxylic acid N-methylcarbamoyl-N'-phenyl-hydrazide; Compound 627: (1aR,5aR)-2-Pyrazin-2-yl-1a,2,5,5a-tetrahydro-1H-2,3-diaza-cyclopropa[a]pentalene-4-carboxylic acid (cyano-dimethyl-methyl)-amide; Compound 628: (1aR,5aR)-2-Pyrazin-2-yl-1a,2,5,5a-tetrahydro-1H-2,3-diaza-cyclopropa[a]pentalene-4-carboxylic acid (1-carbamoyl-2,2-dimethyl-propyl)-amide; Compound 629: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 630: (1aR,5aR)-2-(4-Cyclopropyl-pyridin-2-yl)-1a,2,5,5a-tetrahydro-1H-2,3-diaza-cyclopropa[a]pentalene-4-carboxylic acid tert-butylamide; Compound 631: (1aR,5aR)-2-Pyrazin-2-yl-1a,2,5,5a-tetrahydro-1H-2,3-diaza-cyclopropa[a]pentalene-4-carboxylic acid N'-tert-butyl-hydrazide; Compound 632: (1aR,5aR)-2-(4-Trifluoromethyl-pyridin-2-yl)-1a,2,5,5a-tetrahydro-1H-2,3-diaza-cyclopropa[a]pentalene-4-carboxylic acid tert-butylamide; Compound 633: (1aR,5aR)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide; Compound 634: (1aR,5aR)-2-(2,4-Difluoro-phenyl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 635: (1aR,5aR)-2-(4-Bromo-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 636: (1aR,5aR)-2-(4-Chloro-pyridin-2-yl)-1a,2,5,5a-tetrahydro-1H-2,3-diaza-cyclopropa[a]pentalene-4-carboxylic acid tert-butylamide; Compound 637: (1aR,5aR)-2-(4-Cyano-pyridin-2-yl)-1a,2,5,5a-tetrahydro-1H-2,3-diaza-cyclopropa[a]pentalene-4-carboxylic acid (cyano-dimethyl-methyl)-amide; Compound 638: (1aR,5aR)-2-Pyrazin-2-yl-1a,2,5,5a-tetrahydro-1H-2,3-diaza-cyclopropa[a]pentalene-4-carboxylic acid ((R)-1-cyclopropyl-ethyl)-amide; Compound 639: (1aR,5aR)-2-Pyrazin-2-yl-1a,2,5,5a-tetrahydro-1H-2,3-diaza-cyclopropa[a]pentalene-4-carboxylic acid N-cyclobutyl-hydrazide; Compound 640: (1aR,5aR)-2-(5-Chloro-4-trifluoromethyl-pyridin-2-yl)-1a,2,5,5a-tetrahydro-1H-2,3-diaza-cyclopropa[a]pentalene-4-carboxylic acid tert-butylamide; Compound 641: (1aR,5aR)-2-(2,4-Difluoro-phenyl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 642: (1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 643: (1aR,5aR)-2-Pyrazin-2-yl-1a,2,5,5a-tetrahydro-1H-2,3-diaza-cyclopropa[a]pentalene-4-carboxylic acid N'-methylsulfonyl-N'-tert-butyl-hydrazide; Compound 644: (1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 645: (1aR,5aR)-2-(4-Bromo-pyridin-2-yl)-1a,2,5,5a-tetrahydro-1H-2,3-diaza-cyclopropa[a]pentalene-4-carboxylic acid (1,1-dimethyl-prop-2-ynyl)-amide; Compound 646: Phosphoric acid mono-(2-{[(1aR,5aR)-2-(4-cyano-pyridin-2-yl)-1a,2,5,5a-tetrahydro-1H-2,3-diaza-cyclopropa[a]pentalene-4-carbonyl]-amino}-2-methyl-propyl) ester; Compound 647: (1aR,5aR)-2-Pyrazin-2-yl-1a,2,5,5a-tetrahydro-1H-2,3-diaza-cyclopropa[a]pentalene-4-carboxylic acid N-methylcarbamoyl-N'-tert-butyl-hydrazide; Compound 648: (1aR,5aR)-2-(4-Bromo-pyridin-2-yl)-1a,2,5,5a-tetrahydro-1H-2,3-diaza-cyclopropa[a]pentalene-4-carboxylic acid (1-pyridin-4-yl-cyclobutyl)-amide; Compound 649: (1aR,5aR)-2-(4-Trifluoromethyl-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 650: (1aR,5aR)-2-(2,4-Difluoro-phenyl)-1a,2,5,5a-tetrahydro-1H-2,3-diaza-cyclopropa[a]pentalene-4-carboxylic acid (1-carbamoyl-2,2-dimethyl-propyl)-amide; Compound 651: (1aR,5aR)-2-(4-Methanesulfonyl-pyridin-2-yl)-1a,2,5,5a-tetrahydro-H-2,3-diaza-cyclopropa[a]pentalene-4-carboxylic acid ((S)-1-hydroxymethyl-2,2-dimethyl-propyl)-amide; Compound 652: (1aR,5aR)-2-(2,4-Difluoro-phenyl)-1a,2,5,5a-tetrahydro-1H-2,3-diaza-cyclopropa[a]pentalene-4-carboxylic acid (4-cyano-tetrahydro-pyran-4-yl)-amide; Compound 653: (1aR,5aR)-2-Pyrazin-2-yl-1a,2,5,5a-tetrahydro-1H-2,3-diaza-cyclopropa[a]pentalene-4-carboxylic acid N'-cyclobutyl-N'-methylcarbamoyl-hydrazide; Compound 654: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (cyano-dimethyl-methyl)-amide; Compound 655: (1aR,5aR)-2-(4-Bromo-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 656: (1aR,5aR)-2-Pyrazin-2-yl-1a,2,5,5a-tetrahydro-1H-2,3-diaza-cyclopropa[a]pentalene-4-carboxylic acid (1-methyl-cyclobutyl)-amide; Compound 657: (1aR,5aR)-2-Pyrazin-2-yl-1a,2,5,5a-tetrahydro-1H-2,3-diaza-cyclopropa[a]pentalene-4-carboxylic acid (1-hydroxymethyl-cyclobutyl)-amide; Compound 658: (1aR,5aR)-2-(5-Chloro-4-methyl-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 659: (1aR,5aR)-2-Pyrazin-2-yl-1a,2,5,5a-tetrahydro-1H-2,3-diaza-cyclopropa[a]pentalene-4-carboxylic acid (1-pyridin-2-yl-cyclopropyl)-amide; Compound 660: (1aR,5aR)-2-(4-Oxy-pyrazin-2-yl)-1a,2,5,5a-tetrahydro-1H-2,3-diaza-cyclopropa[a]pentalene-4-carboxylic acid tert-butylamide; Compound 661: (1aR,5aR)-2-(2,4-Difluoro-phenyl)-1a,2,5,5a-tetrahydro-1H-2,3-diaza-cyclopropa[a]pentalene-4-carboxylic acid ((S)-1-hydroxymethyl-2-methyl-propyl)-amide; Compound 662: (1aR,5aR)-2-(4-Methoxy-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 663: (1aR,5aR)-2-(4-Cyanopyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 664: (1aR,5aR)-2-Pyrazin-2-yl-1a,2,5,5a-tetrahydro-1H-2,3-diaza-cyclopropa[a]pentalene-4-carboxylic acid N-cyclobutyl-hydrazide; Compound 665: (1aR,5aR)-2-Pyrazin-2-yl-1a,2,5,5a-tetrahydro-1H-2,3-diaza-cyclopropa[a]pentalene-4-carboxylic acid (1-cyano-cyclopentyl)-amide; Compound 666: (1aR,5aR)-2-(2,4-Difluoro-phenyl)-1a,2,5,5a-tetrahydro-1H-2,3-diaza-cyclopropa[a]pentalene-4-carboxylic acid (cyano-dimethyl-methyl)-amide; Compound 667: (1aR,5aR)-2-Pyrazin-2-yl-1a,2,5,5a-tetrahydro-1H-2,3-diaza-cyclopropa[a]pentalene-4-carboxylic acid [2,2-dimethyl-1-((S)-methylcarbamoyl)-propyl]-amide; Compound 668: (1aR,5aR)-2-(4-Cyano-pyridin-2-yl)-1a,2,5,5a-tetrahydro-H-2,3-diaza-cyclopropa[a]pentalene-4-carboxylic acid ((S)-1-hydroxymethyl-2,2-dimethyl-propyl)-amide; Compound 669: (1aR,5aR)-2-(4-Cyano-pyridin-2-yl)-1a,2,5,5a-tetrahydro-1H-2,3-diaza-cyclopropa[a]pentalene-4-carboxylic acid tert-butylamide; Compound 670: (1aR,5aR)-2-(4-Bromo-pyridin-2-yl)-1a,2,5,5a-tetrahydro-1H-2,3-diaza-cyclopropa[a]pentalene-4-carboxylic acid (1-methyl-cyclobutyl)-amide; Compound 671: (1aR,5aR)-2-Pyrazin-2-yl-1a,2,5,5a-tetrahydro-1H-2,3-diaza-cyclopropa[a]pentalene-4-carboxylic acid ((S)-1-cyclopropyl-ethyl)-amide; Compound 672: (1aR,5aR)-2-Pyrazin-2-yl-1a,2,5,5a-tetrahydro-1H-2,3-diaza-cyclopropa[a]pentalene-4-carboxylic acid N-phenyl-hydrazide; Compound 673: (1aR,5aR)-2-(4-Bromo-pyridin-2-yl)-1a,2,5,5a-tetrahydro-1H-2,3-diaza-cyclopropa[a]pentalene-4-carboxylic acid tert-butylamide; Compound 674: (1aR,5aR)-2-(4-Chloro-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 675: (1aR,5aR)-2-(4-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 676: 1-[((1aR,5aR)-2-Pyrazin-2-yl-1a,2,5,5a-tetrahydro-1H-2,3-diaza-cyclopropa[a]pentalene-4-carbonyl)-amino]-cyclobutanecarboxylic acid ethyl ester; Compound 677: (1aR,5aR)-2-(4-Bromo-pyridin-2-yl)-1a,2,5,5a-tetrahydro-1H-2,3-diaza-cyclopropa[a]pentalene-4-carboxylic acid (cyano-dimethyl-methyl)-amide; Compound 678: (1aR,5aR)-2-Pyrazin-2-yl-1a,2,5,5a-tetrahydro-1H-2,3-diaza-cyclopropa[a]pentalene-4-carboxylic acid ((S)-1-pyridin-2-yl-ethyl)-amide; Compound 679: (aR,5aR)-2-Pyrazin-2-yl-1a,2,5,5a-tetrahydro-H-2,3-diaza-cyclopropa[a]pentalene-4-carboxylic acid (1-methyl-1-pyridin-2-yl-ethyl)-amide; Compound 680: (1aR,5aR)-2-(2,4-Difluoro-phenyl)-1a,2,5,5a-tetrahydro-1H-2,3-diaza-cyclopropa[a]pentalene-4-carboxylic acid ((S)-1-hydroxymethyl-propyl)-amide; Compound 681: (1aR,5aR)-2-(4-Methoxy-pyridin-2-yl)-1a,2,5,5a-tetrahydro-1H-2,3-diaza-cyclopropa[a]pentalene-4-carboxylic acid tert-butylamide; Compound 682: (1aR,5aR)-2-(4-Chloro-pyridin-2-yl)-1a,2,5,5a-tetrahydro-1H-2,3-diaza-cyclopropa[a]pentalene-4-carboxylic acid [1-methyl-1-(1H-tetrazol-5-yl)-ethyl]-amide; Compound 683: Phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl} ester; Compound 684: (1aR,5aR)-2-Pyrazin-2-yl-1a,2,5,5a-tetrahydro-1H-2,3-diaza-cyclopropa[a]pentalene-4-carboxylic acid ((S)-2-hydroxy-1-tetrahydro-pyran-4-yl-ethyl)-amide; Compound 685: (1aR,5aR)-2-Pyrazin-2-yl-1a,2,5,5a-tetrahydro-1H-2,3-diaza-cyclopropa[a]pentalene-4-carboxylic acid ((R)-2-hydroxy-1-tetrahydro-pyran-4-yl-ethyl)-amide; Compound 686: (1aR,5aR)-2-Pyrazin-2-yl-1a,2,5,5a-tetrahydro-1H-2,3-diaza-cyclopropa[a]pentalene-4-carboxylic acid ((R)-1,2-dimethyl-propyl)-amide; Compound 687: (1aR,5aR)-2-(4-Oxy-pyrazin-2-yl)-1a,2,5,5a-tetrahydro-1H-2,3-diaza-cyclopropa[a]pentalene-4-carboxylic acid N'-tert-butyl-hydrazide; Compound 688: (1aR,5aR)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide; Compound 689: (1aR,5aR)-2-(4-Oxy-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 690: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 691: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-phenyl-ethyl)-amide; Compound 692: (4-Methyl-piperazin-1-yl)-((1aR,5aR)-2-pyrazin-2-yl-1a,2,5,5a-tetrahydro-1H-2,3-diaza-cyclopropa[a]pentalen-4-yl)-methanone; Compound 693: (1aR,2S,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 694: (1aR,2R,5aR)-2-(1,1-Dioxo-tetrahydro-1$\lambda^6$-thiophen-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 695: (1aS,5aS)-2-Pyrazin-2-yl-1a,2,5,5a-tetrahydro-1H-2,3-diaza-cyclopropa[a]pentalene-4-carboxylic acid (1-pyridin-2-yl-cyclobutyl)-amide; Compound 696: (1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 697: (1aS,5aS)-2-Pyrazin-2-yl-1a,2,5,5a-tetrahydro-H-2,3-diaza-cyclopropa[a]pentalene-4-carboxylic acid ((R)-1-hydroxymethyl-2,2-dimethyl-propyl)-amide; Compound 698: (1aR,5aR)-2-(4-Oxy-pyrazin-2-yl)-1a,2,5,5a-tetrahydro-1H-2,3-diaza-cyclopropa[a]pentalene-4-carboxylic acid (1-hydroxymethyl-cyclobutyl)-amide; Compound 699: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 700: (1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide; Compound 701: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 702: (1aR,5aR)-2-(4-Oxy-pyrazin-2-yl)-1a,2,5,5a-tetrahydro-1H-2,3-diaza-cyclopropa[a]pentalene-4-carboxylic acid (1-pyridin-4-yl-cyclobutyl)-amide; Compound 703: Phosphoric acid mono-((S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester; Compound 704: (1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 705: (1aR,5aR)-2-(4-Oxy-pyrazin-2-yl)-1a,2,5,5a-tetrahydro-1H-2,3-diaza-cyclopropa[a]pentalene-4-carboxylic acid (4-methylcarbamoyl-tetrahydro-pyran-4-yl)-amide; Compound 706: (1aR,5aR)-2-(4-Oxy-pyrazin-2-yl)-1a,2,5,5a-tetrahydro-1H-2,3-diaza-cyclopropa[a]pentalene-4-carboxylic acid (1-methyl-1-methylcarbamoyl-ethyl)-amide; Compound 707: (1aS,5aS)-2-Pyrazin-2-yl-1a,2,5,5a-tetrahydro-1H-2,3-diaza-cyclopropa[a]pentalene-4-carboxylic acid ((S)-2,2-dimethyl-1-morpholin-4-ylmethyl-propyl)-amide; Compound 708: (1aR,5aR)-2-(4-Oxy-pyrazin-2-yl)-1a,2,5,5a-tetrahydro-1H-2,3-diazacyclopropa[a]pentalene-4-carboxylic acid (1-methylcarbamoyl-cyclopent-3-enyl)-amide; Compound 709: {[(1aS,5aS)-2-(4-Oxy-pyrazin-2-yl)-1a,2,5,5a-tetrahydro-1H-2,3-diaza-cyclopropa[a]pentalene-4-carbonyl]-amino}-pyridin-2-yl-acetic acid methyl ester; Compound 710: (1aS,5aS)-2-(4-Oxy-pyrazin-2-yl)-1a,2,5,5a-tetrahydro-H-2,3-diaza-cyclopropa[a]pentalene-4-carboxylic acid (methylcarbamoyl-pyridin-2-yl-methyl)-amide; Compound 711: {[(1aR,5aR)-2-(4-Oxy-pyrazin-2-yl)-1a,2,5,5a-tetrahydro-1H-2,3-diaza-cyclopropa[a]pentalene-4-carbonyl]-amino}-pyridin-2-yl-acetic acid methyl ester; Compound 712: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-morpholin-4-ylmethyl-propyl)-amide; Compound 713: (1aR,5aR)-2-(4-Oxy-pyrazin-2-yl)-1a,2,5,5a-tetrahydro-1H-2,3-diaza-cyclopropa[a]pentalene-4-carboxylic acid (methylcarbamoyl-pyridin-2-yl-methyl)-amide; Compound 714: (1aR,5aR)-2-(4-Oxy-pyrazin-2-yl)-1a,2,5,5a-tetrahydro-1H-2,3-diaza-cyclopropa[a]pentalene-4-carboxylic acid (1-methylcarbamoyl-cyclopentyl)-amide; Compound 715: (1aR,5aR)-2-(4-Oxy-pyrazin-2-yl)-1a,2,5,5a-tetrahydro-H-2,3-diaza-cyclopropa[a]pentalene-4-carboxylic acid [1-((S)-tert-butylcarbamoyl)-2,2-dimethyl-propyl]-amide; Compound 716: (1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclopropyl)-amide; Compound 717: (1aS,5aS)-2-(4-Oxy-pyrazin-2-yl)-1a,2,5,5a-tetrahydro-1H-2,3-diaza-cyclopropa[a]pentalene-4-carboxylic acid (1-methyl-1-phenyl-ethyl)-amide; Compound 718: (1aR,5aR)-2-(4-Oxy-pyrazin-2-yl)-1a,2,5,5a-tetrahydro-H-2,3-diaza-cyclopropa[a]pentalene-4-carboxylic acid (1-methyl-1-phenyl-ethyl)-amide; Compound 719: (1aR,5aR)-2-(4-Oxy-pyrazin-2-yl)-1a,2,5,5a-tetrahydro-1H-2,3-diaza-cyclopropa[a]pentalene-4-carboxylic acid [(S)-2,2-dimethyl-1-(pyridin-2-ylcarbamoyl)-propyl]-amide; Compound 720: (1aR,5aR)-2-(4-Oxy-pyrazin-2-yl)-1a,2,5,5a-tetrahydro-1H-2,3-diaza-cyclopropa[a]pentalene-4-carboxylic acid [1-(pyridin-2-ylcarbamoyl)-cyclobutyl]-amide; Compound 721: (1aR,5aR)-2-(4-Oxy-pyrazin-2-yl)-1a,2,5,5a-tetrahydro-1H-2,3-diaza-cyclopropa[a]pentalene-4-carboxylic acid (1-methylcarbamoyl-cyclobutyl)-amide; Compound 722: (1aR,5aR)-2-(4-Oxy-pyrazin-2-yl)-1a,2,5,5a-tetrahydro-1H-2,3-diaza-cyclopropa[a]pentalene-4-carboxylic acid ((S)-methylcarbamoyl-phenyl-methyl)-amide; Compound 723: (1aR,5aR)-2-(4-Oxy-pyrazin-2-yl)-1a,2,5,5a-tetrahydro-1H-2,3-diaza-cyclopropa[a]pentalene-4-carboxylic acid pyrrolidin-1-ylamide; Compound 724: (1aR,5aR)-2-(4-Oxy-pyrazin-2-yl)-1a,2,5,5a-tetrahydro-1H-2,3-diaza-cyclopropa[a]pentalene-4-carboxylic acid piperidin-1-ylamide; Compound 725: (1aR,5aR)-2-(4-Oxy-pyrazin-2-yl)-1a,2,5,5a-tetrahydro-1H-2,3-diaza-cyclopropa[a]pentalene-4-carboxylic acid (2,6-dimethyl-piperidin-1-yl)-amide; Compound 726: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-cyclopropylcarbamoyl-2,2-dimethyl-propyl)-amide; Compound 727: (1aR,5aR)-2-(4-Oxy-pyrazin-2-yl)-1a,2,5,5a-tetrahydro-1H-2,3-diaza-cyclopropa[a]pentalene-4-carboxylic acid [(S)-2,2-dimethyl-1-(2,2,2-trifluoro-ethylcarbamoyl)-propyl]-amide; Compound 728: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-ethylcarbamoyl-2,2-dimethyl-propyl)-amide; Compound 729: (1aR,5aR)-2-(4-Oxy-pyrazin-2-yl)-1a,2,5,5a-tetrahydro-1H-2,3-diaza-cyclopropa[a]pentalene-4-carboxylic acid N'-tert-butyl-N'-methyl-hydrazide; Compound 730: (1aS,5aS)-2-(4-Oxy-pyrazin-2-yl)-1a,2,5,5a-tetrahydro-1H-2,3-diaza-cyclopropa[a]pentalene-4-carboxylic acid tert-butyl-(2,2-dimethyl-1-pyridin-2-yl-propyl)-amide; Compound 731: (1aR,5aR)-2-(4-Oxy-pyrazin-2-yl)-1a,2,5,5a-tetrahydro-1H-2,3-diaza-cyclopropa[a]pentalene-4-carboxylic acid tert-butyl-(2,2-dimethyl-1-pyridin-2-yl-propyl)-amide; Compound 732: (1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2-methyl-propyl)-amide; Compound 733: (1aR,5aR)-2-(2,4-Difluoro-phenyl)-1a,2,5,5a-tetrahydro-1H-2,3-diaza-cyclopropa[a]pentalene-4-carboxylic acid ((1S,2R)-2-hydroxy-cyclopentyl)-amide; Compound 734: (1aR,5aR)-2-Pyrazin-2-yl-1a,2,5,5a-tetrahydro-H-2,3-diaza-cyclopropa[a]pentalene-4-carboxylic acid (1-pyridin-2-yl-cyclobutyl)-amide; Compound 735: (1aR,5aR)-2-(2,4-Difluoro-phenyl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide; Compound 736: (1aR,5aR)-2-Pyrazin-2-yl-1a,2,5,5a-tetrahydro-1H-2,3-diaza-cyclopropa[a]pentalene-4-carboxylic acid N'-methylsulfonyl-N'-cyclobutyl-hydrazide; Compound 737: (1aR,5aR)-2-Pyrazin-2-yl-1a,2,5,5a-tetrahydro-1H-2,3-diaza-cyclopropa[a]pentalene-4-carboxylic acid N'-methylsulfonyl-N'-phenyl-hydrazide; Compound 738: (1aR,5aR)-2-Pyrazin-2-yl-1a,2,5,5a-tetrahydro-1H-2,3-diaza-cyclopropa[a]pentalene-4-carboxylic acid cyclopentylamide; Compound 739: (1aR,5aR)-2-(2,4-Difluoro-phenyl)-1a,2,55a-tetrahydro-H-2,3-diaza-cyclopropa[a]pentalene-4-carboxylic acid ((S)-1-cyclopropyl-2-hydroxy-ethyl)-amide; Compound 740: (1aR,5aR)-2-Pyrazin-2-yl-1a,2,5,5a-tetrahydro-1H-2,3-diaza-cyclopropa[a]pentalene-4-carboxylic acid ((R)-1,2,2-trimethyl-propyl)-amide; Compound 741: (1aR,5aR)-2-Pyrazin-2-yl-1a,2,5,5a-tetrahydro-1H-2,3-diaza-cyclopropa[a]pentalene-4-carboxylic acid ((1S,2R)-2-hydroxy-cyclopentyl)-amide; Compound 742: (1aR,5aR)-2-(2,4-Difluoro-phenyl)-1a,2,5,5a-tetrahydro-1H-2,3-diaza-cyclopropa[a]pentalene-4-carboxylic acid ((R)-2-hydroxy-1-tetrahydro-pyran-4-yl-ethyl)-amide; Compound 743: (1aS,5aS)-2-(4-Oxy-pyrazin-2-yl)-1a,2,5,5a-tetrahydro-1H-2,3-diaza-cyclopropa[a]pentalene-4-carboxylic acid [pyridin-2-yl-(2,2,2-trifluoro-ethylcarbamoyl)-methyl]-amide; Compound 744: (1aS,5aS)-2-(4-Oxy-pyrazin-2-yl)-1a,2,5,5a-tetrahydro-1H-2,3-diaza-cyclopropa[a]pentalene-4-carboxylic acid (2,2-dimethyl-1-pyridin-2-yl-propyl)-amide; Compound 745: (1aR,5aR)-2-(4-Oxy-pyrazin-2-yl)-1a,2,5,5a-tetrahydro-1H-2,3-diaza-cyclopropa[a]pentalene-4-carboxylic acid (2,2-dimethyl-1-pyridin-2-yl-propyl)-amide; Compound 746: (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester; Compound 747: (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid; Compound 748: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(hydroxy-methyl-carbamoyl)-2,2-dimethyl-propyl]-amide; Compound 749: (1aR,5aR)-2-(Tetrahydro-pyran-4-ylmethyl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 750: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-dimethylcarbamoyl-2,2-dimethyl-propyl)-amide; Compound 751: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(azetidine-1-carbonyl)-2,2-dimethyl-propyl]-amide; Compound 752: (1aR,5aR)-2-

(Tetrahydro-pyran-4-ylmethyl)-1a,2,5,5a-tetrahydro-1H-2,3-diaza-cyclopropa[a]pentalene-4-carboxylic acid (1-pyridin-2-yl-cyclobutyl)-amide; Compound 753: (1aR,5aR)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclopropyl)-amide; Compound 754: (1aS,5aS)-2-(4-Oxy-pyrazin-2-yl)-1a,2,5,5a-tetrahydro-1H-2,3-diaza-cyclopropa[a]pentalene-4-carboxylic acid [1-(4-fluoro-phenyl)-cyclobutyl]-amide; Compound 755: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-methoxycarbamoyl-2,2-dimethyl-propyl)-amide; Compound 756: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(methoxy-methyl-carbamoyl)-2,2-dimethyl-propyl]-amide; Compound 757: (1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 758: (1aR,5aR)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 759: (1aR,5aR)-2-(4-Cyano-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 760: (S)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-3,3-dimethyl-butyric acid; Compound 761: (1aR,5aR)-2-(2,4-Difluoro-phenyl)-1a,2,5,5a-tetrahydro-1H-2,3-diaza-cyclopropa[a]pentalene-4-carboxylic acid ((S)-methylcarbamoyl-phenyl-methyl)-amide; Compound 762: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-tert-butoxycarbamoyl-2,2-dimethyl-propyl)-amide; Compound 763: (1aR,5aR)-2-Piperidin-4-yl-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 764: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide; Compound 765: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide; Compound 766: (1aS,5aS)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 767: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 768: (1aR,5aR)-2-(Tetrahydro-pyran-4-yl)-1a,2,5,5a-tetrahydro-1H-2,3-diaza-cyclopropa[a]pentalene-4-carboxylic acid (1-pyridin-2-yl-cyclobutyl)-amide; Compound 769: (1aR,5aR)-2-(Tetrahydro-pyran-4-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 770: (1aR,5aR)-2-((R)-3-Methyl-1,1-dioxo-tetrahydro-1$\lambda^6$-thiophen-3-yl)-1a,2,5,5a-tetrahydro-1H-2,3-diaza-cyclopropa[a]pentalene-4-carboxylic acid (1-pyridin-2-yl-cyclobutyl)-amide; Compound 771: (1aR,5aR)-2-(2-Chloro-pyridin-4-yl)-1a,2,5,5a-tetrahydro-1H-2,3-diaza-cyclopropa[a]pentalene-4-carboxylic acid (1-pyridin-2-yl-cyclobutyl)-amide; Compound 772: (1aR,5aR)-2-(2-Chloro-pyridin-4-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 773: (1aR,5aR)-2-(5-Bromo-pyridin-2-yl)-1a,2,5,5a-tetrahydro-H-2,3-diaza-cyclopropa[a]pentalene-4-carboxylic acid ((S)-1-hydroxymethyl-2,2-dimethyl-propyl)-amide; Compound 774: (1aR,5aR)-2-(5-Bromo-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 775: (1aR,5aR)-2-(5-Cyano-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 776: (1aR,5aR)-2-(5-Cyano-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 777: (1aR,5aR)-2-(4-Oxy-pyrazin-2-yl)-1a,2,5,5a-tetrahydro-H-2,3-diaza-cyclopropa[a]pentalene-4-carboxylic acid ((S)-1-hydroxycarbamoyl-2,2-dimethyl-propyl)-amide; Compound 778: (1aR,5aR)-2-((R)-3-Methyl-1,1-dioxo-tetrahydro-1$\lambda^6$-thiophen-3-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 779: (1aR,5aR)-2-((S)-3-Methyl-1,1-dioxo-tetrahydro-1$\lambda^6$-thiophen-3-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 780: (1aR,5aR)-2-(5-Fluoro-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 781: (1aR,5aR)-2-(5-Fluoro-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 782: (1aR,5aR)-2-(5-Fluoro-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 783: (1aR,5aR)-2-(5-Fluoro-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 784: (1aR,5aR)-2-(5-Chloro-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 785: (1aR,5aR)-2-(5-Chloro-pyridin-2-yl)-1a,2,5,5a-tetrahydro-1H-2,3-diaza-cyclopropa[a]pentalene-4-carboxylic acid ((1S,2S)-1-hydroxymethyl-2-methyl-butyl)-amide; Compound 786: (1aR,5aR)-2-(5-Chloro-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 787: (1aR,5aR)-2-(5-Fluoro-pyridin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 788: (1aR,5aR)-2-(5-Chloro-3-fluoro-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 789: (1aR,5aR)-2-(5-Bromo-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 790: (1aR,5aR)-2-(5-Bromo-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 791: (1aR,5aR)-2-(5-Cyano-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 792: (1aR,5aR)-2-(5-Cyano-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 793: (1aR,5aR)-2-(Tetrahydro-pyran-4-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 794: (1aR,5aR)-2-(5-Chloro-pyridin-2-yl)-1a,2,5,5a-tetrahydro-1H-2,3-diaza-cyclopropa

[a]pentalene-4-carboxylic acid ((S)-2,2-dimethyl-1-methylcarbamoyl-propyl)-amide; Compound 795: (1aR,5aR)-2-(5-Chloro-3-fluoro-pyridin-2-yl)-1a,2,5,5a-tetrahydro-1H-2,3-diaza-cyclopropa[a]pentalene-4-carboxylic acid (1-pyridin-2-yl-cyclobutyl)-amide; Compound 796: (1aR,5aR)-2-(4-Trifluoromethyl-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 797: (1aR,5aR)-2-Pyrazin-2-yl-1a,2,5,5a-tetrahydro-1H-2,3-diaza-cyclopropa[a]pentalene-4-carboxylic acid (2,2-dimethyl-1-pyridin-2-yl-propyl)-amide; Compound 798: (1aS,5aS)-2-Pyrazin-2-yl-1a,2,5,5a-tetrahydro-1H-2,3-diaza-cyclopropa[a]pentalene-4-carboxylic acid (2,2-dimethyl-1-pyridin-2-yl-propyl)-amide; Compound 799: (1aR,5aR)-2-(3-Fluoro-pyridin-4-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 800: (1aR,5aR)-2-(3-Fluoro-pyridin-4-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 801: (1aR,5aR)-2-(5-Chloro-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 802: (1aR,5aR)-2-(5-Chloro-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 803: (1aR,5aR)-2-(5-Trifluoromethyl-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 804: (1aR,5aR)-2-(5-Trifluoromethyl-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 805: (1aR,5aR)-2-(5-Trifluoromethyl-pyridin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 806: (1aR,5aR)-2-(3,5-Difluoro-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 807: (1aR,5aR)-2-(3-Fluoro-5-methoxy-pyridin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 808: (1aR,5aR)-2-(3,5-Difluoro-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 809: (1aS,5aS)-2-Pyridin-2-yl-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 810: (1aR,5aR)-2-(2,4-Difluoro-phenyl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 811: (1aR,5aR)-2-(2,4-Difluoro-phenyl)-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 812: (1aR,5aR)-2-Pyridin-2-yl-1a,2,5,5a-tetrahydro-1H-2,3-diaza-cyclopropa[a]pentalene-4-carboxylic acid ((S)-2,2-dimethyl-1-pyridin-2-yl-propyl)-amide; Compound 813: (1aR,5aR)-2-Pyridin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 814: (1aR,5aR)-2-(2,4-Difluoro-phenyl)-1a,2,5,5a-tetrahydro-1H-2,3-diaza-cyclopropa[a]pentalene-4-carboxylic acid [1-(2-hydroxy-ethylcarbamoyl)-2,2-dimethyl-propyl]-amide; Compound 815: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(tetrahydro-furan-2-yl)methyl]-amide; Compound 816: (1aR,5aR)-2-(4-Oxy-pyrazin-2-yl)-1a,2,5,5a-tetrahydro-1H-2,3-diaza-cyclopropa[a]pentalene-4-carboxylic acid [1-(2-fluoro-phenyl)-cyclobutyl]-amide; Compound 817: (1aS,5aS)-2-(4-Oxy-pyrazin-2-yl)-1a,2,5,5a-tetrahydro-1H-2,3-diaza-cyclopropa[a]pentalene-4-carboxylic acid [1-(2-fluoro-phenyl)-cyclobutyl]-amide; Compound 818: (1aR,5aR)-2-Pyrazin-2-yl-1a,2,5,5a-tetrahydro-1H-2,3-diaza-cyclopropa[a]pentalene-4-carboxylic acid [(S)-1-(2-hydroxy-ethylcarbamoyl)-2,2-dimethyl-propyl]-amide; Compound 819: (1aR,5aR)-2-(2,4-Difluoro-phenyl)-1a,2,5,5a-tetrahydro-1H-2,3-diaza-cyclopropa[a]pentalene-4-carboxylic acid (1,1-bis-hydroxymethyl-propyl)-amide; Compound 820: (1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 821: (1aR,5aR)-2-(4-Oxy-pyrazin-2-yl)-1a,2,5,5a-tetrahydro-1H-2,3-diaza-cyclopropa[a]pentalene-4-carboxylic acid (1-methyl-cyclobutyl)-amide; Compound 822: (1aR,5aR)-2-(2-Chloro-4-fluoro-phenyl)-1a,2,5,5a-tetrahydro-1H-2,3-diaza-cyclopropa[a]pentalene-4-carboxylic acid (2-hydroxy-1,1-dimethyl-ethyl)-amide; Compound 823: (1aR,5aR)-2-(2-Chloro-4-fluoro-phenyl)-1a,2,5,5a-tetrahydro-1H-2,3-diaza-cyclopropa[a]pentalene-4-carboxylic acid ((R)-2,2-dimethyl-1-pyridin-2-yl-propyl)-amide; Compound 824: (1aR,5aR)-2-(2-Chloro-4-fluoro-phenyl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 825: (1aR,5aR)-2-(2-Chloro-4-fluoro-phenyl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 826: (1aR,5aR)-2-(2-Chloro-4-fluoro-phenyl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 827: (1aR,5aR)-2-(2-Chloro-4-fluoro-phenyl)-1a,2,5,5a-tetrahydro-1H-2,3-diaza-cyclopropa[a]pentalene-4-carboxylic acid (1-pyridin-2-yl-cyclobutyl)-amide; Compound 828: (1aR,5aR)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide; Compound 829: (1aR,5aR)-2-(4-Oxy-pyrazin-2-yl)-1a,2,5,5a-tetrahydro-H-2,3-diaza-cyclopropa[a]pentalene-4-carboxylic acid (1-phenyl-cyclopropyl)-amide; Compound 830: (1aR,5aR)-2-Pyrazin-2-yl-1a,2,5,5a-tetrahydro-1H-2,3-diaza-cyclopropa[a]pentalene-4-carboxylic acid ((S)-1-hydroxycarbamoyl-2,2-dimethyl-propyl)-amide; Compound 831: (S)-3,3-Dimethyl-2-[((1aR,5aR)-2-pyrazin-2-yl-1a,2,5,5a-tetrahydro-1H-2,3-diaza-cyclopropa[a]pentalene-4-carbonyl)-amino]-butyric acid; Compound 832: (1aR,5aR)-2-(4-Oxy-pyrazin-2-yl)-1a,2,5,5a-tetrahydro-1H-2,3-diaza-cyclopropa[a]pentalene-4-carboxylic acid [1-(5-fluoro-pyridin-2-yl)-2,2-dimethyl-propyl]-amide; Compound 833: (1aR,5aR)-2-(4-Oxy-pyrazin-2-yl)-1a,2,5,5a-tetrahydro-1H-2,3-diaza-cyclopropa[a]pentalene-4-carboxylic acid [(S)-1-(2-hydroxy-ethylcarbamoyl)-2,2-dimethyl-propyl]-amide; Compound 834: (1aR,5aR)-2-(4-Oxy-pyrazin-2-yl)-1a,2,5,5a-tetrahydro-1H-2,3-diaza-cyclopropa[a]pentalene-4-carboxylic acid (4-hydroxymethyl-tetrahydro-pyran-4-yl)-amide; Compound 835: (1aR,5aR)-2-(4-Oxy-pyrazin-2-yl)-1a,2,5,5a-tetrahydro-1H-2,3-diaza-cyclopropa[a]pentalene-4-carboxylic acid (tetrahydro-pyran-4-yl)-amide; Compound 836: (1aR,5aR)-2-(4-Oxy-pyrazin-2-yl)-1a,2,5,5a-tetrahydro-1H-2,3-diaza-cyclopropa[a]pentalene-4-carboxylic acid [(R)-1-(5-fluoro-pyridin-2-yl)-2,2-dimethylpropyl]-amide; Compound 837: (1aR,5aR)-2-(4-Oxy-pyrazin-2-yl)-1a,2,5,5a-tetrahydro-H-2,3-diaza-cyclopropa[a]pentalene-4-carboxylic acid [(S)-1-(5-fluoro-pyridin-2-yl)-2,2-dimethyl-propyl]-amide; Compound 838: (1aR,5aR)—((S)-2-tert-Butoxycarbonylamino-3-methyl-butyric acid) 2-{[2-(2,4-difluoro-phenyl)-1a,2,5,5a-tetrahydro-1H-2,3-diaza-cyclopropa[a]pentalene-4-carbonyl]-amino}-2-methyl-propyl ester; Compound 839: (1aR,5aR)—(S)-2-Amino-3-methyl-butyric acid (S)-3-methyl-2-{[2-(4-oxy-pyrazin-2-yl)-1a,2,5,5a-tetrahydro-1H-2,3-diaza-cyclopropa[a]pentalene-4-carbonyl]-amino}-butyl ester; Compound 840: (1aR,5aR)—(S)-2-Amino-3-methyl-butyric acid 2-{[(R)-2-(2,4-difluoro-phenyl)-1a,2,5,5a-tetrahydro-1H-2,3-diaza-cyclopropa[a]pentalene-4-carbonyl]-amino}-2-methyl-propyl ester; Compound 841: (1aR,5aR)-2-(4-Oxy-pyrazin-2-yl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide; Compound 842: (1aR,5aR)-Pentanedioic acid mono-(2-{[(1aR,5aR)-2-(2,4-difluoro-phenyl)-1a,2,5,5a-tetrahydro-1H-2,3-diaza-cyclopropa[a]pentalene-4-carbonyl]-amino}-2-methyl-propyl) ester; Compound 843: (1aR,5aR)-2-Pyrazin-2-yl-1a,2,5,5a-tetrahydro-1H-2,3-diaza-cyclopropa[a]pentalene-4-carboxylic acid [(R)-2-hydroxy-1-(tetrahydro-pyran-4-yl)-ethyl]-amide; Compound 844: (1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester; Compound 845: (1aS,5aS)-Pentanedioic acid mono-((S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl) ester; Compound 846: (1aR,5aR)-2-(4-Oxy-pyrazin-2-yl)-1a,2,5,5a-tetrahydro-1H-2,3-diaza-cyclopropa[a]pentalene-4-carboxylic acid [2-hydroxy-1-(tetrahydro-pyran-4-yl)-ethyl]-amide; Compound 847: (1aR,5aR)-2-(4-Cyano-pyridin-2-yl)-1a,2,5,5a-tetrahydro-H-2,3-diaza-cyclopropa[a]pentalene-4-carboxylic acid ((S)-1-hydroxymethyl-2-methyl-propyl)-amide; Compound 848: (1aS,5aS)—(S)-2-Amino-3-methyl-butyric acid (S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl ester; Compound 849: (1aR,5aR)—(S)-2-Amino-3-methyl-butyric acid (S)-2-[(2-pyrazin-2-yl-1a,2,5,5a-tetrahydro-H-2,3-diaza-cyclopropa[a]pentalene-4-carbonyl)-amino]-2-(tetrahydro-pyran-4-yl)-ethyl ester; Compound 850: (1aR,5aR)-2-(5-Fluoro-pyridin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 851: (1aR,5aR)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 852: (1aR,5aR)-2-(4-Oxy-pyrazin-2-yl)-1a,2,5,5a-tetrahydro-1H-2,3-diaza-cyclopropa[a]pentalene-4-carboxylic acid [(R)-2-hydroxy-1-(tetrahydro-pyran-4-yl)-ethyl]-amide; Compound 853: 3-Fluoro-2-{[(1aR,5aR)-2-(5-fluoro-pyridin-2-yl)-1a,2,5,5a-tetrahydro-1H-2,3-diaza-cyclopropa[a]pentalene-4-carbonyl]-amino}-3-methyl-butyric acid methyl ester; Compound 854: (1aR,5aR)-2-(5-Fluoro-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 855: 4,4,4-Trifluoro-2-{[(1aR,5aR)-2-(5-fluoro-pyridin-2-yl)-1a,2,5,5a-tetrahydro-1H-2,3-diaza-cyclopropa[a]pentalene-4-carbonyl]-amino}-3-trifluoromethyl-butyric acid ethyl ester; Compound 856: (1aR,5aR)-2-(6-Fluoro-pyridin-3-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 857: (1aR,5aR)-2-(6-Fluoro-pyridin-3-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 858: (1aR,5aR)-2-(5-Fluoro-pyridin-2-yl)-1a,2,5,5a-tetrahydro-1H-2,3-diaza-cyclopropa[a]pentalene-4-carboxylic acid ((S)-2-fluoro-1-hydroxymethyl-2-methyl-propyl)-amide; Compound 859: (1aR,5aR)-2-(5-Fluoro-pyridin-2-yl)-1a,2,5,5a-tetrahydro-1H-2,3-diaza-cyclopropa[a]pentalene-4-carboxylic acid ((R)-2-fluoro-1-hydroxymethyl-2-methyl-propyl)-amide; Compound 860: (S)-2-tert-Butoxycarbonylamino-3-methyl-butyric acid (S)-3,3-dimethyl-2-{[(1aS,5aS)-2-(4-oxy-pyrazin-2-yl)-1a,2,5,5a-tetrahydro-1H-2,3-diaza-cyclopropa[a]pentalene-4-carbonyl]-amino}-butyl ester; Compound 861: 2-{[(1aR,5aR)-2-(2,4-Difluoro-phenyl)-1a,2,5,5a-tetrahydro-1H-2,3-diaza-cyclopropa[a]pentalene-4-carbonyl]-amino}-4,4,4-trifluoro-butyric acid methyl ester; Compound 862: 3-Fluoro-2-{[(1aR,5aR)-2-(6-fluoro-pyridin-3-yl)-1a,2,5,5a-tetrahydro-1H-2,3-diaza-cyclopropa[a]pentalene-4-carbonyl]-amino}-3-methyl-butyric acid methyl ester; Compound 863: (1aR,5aR)-2-(2,4-Difluoro-phenyl)-1a,2,5,5a-tetrahydro-1H-2,3-diaza-cyclopropa[a]pentalene-4-carboxylic acid (2-fluoro-1,1-dimethyl-ethyl)-amide; Compound 864: (1aR,5aR)-2-(6-Fluoro-pyridin-3-yl)-1a,2,5,5a-tetrahydro-1H-2,3-diaza-cyclopropa[a]pentalene-4-carboxylic acid (2-fluoro-1,1-dimethyl-ethyl)-amide; Compound 865: 2-{[(1aR,5aR)-2-(4-Cyano-pyridin-2-yl)-1a,2,5,5a-tetrahydro-1H-2,3-diaza-cyclopropa[a]pentalene-4-carbonyl]-amino}-3-fluoro-2-fluoromethyl-propionic acid methyl ester; Compound 866: 2-{[(1aR,5aR)-2-(2,4-Difluoro-phenyl)-1a,2,5,5a-tetrahydro-1H-2,3-diaza-cyclopropa[a]pentalene-4-carbonyl]-amino}-3-fluoro-2-fluoromethyl-propionic acid methyl ester; Compound 867: (1aR,5aR)-2-(2,4-Difluoro-phenyl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide; Compound 868: (1aR,5aR)-2-(6-Cyano-pyridin-3-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide; Compound 869: 2-{[(1aR,5aR)-2-(4-Cyano-pyridin-2-yl)-1a,2,5,5a-tetrahydro-1H-2,3-diaza-cyclopropa[a]pentalene-4-carbonyl]-amino}-3-hydroxy-2-methyl-propionic acid methyl ester; Compound 870: 2-{[(1aR,5aR)-2-(4-Cyano-pyridin-2-yl)-1a,2,5,5a-tetrahydro-1H-2,3-diaza-cyclopropa[a]pentalene-4-carbonyl]-amino}-3-hydroxy-2-methyl-propionic acid; Compound 871: 3-Fluoro-2-fluoromethyl-2-{[(1aR,5aR)-2-(5-trifluoromethyl-pyrazin-2-yl)-1a,2,5,5a-tetrahydro-1H-2,3-diaza-cyclopropa[a]pentalene-4-carbonyl]-amino}-propionic acid methyl ester; Compound 872: (1aR,5aR)-2-(2,4-Difluoro-phenyl)-1a,2,5,5a-tetrahydro-1H-2,3-diaza-cyclopropa[a]pentalene-4-carboxylic acid ((R)-3,3,3-trifluoro-1-hydroxymethyl-propyl)-amide; Compound 873: (1aR,5aR)-2-(2,4-Difluoro-phenyl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 874: (1aR,5aR)-2-(5-Trifluoromethyl-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide; Compound 875: (1aR,5aR)-2-(5-Trifluoromethyl-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 876: (1aR,5aR)-2-(4-Oxy-pyrazin-2-yl)-1a,2,5,5a-tetrahydro-1H-2,3-diaza-cyclopropa[a]pentalene-4-carboxylic acid (1,1-bis-hydroxymethyl-propyl)-amide; Compound 877: (1aR,5aR)-2-(6-Cyano-pyridin-3-yl)-1a,2,5,5a-tetrahydro-1H-2,3-diaza-cyclopropa[a]pentalene-4- carboxylic acid (2-hydroxy-1-hydroxymethyl-1-methyl-ethyl)-amide; Compound 878: (1aR,5aR)-2-(6-Fluoro-pyridin-3-yl)-1a,2,5,5a-tetrahydro-1H-2,3-diaza-cyclopropa[a]pentalene-4-carboxylic acid (2-hydroxy-1,1-dimethyl-ethyl)-amide; Compound 879: (1aR,5aR)-2-(3-Hydroxy-3-methyl-butyl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 880: (1aR,5aR)-2-(6-Chloro-pyridin-3-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 881: (1aR,5aR)-2-(4-Iodo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide; Compound 882: (1aR,5aR)-2-(4-Iodo-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 883: (1aR,5aR)-2-(1-Oxy-pyridin-3-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 884: (1aR,5aR)-2-(1-Oxy-pyridin-3-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 885: (1aR,5aR)-2-(4-Chloro-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 886: (1aS,5aS)-2-(4-Chloro-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 887: (1aS,5aS)-2-(4-Chloro-pyridin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 888: 2-{[(1aS,5aS)-2-(4-Chloro-pyridin-2-yl)-1a,2,5,5a-tetrahydro-1H-2,3-diaza-cyclopropa[a]pentalene-4-carbonyl]-amino}-3-fluoro-2-fluoromethyl-propionic acid methyl ester; Compound 889: (1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide; Compound 890: (1aS,5aS)-2-(4-Chloro-pyridin-2-yl)-1a,2,5,5a-tetrahydro-1H-2,3-diaza-cyclopropa[a]pentalene-4-carboxylic acid N'-tert-butyl-hydrazide; Compound 891: (1aS,5aS)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 892: (1aS,5aS)-2-(4-Cyano-pyridin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 893: (1aS,5aS)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 894: (1aR,5aR)-2-(1-Oxy-pyridin-3-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide; Compound 895: (1aR,5aR)-2-(4-Chloro-pyridin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 896: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide; Compound 897: (1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1,1-dimethyl-ethyl)-amide; Compound 898: (1aR,5aR)-2-(4-tert-Butylcarbamoyl-pyridin-2-yl)-1a,2,5,5a-tetrahydro-1H-2,3-diaza-cyclopropa[a]pentalene-4-carboxylic acid tert-butylamide; Compound 899: (1aR,5aR)-2-(4-Chloro-pyridin-2-yl)-1a,2,5,5a-tetrahydro-1H-2,3-diaza-cyclopropa[a]pentalene-4-carboxylic acid ((S)-2-fluoro-1-hydroxymethyl-2-methyl-propyl)-amide; Compound 900: (1aR,5aR)-2-(4-Chloro-pyridin-2-yl)-1a,2,5,5a-tetrahydro-1H-2,3-diaza-cyclopropa[a]pentalene-4-carboxylic acid ((R)-2-fluoro-1-hydroxymethyl-2-methyl-propyl)-amide; Compound 901: (1aS,5aS)-2-(4-Chloro-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide; Compound 902: (1aS,5aS)-2-(4-Oxy-pyrazin-2-yl)-1a,2,5,5a-tetrahydro-H-2,3-diaza-cyclopropa[a]pentalene-4-carboxylic acid N'-tert-butyl-hydrazide; Compound 903: (1aS,5aS)-2-(4-Chloro-pyridin-2-yl)-1a,2,5,5a-tetrahydro-1H-2,3-diaza-cyclopropa[a]pentalene-4-carboxylic acid N'-(2,2,2-trifluoro-ethyl)-hydrazide; Compound 904: (1aS,5aS)-2-(4-Oxy-pyrazin-2-yl)-1a,2,5,5a-tetrahydro-H-2,3-diaza-cyclopropa[a]pentalene-4-carboxylic acid (2-fluoro-1,1-dimethyl-ethyl)-amide; Compound 905: (1aS,5aS)-2-(4-Chloro-pyridin-2-yl)-1a,2,5,5a-tetrahydro-1H-2,3-diaza-cyclopropa[a]pentalene-4-carboxylic acid N'-(1,1-dioxo-tetrahydro-1$\lambda^6$-thiophen-3-yl)-hydrazide; Compound 906: (1aR,5aR)-2-(4-Methoxy-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 907: (1aR,5aR)-2-(4-Methoxy-pyridin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 908: (1aR,5aR)-2-(4-Hydroxy-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide; Compound 909: (1aR,5aR)-2-(4-Hydroxy-pyridin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide; Compound 910: (1aS,5aS)-2-(4-Chloro-pyridin-2-yl)-1a,2,5,5a-tetrahydro-1H-2,3-diaza-cyclopropa[a]pentalene-4-carboxylic acid ((R)-2-fluoro-1-hydroxymethyl-2-methyl-propyl)-amide; Compound 911: (1aS,5aS)-2-(4-Chloro-pyridin-2-yl)-1a,2,5,5a-tetrahydro-1H-2,3-diaza-cyclopropa[a]pentalene-4-carboxylic acid ((S)-2-fluoro-1-hydroxymethyl-2-methyl-propyl)-amide; Compound 912: (1aS,5aS)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide; Compound 913: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2-hydroxy-1-phenyl-ethyl)-amide; Compound 914: (1aS,5aS)-2-(4-Oxy-pyrazin-2-yl)-1a,2,5,5a-tetrahydro-H-2,3-diaza-cyclopropa[a]pentalene-4-carboxylic acid ((S)-3,3,3-trifluoro-1-hydroxymethyl-propyl)-amide; Compound 915: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2-methyl-propyl)-amide; Compound 916: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide; Compound 917: (1aR,5aR)-2-(4-Oxy-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide; Compound 918: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide; Compound 919: (1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide; Compound 920: (1aS,5aS)-2-(4-Oxy-pyrazin-2-yl)-

1a,2,5,5a-tetrahydro-1H-2,3-diaza-cyclopropa[a]pentalene-4-carboxylic acid ((1S,2S)-2-hydroxy-indan-1-yl)-amide; Compound 921: (1aS,5aS)-2-(4-Oxy-pyrazin-2-yl)-1a,2,5,5a-tetrahydro-1H-2,3-diaza-cyclopropa[a]pentalene-4-carboxylic acid ((1S,2R)-2-hydroxy-indan-1-yl)-amide; Compound 922: (1aS,5aS)-2-(4-Oxy-pyrazin-2-yl)-1a,2,5,5a-tetrahydro-1H-2,3-diaza-cyclopropa[a]pentalene-4-carboxylic acid (3-methyl-oxetan-3-yl)-amide; Compound 923: (1aS,5aS)-3,3-Dimethyl-2-{[(S)-2-(4-oxy-pyrazin-2-yl)-1a,2,5,5a-tetrahydro-1H-2,3-diaza-cyclopropa[a]pentalene-4-carbonyl]-amino}-butyric acid; Compound 924: (1aS,5aS)-2-(4-Oxy-pyrazin-2-yl)-1a,2,5,5a-tetrahydro-1H-2,3-diaza-cyclopropa[a]pentalene-4-carboxylic acid (1-fluoromethyl-cyclobutyl)-amide; Compound 925: (1aS,5aS)-2-(4-Oxy-pyrazin-2-yl)-1a,2,5,5a-tetrahydro-1H-2,3-diaza-cyclopropa[a]pentalene-4-carboxylic acid (1,1-bis-hydroxymethyl-2-methyl-propyl)-amide; Compound 926: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide; Compound 927: (1aS,5aS)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide; Compound 928: (1aS,5aS)-2-(4-Oxy-pyrazin-2-yl)-1a,2,5,5a-tetrahydro-1H-2,3-diaza-cyclopropa[a]pentalene-4-carboxylic acid (1-methyl-cyclopropyl)-amide; Compound 929: (1aS,5aS)-2-(4-Oxy-pyrazin-2-yl)-1a,2,5,5a-tetrahydro-1H-2,3-diaza-cyclopropa[a]pentalene-4-carboxylic acid (3-trifluoromethyl-oxetan-3-yl)-amide; Compound 930: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclopropyl)-amide; and Compound 931: (1aR,5aR)-2-(4-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide.

Additionally, chemical genera of the present invention and individual compounds, for example those compounds found in the above list including diastereoisomers and enantiomers thereof, encompass all pharmaceutically acceptable salts, solvates, and particularly hydrates, thereof.

The compounds of the Formula Ia of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention embraces each diastereoisomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Indications and Methods of Prophylaxis and/or Treatment

In addition to the foregoing beneficial uses for the modulators of cannabinoid receptor activity disclosed herein, the compounds disclosed herein are useful in the treatment of several additional diseases and disorders, and in the amelioration of symptoms thereof. Without limitation, these include the following:

1. Pain.

The analgesic properties of cannabinoids have been recognized for many years. For example, animal studies have demonstrated that the $CB_1/CB_2$ agonists anandamide, THC, CP55,940 and WIN 55212-2 are effective against acute and chronic pain from chemical, mechanical, and thermal pain stimuli (reviewed in Walker and Huang (2002) *Pharmacol. Ther.* 95:127-135; reviewed in Pacher, P et al. (2006) *Pharmacol. Rev.* 58(3): 389-462). In humans, topical administration of the $CB_1/CB_2$ agonist HU-210 attenuates capsaicin-induced hyperalgesia and allodynia (Rukwied, R. et al. (2003) *Pain* 102:283-288), and co-administration of the $CB_1/CB_2$ agonist THC and cannabidiol (nabiximols, trademark Sativex®) provides relief from cancer-associated pain (GW Pharmaceuticals press release Jan. 19, 2005, Jun. 19, 2007) and multiple-sclerosis-associated pain and spasticity (GW Pharmaceuticals press release Sep. 27, 2005, Mar. 11, 2009).

The role of $CB_1$ in mediating these analgesic effects is well-documented (reviewed in Manzanares, J. et al. (2006) *Current Neuropharmacology* 4:239-57; reviewed in Pacher, P. et al. (2006) *Pharmacol. Rev.* 58(3): 389-462). For example, blockade of peripheral or central $CB_1$ leads to hyperalgesia (Richardson, J. D. et al. (1997) *Eur. J. Pharmacol.* 345:145-153; Calignano, A. et al. (1998) *Nature* 394:277-281), whereas $CB_1$ activation by exogenous administration of a $CB_1$ agonist arachidonyl-2-chloroethylamide reduces pain (Furuse, S. et al. (2009) *Anesthesiology* 111 (1):173-86).

Although less well-documented, $CB_2$ also plays a role in mediating analgesic effects of cannabinoids (reviewed in Guindon and Hohmann (2008) *Br. J. Pharmacol.* 153:319-334). For example, systemic delivery of the $CB_2$-selective agonist AM1241 suppresses hyperalgesia induced in the carrageenan, capsaicin, and formalin models of inflammatory pain in rodents (reviewed in Guindon and Hohmann (2008) *Br. J. Pharmacol.* 153:319-334). Local (subcutaneous) or systemic administration of AM1241 also reverses tactile and thermal hypersensitivity in rats following ligation of spinal nerves in the chronic constriction injury model of neuropathic pain (Malan, T. P. et al. (2001) *Pain* 93:239-245; Ibrahim, M. M. et al. (2003) *Proc. Natl. Acad. Sci.* 100(18): 10529-10533), an effect which is inhibited by treatment with the $CB_2$-selective antagonist AM630 (Ibrahim, M. M. et al. (2005) *Proc. Natl. Acad. Sci.* 102(8):3093-8). The $CB_2$-selective agonist GW405833 administered systemically significantly reverses hypersensitivity to mechanical stimuli in rats following ligation of spinal nerves (Hu, B. et al. (2009) *Pain* 143:206-212). Thus, $CB_2$-selective agonists have also been demonstrated to attenuate pain in experimental models of acute, inflammatory, and neuropathic pain, and hyperalgesia.

Accordingly, $CB_2$-specific agonists and/or $CB_1/CB_2$ agonists find use in the treatment and/or prophylaxis of acute nociception and inflammatory hyperalgesia, as well as the allodynia and hyperalgesia produced by neuropathic pain. For example, these agonists are useful as an analgesic to treat pain arising from autoimmune conditions; allergic reactions; bone and joint pain; muscle pain; dental pain; nephritic syndrome; scleroderma; thyroiditis; migraine and other headache pain; pain associated with diabetic neuropathy; fibromyalgia, HIV-related neuropathy, sciatica, and neuralgias; pain arising from cancer; and pain that occurs as an adverse affect of therapeutics for the treatment of disease.

Furthermore, although cannabinoids exert their antinociceptive effects by complex mechanisms involving effects on the central nervous system, spinal cord, and peripheral sensory nerves (reviewed in Pacher, P. et al. (2006) *Pharmacol. Rev.* 58(3): 389-462), an analysis of models of inflammatory and neuropathic pain in mice that are deficient for $CB_1$ only in nociceptive neurons localized in the peripheral nervous system demonstrates that the contribution of $CB_1$-type receptors expressed on the peripheral terminals of nociceptors to cannabinoid-induced analgesia is paramount (Agarwal, N. et al. (2007) *Nat. Neurosci.* 10(7): 870-879). Accordingly, agonists of $CB_1$ that are unable to cross the blood brain barrier still find use in the treatment and/or prophylaxis of acute pain, inflammatory pain, neuropathic pain, and hyperalgesia.

2. Disorders of the Immune System.

Autoimmune Disorders.

Cannabinoid receptor agonists have been demonstrated to attenuate aberrant immune responses in autoimmune disorders, and in some cases, to provide protection to the tissue that is being inappropriately targeted by the immune system.

For example, Multiple Sclerosis (MS) is an autoimmune disorder that results in the demyelination of neurons in the CNS. The $CB_1/CB_2$ agonist THC significantly inhibits the severity of clinical disease in the Experimental Autoimmune Encephalomyelitis (EAE) mouse model of MS, an effect that is believed to be mediated by $CB_1$ on neurons and $CB_2$ on immune cell (Maresz, K. et al. (2007) *Nat. Med.* 13(4):492-497). Consistent with these results, $CB_1$-selective agonist WIN 55212-2 provides significant neuroprotection in the experimental allergic uveitis (EAU) model in mice (Pryce, G. et al. (2003) *Brain* 126:2191-2202), whereas $CB_2$-selective agonist HU-308 markedly reduces the recruitment of immature myeloid cells and T cells, microglial and infiltrating myeloid cell proliferation, and axonal loss in the EAE model (Palazuelos, J. et al. (2008). *J. Biol. Chem.* 283(19): 13320-9). Likewise, the $CB_1/CB_2$ agonist WIN 55212-2 significantly inhibits leukocyte rolling and adhesion in the brain in the EAE mouse model, an effect that is blocked by the $CB_2$-selective antagonist SR144528 but not the $CB_1$-selective antagonist SR141716A (Ni, X. et al. *Mult. Sclerosis* 10(2):158-64). Accordingly, $CB_2$-selective agonists and/or $CB_1/CB_2$ agonists find use in the treatment and/or prophylaxis of Multiple Sclerosis and related autoimmune demyelinating diseases, e.g. Guillan-Barré syndrome, polyradiculoneuropathy and chronic inflammatory demyelination.

As another example, the autoimmune disease Rheumatoid Arthritis (RA) is a chronic, systemic inflammatory disorder of the skeletal system that principally attacks the joints to produce an inflammatory synovitis and that often progresses to destruction of the articular cartilage and ankylosis of the joints. The $CB_1/CB_2$ agonists WIN 55212-2 and HU-210 significantly inhibit IL-1alpha-stimulated proteoglycan and collagen degradation in bovine nasal cartilage explants in vitro (Mbvundula, E. et al. (2006) *J. Pharm. and Pharmacol.* 58:351-358). Accordingly, $CB_2$-selective agonists and/or $CB_1/CB_2$ agonists find use in the treatment and/or prophylaxis of autoimmune arthritic diseases, for example, rheumatoid arthritis, psoriatic arthritis, ankylosing spondylarthritis, and reactive arthritis.

Type 1 Hypersensitivity and Allergic Response.

Cannabinoid receptor agonists have been demonstrated to attenuate aberrant immune responses in allergic reactions as well. In type-1, or immediate, hypersensitivity, plasma cells that have been activated by an allergen secrete IgE antibodies, which bind to Fc receptors on the surface of tissue mast cells and blood basophils and eosinophils. Repeated exposure to the same allergen results in cross-linking of the bound IgE on sensitized cells, resulting in secretion of pharmacologically active mediators such as histamine, leukotriene and prostaglandin. These mediators are responsible for the symptoms associated with allergies, including vasodilation and increased permeability, smooth muscle spasms, and leukocyte extravasation. Topical administration of the $CB_1/CB_2$ agonist HU-210 reduces these histamine-induced responses in human skin (Dvorak, M. et al. (2003) *Inflamm. Res.* 52:238-245). Similarly, subcutaneous injection of $CB_1/CB_2$ agonist THC or increased levels of endogenous cannabinoids reduces cutaneous inflammation and the pruritis (itch) associated with it in a mouse model for allergic contact dermatitis. (Karsak et al. (2007) *Science,* 316(5830), 1494-1497). In contrast, injection of the $CB_1$ receptor antagonist S141716A or the $CB_2$ receptor antagonist SR144528 exacerbates this inflammation and pruritis. (Karsak et al. (2007) *Science,* 316(5830), 1494-1497). Accordingly, $CB_2$-selective agonists and/or $CB_1/CB_2$ agonists find use in the treatment of allergic reactions including atopic dermatitis (pruritis/itch), urticaria (hives), asthma, conjunctivitis, allergic rhinitis (hay fever), and anaphylaxis.

Conditions Associated with CNS Inflammation.

$CB_2$ agonists have been demonstrated to attenuate inflammation in the CNS. For example, administration of $CB_2$ agonists prevents the activation of microglia in rodent models of Alzheimer's Disease (Ashton J. C., et al. (2007) *Curr. Neuropharmacol.* 5(2):73-80). Likewise, administration of $CB_2$ agonists reduces the volume of infarcts by 30% in a rodent occlusion model of stroke (Zhang, M. et al. (2007) *J. Cereb. Blood Flow Metab.* 27:1387-96). Thus, $CB_2$ agonists find use in the treatment and/or prophylaxis of neuropathologies associated with CNS inflammation, e.g. Alzheimer's, stroke-induced damage, dementia, ALS, and HIV.

Conditions Associated with Vascular Inflammation.

$CB_2$ is expressed in macrophages and T cells in atherosclerotic plaques, and the $CB_1/CB_2$ agonist THC reduces the progression of atherosclerosis in ApoE knockout mice, a well studied mouse model of atherosclerosis. The $CB_2$-specific antagonist SR144528 completely blocks this effect in vitro and in vivo (Steffens, S. et al. (2005) *Nature* 434:782-786). Thus, $CB_2$ agonists find use in treating atherosclerosis.

Other Disorders Associated with Aberrant or Unwanted Immune Response.

Given the expression of $CB_2$ on a number of different types of immune cells and the attenuating effects that $CB_2$ agonists have been observed to have on the activities of these cells, $CB_2$ agonists are useful for the treatment and/or prophylaxis of other disorders wherein undesired immune cell activity and/or inflammation is observed. Such exemplary disorders include osteoarthritis, anaphylaxis, Behcet's disease, graft rejection, vasculitis, gout, spondylitis, viral and bacterial diseases, e.g. AIDS, and meningitis; and other autoimmune disorders such as lupus, e.g. systemic lupus erythematosus; inflammatory bowel disease, e.g. Crohn's disease, ulcerative colitis; psoriasis; autoimmune hepatitis; and type 1 diabetes mellitus.

3. Bone and Joint Diseases.

Osteoporosis.

$CB_2$ is expressed in osteoblasts, osteocytes, and osteoclasts. Osteoblasts make new bone, whereas osteoclasts degrade it. The $CB_2$-specific agonist HU-308 enhances endocortical osteoblast numbers and activity while simultaneously inhibiting proliferation of osteoclast precursors in bone marrow-derived osteoblasts/stromal cells in vitro, and attenuates ovariectomy-induced bone loss and stimulates cortical thickness by stimulating endocortical bone formation and suppressing osteoclast number in vivo (Ofek, O. et al. (2006) *Proc. Natl. Acad. Sci.* 103(3):696-701). Thus, $CB_2$ agonists are useful for the treatment and/or prophylaxis of disease wherein bone density is decreased, such as osteoporosis.

Arthritis.

As discussed above, $CB_2$-selective agonists and $CB_1/CB_2$ agonists are useful for the treatment and/or prophylaxis of autoimmune arthritic diseases, for example, rheumatoid arthritis, psoriatic arthritis, ankylosing spondylarthritis, and reactive arthritis, and for the treatment and/or prophylaxis of inflammation associated with osteoarthritis. In addition, as discussed above, $CB_1$-selective agonists and $CB_1/CB_2$ agonists are useful for the treatment of pain associated with these arthritic disorders.

4. Eye Disease.

Retinal pigment epithelial (RPE) cells provide trophic support to photoreceptor cells in the eye, and RPE cell death has been demonstrated to be a major contributor to Age-related Macular Degeneration (AMD). The $CB_1/CB_2$ agonist CP55940 significantly protects RPE cells from oxidative damage; the $CB_2$ receptor agonist, JWH015 provides comparable protection (Wei, Y. et al. (2009) *Mol. Vis.* 15:1243-51). Accordingly, $CB_2$-selective agonists find use in preventing the onset or progression of vision loss associated with AMD.

5. Cough.

The cough reflex is predominantly under the control of two classes of sensory afferent nerve fibers, the myelinated A-delta fibers and the non-myelinated C-fibers, the activation of which (i.e. depolarization) elicits cough via the vagus nerve afferent pathway. The $CB_1/CB_2$ agonist CP55940 reduces capsaicin-, $PGE_2$- and hypertonic saline-induced depolarization of guinea pig and human vagus nerve preparations in vitro (Patel, H. J. et al. (2003) *British J. Pharma.* 140:261-8). The $CB_1/CB_2$ agonists WIN 55212-2 produced a dose-dependent inhibition of the number of capsaicin-induced coughs in mice (Morita, K. et al. (2003) *Eur. J. Pharmacol.* 474:269-272). The $CB_1/CB_2$ agonist anandamide produced a dose-dependent inhibition of the number of capsaicin-induced coughs in guinea pigs (Calignano, A. et al. (2000) *Nature* 408:96-101). $CB_1$-specific antagonist SR141716A attenuates the antitussive effects of WN 55212-2 and anandamide (Morita, K. et al. (2003) *Eur. J. Pharmacol.* 474:269-272; Calignano, A. et al. (2000) *Nature* 408:96-101). The $CB_2$-selective agonist JWH133 reduces capsaicin-, $PGE_2$- and hypertonic saline-induced depolarization of guinea pig and human vagus nerve preparations in vitro, and administration of $CB_2$-selective agonist JWH133 prior to exposure to the tussive agent citric acid significantly reduces cough in conscious guinea-pigs (Patel, H. J. et al. (2003) *British J. Pharma.* 140:261-8). Thus, both $CB_1$ and $CB_2$ play an important role in mediating the antitussive effect of cannabinoids, and $CB_1$-selective agonists and $CB_1/CB_2$ agonists are useful in the treatment and/or prophylaxis of cough.

6. Cancer.

A number of human leukemia and lymphoma cell lines, including Jurkat, Molt-4 and Sup-T1, express $CB_2$ and not $CB_1$, and agonists of $CB_2$ induce apoptosis in these and primary acute lymphoblastic leukemia (ALL) cells (Nagarkatti, L. C. et al. US2004/0259936). Similarly, $CB_2$ is expressed on glioblastoma cell lines and treatment with agonists of $CB_2$ induces apoptosis of these cells in vitro (Widmer, M. (2008) *J. Neurosci. Res.* 86(14):3212-20). Accordingly, $CB_2$-selective agonists are useful to attenuate the growth of a malignancy of the immune system, for example, leukemias, lymphomas, and solid tumors of the glial lineage.

In addition, as discussed above, $CB_1$-selective agonists and $CB_1/CB_2$ agonists are useful in providing relief from pain associated with cancer (GW Pharmaceuticals press release Jan. 19, 2005, Jun. 19, 2007).

$CB_2$-mediated signaling is involved in the in vivo and in vitro growth inhibition of prostate cancer cells, which suggests that $CB_2$ agonists have potential therapeutic interest in the management of prostate cancer. (Inhibition of human tumour prostate PC-3 cell growth by cannabinoids R(+)-Methanandamide and JWH-015: Involvement of $CB_2$; Olea-Herrero, et al. *British Journal of Cancer* advance online publication 18 Aug. 2009; doi: 10.1038/sj.bjc. 6605248).

7. Regenerative Medicine.

Agonists of $CB_2$ modulate the expansion of the progenitor pool of neurons in the CNS. $CB_2$ antagonists inhibit the proliferation of cultured neural stem cells and the proliferation of progenitor cells in the SVZ of young animals, whereas $CB_2$-selective agonists stimulate progenitor cell proliferation in vivo, with this effect being more pronounced in older animals (Goncalves, M. B. et al. (2008) *Mol. Cell Neurosci.* 38(4):526-36). Thus, agonists of $CB_2$ are useful in regenerative medicine, for example to promote the expansion of progenitor cells for the replacement of neurons lost during injury or disease, such as Alzheimer's Disease, stroke-induced damage, dementia, amyotrophic lateral sclerosis (ALS) and Parkinson's Disease.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods-well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20th Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate, hydrate or physiologically functional derivative thereof can be used as active ingredients in pharmaceutical compositions, specifically as cannabinoid receptor modulators. By the term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents.

Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds of the present invention which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1,N^2$-dibenzylethane-1, 2-diamine), chloroprocaine (2-(diethylamino)ethyl 4-(chloroamino)benzoate), choline, diethanolamine, ethylenediamine, meglumine ((2R,3R,4R,5S)-6-(methylamino) hexane-1,2,3,4,5-pentaol), procaine (2-(diethylamino)ethyl 4-aminobenzoate), and the like. Certain pharmaceutically acceptable salts are listed in Berge, et al., *Journal of Pharmaceutical Sciences*, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the cannabinoid receptor modulators are utilized as active ingredients in a pharmaceutical composition, these are not intended for use only in humans, but in other non-human mammals as well. Indeed, recent advances in the area of animal health-care mandate that consideration be given for the use of active agents, such as cannabinoid receptor modulators, for the treatment of a cannabinoid receptor-associated disease or disorder in companionship animals (e.g., cats, dogs, etc.) and in livestock animals (e.g., cows, chickens, etc.) Those of ordinary skill in the art are readily credited with understanding the utility of such compounds in such settings.

Hydrates and Solvates

It is understood that when the phrase "pharmaceutically acceptable salts, solvates and hydrates" is used when referring to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula.

The compounds of the present invention can be administrated in a wide variety of oral and parenteral dosage forms. It will be apparent to those skilled in the art that the following dosage forms may comprise, as the active component, either a compound of the invention or a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Brittan, Vol. 95, Marcel Dekker, Inc., New York, 1999, incorporated herein by reference in its entirety. Accordingly, one aspect of the present invention pertains to hydrates and solvates of compounds of Formula Ia and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Polymorphs and Pseudopolymorphs

Polymorphism is the ability of a substance to exist as two or more crystalline phases that have different arrangements and/or conformations of the molecules in the crystal lattice.

Polymorphs show the same properties in the liquid or gaseous state but they behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

By way of example, Stahly recently published a polymorph screens of 245 compounds consisting of a "wide variety of structural types" revealed that about 90% of them exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026.)

Other Utilities

Another object of the present invention relates to radio-labeled compounds of the present invention that would be useful not only in radio-imaging but also in assays, both in vitro and in vivo, for localizing and quantitating cannabinoid receptors in tissue samples, including human and for identifying cannabinoid receptor ligands by inhibition binding of a radio-labeled compound. It is a further object of this invention to develop novel cannabinoid receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{82}$Br, $^{123}$I, $^{124}$I, $^{125}$I and $^{131}$I. The radionuclide that is incorporated in the instant radio-labeled compounds will depend on the specific application of that radio-labeled compound. For example, for in vitro cannabinoid receptor labeling and competition assays, compounds that incorporate $^{3}$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound of Formula Ia, Ic, or Ie that has incorporated at least one radionuclide; in some embodiments the radionuclide is selected from the group consisting of $^{3}$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^{3}$H and/or $^{14}$C isotopes are useful in these studies. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^{3}$H]: This procedure is rather inexpensive and requires precursors containing reducible functional groups such as aldehydes, ketones, lactones, esters and the like.

C. Reduction with Lithium Aluminum Hydride [$^{3}$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^{3}$H]: This procedure is usually employed to prepare O-methyl or N-methyl (3H) products by treating appropriate precursors with high specific activity methyl iodide (3H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na $^{125}$I. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled cannabinoid receptor compound of Formula Ia can be used in a screening assay to identify/evaluate compounds. In general terms, a newly synthesized or identified compound (i.e., test compound) can be evaluated for its ability to reduce binding of the "radio-labeled compound of Formula Ia" to a cannabinoid receptor. Accordingly, the ability of a test compound to compete with the "radio-labeled compound of Formula Ia" for the binding to a cannabinoid receptor directly correlates to its binding affinity.

Certain labeled compounds of the present invention bind to certain cannabinoid receptors. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM and in still yet another embodiment the labeled inhibitor has an IC$_{50}$ less than about 0.1 μM.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Syntheses of Compounds of the Present Invention

Illustrated syntheses for compounds of the present invention are shown in FIGS. 9 through 14 where the symbols have the same definitions as used throughout this disclosure.

The compounds of the invention and their syntheses are further illustrated by the following examples. The following examples are provided to further define the invention without, however, limiting the invention to the particulars of these examples. The compounds described herein, supra and infra, are named according to AutoNom version 2.2, AutoNom 2000, CS ChemDraw Ultra Version 7.0.1, or CS ChemDraw Ultra Version 9.0.7. In certain instances common names are used and it is understood that these common names would be recognized by those skilled in the art.

Chemistry:

Proton nuclear magnetic resonance ($^1$H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, ddd=doublet of doublet of doublets, dt=doublet of triplets, t=triplet, td=triplet of doublets, tt=triplet of triplets, q=quartet, m=multiplet, bs=broad singlet, bt=broad triplet. Microwave irradiations were carried out using a Smith Synthesizer™ or an Emrys Optimizer™ (Biotage). Thin-layer chromatography (TLC) was performed on silica gel 60 F$_{254}$ (Merck), preparatory thin-layer chromatography (prep TLC) was preformed on PK6F silica gel 60 Å 1 mm plates (Whatman) and column chromatography was carried out on a silica gel column using Kieselgel 60, 0.063-0.200 mm (Merck). Evaporation was done under reduced pressure on a Büchi rotary evaporator.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1: Preparation of (1aR,5aR)-2-(2,4-Difluoro-phenyl)-1a,2,5,5a-tetrahydro-1H-2,3-diaza-cyclopropa[a]pentalene-4-carboxylic Acid (Intermediate 1)

Step A: Preparation of (1aR,5aR)-2-(2,4-Difluoro-phenyl)-1a,2,5,5a-tetrahydro-1H-2,3-diaza-cyclopropa[a]pentalene-4-carboxylic Acid Ethyl Ester. [Method A]

To a solution of (1R,5S)-bicyclo[3.1.0]hexan-2-one (9.19 g, 96 mmol) and diethyl oxalate (12.98 mL, 96 mmol) in absolute ethanol (300 mL) was added a 1.0 M THF solution of potassium tert-butoxide (105 mL, 105 mmol). The resulting yellow solution was stirred at 20° C. for 2 h. (2,4-difluorophenyl)hydrazine hydrochloride (17.26 g, 96 mmol) was added followed by a 3.0 M aqueous solution of hydrogen chloride (96 mL, 287 mmol). The reaction was stirred at 40° C. for 18 h. The volume was reduced by about 200 mL, and then brine (300 mL) was added. The mixture was extracted with dichloromethane (3×250 mL). The combined organic extracts were dried (MgSO$_4$), filtered, and then concentrated. The residue was purified by silica gel flash chromatography to give the title compound as a yellow solid (18.4 g). LCMS m/z=305.3 [M+H]$^+$; $^1$H NMR (400 MHz, CDCl$_3$) δ ppm 0.49 (td, J=4.8, 3.3 Hz, 1H), 1.16 (td, J=7.8, 5.0 Hz, 1H), 1.38 (t, J=7.1 Hz, 3H), 2.11-2.16 (m, 1H), 2.24-2.30 (m, 1H), 2.90 (d, J=16.6 Hz, 1H), 3.03 (dd, J=16.4, 6.3 Hz, 1H), 4.38 (q, J=7.1 Hz, 2H), 6.97-7.02 (m, 2H), 7.66-7.72 (m, 1H).

Step B: Preparation of (1aR,5aR)-2-(2,4-Difluoro-phenyl)-1a,2,5,5a-tetrahydro-1H-2,3-diaza-cyclopropa[a]pentalene-4-carboxylic Acid. [Method B]

To a solution of (1aR,5aR)-2-(2,4-difluoro-phenyl)-1a,2,5,5a-tetrahydro-1H-2,3-diaza-cyclopropa[a]pentalene-4-carboxylic acid ethyl ester (17.4 g, 57.2 mmol) in methanol (100 mL) and THF (100 mL) was added a 2.0 M aqueous solution of sodium hydroxide (86 mL, 172 mmol). The resulting orange solution was stirred at 23° C. for 3 h. The organic solvents were removed under reduced pressure. The remaining aqueous solution was diluted to 150 mL with water and then acidified to pH 2 by addition of 6 M HCl while stirring vigorously. The precipitate was collected by filtration, rinsed with water, and then dried under reduced pressure to give the title compound as a tan solid (15.62 g).

LCMS m/z=277.3 [M+H]+; 1H NMR (400 MHz, DMSO-d6) δ ppm 0.41 (td, J=4.6, 3.4 Hz, 1H), 1.15 (td, J=7.8, 4.7 Hz, 1H), 2.16-2.21 (m, 1H), 2.23-2.29 (m, 1H), 2.76 (d, J=16.2 Hz, 1H), 2.90 (dd, J=16.4, 6.2 Hz, 1H), 7.27-7.32 (m, 1H), 7.56-7.62 (m, 1H), 7.75 (td, J=9.0, 5.9 Hz, 1H), 12.93 (bs, 1H).

Example 1.2: Preparation of (1aR,5aR)-2-(Pyrazin-2-yl)-1a,2,5,5a-tetrahydro-1H-2,3-diaza-cyclopropa[a]pentalene-4-carboxylic Acid (Intermediate 2)

Step A: Preparation of Potassium 2-Ethoxy-2-oxo-1-((1R,5R)-2-oxobicyclo[3.1.0]hexan-3-ylidene)ethanolate To a solution of (1R,5S)-bicyclo[3.1.0]hexan-2-one (10 g, 91 mmol) and diethyl oxalate (12.29 mL, 91 mmol) in absolute ethanol (250 mL) was added a 1.0 M THF solution of potassium tert-butoxide (91 mL, 91 mmol). The resulting yellow solution was stirred at 20° C. for 3 h. The mixture was diluted with diethyl ether (250 mL). The precipitate was collected by filtration, rinsed with diethyl ether, and then dried under reduced pressure to give the title compound as a yellow solid (16.7 g). LCMS m/z=197.2 [M+H]+; 1H NMR (400 MHz, DMSO-d6) δ ppm 0.14 (td, J=4.5, 3.4 Hz, 1H), 0.78 (td, J=8.0, 3.3 Hz, 1H), 1.15 (t, J=7.2 Hz, 3H), 1.26-1.31 (m, 1H), 1.41-1.47 (m, 1H), 2.27 (dd, J=14.2, 1.4 Hz, 1H), 2.39 (dd, J=14.2, 6.2 Hz, 1H), 3.91-4.01 (m, 2H).

Step B: Preparation of (1aR,5aR)-2-(Pyrazin-2-yl)-1a,2,5,5a-tetrahydro-1H-2,3-diaza-cyclopropa[a]pentalene-4-carboxylic Acid Ethyl Ester. [Method C]

To a stirred suspension of 2-ethoxy-2-oxo-1-((1R,5R)-2-oxobicyclo[3.1.0]hexan-3-ylidene)ethanolate (300 mg, 1.28 mmol) in ethanol (5 mL) was added 2-hydrazinylpyrazine (141 mg, 1.28 mmol) followed by 6 N HCl (0.5 mL, 3.0 mmol). The reaction was stirred overnight at room temperature. The reaction was diluted with H2O and extracted with DCM. The combined organic phases were washed with H2O, dried over MgSO4, and concentrated. Purification by silica gel flash chromatography gave the title compound (150 mg). LCMS m/z=271.2 [M+H]+; 1H NMR (400 MHz, CDCl3) δ ppm 0.47 (td, J=4.7 and 3.4 Hz, 1H), 1.22-1.28 (m, 1H), 1.39 (t, J=7.1 Hz, 3H), 2.26-2.30 (m, 1H), 2.77-2.82 (m, 1H), 2.87 (d, J=16.6 Hz, 1H), 2.98 (dd, J=16.6 and 6.3 Hz, 1H), 4.40 (q, J=7.1 Hz, 2H), 8.40 (dd, J=2.6 and 1.5 Hz, 1H), 8.51 (d, J=2.5 Hz, 1H), 9.39 (d, J=1.3 Hz, 1H).

Step C: Preparation of (1aR,5aR)-2-(Pyrazin-2-yl)-1a,2,5,5a-tetrahydro-1H-2,3-diaza-cyclopropa[a]pentalene-4-carboxylic Acid. [Method D]

To a solution of (1aR,5aR)-2-(pyrazin-2-yl)-1a,2,5,5a-tetrahydro-1H-2,3-diaza-cyclopropa[a]pentalene-4-carboxylic acid ethyl ester (150 mg, 0.56 mmol) in dioxane (2 mL) was added 1 N LiOH (1.1 mL, 1.11 mmol). The reaction was stirred for 1 h at 80° C., and cooled to room temperature. The reaction was acidified to pH 2 with 4 N HCl and diluted with H2O to form precipitate. The resulting precipitate was collected by filtration, rinsed with water, and then dried to give the title compound as a white solid (100 mg). LCMS m/z=243.3 [M+H]+; 1H NMR (400 MHz, DMSO-d6) δ ppm 0.43 (td, J=4.5 and 3.4 Hz, 1H), 1.26 (td, J=7.7 and 4.4 Hz, 1H), 2.26-2.33 (m, 1H), 2.70-2.79 (m, 2H), 2.89 (dd, J=16.6 and 6.3 Hz, 1H), 8.60 (dd, J=2.6 and 1.5 Hz, 1H), 8.67 (d, J=2.6 Hz, 1H), 9.17 (d, J=1.4 Hz, 1H), 13.01 (s, 1H).

Example 1.3: Preparation of (1aS,5aS)-2-(2,4-Difluoro-phenyl)-1a,2,5,5a-tetrahydro-1H-2,3-diaza-cyclopropa[a]pentalene-4-carboxylic Acid (Intermediate 3)

The title compound was prepared in a manner similar to that described in Method A and B using (1S,5R)-bicyclo[3.1.0]hexan-2-one. LCMS m/z=277.3 [M+H]+; 1H NMR (400 MHz, CDCl3) δ ppm 0.51 (td, J=4.8, 3.5 Hz, 1H), 1.19 (td, J=7.8, 4.8 Hz, 1H), 2.14-2.18 (m, 1H), 2.26-2.32 (m, 1H), 2.92 (d, J=16.9 Hz, 1H), 3.04 (dd, J=16.7, 6.6 Hz, 1H), 6.99-7.04 (m, 2H), 7.67-7.73 (m, 1H).

Example 1.4: Preparation of (1aR,5aR)-2-tert-Butyl-1a,2,5,5a-tetrahydro-1H-2,3-diaza-cyclopropa[a]pentalene-4-carboxylic Acid (1-Methyl-1-phenyl-ethyl)-amide (Compound 325)

Step A: Preparation of (1aR,5aR)-1a,2,5,5a-tetrahydro-1H-2,3-diazacyclopropa[a]pentalene-4-carboxylic Acid [Method E]

To a solution of (1R,5S)-bicyclo[3.1.0]hexan-2-one (729 mg, 7.6 mmol) and diethyl oxalate (1030 μL, 7.6 mmol) in EtOH at 0° C. under N2 was added 1 M potassium tert-butoxide (8342 μL, 8.3 mmol). The mixture was warmed to room temperature and stirred for 6 h at which time hydrazine monohydrochloride (779 mg, 11.4 mmol) in H2O (4 mL) was added. The mixture was stirred for 15 h and the ethanol was removed under reduced pressure. The mixture was diluted with H2O and extracted with EtOAc. The combined organics were washed with brine, dried over MgSO4, filtered, and concentrated. The residue was dissolved in THF (6 mL) and H2O (6 mL). LiOH (363 mg, 15.1 mmol) was added and the mixture was stirred in the microwave at 60° C. for 2 h. The mixture was acidified with 1 N HCl and extracted with EtOAc (twice) and concentrated. The residue was purified by HPLC. The combined HPLC fractions were concentrated to remove CH3CN and the remaining aqueous was extracted with EtOAc (twice). The organics were washed with brine, dried over MgSO4, filtered, and concentrated to give the title compound as a white solid (322 mg). LCMS m/z=165.3 [M+H]+; 1H NMR (400 MHz, DMSO-d6) δ ppm 0.18 (td, J=4.5 and 3.4 Hz, 1H), 1.10 (td, J=7.8 and 4.5 Hz, 1H), 2.08-2.15 (m, 2H), 2.67 (d, J=16.9 Hz, 1H), 2.80-2.88 (m, 1H), —NH and —CO2H were not observed.

Step B: Preparation of (1aR,5aR)-2-tert-Butyl-1a,2,5,5a-tetrahydro-1H-2,3-diazacyclopropa[a]pentalene-4-carboxylic Acid. [Method F]

A mixture of (1aR,5aR)-1a,2,5,5a-tetrahydro-1H-2,3-diazacyclopropa[a]pentalene-4-carboxylic acid (330 mg, 2.0 mmol), tert-butanol (300 mg, 4.1 mmol), and TFA (1 mL) in a heavy walled tube was sealed and stirred overnight at 80° C. The reaction was diluted with H2O (8 mL), and extracted with DCM (twice). The organic was extracted with saturated NaHCO3 to remove organic impurities, and then the aqueous layer was acidified with 4 N HCl to pH 2 and extracted with DCM (twice). The combined organic layer was washed with H2O, dried over MgSO4, and concentrated to give the title product as a white powder (270 mg). LCMS m/z=221.2 [M+H]+; 1H NMR (400 MHz, CDCl3) δ ppm 0.37 (td, J=4.6 and 3.4 Hz, 1H), 1.16 (td, J=7.8 and 4.7 Hz, 1H), 1.64 (s, 9H), 2.16-2.24 (m, 2H), 2.80 (d, J=16.4 Hz, 1H), 2.94 (dd, J=16.6 and 5.8 Hz, 1H), —$CO_2H$ was not observed.

Step C: Preparation of (1aR,5aR)-2-tert-butyl-1a,2,5,5a-tetrahydro-1H-2,3-diazacyclopropa[a]pentalene-4-carboxylic Acid (1-Methyl-1-phenylethyl)-amide. [Method G]

To a solution of (1aR,5aR)-2-tert-butyl-1a,2,5,5a-tetrahydro-1H-2,3-diazacyclopropa[a]pentalene-4-carboxylic acid (30 mg, 0.136 mmol), HATU (55 mg, 0.143 mmol) in DMF (1 mL) was added $Et_3N$ (16 mg, 0.15 mmol). After stirring for 5 min at room temperature, 2-phenylpropan-2-amine (20 mg, 0.143 mmol) was added into the reaction. The reaction was stirred for 1 h at room temperature, and purified by preparative HPLC to give the title compound (25 mg). LCMS m/z=338.5 $[M+H]^+$; $^1H$ NMR (400 MHz, $CDCl_3$) δ ppm 0.34 (td, J=4.5 and 3.4 Hz, 1H), 1.11 (td, J=7.8 and 4.5 Hz, 1H), 1.63 (s, 9H), 1.78 (s, 6H), 2.11-2.18 (m, 2H), 2.75 (d, J=16.7 Hz, 1H), 2.86 (dd, J=16.6 and 5.8 Hz, 1H), 7.21 (t, J=7.3 Hz, 1H), 7.32 (t, J=8.0 Hz, 2H), 7.36 (bs, 1H), 7.42-7.46 (m, 2H).

Example 1.5: Preparation of (1aR,5aR)-2-(2-Morpholin-4-yl-ethyl)-1a,2,5,5a-tetrahydro-1H-2,3-diaza-cyclopropa[a]pentalene-4-carboxylic Acid (1-Methyl-1-phenyl-ethyl)-amide (Compound 251). [Method H]

To a solution of (1aR,5aR)-1a,2,5,5a-tetrahydro-1H-2,3-diazacyclopropa[a]pentalene-4-carboxylic acid (40 mg, 0.24 mmol), HATU (93 mg, 0.24 mmol) in DMF (1 mL) was added $Et_3N$ (25 mg, 0.24 mmol). After stirring for 5 min at room temperature, 2-phenylpropan-2-amine (33 mg, 0.24 mmol) was added to the reaction. After stirring for an additional 1 h, 4-(2-chloroethyl)morpholine hydrochloride (45 mg, 0.24 mmol) and $Cs_2CO_3$ (79 mg, 0.24 mmol) was added into the reaction. The reaction was microwaved for 3.5 h at 150° C., filtered, and purified by preparative HPLC to give the title compound (12 mg). LCMS m/z=395.5 $[M+H]^+$; $^1H$ NMR (400 MHz, $CDCl_3$) δ ppm 0.38 (td, J=4.6 and 3.5 Hz, 1H), 1.10 (td, J=7.8 and 4.7 Hz, 1H), 1.78 (s, 6H), 2.00-2.06 (m, 1H), 2.16-2.23 (m, 1H), 2.48-2.52 (m, 4H), 2.76-2.94 (m, 4H), 3.67-3.72 (m, 4H), 4.17 (t, J=6.8 Hz, 2H), 7.07 (bs, 1H), 7.21 (t, J=8.0 Hz, 1H), 7.32 (t, J=8.0 Hz, 2H), 7.42-7.47 (m, 2H).

Example 1.6: Preparation of (1aR,5aR)-2-Isopropyl-1a,2,5,5a-tetrahydro-1H-2,3-diaza-cyclopropa[a]pentalene-4-carboxylic Acid (1-Methyl-1-phenyl-ethyl)-amide (Compound 170). [Method I]

Step A: Preparation of Ethyl (1aR,5aR)-2-Isopropyl-1a,2,5,5a-tetrahydro-1H-2,3-diazacyclopropa[a]pentalene-4-carboxylate. [Method J]

(1aR,5aR)-1a,2,5,5a-Tetrahydro-1H-2,3-diazacyclopropa[a]pentalene-4-carboxylic acid ethyl ester (0.100 g, 0.520 mmol) (from Example 1.4, Step A) was dissolved in anhydrous DMF (5.20 mL). $CsCO_3$ (0.678 g, 2.081 mmol) was added to give a suspension which was stirred at 25° C. for several minutes. 2-Bromopropane (0.098 mL, 1.041 mmol) was added dropwise at 25° C. After stirring for 4 h, the reaction was diluted with EtOAc (50 mL), washed with water (2×10 mL), brine, and dried over $MgSO_4$. The solvent was evaporated under reduced pressure. The oil residue was purified by silica gel column chromatography to give the title compound as an oil (0.073 g). LCMS m/z=235.3 $[M+H]^+$; $^1H$ NMR (400 MHz, $CDCl_3$) δ ppm 0.29-0.35 (m, 1H), 1.12 (td, J=8.02, 4.93 Hz, 1H), 1.34 (t, J=7.20 Hz, 3H), 1.46 (dd, J=15.16, 6.57 Hz, 6H), 2.04-2.12 (m, 1H), 2.16-2.24 (m, 1H), 2.74-2.82 (m, 1H), 2.90-2.99 (m, 1H), 4.27 (q, J=7.07 Hz, 2H), 5.31-5.43 (m, 1H).

Step B: Preparation of (1aR,5aR)-2-Isopropyl-1a,2,5,5a-tetrahydro-1H-2,3-diazacyclopropa[a]pentalene-4-carboxylic Acid The title compound was prepared in a manner similar to that described in Method D, using ethyl (1aR,5aR)-2-Isopropyl-1a,2,5,5a-tetrahydro-1H-2,3-diazacyclopropa[a]pentalene-4-carboxylate. LCMS m/z=207.1 $[M+H]^+$.

Step C: Preparation of (1aR,5aR)-2-isopropyl-1a,2,5,5a-tetrahydro-1H-2,3-diazacyclopropa[a]pentalene-4-carboxylic Acid (1-Methyl-1-phenylethyl)-amide The title compound was prepared in a manner similar to that described in Method G, using (1aR,5aR)-2-Isopropyl-1a,2,5,5a-tetrahydro-1H-2,3-diazacyclopropa[a]pentalene-4-carboxylic acid and 2-phenylpropan-2-amine. LCMS m/z=324.6 $[M+H]^+$.

Example 1.7: Preparation of (1aR,5aR)-2-(2,4-Difluoro-phenyl)-1a,2,5,5a-tetrahydro-1H-2,3-diazacyclopropa[a]pentalene-4-carboxylic Acid (1-Methyl-1-phenyl-ethyl)-amide (Compound 18). [Method K]

The title compound was prepared in a manner similar to that described in Method G, using Intermediate 1 (see Example 1.1) and 2-phenylpropan-2-amine, except that it was purified by silica gel column chromatography. LCMS m/z=394.3 $[M+H]^+$; $^1H$ NMR (400 MHz, $CDCl_3$) δ ppm 0.48 (td, J=4.6 and 3.5 Hz, 1H), 1.08-1.18 (m, 1H), 1.79 (s, 6H), 2.05-2.15 (m, 1H), 2.19-2.30 (m, 1H), 2.85-3.06 (m, 2H), 7.03 (t, J=8.08 Hz, 2H), 7.16-7.25 (m, 2H), 7.32 (t, J=7.71 Hz, 2H), 7.46 (d, J=7.33 Hz, 2H), 7.60-7.71 (m, 1H).

Example 1.8: Preparation of (1aR,5aR)-2-(2,4-Difluoro-phenyl)-1a,2,5,5a-tetrahydro-1H-2,3-diazacyclopropa[a]pentalene-4-carboxylic Acid [1-(6-Methoxy-pyridin-3-yl)-1-methyl-ethyl]-amide (Compound 77)

Step A: Preparation of 2-(6-Methoxypyridin-3-yl)propan-2-amine. [Method L]

To a flame dried flask containing cerium(III) chloride (4.59 g, 18.64 mmol) was added THF (60 mL) under nitrogen atmosphere. The suspension was stirred at room temperature for 2 h, cooled down below −50° C., then added methyllithium (11.65 mL, 18.64 mmol) in hexanes. The whole reaction mixture was stirred for 30 min at that temperature, and 6-methoxynicotinonitrile (0.5 g, 3.73 mmol) in THF (2 mL) was added. The cooling bath was removed, and the reaction was stirred at room temperature for 18 h, quenched with concentrated $NH_4OH$ (15 mL) at below −40° C. The mixture was brought to 25° C. and filtered through Celite. The solid was washed with 10% $MeOH/CH_2Cl_2$. The combined filtrates were concentrated, and the residue was purified by HPLC. The fractions collected were neutralized with saturated NaHCO$_3$, then extracted with 1:4 iPrOH/CH$_2$Cl$_2$. The organics were dried and concentrated to give the title compound (180 mg). LCMS m/z=167.3 [M+H]$^+$; $^1$H NMR (400 MHz, CDCl$_3$) δ ppm 1.50 (s, 6H), 3.92 (s, 3H), 6.71 (d, J=8.7 Hz, 1H), 7.75 (ddd, J=1.4, 2.6 and 8.7 Hz, 1H), 8.29 (dd, J=1.4 and 2.6 Hz, 1H).

Step B: Preparation of (1aR,5aR)-2-(2,4-Difluoro-phenyl)-1a,2,5,5a-tetrahydro-1H-2,3-diaza-cyclopropa[a]pentalene-4-carboxylic Acid (1-(6-Methoxylpyridin-3-yl)-1,1-dimethyl-methyl)-amide. [Method M]

To a stirred solution of Intermediate 1 (see Example 1.1, 100 mg, 0.362 mmol), HATU (165 mg, 0.434 mmol) and DIEA (0.126 mL, 0.724 mmol) in DMF was added 2-(6-methoxypyridin-3-yl)propan-2-amine (72.2 mg, 0.434 mmol). The reaction mixture was stirred at room temperature for 1 h. The solvent was evaporated and the residue was purified by silica gel column chromatography to give the title compound (138 mg) as white solid. LCMS m/z=425.3 [M+H]$^+$; $^1$H NMR (400 MHz, CDCl$_3$) δ ppm 0.47 (td, J=4.6 and 3.5 Hz, 1H), 1.12-1.15 (m, 1H), 1.76 (s, 3H), 1.77 (s, 3H), 2.08-2.12 (m, 1H), 2.22-2.27 (m, 1H), 2.91 (d, J=16.6 Hz, 1H), 3.00 (dd, J=6.2 and 16.5 Hz, 1H), 3.91 (s, 3H), 6.69 (d, J=8.7 Hz, 1H), 7.00-7.07 (m, 2H), 7.14 (s, 1H), 7.62-7.68 (m, 2H), 8.25 (d, J=2.6 Hz, 1H).

Example 1.9: Preparation of (1aS,5aS)-2-(2,4-Difluoro-phenyl)-1a,2,5,5a-tetrahydro-1H-2,3-diaza-cyclopropa[a]pentalene-4-carboxylic Acid Pyridin-2-ylamide (Compound 518). [Method N]

To a solution of Intermediate 3 (see Example 1.3, 50 mg, 0.181 mmol), HATU (70 mg, 0.185 mmol) in DMF (1 mL) was added Et$_3$N (20 mg, 0.120 mmol). After stirring for 5 min at room temperature, pyridine-2-amine (26 mg, 0.272 mmol) was added into the reaction. The reaction was stirred for 3 h at 80° C., and purified by preparative HPLC to give the title compound (40 mg): LCMS m/z=353.3 [M+H]$^+$; $^1$H NMR (400 MHz, CDCl$_3$) δ ppm 0.52 (td, J=4.8 and 3.5 Hz, 1H), 1.19 (td, J=7.8 and 5.0 Hz, 1H), 2.15-2.21 (m, 1H), 2.28-2.35 (m, 1H), 3.01 (d, J=16.7 Hz, 1H), 3.11 (dd, J=16.2 and 6.3 Hz, 1H), 7.01-7.08 (m, 3H), 7.66-7.75 (m, 2H), 8.30-8.32 (m, 1H), 8.34 (d, J=8.3 Hz, 1H), 9.29 (s, 1H).

Example 1.10: Preparation of (1aR,5aR)-2-(2,4-Difluoro-phenyl)-1a,2,5,5a-tetrahydro-1H-2,3-diaza-cyclopropa[a]pentalene-4-carboxylic Acid (2-Hydroxy-1,1-dimethyl-ethyl)-amide (Compound 493)

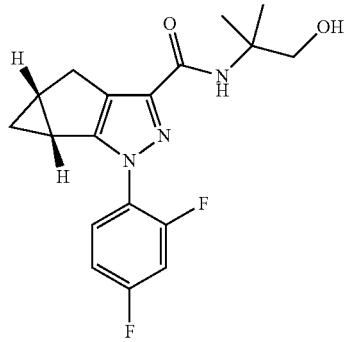 [SMILES: CC(C)(CO)NC(=O)c1nn(-c2ccc(F)cc2F)c2c1C[C@H]1C[C@@H]21]

To a stirred solution of Intermediate 1 (see Example 1.1, 2 g, 7.24 mmol), benzotriazole-1-yl-oxytripyrrolidinophosphonium hexafluorophosphate (PyBOP, 4.52 g, 8.69 mmol) and DIEA (2.52 mL, 14.48 mmol) in DMF (20 mL) was added 2-amino-2-methylpropan-1-ol (0.833 mL, 8.69 mmol). The reaction was stirred at room temperature overnight, then poured into water, and extracted with ethyl acetate. The combined organics were dried and concentrated. The residue was purified by silica gel column chromatography to give the title compound as a white solid (2.08 g). LCMS m/z=348.4 [M+H]$^+$; $^1$H NMR (400 MHz, CDCl$_3$) δ ppm 0.48 (td, J=4.7, 3.3 Hz, 1H), 1.16 (td, J=7.8, 4.9 Hz, 1H), 1.371 (s, 3H), 1.376 (s, 3H), 2.08-2.13 (m, 1H), 2.25-2.31 (m, 1H), 2.94 (d, J=16.8 Hz, 1H), 3.04 (dd, J=16.4, 6.2 Hz, 1H), 3.68 (d, J=3.5 Hz, 2H), 4.81-4.84 (m, 1H), 6.88 (bs, 1H), 6.99-7.05 (m, 2H), 7.59-7.65 (m, 1H).

Example 1.11: Preparation of (1aS,5aS)-2-(2,4-Difluoro-phenyl)-1a,2,5,5a-tetrahydro-1H-2,3-diaza-cyclopropa[a]pentalene-4-carboxylic Acid (1-Hydroxymethyl-cyclopropyl)-amide (Compound 61). [Method O]

(1aS,5aS)-2-(2,4-Difluoro-phenyl)-1a,2,5,5a-tetrahydro-1H-2,3-diaza-cyclopropa[a]pentalene-4-carboxylic acid (methyl cyclopropanecarboxylate) amide (30 mg, 0.08 mmol) (prepared in a manner similar to that described in Method G using Intermediate 3 (see Example 1.3) and methyl 1-aminocyclopropanecarboxylate) was suspended in water/dioxane mixture (1/1 ratio, 1 mL), then sodium borohydride (21.3 mg, 0.562 mmol) was added. The reaction mixture was stirred overnight at room temperature, neutralized with HCl solution, and then purified by preparative LCMS to give the title compound as white solid (7.0 mg). LCMS m/z=346.1 [M+H]$^+$; $^1$H NMR (400 MHz, DMSO-d$_6$) ppm 0.48 (td, J=4.7 and 3.3 Hz, 1H), 0.69-0.74 (m, 4H), 1.12-1.18 (m, 1H), 2.14-2.20 (m, 1H), 2.24-2.30 (m, 1H), 2.78 (d, J=16.1 Hz, 1H), 2.90 (dd, J=6.3 and 16.3 Hz, 1H), 3.48 (s, 2H), 4.64 (s, 1H), 7.28-7.34 (m, 1H), 7.56-7.64 (m, 1H), 7.77-7.83 (m, 1H), 8.00 (s, 1H).

Example 1.12: Preparation of (1aR,5aR)-2-(5-Ethyl-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 274). [Method P]

To a mixture of (1aR,5aR)-2-(5-bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide (0.030 g, 0.077 mmol) and 1,3-bis(diphenylphosphino)-propane-nickel(II) chloride (0.0083 g, 0.015 mmol) in dry 1,4-dioxane (2.0 mL, 0.077 mmol) under argon, was added a solution of 1.0 M diethylzinc in hexane (0.15 mL, 0.15 mmol). The reaction was heated under microwave irradiation for 10 min at 100° C. The reaction was quenched with MeOH, concentrated, and then purified by preparative HPLC to give the title compound as a solid (8 mg). LCMS m/z=341.4 [M+H]$^+$; $^1$H NMR (400 MHz, CDCl$_3$) δ ppm 0.48 (td, J=4.7 and 3.3 Hz, 1H), 1.24-1.35 (m, 4H), 1.42 (s, 6H), 2.25-2.32 (m, 1H), 2.64-2.82 (m, 3H), 2.92 (d, J=15.8 Hz, 1H), 3.01 (dd, J=16.5 and 6.2 Hz, 1H), 3.72 (s, 2H), 7.00-7.06 (m, 1H), 7.68 (d, J=8.3 Hz, 1H), 7.81 (d, J=8.3 Hz, 1H), 8.32-8.36 (m, 1H).

Example 1.13: Preparation of (1aR,5aR)-2-(5-Bromo-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 446)

Step A: Preparation of 2-Bromo-5-hydrazinylpyrazine. [Method Q]

To a solution of 2,5-dibromopyrazine (2.4 g, 10.1 mmol) in IPA (30 mL) was added hydrazine monohydrate (2.5 g, 50.4 mmol). The reaction was stirred at 65° C. overnight and cooled down to 0° C. to form precipitates. The solid precipitate was collected and dried to give the title compound (1.6 g). LCMS m/z=188.9 [M+H]$^+$; $^1$H NMR (400 MHz, DMSO-d$_6$) δ ppm 4.31 (bs, 2H), 7.93 (d, J=1.2 Hz, 1H), 8.08 (d, J=1.2 Hz, 1H), 8.16 (s, 1H).

Step B: Preparation of (1aR,5aR)-2-(5-Bromopyrazin-2-yl)-1a,2,5,5a-tetrahydro-1H-2,3-diaza-cyclopropa[a]pentalene-4-carboxylic Acid The title compound was prepared in a manner similar to that described in Method C and D, using potassium 2-ethoxy-2-oxo-1-((1R,5R)-2-oxobicyclo[3.1.0]hexan-3-ylidene)ethanolate and 2-bromo-5-hydrazinylpyrazine. LCMS m/z=188.9 [M+H]$^+$; $^1$H NMR (400 MHz, DMSO-d$_6$) δ ppm 4.31 (bs, 2H), 7.93 (d, J=1.2 Hz, 1H), 8.08 (d, J=1.2 Hz, 1H), 8.16 (s, 1H).

Step C: Preparation of (1aR,5aR)-2-(5-Bromopyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method G, using (1aR,5aR)-2-(5-bromopyrazin-2-yl)-1a,2,5,5a-tetrahydro-1H-2,3-diaza-cyclopropa[a]pentalene-4-carboxylic Acid and 2-amino-2-methylpropan-1-ol. LCMS m/z=392.2 [M+H]$^+$; $^1$H NMR (400 MHz, CDCl$_3$) δ ppm 0.45 (td, J=4.7 and 3.5 Hz, 1H), 1.25 (td, J=8.0 and 4.7 Hz, 1H), 1.41 (s, 3H), 1.42 (s, 3H), 2.27-2.33 (m, 1H), 2.67-2.72 (m, 1H), 2.91 (d, J=16.8 Hz, 1H), 3.00 (dd, J=16.8 and 6.2 Hz, 1H), 3.70 (s, 2H), 4.53 (s, 1H), 6.90 (s, 1H), 8.50 (d, J=1.4 Hz, 1H), 8.99 (d, J=1.4 Hz, 1H).

Example 1.14: Preparation of (1aR,5aR)-2-(5-Cyano-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 264)

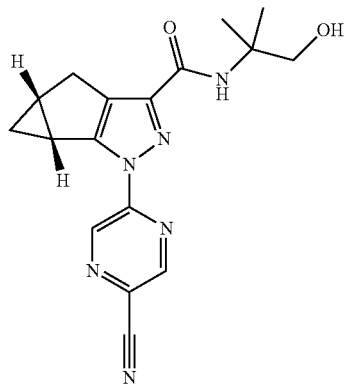 [SMILES: CC(C)(CO)NC(=O)c1nn(-c2cnc(C#N)cn2)c2c1C[C@H]1C[C@@H]21]

A heterogeneous mixture of (1aR,5aR)-2-(5-bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide (40 mg, 0.10 mmol) and cyanocopper (13.7 mg, 0.15 mmol) in NMP (1.0 mL) in a heavy walled tube was heated at 200° C. under microwave irradiation for 2 h. The reaction was filtered and purified by preparative HPLC to give the title compound. LCMS m/z=339.6 [M+H]$^+$; $^1$H NMR (400 MHz, CDCl$_3$) δ ppm 0.46 (td, J=4.7 and 3.4 Hz, 1H), 1.29 (td, J=8.0 and 4.7 Hz, 1H), 1.42 (s, 3H), 1.43 (s, 3H), 2.30-2.37 (m, 1H), 2.71-2.77 (m, 1H), 2.92 (d, J=17.0 Hz, 1H), 3.01 (dd, J=16.8 and 6.2 Hz, 1H), 3.71 (s, 2H), 4.29 (s, 1H), 6.90 (s, 1H), 8.72 (d, J=1.4 Hz, 1H), 9.33 (d, J=1.4 Hz, 1H).

Example 1.15: Preparation of (1aR,5aR)-2-(2-Methoxy-pyridin-4-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 75). [Method R]

To an oven-dried vial with stir bar were added (1aR,5aR)-2-(2-chloro-pyridin-4-yl)-1a,2,5,5a-tetrahydro-1H-2,3-diaza-cyclopropa[a]pentalene-4-carboxylic acid (2-hydroxy-1,1-dimethyl-ethyl)-amide (0.017 g, 0.048 mmol), sodium methoxide (0.008 mg, 0.15 mmol), and anhydrous DMSO (0.022 mL, 0.048 mmol). The reaction was heated at 60° C. for 8 h. The mixture was concentrated under reduced pressure, acidified with 1 M HCl until pH 5, diluted with acetonitrile, and then purified by preparative HPLC to give the title compound as a solid (7 mg). LCMS m/z=343.3 [M+H]$^+$; $^1$H NMR (400 MHz, CDCl$_3$) δ ppm 0.58 (td, J=4.7 and 3.5 Hz, 1H), 1.28-1.37 (m, 1H), 1.38-1.45 (m, 6H), 2.33-2.42 (m, 2H), 2.93 (d, J=16.5 Hz, 1H), 3.03 (dd, J=16.5 and 6.1 Hz, 1H), 3.76 (s, 2H), 4.04 (s, 3H), 6.98 (bs, 1H), 7.20 (d, J=1.6 Hz, 1H), 7.41 (dd, J=5.8 and 1.9 Hz, 1H), 8.28 (d, J=5.8 Hz, 1H).

Example 1.16: Preparation of (1aS,5aS)-2-(5-Phenyl-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 179). [Method S]

To a 5 mL heavy-walled sealed tube with a stir bar were added (1aS,5aS)-2-(5-bromo-pyridin-2-yl)-1a,2,5,5a-tetrahydro-H-2,3-diaza-cyclopropa[a]pentalene-4-carboxylic acid (2-hydroxy-1,1-dimethyl-ethyl)-amide (0.020 g, 0.051 mmol) and DME (0.31 mL, 0.051 mmol), cesium carbonate (0.033 g, 0.10 mmol), phenylboronic acid (0.0094 g, 0.077 mmol). Water (0.051 mL, 0.051 mmol) was added and the tube was flushed with argon. Tetrakis(triphenylphosphine)palladium(0) (0.0060 g, 0.0051 mmol) was added and tube was capped and again flushed with argon. The reaction was heated under microwave irradiation at 120° C. for 35 min. The sample was cooled and filtered. The filtrate was concentrated and the residue was purified by preparative HPLC to give the title compound as a tan solid (12 mg). LCMS m/z=389.5 [M+H]$^+$; $^1$H NMR (400 MHz, CDCl$_3$) δ ppm 0.51 (td, J=4.8 and 3.5 Hz, 1H), 1.26-1.33 (m, 1H), 1.41-1.47 (m, 6H), 2.28-2.36 (m, 1H), 2.80-2.87 (m, 1H), 2.94 (d, J=16.5 Hz, 1H), 3.03 (dd, J=16.5 and 6.3 Hz, 1H), 3.77 (s, 2H), 7.08 (bs, 1H), 7.42-7.47 (m, 1H), 7.52 (t, J=7.2 Hz, 2H), 7.60-7.65 (m, 2H), 7.96 (d, J=8.5 Hz, 1H), 8.05 (dd, J=8.5 and 2.4 Hz, 1H), 8.74 (d, J=2.3 Hz, 1H).

Example 1.17: Preparation of (1aS,5aS)-2-(5-Cyano-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 505). [Method T]

In a heavy-walled sealed tube with a stir bar were added (1aS,5aS)-2-(5-bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide (0.020 g, 0.051 mmol), tetrakis(triphenylphosphine)palladium(0) (0.012 g, 0.010 mmol), and dicyanozinc (0.012 g, 0.10 mmol) in DMA (1.2 mL). The tube was sealed, flushed with argon, and heated under microwave irradiation at 140° C. for 90 min. Ice water (10 mL) was added. The mixture was extracted with EtOAc (3×30 mL). The combined organic extracts were washed with brine (4 mL), dried over $Na_2SO_4$, filtered, and concentrated under reduced pressure. The residue was purified on silica gel (EtOAc/Hexanes) to give the title compound (0.011 g) as a white solid. LCMS m/z=338.5 $[M+H]^+$; $^1$H NMR (400 MHz, $CDCl_3$) δ ppm 0.47 (td, J=4.8 and 3.5 Hz, 1H), 1.26-1.33 (m, 1H), 1.43 (s, 6H), 2.27-2.35 (m, 1H), 2.79-2.86 (m, 1H), 2.92 (d, J=16.5 Hz, 1H), 3.02 (dd, J=16.7 and 6.4 Hz, 1H), 3.71 (s, 2H), 6.88-6.94 (bs, 1H), 8.03-8.09 (m, 2H), 8.74-8.77 (m, 1H).

Example 1.18: Preparation of (1aR,5aR)-2-(2,4-Difluoro-phenyl)-1a,2,5,5a-tetrahydro-1H-2,3-diaza-cyclopropa[a]pentalene-4-carboxylic Acid ((S)-2-Hydroxy-1-pyridin-4-yl-ethyl)-amide (Compound 350)

Step A: Preparation of (R)-1-(Pyridin-4-yl)ethane-1,2-diol. [Method U]

To a stirred suspension of AD-mix-β (13.3 g) in t-BuOH/$H_2O$ (1:1) was added 4-vinylpyridine (1 g, 9.51 mmol). The reaction was stirred at room temperature for 48 h. Sodium sulfite (14.3 g) was added. The mixture was stirred for 30 min, and diluted with ethyl acetate. After separation, the aqueous phase was further extracted with ethyl acetate, and the combined organic layers were washed with water, brine, dried over anhydrous $Na_2SO_4$, and concentrate under reduced pressure. The residue was purified by silica gel column chromatography to give the title compound (0.26 g).

Step B: Preparation of (R)-2-(tert-Butyldimethylsilyloxy)-1-(pyridin-4-yl)ethanol. [Method V]

To a stirred solution of (R)-1-(pyridin-4-yl)ethane-1,2-diol (220 mg, 1.581 mmol) and imidazole (235 mg, 3.45 mmol) in DMF (5 mL) was added tert-butylchlorodimethylsilane (390 mg, 2.59 mmol) at 0° C. The reaction was warmed to room temperature and stirred for 4 h. Water was added and the aqueous layer was extracted with ethyl acetate. The combined organic layers were washed with brine, dried, and concentrated under reduced pressure. The residue was purified by silica gel column chromatography to give the title compound as a white solid (155 mg).

Step C: Preparation of (R)-2-(tert-Butyldimethylsilyloxy)-1-(pyridin-4-yl)ethyl Methanesulfonate To a stirred solution of (R)-2-(tert-butyldimethylsilyloxy)-1-(pyridin-4-yl)ethanol (80 mg, 0.316 mmol), triethylamine (97 μL, 0.695 mmol) and 4-(dimethylamino)pyridine (3.85 mg, 0.032 mmol) in DCM was added methanesulfonyl chloride (36.8 μL, 0.474 mmol) at 0° C. The reaction was stirred at 0° C. for 20 min, then at room temperature overnight. The mixture was washed with a $NaHCO_3$ solution, water and dried over anhydrous $Na_2SO_4$. The solvent was removed under reduced pressure to give the title compound without further purification. LCMS m/z=332.3 $[M+H]^+$.

Step D: Preparation of (S)-4-(1-Azido-2-(tert-butyldimethylsilyloxy)ethyl)pyridine (R)-2-(tert-Butyldimethylsilyloxy)-1-(pyridin-4-yl)ethyl methanesulfonate was taken in DMF, and sodium azide (61.6 mg, 0.947 mmol) was added. The reaction mixture was warmed to 40° C., and stirred overnight. The solvent was evaporated, and the residue was purified by silica gel column chromatography to give the title compound as a colorless oil (58 mg). LCMS m/z=279.3 $[M+H]^+$.

Step E: Preparation of (S)-2-(tert-Butyldimethylsilyloxy)-1-(pyridin-4-yl)ethanamine 10% Pd/C (10 mg) was added to (S)-4-(1-azido-2-(tert-butyldimethylsilyloxy)ethyl)pyridine (58 mg, 0.208 mmol) in methanol. The reaction was degassed, and then charged with hydrogen. The reaction was stirred at room temperature overnight and filtered. The filtrate was concentrated to give the title compound (50 mg) without further purification.

Step F: Preparation of (1aR,5aR)-2-(2,4-Difluoro-phenyl)-1a,2,5,5a-tetrahydro-1H-2,3-diaza-cyclopropa[a]pentalene-4-carboxylic Acid (S)-(2-Hydroxy-1-(pyridin-4-yl)ethyl Amide To a stirred solution of Intermediate 1 (see Example 1.1, 20 mg, 0.072 mmol), HATU (33 mg, 0.087 mmol) and DIEA (0.025 mL, 0.145 mmol) in DMF (1 mL) was added (S)-2-(tert-butyldimethylsilyloxy)-1-(pyridin-4-yl)ethanamine (18 mg, 0.072 mmol). The reaction mixture was stirred at room temperature for 1 h, and then treated with 1 M TBAF solution in THF (0.144 mL, 0.144 mmol). The reaction was stirred at room temperature for 1 h, and then purified by preparative LCMS to give the title compound as white solid (6.3 mg). LCMS m/z=397.2 $[M+H]^+$; $^1$H NMR (400 MHz, $CDCl_3$) ppm 0.48 (td, J=4.8 and 3.5 Hz, 1H), 1.14-1.19 (m, 1H), 2.10-2.15 (m, 1H), 2.25-2.31 (m, 1H), 2.93 (d, J=16.6 Hz, 1H), 3.03 (dd, J=6.2 and 16.5 Hz, 1H), 3.96-4.02 (m, 2H), 5.15-5.19 (m, 1H), 7.00-7.05 (m, 2H), 7.31 (d, J=5.4 Hz, 2H), 7.56 (d, J=7.5 Hz, 1H), 7.62-7.68 (m, 1H), 8.54 (d, J=5.4 Hz, 2H).

Example 1.19: Preparation of (1aR,5aR)-2-(5-Trifluoromethyl-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 583). [Method W]

Step A: Preparation of (1aR,5aR)-2-(5-(Trifluoromethyl)pyrazin-2-yl)-1a,2,5,5a-tetrahydro-1H-2,3-diaza-cyclopropa[a]pentalene-4-carboxylic Acid In an oven-dried 20 mL scintillation vial were placed potassium fluoride (523 mg, 9.00 mmol) and copper (I) iodide (1714 mg, 9.00 mmol). N-Methyl-2-pyrrolidinone (10 mL) was added to the mixture followed by trimethyl (trifluoromethyl)silane (2.66 mL, 18.00 mmol). The reaction was stirred at 50° C. for 1 h. (1aR,5aR)-2-(5-Bromopyrazin- 2-yl)-1a,2,5,5a-tetrahydro-1H-2,3-diaza-cyclopropa[a]pentalene-4-carboxylic acid (289 mg, 0.900 mmol) (from Example 1.13, Step B) was then added. The brown mixture was stirred at 50° C. for 17 h before poured into 1 M HCl (75 mL). EtOAc (50 mL) were added and the mixture was stirred vigorously for 5 minutes. The mixture was filtered and the layers were separated. The aqueous layer was extracted with EtOAc (50 mL). The combined organic layers were concentrated and the residue was purified by preparative HPLC to give the title compound as a yellow solid (45 mg). LCMS m/z=311.2 [M+H]$^+$.

Step B: Preparation of (1aR,5aR)-2-(5-Trifluoromethylpyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method G, using (1aR,5aR)-2-(5-trifluoromethylpyrazin-2-yl)-1a,2,5,5a-tetrahydro-1H-2,3-di aza-cyclopropa[a]pentalene-4-carboxylic acid and 2-amino-2-methylpropan-1-ol. LCMS m/z=382.2 [M+H]$^+$; $^1$H NMR (400 MHz, CDCl$_3$) δ ppm 0.47 (td, J=4.3, 4.0 Hz, 1H), 1.28 (td, J=7.8, 5.2 Hz, 1H), 1.49 (s, 6H), 2.30-2.36 (m, 1H), 2.74-2.78 (m, 1H), 2.93 (d, J=16.8 Hz, 1H), 3.02 (dd, J=16.6, 6.2 Hz, 1H), 3.71 (s, 2H), 4.43 (bs, 1H), 6.94 (s, 1H), 8.77 (s, 1H), 9.32 (s, 1H).

Example 1.20: Preparation of 1-(2,4-Difluoro-phenyl)-3b,4,4a,5-tetrahydro-1H-cyclopropa[3,4]cyclopenta[1,2-c]pyrazole-3-carboxylic Acid (1-Methyl-1-pyridin-4-yl-ethyl)-amide (Compound 340). [Method X]

Step A: Preparation of Bicyclo[3.1.0]hexan-3-one

To an ice-cooled solution of bicyclo[3.1.0]hexan-3-ol (1.00 g, 10.19 mmol) in dichloromethane (25 mL) was added Dess-Martin periodinane (4.75 g, 11.21 mmol). The resulting suspension was stirred for 4 h as reaction gradually warmed to 23° C. The mixture was filtered, and the filtrate was washed with 1.0 M aqueous NaOH (3×25 mL), water, and then brine. The organic layer was dried over MgSO$_4$ and filtered. The dichloromethane was removed by distillation at atmospheric pressure. The residue was distilled at 50° C. at 1 mtorr to give the title compound (0.56 g) as a colorless oil. $^1$H NMR (400 MHz, CDCl$_3$) δ ppm −0.06 (td, J=5.7, 4.0 Hz, 1H), 0.87-0.93 (m, 1H), 1.51-1.55 (m, 2H), 2.13-2.14 (m, 1H), 2.17-2.18 (m, 1H), 2.55-2.58 (m, 1H), 2.60-2.62 (m, 1H).

Step B: Preparation of 1-(2,4-Difluoro-phenyl)-3b,4,4a,5-tetrahydro-1H-cyclopropa[3,4]cyclopenta[1,2-c]pyrazole-3-carboxylic Acid Ethyl Ester To a solution of bicyclo[3.1.0]hexan-3-one (0.30 g, 3.12 mmol) and diethyl oxalate (0.433 mL, 3.20 mmol) in denatured absolute ethanol (10 mL) was added a 1.0 M THF solution of potassium tert-butoxide (3.28 mL, 3.28 mmol). The resulting yellow solution was stirred at 20° C. for 2 h. (2,4-Difluorophenyl)hydrazine hydrochloride (0.564 g, 3.12 mmol) was added followed by a 3.0 M aqueous solution of hydrogen chloride (3.12 mL, 9.36 mmol). The reaction was stirred at 40° C., for 18 h. Brine (100 mL) was added. The mixture was extracted with dichloromethane (3×25 mL). The combined organic extracts were dried over MgSO$_4$, filtered, then concentrated under reduced pressure. The residue was purified by silica gel flash chromatography to give a mixture of the title compound (0.672 g) and 1-(2,4-difluoro-phenyl)-3b,4,4a,5-tetrahydro-1H-cyclopropa[3,4]cyclopenta[1,2-c]pyrazole-3-carboxylic acid methyl ester (0.090 g) as yellow solids. LCMS m/z=305.3 [M+H]$^+$; $^1$H NMR (400 MHz, CDCl$_3$) δ ppm 0.36 (td, J=4.5, 3.8 Hz, 1H), 1.17 (td, J=7.9, 5.0 Hz, 1H), 1.41 (t, J=7.2 Hz, 3H), 2.09-2.16 (m, 1H), 2.33-2.37 (m, 1H), 2.80 (d, J=16.9 Hz, 1H), 2.98 (dd, J=16.9, 6.7 Hz, 1H), 4.36-4.49 (m, 2H), 6.92-6.99 (m, 2H), 7.61-7.67 (m, 1H).

Step C: Preparation of 1-(2,4-Difluoro-phenyl)-3b,4,4a,5-tetrahydro-1H-cyclopropa[3,4]cyclopenta[1,2-c]pyrazole-3-carboxylic Acid To a solution of 1-(2,4-difluoro-phenyl)-3b,4,4a,5-tetrahydro-1H-cyclopropa[3,4]cyclopenta[1,2-c]pyrazole-3-carboxylic acid ethyl ester (0.66 g, 2.169 mmol) and 1-(2,4-difluoro-phenyl)-3b,4,4a,5-tetrahydro-1H-cyclopropa[3,4]cyclopenta[1,2-c]pyrazole-3-carboxylic acid methyl ester (0.08 g, 0.276 mmol) in methanol (6 mL) and THF (6.00 mL) was added a 2.0 M aqueous solution of sodium hydroxide (3.25 mL, 6.51 mmol). The resulting yellow solution was stirred at 20° C. for 16 h. The organic solvents were removed under reduced pressure. The remaining aqueous solution was diluted with water (25 mL) then acidified to pH 2 by addition of 6 M HCl. The resulting precipitate was collected by filtration, rinsed with water, and then dried under reduced pressure to give the title compound as a tan solid (0.575 g). LCMS m/z=277.2 [M+H]$^+$; $^1$H NMR (400 MHz, DMSO-d$_6$) δ ppm 0.28 (td, J=4.4, 3.8 Hz, 1H), 1.12 (td, J=7.6, 4.7 Hz, 1H), 2.10-2.15 (m, 1H), 2.19-2.23 (m, 1H), 2.79 (d, J=17.0 Hz, 1H), 2.98 (dd, J=17.0, 6.6 Hz, 1H), 7.25-7.29 (m, 1H), 7.56-7.60 (m, 1H), 7.72 (td, J=8.8, 6.2 Hz, 1H), 12.83 (s, 1H).

Step D: Preparation of 1-(2,4-Difluoro-phenyl)-3b,4,4a,5-tetrahydro-1H-cyclopropa[3,4]cyclopenta[1,2-c]pyrazole-3-carboxylic Acid (1-Methyl-1-pyridin-4-yl-ethyl)-amide Trifluoroacetate The title compound was prepared in a manner similar to that described in Method G, using 1-(2,4-difluoro-phenyl)-3b,4,4a,5-tetrahydro-1H-cyclopropa[3,4]cyclopenta[1,2-c]pyrazole-3-carboxylic acid and 2-(pyridin-4-yl)propan-2-amine. LCMS m/z=395.4 [M+H]$^+$; $^1$H NMR (400 MHz, CDCl$_3$) δ ppm 0.33 (td, J=4.4, 3.9 Hz, 1H), 1.14 (td, J=7.8 and 5.2 Hz, 1H), 1.80 (s, 3H), 1.82 (s, 3H), 2.08-2.14 (m, 1H), 2.25-2.29 (m, 1H), 2.78 (d, J=16.9 Hz, 1H), 2.96 (ddd, J=16.9, 6.8, 1.0 Hz, 1H), 6.99-7.06 (m, 2H), 7.31 (s, 1H), 7.57-7.63 (m, 1H), 7.88 (d, J=6.8 Hz, 2H), 8.78 (d, J=6.8 Hz, 2H), 11.19 (bs, 1H).

Example 1.21: Preparation of (1aR,5aR)-2-(2,4-Difluoro-phenyl)-1a,2,5,5a-tetrahydro-1H-2,3-diazacyclopropa[a]pentalene-4-carboxylic Acid (5-Fluoro-1-oxy-pyridin-2-yl)-amide (Compound 498). [Method Y]

Step A: Preparation of 2-Amino-5-fluoropyridin 1-oxide

To a stirred solution of 5-fluoropyridin-2-amine (500 mg, 4.46 mmol) in DCM/MeOH (20 mL) in an ice-bath was added MCPBA (1199 mg, 5.35 mmol). The reaction was slowly warmed to room temperature and stirred overnight. The red-orange color solution was loaded to a SCX resin, which was then washed with methanol, eluted with 2 N ammonia in methanol to collect the product. Evaporation of the solvent gave the title compound as yellow-brownish solid (420 mg) without further purification. LCMS m/z=129.2 [M+H]$^+$.

Step B: Preparation of (1aR,5aR)-2-(2,4-Difluoro-phenyl)-1a,2,5,5a-tetrahydro-1H-2,3-diaza-cyclopropa[a]pentalene-4-carboxylic Acid (5-Fluoro-1-oxy-pyridin-2-yl)-amide To a stirred solution of Intermediate 1 (see Example 1.1, 50 mg, 0.181 mmol), HATU (83 mg, 0.217 mmol) and DIEA (0.063 mL, 0.362 mmol) in DMF (1 mL) was added 2-amino-5-fluoropyridin 1-oxide (34.8 mg, 0.272 mmol). The reaction was stirred at room temperature for 1 h. The mixture was purified by preparative LCMS to give the title compound (30 mg) as white solid. LCMS m/z=387.3 [M+H]$^+$; $^1$H NMR (400 MHz, CDCl$_3$) δ ppm 0.52 (td, J=4.6 and 3.5 Hz, 1H), 1.19-1.22 (m, 1H), 2.15-2.20 (m, 1H), 2.30-2.34 (m, 1H), 2.98 (d, J=16.4 Hz, 1H), 3.10 (dd, J=6.3 and 16.5 Hz, 1H), 7.00-7.07 (m, 2H), 7.15-7.23 (m, 1H), 7.70-7.75 (m, 1H), 8.27 (dd, J=2.7 and 3.7 Hz, 1H), 8.59 (dd, J=6.4 and 9.5 Hz, 1H), 10.93 (s, 1H).

Example 1.22: Preparation of (1aR,5aR)-2-(2,4-Difluoro-phenyl)-1a,2,5,5a-tetrahydro-1H-2,3-diaza-cyclopropa[a]pentalene-4-carboxylic Acid (5-tert-Butyl-isoxazol-3-yl)-amide (Compound 74)

Step A: Preparation of (1aR,5aR)-2-(2,4-Difluoro-phenyl)-1a,2,5,5a-tetrahydro-1H-2,3-diaza-cyclopropa[a]pentalene-4-carbonyl Chloride To an ice-cooled solution of Intermediate 1 (see Example 1.1, 2.10 g, 7.60 mmol) in dichloromethane (25 mL) was added one drop dry DMF followed by a 2.0 M dichloromethane solution of oxalyl chloride (7.60 mL, 15.20 mmol). The orange solution was stirred at 0° C. for 10 min then at 23° C. for 2 h. The reaction was concentrated leaving the acid chloride as a tan solid (2.25 g).

Step B: Preparation of (1aR,5aR)-2-(2,4-Difluoro-phenyl)-1a,2,5,5a-tetrahydro-1H-2,3-diaza-cyclopropa[a]pentalene-4-carboxylic Acid (5-tert-Butyl-isoxazol-3-yl)-amide. [Method Z]

(1aR,5aR)-2-(2,4-difluorophenyl)-1a,2,5,5a-tetrahydro-1H-2,3-diaza-cyclopropa[a]pentalene-4-carbonyl chloride (40 mg, 0.136 mmol) was added to a solution of 5-tert-butylisoxazol-3-amine (19.03 mg, 0.136 mmol), triethylamine (0.038 mL, 0.271 mmol), and DMAP (1.658 mg, 0.014 mmol) in dichloromethane (1 mL). The orange solution was stirred at 23° C. for 2.5 h. The mixture was purified by silica gel flash chromatography to give the title compound (39 mg) as a white solid. LCMS m/z=399.3 [M+H]$^+$; $^1$H NMR (400 MHz, CDCl$_3$) δ ppm 0.52 (td, J=4.8, 3.3 Hz, 1H), 1.20 (td, J=7.8, 4.9 Hz, 1H), 1.36 (s, 9H), 2.14-2.20 (m, 1H), 2.29-2.35 (m, 1H), 2.98 (d, J=16.9 Hz, 1H), 3.08 (dd, J=16.6, 6.4 Hz, 1H), 6.79 (s, 1H), 7.01-7.08 (m, 2H), 7.63-7.69 (m, 1H), 9.17 (s, 1H).

Example 1.23: Preparation of (1aR,5aR)-2-(2,4-Difluoro-phenyl)-1a,2,5,5a-tetrahydro-1H-2,3-diaza-cyclopropa[a]pentalene-4-carboxylic Acid Amide (Compound 227)

(1aR,5aR)-2-(2,4-Difluoro-phenyl)-1a,2,5,5a-tetrahydro-1H-2,3-diaza-cyclopropa[a]pentalene-4-carboxylic acid ethyl ester (200 mg, 0.657 mmol) was partially dissolved in a 7 M methanolic solution of ammonia (2 mL, 14.00 mmol). The mixture was heated under microwave irradiation in a sealed, thick-walled glass tube for 1 h at 100° C., then 2 h at 120° C. and 12 h at 125° C. The methanol was removed under reduced pressure. The remaining residue was triturated with ether and the precipitate was collected by filtration to give the title compound (122 mg) as a tan solid. LCMS m/z=276.2 [M+H]$^+$; $^1$H NMR (400 MHz, DMSO-d$_6$) δ ppm 0.40 (td, J=4.4, 3.4 Hz, 1H), 1.15 (td, J=7.8, 4.7 Hz, 1H), 2.15-2.20 (m, 1H), 2.23-2.30 (m, 1H), 2.77 (d, J=16.7 Hz, 1H), 2.89 (dd, J=16.4, 6.4 Hz, 1H), 7.22 (bs, 1H), 7.28-7.33 (m, 1H), 7.35 (bs, 1H), 7.56-7.62 (m, 1H), 7.77 (td, J=8.9, 6.0 Hz, 1H).

Example 1.24: Preparation of (1aR,5aR)-2-(2,4-Difluoro-phenyl)-1a,2,5,5a-tetrahydro-1H-2,3-diaza-cyclopropa[a]pentalene-4-carboxylic Acid (Morpholin-2-ylmethyl)-amide (Compound 413)

To 2-({[(1aR,5aR)-2-(2,4-Difluoro-phenyl)-1a,2,5,5a-tetrahydro-1H-2,3-diaza-cyclopropa[a]pentalene-4-carbonyl]-amino}-methyl)-morpholine-4-carboxylic acid tert-butyl ester (140 mg, 0.295 mmol) was added a 4.0 M dioxane solution of HCl (2.213 mL, 8.85 mmol). The solution was stirred at 23° C. for 2.5 h then concentrated. The residue was taken up in diethyl ether (8 mL). The resulting precipitate was collected by filtration then dried under reduced pressure to provide the title compound (hydrochloride salt, 90 mg). LCMS m/z=375.1 [M+H]$^+$; $^1$H NMR (400 MHz, DMSO-d$_6$) δ ppm 0.40 (td, J=4.5, 3.4 Hz, 1H), 1.14-1.19 (m, 1H), 2.16-2.20 (m, 1H), 2.25-2.31 (m, 1H), 2.70-2.78 (m, 2H), 2.87-3.00 (m, 2H), 3.13-3.21 (m, 2H), 3.23-3.32 (m, 2H), 3.66-3.73 (m, 1H), 3.80-3.86 (m, 1H), 3.95 (dd, J=12.6, 3.1 Hz, 1H), 7.29-7.34 (m, 1H), 7.58-7.64 (m, 1H), 7.78 (td, J=8.9, 5.9 Hz, 1H), 8.17 (t, J=6.1 Hz, 1H), 9.14 (bs, 2H).

Example 1.25: Preparation of (1aR,5aR)-2-(6-Bromo-pyridin-3-yl)-1a,2,5,5a-tetrahydro-1H-2,3-diaza-cyclopropa[a]pentalene-4-carboxylic Acid (1,1-Dimethyl-2-morpholin-4-yl-ethyl)-amide (Compound 468)

Step A: Preparation of 2-Bromo-5-hydrazinylpyridine

To hydrazine monohydrate (5.51 mL, 114 mmol) was added 2-bromo-5-fluoropyridine (1.00 g, 5.68 mmol). The mixture was heated under microwave irradiation in a sealed, thick-walled glass tube for 1 h at 110° C. The thick, white suspension was poured into 60 mL water and stirred vigorously for 5 min. The precipitate was collected by filtration, rinsed with water, and then dried under reduced pressure to provide the title compound (0.35 g) as a white solid. LCMS m/z=188.2 [M+H]$^+$; $^1$H NMR (400 MHz, DMSO-d$_6$) δ ppm 4.13 (s, 2H), 7.09 (dd, J=8.7, 3.2 Hz, 1H), 7.11 (bs, 1H), 7.26 (d, J=8.6 Hz, 1H), 7.87 (d, J=2.9 Hz, 1H).

Step B: Preparation of (1aR,5aR)-2-(6-Bromopyridin-3-yl)-1a,2,5,5a-tetrahydro-1H-2,3-diaza-cyclopropa[a]pentalene-4-carboxylic Acid Ethyl Ester The title compound was prepared in a manner similar to that described in Method C using potassium 2-ethoxy-2-oxo-1-((1R,5R)-2-oxobicyclo[3.1.0]hexan-3-ylidene)ethanolate and 2-bromo-5-hydrazinylpyridine. LCMS m/z=348.2 [M+H]$^+$; $^1$H NMR (400 MHz, CDCl$_3$) δ ppm 0.58 (td, J=4.8, 3.4 Hz, 1H), 1.30 (td, J=7.8, 5.1 Hz, 1H), 1.39 (t, J=7.2 Hz, 3H), 2.29-2.39 (m, 2H), 2.90 (d, J=16.6 Hz, 1H), 3.02 (dd, J=16.6, 6.2 Hz, 1H), 4.39 (q, J=7.1 Hz, 2H), 7.59 (d, J=8.2 Hz, 1H), 8.09 (dd, J=8.5, 2.9 Hz, 1H), 8.87 (d, J=2.8 Hz, 1H).

Step C: Preparation of (1aR,5aR)-2-(6-Bromopyridin-3-yl)-1a,2,5,5a-tetrahydro-1H-2,3-diaza-cyclopropa[a]pentalene-4-carboxylic Acid The title compound was prepared in a manner similar to that described in Method B using (1aR,5aR)-2-(6-bromopyridin-3-yl)-1a,2,5,5a-tetrahydro-1H-2,3-diaza-cyclopropa[a]pentalene-4-carboxylic acid ethyl ester and 2.0 M sodium hydroxide. LCMS m/z=320.1 [M+H]$^+$; $^1$H NMR (400 MHz, DMSO-d$_6$) δ ppm 0.49 (td, J=4.7, 3.4 Hz, 1H), 1.25 (td, J=7.8, 4.8 Hz, 1H), 2.30-1.36 (m, 1H), 2.61-2.66 (m, 1H), 2.76 (d, J=16.6 Hz, 1H), 2.90 (dd, J=16.6, 6.4 Hz, 1H), 7.83 (dd, J=8.6, 0.5 Hz, 1H), 8.16 (dd, J=8.6, 2.9 Hz, 1H), 8.87 (dd, J=2.8, 0.5 Hz, 1H), 12.90 (bs, 1H).

Step D: Preparation of (1aR,5aR)-2-(6-Bromo-pyridin-3-yl)-1a,2,5,5a-tetrahydro-1H-2,3-diaza-cyclopropa[a]pentalene-4-carboxylic Acid (1,1-Dimethyl-2-morpholin-4-yl-ethyl)-amide The title compound was prepared in a manner similar to that described in Method G using (1aR,5aR)-2-(6-bromopyridin-3-yl)-1a,2,5,5a-tetrahydro-1H-2,3-diaza-cyclopropa[a]pentalene-4-carboxylic acid and 2-methyl-1-morpholinopropan-2-amine. LCMS m/z=460.4 [M+H]$^+$; $^1$H NMR (400 MHz, DMSO-d$_6$) δ ppm 0.46 (td, J=4.7, 3.4 Hz, 1H), 1.27 (td, J=7.8, 4.8 Hz, 1H), 1.48 (s, 6H), 2.32-2.37 (m, 1H), 2.63-2.67 (m, 1H), 2.77 (d, J=16.4 Hz, 1H), 2.90 (dd, J=16.4, 6.6 Hz, 1H), 3.14-3.94 (m, 10H), 7.70 (s, 1H), 7.86 (dd, J=8.7, 0.5 Hz, 1H), 8.24 (d, J=7.7 Hz, 1H), 8.97 (s, 1H), 9.39 (s, 1H).

Example 1.26: Preparation of (1aR,5aR)-2-(2,4-Difluoro-phenyl)-1a,2,5,5a-tetrahydro-1H-2,3-diaza-cyclopropa[a]pentalene-4-carboxylic Acid (4-Methyl-morpholin-2-ylmethyl)-amide (Compound 291)

To a mixture of (1aR,5aR)-2-(2,4-Difluoro-phenyl)-1a,2,5,5a-tetrahydro-1H-2,3-diaza-cyclopropa[a]pentalene-4-carboxylic acid (morpholin-2-ylmethyl)-amide (40 mg, 0.097 mmol) and potassium carbonate (26.9 mg, 0.195 mmol) in DMF (0.5 mL) was added iodomethane (6.06 μL, 0.097 mmol). The reaction was stirred at 23° C. for 18 h. The mixture was filtered then purified by HPLC to provide the title compound (TFA salt, 40 mg) as a hygroscopic white solid. LCMS m/z=389.4 [M+H]$^+$; $^1$H NMR (400 MHz, DMSO-d$_6$) δ ppm 0.37-0.41 (m, 1H), 1.14-1.20 (m, 1H), 2.11-2.21 (m, 1H), 2.25-2.32 (m, 1H), 2.74-3.47 (m, 11H), 3.61-3.69 (m, 1H), 3.77-3.83 (m, 1H), 3.94-4.05 (m, 1H), 7.30-7.35 (m, 1H), 7.59-7.64 (m, 1H), 7.74-7.80 (m, 1H), 8.15-8.21 (m, 1H).

Example 1.27: Preparation of (1aR,5aR)-2-(5-Fluoro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 309)

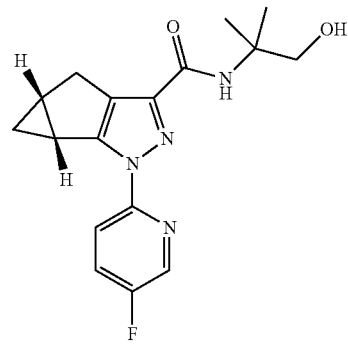 [SMILES: CC(C)(CO)NC(=O)c1nn(-c2ccc(F)cn2)c2c1C[C@H]1C[C@@H]21]

Step A: Preparation of (1aR,5aR)-2-(5-Fluoropyridin-2-yl)-1a,2,5,5a-tetrahydro-1H-2,3-diaza-cyclopropa[a]pentalene-4-carboxylic Acid Ethyl Ester To a solution of hydrazine monohydrate (3.13 mL, 64.6 mmol) in 1-butanol (8 mL) in a thick-walled glass tube was added 2-chloro-5-fluoropyridine (1.00 g, 7.60 mmol). The vessel was flushed with nitrogen then sealed. The solution was heated under microwave irradiation at 200° C. for 8 h. The reaction was concentrated under reduced pressure leaving an orange solid. The solid was taken up in ethyl acetate (30 mL), and the insoluble material was removed by filtration. The filtrate was concentrated to give an orange solid (0.8 g) as a 39:61 mixture of 5-fluoro-2-hydrazinylpyridine and 2-chloro-5-hydrazinylpyridine.

The title compound was prepared in a manner similar to that described in Method C using potassium 2-ethoxy-2-oxo-1-((1R,5R)-2-oxobicyclo[3.1.0]hexan-3-ylidene)ethanolate and mixture of 5-fluoro-2-hydrazinylpyridine and 2-chloro-5-hydrazinylpyridine. LCMS m/z=288.2 [M+H]$^+$.

Step B: Preparation of (1aR,5aR)-2-(5-Fluoropyridin-2-yl)-1a,2,5,5a-tetrahydro-1H-2,3-diaza-cyclopropa[a]pentalene-4-carboxylic Acid The title compound was prepared in a manner similar to that described in Method B using (1aR,5aR)-2-(5-fluoropyridin-2-yl)-1a,2,5,5a-tetrahydro-1H-2,3-diaza-cyclopropa[a]pentalene-4-carboxylic acid ethyl ester. LCMS m/z=260.2 [M+H]$^+$.

Step C: Preparation of (1aR,5aR)-2-(5-Fluoro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method G using (1aR,5aR)-2-(5-fluoropyridin-2-yl)-1a,2,5,5a-tetrahydro-1H-2,3-diaza-cyclopropa[a]pentalene-4-carboxylic acid and 2-amino-2-methylpropan-1-ol. LCMS m/z=331.2 [M+H]⁺; ¹H NMR (400 MHz, CDCl₃) δ ppm 0.45 (td, J=4.7, 3.3 Hz, 1H), 1.24 (td, J=7.9, 4.8 Hz, 1H), 1.404 (s, 3H), 1.408 (s, 3H), 2.24-2.30 (m, 1H), 2.74-2.79 (m, 1H), 2.91 (d, J=16.7 Hz, 1H), 3.00 (dd, J=16.6, 6.2 Hz, 1H), 3.70 (d, J=6.2 Hz, 2H), 4.72 (t, J=6.3 Hz, 1H), 6.92 (s, 1H), 7.55 (ddd, J=9.1, 7.6, 3.0 Hz, 1H), 7.91 (dd, J=9.1, 3.9 Hz, 1H), 8.31 (d, J=2.8 Hz, 1H).

Example 1.28: Preparation of (1aR,5aR)-2-(5-Methoxy-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 124)

Step A: Preparation of (1aR,5aR)-2-(5-Methoxy-pyridin-2-yl)-1a,2,5,5a-tetrahydro-1H-2,3-diaza-cyclopropa[a]pentalene-4-carboxylic Acid Ethyl Ester A 20 mL scintillation vial was charged with (1aR,5aR)-1a,2,5,5a-tetrahydro-1H-2,3-diaza-cyclopropa[a]pentalene-4-carboxylic acid ethyl ester (492 mg, 2.56 mmol), 2-iodo-5-methoxypyridine (662 mg, 2.82 mmol), DL-proline (58.9 mg, 0.512 mmol), copper(I) iodide (48.7 mg, 0.256 mmol), and potassium carbonate (708 mg, 5.12 mmol). The vial was flushed with nitrogen, and added DMSO (15 mL). The reaction was stirred under nitrogen at 75° C. for 15 h. The reaction was filtered then purified by HPLC to provide the title compound (279 mg) as a white solid. LCMS m/z=300.3 [M+H]⁺; ¹H NMR (400 MHz, CDCl₃) δ ppm 0.45 (td, J=4.7, 3.3 Hz, 1H), 1.23 (td, J=8.0, 4.8 Hz, 1H), 1.39 (t, J=7.2 Hz, 3H), 2.21-2.27 (m, 1H), 2.77-2.82 (m, 1H), 2.85 (d, J=16.6 Hz, 1H), 2.97 (dd, J=16.6, 6.4 Hz, 1H), 3.90 (s, 3H), 4.38 (q, J=7.2 Hz, 2H), 7.34 (dd, J=8.8, 2.9 Hz, 1H), 7.98 (dd, J=9.0, 0.6 Hz, 1H), 8.13 (dd, J=3.0, 0.5 Hz, 1H).

Step B: Preparation of (1aR,5aR)-2-(5-Methoxy-pyridin-2-yl)-1a,2,5,5a-tetrahydro-1H-2,3-diaza-cyclopropa[a]pentalene-4-carboxylic Acid The title compound was prepared in a manner similar to that described in Method B using (1aR,5aR)-2-(5-methoxy-pyridin-2-yl)-1a,2,5,5a-tetrahydro-1H-2,3-diaza-cyclopropa[a]pentalene-4-carboxylic acid ethyl ester. LCMS m/z=272.3 [M+H]⁺.

Step C: Preparation of (1aR,5aR)-2-(5-Methoxy-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method G using (1aR,5aR)-2-(5-methoxy-pyridin-2-yl)-1a,2,5,5a-tetrahydro-1H-2,3-diaza-cyclopropa[a]pentalene-4-carboxylic acid and 2-amino-2-methylpropan-1-ol. LCMS m/z=343.3 [M+H]⁺; ¹H NMR (400 MHz, CDCl₃) δ ppm 0.46 (td, J=4.7, 3.3 Hz, 1H), 1.24 (td, J=8.0, 4.8 Hz, 1H), 1.40 (s, 3H), 1.41 (s, 3H), 2.23-2.29 (m, 1H), 2.72-2.76 (m, 1H), 2.91 (d, J=16.7 Hz, 1H), 3.00 (dd, J=16.6, 6.2 Hz, 1H), 3.69 (s, 2H), 3.91 (s, 3H), 4.83 (bs, 1H), 6.95 (s, 1H), 7.36 (dd, J=9.0, 3.0 Hz, 1H), 7.82 (d, J=9.0 Hz, 1H), 8.15 (d, J=2.9 Hz, 1H).

Example 1.29: Preparation of (1aR,5aR)-2-(6-Chloro-pyridazin-3-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 305). [Method AA]

Step A: Preparation of (1aR,5aR)-2-(6-Chloro-pyridazin-3-yl)-1a,2,5,5a-tetrahydro-1H-2,3-diaza-cyclopropa[a]pentalene-4-carboxylic Acid Ethyl Ester The title compound was prepared in a manner similar to that described in Method C using potassium 2-ethoxy-2-oxo-1-((1R,5R)-2-oxobicyclo[3.1.0]hexan-3-ylidene)ethanolate and 3-chloro-6-hydrazinylpyridazine. LCMS m/z=305.2 [M+H]⁺.

Step B: Preparation of (1aR,5aR)-2-(6-Chloro-pyridazin-3-yl)-1a,2,5,5a-tetrahydro-1H-2,3-diaza-cyclopropa[a]pentalene-4-carboxylic Acid and (1aR,5aR)-2-(6-Methoxypyridazin-3-yl)-1a,2,5,5a-tetrahydro-1H-2,3-diaza-cyclopropa[a]pentalene-4-carboxylic Acid To a solution of (1aR,5aR)-2-(6-chloropyridazin-3-yl)-1a,2,5,5a-tetrahydro-1H-2,3-diaza-cyclopropa[a]pentalene-4-carboxylic acid ethyl ester (245 mg, 0.804 mmol) in methanol (2 mL) and THF (2 mL) was added a 2.0 M aqueous solution of sodium hydroxide (1.206 mL, 2.412 mmol). The reaction was stirred at 23° C. for 4 h. The organic solvents were removed by distillation. To the remaining residue was added 15 mL water. The aqueous solution was acidified to pH 2 by addition of 1 M HCl. The resulting precipitate was collected by filtration, rinsed with water, then dried to provide a 4:1 mixture (based on LC) of (1aR,5aR)-2-(6-chloropyridazin-3-yl)-1a,2,5,5a-tetrahydro-1H-2,3-diaza-cyclopropa[a]pentalene-4-carboxylic acid and (1aR,5aR)-2-(6-methoxypyridazin-3-yl)-1a,2,5,5a-tetrahydro-1H-2,3-diaza-cyclopropa[a]pentalene-4-carboxylic acid (180 mg) which was used without further purification. LCMS m/z=273.3 [M+H]⁺ and 277.2 [M+H]⁺.

Step C: Preparation of (1aR,5aR)-2-(6-Chloro-pyridazin-3-yl)-1a,2,5,5a-tetrahydro-1H-2,3-diaza-cyclopropa[a]pentalene-4-carboxylic Acid (2-Hydroxy-1,1-dimethyl-ethyl)-amide To a solution of a 4:1 mixture of (1aR,5aR)-2-(6-chloro-pyridazin-3-yl)-1a,2,5,5a-tetrahydro-1H-2,3-diaza-cyclopropa[a]pentalene-4-carboxylic acid and (1aR,5aR)-2-(6-methoxypyridazin-3-yl)-1a,2,5,5a-tetrahydro-1H-2,3-diaza-cyclopropa[a]pentalene-4-carboxylic acid (100 mg, 0.361 mmol), 2-amino-2-methylpropan-1-ol (32.2 mg, 0.361 mmol), and triethylamine (0.101 mL, 0.723 mmol) in DMF (2 mL) was added HATU (151 mg, 0.398 mmol). The reaction was stirred at 23° C. for 3 h then concentrated. The residue was purified by HPLC to provide the title compound (73 mg) as a white solid. LCMS m/z=348.4 [M+H]⁺; ¹H NMR (400 MHz, CDCl₃) δ ppm 0.47 (td, J=4.6, 3.3 Hz, 1H), 1.29 (td, J=7.9, 4.9 Hz, 1H), 1.41 (s, 3H), 1.42 (s, 3H), 2.30-2.36 (m, 1H), 2.88-2.94 (m, 2H), 3.01 (dd, J=16.4, 6.2 Hz, 1H), 3.72 (s, 2H), 3.84 (bs, 1H), 6.88 (s, 1H), 7.61 (d, J=9.1 Hz, 1H), 8.12 (d, J=9.2 Hz, 1H).

Example 1.30: Preparation of (1aR,5aR)-2-(6-Dimethylamino-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 495)

(1aR,5aR)-2-(6-Chloro-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide (25 mg, 0.072 mmol) was added to a 2.0 M THF solution of dimethylamine (0.719 mL, 1.438 mmol). The reaction was heated under microwave irradiation for 30 min at 100° C., then for 60 min at 110° C. The mixture was concentrated and purified by silica gel flash chromatography to provide the title compound (18 mg) as a white solid. LCMS m/z=357.4 [M+H]$^+$; $^1$H NMR (400 MHz, CDCl$_3$) δ ppm 0.45 (td, J=4.7, 3.3 Hz, 1H), 1.21 (td, J=7.8, 4.8 Hz, 1H), 1.41 (s, 3H), 1.42 (s, 3H), 2.22-2.28 (m, 1H), 2.70-2.75 (m, 1H), 2.90 (d, J=16.8 Hz, 1H), 3.00 (dd, J=16.6, 6.3 Hz, 1H), 3.18 (s, 6H), 3.70 (s, 2H), 4.87 (bs, 1H), 6.98 (s, 1H), 7.93 (s, 1H), 8.41 (s, 1H).

Example 1.31: Preparation of (1aR,5aR)-2-(6-Methoxy-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 319)

(1aR,5aR)-2-(6-Chloro-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide (25 mg, 0.072 mmol) was added to a 3.7 M methanol solution of sodium methoxide (0.583 mL, 2.156 mmol). The white suspension was stirred at 23° C., for 30 min. 1 M HCl (2.5 mL) and water (5 mL) were added. The mixture was extracted with dichloromethane (3×5 mL). The combined organic extracts were concentrated under reduced pressure and purified by silica gel flash chromatography to provide the title compound (12 mg) as a white solid. LCMS m/z=344.3 [M+H]$^+$; $^1$H NMR (400 MHz, DMSO-d$_6$) δ ppm 0.47 (td, J=4.7, 3.3 Hz, 1H), 1.25 (td, J=7.9, 4.8 Hz, 1H), 1.419 (s, 3H), 1.422 (s, 3H), 2.26-2.32 (m, 1H), 2.71-2.76 (m, 1H), 2.92 (d, J=16.9 Hz, 1H), 3.02 (dd, J=16.6, 6.2 Hz, 1H), 3.71 (s, 2H), 4.03 (s, 3H), 4.70 (bs, 1H), 6.96 (s, 1H), 8.17 (d, J=0.5 Hz, 1H), 8.75 (d, J=0.5 Hz, 1H).

Example 1.32: Preparation of (1aR,5aR)-2-(1-Oxo-hexahydro-1λ4-thiopyran-4-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 98). [Method BB]

To a solution of (1aR,5aR)-2-(tetrahydro-thiopyran-4-yl)-1a,2,5,5a-tetrahydro-1H-2,3-diaza-cyclopropa[a]pentalene-4-carboxylic acid (2-hydroxy-1,1-dimethyl-ethyl)-amide (42 mg, 0.125 mmol) in dichloromethane (2 mL) was added MCPBA (28.1 mg, 0.125 mmol). The mixture was stirred at 23° C. for 2 h. After added additional MCPBA (14 mg), it was stirred another hour. The reaction mixture was concentrated and purified by preparative TLC to provide the title compound (18 mg) as white solids. LCMS m/z=352.3 [M+H]$^+$; $^1$H NMR (400 MHz, CD$_3$CN) δ ppm 0.30-0.34 (m, 1H), 1.10-1.17 (m, 1H), 1.30 (s, 3H), 1.31 (s, 3H), 2.00-2.05 (m, 1H), 2.17-2.25 (m, 3H), 2.42-2.50 (m, 1H), 2.67-2.86 (m, 5H), 3.03-3.08 (m, 1H), 3.20-3.33 (m, 1H), 3.51 (s, 2H), 4.15 (bs, 1H), 4.29-4.49 (m, 1H), 6.88-6.90 (m, 1H).

Example 1.33: Preparation of (1aR,5aR)-2-(6-Cyano-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 147). [Method CC]

A solution of (1aR,5aR)-2-(6-Chloro-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide (30 mg, 0.086 mmol), zinc cyanide (30 mg, 0.259 mmol), and tetrakis(triphenylphosphine)palladium (9.97 mg, 8.63 µmol) in THF (1 mL) was heated under microwave irradiation in a sealed, thick-walled glass tube at 100° C. for 30 min. The reaction mixture was purified by preparative TLC plate to provide the title compound (14 mg) as a white solid. LCMS m/z=339.3 [M+H]$^+$; $^1$H NMR (400 MHz, CDCl$_3$) δ ppm 0.46 (td, J=4.8, 3.3 Hz, 1H), 1.32 (td, J=7.9, 5.1 Hz, 1H), 1.43 (s, 6H), 2.31-2.38 (m, 1H), 2.75-2.79 (m, 1H), 2.95 (d, J=17.1 Hz, 1H), 3.01 (dd, J=16.7, 6.2 Hz, 1H), 3.71 (d, J=5.9 Hz, 2H), 4.33 (t, J=6.2 Hz, 1H), 6.90 (s, 1H), 8.80 (s, 1H), 9.46 (s, 1H).

Example 1.34: Preparation of (1aR,5aR)-2-(2,4-Difluoro-phenyl)-1a,2,5,5a-tetrahydro-1H-2,3-diaza-cyclopropa[a]pentalene-4-carboxylic Acid (1-Dimethylaminomethyl-cyclopentyl)-amide (Compound 245)

Step A: Preparation of (1aR,5aR)-2-(2,4-Difluoro-phenyl)-1a,2,5,5a-tetrahydro-1H-2,3-diaza-cyclopropa[a]pentalene-4-carboxylic Acid (1-Oxo-methyl-cyclopentyl)-amide To a solution of (1aR,5aR)-2-(2,4-difluoro-phenyl)-1a,2,5,5a-tetrahydro-1H-2,3-diaza-cyclopropa[a]pentalene-4-carboxylic acid (1-hydroxymethyl-cyclopentyl)-amide (193 mg, 0.517 mmol) in dichloromethane (4 mL) was added Dess-Martin Periodinane (230 mg, 0.543 mmol). The mixture was stirred at 23° C. for 2 h, and purified by silica gel column chromatography to give the title compound (170 mg) as a white solid. LCMS m/z=372.3 [M+H]$^+$.

Step B: Preparation of (1aR,5aR)-2-(2,4-Difluoro-phenyl)-1a,2,5,5a-tetrahydro-1H-2,3-diaza-cyclopropa[a]pentalene-4-carboxylic Acid (1-Dimethylaminomethyl-cyclopentyl)-amide To a solution of (1aR,5aR)-2-(2,4-difluoro-phenyl)-1a,2,5,5a-tetrahydro-11H-2,3-diaza-cyclopropa[a]pentalene-4-carboxylic acid (1-oxo-methyl-cyclopentyl)-amide (26 mg, 0.070 mmol) in methanol (0.5 mL) was added a 2.0 M THF solution of dimethylamine (0.088 mL, 0.175 mmol) and acetic acid (0.681 µL, 0.012 mmol). The mixture was stirred at 23° C. for 15 min, added sodium triacetoxyborohydride (16.3 mg, 0.077 mmol), and stirred for another 1.5 h. One drop of acetic acid was added and the stirring was continued at room temperature for 3 h. Additional sodium triacetoxyborohydride (20 mg) and 2 M dimethylamine (200 µL) was added and the stirring was continued for 3 days. The mixture was purified by preparative TLC to provide the title compound (5.7 mg) as a colorless solid. LCMS m/z=401.5 [M+H]$^+$; $^1$H NMR (400 MHz, CDCl$_3$) δ ppm 0.48 (td, J=4.8, 3.3 Hz, 1H), 1.13 (td, J=7.8, 4.9 Hz, 1H), 1.58-1.68 (m, 2H), 1.76-1.83 (m, 4H), 2.09-2.18 (m, 3H), 2.22-2.28 (m, 1H), 2.39 (s, 6H), 2.76-2.85 (m, 2H), 2.94 (d, J=16.4 Hz, 1H), 3.04 (dd, J=16.4, 6.3 Hz, 1H), 6.97-7.04 (m, 2H), 7.12 (s, 1H), 7.62-7.68 (m, 1H).

Example 1.35: Preparation of (1aR,5aR)-2-(2,4-Difluoro-phenyl)-1a,2,5,5a-tetrahydro-1H-2,3-diaza-cyclopropa[a]pentalene-4-carboxylic Acid [1-((R)-2-(S)-Methyl-5-methyl-pyrrolidine-1-carbonyl)-cyclopentyl]-amide (Compound 538)

Step A: Preparation of tert-Butyl 1-((2R,5S)-2,5-Dimethylpyrrolidine-1-carbonyl)cyclopentylcarbamate To a suspension of 1-(tert-butoxycarbonylamino)cyclopentanecarboxylic acid (500 mg, 2.181 mmol), (2R,5S)-2, 5-dimethylpyrrolidine, HCl (296 mg, 2.181 mmol), and triethylamine (0.912 mL, 6.54 mmol) in DMF (5 mL) was added HATU (829 mg, 2.181 mmol). The mixture was stirred at 23° C. for 4 h then concentrated. The residue was taken up in EtOAc (25 mL) then washed successively with 0.5 M HCl (2×25 mL), saturated NaHCO$_3$ (2×25 mL), and brine (2×25 mL). The combined organic layers were dried (MgSO$_4$), filtered, then concentrated under reduced pressure. The residue was purified by silica gel flash chromatography to give the title compound (0.47 g) as a white solid. LCMS m/z=311.3 [M+H]$^+$.

Step B: Preparation of (1-Aminocyclopentyl) ((2R, 5S)-2,5-Dimethylpyrrolidin-1-yl)methanone Hydrochloride To tert-butyl 1-((2R,5S)-2,5-dimethylpyrrolidine-1-carbonyl)cyclopentylcarbamate (170 mg, 0.548 mmol) was added a 4.0 M dioxane solution of hydrogen chloride (0.137 mL, 0.548 mmol). The mixture was stirred at 23° C. for 64 h then concentrated. The residue was taken up in ether (10 mL). The precipitate was collected by filtration, rinsed with ether, and dried to provide the title compound as a white solid.

Step C: Preparation of (1aR,5aR)-2-(2,4-Difluoro-phenyl)-1a,2,5,5a-tetrahydro-1H-2,3-diaza-cyclopropa[a]pentalene-4-carboxylic Acid [1-((R)-2-(S)-methyl-5-methyl-pyrrolidine-1-carbonyl)-cyclopentyl]-amide The title compound was prepared in a manner similar to that described in Method G using (1-aminocyclopentyl) ((2R,5S)-2,5-dimethylpyrrolidin-1-yl)methanone hydrochloride and (1aR,5aR)-2-(2,4-Difluoro-phenyl)-1a,2,5,5a-tetrahydro-H-2,3-diaza-cyclopropa[a]pentalene-4-carboxylic acid. LCMS m/z=469.5 [M+H]$^+$; $^1$H NMR (400 MHz, CD$_3$CN) δ ppm 0.39-0.43 (m, 1H), 0.89-1.27 (m, 8H), 1.57-1.69 (m, 7H), 1.96-2.11 (m, 1H), 2.13-2.18 (m, 3H), 2.23-2.30 (m, 1H), 2.52-2.70 (m, 1H), 2.80 (d, J=17.2 Hz, 1H), 2.91 (dd, J=16.6, 6.6 Hz, 1H), 3.93-4.39 (m, 2H), 7.13-7.25 (m, 3H), 7.72 (td, J=8.8, 5.9 Hz, 1H).

Example 1.36: Preparation of (1aR,5aR)-2-(2,4-Difluoro-phenyl)-1a,2,5,5a-tetrahydro-1H-2,3-diaza-cyclopropa[a]pentalene-4-carboxylic Acid [1-(3,3,3-Trifluoro-propyl)-azetidin-3-yl]-amide (Compound 36). [Method DD]

3-{[(1aR,5aR)-2-(2,4-Difluoro-phenyl)-1a,2,5,5a-tetrahydro-11H-2,3-diaza-cyclopropa[a]pentalene-4-carbonyl]-amino}-azetidine-1-carboxylic acid tert-butyl ester was dissolved in 20% TFA/DCM. The reaction mixture was stirred at room temperature for 1 h. The solvent was evaporated, and the residue was purified by cation exchange resin to give (1aR,5aR)-2-(2,4-difluoro-phenyl)-1a,2,5,5a-tetrahydro-H-2,3-diaza-cyclopropa[a]pentalene-4-carboxylic acid (azetidin-3-yl) amide. This material was mixed with 3-bromo-1,1,1-trifluoropropane and Et$_3$N in IPA. The reaction was heated under microwave irradiation for 1 h at 150° C. The mixture was purified by preparative HPLC to provide the title compound. LCMS m/z=427.3 [M+H]$^+$.

Example 1.37: Preparation of (1aR,5aR)-2-(2,4-Difluoro-phenyl)-1a,2,5,5a-tetrahydro-1H-2,3-diaza-cyclopropa[a]pentalene-4-carboxylic Acid (3-Hydroxy-pyridin-2-yl)-amide (Compound 157). [Method EE]

Intermediate 1 (see Example 1.1, 50 mg, 0.181 mmol) was dissolved in DMF (1 mL). PyBOP (104 mg, 0.199 mmol) and N-ethyl-N-isopropylpropan-2-amine (0.098 mL, 0.561 mmol) were added. The reaction mixture was stirred at room temperature for about 3 min. 2-aminopyridin-3-ol (19.93 mg, 0.181 mmol) was then added to the mixture to give an amber solution which was stirred overnight at room temperature. The mixture was purified by HPLC to provide the title compound (20 mg). LCMS m/z=369.2 [M+H]$^+$; $^1$H NMR: (400 MHz, CD$_3$CN) δ ppm 0.53 (td, J=4.8 and 3.5 Hz, 1H), 1.23 (td, J=7.9 and 4.8 Hz, 1H), 2.21-2.27 (m, 1H), 2.33-2.40 (m, 1H), 2.93 (d, J=16.5 Hz, 1H), 3.05 (dd, J=16.6 and 6.3 Hz, 1H), 7.16-7.23 (m, 1H), 7.23-7.32 (m, 2H), 7.73-7.83 (m, 3H), 9.80 (s, 1H).

Example 1.38: Preparation of (1aR,5aR)-2-(2,4-Difluoro-phenyl)-1a,2,5,5a-tetrahydro-1H-2,3-diaza-cyclopropa[a]pentalene-4-carboxylic Acid (4-Hydroxy-pyridin-2-yl)-amide (Compound 393)

A solution of 4-methoxypyridin-2-amine (100 mg, 0.806 mmol) in DCM (1.6 mL) under N$_2$ atmosphere was cooled in an dry ice/IPA bath, and tribromoborane (0.305 mL, 3.23 mmol) was added with a syringe. After removing the cold bath, the reaction was stirred overnight at room temperature. The reaction mixture was diluted with water (5 mL) and stirred for an additional 30 min. It was then washed with saturated NaHCO$_3$ (20 mL) to pH=7 and extracted with DCM (3×20 mL). The combined organic layer was dried over MgSO$_4$ and concentrated to provide 2-aminopyridin-4-ol. The title compound was prepared in a manner similar to that described in Method EE using Intermediate 1 (see Example 1.1) and 2-aminopyridin-4-ol. LCMS m/z=369.3 [M+H]$^+$; $^1$H NMR: (400 MHz, CD$_3$CN) δ ppm 0.50 (td, J=4.7 and 3.5 Hz, 1H), 1.22 (td, J=7.8 and 4.9 Hz, 1H), 2.21-2.26 (m, 1H), 2.31-2.38 (m, 1H), 2.93 (d, J=16.7 Hz, 1H), 3.05 (dd, J=16.6 and 6.3 Hz, 1H), 6.80 (dd, J=7.1 and 2.2 Hz, 1H), 6.95 (d, J=2.2 Hz, 1H), 7.15-7.21 (m, 1H), 7.22-7.29 (m, 1H), 7.52 (s, 1H), 7.70 (td, J=8.8 and 5.9 Hz, 1H), 7.82 (d, J=7.1 Hz, 1H).

Example 1.39: Preparation of (1aS,5aS)-2-(2,4-Difluoro-phenyl)-1a,2,5,5a-tetrahydro-1H-2,3-diaza-cyclopropa[a]pentalene-4-carboxylic Acid [(R)-1-(4-Fluoro-phenyl)-3-Hydroxy-propyl]-amide (Compound 46). [Method FF]

Intermediate 3 (see Example 1.3, 0.040 g, 0.145 mmol), HATU (0.066 g, 0.174 mmol) and triethylamine (0.040 mL, 0.290 mmol) were stirred in DMF for one hour. To this was added (R)-3-amino-3-(4-fluorophenyl)propan-1-ol (0.029 g, 0.174 mmol). After stirring overnight, the reaction was filtered and concentrated. The residue was purified by preparative TLC to provide the title compound (38.1 mg). LCMS m/z=428.3 [M+H]$^+$; $^1$H NMR (400 MHz, DMSO-d$_6$) δ ppm 0.34-0.41 (m, 1H) 1.08-1.17 (m, 1H) 1.82-1.94 (m, 1H) 1.97-2.08 (m, 1H) 2.12-2.19 (m, 1H) 2.21-2.29 (m, 1H) 2.72-2.76 (m, 1H) 2.83-2.92 (m, 1H) 3.32-3.43 (m, 2H) 4.55 (t, J=4.80 Hz, 1H) 5.05-5.15 (m, 1H) 7.07-7.16 (m, 2H) 7.27-7.35 (m, 1H) 7.36-7.43 (m, 2H) 7.56-7.64 (m, 1H) 7.75-7.84 (m, 1H) 8.48 (d, J=8.46 Hz, 1H).

Example 1.40: Preparation of (1aR,5aR)-2-(1,1-Dioxo-tetrahydro-1λ6-thiophen-3-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 526)

(1aR,5aR)-2-(1,1-Dioxo-tetrahydrothiophen-3-yl)-1a,2,5,5a-tetrahydro-H-2,3-diaza-cyclopropa[a]pentalene-4-carboxylic acid was prepared in a manner similar to that described in Method C and D using potassium 2-ethoxy-2-oxo-1-((1R,5R)-2-oxobicyclo[3.1.0]hexan-3-ylidene)ethanolate and (1,1-dioxo-tetrahydrothiophen-3-yl)hydrazine.

The title compound was prepared in a manner similar to that described in Method G using the acid described above and 2-amino-2-methylpropan-1-ol. LCMS m/z=354.2 [M+H]$^+$; $^1$H NMR (400 MHz, CDCl$_3$) δ ppm 0.37-0.42 (m, 1H), 1.16-1.23 (m, 1H), 1.37 (s, 3H), 1.38 (s, 3H), 2.06-2.12 (m, 1H), 2.26-2.33 (m, 1H), 2.65-2.77 (m, 3H), 2.84 (d, J=16.8 Hz, 1H), 2.94 (dd, J=16.8 and 6.0 Hz, 1H), 3.16-3.25 (m, 1H), 3.40-3.64 (m, 3H), 3.69 (s, 2H), 5.05-5.13 (m, 1H), 6.87 (s, 1H).
Resolution Via Chiral HPLC.
Column: normal phase preparative Chiralcel OD®, 5 cm ID×50 cm L, 20 μm particle size
Eluent: 25% EtOH/hexanes
Gradient: isocratic
Flow: 60 mL/min
Detector: 254 nm
Retention Times: 1$^{st}$ diastereomer—43.4 min; 2$^{nd}$ diastereomer—48.8 min.

Example 1.41: Preparation of (1aS,5aS)-2-(2,4-Difluoro-phenyl)-1a,2,5,5a-tetrahydro-1H-2,3-diaza-cyclopropa[a]pentalene-4-carboxylic Acid (Tetrahydro-pyran-4-ylmethyl)-amide (Compound 408). [Method GG]

Intermediate 3 (see Example 1.3, 27 mg, 0.1 mmol), (tetrahydro-2H-pyran-4-yl)methanamine (11 mg, 0.1 mmol), 2-(3H-[1,2,3]triazolo[4,5-b]pyridin-3-yl)-1,1,3,3-tetramethylisouronium hexafluorophosphate(V) (48 mg, 0.13 mmol), Et$_3$N (41 μL, 0.3 mmol) and THF (1 mL) were heated for 10 min at 100° C. under microwave irradiation in a heavy walled sealed tube. The solvent was evaporated and the resulting residue was dissolved in ACN (3 mL) and purified by HPLC to give the title compound (TFA salt, 26 mg) as a solid. LCMS m/z=374.4 [M+H]$^+$; $^1$H NMR (400 MHz, CD$_3$CN) δ ppm 0.43 (td, J=3.41, 4.55 Hz, 1H), 1.13-1.18 (m, 1H), 1.19-1.29 (m, 2H), 1.59 (d, J=13.01 Hz, 2H), 1.72-1.83 (m, 1H), 2.13-2.18 (m, 1H), 2.24-2.30 (m, 1H), 2.82 (d, J=16.3 Hz, 1H), 2.94 (dd, J=6.32, 16.3 Hz, 1H), 3.19 (t, J=6.69 Hz, 2H), 3.30 (td, J=2.02, 11.75 Hz, 2H), 3.84-3.89 (m, 2H), 7.11-7.24 (m, 2H), 7.65-7.72 (m, 1H).

Example 1.42: Preparation of (1aR,5aR)-2-(Tetrahydro-pyran-4-ylmethyl)-1a,2,5,5a-tetrahydro-1H-2,3-diaza-cyclopropa[a]pentalene-4-carboxylic Acid (5-Fluoro-pyridin-2-yl)-amide (Compound 258). [Method HH]

Step A: Preparation of Ethyl (1aR,5aR)-1a,2,5,5a-tetrahydro-1H-2,3-diaza-cyclopropa[a]pentalene-4-carboxylate (1R,5S)-Bicyclo[3.1.0]hexan-2-one (1.000 g, 10.40 mmol) was taken up in ethanol (40 mL) and potassium tert-butoxide (1.0 M in THF) (13.00 mL, 13.00 mmol) was added, followed by diethyl oxalate (1.413 mL, 10.40 mmol). The resulting solution was heated and stirred for 1 h at 70° C. Hydrazine (10.40 mL, 10.40 mmol) was then added, followed by hydrochloric acid (ca 3 M aqueous) (10.40 mL, 31.2 mmol). The solution was stirred at 70° C. for 1 h and purified by HPLC to give the title compound (356 mg, 1.852 mmol, 17.80% yield) as a solid. LCMS m/z=193.3 [M+H]$^+$.

Step B: Preparation of Ethyl (1aR,5aR)-2-((Tetrahydro-2H-pyran-4-yl)methyl)-1a,2,5,5a-tetrahydro-1H-2,3-diaza-cyclopropa[a]pentalene-4-carboxylate To potassium hydroxide (561 mg, 10.00 mmol) in DMSO (10 mL) was added ethyl 1a,2,5,5a-tetrahydro-1H-2,3-diaza-cyclopropa[a]pentalene-4-carboxylate (356 mg, 1.852 mmol) under nitrogen atmosphere. The mixture was stirred at room temperature for 1 hour and added 4-(bromomethyl) tetrahydro-2H-pyran (962 mg, 5.37 mmol). The reaction was stirred at room temperature for 1.5 h, poured into 50 mL of ice cold water and added glacial acetic (0.71 mL). The resulting mixture was extracted with EtOAc (3×50 mL). The combined organic extracts were concentrated under reduced pressure and purified by HPLC to give the title compound (127 mg, 24% yield) as a yellow solid. LCMS m/z=291.2 [M+H]$^+$.

Step C: Preparation of (1aR,5aR)-2-((Tetrahydro-2H-pyran-4-yl)methyl)-1a,2,5,5a-tetrahydro-1H-2,3-diaza-cyclopropa[a]pentalene-4-carboxylic Acid Ethyl 2-((tetrahydro-2H-pyran-4-yl)methyl)-1a,2,5,5a-tetrahydro-1H-2,3-diaza-cyclopropa[a]pentalene-4-carboxylate (127 mg, 0.437 mmol) was dissolved in THF (4.00 mL) and H$_2$O (4.00 mL). Lithium hydroxide hydrate (55.1 mg, 1.312 mmol) was added and the reaction was stirred at 45° C. for 1.5 h. The organic solvent was removed under reduced pressure to give the title compound (115 mg) as a brown solid. LCMS m/z=263.2 [M+H]$^+$.

Step D: Preparation of (1aR,5aR)-2-(Tetrahydro-pyran-4-ylmethyl)-1a,2,5,5a-tetrahydro-1H-2,3-diaza-cyclopropa[a]pentalene-4-carboxylic Acid (5-Fluoro-pyridin-2-yl)-amide. [Method H]

The title compound was prepared in a manner similar to that described in Method GG, using 2-((tetrahydro-2H-pyran-4-yl)methyl)-1a,2,5,5a-tetrahydro-1H-2,3-diaza-cyclopropa[a]pentalene-4-carboxylic acid (27 mg, 0.1 mmol) and 5-fluoropyridin-2-amine. LCMS m/z=357.5 [M+H]$^+$; $^1$H NMR (400 MHz, CDCl$_3$) δ ppm 0.40 (td, J=3.41, 4.80 Hz, 1H), 1.17-1.22 (m, 1H), 1.37-1.49 (m, 2H), 1.53-1.63 (m, 2H), 2.05-2.10 (m, 1H), 2.27-2.33 (m, 1H), 2.34-2.41 (m, 1H), 2.89 (d, J=16.5 Hz, 1H), 3.00 (dd, J=6.44, 16.5 Hz, 1H), 3.47 (td, J=2.27, 11.7 Hz, 2H), 4.00 (d, J=7.07 Hz, 2H), 4.04 (dd, J=4.04, 11.5 Hz, 2H), 7.78-7.83 (m, 1H), 8.19 (d, J=2.27 Hz, 1H), 8.69 (dd, J=4.27, 9.47 Hz, 1H).

Example 1.43: Preparation of (1aR,5aR)-2-Pyridin-4-yl-1a,2,5,5a-tetrahydro-1H-2,3-diaza-cyclopropa[a]pentalene-4-carboxylic Acid (5-Fluoro-pyridin-2-yl)-amide (Compound 363). [Method JJ]

Step A: Preparation of Ethyl (1aR,5aR)-1-(Pyridin-4-yl)-1a,2,5,5a-tetrahydro-1H-2,3-diaza-cyclopropa[a]pentalene-4-carboxylate The title compound was prepared in a manner similar to that described in Method A using (1R,5S)-bicyclo[3.1.0]hexan-2-one and 4-Hydrazinylpyridine hydrochloride. LCMS m/z=270.2 [M+H]$^+$; $^1$H NMR (400 MHz, CDCl$_3$) δ ppm 0.68 (dd, J=4.80, 8.46 Hz, 1H), 1.41 (t, J=7.07 Hz, 3H), 1.45-1.50 (m, 1H), 2.47-2.52 (m, 2H), 2.93 (d, J=16.9 Hz, 1H), 3.05 (dd, J=6.44, 16.9 Hz, 1H), 4.42 (q, J=7.07 Hz, 2H), 8.39 (d, J=7.20 Hz, 2H), 8.91 (d, J=7.20 Hz, 2H).

Step B: Preparation of (1aR,5aR)-1-(Pyridin-4-yl)-1a,2,5,5a-tetrahydro-1H-2,3-diaza-cyclopropa[a]pentalene-4-carboxylic Acid Ethyl (1aR,5aR)-1-(pyridin-4-yl)-1a,2,5,5a-tetrahydro-1H-2,3-diaza-cyclopropa[a]pentalene-4-carboxylate (357 mg, 1.326 mmol) was taken up in THF (4.00 mL) and $H_2O$ (4.00 mL). LiOH (95 mg, 3.98 mmol) was added and the reaction was stirred at room temperature for 1.5 h. The organic solvent was removed under reduced pressure to give the title compound (473 mg) as a brown solid. LCMS m/z=242.3 [M+H]$^+$.

Step C: Preparation of (1aR,5aR)-2-Pyridin-4-yl-1a,2,5,5a-tetrahydro-1H-2,3-diaza-cyclopropa[a]pentalene-4-carboxylic Acid (5-Fluoro-pyridin-2-yl)-amide. [Method KK]

The title compound was prepared in a manner similar to that described in Method GG using (1aR,5aR)-1-(pyridin-4-yl)-1a,2,5,5a-tetrahydro-1H-2,3-diaza-cyclopropa[a]pentalene-4-carboxylic acid and 5-fluoropyridin-2-amine. LCMS m/z=336.5 [M+H]$^+$.

Example 1.44: Preparation of (1aR,5aR)-2-(5-Methyl-pyridin-2-yl)-1a,2,5,5a-tetrahydro-1H-2,3-diaza-cyclopropa[a]pentalene-4-carboxylic Acid (1-Methyl-1-phenyl-ethyl)-amide (Compound 299). [Method LL]

2-(5-Methylpyridin-2-yl)-1a,2,5,5a-tetrahydro-1H-2,3-diaza-cyclopropa[a]pentalene-4-carboxylic acid was prepared using a similar method to the one described in Method A using (1R,5S)-bicyclo[3.1.0]hexan-2-one and 2-hydrazinyl-5-methylpyridine.

The title compound was prepared in a manner similar to that described in Method KK using 2-(5-methylpyridin-2-yl)-1a,2,5,5a-tetrahydro-1H-2,3-diaza-cyclopropa[a]pentalene-4-carboxylic acid and 2-phenylpropan-2-amine. LCMS m/z=373.4 [M+H]$^+$; $^1$H NMR (400 MHz, CDCl$_3$) δ ppm 0.51 (td, J=3.41, 4.67 Hz, 1H), 1.23-1.28 (m, 1H), 1.82 (s, 6H), 2.26-2.32 (m, 1H), 2.44 (s, 3H), 2.57-2.63 (m, 1H), 2.87 (d, J=16.7 Hz, 1H), 2.95 (dd, J=6.19, 16.7 Hz, 1H), 7.20-7.24 (m, 1H), 7.32 (t, J=7.58 Hz, 2H), 7.44-7.49 (m, 2H), 7.67 (s, 1H), 7.81 (s, 2H), 8.47 (s, 1H).

Example 1.45: Preparation of (1aR,5aR)-2-(2,4-Difluoro-phenyl)-1a,2,5,5a-tetrahydro-1H-2,3-diaza-cyclopropa[a]pentalene-4-carboxylic Acid (1-Oxo-hexahydro-1λ4-thiopyran-4-yl)-amide (Compound 567). [Method MM]

A solution of (1aR,5aR)-2-(2,4-difluoro-phenyl)-1a,2,5,5a-tetrahydro-1H-2,3-diaza-cyclopropa[a]pentalene-4-carboxylic acid (tetrahydro-thiopyran-4-yl)-amide (0.014 g, 0.037 mmol) in anhydrous DCM (0.5 mL) was cooled to 0° C. on an ice bath. 3-Chlorobenzoperoxoic acid (7.08 mg, 0.041 mmol) in DCM (0.5 mL) was added drop wise and the reaction was stirred for 1 hour. The reaction mixture was extracted with DCM/water and NaHCO$_3$. The organic phase was concentrated and the residue was purified by HPLC to provide the title compound (2.1 mg) as a white solid. LCMS m/z=392.5 [M+H]$^+$.

Example 1.46: Preparation of (1aS,5aS)-2-(5-Cyclopropyl-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 531)

To a mixture of (1aS,5aS)-2-(5-bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide (0.020 g, 0.051 mmol), cyclopropylboronic acid (6.59 mg, 0.077 mmol) and potassium phosphate (0.033 g, 0.153 mmol) in toluene/$H_2O$ (1.5 mL/0.050 mL) under nitrogen atmosphere, tetrakis(triphenylphosphine)palladium (5.91 mg, 5.11 µmol) was added. The reaction was heated at 100° C. for 30 min in a heavy walled sealed tube under microwave irradiation. Additional cyclopropylboronic acid (6.59 mg, 0.077 mmol) was added and the reaction was heated at 100° C. for 2 more hours. The mixture was purified by HPLC to give the titled compound (5.1 mg) as a white solid. LCMS m/z=353.5 [M+H]$^+$.

Example 1.47: Preparation of (1aS,5aS)-2-(5-Morpholin-4-yl-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 103). [Method NN]

A mixture of (1aS,5 aS)-2-(5-bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide (0.015 g, 0.038 mmol), morpholine (5.01 µL, 0.058 mmol), Pd$_2$(dba)$_3$ (0.702 mg, 0.767 µmol), BINAP (0.955 mg, 1.533 µmol) and sodium tert-butoxide (5.16 mg, 0.054 mmol) in toluene (1.00 mL) was heated at 80° C. for 1 h followed by 100° C. for 2 h in a heavy walled sealed tube under microwave irradiation. The mixture was purified by HPLC to provide title compound (4.1 mg) as a yellow solid. LCMS m/z=398.3 [M+H]$^+$.

Example 1.48: Preparation of (1aR,5aR)-2-(5-Cyclopropyl-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 423)

To a mixture of (1aR,5aR)-2-(5-bromo-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide (0.030 g, 0.077 mmol), cyclopropylboronic acid (0.020 g, 0.230 mmol), potassium phosphate (0.049 g, 0.230 mmol) and tricyclohexylphosphine (4.30 mg, 0.015 mmol) in toluene/$H_2O$ (1.5 mL/0.050 mL) under nitrogen atmosphere, palladium (II) acetate (1.721 mg, 7.67 µmol) was added and the reaction mixture was heated at 100° C. for 2 hours in a heavy walled sealed tube under microwave irradiation. The reaction mixture was concentrated and the product was purified by preparative HPLC twice. The corresponding fractions were collected and lyophilized to provide the title compound (12.6 mg) as a white solid. LCMS m/z=353.4 [M+H]$^+$.

Example 1.49: Preparation of 4-{[(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1-carboxylic Acid Tert-Butyl Ester (Compound 11). [Method OO]

To a stirred solution of Intermediate 1 (see Example 1.1, 100 mg, 0.362 mmol) and BOP-Cl (111 mg, 0.434 mmol) in DMF (2 mL) was added DIEA (0.126 mL, 0.724 mmol). After 10 min, tert-butyl 4-aminopiperidine-1-carboxylate (72.5 mg, 0.362 mmol) was added. The reaction mixture was stirred at room temperature for 2 h, poured into water, extracted with ethyl acetate. The combined organics were dried and concentrated. The residue was purified by column chromatography to give the title compound (120 mg). LCMS m/z=459.3 [M+H]$^+$; $^1$H NMR (400 MHz, CDCl$_3$) δ ppm 0.49 (td, J=4.6 and 3.5 Hz, 1H), 1.11-1.20 (m, 1H), 1.40-1.48 (m 2H), 1.47 (s, 9H), 1.92-2.00 (m, 2H), 2.10-2.14 (m, 1H), 2.24-2.32 (m, 1H), 2.90 (t, J=11.5 Hz, 2H), 2.95 (d, J=16.7 Hz, 1H), 3.05 (dd, J=16.5 and 6.2 Hz, 1H), 4.00-4.10 (m, 3H), 6.75 (d, J=8.1 Hz, 1H), 7.00-7.05 (m, 2H), 7.61-7.67 (m, 1H).

Example 1.50: Preparation of (1aR,5aR)-2-(2,4-Difluoro-phenyl)-1a,2,5,5a-tetrahydro-1H-2,3-diaza-cyclopropa[a]pentalene-4-carboxylic Acid Piperidin-4-ylamide (Compound 99)

4-{[(1aR,5aR)-2-(2,4-Difluoro-phenyl)-1a,2,5,5a-tetrahydro-1H-2,3-diaza-cyclopropa[a]pentalene-4-carbonyl]-amino}-piperidine-1-carboxylic acid tert-butyl ester (100 mg, 0.218 mmol) was dissolved in 20% TFA/DCM (3 mL). The reaction mixture was stirred at room temperature for 1 h. The solvent was evaporated, and the residue was purified by cation exchange resin to give the title compound (66 mg). LCMS m/z=359.4 [M+H]$^+$; $^1$H NMR (400 MHz, CDCl$_3$) δ ppm 0.48 (td, J=4.2 and 3.6 Hz, 1H), 1.10-1.17 (m, 1H), 1.49-1.55 (m, 2H), 1.97-2.05 (m, 2H), 2.06-2.12 (m, 1H), 2.22-2.29 (m, 1H), 2.78 (t, J=11.1 Hz, 2H), 2.95 (d, J=16.5 Hz, 1H), 3.03 (dd, J=16.4 and 6.2 Hz, 1H), 3.11-3.19 (d, J=11.9 Hz, 2H), 3.97-4.05 (m, 1H), 6.85 (d, J=8.1 Hz, 1H), 6.98-6.74 (m, 2H), 7.61-7.67 (m, 1H).

Example 1.51: Preparation of (1aR,5aR)-2-(2,4-Difluoro-phenyl)-1a,2,5,5a-tetrahydro-1H-2,3-diaza-cyclopropa[a]pentalene-4-carboxylic Acid [1-(2-Methoxy-ethyl)-piperidin-4-ylmethyl]-amide (Compound 149). [Method PP]

To a reaction vial were charged (1aR,5aR)-2-(2,4-difluoro-phenyl)-1a,2,5,5a-tetrahydro-1H-2,3-diaza-cyclopropa[a]pentalene-4-carboxylic acid (piperidin-4-ylmethyl)-amide (20 mg, 0.054 mmol), 1-bromo-2-methoxyethane (0.01 mL, 0.107 mmol) and DIEA (0.019 mL, 0.107 mmol) in 2-propanol (1.5 mL). The reaction was heated at 150° C. for 1 h under microwave irradiation. The reaction mixture was concentrated and the residue was purified by preparative LCMS to give the title compound (14 mg). LCMS m/z=431.4 [M+H]$^+$; $^1$H NMR (400 MHz, CD$_3$OD) δ ppm 0.44 (td, J=4.6 and 3.5 Hz, 1H), 1.18-1.25 (m, 1H), 1.50-1.61 (m, 2H), 1.88-2.05 (m, 3H), 2.17-2.23 (m, 1H), 2.30-2.38 (m, 1H), 2.90 (d, J=16.4 Hz, 1H), 2.93-3.05 (m, 3H), 3.28-3.34 (buried, 4H), 3.42 (s, 3H), 3.59-3.66 (m, 2H), 3.68-3.74 (m, 2H), 7.14-7.21 (m, 1H), 7.26-7.33 (m, 1H), 7.71-7.78 (m, 1H).

Example 1.52: Preparation of (1aR,5aR)-2-(2,4-Difluoro-phenyl)-1a,2,5,5a-tetrahydro-1H-2,3-diaza-cyclopropa[a]pentalene-4-carboxylic Acid [1-(6-Hydroxy-pyridin-3-yl)-1-methyl-ethyl]-amide (Compound 100). [Method QQ]

To a stirred solution of (1aR,5aR)-2-(2,4-difluoro-phenyl)-1a,2,5,5a-tetrahydro-1H-2,3-diaza-cyclopropa[a]pentalene-4-carboxylic acid (1-(6-methoxylpyridin-3-yl)-1,1-dimethyl-methyl)-amide (65 mg, 0.15 mmol) in dichloromethane was added iodotrimethylsilane (106 μL, 0.75 mmol) at 0° C. under nitrogen atmosphere. The reaction mixture was warmed to room temperature and refluxed overnight. The mixture was purified by preparative LCMS to give the title compound (40 mg). LCMS m/z=411.3 [M+H]$^+$; $^1$H NMR (400 MHz, CDCl$_3$) δ ppm 0.50 (td, J=4.7 and 3.4 Hz, 1H), 1.13-1.18 (m, 1H), 1.71 (s, 3H), 1.73 (s, 3H), 2.09-2.12 (m, 1H), 2.25-2.28 (m, 1H), 2.88 (d, J=16.7 Hz, 1H), 2.98 (dd, J=16.5 and 6.3 Hz, 1H), 6.84 (d, J=9.4 Hz, 1H), 7.02-7.08 (m, 2H), 7.13 (s, 1H), 7.62-7.67 (m, 2H), 7.90 (dd, J=9.4 and 2.6 Hz, 1H).

Example 1.53: Preparation of (1aR,5aR)-2-(2,4-Difluoro-phenyl)-1a,2,5,5a-tetrahydro-1H-2,3-diaza-cyclopropa[a]pentalene-4-carboxylic Acid Methyl-pyridin-2-yl-amide (Compound 139)

To a reaction vial containing NaH (2.3 mg, 0.057 mmol) was added (1aR,5aR)-2-(2,4-difluoro-phenyl)-1a,2,5,5a-tetrahydro-1H-2,3-diaza-cyclopropa[a]pentalene-4-carboxylic acid pyridin-2-ylamide (10 mg, 0.028 mmol) in DMF (0.5 mL) under nitrogen protection. After 15 min, iodomethane (2.7 μL, 0.043 mmol) in DMF (0.1 mL) was added. The reaction mixture was stirred at room temperature overnight, and then purified by preparative LCMS to give the title compound (3.5 mg). LCMS m/z=367.3 [M+H]$^+$; $^1$H NMR (400 MHz, CDCl$_3$) δ ppm 0.52 (td, J=4.7 and 3.4 Hz, 1H), 1.15-1.22 (m, 1H), 2.19-2.23 (m, 1H), 2.28-2.34 (m, 1H), 2.97 (dd, J=16.6 Hz, 1H), 3.08 (dd, J=16.4 and 6.3 Hz, 1H), 4.39 (s, 3H), 6.97-7.08 (m, 2H), 7.49 (t, J=6.6 Hz, 1H), 7.88-7.94 (m, 1H), 8.22 (t, J=8.0 Hz, 1H), 8.50-8.55 (m, 2H).

Example 1.54: Preparation of (1aS,5aS)-2-(2,4-Difluoro-phenyl)-1a,2,5,5a-tetrahydro-1H-2,3-diaza-cyclopropa[a]pentalene-4-carboxylic Acid (3-Dimethylamino-1-oxo-tetrahydro-1λ4-thiophen-3-ylmethyl)-amide (Compound 290)

Step A: Preparation of 3-(Aminomethyl)-3-(N,N-dimethylamino)tetramethylene Sulfoxide To a stirred solution of 3-(aminomethyl)-N,N-dimethyl-tetrahydrothiophen-3-amine (160 mg, 0.998 mmol) in DCM: MeOH (4:1, 10 mL) was added MCPBA (246 mg, 1.098 mmol) at 0° C. The reaction was slowly warmed to room temperature and stirred overnight. The crude was purified by cation exchange resin to give the title compound without further purification.

Step B: Preparation of (1aS,5aS)-2-(2,4-Difluoro-phenyl)-1a,2,5,5a-tetrahydro-1H-2,3-diaza-cyclopropa[a]pentalene-4-carboxylic Acid (3-Dimethylamino-1-oxo-tetrahydro-1λ4-thiophen-3-ylmethyl)-amide The title compound was prepared in a manner similar to that described in Method G using Intermediate 3 (see Example 1.3) and 3-(aminomethyl)-3-(N,N-dimethylamino) tetramethylene sulfoxide LCMS m/z=435.4 [M+H]$^+$; $^1$H NMR (400 MHz, CD$_3$OD) δ ppm 0.48-0.51 (m, 1H), 1.21-1.28 (m, 1H), 2.20-2.28 (m, 1H), 2.35-2.40 (m, 1H), 2.41 (s, 3H), 2.47 (s, 3H), 2.50-2.58 (m, 1H), 2.71-2.80 (m, 1H), 2.90-3.10 (m, 3H), 3.15-3.20 (m, 1H), 3.30-3.38 (m, 2H, buried), 3.56-3.85 (m, 2H), 7.19-7.26 (m, 1H), 7.29-7.37 (m, 1H), 7.75-7.83 (m, 1H).

Example 1.55: Preparation of (1aS,5aS)-2-(2,4-Difluoro-phenyl)-1a,2,5,5a-tetrahydro-1H-2,3-diaza-cyclopropa[a]pentalene-4-carboxylic Acid (1-Hydroxymethyl-cyclopentyl)-amide (Compound 244). [Method RR]

To a stirred solution of (1aS,5aS)-2-(2,4-difluoro-phenyl)-1a,2,5,5a-tetrahydro-1H-2,3-diaza-cyclopropa[a]pentalene-4-carboxylic acid (40 mg, 0.145 mmol) and PyBOP (90 mg, 0.174 mmol) in DMF (1 mL) was added DIEA (0.05 mL, 0.724 mmol). After 10 min, (1-aminocyclopentyl)methanol (20 mg, 0.174 mmol) was added. The reaction mixture was stirred at room temperature overnight. The mixture was purified by preparative LCMS to give the title compound (23 mg) as a white solid. LCMS m/z=374.4 [M+H]$^+$; $^1$H NMR (400 MHz, CDCl$_3$) δ ppm 0.48 (td, J=4.7 and 3.3 Hz, 1H), 1.12-1.18 (m, 1H), 1.66-1.88 (m, 6H), 1.94-2.02 (m, 2H), 2.08-2.12 (m, 1H), 2.25-2.32 (m, 1H), 2.95 (d, J=16.5 Hz, 1H), 3.05 (dd, J=16.5 and 6.2 Hz, 1H), 3.73 (d, J=5.9 Hz, 2H), 4.69 (t, J=5.9 Hz, 1H), 7.00-7.05 (m, 3H), 7.59-7.73 (m, 1H).

Example 1.56: Preparation of (1aS,5aS)-2-(2,4-Difluoro-phenyl)-1a,2,5,5a-tetrahydro-1H-2,3-diaza-cyclopropa[a]pentalene-4-carboxylic Acid (1-Carbamoyl-cyclobutyl)-amide (Compound 236)

1-{[(1aS,5aS)-2-(2,4-Difluoro-phenyl)-1a,2,5,5a-tetrahydro-1H-2,3-diaza-cyclopropa[a]pentalene-4-carbonyl]-amino}-cyclobutanecarboxylic acid ethyl ester (20 mg, 0.05 mmol) was dissolved in 7 N ammonia in methanol (4 mL). The sealed reaction vial was stirred at 65° C. for 48 h. The solvent was evaporated, and the residue was purified by preparative TLC plate to give the title compound (14 mg) as a white solid. LCMS m/z=373.3 [M+H]$^+$; $^1$H NMR (400 MHz, DMSO-d$_6$) δ ppm 0.46 (td, J=4.6 and 3.5 Hz, 1H), 1.16-1.20 (m, 1H), 1.82-1.94 (m, 1H), 2.18-2.31 (m, 4H), 2.50 (m, buried, 3H), 2.80 (d, J=16.3 Hz, 1H), 2.92 (dd, J=16.3 and 6.3 Hz, 1H), 6.85 (s, 1H), 6.96 (s, 1H), 7.32-7.38 (m, 1H), 7.61-7.68 (m, 1H), 7.81-7.88 (m, 1H), 8.28 (s, 1H).

Example 1.57: Preparation of (1aR,5aR)-2-(5-Methoxy-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 374)

Step A: Preparation of (1aR,5aR)-2-(5-Methoxy-pyrazin-2-yl)-1a,2,5,5a-tetrahydro-1H-2,3-diaza-cyclopropa[a]pentalene-4-carboxylic Acid To a reaction vial containing (1aR,5aR)-2-(5-bromopyrazin-2-yl)-1a,2,5,5a-tetrahydro-1H-2,3-diaza-cyclopropa[a]pentalene-4-carboxylic acid ethyl ester (120 mg, 0.344 mmol) in methanol was added sodium methoxide (74 mg, 1.375 mmol). The reaction mixture was heated at 140° C. for 1 h under microwave irradiation, poured into water, acidified with HCl solution and extracted with solution of DCM:IPA (4:1). The combined organics were dried and concentrated to give the title compound (70 mg). LCMS m/z=273.3 [M+H]$^+$.

Step B: Preparation of (1aR,5aR)-2-(5-methoxy-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method RR using (1aR,5aR)-2-(5-methoxypyrazin-2-yl)-1a,2,5,5a-tetrahydro-1H-2,3-diaza-cyclopropa[a]pentalene-4-carboxylic acid and 2-amino-2-methylpropan-1-ol. LCMS m/z=344.3 [M+H]$^+$; $^1$H NMR (400 MHz, CDCl$_3$) δ ppm 0.44 (td, J=4.6 and 3.4 Hz, 1H), 1.18-1.22 (m, 1H), 1.39 (s, 3H), 1.40 (s, 3H), 2.23-2.28 (m, 1H), 2.62-2.67 (m, 1H), 2.88 (d, J=16.8 Hz, 1H), 2.97 (dd, J=16.5 and 6.3 Hz, 1H), 3.68 (s, 2H), 4.01 (s, 3H), 4.17 (br, 1H), 6.96 (s, 1H), 8.05 (d, J=1.4 Hz, 1H), 8.67 (d, J=1.4 Hz, 1H).

Example 1.58: Preparation of (1aR,5aR)-2-(5-Hydroxy-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 414)

Step A: Preparation of (1aR,5aR)-2-(5-Hydroxy-pyrazin-2-yl)-1a,2,5,5a-tetrahydro-1H-2,3-diaza-cyclopropa[a]pentalene-4-carboxylic Acid To a mixture of (1aR,5aR)-2-(5-bromopyrazin-2-yl)-1a,2,5,5a-tetrahydro-1H-2,3-diaza-cyclopropa[a]pentalene-4-carboxylic acid ethyl ester (100 mg, 0.286 mmol) in THF was added 1 N NaOH solution (1.43 mL, 1.43 mmol). The reaction was heated at 120° C. for 1 h under microwave irradiation. The solvent was removed. The residue was added water and acidified with HCl solution to give the title compound (52 mg) as an off-white solid.

Step B: Preparation of (1aR,5aR)-2-(5-Hydroxy-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method RR using (1aR,5aR)-2-(5-hydroxypyrazin-2-yl)-1a,2,5,5a-tetrahydro-1H-2,3-diaza-cyclopropa[a]pentalene-4-carboxylic acid and 2-amino-2-methylpropan-1-ol. LCMS m/z=330.4 [M+H]$^+$; $^1$H NMR (400 MHz, DMSO-d$_6$) δ ppm 0.36 (td, J=4.5 and 3.3 Hz, 1H), 1.17-1.23 (m, 1H), 1.30 (s, 3H), 1.31 (s, 3H), 2.23-2.28 (m, 1H), 2.54-2.58 (m, 1H), 2.74 (d, J=16.5 Hz, 1H), 2.85 (dd, J=16.3 and 6.3 Hz, 1H), 3.43 (s, 2H), 7.20 (s, 1H), 8.01 (d, J=1.3 Hz, 1H), 8.38 (bs, 1H).

Example 1.59: Preparation of (1aR,5aR)-2-(5-Cyclopropylmethyl-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 586)

Under nitrogen protection, zinc suspension (1.76 mL, 1.338 mmol) was added to a solution of diiodine (4.5 mg, 0.018 mmol) in DMA at room temperature. After several minutes, (bromomethyl)cyclopropane (120 mg, 0.892 mmol) was added. The reaction mixture was heated at 70° C. for 3 h, cooled down to room temperature, then transferred to a flask containing (1aR,5aR)-2-(5-bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)- amide (70 mg, 0.178 mmol) and bis(tri-t-butylphosphine) palladium (0) (9.1 mg, 0.018 mmol) in THF (1 mL). The whole reaction mixture was heated at reflux overnight, cooled down and quenched with saturated sodium bicarbonate. The solid was filtered, and the filtrate was extracted with ethyl acetate. The combined organics were dried and concentrated. The residue was purified by silica gel column chromatography to give the title compound (5 mg) as white solid. LCMS m/z=368.4 [M+H]$^+$; $^1$H NMR (400 MHz, CDCl$_3$) δ ppm 0.46 (td, J=4.7 and 3.3 Hz, 1H), 1.22-1.28 (m, 1H), 1.40 (s, 3H), 1.41 (s, 3H), 1.95-2.04 (m, 1H), 2.09-2.16 (m 1H), 2.26-2.32 (m, 1H), 2.37-2.41 (m, 4H), 2.68-2.74 (m, 1H), 2.91 (d, J=16.8 Hz, 1H), 3.00 (dd, J=16.5 and 6.2 Hz, 1H), 3.69 (d, J=6.3 Hz, 2H), 3.72-3.77 (m, 1H), 4.78 (br, 1H), 6.97 (s, 1H), 8.26 (d, J=1.3 Hz, 1H), 9.15 (d, J=1.3 Hz, 1H).

Example 1.60: Preparation of (1aR,5aR)-2-(5-Cyano-pyridin-2-yl)-1a,2,5,5a-tetrahydro-1H-2,3-diaza-cyclopropa[a]pentalene-4-carboxylic Acid (1-Phenyl-cyclopropyl)-amide. (Compound 329)

In a 5 mL heavy-walled sealed tube with stir bar, was added (1aR,5aR)-2-(5-bromopyridin-2-yl)-1a,2,5,5a-tetrahydro-1H-2,3-diaza-cyclopropa[a]pentalene-4-carboxylic acid ethyl ester (0.048 g, 0.138 mmol), tetrakis(triphenylphosphine)palladium (0.032 g, 0.028 mmol), and dicyanozinc (0.032 g, 0.276 mmol) in DMA (0.66 mL). The tube was sealed, flushed with argon, and heated under microwave irradiation at 140° C. for 90 min. The reaction mixture was added ice water (10 mL), and extracted with EtOAc (3×30 mL). The combined organic extracts were washed with brine (4 mL), dried (Na$_2$SO$_4$), filtered, and concentrated. The residue was purified by silica gel column chromatography to provide a yellow solid (0.030 g). The solid was hydrolyzed in a similar method as described in Method D to provide (1aR,5aR)-2-(5-cyanopyridin-2-yl)-1a,2,5,5a-tetrahydro-1H-2,3-diaza-cyclopropa[a]pentalene-4-carboxylic acid. The title compound was prepared in a manner similar to that described in Method G using the acid prepared above and 1-phenylcyclopropanamine. LCMS m/z=382.4 [M+H]$^+$; $^1$H NMR (400 MHz, CDCl$_3$) δ ppm 0.46 (td, J=4.7 and 3.3 Hz, 1H), 1.24-1.32 (m, 1H), 1.34-1.45 (m, 4H), 2.26-2.34 (m, 1H), 2.78-2.84 (m, 1H), 2.92 (d, J=17.1 Hz, 1H), 3.01 (dd, J=16.7 and 6.2 Hz, 1H), 7.18-7.23 (m, 1H), 7.26-7.37 (m, 4H), 7.56 (bs, 1H), 8.04-8.09 (m 2H), 8.76 (t, J=1.6 Hz, 1H).

Example 1.61: Preparation of (1aR,5aR)-2-(2,4-Difluoro-phenyl)-1a,2,5,5a-tetrahydro-1H-2,3-diaza-cyclopropa[a]pentalene-4-carboxylic Acid ((1R,2R)-2-Amino-cyclohexyl)-amide (Compound 470). [Method SS]

((1R,2R)-2-{[(1aR,5aR)-2-(2,4-Difluoro-phenyl)-1a,2,5,5a-tetrahydro-1H-2,3-diaza-cyclopropa[a]pentalene-4-carbonyl]-amino}-cyclohexyl)-carbamic acid tert-butyl ester (75 mg, 0.159 mmol) was added to a solution of 20% TFA/DCM and stirred for 2 h at room temperature. The solvent was evaporated and the residue was purified by SCX resin to give the title compound (54 mg). LCMS m/z=373.4 [M+H]$^+$; $^1$H NMR (400 MHz, DMSO-d$_6$) δ ppm 0.39 (td, J=4.3, 3.8 Hz, 1H), 1.04-1.26 (m, 5H), 1.59-1.82 (m, 4H), 2.14-2.19 (m, 1H), 2.23-2.29 (m, 1H), 2.50-2.58 (m 1H), 2.76 (d, J=16.4 Hz, 1H), 2.89 (d, J=16.2, 6.3 Hz, 1H), 3.31-3.41 (m, 3H), 7.29-7.34 (m, 1H), 7.59-7.65 (m, 1H), 7.77-7.84 (m, 2H).

Example 1.62: Preparation of (1aR,5aR)-2-(2,4-Difluoro-phenyl)-1a,2,5,5a-tetrahydro-1H-2,3-diaza-cyclopropa[a]pentalene-4-carboxylic Acid ((S)-Carbamoyl-phenyl-methyl)-amide (Compound 29)

Step A. Preparation of (2S)-Methyl 2-(1-(2,4-Difluorophenyl)-1a,2,5,5a-tetrahydro-1H-2,3-diaza-cyclopropa[a]pentalene-4-carboxamido)-2-phenylacetate The title compound was prepared in a manner similar to that described in Method G using Intermediate 1 (see Example 1.1) and (S)-methyl 2-amino-2-phenylacetate. The material was purified by HPLC and used directly in the next step.

Step B. Preparation of (1aR,5aR)-2-(2,4-Difluorophenyl)-1a,2,5,5a-tetrahydro-1H-2,3-diaza-cyclopropa[a]pentalene-4-carboxylic Acid ((S)-Carbamoyl-phenyl-methyl)-amide A mixture of ammonia in MeOH (50 equiv) and (2S)-methyl 2-(1-(2,4-difluorophenyl)-1a,2,5,5a-tetrahydro-1H-2,3-diaza-cyclopropa[a]pentalene-4-carboxamido)-2-phenylacetate was stirred at 100° C. overnight. The mixture was concentrated and purified by HPLC to provide the titled compound as a pale yellow solid. LCMS m/z=409.4 [M+H]$^+$; $^1$H NMR (400 MHz, CDCl$_3$) 0.45 (td, J=3.5, 4.8 Hz, 1H), 1.14 (td, J=4.6, 8.0 Hz, 1H), 2.08-2.14 (m, 1H), 2.21-2.28 (m, 1H), 2.88 (d, J=16.4 Hz, 1H), 2.99 (dd, J=6.4 and 16.4 Hz, 1H), 5.74 (t, J=6.4 Hz, 1H), 6.14 (s, 1H), 6.42 (s, 1H), 6.97-7.04 (m, 2H), 7.29-7.38 (m, 3H), 7.47 (dd, J=1.8, 8.2 Hz, 2H), 7.62-7.68 (m, 1H), 7.87-7.93 (dd, J=7.2, 7.4 Hz, 1H).

Example 1.63: Preparation of (1aR,5aR)-2-(2,4-Difluoro-phenyl)-1a,2,5,5a-tetrahydro-1H-2,3-diaza-cyclopropa[a]pentalene-4-carboxylic Acid (2-Hydroxy-1-pyridin-3-yl-ethyl)-amide (Racemic Mixture of Compound 579 and Compound 445)

The title compound was prepared in a manner similar to that described in Method G using Intermediate 1 (see Example 1.1) and 2-amino-2-(pyridin-3-yl)ethanol. LCMS m/z=397.4 [M+H]$^+$; $^1$H NMR (400 MHz, CDCl$_3$) δ 0.48 (td, J=4.7 and 3.5 Hz, 1H), 1.17 (td, J=7.9 and 4.7 Hz, 1H), 2.08-2.14 (m, 1H), 2.23-2.30 (m, 1H), 2.56 (bs, 1H), 2.93 (d, J=16.4 Hz, 1H), 3.03 (dd, J=16.4 and 6.2 Hz, 1H), 3.98-4.03 (m, 2H), 5.19-5.24 (m, 1H), 7.02 (t, J=8.0 Hz, 2H), 7.27 (dd, J=7.8 and 5.0 Hz, 1H), 7.47 (d, J=7.6 Hz, 1H), 7.60-7.67 (m, 1H), 7.71 (d, J=8.0 Hz, 1H), 8.53 (bs, 1H), 8.66 (bs, 1H). Resolution Via Chiral HPLC.
Column: normal phase preparative Chiralcel OD®, 5 cm ID×50 cm L, 20 μm particle size
Eluent: 85% hexane/15% IPA
Gradient: isocratic
Flow: 60 mL/min
Detector: 280 nm
Retention time: 1$^{st}$ diastereomer—33 min; 2$^{nd}$ diastereomer—36 min.

Example 1.64: Preparation of (1aR,5aR)-2-(5-Dimethylamino-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 40). [Method VV]

To a reaction vial containing (1aR,5aR)-2-(5-bromopyrazin-2-yl)-1a,2,5,5a-tetrahydro-1H-2,3-diaza-cyclopropa[a]pentalene-4-carboxylic acid (2-hydroxy-1,1-dimethyl-ethyl)-amide (30 mg, 0.076 mmol) was added dimethylamine in THF (1.15 mL, 2.294 mmol). The reaction mixture was heated at 110° C. for 5 h under microwave irradiation. The solvent was evaporated, and the crude was purified by preparative LCMS to give the title compound (18 mg) as light yellow solid. LCMS m/z=357.4 [M+H]$^+$; $^1$H NMR (400 MHz, CDCl$_3$) δ 0.46 (td, J=4.6 and 3.4 Hz, 1H), 1.18-1.24 (m, 1H), 1.39 (s, 3H), 1.40 (s, 3H), 2.23-2.28 (m, 1H), 2.57-2.62 (m, 1H), 2.91 (d, J=16.8 Hz, 1H), 3.00 (dd, J=16.5 and 6.2 Hz, 1H), 3.18 (s, 6H), 3.71 (s, 2H), 7.00 (s, 1H), 7.84 (d, J=1.4 Hz, 1H), 8.64 (d, J=1.4 Hz, 1H).

Example 1.65: Preparation of (1aR,5aR)-2-(5-Ethyl-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 314). [Method WW]

To a reaction vial containing (1aR,5aR)-2-(5-bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide (35 mg, 0.089 mmol) and bis(tri-t-butylphosphine)palladium (0) (4.6 mg, 8.92 μmol) in THF was added diethylzinc in hexanes (268 μL, 0.268 mmol) at room temperature. The reaction mixture was heated at reflux for 2 h, quenched with saturated sodium bicarbonate. The solid was filtered through celite, and the filtrate was extracted with ethyl acetate. The combined organics were dried and concentrated. The residue was purified by preparative LCMS to give the title compound (17 mg) as white solid. LCMS m/z=342.4 [M+H]$^+$; $^1$H NMR (400 MHz, CDCl$_3$) δ 0.46 (td, J=4.6 and 3.4 Hz, 1H), 1.21-1.28 (m, 1H), 1.38 (t, J=7.6 Hz, 3H), 1.41 (s, 3H), 1.42 (s, 3H), 2.26-2.32 (m, 1H), 2.70-2.75 (m, 1H), 2.90 (q, J=7.6 Hz, 2H), 2.92 (d, J=16.3 Hz, 1H), 3.01 (dd, J=16.5 and 6.3 Hz, 1H), 3.72 (d, J=4.6 Hz, 2H), 4.72 (t, J=4.6 Hz, 1H), 6.96 (s, 1H), 8.29 (d, J=1.4 Hz, 1H), 9.12 (d, J=1.4 Hz, 1H).

Example 1.66: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (2,2,2-Trifluoro-1,1-dimethyl-ethyl)-amide (Compound 663). [Method XX]

To a mixture of (1aR,5aR)-2-(4-bromo-pyridin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide (35 mg, 0.082 mmol) and dicyanozinc (19.2 mg, 0.164 mmol) in DMA (2 mL) under nitrogen atmosphere, tetrakis(triphenylphosphine)palladium (9.4 mg, 0.0081 mmol) was added. The reaction was heated in a heavy-walled sealed tube under microwave irradiation at 130° C. for 1 h. The mixture was purified by preparative HPLC to give the title compound (13 mg). LCMS m/z=376.3 [M+H]$^+$; $^1$H NMR (400 MHz, CDCl$_3$) δ ppm 0.44-0.47 (m, 1H), 1.26 (td, J=7.9 and 4.9 Hz, 1H), 1.72 (s, 6H), 2.25-2.32 (m, 1H), 2.76-2.82 (m, 1H), 2.92 (d, J=16.9 Hz, 1H), 3.00 (dd, J=16.7 and 6.2 Hz, 1H), 6.87 (bs, 1H), 7.42 (dd, J=5.0 and 1.4 Hz, 1H), 8.15 (s, 1H), 8.62 (d, J=5.0 Hz, 1H).

Example 1.67: Preparation of (1aR,5aR)-2-(4-Methanesulfonyl-pyridin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 651)

Step A: Preparation of (1aR,5aR)-2-(4-(methylsulfonyl)pyridin-2-yl)-1a,2,5,5a-tetrahydro-1H-2,3-diaza-cyclopropa[a]pentalene-4-carboxylic Acid A solution of (1aR,5aR)-2-(4-bromopyridin-2-yl)-1a,2,5,5a-tetrahydro-1H-2,3-diaza-cyclopropa[a]pentalene-4-carboxylic acid (80 mg, 0.25 mmol) and sodium methanesulfinate (28 mg, 0.28 mmol) in DMSO (1.5 mL) was stirred overnight at 80° C. The reaction was diluted with H$_2$O, and then extracted with DCM (3×). The combined organics were washed with H$_2$O, dried, and concentrated. The residue was purified by silica gel column chromatography to give the title compound (50 mg). LCMS m/z=320.2 [M+H]$^+$.

Step B: Preparation of (1aR,5aR)-2-(4-Methanesulfonyl-pyridin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide The title compound was prepared in a manner similar to that described in Method G, using (1aR,5aR)-2-(4-(methylsulfonyl)pyridin-2-yl)-1a,2,5,5a-tetrahydro-1H-2,3-diaza-cyclopropa[a]pentalene-4-carboxylic acid and (S)-2-amino-3,3-dimethylbutan-1-ol. LCMS m/z=419.6 [M+H]$^+$; $^1$H NMR (400 MHz, CDCl$_3$) δ ppm 0.44-0.48 (m, 1H), 1.05 (s, 9H), 1.23-1.28 (m, 1H), 2.21 (t, J=5.8 Hz, 1H), 2.26-2.32 (m, 1H), 2.79-2.85 (m, 1H), 2.94 (d, J=16.8 Hz, 1H), 3.04 (dd, J=16.6 and 6.3 Hz, 1H), 3.16 (s, 3H), 3.67-3.74 (m, 1H), 3.94-4.04 (m, 2H), 6.96 (d, J=9.2 Hz, 1H), 7.69 (dd, J=5.0 and 1.5 Hz, 1H), 8.38 (s, 1H), 8.72 (d, J=5.0 Hz, 1H).

Example 1.68: Preparation of (1aR,5aR)-2-(2,4-Difluoro-phenyl)-1a,2,5,5a-tetrahydro-1H-2,3-diaza-cyclopropa[a]pentalene-4-carboxylic Acid [2-Hydroxy-1-(tetrahydro-pyran-4-yl)-ethyl]-amide (Racemic Mixture of Compound 735 and Compound 742)

The title compound was prepared in a manner similar to that described in Method G, using Intermediate 1 (see Example 1.1) and 2-amino-2-(tetrahydro-2H-pyran-4-yl)ethanol. LCMS m/z=404.4 [M+H]$^+$; $^1$H NMR (400 MHz, CDCl$_3$) δ ppm 0.46-0.50 (m, 1H), 1.15 (td, J=7.8 and 4.8 Hz, 1H), 1.40-1.53 (m, 2H), 1.70 (d, J=12.6 Hz, 2H), 1.93-2.03 (m, 1H), 2.08-2.15 (m, 1H), 2.24-2.32 (m, 1H), 2.94 (d, J=16.8 Hz, 1H), 3.06 (dd, J=16.8 and 6.2 Hz, 1H), 3.33-3.43 (m, 2H), 3.77-3.85 (m, 3H), 3.95-4.02 (m, 2H), 6.99-7.05 (m, 3H), 7.59-7.66 (m, 1H).

Resolution Via Chiral HPLC.

Column: normal phase preparative Chiralcel OD®, 5 cm ID×50 cm L, 20 μm particle size Eluent: 90% hexane/10% IPA Gradient: isocratic Flow: 60 mL/min Detector: 280 nm Retention Times: 1$^{st}$ diastereomer—28 min; 2$^{nd}$ diastereomer—30 min.

Example 1.69: Preparation of (1aR,5aR)-2-(5-Pentafluoroethyl-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 596)

Step A: Preparation of (1aR,5aR)-2-(5-(Perfluoroethyl)pyrazin-2-yl)-1a,2,5,5a-tetrahydro-1H-2,3-diaza-cyclopropa[a]pentalene-4-carboxylic Acid. [Method YY]

Potassium fluoride (1.809 g, 31.1 mmol) and copper(I) iodide (5.93 g, 31.1 mmol) were combined in an oven-dried 20 mL scintillation vial. N-Methyl-2-pyrrolidinone (15 mL) was added followed by trimethyl(trifluoromethyl)silane (4.43 g, 31.1 mmol) (exothermic!) The mixture was stirred in a sealed vial at 50° C. for 1 h, and then added (1aR,5aR)-2-(5-bromopyrazin-2-yl)-1a,2,5,5a-tetrahydro-1H-2,3-diaza-cyclopropa[a]pentalene-4-carboxylic acid (1.00 g, 3.11 mmol). The brown mixture was stirred in a sealed vial at 50° C. for 17 h. The mixture was poured into 1 M HCl (100 mL), added 25% iPrOH/CH$_2$Cl$_2$ (50 mL), and stirred for 5 minutes. The mixture was filtered and the layers were separated. The aqueous layer was extracted with two more 50 mL portions of 25% iPrOH/CH$_2$Cl$_2$. The combined organic extracts were dried (MgSO$_4$), filtered, and concentrated. The residue was purified by preparative HPLC to give the title compound (0.50 g) as a white solid. LCMS m/z=361.4 [M+H]$^+$.

Step B: Preparation of (1aR,5aR)-2-(5-Pentafluoroethyl-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method G, using 2-amino-2-methylpropan-1-ol and (1aR,5aR)-2-(5-(perfluoroethyl)pyrazin-2-yl)-1a,2,5,5a-tetrahydro-1H-2,3-diaza-cyclopropa[a]pentalene-4-carboxylic acid. LCMS m/z=432.3 [M+H]$^+$; $^1$H NMR (400 MHz, CDCl$_3$) δ ppm 0.47 (td, J=4.7, 3.3 Hz, 1H), 1.29 (td, J=8.0, 4.9 Hz, 1H), 1.42 (s, 6H), 2.30-2.37 (m, 1H), 2.75-2.79 (m, 1H), 2.93 (d, J=16.9 Hz, 1H), 3.02 (dd, J=16.7, 6.3 Hz, 1H), 3.71 (d, J=6.1 Hz, 2H), 4.40 (d, J=6.1 Hz, 1H), 6.93 (s, 1H), 8.78 (d, J=1.3 Hz, 1H), 9.35 (d, J=1.0 Hz, 1H).

Example 1.70: Preparation of (1aR,5aR)-2-(2,4-Difluoro-phenyl)-1a,2,5,5a-tetrahydro-1H-2,3-diaza-cyclopropa[a]pentalene-4-carboxylic Acid (4-Hydroxymethyl-1-methyl-piperidin-4-yl)-amide (Compound 599)

To a solution of 4-{[(1aR,5aR)-2-(2,4-difluoro-phenyl)-1a,2,5,5a-tetrahydro-1H-2,3-diaza-cyclopropa[a]pentalene-4-carbonyl]-amino}-1-methyl-piperidine-4-carboxylic acid methyl ester (50 mg, 0.116 mmol) in THF (1 mL) was added a 2.0 M THF solution of lithium borohydride (0.116 mL, 0.232 mmol). The reaction was stirred at 23° C. for 3 h (5 drops methanol were added at 20 min). 1.0 M NaOH (5 mL) was added. The mixture was extracted with dichloromethane (3×10 mL). The combined organic extracts were dried (MgSO$_4$), filtered, then concentrated. The residue was purified by preparative HPLC to give the title compound as a TFA salt (12 mg). LCMS m/z=403.5 [M+H]$^+$; $^1$H NMR (400 MHz, DMSO-d$_6$) δ ppm 0.39 (td, J=4.4, 3.5 Hz, 1H), 1.16 (td, J=7.8, 4.6 Hz, 1H), 1.40-1.61 (m, 2H), 1.89-1.96 (m, 2H), 2.16-2.20 (m, 1H), 2.24-2.37 (m, 3H), 2.56 (s, 3H), 2.67-2.79 (m, 4H), 2.90 (dd, J=16.4, 6.4 Hz, 1H), 3.54 (s, 2H), 7.09 (s, 1H), 7.28-7.33 (m, 1H), 7.57-7.63 (m, 1H), 7.77-7.83 (m, 1H).

Example 1.71: Preparation of (1aR,5aR)-2-(5-Chloro-4-trifluoromethyl-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 611)

Step A: Preparation of 5-Chloro-2-hydrazinyl-4-(trifluoromethyl)pyridine

To a solution of 2,5-dichloro-4-(trifluoromethyl)pyridine (1 g, 4.63 mmol) in isopropanol (20 mL) was added hydrazine monohydrate (2.021 mL, 41.7 mmol). The mixture was stirred at 70° C. for 16 h. The reaction was concentrated. The residue was taken up in ethyl acetate and the insoluble material was removed by filtration. The filtrate was concentrated to give the title compound as a tan solid (0.94 g). LCMS m/z=212.0 [M+H]$^+$; $^1$H NMR (400 MHz, DMSO-d$_6$) δ ppm 4.39 (s, 2H), 7.11 (s, 1H), 8.19 (s, 1H), 8.25 (s, 1H).

Step B: Preparation of Ethyl (1aR,5aR)-1-(5-Chloro-4-(trifluoromethyl)pyridin-2-yl)-1a,2,5,5a-tetrahydro-1H-2,3-diaza-cyclopropa[a]pentalene-3-carboxylate The title compound was prepared in a manner similar to that described in Method C from potassium 2-ethoxy-2-oxo-1-((1R,5R)-2-oxobicyclo[3.1.0]hexan-3-ylidene)ethanolate and 5-chloro-2-hydrazinyl-4-(trifluoromethyl)pyridine. LCMS m/z=372.1 [M+H]$^+$.

Step C: Preparation of (1aR,5aR)-1-(5-Chloro-4-(trifluoromethyl)pyridin-2-yl)-1a,2,5,5a-tetrahydro-1H-2,3-diaza-cyclopropa[a]pentalene-3-carboxylic Acid The title compound was prepared in a manner similar to that described in Method B using ethyl 1-(5-chloro-4-(trifluoromethyl)pyridin-2-yl)-1a,2,5,5a-tetrahydro-1H-2,3-diaza-cyclopropa[a]pentalene-3-carboxylate. LCMS m/z=344.1 [M+H]$^+$.

Step D: Preparation of (1aR,5aR)-2-(5-Chloro-4-trifluoromethyl-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method G, using (1aR,5aR)-1-(5-chloro-4-(trifluoromethyl)pyridin-2-yl)-1a,2,5,5a-tetrahydro-1H-2,3-diaza-cyclopropa[a]pentalene-3-carboxylic acid and 2-amino-2-methylpropan-1-ol. LCMS m/z=415.4 [M+H]$^+$; 1H NMR (400 MHz, CDCl$_3$) δ ppm 0.45 (td, J=4.6, 3.4 Hz, 1H), 1.26 (td, J=8.0, 4.9 Hz, 1H), 1.43 (s, 6H), 2.26-2.32 (m, 1H), 2.74-2.79 (m, 1H), 2.91 (d, J=17.0 Hz, 1H), 3.01 (dd, J=16.7, 6.4 Hz, 1H), 3.71 (d, J=6.2 Hz, 2H), 4.57 (d, J=6.2 Hz, 1H), 6.88 (s, 1H), 8.17 (s, 1H), 8.58 (s, 1H).

Example 1.72: Preparation of (1aR,5aR)-2-(4-Chloro-pyridin-2-yl)-1a,2,5,5a-tetrahydro-1H-2,3-diaza-cyclopropa[a]pentalene-4-carboxylic Acid [1-Methyl-1-(1H-tetrazol-5-yl)-ethyl]-amide (Compound 682)

A mixture of (1aR,5aR)-2-(4-chloro-pyridin-2-yl)-1a,2,5,5a-tetrahydro-1H-2,3-diaza-cyclopropa[a]pentalene-4-carboxylic acid (cyano-dimethyl-methyl)-amide (100 mg, 0.293 mmol), sodium azide (28.5 mg, 0.439 mmol) and triethylamine hydrochloride (81 mg, 0.585 mmol) in DMF (2 mL) was heated in a heavy-walled sealed tube under microwave irradiation at 110° C. for 1 h. Another 50 mg sodium azide and 150 mg triethylamine hydrochloride were added, and the mixture was heated under microwave for another 5 h at 125° C. The mixture was purified by prep HPLC to give the title compound as a white solid (33 mg). LCMS m/z=385.3 [M+H]$^+$; $^1$H NMR (400 MHz, DMSO-d$_6$) δ ppm 0.35 (td, J=4.4, 3.4 Hz, 1H), 1.23 (td, J=7.8, 4.6 Hz, 1H), 1.757 (s, 3H), 1.764 (s, 3H), 2.21-2.28 (m, 1H), 2.66 (d, J=16.6 Hz, 1H), 2.71-2.75 (m, 1H), 2.79 (dd, J=16.6, 6.4 Hz, 1H), 7.54 (dd, J=5.4, 1.9 Hz, 1H), 8.26 (d, J=1.9 Hz, 1H), 8.42 (bs, 1H), 8.51 (d, J=5.4 Hz, 1H), 16.0 (bs, 1H).

Example 1.73: Preparation of Phosphoric Acid mono-(2-{[(1aR,5aR)-2-(4-Cyano-pyridin-2-yl)-1a,2,5,5a-tetrahydro-1H-2,3-diaza-cyclopropa[a]pentalene-4-carbonyl]-amino}-2-methyl-propyl) Ester (Compound 646)

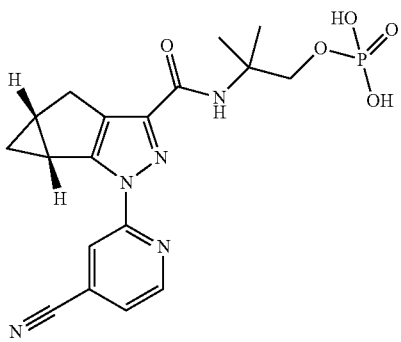 [SMILES: CC(C)(COP(=O)(O)O)NC(=O)c1nn(-c2cc(C#N)ccn2)c2c1C[C@H]1C[C@@H]21]

A solution of (1aR,5aR)-2-(4-cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide (500 mg, 1.482 mmol) in pyridine (10 mL) was cooled in a dry-ice/acetone bath until the mixture solidified. The cooling bath was removed and phosphoryl trichloride (0.691 mL, 7.41 mmol) was added as soon as the mixture melted (ca −42° C.). The cooling bath was replaced periodically, maintaining the temperature at −42° C. while stirring for 45 minutes. Still at −42° C., 50 mL 0.5 M aqueous HCl was added. The volume was reduced to 20 mL by distillation under reduced pressure (50° C. water bath). The remaining solution was purified by preparative HPLC to give a white solid (338 mg). The solid was suspended in water (10 mL) and acetonitrile (2 mL). Sodium carbonate (81.5 mg, 0.769 mmol) was added to form a solution. The resulting solution was lyophilized to give the sodium salt of the title compound as a white solid (385 mg). LCMS m/z=418.3 [M+H]$^+$; $^1$H NMR (400 MHz, D$_2$O) δ ppm 0.53-0.56 (m, 1H), 1.33-1.38 (m, 1H), 1.53 (s, 6H), 2.41-2.47 (m, 1H), 2.69-2.73 (m, 1H), 2.89 (d, J=16.4 Hz, 1H), 3.00 (dd, J=16.4, 6.2 Hz, 1H), 3.91 (d, J=4.2 Hz, 2H), 7.26 (d, J=4.2 Hz, 1H), 8.26-7.33 (s, 1H), 8.72 (d, J=4.6 Hz, 1H). $^{31}$P NMR (162 MHz, D$_2$O, no decoupling) δ ppm 3.36 (t, J=4.5 Hz, 1H).

Example 1.74: Preparation of (1aR,5aR)-2-(4-Bromo-pyridin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 635)

To a solution of (1aR,5aR)-2-(4-bromo-pyridin-2-yl)-1a,2,5,5a-tetrahydro-1H-2,3-diaza-cyclopropa[a]pentalene-4-carboxylic acid (2.00 g, 6.25 mmol) and triethylamine (1.741 mL, 12.49 mmol) in DMF (15 mL) was added HATU (2.423 g, 6.37 mmol). The reaction was stirred at 23° C. for 5 min, then was added (S)-2-amino-3,3-dimethylbutan-1-ol (0.805 g, 6.87 mmol). The reaction was stirred at 23° C. for 1 h then concentrated. The residue was purified by silica gel column chromatography to give the title compound as a white solid (2.48 g). LCMS m/z=419.2 [M+H]$^+$; $^1$H NMR (400 MHz, CDCl$_3$) δ ppm 0.44 (td, J=4.6, 3.4 Hz, 1H), 1.05 (s, 9H), 1.24 (td, J=7.8, 4.9 Hz, 1H), 2.23-2.29 (m, 1H), 2.46 (t, J=5.5 Hz, 1H), 2.78-2.83 (m, 1H), 2.91 (d, J=16.7 Hz, 1H), 3.01 (dd, J=16.6, 6.3 Hz, 1H), 3.66-3.72 (m, 1H), 3.93-4.01 (m, 2H), 7.01 (d, J=8.8 Hz, 1H), 7.37 (dd, J=5.3, 1.6 Hz, 1H), 8.09 (d, J=1.6 Hz, 1H) 8.28 (d, J=5.3 Hz, 1H).

Example 1.75: Preparation of (1aR,5aR)-2-(4-Cyano-pyridin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 668)

(1aR,5aR)-2-(4-Bromo-pyridin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (2.38 g, 5.68 mmol) was dissolved in DMA (10 mL). Nitrogen was bubbled through the solution for 20 min. Zinc(II) cyanide (1.333 g, 11.35 mmol) and palladium tetrakistriphenylphosphine (0.328 g, 0.284 mmol) were added. The reaction was heated under microwave at 120° C. for 1 h. The reaction was diluted with 100 mL ethyl acetate, filtered, then concentrated. The residue was purified by silica gel column chromatography and then crystallized from EtOAc/hexanes to give the title compound as a white solid (1.78 g). LCMS m/z=366.2 [M+H]$^+$; $^1$H NMR (400 MHz, CDCl$_3$) δ ppm 0.45 (td, J=4.7, 3.3 Hz, 1H), 1.06 (s, 9H), 1.25 (td, J=8.0, 4.9 Hz, 1H), 2.26-2.32 (m, 1H), 2.35 (t, J=5.5 Hz, 1H), 2.78-2.83 (m, 1H), 2.93 (d, J=17.2 Hz, 1H), 3.03 (dd, J=16.7, 6.3 Hz, 1H), 3.66-3.72 (m, 1H), 3.94-4.01 (m, 2H), 7.01 (d, J=8.6 Hz, 1H), 7.41 (dd, J=5.1, 1.4 Hz, 1H), 8.15 (dt, J=1.1 Hz, 1H), 8.62 (dd, J=5.1, 0.8 Hz, 1H).

Example 1.76: Preparation of (1aR,5aR)-2-(2,4-Difluoro-phenyl)-1a,2,5,5a-tetrahydro-1H-2,3-diaza-cyclopropa[a]pentalene-4-carboxylic Acid ((S)-1-Cyclopropyl-2-hydroxy-ethyl)-amide (Compound 739)

Step A: Preparation of (2S)-(1aR,5aR)-2-cyclopropyl-2-(1-(2,4-difluorophenyl)-1a,2,5,5a-tetrahydro-1H-2,3-diaza-cyclopropa[a]pentalene-3-carboxamido)acetic Acid The title compound was prepared in a manner similar to that described in Method G, using (1aR,5aR)-2-(2,4-difluoro-phenyl)-1a,2,5,5a-tetrahydro-H-2,3-diaza-cyclopropa

[a]pentalene-4-carboxylic acid and (S)-2-amino-2-cyclopropylacetic acid. LCMS m/z=374.4 [M+H]$^+$; $^1$H NMR (400 MHz, CDCl$_3$) δ ppm 0.46-0.73 (m, 5H), 1.15 (td, J=7.8, 4.9 Hz, 1H), 1.23-1.32 (m, 1H), 2.10-2.15 (m, 1H), 2.24-2.31 (m, 1H), 2.94 (d, J=16.6 Hz, 1H), 3.04 (dd, J=16.6, 6.3 Hz, 1H), 3.97-4.01 (m, 1H), 7.00-7.06 (m, 2H), 7.34 (d, J=7.1 Hz, 1H), 7.63-7.70 (m, 1H).

Step B: Preparation of (1aR,5aR)-2-(2,4-Difluoro-phenyl)-1a,2,5,5a-tetrahydro-1H-2,3-diaza-cyclopropa[a]pentalene-4-carboxylic Acid ((S)-1-Cyclopropyl-2-hydroxy-ethyl)-amide To a solution of (S)-cyclopropyl-{[(1aR,5aR)-2-(2,4-difluoro-phenyl)-1a,2,5,5a-tetrahydro-1H-2,3-diaza-cyclopropa[a]pentalene-4-carbonyl]-amino}-acetic acid (175 mg, 0.469 mmol) in THF (4 mL) was added a 1.0 M THF solution of borane (1.875 mL, 1.875 mmol). The reaction was stirred at 23° C. for 2.5 h. Saturated aqueous NaHCO$_3$ (25 mL) was added. The mixture was extracted with dichloromethane (3×25 mL). The combined organic extracts were dried (MgSO$_4$), filtered, then concentrated. The residue was purified by silica gel column chromatography followed by reversed-phase prep HPLC to give the title compound as a white solid (72 mg). LCMS m/z=360.4 [M+H]$^+$; $^1$H NMR (400 MHz, CDCl$_3$) δ ppm 0.35-0.42 (m, 2H), 0.48 (td, J=4.6, 3.4 Hz, 1H), 0.52-0.64 (m, 2H), 0.94-1.03 (m, 1H), 1.15 (td, J=7.8, 4.9 Hz, 1H), 2.09-2.14 (m, 1H), 2.24-2.31 (m, 1H), 2.94 (d, J=16.6 Hz, 1H), 3.05 (dd, J=16.6, 6.3 Hz, 1H), 3.18 (bs, 1H), 3.27-3.34 (m, 1H), 3.78-3.80 (m, 1H), 3.90 (dd, J=11.1, 3.0 Hz, 1H), 7.00-7.05 (m, 2H), 7.09 (d, J=6.4 Hz, 1H), 7.62-7.68 (m, 1H).

Example 1.77: Preparation of (1aR,5aR)-2-(4-Chloro-pyridin-2-yl)-1a,2,5,5a-tetrahydro-1H-2,3-diaza-cyclopropa[a]pentalene-4-carboxylic Acid tert-Butylamide (Compound 636)

A mixture of (1aR,5aR)-2-(4-bromo-pyridin-2-yl)-1a,2,5,5a-tetrahydro-1H-2,3-diaza-cyclopropa[a]pentalene-4-carboxylic acid tert-butylamide (0.010 g, 0.027 mmol) and lithium chloride (5.65 mg, 0.133 mmol) in DMA (1 mL) was heated in a heavy-walled sealed tube under microwave irradiation at 160 for 1 hour. Lithium chloride (20 mg) and tetrabutylammonium bromide (5 mg) were added. The reaction was heated in a heavy-walled sealed tube under microwave irradiation at 180° C. for 10 h. The mixture was purified by preparative HPLC to give the title compound as a white solid (4.6 mg). LCMS m/z=331.3 [M+H]$^+$.

Example 1.78: Preparation of (1aR,5aR)-2-(4-Cyclopropyl-pyridin-2-yl)-1a,2,5,5a-tetrahydro-1H-2,3-diaza-cyclopropa[a]pentalene-4-carboxylic Acid tert-Butylamide (Compound 630)

To a mixture of (1aR,5aR)-2-(4-bromo-pyridin-2-yl)-1a,2,5,5a-tetrahydro-1H-2,3-diaza-cyclopropa[a]pentalene-4-carboxylic acid tert-butylamide (0.020 g, 0.053 mmol), cyclopropylboronic acid (0.014 g, 0.160 mmol), potassium phosphate (0.034 g, 0.160 mmol) and tricyclohexylphosphine (2.99 mg, 10.66 μmol) in toluene/H$_2$O (1.5 mL/0.050 mL) under nitrogen atmosphere was added palladium (II) acetate (1.197 mg, 5.33 μmol). The reaction mixture was heated at 100° C. for 1 hour in a heavy-walled sealed tube under microwave irradiation. The reaction mixture was concentrated and the residue was purified by preparative HPLC to give the title compound as a white solid (5.7 mg). LCMS m/z=337.5 [M+H]$^+$.

Example 1.79: Preparation of (1aS,5aS)-2-Pyrazin-2-yl-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 696)

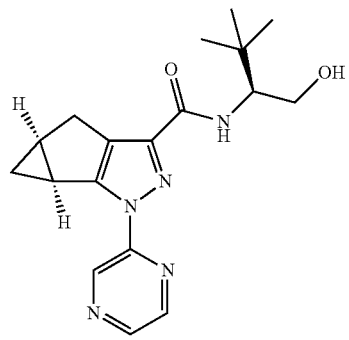 [SMILES: CC(C)(C)[C@@H](CO)NC(=O)c1nn(-c2cnccn2)c2c1C[C@@H]1C[C@H]21]

Step A: Preparation of (1aS,5aS)-2-(pyrazin-2-yl)-1a,2,5,5a-tetrahydro-1H-2,3-diaza-cyclopropa[a]pentalene-4-carboxylic Acid The title compound was prepared in a manner similar to that described in Example 1.2. LCMS m/z=243.1 [M+H]$^+$; $^1$H NMR (400 MHz, DMSO-d$_6$) δ ppm 0.43 (td, J=4.6, 3.2 Hz, 1H), 1.26 (td, J=8.0, 4.6 Hz, 1H), 2.27-2.33 (m, 1H), 2.71-2.75 (m, 1H), 2.75 (d, J=16.7 Hz, 1H), 2.89 (dd, J=16.4, 6.4 Hz, 1H), 8.61 (dd, J=2.5, 1.4 Hz, 1H), 8.67 (d, J=2.7 Hz, 1H), 9.17 (d, J=1.4 Hz, 1H), 12.99 (s, 1H).

Step B: Preparation of (1aS,5aS)-2-Pyrazin-2-yl-1a,2,5,5a-tetrahydro-1H-2,3-diaza-cyclopropa[a]pentalene-4-carboxylic Acid ((S)-1-Hydroxymethyl-2,2-dimethyl-propyl)-amide The title compound was prepared in a manner similar to that described in Method G, using (1aS,5aS)-2-(pyrazin-2-yl)-1a,2,5,5a-tetrahydro-1H-2,3-diaza-cyclopropa[a]pentalene-4-carboxylic acid and (S)-2-amino-3,3-dimethylbutan-1-ol. LCMS m/z=342.2 [M+H]$^+$; $^1$H NMR (400 MHz, CDCl$_3$) δ ppm 0.48 (td, J=4.6, 3.4 Hz, 1H), 1.05 (s, 9H), 1.24 (td, J=8.0, 4.7 Hz, 1H), 2.26-2.32 (m, 1H), 2.74-2.78 (m, 1H), 2.94 (d, J=16.8 Hz, 1H), 3.01 (dd, J=16.7, 6.1 Hz, 1H), 3.67-3.72 (m, 1H), 3.93-3.98 (m, 2H), 7.08 (d, J=8.5 Hz, 1H), 8.42 (dd, J=1.4, 0.9 Hz, 1H), 8.51 (d, J=2.7 Hz, 1H), 9.26 (d, J=1.1 Hz, 1H).

Example 1.80: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 699). [Method PPP]

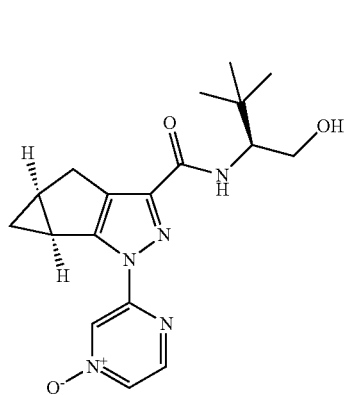 [SMILES: CC(C)(C)[C@@H](CO)NC(=O)c1nn(-c2c[n+]([O-])ccn2)c2c1C[C@@H]1C[C@H]21]

To a solution of (1aS,5aS)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (900 mg, 2.64 mmol) in chloroform (10 mL) was added 3-chlorobenzoperoxoic acid (1772 mg, 7.91 mmol). The reaction was stirred at 23° C. for 3 h. Additional MCPBA (1.2 g) was added and stirring was continued at room temperature for 18 h. The mixture was purified by silica gel column chromatography to give the title compound (550 mg) as a white solid. LCMS m/z=358.3 [M+H]$^+$; $^1$H NMR (400 MHz, CDCl$_3$) δ ppm 0.49 (td, J=4.6, 3.3 Hz, 1H), 1.03 (s, 9H), 1.27 (td, J=8.0, 4.9 Hz, 1H), 2.08 (bs, 1H), 2.27-2.33 (m, 1H), 2.71-2.76 (m, 1H), 2.93 (d, J=16.8 Hz, 1H), 3.00 (dd, J=16.7, 6.1 Hz, 1H), 3.65-3.71 (m, 1H), 3.92-3.97 (m, 2H), 6.97 (d, J=8.5 Hz, 1H), 7.99 (dd, J=4.0, 1.4 Hz, 1H), 8.28 (d, J=4.2 Hz, 1H), 8.78 (dd, J=1.4, 0.8 Hz, 1H).

A sample was recrystallized from CH$_2$Cl$_2$/hexane to give a crystalline solvate. A thermogravimetric analysis (TGA) thermogram for this solvate showed a loss of ~5% weight occurring with a melting endotherm at 164° C.

Figure 15:
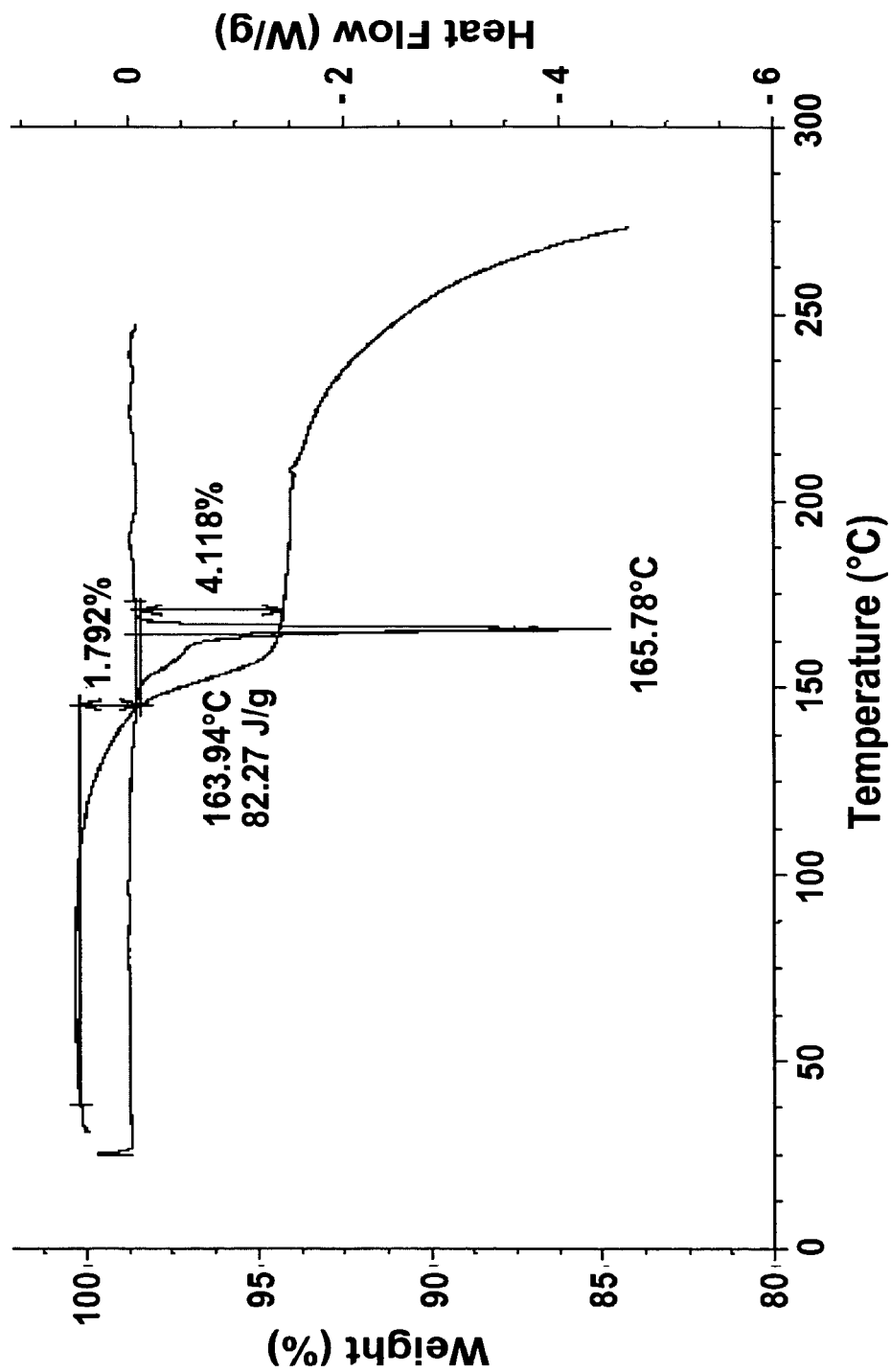
FIG. 15 shows a differential scanning calorimetry (DSC) thermogram for a sample containing a crystalline form of Compound 699 $CH_2Cl_2$ solvate and a thermogravimetric analysis (TGA) thermogram of a sample containing a crystalline form of Compound 699 $CH_2Cl_2$ solvate.
Figure 16:
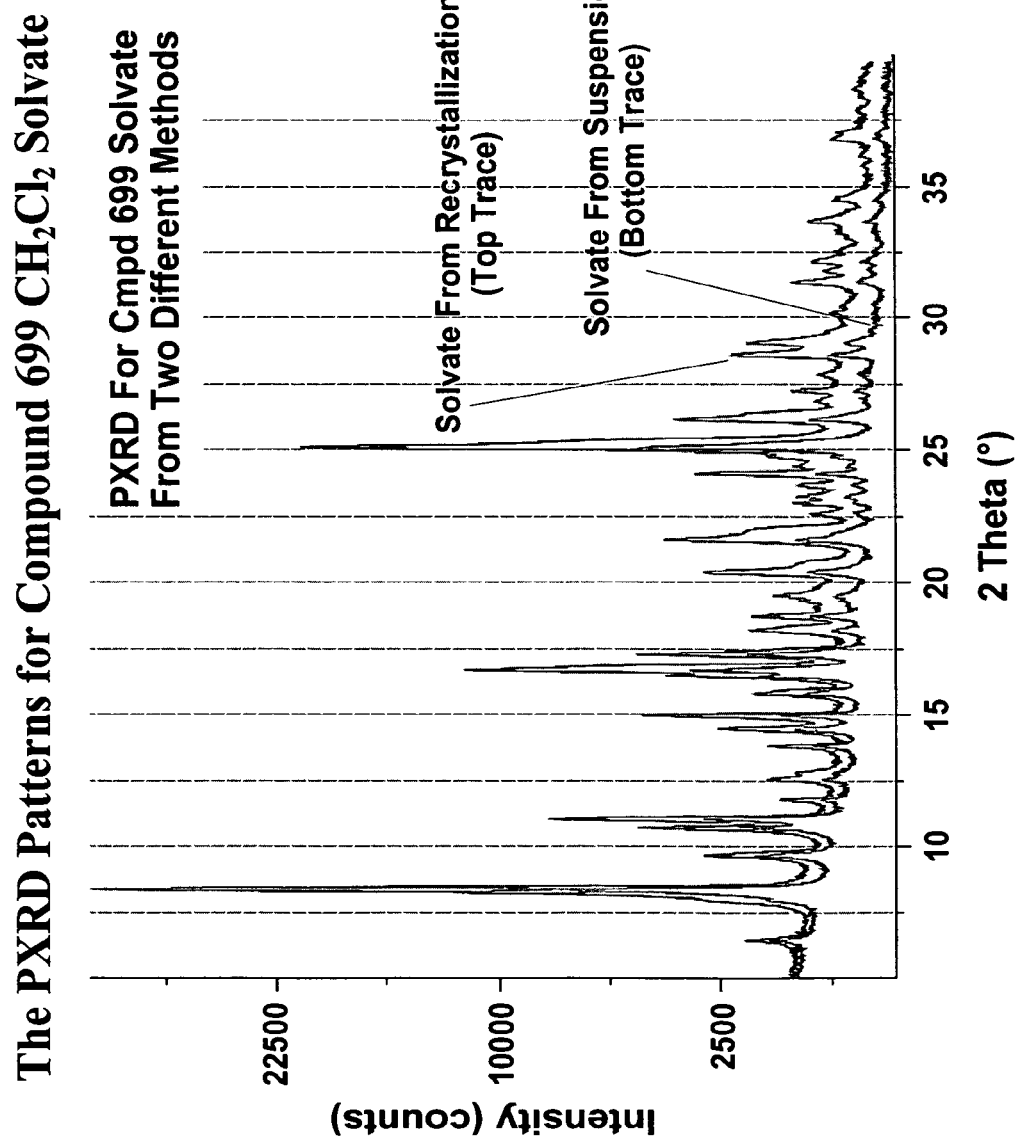
FIG. 16 shows an overlay of a powder X-ray diffraction pattern (PXRD) for a sample containing a crystalline form of Compound 699 $CH_2Cl_2$ solvate obtained from recrystallization using $CH_2Cl_2$/hexane (Top Trace) and a powder X-ray diffraction pattern (PXRD) for a sample containing a crystalline form of Compound 699 $CH_2Cl_2$ solvate obtained by slurrying non-solvated Compound 699 in $CH_2Cl_2$ (Bottom Trace). The PXRD showed the crystalline solvate obtained from the $CH_2Cl_2$ slurry is substantially indistinguishable from the crystalline solvate resulting from recrystallized from $CH_2Cl_2$/hexane.

A non-solvated form of Compound 699 was slurried in CH$_2$Cl$_2$ and stirred at −28° C. overnight. The suspension was filtered using a centrifuge filter and air dried prior to powder-X-ray diffraction pattern (PXRD) analysis. The PXRD pattern showed the material following CH$_2$Cl$_2$ slurry to be indistinguishable from the original solvate form resulting from recrystallized from CH$_2$Cl$_2$/hexane. The differential scanning calorimetry (DSC) thermogram and thermogravimetric analysis (TGA) thermogram for the crystalline CH$_2$Cl$_2$ solvate obtained from recrystallization using CH$_2$Cl$_2$/hexane is shown in FIG. 15; and the PXRD pattern for each of the crystalline CH$_2$Cl$_2$ solvates obtained from two the different methods (i.e., recrystallization using CH$_2$Cl$_2$/hexane; and non-solvated Compound 699 slurried in CH$_2$Cl$_2$) is shown as an overlay in FIG. 16.

Example 1.81: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Pyridin-2-yl-cyclobutyl)-amide (Compound 700)

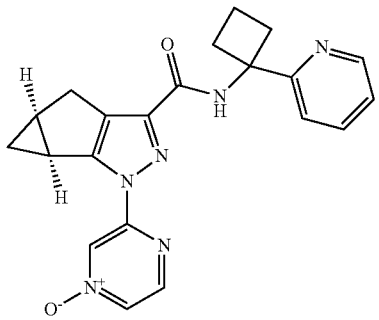 [SMILES: O=C(NC1(c2ccccn2)CCC1)c1nn(-c2c[n+]([O-])ccn2)c2c1C[C@@H]1C[C@H]21]

The title compound was prepared in a manner similar to that described in Method G, using (1aS,5aS)-2-(4-oxy-pyrazin-2-yl)-1a,2,5,5a-tetrahydro-1H-2,3-diaza-cyclopropa[a]pentalene-4-carboxylic acid and 1-(pyridin-2-yl)cyclobutanamine. LCMS m/z=389.4 [M+H]$^+$; $^1$H NMR (400 MHz, CDCl$_3$) δ ppm 0.46 (td, J=4.7, 3.4 Hz, 1H), 1.25 (td, J=7.8, 4.8 Hz, 1H), 1.97-2.08 (m, 1H), 2.19-2.31 (m, 2H), 2.70-2.78 (m, 3H), 2.84-2.92 (m, 3H), 2.98 (dd, J=16.7, 6.2 Hz, 1H), 7.19 (t, J=5.7 Hz, 1H), 7.62 (d, J=8.0 Hz, 1H), 7.72 (t, J=7.2 Hz, 1H), 7.98 (dd, J=4.2, 1.5 Hz, 1H), 8.00-8.04 (m, 1H), 8.28 (d, J=4.2 Hz, 1H), 8.61-8.63 (m, 1H), 8.85 (s, 1H).

Example 1.82: Preparation of (1aS,5aS)-2-Pyrazin-2-yl-1a,2,5,5a-tetrahydro-1H-2,3-diaza-cyclopropa[a]pentalene-4-carboxylic Acid ((S)-2,2-Dimethyl-1-morpholin-4-ylmethyl-propyl)-amide (Compound 707). [Method ZZ]

Step A: Preparation of (S)—N-(3,3-dimethyl-1-oxobutan-2-yl)-1-(pyrazin-2-yl)-1a,2,5,5a-tetrahydro-1H-2,3-diaza-cyclopropa[a]pentalene-3-carboxamide To a solution of (1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (200 mg, 0.586 mmol) in chloroform (3 mL) was added Dess-Martin Periodinane (261 mg, 0.615 mmol). The reaction was stirred at 23° C. for 3 h. The mixture was purified by silica gel flash chromatography to give the title compound (160 mg) as a white solid. LCMS m/z=340.2 [M+H]$^+$.

Step B: Preparation of ((1aS,5aS)-2-Pyrazin-2-yl-1a,2,5,5a-tetrahydro-1H-2,3-diaza-cyclopropa[a]pentalene-4-carboxylic Acid ((S)-2,2-Dimethyl-1-morpholin-4-ylmethyl-propyl)-amide)

To a solution of (S)—N-(3,3-dimethyl-1-oxobutan-2-yl)-1-(pyrazin-2-yl)-1a,2,5,5a-tetrahydro-1H-2,3-diaza-cyclopropa[a]pentalene-3-carboxamide (50 mg, 0.147 mmol) in methanol (1 mL) was added morpholine (0.026 mL, 0.295 mmol) and one drop acetic acid. The reaction was stirred at 23° C. for 15 min. Sodium cyanoborohydride (13.89 mg, 0.221 mmol) was added and the stirring was continued at 23° C. for 18 h. The mixture was concentrated. The residue was purified by preparative HPLC to give the title compound (22 mg) as a colorless film. LCMS m/z=411.3 [M+H]$^+$; $^1$H NMR (400 MHz, CDCl$_3$) δ ppm 0.49 (td, J=4.6, 3.4 Hz, 1H), 1.00 (s, 9H), 1.25 (td, J=8.0, 4.9 Hz, 1H), 2.26-2.46 (m, 4H), 2.54-2.62 (m, 3H), 2.74-2.79 (m, 1H), 2.95 (d, J=16.7 Hz, 1H), 3.03 (dd, J=16.6, 6.2 Hz, 1H), 3.58-3.67 (m, 4H), 4.10 (td, J=10.1, 3.9 Hz, 1H), 6.79 (d, J=10.1 Hz, 1H), 8.41 (dd, J=1.3, 1.0 Hz, 1H), 8.50 (d, J=2.7 Hz, 1H), 9.28 (d, J=1.4 Hz, 1H).

Example 1.83: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (Methyl-carbamoyl-pyridin-2-yl-methyl)-amide (Compound 710). [Method BBB]

To a solution of {[(1aS,5aS)-2-(4-oxy-pyrazin-2-yl)-1a,2, 5,5a-tetrahydro-1H-2,3-diaza-cyclopropa[a]pentalene-4-carbonyl]-amino}-pyridin-2-yl-acetic acid methyl ester (50 mg, 0.123 mmol) and methylamine (2 M solution in THF, 0.123 mL, 0.246 mmol) in THF (1 mL) was added a solution of diethylaluminum chloride (1 M in hexanes, 0.492 mL, 0.492 mmol). The reaction was stirred at 50° C. for 5 h. Saturated aqueous NaHCO$_3$ (25 mL) was added, and the mixture was extracted with 25% IPA/dichloromethane (3×25 mL). The combined organic extracts were dried (MgSO$_4$), filtered, and concentrated. The residue was purified by silica gel flash chromatography to give the title compound (42 mg) as a yellow solid. LCMS m/z=406.3 [M+H]$^+$; $^1$H NMR (400 MHz, CDCl$_3$) δ ppm 0.48-0.50 (m, 1H), 1.24-1.31 (m, 1H), 2.27-2.33 (m, 1H), 2.74-2.78 (m, 1H), 2.81-2.83 (m, 3H), 2.89-3.04 (m, 2H), 5.64-5.66 (m, 1H), 6.90-6.95 (m, 1H), 7.24-7.27 (m, 1H), 7.48-7.52 (m, 1H), 7.68-7.72 (m, 1H), 7.99-8.01 (m, 1H), 8.28-8.29 (m, 1H), 8.59-8.63 (m, 2H), 8.917-8.922 (m, 1H).

Example 1.84: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid N'-tert-Butyl-hydrazide (Compound 687)

Step A: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid To a solution of (1aR,5aR)-2-(pyrazin-2-yl)-1a,2,5,5a-tetrahydro-1H-2,3-diaza-cyclopropa[a]pentalene-4-carboxylic acid (3.35 g, 13.83 mmol) in formic acid (50 mL) was added hydrogen peroxide (35% in water, 6.7 mL, 69.1 mmol). The reaction was stirred at 45° C. for 24 h. The mixture was concentrated. The residue was dissolved in a LiOH solution and extracted with EtOAc. The separated water layer was acidified with HCl solution to ~pH 2. The resulting solid was filtered, washed with water and dried to give the title compound (2.15 g) as a pale brown solid. LCMS m/z=259.3 [M+H]$^+$; $^1$H NMR (400 MHz, DMSO-d$_6$) δ ppm 0.43 (dd, J=7.8 and 4.6 Hz, 1H), 1.28 (td, J=7.9 and 4.8 Hz, 1H), 2.27-2.33 (m, 1H), 2.68-2.73 (m, 1H), 2.75 (d, J=16.7 Hz, 1H), 2.88 (dd, J=16.5 and 6.4 Hz, 1H), 8.33 (dd, J=4.2 and 1.5 Hz, 1H), 8.50 (d, J=4.2 Hz, 1H), 8.55 (d, J=1.0 Hz, 1H), 13.10 (bs, 1H).

Step B: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid N'-tert-Butyl-hydrazide. [Method CCC]

To a solution of (1aR,5aR)-2-(4-oxy-pyrazin-2-yl)-1a,2, 5,5a-tetrahydro-1H-2,3-diaza-cyclopropa[a]pentalene-4-carboxylic acid (129 mg, 0.5 mmol) and HATU (190 mg, 0.500 mmol) in DMF (4 mL) was added triethylamine (126 mg, 1.250 mmol) followed by the addition of tert-butylhydrazine (44.1 mg, 0.500 mmol) at room temperature. The reaction was stirred for 16 h. The mixture was diluted with water (100 mL) and extracted with EtOAc (70 mL). The organic layer was concentrated and purified by silica gel column chromatography to give the title compound (87 mg) as a white solid. LCMS m/z=329.4 [M+H]$^+$; $^1$H NMR (400 MHz, CDCl$_3$) δ ppm 0.48 (dd, J=8.0 and 4.7 Hz, 1H), 1.26 (s, 9H), 1.24-1.31 (m, 1H), 2.30-2.34 (m, 1H), 2.72-2.77 (m, 1H), 2.91 (d, J=19.2 Hz, 1H), 3.00 (dd, J=17.0 and 6.2 Hz, 1H), 8.05 (dd, J=4.1 and 1.4 Hz, 1H), 8.30 (d, J=4.1 Hz, 1H), 8.91 (s, 1H).

Example 1.85: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid N'-tert-Butyl-N'-methyl-hydrazide (Compound 729)

To a solution of (1aR,5aR)-2-(4-oxy-pyrazin-2-yl)-1a,2, 5,5a-tetrahydro-1H-2,3-diaza-cyclopropa[a]pentalene-4-carboxylic acid N'-tert-butyl-hydrazide (25 mg, 0.076 mmol) and iodomethane (54.0 mg, 0.381 mmol) in acetonitrile (3 mL) was added triethylamine (15.41 mg, 0.152 mmol). The reaction was stirred at 22° C. for 72 h and concentrated. The residue was diluted with EtOAc (15 mL) and washed with NaHCO$_3$ solution. The organics were purified by silica gel column chromatography to give the title compound (17 mg) as a white solid. LCMS m/z=343.3 [M+H]$^+$; $^1$H NMR (400 MHz, CDCl$_3$) δ ppm 0.48 (dd, J=8.0 and 4.7 Hz, 1H), 1.17 (s, 9H), 1.23-1.29 (m, 1H), 2.28-2.31 (m, 1H), 2.61 (s, 3H), 2.71-2.76 (m, 1H), 2.95 (d, J=17.0 Hz, 1H), 3.01 (dd, J=16.7 and 6.0 Hz, 1H), 7.47 (bs, NH, 1H), 7.99 (dd, J=4.1 and 1.5 Hz, 1H), 8.29 (d, J=3.9 Hz, 1H), 8.79 (s, 1H).

Example 1.86: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 629)

To a solution of (1aR,5aR)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (1.024 g, 3.0 mmol) in formic acid (10 mL) was added hydrogen peroxide (35% in water, 0.582 mL, 6.00 mmol). The reaction was stirred at 45° C. for 72 h and concentrated. The residue was dissolved in THF/MeOH (40 mL/40 mL) and added lithium hydroxide (1.437 g, 60.0 mmol) in water (5 mL). The reaction was stirred at room temperature for 1 h and neutralized with NH$_4$Cl solution. After removal of the organic solvent, the mixture was extracted with EtOAc. The organics were purified by silica gel column chromatography.

The resulting oil was treated with ACN (5 mL) and concentrated to give the title compound (0.49 g) as a white solid. LCMS m/z=358.4 [M+H]+; 1H NMR (400 MHz, CDCl3) δ ppm 0.47 (dd, J=8.0 and 4.7 Hz, 1H), 1.05 (s, 9H), 1.28 (td, J=7.9 and 5.0 Hz, 1H), 2.28-2.32 (m, 1H), 2.72-2.76 (m, 1H), 2.92 (d, J=17.0 Hz, 1H), 3.02 (dd, J=16.7 and 6.4 Hz, 1H), 3.67 (dd, J=11.9 and 8.8 Hz, 1H), 3.92-3.98 (m, 2H), 6.97 (d, J=8.7 Hz, NH, 1H), 8.00 (dd, J=4.1 and 1.5 Hz, 1H), 8.28 (d, J=4.1 Hz, 1H), 8.79 (s, 1H).

Example 1.87: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid (1-Hydroxymethyl-cyclobutyl)-amide (Compound 698)

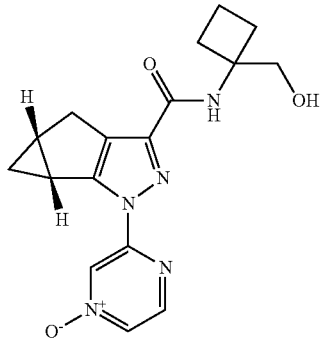 [SMILES: O=C(NC1(CO)CCC1)c1nn(-c2c[n+]([O-])ccn2)c2c1C[C@H]1C[C@@H]21]

The title compound was prepared in a manner similar to that described in Example 1.86. LCMS m/z=342.3 [M+H]+; 1H NMR (400 MHz, CDCl3) δ ppm 0.46 (dd, J=8.0 and 4.7 Hz, 1H), 1.28 (td, J=7.9 and 5.0 Hz, 1H), 1.87-2.07 (m, 2H), 2.22-2.37 (m, 5H), 2.71-2.76 (m, 1H), 2.90 (d, J=17.0 Hz, 1H), 2.99 (dd, J=16.7 and 6.2 Hz, 1H), 3.89 (s, 2H), 7.15 (s, NH, 1H), 8.00 (dd, J=4.1 and 1.5 Hz, 1H), 8.28 (d, J=4.1 Hz, 1H), 8.80 (s, 1H).

Example 1.88: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid tert-Butylamide (Compound 660)

To a solution of (1aR,5aR)-2-pyrazin-2-yl-1a,2,5,5a-tetrahydro-1H-2,3-diaza-cyclopropa[a]pentalene-4-carboxylic acid tert-butylamide (1.487 g, 5.0 mmol) in formic acid (50 mL) was added hydrogen peroxide (35% in water, 0.97 mL, 10.0 mmol). The reaction was stirred at 45° C. for 48 h and concentrated. The residue was purified by silica gel column chromatography to give the title compound (602 mg) as a white solid. LCMS m/z=314.3 [M+H]+; 1H NMR (400 MHz, CDCl3) δ ppm 0.47 (dd, J=8.0 and 4.7 Hz, 1H), 1.23-1.28 (m, 1H), 1.46 (s, 9H), 2.27-2.32 (m, 1H), 2.69-2.74 (m, 1H), 2.93 (d, J=17.0 Hz, 1H), 3.01 (dd, J=16.7 and 6.1 Hz, 1H), 6.68 (bs, NH, 1H), 7.97 (dd, J=4.1 and 1.5 Hz, 1H), 8.28 (d, J=4.1 Hz, 1H), 8.79 (s, 1H).

Example 1.89: Preparation of Phosphoric Acid mono-((S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) Ester (Compound 703)

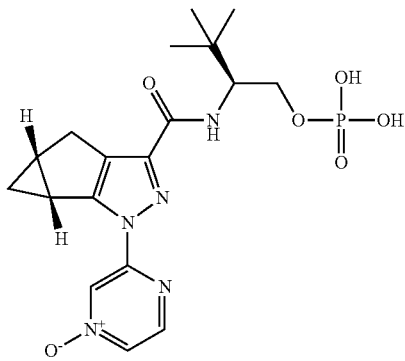 [SMILES: CC(C)(C)[C@@H](COP(=O)(O)O)NC(=O)c1nn(-c2c[n+]([O-])ccn2)c2c1C[C@H]1C[C@@H]21]

To a solution of phosphoric acid mono-{(S)-3,3-dimethyl-2-[((1aR,5aR)-2-pyrazin-2-yl-1a,2,5,5a-tetrahydro-H-2,3-diaza-cyclopropa[a]pentalene-4-carbonyl)-amino]-butyl} ester (500 mg, 1.074 mmol) in formic acid (5 mL) was added hydrogen peroxide (35% in water, 0.31 mL, 3.22 mmol). The reaction was stirred at 45° C. for 6 h and concentrated. The residue was purified by preparative HPLC to give the title compound (284 mg) as a white solid. LCMS m/z=438.4 [M+H]+; 1H NMR (400 MHz, CDCl3) δ ppm 0.54 (dd, J=8.0 and 4.7 Hz, 1H), 1.05 (s, 9H), 1.25 (td, J=7.9 and 5.0 Hz, 1H), 2.27-2.33 (m, 1H), 2.70-2.74 (m, 1H), 2.90 (d, J=17.2 Hz, 1H), 2.99 (dd, J=16.7 and 6.2 Hz, 1H), 4.11-4.16 (m, 1H), 4.22-4.34 (m, 2H), 7.55 (d, J=10.2 Hz, NH, 1H), 8.02 (dd, J=4.1 and 1.5 Hz, 1H), 8.38 (d, J=4.1 Hz, 1H), 9.32 (s, 1H).

Example 1.90: Preparation of (1aR,5aR)-2-Pyrazin-2-yl-1a,2,5,5a-tetrahydro-1H-2,3-diaza-cyclopropa[a]pentalene-4-carboxylic Acid N'-tert-Butyl-hydrazide (Compound 631). [Method DDD]

To a suspension of (1aR,5aR)-2-(pyrazin-2-yl)-1a,2,5,5a-tetrahydro-1H-2,3-diaza-cyclopropa[a]pentalene-4-carboxylic acid (1.211 g, 5.0 mmol) and HATU (2.091 g, 5.50 mmol) in acetonitrile (100 mL) was added triethylamine (1.771 g, 17.50 mmol) at room temperature. 2-tert-Butyl-hydrazinium chloride (0.748 g, 6.00 mmol) was added to the solution and the reaction was stirred for 12 at room temperature. The mixture was concentrated. The residue was diluted with EtOAc (150 mL) and washed with NaHCO3 solution (100 mL). The organic layer was concentrated and purified by silica gel column chromatography to give the title compound (1.42 g) as a glassy solid. LCMS m/z=313.3 [M+H]+; 1H NMR (400 MHz, CDCl3) δ ppm 0.49 (dd, J=8.0 and 4.7 Hz, 1H), 1.18 (s, 9H), 1.24-1.29 (m, 1H), 2.29-2.34 (m, 1H), 2.75-2.80 (m, 1H), 2.94 (d, J=16.9 Hz, 1H), 3.03 (dd, J=16.5 and 6.2 Hz, 1H), 4.75 (bs, NH, 1H), 805 (bs, NH, 1H), 8.41 (dd, J=2.5 and 1.5 Hz, 1H), 8.51 (d, J=2.6 Hz, 1H), 9.26 (d, J=1.4 Hz, 1H).

Example 1.91: Preparation of (1aR,5aR)-2-Pyrazin-2-yl-1a,2,5,5a-tetrahydro-1H-2,3-diaza-cyclopropa[a]pentalene-4-carboxylic Acid (1-Hydroxymethyl-cyclobutyl)-amide (Compound 657)

To a solution of sodium borohydride (0.206 g, 5.44 mmol) in dioxane (2.0 mL) with water (1.0 mL) was added 1-[((1aR,5aR)-2-pyrazin-2-yl-1a,2,5,5a-tetrahydro-1H-2,3-diaza-cyclopropa[a]pentalene-4-carbonyl)-amino]-cyclobutanecarboxylic acid ethyl ester (1.0 g, 2.72 mmol) at 0° C. The mixture was stirred at room temperature until the starting materials were consumed. The mixture was concentrated and added 2 M HCl was added to adjust pH to 3. The isolated precipitate was dissolved in DCM and purified by silica gel column chromatography to give the title compound (0.5 g) as a solid. LCMS m/z=326.3 [M+H]$^+$; $^1$H NMR (400 MHz, CDCl$_3$) δ ppm 0.47 (dd, J=8.0 and 4.7 Hz, 1H), 1.26 (td, J=7.8 and 4.9 Hz, 1H), 1.85-2.26 (m, 2H), 2.21-2.40 (m, 5H), 2.73-2.78 (m, 1H), 2.91 (d, J=16.8 Hz, 1H), 3.00 (dd, J=16.6 and 6.3 Hz, 1H), 3.90 (s, 2H), 7.21 (bs, NH, 1H), 8.42 (dd, J=2.3 and 1.5 Hz, 1H), 8.51 (d, J=2.5 Hz, 1H), 9.26 (d, J=1.4 Hz, 1H).

Example 1.92: Preparation of (1aR,5aR)-2-Pyrazin-2-yl-1a,2,5,5a-tetrahydro-1H-2,3-diaza-cyclopropa[a]pentalene-4-carboxylic Acid N'-Methylsulfonyl-N'-tert-butyl-hydrazide (Compound 643). [Method EEE]

To a solution of (1aR,5aR)-2-pyrazin-2-yl-1a,2,5,5a-tetrahydro-1H-2,3-diaza-cyclopropa[a]pentalene-4-carboxylic acid N'-tert-butyl-hydrazide (0.094 g, 0.301 mmol) in THF (5 mL) was added methanesulfonyl chloride (0.069 g, 0.602 mmol) followed by triethylamine (0.076 g, 0.752 mmol). The reaction was stirred for 48 h at room temperature and concentrated. The residue was purified by silica gel column chromatography to give the title compound (24 mg) as a white solid. LCMS m/z=391.5 [M+H]$^+$; $^1$H NMR (400 MHz, CDCl$_3$) δ ppm 0.50 (dd, J=8.0 and 4.7 Hz, 1H), 1.26-1.31 (m, 1H), 1.54 (s, 9H), 2.30-2.36 (m, 1H), 2.78-2.82 (m, 1H), 2.91-3.07 (m, 2H), 3.14 (s, 3H), 8.43 (dd, J=2.5 and 1.5 Hz, 1H), 8.55 (d, J=2.6 Hz, 1H), 8.57 (bs, NH, 1H), 9.30 (d, J=1.3 Hz, 1H).

Example 1.93: Preparation of (1aR,5aR)-2-Pyrazin-2-yl-1a,2,5,5a-tetrahydro-1H-2,3-diaza-cyclopropa[a]pentalene-4-carboxylic Acid N'-Methylcarbamoyl-N'-tert-butyl-hydrazide (Compound 647). [Method FFF]

To a solution of (1aR,5aR)-2-pyrazin-2-yl-1a,2,5,5a-tetrahydro-1H-2,3-diaza-cyclopropa[a]pentalene-4-carboxylic acid N'-tert-butyl-hydrazide (94 mg, 0.3 mmol) in CH$_2$Cl$_2$ (4 mL) was added isocyanatomethane (22.25 mg, 0.390 mmol). The reaction was stirred for 72 h at room temperature and concentrated. The residue was purified by silica gel column chromatography to give the title compound (99 mg) as a white solid. LCMS m/z=370.2 [M+H]$^+$; $^1$H NMR (400 MHz, CDCl$_3$) δ ppm 0.51 (dd, J=8.0 and 4.7 Hz, 1H), 130 (td, J=7.9 and 5.0 Hz, 1H), 1.51 (s, 9H), 2.31-2.37 (m, 1H), 2.75 (d, J=4.7 Hz, 3H), 2.77-2.82 (m, 1H), 2.96 (d, J=16.9 Hz, 1H), 3.04 (dd, J=16.7 and 6.3 Hz, 1H), 5.08 (q, J=4.5 Hz, NH, 1H), 8.39 (bs, NH, 1H), 8.44 (dd, J=2.5 and 1.5 Hz, 1H), 8.55 (d, J=2.5 Hz, 1H), 9.27 (d, J=1.4 Hz, 1H).

Example 1.94: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid (1-Methyl-1-phenyl-ethyl)-amide (Compound 718). [Method GGG]

(1aR,5aR)-2-(4-Oxy-pyrazin-2-yl)-1a,2,5,5a-tetrahydro-1H-2,3-diaza-cyclopropa[a]pentalene-4-carboxylic acid (77.4 mg, 0.3 mmol), cumylamine (40.5 mg, 0.3 mmol), N-(2-(3H-[1,2,3]triazolo[4,5-b]pyridin-3-yl)-1-(dimethylamino)ethylidene)-N-methylmethanaminium hexafluorophosphate(V) (125 mg, 0.33 mmol), DIEA (104 μL, 0.60 mmol) in ACN (4 mL) were stirred at room temperature for 2 h. The mixture was purified by HPLC to give an off-white solid (70 mg). LCMS m/z=376.2 [M+H]$^+$. $^1$H NMR (400 MHz, DMSO-d$_6$) δ ppm 0.40 (dd, J=3.3, 4.5 Hz, 1H), 1.23-1.24 (m, 1H), 1.69 (s, 6H), 2.2-2.3 (m, 1H), 2.64-2.68 (m, 2H), 2.77 (dd, J=6.3, 16.4 Hz, 1H), 7.16-7.20 (m, 1H), 7.30 (t, J=7.4 Hz, 2H), 7.37-7.40 (m, 2H), 8.19 (s, 1H), 8.30 (dd, J=1.6, 4.2 Hz, 1H), 8.47 (d, J=4.2 Hz, 1H), 9.20 (d, J=1.6 Hz, 1H).

Example 1.95: Preparation of (1aR,5aR)-2-Pyrazin-2-yl-1a,2,5,5a-tetrahydro-1H-2,3-diaza-cyclopropa[a]pentalene-4-carboxylic Acid (2-Hydroxy-1-tetrahydro-pyran-4-yl-ethyl)-amide (Mixture of Compound 684 and Compound 685)

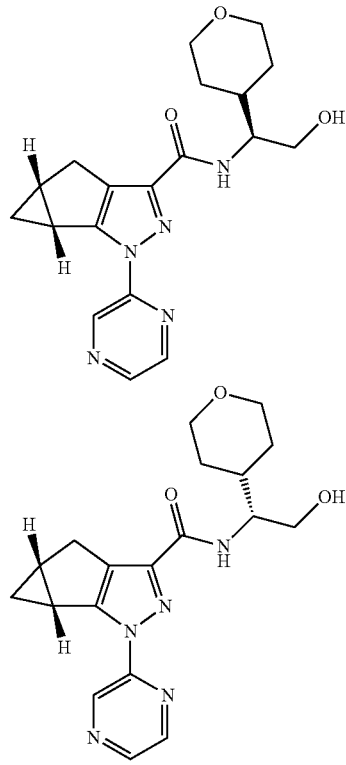

The title compound was prepared in a manner similar to that described in Method G using Intermediate 2 and 2-amino-2-(tetrahydro-2H-pyran-4-yl)ethanol. LCMS m/z=370.2 [M+H]$^+$; $^1$H NMR (400 MHz, CDCl$_3$) δ ppm 0.46-0.50 (m, 1H), 1.26 (td, J=7.8 and 4.6 Hz, 1H), 1.42-1.54 (m, 2H), 1.72 (d, J=12.6 Hz, 2H), 1.98-2.09 (m, 1H), 2.27-2.34 (m, 1H), 2.51 (bs, 1H), 2.73-2.79 (m, 1H), 2.94 (d, J=16.8 Hz, 1H), 3.01 (dd, J=16.4 and 6.1 Hz, 1H), 3.36-3.45 (m, 2H), 3.82-3.89 (m, 3H), 4.01 (dd, J=11.2 and 4.0 Hz, 2H), 7.11 (d, J=7.6 Hz, 1H), 8.42 (dd, J=2.5 and 1.5 Hz, 1H), 8.51 (d, J=2.4 Hz, 1H), 9.26 (d, J=1.4 Hz, 1H).
Resolution Via Chiral HPLC.
Column: normal phase preparative Chiralcel OD®, 5 cm ID×50 cm L, 20 μm particle size
Eluent: 90% hexane/10% IPA
Gradient: isocratic Flow: 60 mL/min
Detector: 280 nm
Retention Times: 1$^{st}$ diastereomer—31 min; 2$^{nd}$ diastereomer—35 min.

Example 1.96: Preparation of (1aR,5aR)-2-(4-Oxypyrazin-2-yl)-1a,2,5,5a-tetrahydro-1H-2,3-diazacyclopropa[a]pentalene-4-carboxylic Acid (4-Methylcarbamoyl-tetrahydro-pyran-4-yl)-amide (Compound 705)

Step A: Preparation of tert-Butyl 4-(methylcarbamoyl)tetrahydro-2H-pyran-4-ylcarbamate. [Method HHH]

A solution of 4-(tert-butoxycarbonylamino)tetrahydro-2H-pyran-4-carboxylic acid (0.5 g, 2.04 mmol), HATU (0.81 g, 2.14 mmol), and Et$_3$N (0.32 mL, 2.5 mmol) in DCM (8 mL) was stirred for 10 min at room temperature. Methylamine (33% in EtOH, 0.6 mL, 6.1 mmol) was added and the reaction was stirred for 2 h at room temperature. The mixture was diluted with DCM, washed with H$_2$O and 1 N HCl, dried over MgSO$_4$, and concentrated to give the title compound. LCMS m/z=259.3 [M+H]$^+$.

Step B: Preparation of 4-amino-N-methyltetrahydro-2H-pyran-4-carboxamide. [Method III]

To a solution of tert-butyl 4-(methylcarbamoyl)tetrahydro-2H-pyran-4-ylcarbamate in DCM (10 mL) was added trifluoroacetic acid (2 mL). The reaction was stirred at room temperature for 2 h. The mixture was purified by SCX (strong cationic exchange) resin column chromatography to give the title compound (0.1 g). LCMS m/z=159.0 [M+H]$^+$.

Step C: Preparation of (1aR,5aR)-2-(4-Oxypyrazin-2-yl)-1a,2,5,5a-tetrahydro-1H-2,3-diazacyclopropa[a]pentalene-4-carboxylic Acid (4-Methylcarbamoyl-tetrahydro-pyran-4-yl)-amide The title compound was prepared in a manner similar to that described in Method G, using (1aR,5aR)-2-(4-oxypyrazin-2-yl)-1a,2,5,5a-tetrahydro-1H-2,3-diaza-cyclopropa[a]pentalene-4-carboxylic acid and 4-amino-N-methyltetrahydro-2H-pyran-4-carboxamide. LCMS m/z=399.4 [M+H]$^+$; $^1$H NMR (400 MHz, CDCl$_3$) δ ppm 0.48-0.52 (m, 1H), 1.30 (td, J=7.9 and 5.0 Hz, 1H), 2.13-2.22 (m, 2H), 2.29-2.39 (m, 3H), 2.74-2.79 (m, 1H), 2.82 (d, J=4.7 Hz, 3H), 2.91 (d, J=17.0 Hz, 1H), 2.96-3.03 (m, 1H), 3.67 (t, J=10.8 Hz, 2H), 3.83-3.90 (m, 2H), 6.89 (s, 1H), 7.09 (s, 1H), 8.01 (dd, J=4.0 and 1.4 Hz, 1H), 8.30 (d, J=4.0 Hz, 1H), 8.77 (s, 1H).

Example 1.97: Preparation of (1aR,5aR)-2-(4-Oxypyrazin-2-yl)-1a,2,5,5a-tetrahydro-1H-2,3-diazacyclopropa[a]pentalene-4-carboxylic Acid [(S)-2,2-Dimethyl-1-(pyridin-2-ylcarbamoyl)-propyl]-amide (Compound 719)

Step A: Preparation of (S)-2-Amino-3,3-dimethyl-N-(pyridin-2-yl)butanamide (S)-2-(tert-Butoxycarbonylamino)-3,3-dimethylbutanoic acid (1.00 g, 4.32 mmol), pyridine-2-amine (1.506 g, 16.00 mmol), DIEA (8.36 mL, 48 mmol), and HATU (7.87 g, 20.80 mmol) were taken up in ACN (5 mL) and heated at 120° C. for 30 minutes under microwave irradiation. ACN was removed under reduced pressure and the residue was dissolved in water and extracted with EtOAc (2×50 mL). The organic extracts were concentrated under reduced pressure and purified by preparative HPLC. Hydrogen chloride (4 M in THF, 4 mL, 16 mmol) was added to the resulting solid and the mixture was stirred at room temperature for 30 minutes. The solvent was removed under reduced pressure. The residue was dissolved in water and extracted with EtOAc (2×50 mL). The aqueous layer was basified with 30% NaOH solution. The resulting solid precipitate was removed by filtration. The filtrate was extracted with DCM (2×50 mL). The DCM layer was dried and concentrated to give the title compound (83 mg) as a brown liquid. LCMS m/z=208.2 [M+H]$^+$.

Step B: Preparation of (1aR,5aR)-2-(4-oxy-pyrazin-2-yl)-1a,2,5,5a-tetrahydro-1H-2,3-diaza-cyclopropa[a]pentalene-4-carboxylic Acid [(S)-2,2-Dimethyl-1-(pyridin-2-ylcarbamoyl)-propyl]-amide (1aR,5aR)-2-(4-Oxy-pyrazin-2-yl)-1a,2,5,5a-tetrahydro-H-2,3-diaza-cyclopropa[a]pentalene-4-carboxylic acid (72.9 mg, 0.28 mmol), (S)-2-amino-3,3-dimethyl-N-(pyridin-2-yl)butanamide (78 mg, 0.28 mmol), N-(2-(3H-[1,2,3]triazolo[4,5-b]pyridin-3-yl)-1-(dimethylamino)ethylidene)-N-methylmethanaminium hexafluorophosphate(V) (139 mg, 0.37 mmol), DIEA (147 µL, 0.85 mmol) and ACN (5 mL) were stirred overnight at room temperature. The mixture was purified by preparative HPLC to give an off-white solid (39 mg). LCMS m/z=448.6 [M+H]$^+$. $^1$H NMR (400 MHz, DMSO-d$_6$) δ ppm 0.40 (td, J=3.41, 4.55 Hz, 1H), 1.05 (s, 9H), 1.22-1.28 (m, 1H), 2.26-2.33 (m, 1H), 2.66-2.71 (m, 1H), 2.74 (d, J=16.4 Hz, 1H), 2.89 (dd, J=6.69, 16.4 Hz, 1H), 4.75 (d, J=9.35 Hz, 1H), 7.13 (dd, J=5.05, 7.20 Hz, 1H), 7.77-7.83 (m, 2H), 8.06 (d, J=8.59 Hz, 1H), 8.30-8.35 (m, 2H), 8.49 (d, J=4.17 Hz, 1H), 9.02 (s, 1H), 10.7 (s, NH, 1H).

Example 1.98: Preparation of (1aR,5aR)-2-(4-Oxypyrazin-2-yl)-1a,2,5,5a-tetrahydro-1H-2,3-diazacyclopropa[a]pentalene-4-carboxylic Acid (1-Methylcarbamoyl-cyclobutyl)-amide (Compound 721)

Step A: Preparation of 1-[((1aR,5aR)-2-(4-Oxypyrazin-2-yl)-1a,2,5,5a-tetrahydro-1H-2,3-diazacyclopropa[a]pentalene-4-carbonyl)-amino]-cyclobutanecarboxylic Acid Ethyl Ester (1aR,5aR)-2-(4-Oxy-pyrazin-2-yl)-1a,2,5,5a-tetrahydro-1H-2,3-diaza-cyclopropa[a]pentalene-4-carboxylic acid (300 mg, 1.16 mmol), ethyl-1-aminocyclobutanecarboxylate (166 mg, 1.16 mmol), N-(2-(3H-[1,2,3]triazolo[4,5-b]pyridin-3-yl)-1-(dimethylamino)ethylidene)-N-methylmethanaminium hexafluorophosphate(V) (571 mg, 1.51 mmol), DIEA (606 µL, 3.49 mmol) and ACN (5 mL) were stirred for 5 minutes at room temperature. The crude was purified by preparative HPLC to give a white solid (420 mg, 94% yield). LCMS m/z=384.4 [M+H]+. 1H NMR (400 MHz, DMSO-$d_6$) δ ppm 0.40 (td, J=3.28, 4.42 Hz, 1H), 1.16 (t, J=7.07 Hz, 3H), 1.22-1.28 (m, 1H), 1.89-1.99 (m, 2H), 2.25-2.40 (m, 3H), 2.52-2.60 (m, 2H), 2.64-2.68 (m, 1H), 2.70 (d, J=16.4 Hz, 1H), 2.82 (dd, J=6.44, 16.4 Hz, 1H), 4.10 (q, J=7.07 Hz, 2H), 8.30 (dd, J=1.64, 4.17 Hz, 1H), 8.48 (d, J=4.17 Hz, 1H), 8.89 (s, 1H), 9.07 (s, NH, 1H).

Step B: Preparation of 1-(2-(4-Oxy-pyrazin-2-yl)-1a,2,5,5a-tetrahydro-1H-2,3-diaza-cyclopropa[a]pentalene-4-carboxamido)cyclobutanecarboxylic Acid 1-[(((1aR,5aR)-2-(4-Oxy-pyrazin-2-yl)-1a,2,5,5a-tetrahydro-1H-2,3-diaza-cyclopropa[a]pentalene-4-carbonyl)-amino]-cyclobutanecarboxylic acid ethyl ester (412 mg, 1.07 mmol), lithium hydroxide hydrate (90 mg, 2.15 mmol) in THF (5 mL)/water (5 mL) were stirred at room temperature for 1 h. The organic solvent was removed under reduced pressure. The remaining aqueous solution was acidified with 6 M HCl solution to pH 2. The resulting solid was filtered and washed with water then dried in vacuum oven to give as a pale yellow solid (290 mg). LCMS m/z=356.2 [M+H]+. 1H NMR (400 MHz, DMSO-$d_6$) δ ppm 0.41 (td, J=3.54, 4.17 Hz, 1H), 1.22-1.28 (m, 1H), 1.90-1.98 (m, 2H), 2.26-2.38 (m, 3H), 2.52-2.59 (m, 2H), 2.64-2.68 (m, 1H), 2.71 (d, J=16.4 Hz, 1H), 2.84 (dd, J=6.44, 16.4 Hz, 1H), 8.30 (dd, J=1.64, 4.17 Hz, 1H), 8.48 (d, J=4.17 Hz, 1H), 8.77 (s, 1H), 9.07 (s, NH, 1H), 12.3 (bs, 1H).

Step C: Preparation of (1aR,5aR)-2-(4-oxy-pyrazin-2-yl)-1a,2,5,5a-tetrahydro-1H-2,3-diaza-cyclopropa[a]pentalene-4-carboxylic Acid (1-Methylcarbamoyl-cyclobutyl)-amide 1-(2-(4-Oxy-pyrazin-2-yl)-1a,2,5,5a-tetrahydro-1H-2,3-diaza-cyclopropa[a]pentalene-4-carboxamido)cyclobutanecarboxylic acid (100 mg, 0.28 mmol), methanamine (0.84 mL, 0.84 mmol), N-(2-(3H-[1,2,3]triazolo[4,5-b]pyridin-3-yl)-1-(dimethylamino)ethylidene)-N-methylmethanaminium hexafluorophosphate(V) (139 mg, 0.37 mmol), DIEA (147 μL, 0.85 mmol) and ACN (5 mL) were heated at 120° C. for 30 minutes under microwave irradiation. The residue was purified by preparative HPLC to give the title compound as a white solid (52 mg). LCMS m/z=369.4 [M+H]+. 1H NMR (400 MHz, DMSO-$d_6$) δ ppm 0.40 (td, J=3.28, 4.42 Hz, 1H), 1.23-1.29 (m, 1H), 1.83-1.93 (m, 2H), 2.22-2.33 (m, 3H), 2.52-2.58 (m, 2H), 2.57 (d, J=4.55 Hz, 3H), 2.65-2.70 (m, 1H), 2.73 (d, J=16.8 Hz, 1H), 2.84 (dd, J=6.44, 16.4 Hz, 1H), 7.44 (q, J=4.55 Hz, 1H), 8.30 (dd, J=1.64, 4.17 Hz, 1H), 8.48 (d, J=4.17 Hz, 1H), 8.62 (s, 1H), 9.11 (s, NH, 1H).

Example 1.99: Preparation of (1aR,5aR)-2-(4-Chloro-pyridin-2-yl)-1a,2,5,5a-tetrahydro-1H-2,3-diaza-cyclopropa[a]pentalene-4-carboxylic Acid (Cyano-dimethyl-methyl)-amide (Compound 625). [Method JJJ]

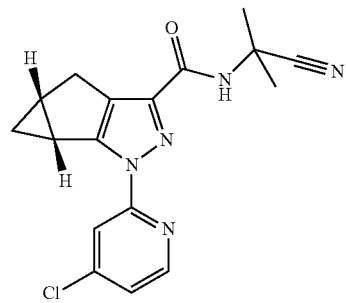 [SMILES: CC(C)(C#N)NC(=O)c1nn(-c2cc(Cl)ccn2)c2c1C[C@H]1C[C@@H]21]

A mixture of (1aR,5aR)-2-(4-bromo-pyridin-2-yl)-1a,2,5,5a-tetrahydro-1H-2,3-diaza-cyclopropa[a]pentalene-4-carboxylic acid (cyano-dimethyl-methyl)-amide (0.800 g, 2.071 mmol), lithium chloride (0.878 g, 20.71 mmol) and tetrabutylammonium bromide (0.334 g, 1.036 mmol) in DMA (10 mL) was heated in a heavy-walled sealed tube under microwave irradiation at 180° C. for 11 h. The mixture was purified by preparative HPLC to give the title compound (160 mg) as a white solid. LCMS m/z=342.1 [M+H]+; 1H NMR (400 MHz, CDCl$_3$) δ ppm 0.45 (td, J=4.6, 3.4 Hz, 1H), 1.26 (td, J=8.0, 4.9 Hz, 1H), 1.839 (s, 3H), 1.844 (s, 3H), 2.25-2.31 (m, 1H), 2.78-2.82 (m, 1H), 2.94 (d, J=16.8 Hz, 1H), 3.02 (dd, J=16.7, 6.1 Hz, 1H), 6.91 (s, 1H), 7.23 (dd, J=5.4, 1.9 Hz, 1H), 7.92 (d, J=1.8 Hz, 1H) 8.37 (d, J=5.3 Hz, 1H).

Example 1.100: Preparation of (1aR,5aR)-2-Pyrazin-2-yl-1a,2,5,5a-tetrahydro-1H-2,3-diaza-cyclopropa[a]pentalene-4-carboxylic Acid [2,2-Dimethyl-1-((S)-methylcarbamoyl)-propyl]-amide (Compound 667)

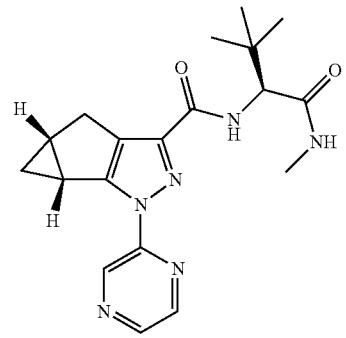 [SMILES: CNC(=O)[C@@H](NC(=O)c1nn(-c2cnccn2)c2c1C[C@H]1C[C@@H]21)C(C)(C)C]

The title compound was prepared in a manner similar to that described in Method G using Intermediate 2 and (S)-

2-amino-N,3,3-trimethylbutanamide. LCMS m/z=369.3 [M+H]⁺; ¹H NMR (400 MHz, DMSO-d₆) δ ppm 0.41 (td, J=4.4 and 3.5 Hz, 1H), 0.96 (s, 9H), 1.23-1.28 (m, 1H), 2.25-2.34 (m, 1H), 2.60 (d, J=4.5 Hz, 3H), 2.68-2.74 (m, 1H), 2.75 (d, J=16.3 Hz, 1H), 2.90 (dd, J=16.2 and 6.4 Hz, 1H), 4.33 (d, J=9.7 Hz, 1H), 7.52 (d, J=9.7 Hz, 1H), 8.10-8.15 (m, 1H), 8.60 (dd, J=2.5 and 1.5 Hz, 1H), 8.66 (d, J=2.6 Hz, 1H), 9.27 (d, J=1.4 Hz, 1H).

Example 1.101: Preparation of (1aR,5aR)-2-Pyrazin-2-yl-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 642)

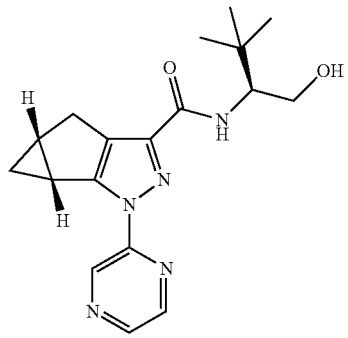 [SMILES: CC(C)(C)[C@@H](CO)NC(=O)c1nn(-c2cnccn2)c2c1C[C@H]1C[C@@H]21]

The title compound was prepared as described in Method G using Intermediate 2 and (S)-2-amino-3,3-dimethylbutan-1-ol. LCMS m/z=342.3 [M+H]⁺; ¹H NMR (400 MHz, DMSO-d₆) δ ppm 0.41 (td, J=4.4 and 3.3 Hz, 1H), 0.93 (s, 9H), 1.23-1.28 (m, 1H), 2.25-2.34 (m, 1H), 2.69-2.74 (m, 1H), 2.75 (d, J=16.0 Hz, 1H), 2.90 (dd, J=16.2 and 6.4 Hz, 1H), 3.50-3.58 (m, 1H), 3.62-3.67 (m, 1H), 3.76-3.82 (m, 1H), 4.52 (t, J=5.0 Hz, 1H), 7.54 (d, J=9.8 Hz, 1H), 8.58 (dd, J=2.5 and 1.5 Hz, 1H), 8.64 (d, J=2.6 Hz, 1H), 9.39 (d, J=1.4 Hz, 1H).

Example 1.102: Preparation of (1aR,5aR)-2-(4-Cyano-pyridin-2-yl)-1a,2,5,5a-tetrahydro-1H-2,3-diaza-cyclopropa[a]pentalene-4-carboxylic Acid tert-Butylamide (Compound 669)

To a mixture of (1aR,5aR)-2-(4-bromo-pyridin-2-yl)-1a,2,5,5a-tetrahydro-1H-2,3-diaza-cyclopropa[a]pentalene-4-carboxylic acid tert-butylamide (100 mg, 0.265 mmol) and dicyanozinc (62.4 mg, 0.53 mmol) in DMA (2 mL), tetrakis(triphenylphosphine)palladium (61.4 mg, 0.051 mmol) was added. After degassing for 5 min with N₂, the reaction mixture was heated under microwaved for 1 h at 130° C. in a heavy walled sealed tube. After removal of the volatile solvent, the residue was purified by preparative HPLC to give the title compound (58 mg). LCMS m/z=322.0 [M+H]⁺; ¹H NMR (400 MHz, CDCl₃) δ ppm 0.43-0.47 (m, 1H), 1.24 (td, J=7.8 and 5.0 Hz, 1H), 1.48 (s, 9H), 2.24-2.31 (m, 1H), 2.75-2.80 (m, 1H), 2.93 (d, J=16.8 Hz, 1H), 3.01 (dd, J=16.7 and 6.2 Hz, 1H), 6.73 (bs, 1H), 7.39 (dd, J=5.0 and 1.4 Hz, 1H), 8.16 (s, 1H), 8.61 (d, J=5.0 Hz, 1H).

Example 1.103: Preparation of Phosphoric Acid mono-{(S)-3,3-Dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl} Ester (Compound 683)

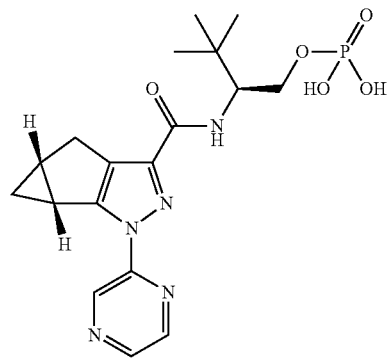 [SMILES: CC(C)(C)[C@@H](COP(=O)(O)O)NC(=O)c1nn(-c2cnccn2)c2c1C[C@H]1C[C@@H]21]

A mixture of (1aR,5aR)-2-pyrazin-2-yl-1a,2,5,5a-tetrahydro-11H-2,3-diaza-cyclopropa[a]pentalene-4-carboxylic acid ((S)-1-hydroxymethyl-2,2-dimethyl-propyl)-amide (600 mg, 1.757 mmol) in pyridine (5 mL) was cooled in a dry-ice/acetone bath until it solidified (pyridine mp=−42° C.). The cooling bath was removed and POCl₃ (0.819 ml, 8.79 mmol) was added as soon as the mixture was melted. The mixture was stirred at −42° C. for 2 h and an HCl solution (3.0 M, 15 mL) was added. The mixture was filtered and the filtrate was purified by prep-HPLC to give a white solid (260 mg). A solution of the solid (240 mg, 0.570 mmol) in H₂O/AcCN (4 mL/3 mL) was mixed with a solution of Na₂CO₃ (57.3 mg, 0.541 mmol) in H₂O (3 mL). The mixture was dried to give the sodium salt of the title compound (258 mg) as a white solid. LCMS m/z=422.3 [M+H]⁺; ¹H NMR (400 MHz, D₂O) δ ppm 0.42-0.47 (m, 1H), 0.99 (s, 9H), 1.21-1.27 (m, 1H), 2.29-2.36 (m, 1H), 2.57-2.62 (m, 1H), 2.80 (d, J=16.4 Hz, 1H), 2.92 (dd, J=16.4 and 6.4 Hz, 1H), 3.77-3.83 (m, 1H), 3.98-4.08 (m, 2H), 8.48-8.51 (m, 2H), 9.06 (s, 1H).

Example 1.104: Preparation of (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric Acid (Compound 747).
[Method OOO]

To a solution of (S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester (1.10 g, 2.85 mmol) in THF/MeOH/H₂O (10 mL/5 mL/5 mL) was added lithium hydroxide (0.068 g, 2.85 mmol). It was stirred for 15 h at room temperature. After removal of organic solvents, the remaining aqueous solution was washed with EtOAc (30 mL) and acidified with 2 N HCl solution to pH2. The resulting solid was filtered, washed with H₂O and dried to give the title compound (697 mg) as a white solid. LCMS m/z=372.1 [M+H]⁺; ¹H NMR (400 MHz, CDCl₃) δ ppm 0.44 (dd, J=8.0 and 4.7 Hz, 1H), 1.10 (s, 9H), 1.22-1.28 (m, 1H), 2.27-2.33 (m, 1H), 2.72-2.77 (m, 1H), 2.91 (d, J=16.9 Hz, 1H), 3.02 (dd, J=16.7 and 6.4 Hz, 1H), 4.62 (d, J=9.6 Hz, 1H), 7.37 (d, J=9.6 Hz, NH, 1H), 8.03 (dd, J=4.1 and 1.4 Hz, 1H), 8.31 (d, J=4.1 Hz, 1H), 9.02 (d, J=1.7 Hz, 1H).

Example 1.105: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid [Pyridin-2-yl-(2,2,2-trifluoro-ethylcarbamoyl)-methyl]-amide (Compound 743)

To a solution of {[(1aS,5aS)-2-(4-oxy-pyrazin-2-yl)-1a,2,5,5a-tetrahydro-1H-2,3-diaza-cyclopropa[a]pentalene-4-carbonyl]-amino}-pyridin-2-yl-acetic acid methyl ester (50 mg, 0.123 mmol) and 2,2,2-trifluoroethanamine (24.37 mg, 0.246 mmol) in THF (1 mL) was added diethylaluminum chloride (1 M in hexane, 0.492 mL, 0.492 mmol). The reaction was stirred at 60° C. for 5 h. Saturated aqueous NaHCO$_3$ (25 mL) was added. The mixture was extracted with 25% IPA/dichloromethane (3×25 mL). The combined organic extracts were dried (MgSO$_4$), filtered, then concentrated. The residue was purified by preparative TLC (10% MeOH/CH$_2$Cl$_2$) to give the title compound (22 mg) as an off-white solid. LCMS m/z=474.3 [M+H]$^+$; $^1$H NMR (400 MHz, CDCl$_3$) δ ppm 0.46-0.51 (m, 1H), 1.26-1.32 (m, 1H), 2.28-2.34 (m, 1H), 2.75-2.79 (m, 1H), 2.91 (d, J=16.8 Hz, 1H), 2.97-3.03 (m, 1H), 3.82-4.00 (m, 2H), 5.74 (d, J=6.1 Hz, 1H), 7.28-7.30 (m, 1H), 7.45-7.47 (m, 1H), 7.66-7.75 (m, 2H), 8.00-8.01 (m, 1H), 8.29 (d, J=4.2 Hz, 1H), 8.53-8.55 (m, 1H), 8.61-8.62 (m, 1H), 8.91 (s, 1H).

Example 1.106: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (1-Pyridin-2-yl-cyclobutyl)-amide (Compound 759)

Step A: Preparation of (1aR,5aR)-2-(4-Cyano-pyridin-2-yl)-1a,2,5,5a-tetrahydro-1H-2,3-diaza-cyclopropa[a]pentalene-4-carboxylic acid (1aR,5aR)-2-(4-Bromo-pyridin-2-yl)-1a,2,5,5a-tetrahydro-1H-2,3-diaza-cyclopropa[a]pentalene-4-carboxylic acid (1.00 g, 3.12 mmol) was dissolved in DMA (10 mL). Sodium hydride (60 wt %, 0.125 g, 3.12 mmol) was added and the mixture was stirred vigorously for 5 min. Nitrogen was bubbled through the mixture for 10 min. Zinc(II) cyanide (0.734 g, 6.25 mmol) and tetrakis(triphenylphosphine)palladium (0.180 g, 0.156 mmol) were added. The reaction was microwaved at 120° C. for 1 h. The reaction was diluted with ethyl acetate (20 mL) and methanol (5 mL), filtered, and concentrated. The residue was purified by preparative HPLC to give the title compound (0.557 g) as a white solid. LCMS m/z=267.2 [M+H]$^+$.

Step B: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (1-Pyridin-2-yl-cyclobutyl)-amide The title compound was prepared in a manner similar to that described in Method G from (1aR,5aR)-2-(4-Cyano-pyridin-2-yl)-1a,2,5,5a-tetrahydro-1H-2,3-diaza-cyclopropa[a]pentalene-4-carboxylic acid and 1-(pyridin-2-yl)cyclobutanamine dihydrochloride. LCMS m/z=397.3 [M+H]$^+$; $^1$H NMR (400 MHz, CDCl$_3$) δ ppm 0.45 (td, J=4.7, 3.3 Hz, 1H), 1.24 (td, J=8.0, 4.9 Hz, 1H), 1.97-2.08 (m, 1H), 2.19-2.29 (m, 2H), 2.74-2.92 (m, 6H), 2.98 (dd, J=16.6, 6.2 Hz, 1H), 7.16-7.19 (m, 1H), 7.40 (dd, J=5.1, 1.0 Hz, 1H), 7.63 (d, J=8.0 Hz, 1H), 7.70 (td, J=7.6, 1.8 Hz, 1H), 7.99 (s, 1H), 8.23 (s, 1H), 8.60-8.63 (m, 2H).

Example 1.107: Preparation of (1aS,5aS)-2-(Pyrazin-2-yl)-1a,2,5,5a-tetrahydro-1H-2,3-diaza-cyclopropa[a]pentalene-4-carboxylic Acid (Intermediate 4)

Step A: Preparation of (1S,5R)-Bicyclo[3.1.0]hexan-2-one

To a stirred solution of (S)-2-(but-3-enyl)oxirane (100 g, 1019 mmol) and 2,2,6,6-tetramethylpiperidine (86 mL, 509 mmol) in MTBE (1000 mL) cooled in a dry ice/acetone bath, was added dropwise a 2.5 M hexane solution of BuLi (489 mL, 1223 mmol) at a rate to maintain the internal temperature at −12 to −5° C. (time of addition=1 h). After addition was complete, the reaction was stirred one hour at −5 to 0° C. and quenched with 3 M aqueous HCl (545 mL) dropwise (internal temperature rose to 3° C.). The layers were separated and the organic layer was washed with 3 M HCl (200 mL). The combined aqueous layers were extracted with MTBE (2×500 mL). The combined organic layers were washed with brine (3×300 mL) and concentrated to give a pale yellow solution (ca. 1000 mL). To this solution in a 5 L 3-neck round bottom flask equipped with an overhead stirrer was added an aqueous solution of dibasic potassium phosphate (216 g, 1240 mmol), monobasic potassium phosphate (12.8 g, 94 mmol), and potassium bromide (18.19 g, 153 mmol) in water (407 mL). The mixture was cooled to −20° C. in a dry-ice/isopropanol bath. TEMPO (4.30 g, 27.5 mmol) was added. The temperature was allowed to warm to 0° C. and aqueous sodium hypochlorite (1.54 M, 1059 mL, 1630 mmol) was added dropwise over 70 min while maintaining the internal temperature between −10 and 0° C. Stirring was continued at 0° C. for another hour. Sodium sulfite (50 g) was added to quench excess sodium hypochlorite (temperature rose to 12° C.). The layers were separated and the aqueous layer was extracted twice more with MTBE (500 mL then 250 mL). The combined organic layers (total volume ca. 1600 mL) were dried (MgSO$_4$) then filtered. The solution was concentrated (ca. 300 mL). The residue was distilled (2 torr/36° C., note: receiving flask was cooled in dry ice/acetone bath) to give the title compound (65.8 g) as a light orange oil. $^1$H NMR (400 MHz, CDCl$_3$) δ 0.93 (td, J=4.6, 3.3 Hz, 1H), 1.20 (td, J=8.0, 4.8 Hz, 1H), 1.74-1.79 (m, 1H), 1.98-2.19 (m, 5H).

Step B: Preparation of 2-Hydrazinylpyrazine

Under nitrogen atmosphere, 2-chloropyrazine (96 mL, 1073 mmol) was added dropwise to 35 wt % aqueous hydrazine (544 mL, 6009 mmol) at 65° C. over 1 h. After the addition, stirring was continued at 63-67° C. for 16 h and the reaction mixture was let stand at room temperature for two days. The mixture was filtered to remove a small amount of precipitate, then extracted with 10% iPrOH/dichloromethane (5×250 mL). The combined organic extracts were dried (MgSO$_4$), filtered, then concentrated under reduced pressure. The resulting solid was triturated with isopropyl acetate (600 mL). The solid was collected by filtration, rinsed with isopropyl acetate, then dried in vacuo to give the title compound (60 g) as a pale yellow solid. LCMS m/z=111.2 [M+H]$^+$; $^1$H NMR (400 MHz, DMSO-d$_6$) δ 4.21 (s, 2H), 7.70 (d, J=2.8 Hz, 1H), 7.89 (s, 1H), 7.93 (dd, J=2.8, 1.5 Hz, 1H), 8.10 (d, J=1.5 Hz, 1H).

Step C: Preparation of (1aS,5aS)-2-(Pyrazin-2-yl)-1a,2,5,5a-tetrahydro-1H-2,3-diaza-cyclopropa[a]pentalene-4-carboxylic Acid Ethyl Ester. [Method KKK]

To a solution of (1S,5R)-bicyclo[3.1.0]hexan-2-one (52.9 g, 539 mmol) and diethyl oxalate (0.073 L, 539 mmol) in absolute ethanol (0.9 L) (not denatured with methanol) was added a THF solution of potassium tert-butoxide (1.0 M, 0.539 L, 539 mmol) over 15 min (maintaining the temperature below 43° C.). The resulting yellow solution was stirred at 40° C. for 3.5 h. 2-Hydrazinylpyrazine (59.4 g, 539 mmol) was added followed by a 6.0 M aqueous solution of hydrogen chloride (0.270 L, 1618 mmol). The reaction was stirred at 50° C. for 1.5 h. The mixture was poured into ice-water (5 L). A precipitate appeared immediately. After sitting for 30 minutes in an ice bath, the solid was collected by filtration, rinsed with water (5×1 L); and dried to give the title compound (106 g) as an off-white solid $^1$H NMR. LCMS m/z=271.2 [M+H]$^+$; $^1$H NMR (400 MHz, CDCl$_3$) δ 0.47 (td, J=4.7, 3.3 Hz, 1H), 1.27 (td, J=8.0, 4.9 Hz, 1H), 1.41 (t, J=7.1 Hz, 3H), 2.26-2.32 (m, 1H), 2.77-2.82 (m, 1H), 2.88 (dd, J=16.7, 1.4 Hz, 1H), 2.99 (dd, J=16.6, 6.4 Hz, 1H), 4.40 (q, J=7.1 Hz, 2H), 8.41 (dd, J=2.5, 1.5 Hz, 1H), 8.52 (d, J=2.5 Hz, 1H), 9.40 (d, J=1.5 Hz, 1H).

Step D: Preparation of (1aS,5aS)-2-(Pyrazin-2-yl)-1a,2,5,5a-tetrahydro-1H-2,3-diaza-cyclopropa[a]pentalene-4-carboxylic Acid (Intermediate 4). [Method LLL]

To a suspension of (1aS,5aS)-2-(pyrazin-2-yl)-1a,2,5,5a-tetrahydro-1H-2,3-diaza-cyclopropa[a]pentalene-4-carboxylic acid ethyl ester (106 g, 392 mmol) in MeOH (300 mL) and THF (300 mL) was added a 2.0 M aqueous solution of NaOH (235 mL, 471 mmol). The reaction was stirred at 23° C. for 20 h. The organic solvents were removed on rotovap. The remaining aqueous solution was diluted to ~1.5 L with H$_2$O then acidified to pH ~2 with 6 M HCl (ca. 95 mL). The resulting fine precipitate was collected by filtration, rinsed with water, and dried to give the title compound (95 g) as a white solid. LCMS m/z=243.1 [M+H]$^+$; $^1$H NMR (400 MHz, DMSO-d$_6$) δ 0.43 (td, J=4.6, 3.2 Hz, 1H), 1.26 (td, J=8.0, 4.4 Hz, 1H), 2.27-2.33 (m, 1H), 2.71-2.75 (m, 1H), 2.76 (d, J=16.8 Hz, 1H), 2.89 (dd, J=16.4, 6.4 Hz, 1H), 8.61 (dd, J=2.7, 1.5 Hz, 1H), 8.67 (d, J=2.5 Hz, 1H), 9.17 (d, J=1.5 Hz, 1H), 13.02 (s, 1H).

Example 1.108: Preparation of (1aS,5aS)-2-(Pyrazin-2-yl)-1a,2,5,5a-tetrahydro-1H-2,3-diaza-cyclopropa[a]pentalene-4-carboxylic Acid N-Oxide (Intermediate 5)

To a suspension of (1aS,5aS)-2-(pyrazin-2-yl)-1a,2,5,5a-tetrahydro-1H-2,3-diaza-cyclopropa[a]pentalene-4-carboxylic acid (68.8 g, 284 mmol) in formic acid (688 mL) at room temperature was added a 50 wt % aqueous solution of hydrogen peroxide (82 mL, 1420 mmol). The mixture was heated to 64° C. The reaction was stirred at 58 to 64° C. for 3 h. Another 8 mL 50% H$_2$O$_2$ was added and stirring continued another hour at 60° C. The mixture was cooled to room temperature and diluted with water (1 L). After cooling in an ice-bath for 1 h, the precipitate was collected by filtration, rinsed with water, and dried in vacuo to give a pale yellow solid (56.7 g) which contains about 2% starting material. The material was re-subjected to reaction conditions aforementioned to give the title compound (45 g). LCMS m/z=259.2 [M+H]$^+$; $^1$H NMR (400 MHz, DMSO-d$_6$) δ 0.42 (td, J=4.4, 3.3 Hz, 1H), 1.27 (td, J=7.8, 4.7 Hz, 1H), 2.27-2.33 (m, 1H), 2.68-2.73 (m, 1H), 2.75 (dd, J=16.9, 1.5 Hz, 1H), 2.88 (dd, J=16.4, 6.4 Hz, 1H), 8.33 (dd, J=4.2, 1.5 Hz, 1H), 8.50 (d, J=4.2, 0.6 Hz, 1H), 8.54 (d, J=1.5, 0.6 Hz, 1H), 13.08 (s, 1H).

Example 1.109: Preparation of (1aR,5aR)-2-(Pyrazin-2-yl)-1a,2,5,5a-tetrahydro-1H-2,3-diaza-cyclopropa[a]pentalene-4-carboxylic Acid The title compound was prepared in a manner similar to that described in Example 1.107 using (R)-2-(but-3-enyl)oxirane. LCMS m/z=243.3 [M+H]$^+$; $^1$H NMR (400 MHz, DMSO-d$_6$) δ 0.43 (td, J=4.5 and 3.4 Hz, 1H), 1.26 (td, J=7.7 and 4.4 Hz, 1H), 2.26-2.33 (m, 1H), 2.70-2.79 (m, 2H), 2.89 (dd, J=16.6 and 6.3 Hz, 1H), 8.60 (dd, J=2.6 and 1.5 Hz, 1H), 8.67 (d, J=2.6 Hz, 1H), 9.17 (d, J=1.4 Hz, 1H), 13.01 (s, 1H).

Example 1.110: Preparation of (1aR,5aR)-2-(Pyrazin-2-yl)-1a,2,5,5a-tetrahydro-1H-2,3-diaza-cyclopropa[a]pentalene-4-carboxylic Acid N-Oxide (Intermediate 6)

The title compound was prepared in a manner similar to that described in Example 1.108 using Intermediate 2. LCMS m/z=259.3 [M+H]$^+$; $^1$H NMR (400 MHz, DMSO-d$_6$) δ 0.43 (td, J=4.6 and 3.3 Hz, 1H), 1.28 (td, J=7.9 and 4.8 Hz, 1H), 2.27-2.33 (m, 1H), 2.68-2.73 (m, 1H), 2.75 (d, J=16.7 Hz, 1H), 2.88 (dd, J=16.5 and 6.4 Hz, 1H), 8.33 (dd, J=4.2 and 1.5 Hz, 1H), 8.50 (d, J=4.2 Hz, 1H), 8.55 (d, J=1.0 Hz, 1H), 13.10 (bs, 1H).

Example 1.111: Preparation of (1aR,5aR)-2-(4-Oxypyrazin-2-yl)-1a,2,5,5a-tetrahydro-1H-2,3-diaza-cyclopropa[a]pentalene-4-carboxylic Acid (1-Methyl-cyclobutyl)-amide (Compound 821). [Method UU]

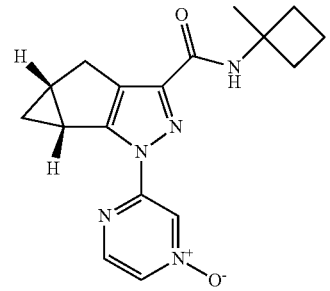 [SMILES: CC1(NC(=O)c2nn(-c3c[n+]([O-])ccn3)c3c2C[C@H]2C[C@@H]32)CCC1]

A solution of Intermediate 6 (200 mg, 0.77 mmol), HATU (300 mg, 0.78 mmol), and Et$_3$N (0.15 mL, 1.17 mmol) in acetonitrile (5 mL) was stirred for 10 min at room temperature. 1-Methylcyclobutanamine (70 mg, 0.82 mmol) was added into the solution, and the mixture was stirred for 2 h at room temperature. The reaction was diluted with DCM, washed with H$_2$O and 1 N HCl, dried with anhydrous MgSO$_4$, and concentrated. The residue was purified by column chromatography to give the title compound (120 mg). LCMS m/z=326.3 [M+H]$^+$; $^1$H NMR (400 MHz, CDCl$_3$) δ 0.44-0.48 (m, 1H), 1.26 (td, J=7.8, 4.8 Hz, 1H), 1.56 (s, 3H), 1.83-1.97 (m, 2H), 2.06-2.14 (m, 2H), 2.26-2.33 (m, 1H), 2.41-2.50 (m, 2H), 2.69-2.74 (m, 1H), 2.92 (d, J=16.6 Hz, 1H), 3.00 (dd, J=16.6, 6.0 Hz, 1H), 6.87 (s, 1H), 7.97 (dd, J=4.0, 1.4 Hz, 1H), 8.28 (d, J=4.2 Hz, 1H), 8.78 (s, 1H).

Example 1.112: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1,1-dimethyl-ethyl)-amide (Compound 897). [Method MMM]

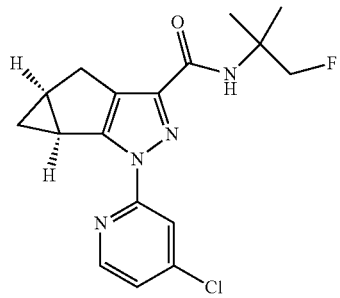 [SMILES: CC(C)(CF)NC(=O)c1nn(-c2cc(Cl)ccn2)c2c1C[C@@H]1C[C@H]21]

Step A: Preparation of (1aS,5aS)-2-(4-Chloro-pyridin-2-yl)-1a,2,5,5a-tetrahydro-1H-2,3-diaza-cyclopropa[a]pentalene-4-carboxylic Acid Ethyl Ester The title compound was prepared in a manner similar to that described in Example 1.108, Step C, using (1S,5R)-bicyclo[3.1.0]hexan-2-one and 4-chloro-2-hydrazinylpyridine. LCMS m/z=348.0 [M+H]$^+$.

Step B: Preparation of (1aS,5aS)-2-(4-Chloro-pyridin-2-yl)-1a,2,5,5a-tetrahydro-1H-2,3-diaza-cyclopropa[a]pentalene-4-carboxylic Acid To a solution of (1aS,5aS)-2-(4-bromo-pyridin-2-yl)-1a,2,5,5a-tetrahydro-1H-2,3-diaza-cyclopropa[a]pentalene-4-carboxylic acid ethyl ester (2.1 g, 6.0 mmol) in acetonitrile (30 mL) was added concentrated HCl (1.4 mL, 18.0 mmol). The reaction was stirred for 6 h at 80° C. The reaction was cooled down and diluted with H$_2$O. The solid precipitate was filtered, washed with H$_2$O, and dried to give a solid (1.7 g). The solid aforementioned was dissolved in dioxane (10 mL). After addition of 1 N LiOH (9.0 mL), the reaction was stirred at 40° C. for 4 h. The reaction was cooled down to room temperature, diluted with H$_2$O, and acidified with 4 N HCl to form a precipitate. The solid was filtered, washed with H$_2$O, and dried to give the title compound.
LCMS m/z=276.1 [M+H]$^+$.

Step C: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1,1-dimethyl-ethyl)-amide (Compound 897)

The title compound was prepared in a manner similar to that described in Method UU using (1aS,5aS)-2-(4-chloro-pyridin-2-yl)-1a,2,5,5a-tetrahydro-1H-2,3-diaza-cyclopropa[a]pentalene-4-carboxylic acid and 1-fluoro-2-methylpropan-2-amine hydrochloride. LCMS m/z=349.2 [M+H]$^+$; $^1$H NMR (400 MHz, CDCl$_3$) δ 0.42-0.47 (m, 1H), 1.24 (td, J=7.9, 4.8 Hz, 1H), 1.48 (s, 3H), 1.49 (s, 3H), 2.22-2.29 (m, 1H), 2.76-2.82 (m, 1H), 2.90 (d, J=16.8 Hz, 1H), 2.99 (dd, J=16.6, 6.2 Hz, 1H), 4.56 (d, J=47 Hz, 2H), 6.80 (s, 1H), 7.20 (dd, J=−5.4, 1.9 Hz, 1H), 7.93 (d, J=1.8 Hz, 1H), 8.35 (d, J=5.4 Hz, 1H).

Example 1.113: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (2,2,2-Trifluoro-1,1-dimethyl-ethyl)-amide (Compound 919)

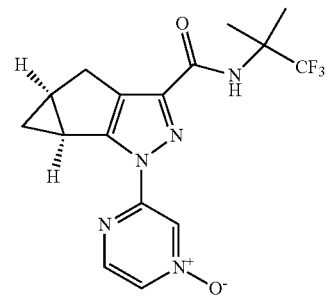 [SMILES: CC(C)(NC(=O)c1nn(-c2c[n+]([O-])ccn2)c2c1C[C@@H]1C[C@H]21)C(F)(F)F]

The title compound was prepared in a manner similar to that described in Method UU using Intermediate 5 and 1,1,1-trifluoro-2-methylpropan-2-amine. LCMS m/z=368.3 [M+H]$^+$; $^1$H NMR (400 MHz, CDCl$_3$) δ 0.44-0.49 (m, 1H), 1.27 (td, J=8.0, 4.8 Hz, 1H), 1.70 (s, 6H), 2.27-2.34 (m, 1H), 2.71-2.76 (m, 1H), 2.91 (d, J=17.0 Hz, 1H), 3.00 (dd, J=16.7, 6.4 Hz, 1H), 6.81 (s, 1H), 7.99 (dd, J=4.2, 1.6 Hz, 1H), 8.28 (dd, J=4.2, 0.6 Hz, 1H), 8.77 (dd, J=1.5, 0.7 Hz, 1H).

Example 1.114: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((1S,2S)-2-Hydroxy-indan-1-yl)-amide (Compound 920)

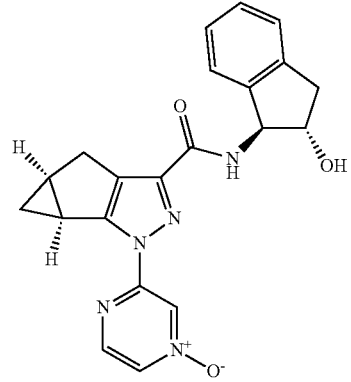 [SMILES: O=C(N[C@H]1c2ccccc2C[C@@H]1O)c1nn(-c2c[n+]([O-])ccn2)c2c1C[C@@H]1C[C@H]21]

The title compound was prepared in a manner similar to that described in Method UU using Intermediate 5 and (1S,2S)-1-amino-2,3-dihydro-1H-inden-2-ol. LCMS m/z=390.4 [M+H]$^+$; $^1$H NMR (400 MHz, CDCl$_3$) δ 0.48-0.52 (m, 1H), 1.30 (td, J=7.9, 5.0 Hz, 1H), 2.30-2.37 (m, 1H), 2.73-2.79 (m, 1H), 2.96 (d, J=16.9 Hz, 1H), 2.99-3.03 (m, 1H), 3.05 (dd, J=16.7, 6.2 Hz, 1H), 3.37 (dd, J=15.7, 7.7 Hz, 1H), 4.46 (s, 1H), 4.55 (q, J=7.7 Hz, 1H), 5.26 (t, J=5.8 Hz, 1H), 7.26-7.34 (m, 5H), 7.95 (dd, J=4.0, 1.6 Hz, 1H), 8.28 (dd, J=4.2, 0.6 Hz, 1H), 8.75 (dd, J=1.5, 0.7 Hz, 1H).

Example 1.115: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((1S,2R)-2-Hydroxy-indan-1-yl)-amide (Compound 921)

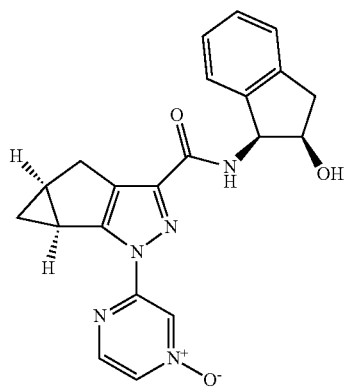 [SMILES: O=C(N[C@H]1c2ccccc2C[C@H]1O)c1nn(-c2c[n+]([O-])ccn2)c2c1C[C@@H]1C[C@H]21]

The title compound was prepared in a manner similar to that described in Method UU using Intermediate 5 and (1S,2R)-1-amino-2,3-dihydro-1H-inden-2-ol. LCMS m/z=390.3 [M+H]$^+$; $^1$H NMR (400 MHz, CDCl$_3$) δ 0.46-0.51 (m, 1H), 1.28 (td, J=8.0, 5.1 Hz, 1H), 2.27-2.33 (m, 1H), 2.67-2.73 (m, 1H), 2.96 (d, J=16.8 Hz, 1H), 3.00-3.07 (m, 2H), 3.24 (dd, J=16.5, 5.4 Hz, 1H), 4.76 (td, J=5.2, 2.2 Hz, 1H), 5.55 (dd, J=8.4, 5.2 Hz, 1H), 7.20-7.34 (m, 4H), 7.56 (d, J=8.4 Hz, 1H), 7.79 (dd, J=4.2, 1.6 Hz, 1H), 8.19 (dd, J=4.0, 0.6 Hz, 1H), 8.84 (dd, J=1.4, 0.6 Hz, 1H).

Example 1.116: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid [2-Hydroxy-1-(tetrahydro-pyran-4-yl)-ethyl]-amide (Compound 841)

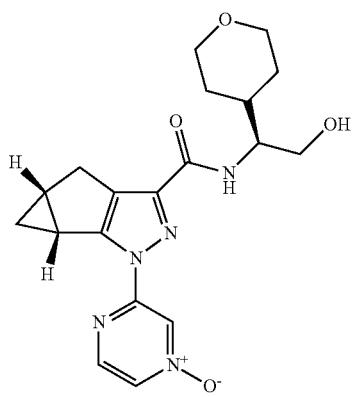 [SMILES: O=C(N[C@H](CO)C1CCOCC1)c1nn(-c2c[n+]([O-])ccn2)c2c1C[C@H]1C[C@@H]21]

The title compound was prepared in a manner similar to that described in Method UU using Intermediate 6 and 2-amino-2-(tetrahydro-2H-pyran-4-yl)ethanol. The crude reaction mixture was purified by preparative HPLC to give a white solid. LCMS m/z=386.2 [M+H]$^+$; $^1$H NMR (400 MHz, CDCl$_3$) δ 0.47 (td, J=4.6 and 3.2 Hz, 1H), 1.23-1.29 (m, 1H), 1.40-1.54 (m, 2H), 1.65-1.75 (m, 2H), 1.95-2.05 (m, 1H), 2.27-2.33 (m, 1H), 2.30-2.40 (m, 1H), 2.70-2.75 (m, 1H), 2.89-3.04 (m, 2H), 3.36-3.45 (m, 2H), 3.82-3.91 (m, 3H), 4.00 (dd, J=11.3 and 3.8 Hz, 2H), 7.05 (d, J=8.3 Hz, 1H), 7.99 (d, J=4.1 and 0.9 Hz, 1H), 8.28 (d, J=4.1 Hz, 1H), 8.80 (d, J=0.5 Hz, 1H).

Resolution Via Chiral HPLC
Column: Chiralcel OD preparative column, 5 cm ID×50 cm L
Injection: ~60 mg
Eluent: 50% IPA/Hexanes
Gradient: isocratic
Flow: 60 mL/min
Detector: 280 nm
Retention Time: 1$^{st}$ diastereomer—37.0 min, 2$^{nd}$ diastereomer—44.2 min

Example 1.117: Preparation of (1aS,5aS)-2-Pyrazin-2-yl-1a,2,5,5a-tetrahydro-1H-2,3-diaza-cyclopropa[a]pentalene-4-carboxylic Acid (2,2,2-Trifluoro-1,1-dimethyl-ethyl)-amide (Compound 927)

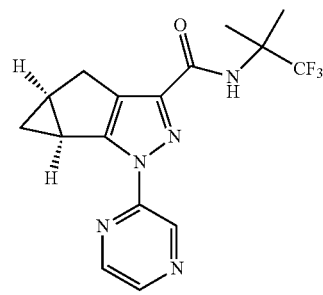 [SMILES: CC(C)(NC(=O)c1nn(-c2cnccn2)c2c1C[C@@H]1C[C@H]21)C(F)(F)F]

The title compound was prepared in a manner similar to that described in Method UU using Intermediate 4 and 1,1,1-trifluoro-2-methylpropan-2-amine. LCMS m/z=352.4 [M+H]$^+$; $^1$H NMR (400 MHz, CDCl$_3$) δ 0.47 (td, J=4.6 and 3.2 Hz, 1H), 1.23-1.29 (m, 1H), 1.71 (s, 6H), 2.27-2.33 (m, 1H), 2.74-2.80 (m, 1H), 2.93 (d, J=17.1 Hz, 1H), 3.00 (dd, J=16.6 and 6.2 Hz, 1H), 6.94 (s, 1H), 8.42 (dd, J=2.5 and 1.5 Hz, 1H), 8.52 (d, J=2.5 Hz, 1H), 9.25 (d, J=1.4 Hz, 1H).

Example 1.118: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Trifluoromethyl-cyclobutyl)-amide (Compound 765)

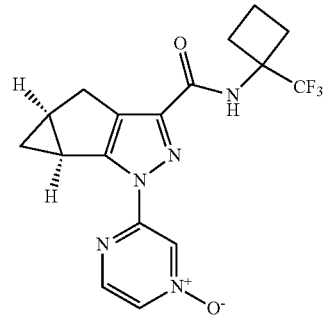 [SMILES: O=C(NC1(C(F)(F)F)CCC1)c1nn(-c2c[n+]([O-])ccn2)c2c1C[C@@H]1C[C@H]21]

Step A: Preparation of 1-(Trifluoromethyl)cyclobutanamine Hydrochloride 1-(Trifluoromethyl)cyclobutanecarboxylic acid (1 g, 5.95 mmol) and triethylamine (0.912 mL, 6.54 mmol) in anhy- Example 1.120: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Trifluoromethyl-cyclopropyl)-amide (Compound 764)

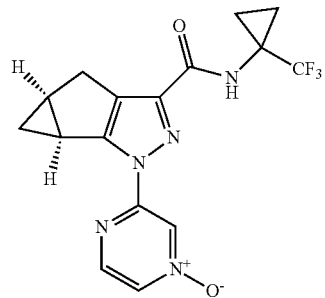

Step A: Preparation of 1-(Trifluoromethyl)cyclopropanamine Hydrochloride drous tert-butanol (20 mL) was stirred at room temperature in the presence of 4 Å molecular sieves powder. To the mixture was added diphenyl phosphorazidate (1.801 g, 6.54 mmol). The reaction mixture was refluxed under $N_2$ for 2 days, filtered, then concentrated in vacuo. The oily residue was stirred in ether, ether layer was isolated. The procedure was repeated three times. The combined organics were washed with 5% citric acid, saturated aqueous $NaHCO_3$ twice, brine, dried over anhydrous $Na_2SO_4$, and concentrated to give tert-butyl 1-(trifluoromethyl)cyclobutylcarbamate (713 mg) as a white solid. The solid was dissolved in 1.25 N HCl in methanol solution (10 mL), stirred at 50° C. overnight, and concentrated to give the title compound (493 mg). $^1H$ NMR (400 MHz, DMSO-$d_6$) δ 1.87-1.97 (m, 1H), 2.04-2.15 (m, 1H), 2.44-2.50 (m, 4H), 9.40 (br, 3H).

Step B: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Trifluoromethyl-cyclobutyl)-amide (Compound 765)

The title compound was prepared in a manner similar to that described in Method UU using Intermediate 5 and 1-(trifluoromethyl)cyclobutanamine hydrochloride. LCMS m/z=380.4 [M+H]$^+$; $^1H$ NMR (400 MHz, CDCl$_3$) δ 0.47 (td, J=4.6, 3.2 Hz, 1H), 1.23-1.29 (m, 1H), 2.04-2.14 (m, 2H), 2.27-2.33 (m, 1H), 2.62-2.69 (m, 4H), 2.71-2.76 (m, 1H), 2.92 (d, J=17.1 Hz, 1H), 3.00 (dd, J=16.8 and 6.2 Hz, 1H), 6.92 (s, 1H), 7.99 (dd, J=4.1 and 1.5 Hz, 1H), 8.29 (dd, J=4.1 and 0.6 Hz, 1H), 8.81 (dd, J=1.5 and 0.6 Hz, 1H).

The title compound was prepared in a manner similar to that described in Example 1.118, Step A, using 1-(trifluoromethyl)cyclopropanecarboxylic acid.

Step B: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Trifluoromethyl-cyclopropyl)-amide (Compound 764)

The title compound was prepared in a manner similar to that described in Method UU using Intermediate 5 and 1-(trifluoromethyl)cyclopropanamine hydrochloride. LCMS m/z=366.4 [M+H]$^+$; $^1H$ NMR (400 MHz, CDCl$_3$) δ 0.47 (td, J=4.6, 3.2 Hz, 1H), 1.23-1.29 (m, 3H), 1.39-1.43 (m, 2H), 2.27-2.33 (m, 1H), 2.70-2.75 (m, 1H), 2.92 (d, J=17.0 Hz, 1H), 3.00 (dd, J=16.8 and 6.2 Hz, 1H), 7.28 (s, 1H), 8.00 (dd, J=4.1 and 1.5 Hz, 1H), 8.29 (dd, J=4.1 and 0.6 Hz, 1H), 8.81 (dd, J=1.5 and 0.6 Hz, 1H).

Example 1.119: Preparation of (1aS,5aS)-2-Pyrazin-2-yl-1a,2,5,5a-tetrahydro-1H-2,3-diaza-cyclopropa[a]pentalene-4-carboxylic Acid (1-Trifluoromethyl-cyclobutyl)-amide (Compound 926)

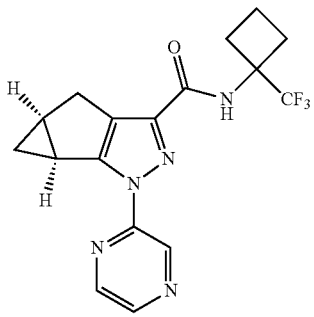 [SMILES: O=C(NC1(C(F)(F)F)CCC1)c1nn(-c2cnccn2)c2c1C[C@@H]1C[C@H]21]

The title compound was prepared in a manner similar to that described in Method UU using Intermediate 4 and 1-(trifluoromethyl)cyclobutanamine hydrochloride. LCMS m/z=364.4 [M+H]$^+$; $^1H$ NMR (400 MHz, CDCl$_3$) δ 0.47 (td, J=4.6, 3.2 Hz, 1H), 1.23-1.29 (m, 1H), 2.04-2.14 (m, 2H), 2.27-2.33 (m, 1H), 2.64-2.70 (m, 4H), 2.74-2.80 (m, 1H), 2.93 (d, J=16.9: Hz, 1H), 3.02 (dd, J=16.6 and 6.2 Hz, 1H), 6.99 (s, 1H), 8.42 (dd, J=2.5 and 1.5 Hz, 1H), 8.52 (d, J=2.5 Hz, 1H), 9.26 (d, J=1.4 Hz, 1H).

Example 1.121: Preparation of (1aS,5aS)-2-Pyrazin-2-yl-1a,2,5,5a-tetrahydro-1H-2,3-diaza-cyclopropa[a]pentalene-4-carboxylic Acid (1-Trifluoromethyl-cyclopropyl)-amide (Compound 930)

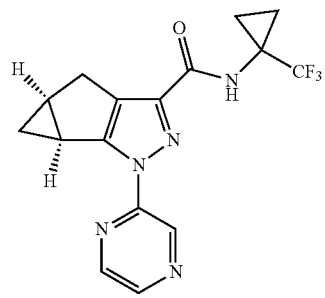 [SMILES: O=C(NC1(C(F)(F)F)CC1)c1nn(-c2cnccn2)c2c1C[C@@H]1C[C@H]21]

The title compound was prepared in a manner similar to that described in Method UU using Intermediate 4 and 1-(trifluoromethyl)cyclopropanamine hydrochloride. LCMS m/z=350.2 [M+H]$^+$; $^1H$ NMR (400 MHz, CDCl$_3$) δ 0.47 (td, J=4.6, 3.2 Hz, 1H), 1.23-1.29 (m, 3H), 1.39-1.43 (m, 2H), 2.27-2.33 (m, 1H), 2.74-2.80 (m, 1H), 2.94 (d, J=16.8 Hz, 1H), 3.02 (dd, J=16.7 and 6.2 Hz, 1H), 7.31 (s, 1H), 8.42 (dd, J=2.5 and 1.5 Hz, 1H), 8.52 (d, J=2.5 Hz, 1H), 9.26 (d, J=1.4 Hz, 1H).

Example 1.122: Preparation of (1aR,5aR)-Pentanedioic Acid mono-((S)-3-Methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) Ester (Compound 844) and its Sodium Salt

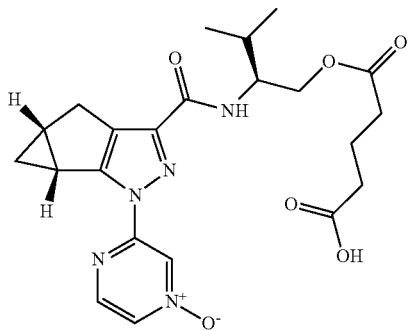 [SMILES: CC(C)[C@@H](COC(=O)CCCC(=O)O)NC(=O)c1nn(-c2c[n+]([O-])ccn2)c2c1C[C@H]1C[C@@H]21]

To a solution of (1aR,5aR)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide (Compound 690) (100 mg, 0.291 mmol), DMAP (17.79 mg, 0.146 mmol) and triethylamine (79 µL, 0.582 mmol) in DCM (5 mL) was added dihydro-2H-pyran-2,6 (3H)-dione (100 mg, 0.874 mmol). The reaction mixture was stirred at room temperature overnight, then concentrated. The residue was purified by preparative HPLC. The combined fractions were extracted with DCM. The organic layers were washed with water twice, dried over anhydrous $Na_2SO_4$, and concentrated to give the title compound as a white solid (95 mg). LCMS m/z=458.4 [M+H]$^+$; $^1$H NMR (400 MHz, DMSO-$d_6$) δ 0.42 (td, J=4.6, 3.2 Hz, 1H), 0.91 (d, J=6.8 Hz, 3H), 0.93 (d, J=6.8 Hz, 3H), 1.23-1.27 (m, 1H), 1.65-1.72 (m, 2H), 1.85-1.92 (m, 1H), 2.18 (t, J=7.5 Hz, 2H), 2.30 (t, J=7.4 Hz, 2H), 2.27-2.33 (m, 1H), 2.65-2.70 (m, 1H), 2.75 (d, J=16.8 Hz, 1H), 2.86 (dd, J=16.5 and 6.4 Hz, 1H), 3.92-4.02 (m, 1H), 4.08 (dd, J=11.0 and 8.2 Hz, 1H), 4.25 (dd, J=11.0 and 4.2 Hz, 1H), 8.05 (d, J=9.2 Hz, 1H), 8.29 (dd, J=4.1 and 1.5 Hz, 1H), 8.47 (d, J=4.1 Hz, 1H), 8.81 (d, J=1.3 Hz, 1H), 12.0 (br, 1H).

(1aR,5aR)-Pentanedioic acid mono-((S)-3-methyl-2-{[(1aR,5aR)-2-(4-oxy-pyrazin-2-yl)-1a,2,5,5a-tetrahydro-H-2,3-diaza-cyclopropa[a]pentalene-4-carbonyl]-amino}-butyl) ester (165 mg, 0.36 mmol) was dissolved in THF (5 mL), heated at 40° C. for 5 min, 0.1 N NaOH solution (3.6 mL, 0.36 mmol) was added slowly, stirred for 30 min while cooled down, then concentrated. The residue was lyophilized to give the sodium salt as white solid (165 mg). LCMS m/z=458.2 [M+H-Na]$^+$; $^1$H NMR (400 MHz, $d_6$-DMSO) δ 0.42 (td, J=4.6, 3.2 Hz, 1H), 0.91 (d, J=6.8 Hz, 3H), 0.93 (d, J=6.8 Hz, 3H), 1.23-1.27 (m, 1H), 1.55-1.62 (m, 2H), 1.80 (t, J=7.0 Hz, 2H), 1.85-1.92 (m, 1H), 2.24 (t, J=7.4 Hz, 2H), 2.25-2.33 (m, 1H), 2.65-2.70 (m, 1H), 2.75 (d, J=16.7 Hz, 1H), 2.86 (dd, J=16.5 and 6.5 Hz, 1H), 3.91-3.99 (m, 1H), 4.05 (dd, J=11.0 and 7.6 Hz, 1H), 4.22 (dd, J=11.0 and 4.3 Hz, 1H), 8.15 (d, J=9.1 Hz, 1H), 8.28 (dd, J=4.2 and 1.5 Hz, 1H), 8.47 (d, J=4.1 Hz, 1H), 9.06 (d, J=1.6 Hz, 1H).

Example 1.123: Preparation of (1aR,5aR)-2-(4-Chloro-pyridin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide (Compound 895)

Step A: Preparation of (1aR,5aR)-2-(4-Chloro-pyridin-2-yl)-1a,2,5,5a-tetrahydro-1H-2,3-diaza-cyclopropa[a]pentalene-4-carboxylic Acid To a solution of (1aR,5aR)-2-(4-iodo-pyridin-2-yl)-1a,2,5,5a-tetrahydro-1H-2,3-diaza-cyclopropa[a]pentalene-4-carboxylic acid ethyl ester (1.0 g, 2.53 mmol) in acetonitrile (30 mL) was added concentrated HCl solution (2 mL). The reaction was stirred at 80° C. for 20 h. After removal of acetonitrile, the aqueous residue was diluted with water and a $NaHCO_3$ solution was added to adjust the pH to 2-3. The resulting mixture was extracted with EtOAc (100 mL). The organic layer was washed with brine, dried over $MgSO_4$, and concentrated. The residue was dissolved in a mixture of $THF/MeOH/H_2O$ (20/20/10) and added LiOH (61 mg). The reaction was stirred overnight and concentrated. The aqueous residue was diluted with water and an HCl solution was added to adjust the pH to 2-3. The resulting solid was filtered, washed with water and dried to give the title compound (610 mg). LCMS m/z=276.1 [M+H]$^+$; $^1$H NMR (400 MHz, DMSO-$d_6$) 0.40 (dd, J=7.7, 4.5 Hz, 1H), 1.25 (td, J=7.9, 4.6 Hz, 1H), 2.25-2.30 (m, 1H), 2.71-2.75 (m, 1H), 2.76 (d, J=16.8 Hz, 1H), 2.87 (dd, J=16.4, 6.4 Hz, 1H), 7.55 (dd, J=5.4, 1.9 Hz, 1H), 7.90 (d, J=1.8 Hz, 1H), 8.52 (d, J=5.4 Hz, 1H), 12.98 (s, 1H).

Step B: Preparation of (1aR,5aR)-2-(4-Chloro-pyridin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide (Compound 895). [Method NNN]

To a solution of (1aR,5aR)-2-(4-chloro-pyridin-2-yl)-1a,2,5,5a-tetrahydro-1H-2,3-diaza-cyclopropa[a]pentalene-4-carboxylic acid (68.9 mg, 0.25 mmol), HATU (95 mg, 0.25 mmol) and $Et_3N$ (25.3 mg, 0.25 mmol) in AcCN (5 mL) was added (S)-2-amino-3-methylbutan-1-ol (25.3 mg, 0.25 mmol) at room temperature. The reaction was stirred overnight and concentrated. The residue was diluted with EtOAc (50 mL) and washed with water (50 mL). The organic layer was concentrated. The residue was purified by column chromatography to give the title compound (72 mg) as a white solid. LCMS m/z=361.5 [M+H]$^+$; $^1$H NMR (400 MHz, $CDCl_3$) δ 0.45 (dd, J=7.9, 4.6 Hz, 1H), 1.04 (d, J=6.8 Hz, 3H), 1.05 (d, J=6.8 Hz, 3H), 1.22-1.27 (m, 1H), 2.01-2.08 (m, 1H), 2.24-2.30 (m, 1H), 2.78-2.82 (m, 1H), 2.96 (d, J=16.8 Hz, 1H), 3.01 (dd, J=16.5, 6.3 Hz, 1H), 3.75-3.88 (m, 3H), 7.02 (d, J=7.8 Hz, 1H), 7.21 (dd, J=5.4, 1.8 Hz, 1H), 7.93 (d, J=1.8 Hz, 1H), 8.36 (d, J=5.4 Hz, 1H).

Example 1.124: Preparation of (1aS,5aS)-2-(4-Oxypyrazin-2-yl)-1a,2,5,5a-tetrahydro-1H-2,3-diazacyclopropa[a]pentalene-4-carboxylic Acid (3-Trifluoromethyl-oxetan-3-yl)-amide (Compound 929)

Step A: Preparation of 2-Methyl-N-(3-(trifluoromethyl)oxetan-3-yl)propane-2-sulfinamide 2-Methyl-N-(oxetan-3-ylidene)propane-2-sulfinamide (100 mg, 0.571 mmol) was dissolved in THF (2 mL). The solution was cooled down to −35° C. and added tetramethylammonium fluoride (63.8 mg, 0.685 mmol). The mixture was degassed and charged with argon. Trimethyl(trifluoromethyl)silane (0.134 ml, 0.856 mmol) in THF (1 mL) was added slowly via syringe. The reaction was stirred at this temperature for 2 h, warmed to −10° C. and quenched with saturated aqueous NH$_4$Cl solution. The mixture was extracted with ethyl acetate, dried over anhydrous Na$_2$SO$_4$, and concentrated. The residue was purified by column chromatography to give the title compound (53 mg). LCMS m/z=246.2 [M+H]$^+$; $^1$H NMR (400 MHz, CDCl$_3$) δ 1.29 (s, 9H), 3.79 (s, 1H), 4.78-4.85 (m, 3H), 4.98 (dd, J=7.6 and 1.3 Hz, 1H).

Step B: Preparation of 3-(Trifluoromethyl)oxetan-3-amine Hydrochloride

2-Methyl-N-(3-(trifluoromethyl)oxetan-3-yl)propane-2-sulfinamide (52 mg, 0.212 mmol) was dissolved in methanol (1 mL). The solution was cooled down at ice-water bath and added slowly 4 N HCl in dioxane (240 µL, 0.954 mmol). The mixture was warmed to room temperature, stirred for 5 h, then concentrated. The solid was washed with ether twice then dried in vacuo to give the title compound (27 mg).

Step C: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (3-Trifluoromethyl-oxetan-3-yl)-amide (Compound 929)

The title compound was prepared in a manner similar to that described in Method UU using Intermediate 5 and 3-(trifluoromethyl)oxetan-3-amine hydrochloride. LCMS m/z=382.2 [M+H]$^+$; $^1$H NMR (400 MHz, CDCl$_3$) δ 0.50 (td, J=4.6, 3.2 Hz, 1H), 1.23-1.29 (m, 1H), 2.30-2.37 (m, 1H), 2.72-2.78 (m, 1H), 2.92 (d, J=17.3 Hz, 1H), 3.00 (dd, J=16.7 and 6.2 Hz, 1H), 4.93 (d, J=7.8 Hz, 2H), 4.99-5.03 (m, 2H), 7.18 (s, 1H), 8.01 (dd, J=4.2 and 1.5 Hz, 1H), 8.30 (dd, J=4.1 and 0.6 Hz, 1H), 8.79 (dd, J=1.4 and 0.5 Hz, 1H).

Example 1.125: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (2-Hydroxy-1-hydroxymethyl-1-methyl-ethyl)-amide (Compound 820)

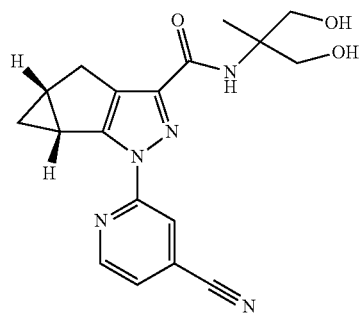 [SMILES: CC(CO)(CO)NC(=O)c1nn(-c2cc(C#N)ccn2)c2c1C[C@H]1C[C@@H]21]

Step A: Preparation of 4-Bromo-2-hydrazinylpyridine

To a solution of 4-bromo-2-fluoropyridine (23.75 g, 135 mmol) in ethanol (120 mL) was added hydrazine monohydrate (65.5 mL, 1350 mmol). The mixture was stirred at 45° C. for 16 h then concentrated. The resulting solid was triturated with water, collected by filtration, rinsed with water, and dried under vacuum, to give the title compound (23.2 g) as a white solid. LCMS m/z=188.0 [M+H]$^+$; $^1$H NMR (400 MHz, DMSO-d$_6$) δ 4.19 (s, 2H), 6.69 (dd, J=5.3, 1.8 Hz, 1H), 6.92 (d, J=1.7 Hz, 1H), 7.69 (s, 1H), 7.84 (d, J=5.3 Hz, 1H).

Step B: Preparation of (1aR,5aR)-2-(4-Bromo-pyridin-2-yl)-1a,2,5,5a-tetrahydro-1H-2,3-diaza-cyclopropa[a]pentalene-4-carboxylic Acid Ethyl Ester The title compound was prepared as described in Method KKK, using (1R,5S)-bicyclo[3.1.0]hexan-2-one and 4-bromo-2-hydrazinylpyridine. LCMS m/z=348.2 [M+H]$^+$.

Step C: Preparation of (1aR,5aR)-2-(4-Bromo-pyridin-2-yl)-1a,2,5,5a-tetrahydro-1H-2,3-diaza-cyclopropa[a]pentalene-4-carboxylic Acid To a solution of (1aR,5aR)-2-(4-bromo-pyridin-2-yl)-1a,2,5,5a-tetrahydro-1H-2,3-diaza-cyclopropa[a]pentalene-4-carboxylic acid ethyl ester (9.0 g, 25.8 mmol) in THF (50 mL) and MeOH (50.0 mL) was added a 2.0 M aqueous solution of sodium hydroxide (25.8 mL, 51.7 mmol). The reaction was stirred at 23° C. for 2 h then concentrated to remove the organic solvents. The remaining residue was diluted to 150 mL with water. This solution was filtered to remove trace insoluble impurities then acidified to pH ~3 with 6 M HCl. The resulting precipitate was collected by filtration, rinsed with water, then dried under vacuum to give the title compound (8.3 g) as a white solid. LCMS m/z=320.0 [M+H]$^+$.

Step D: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (1aR,5aR)-2-(4-Bromo-pyridin-2-yl)-1a,2,5,5a-tetrahydro-1H-2,3-diaza-cyclopropa[a]pentalene-4-carboxylic Acid (1.00 g, 3.12 mmol) was dissolved in DMA (10 mL). 60 wt % sodium hydride (0.125 g, 3.12 mmol) was added and the mixture was stirred vigorously for 5 min. Nitrogen was bubbled through the mixture for 10 min. Zinc(II) cyanide (0.734 g, 6.25 mmol) and palladium tetrakistriphenylphosphine (0.180 g, 0.156 mmol) were added. The reaction was microwaved at 120° C. for 1 h. The reaction was diluted with ethyl acetate (20 mL) and methanol (5 mL), filtered, then concentrated. The residue was purified by HPLC to give the title compound (0.557 g) as a white solid. LCMS m/z=267.2 [M+H]$^+$.

Step E: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (2-Hydroxy-1-hydroxymethyl-1-methyl-ethyl)-amide (Compound 820)

To a solution of (1aR,5aR)-2-(4-cyano-pyridin-2-yl)-1a,2,5,5a-tetrahydro-1H-2,3-diaza-cyclopropa[a]pentalene-4-carboxylic acid (100 mg, 0.376 mmol), 2-amino-2-methylpropane-1,3-diol (39.5 mg, 0.376 mmol), and triethylamine (0.105 mL, 0.751 mmol) in DMF (2 mL) was added HATU (157 mg, 0.413 mmol). The reaction was stirred at 23° C., for 30 min then concentrated. The residue was purified by silica gel flash column chromatography to give the title compound (125 mg) as a white solid. LCMS m/z=354.3 [M+H]$^+$; $^1$H NMR (400 MHz, CDCl$_3$) δ 0.46 (td, J=4.7, 3.3 Hz, 1H), 1.27 (td, J=8.0, 4.9 Hz, 1H), 1.36 (s, 3H), 2.27-2.33 (m, 1H), 2.78-2.89 (m, 2H), 3.00 (dd, J=16.8, 6.4 Hz, 1H), 3.72-3.77 (m, 4H), 3.87-3.94 (m, 2H), 7.23 (m, 1H), 7.42 (dd, J=5.1, 1.0 Hz, 1H), 8.16-8.17 (m, 1H), 8.62 (d, J=5.1 Hz, 1H).

Example 1.126: Preparation of (1aR,5aR)—(R)-2-(5-Fluoro-pyridin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 780)

Step A: Preparation of 5-Fluoro-2-hydrazinylpyridine

To a mixture of hydrazine monohydrate (14.75 mL, 304 mmol) and 1-butanol (10 mL) was added 2-chloro-5-fluoropyridine (5.00 g, 38.0 mmol). The solution was microwaved in a sealed, thick-walled glass tube at 180° C. for 1 h. The resulting white suspension was transferred with EtOH to a round bottom flask then concentrated. The resulting white solid was taken up in ethyl acetate (250 mL) and the insoluble material removed by filtration. The filtrate was concentrated to give the title compound a pale orange solid. This solid was used in the following step without further purification.

Step B: Preparation of (S)-2-Amino-3,3-dimethylbutan-1-ol and (4aR,5aR)-1-(5-fluoropyridin-2-yl)-4,4a,5,5a-tetrahydro-1H-cyclopropa[4,5]cyclopenta[1,2,-c]pyrazole-3-carboxylic Acid Ethyl Ester The title compound was prepared in a manner similar to that described in Example 1.108, Step C, using (1R,5S)-bicyclo[3.1.0]hexan-2-one and 5-fluoro-2-hydrazinylpyridine. LCMS m/z=288.2 [M+H]$^+$.

Step C: Preparation of (S)-2-Amino-3,3-dimethylbutan-1-ol and (4aR,5aR)-1-(5-fluoropyridin-2-yl)-4,4a,5,5a-tetrahydro-1H-cyclopropa[4,5]cyclopenta[1,2,-c]pyrazole-3-carboxylic Acid To a solution of (S)-2-amino-3,3-dimethylbutan-1-ol and (4aR,5aR)-1-(5-fluoropyridin-2-yl)-4,4a,5,5a-tetrahydro-1H-cyclopropa[4,5]cyclopenta[1,2,-c]pyrazole-3-carboxylic acid ethyl ester (1.72 g, 5.99 mmol) in methanol (15 mL) and THF (15.00 mL) was added a 2.0 M aqueous solution of sodium hydroxide (5.99 mL, 11.97 mmol). The mixture was stirred at 23° C., for 2 h then concentrated. The remaining residue was taken up in water (100 mL). The mixture was acidified to pH 2 with 3 M HCl. The resulting precipitate was collected by filtration, rinsed with water, then dried to give the title compound (1.48 g) as a white solid. LCMS m/z=260.2 [M+H]$^+$.

Step D: Preparation of (1aR,5aR)—(R)-2-(5-Fluoro-pyridin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 780)

To a solution of (4aR,5aR)-1-(5-fluoropyridin-2-yl)-4,4a,5,5a-tetrahydro-1H-cyclopropa[4,5]cyclopenta[1,2,-c]pyrazole-3-carboxylic acid (200 mg, 0.771 mmol), (S)-2-amino-3,3-dimethylbutan-1-ol (99 mg, 0.849 mmol) and triethylamine (0.215 mL, 1.543 mmol) in DMF (3 mL) was added HATU (323 mg, 0.849 mmol). The reaction was stirred at 23° C. for 2 h then concentrated. The residue was purified by silica gel flash column chromatography to give the title compound (243 mg) as a white solid. LCMS m/z=359.3 [M+H]$^+$; $^1$H NMR (400 MHz, CDCl$_3$) δ 0.45 (td, J=4.6, 3.4 Hz, 1H), 1.04 (s, 9H), 1.24 (td, J=8.0, 4.8 Hz, 1H), 2.23-2.30 (m, 1H), 2.49 (t, J=5.6 Hz, 1H), 2.75-2.80 (m, 1H), 2.92 (d, J=16.7 Hz, 1H), 3.02 (dd, J=16.4, 6.4 Hz, 1H), 3.63-3.70 (m, 1H), 3.92-3.98 (m, 2H), 7.02 (d, J=8.7 Hz, 1H), 7.55 (ddd, J=9.0, 7.6, 2.9 Hz, 1H), 7.91 (dd, J=9.0, 3.9 Hz, 1H), 8.31 (d, J=2.9 Hz, 1H).

Example 1.127: Preparation of (1aR,5aR)-2-(4-Cyano-pyridin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide (Compound 847)

To a solution of (1aR,5aR)-2-(4-cyano-pyridin-2-yl)-1a,2,5,5a-tetrahydro-1H-2,3-diaza-cyclopropa[a]pentalene-4-carboxylic acid (50 mg, 0.188 mmol), (S)-2-amino-3-methylbutan-1-ol (19.37 mg, 0.188 mmol), and triethylamine (0.052 mL, 0.376 mmol) in DMF (2 mL) was added HATU (71.4 mg, 0.188 mmol). The mixture was stirred at 23° C. for 30 min and purified by HPLC to give the title compound (53 mg) as a white solid. LCMS m/z=352.3 [M+H]$^+$; $^1$H NMR (400 MHz, CDCl$_3$) δ 0.46 (td, J=4.7, 3.3 Hz, 1H), 1.04 (d, J=6.8 Hz, 3H), 1.05 (d, J=6.7 Hz, 3H), 1.26 (td, J=8.0, 4.9 Hz, 1H), 2.05 (oct, J=6.8 Hz, 1H), 2.26-2.32 (m, 1H), 2.52 (t, J=5.6 Hz, 1H), 2.78-2.82 (m, 1H), 2.93 (d, J=16.8 Hz, 1H), 3.02 (dd, J=16.7, 6.4 Hz, 1H), 3.75-3.92 (m, 3H), 7.00 (d, J=7.8 Hz, 1H), 7.41 (dd, J=5.1, 1.4 Hz, 1H), 8.17 (s, 1H), 8.62 (d, J=5.1 Hz, 1H).

Example 1.128: Preparation of (1aR,5aR)-2-(4-Cyano-pyridin-2-yl)-1a,2,5,5a-tetrahydro-1H-2,3-diaza-cyclopropa[a]pentalene-4-carboxylic Acid ((S)-3,3,3-Trifluoro-1-hydroxymethyl-propyl)-amide (Compound 851)

Step A: Preparation of (S)-2-Amino-4,4,4-trifluorobutan-1-ol

To an ice-cooled solution of (S)-2-(tert-butoxycarbonylamino)-4,4,4-trifluorobutanoic acid (1.0 g, 3.89 mmol) and N-ethyl-N-isopropylpropan-2-amine (0.813 mL, 4.67 mmol) in THF (15 mL) was added dropwise ethyl chloroformate (0.409 mL, 4.28 mmol). The cooling bath was removed and the mixture was stirred at 23° C. for 2 h. The mixture was filtered to remove the white precipitate, and the filtrate was treated with a 2 M THF solution of lithium borohydride (1.944 mL, 3.89 mmol) resulting in vigorous gas evolution. The mixture was stirred at room temperature for 2 h. Brine (25 mL) was added. The mixture was extracted with ethyl acetate (3×25 mL). The combined organic extracts were dried (MgSO$_4$), filtered, then concentrated under vacuum. The residue was purified by silica gel flash column chromatography to give (S)-tert-butyl 4,4,4-trifluoro-1-hydroxybutan-2-ylcarbamate (0.80 g) as a white solid. This solid material was treated with 4 M HCl in dioxane (10 mL) for 60 min then concentrated to give the title compound (0.54 g) as a white solid. $^1$H NMR (400 MHz, CD$_3$OD) δ 2.55-2.79 (m, 2H), 3.42 (bs, 1H), 3.54 (dd, J=11.6, 5.6 Hz, 1H), 3.66 (dd, J=11.6, 3.9 Hz, 1H), 3.53 (bs, 1H), 8.27 (bs, 3H).

Step B: Preparation of (1aR,5aR)-2-(4-Cyano-pyridin-2-yl)-1a,2,5,5a-tetrahydro-1H-2,3-diaza-cyclopropa[a]pentalene-4-carboxylic Acid ((S)-3,3,3-Trifluoro-1-hydroxymethyl-propyl)-amide (Compound 851)

To a solution of (1aR,5aR)-2-(4-cyano-pyridin-2-yl)-1a,2,5,5a-tetrahydro-1H-2,3-diaza-cyclopropa[a]pentalene-4-carboxylic acid (50 mg, 0.188 mmol), (S)-2-amino-4,4,4-trifluorobutan-1-ol hydrochloride (33.7 mg, 0.188 mmol), and triethylamine (0.052 mL, 0.376 mmol) in DMF (2 mL) was added HATU (71.4 mg, 0.188 mmol). The mixture was stirred at 23° C. for 30 min and purified by HPLC followed by preparative TLC to give the title product (6 mg) as a white solid. LCMS m/z=392.4 [M+H]$^+$; $^1$H NMR (400 MHz, CDCl$_3$) δ 0.45 (td, J=4.7, 3.3 Hz, 1H), 1.24-1.29 (m, 2H), 2.26-2.32 (m, 1H), 2.54-2.69 (m, 2H), 2.77-2.82 (m, 1H), 2.91 (d, J=16.7 Hz, 1H), 3.01 (dd, J=16.7, 6.4 Hz, 1H), 3.87 (d, J=4.0 Hz, 2H), 4.34-4.42 (m, 1H), 7.24 (d, J=8.1 Hz, 1H), 7.41 (dd, J=5.1, 1.1 Hz, 1H), 8.17 (s, 1H), 8.62 (d, J=5.1 Hz, 1H).

Example 1.129: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Fluoromethyl-2-methyl-propyl)-amide (Compound 915)

Step A: Preparation of (4S)-2-Oxo-3-benzyl-4-isopropyl-1,2,3-oxathiazolidine

A solution of (S)-2-amino-3-methylbutan-1-ol (10.0 g, 97 mmol), benzaldehyde (10.34 mL, 102 mmol), and 4-methylbenzenesulfonic acid hydrate (3.69 mg, 0.019 mmol) in benzene (300 mL) was refluxed (80° C.) for 15 h with a Dean-Stark trap (ca. 2 mL water was collected). The solution was concentrated (leaving a pale yellow solid) and redissolved in methanol (200 mL). The methanol solution was cooled in an ice bath then treated with sodium cyanotrihydroborate (7.31 g, 116 mmol). The ice bath was removed and the mixture was stirred for 30 min (50% conversion). NaBH$_4$ (3 g, 79.3 mmol) were added and stirring continued at room temperature for 20 min. The mixture was concentrated. The remaining residue was taken up in ethyl acetate (200 mL) then washed with saturated NaHCO$_3$ (100 mL) then brine (100 mL). The organic layer was dried (MgSO$_4$), filtered, then concentrated to give (S)-2-(benzylamino)-3-methylbutan-1-ol as a colorless oil. This oil was dissolved in dichloromethane (300 mL). N-ethyl-N-isopropylpropan-2-amine (67.5 mL, 388 mmol) was added. The flask was flushed with nitrogen, and the mixture was cooled in a dry-ice/acetone bath. Thionyl chloride (7.78 mL, 107 mmol) was added dropwise, maintaining the internal temperature between −60° C. and −30° C. After addition was complete, the cooling bath was removed and the mixture gradually warmed to room temperature over 1 h. The mixture was concentrated. The residue was purified by silica gel flash column chromatography to give the title compound (18 g) as an orange oil (mixture of epimers). LCMS m/z=240.0 [M+H]$^+$.

Step B: Preparation of (4S)-2,2-Dioxo-3-benzyl-4-isopropyl-1,2,3-oxathiazolidine To an ice-cooled solution of (4S)-2-oxo-3-benzyl-4-isopropyl-1,2,3-oxathiazolidine (6.00 g, 25.07 mmol) in acetonitrile (45 mL) and water (45.0 mL) was added ruthenium chloride (5.20 mg, 0.025 mmol) followed by sodium periodate (8.04 g, 37.6 mmol). The mixture was stirred for 1 h as ice bath melted and the reaction was gradually warmed to room temperature. The mixture was extracted with ether (3×50 mL). The combined organic extracts were washed with brine (100 mL), dried (MgSO$_4$), filtered, then concentrated. The resulting oil was purified by silica gel flash column chromatography to give the title compound (1.9 g) as a colorless oil. LCMS m/z=256.2 [M+H]$^+$. $^1$H NMR (400 MHz, CDCl$_3$) δ 0.86 (d, J=7.1 Hz, 3H), 0.90 (d, J=7.1 Hz, 3H), 1.83-1.95 (m, 1H), 3.41-3.45 (m, 1H), 4.23-4.28 (m, 2H), 4.39-4.44 (m, 2H), 7.35-7.43 (m, 5H).

Step C: Preparation of (S)—N-Benzyl-1-fluoro-3-methylbutan-2-amine

To an ice-cooled solution of (4S)-2,2-dioxo-3-benzyl-4-isopropyl-1,2,3-oxathiazolidine (1.9 g, 7.44 mmol) in THF (30 mL) was added a 1.0 M THF solution of tetrabutylammonium fluoride (14.88 mL, 14.88 mmol). The mixture was stirred for 1 h as ice bath melted and the reaction was gradually warmed to room temperature, then stirred overnight. The mixture was concentrated, and the remaining residue was treated with ether (25 mL) and 20% vol/vol aqueous sulfuric acid (25 mL). The reaction was stirred for 2 h at room temperature. The mixture was neutralized with 2 M NaOH (ca. 50 mL) and the layers were separated. The aqueous layer was extracted with ether (25 mL). The combined organic extracts were dried (MgSO$_4$), filtered, then concentrated under vacuum to give the title compound (1.4 g) as a colorless oil. LCMS m/z=196.2 [M+H]$^+$. $^1$H NMR (400 MHz, CDCl$_3$) δ 0.95 (d, J=6.8 Hz, 3H), 0.97 (d, J=6.8 Hz, 3H), 1.88 (oct, J=6.8 Hz, 1H), 2.57-2.66 (m, 1H), 3.80 (d, J=13.4 Hz, 1H), 3.88 (d, J=13.4 Hz, 1H), 4.34-4.59 (m, 2H), 7.22-7.36 (m, 5H).

Step D: Preparation of (S)-1-Fluoro-3-methylbutan-2-amine Hydrochloride

To a solution of (S)—N-benzyl-1-fluoro-3-methylbutan-2-amine (1.4 g, 7.17 mmol) in methanol (30 mL) was added 5 wt % wet Pd/C (0.305 g, 0.143 mmol). The mixture was stirred at 23° C. under 125 psi hydrogen for 15 h. The catalyst was removed by filtration. Methanolic HCl (1.25 M, 6 mL) was added and the solution was concentrated. The residue was taken up in ether (50 mL). The resulting solid was collected by filtration, rinsed with ether, then dried to give the title compound (0.60 g) as a white solid. $^1$H NMR (400 MHz, DMSO-d$_6$) δ 0.96 (d, J=6.8 Hz, 3H), 0.98 (d, J=6.8 Hz, 3H), 1.95 (m, 1H), 3.13-3.23 (m, 1H), 4.53-4.76 (m, 2H), 8.17 (s, 3H).

Step E: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Fluoromethyl-2-methyl-propyl)-amide (Compound 915)

The title compound was prepared in a manner similar to that described in Method UU using Intermediate 5 and (S)-1-fluoro-3-methylbutan-2-amine hydrochloride. LCMS m/z=346.2 [M+H]$^+$; $^1$H NMR (400 MHz, CDCl$_3$) δ 0.49 (td, J=4.8, 3.3 Hz, 1H), 1.03 (d, J=6.8 Hz, 3H), 1.06 (d, J=6.8 Hz, 3H), 1.28 (td, J=8.0, 4.9 Hz, 1H), 2.04 (oct, J=6.8 Hz, 1H), 2.28-2.34 (m, 1H), 2.71-2.76 (m, 1H), 2.94 (d, J=16.9 Hz, 1H), 3.01 (dd, J=16.7, 6.1 Hz, 1H), 3.97-4.10 (m, 1H), 4.46-4.70 (m, 2H), 6.92 (d, J=9.60 Hz, 1H), 7.98 (dd, J=4.2, 1.5 Hz, 1H), 8.29 (dd, J=4.2, 0.6 Hz, 1H), 8.80 (dd, J=1.5, 0.6 Hz, 1H).

Example 1.130: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid N'-tert-Butyl-hydrazide (Compound 902). [Method TT]

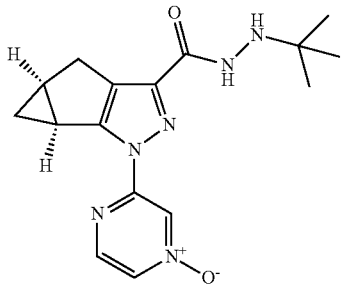 [SMILES: CC(C)(C)NNC(=O)c1nn(-c2c[n+]([O-])ccn2)c2c1C[C@@H]1C[C@H]21]

To a solution of Intermediate 5 (129 mg, 0.5 mmol) and HATU (190 mg, 0.500 mmol) in DMF (4 mL) was added triethylamine (126 mg, 1.250 mmol) followed by tert-butylhydrazine (44.1 mg, 0.500 mmol) at room temperature. The reaction was stirred for 16 h. The reaction mixture was diluted with water (100 mL) and extracted with EtOAc (70 mL). The organic layer was concentrated and the residue was purified by silica gel column chromatography to give the title compound (87 mg) as a white solid. LCMS m/z=329.3 [M+H]$^+$; $^1$H NMR (400 MHz, CDCl$_3$) δ 0.49 (dd, J=8.0 and 4.7 Hz, 1H), 1.17 (s, 9H), 1.25-1.31 (m, 1H), 2.29-2.33 (m, 1H), 2.72-2.77 (m, 1H), 2.93 (d, J=16.8 Hz, 1H), 3.01 (dd, J=17.0 and 6.2 Hz, 1H), 8.00 (dd, J=4.1 and 1.4 Hz, 1H), 8.29 (d, J=4.1 Hz, 1H), 8.80 (d, J=1.4 Hz, 1H).

Example 1.131: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide (Compound 896)

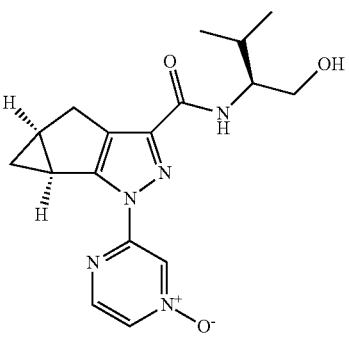 [SMILES: CC(C)[C@@H](CO)NC(=O)c1nn(-c2c[n+]([O-])ccn2)c2c1C[C@@H]1C[C@H]21]

The title compound was prepared in a manner similar to that described in Method TT. LCMS m/z=344.1 [M+H]$^+$; $^1$H NMR (400 MHz, CDCl$_3$) δ 0.48 (dd, J=8.0 and 4.7 Hz, 1H), 1.02 (t, J=7.1 Hz, 6H), 1.28 (td, J=8.0 and 5.0 Hz, 1H), 1.98-2.04 (m, 1H), 2.28-2.32 (m, 1H), 2.71-2.75 (m, 1H), 2.93 (d, J=16.8 Hz, 1H), 3.00 (dd, J=16.7 and 6.3 Hz, 1H), 3.74-3.88 (m, 3H), 6.97 (d, J=8.1 Hz, NH, 1H), 7.99 (dd, J=4.1 and 1.5 Hz, 1H), 8.28 (d, J=4.1 Hz, 1H), 8.79 (d, J=1.5 Hz, 1H).

Example 1.132: Preparation of (1aR,5aR)-2-(4-Oxy-pyrazin-2-yl)-1a,2,5,5a-tetrahydro-1H-2,3-di-aza-cyclopropa[a]pentalene-4-carboxylic Acid [(S)-1-(2-Hydroxy-ethylcarbamoyl)-2,2-dimethyl-propyl]-amide (Compound 833)

Step A: Preparation of (S)-tert-Butyl 1-(2-Hydroxy-ethylamino)-3,3-dimethyl-1-oxobutan-2-ylcarbamate To a solution of (S)-2-(tert-butoxycarbonylamino)-3,3-dimethylbutanoic acid (0.925 g, 4.0 mmol), HATU (1.597 g, 4.20 mmol) and triethylamine (0.810 g, 8.00 mmol) was added 2-aminoethanol (0.257 g, 4.20 mmol) at room temperature. The reaction was stirred overnight and concentrated. The residue was purified by silica gel column chromatography to give the title compound (1.05 g) as a yellow oil. LCMS m/z=275.3 [M+H]$^+$.

Step B: Preparation of (S)-2-Amino-N-(2-hydroxyethyl)-3,3-dimethylbutanamide (S)-tert-Butyl 1-(2-hydroxyethylamino)-3,3-dimethyl-1-oxobutan-2-ylcarbamate was treated overnight with trifluoroacetic acid in methylene chloride. The solution was concentrated to give the title compound without further purification.

Step C: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid [(S)-1-(2-Hydroxy-ethylcarbamoyl)-2,2-dimethyl-propyl]-amide The title compound was prepared in a manner similar to that described in Method TT using Intermediate 6 and (S)-2-amino-N-(2-hydroxyethyl)-3,3-dimethylbutanamide. LCMS m/z=415.5 [M+H]$^+$; $^1$H NMR (400 MHz, CDCl$_3$) δ 0.45 (dd, J=8.0, 4.6 Hz, 1H), 1.08 (s, 9H), 1.24-1.29 (m, 1H), 2.27-2.32 (m, 1H), 2.75-2.88 (m, 2H), 3.00 (dd, J=16.6, 6.4 Hz, 1H), 3.39-3.52 (m, 2H), 3.72-3.76 (m, 2H), 3.67 (d, J=9.0 Hz, 1H), 6.59 (bs, NH, 1H), 7.51 (t, J=9.5 Hz, 1H), 8.04 (dd, J=4.1 and 1.1 Hz, 1H), 8.32 (d, J=4.1 Hz, 1H), 8.89 (s, 1H).

Example 1.133: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-2,2-Dimethyl-1-pyridin-2-yl-propyl)-amide (Compound 767). [Method AAA]

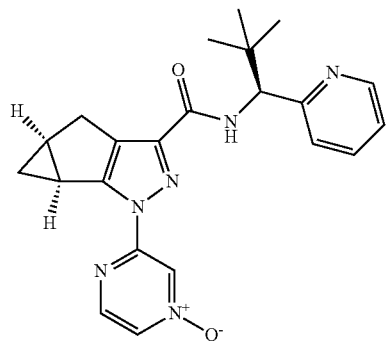 [SMILES: CC(C)(C)[C@H](NC(=O)c1nn(-c2c[n+]([O-])ccn2)c2c1C[C@@H]1C[C@H]21)c1ccccn1]

Step A: Preparation of (R)—N—((S)-2,2-Dimethyl-1-(pyridin-2-yl)propyl)-3,3,3-trifluoro-2-methoxy-2-phenylpropanamide and (R)—N—((R)-2,2-Dimethyl-1-(pyridin-2-yl)propyl)-3,3,3-trifluoro-2-methoxy-2-phenylpropanamide To an ice-cooled solution of racemic 2,2-dimethyl-1-(pyridin-2-yl)propan-1-amine (1.0 g, 6.09 mmol) and triethylamine (0.849 mL, 6.09 mmol) in dichloromethane (20 mL) was added a dichloromethane (5 mL) solution of(S)-3,3,3-trifluoro-2-methoxy-2-phenylpropanoyl chloride (1.148 mL, 6.09 mmol). The solution was stirred at 23° C. for 30 min then loaded onto a silica column. Purification by silica gel flash column chromatography gave the title compound as diastereomers: First-eluting diastereomer (0.56 g) and second-eluting diastereomer (0.504 g) as yellow oils.

First-eluting diastereomer: LCMS m/z=381.4 [M+H]$^+$; $^1$H NMR (400 MHz, CDCl$_3$) δ 0.83 (s, 9H), 3.40 (q, J=1.7 Hz, 3H), 4.93 (d, J=9.5 Hz, 1H), 7.16-7.20 (m, 2H), 7.38-7.42 (m, 3H), 7.61 (td, J=7.7, 1.8 Hz, 1H), 7.65-7.68 (m, 2H), 7.96 (d, J=9.5 Hz, 1H), 8.55 (dt, J=4.5, 1.3 Hz, 1H).

Second-eluting diastereomer: LCMS m/z=381.4 [M+H]$^+$; $^1$H NMR (400 MHz, CDCl$_3$) δ 0.96 (s, 9H), 3.44 (q, J=1.4 Hz, 3H), 4.90 (d, J=9.5 Hz, 1H), 7.14-7.17 (m, 2H), 7.23-7.31 (m, 3H), 7.41 (d, J=7.3 Hz, 2H), 7.59 (td, J=7.7, 1.8 Hz, 1H), 8.16 (d, J=9.4 Hz, 1H), 8.50 (dt, J=5.3, 1.8 Hz, 1H).

Step B: Preparation of (S)-2,2-Dimethyl-1-(pyridin-2-yl)propan-1-amine and (R)-2,2-Dimethyl-1-(pyridin-2-yl)propan-1-amine Solutions of (R)—N—((S)-2,2-dimethyl-1-(pyridin-2-yl)propyl)-3,3,3-trifluoro-2-methoxy-2-phenylpropanamide (0.56 g, 1.472 mmol) or (R)—N—((R)-2,2-dimethyl-1-(pyridin-2-yl)propyl)-3,3,3-trifluoro-2-methoxy-2-phenylpropanamide (0.56 g, 1.472 mmol) in 48 wt % aqueous hydrogen bromide (5.02 mL, 44.2 mmol) were heated under microwave irradiation at 160° C. for 2 h. The mixtures were diluted with water (25 mL), extracted with dichloromethane (3×25 mL), and the dichloromethane extracts discarded. The aqueous solutions were basified with 2 M aqueous NaOH (25 mL) then extracted with dichloromethane (3×25 mL). These extracts were dried (MgSO$_4$), filtered, then concentrated to give enantiomeric 2,2-dimethyl-1-(pyridin-2-yl)propan-1-amine derived from first-eluting diastereomer (0.175 g) and enantiomeric 2,2-dimethyl-1-(pyridin-2-yl)propan-1-amine derived from second-eluting diastereomer (0.200 g) as yellow oils.

Enantiomer derived from first-eluting Mosher amide: LCMS m/z=165.3 [M+H]$^+$;

Enantiomer derived from second-eluting Mosher amide: LCMS m/z=165.3 [M+H]$^+$.

Step C: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-2,2-Dimethyl-1-pyridin-2-yl-propyl)-amide To a solution of Intermediate 5 (200 mg, 0.774 mmol), (S)-2,2-dimethyl-1-(pyridin-2-yl)propan-1-amine (127 mg, 0.774 mmol), and triethylamine (0.216 mL, 1.549 mmol) in DMF (3 mL) was added HATU (324 mg, 0.852 mmol). The reaction was stirred at 23° C. for 1 h then diluted with DMSO (2 mL). The mixture was purified by preparative HPLC to give the title compound (183 mg) as a white solid. LCMS m/z=405.4 [M+H]$^+$. $^1$H NMR (400 MHz, CDCl$_3$) δ 0.38 (td, J=4.7, 3.3 Hz, 1H), 0.99 (s, 9H), 1.23 (td, J=8.0, 4.8 Hz, 1H), 2.24-2.31 (m, 1H), 2.71-2.75 (m, 1H), 2.88 (dd, J=16.7, 1.8 Hz, 1H), 3.03 (dd, J=16.7, 6.4 Hz, 1H), 5.02 (d, J=9.5 Hz, 1H), 7.15-7.20 (m, 2H), 7.59 (td, J=7.7, 1.8 Hz, 1H), 7.99 (dd, J=4.0, 1.4 Hz, 1H), 8.18 (d, J=9.5 Hz, 1H), 8.28 (d, J=4.2 Hz, 1H), 8.61-8.62 (m, 1H), 8.92-8.93 (m, 1H).

Example 1.134: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((R)-2,2-Dimethyl-1-pyridin-2-yl-propyl)-amide (Compound 766)

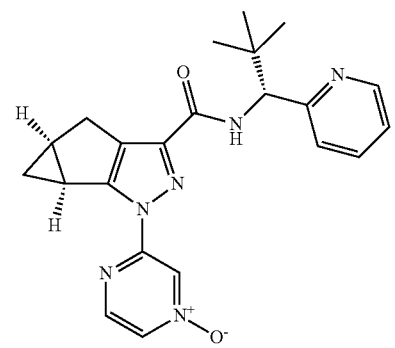 [SMILES: CC(C)(C)[C@@H](NC(=O)c1nn(-c2c[n+]([O-])ccn2)c2c1C[C@@H]1C[C@H]21)c1ccccn1]

To a solution of Intermediate 5 (200 mg, 0.774 mmol), (R)-2,2-dimethyl-1-(pyridin-2-yl)propan-1-amine (127 mg, 0.774 mmol), and triethylamine (0.216 mL, 1.549 mmol) in DMF (3 mL) was added HATU (324 mg, 0.852 mmol). The reaction was stirred at 23° C. for 1 h then diluted with DMSO (2 mL). The mixture was purified by preparative HPLC to give the title compound (230 mg) as a white solid. LCMS m/z=405.4 [M+H]$^+$; $^1$H NMR (400 MHz, CDCl$_3$) δ 0.50 (td, J=4.8, 3.3 Hz, 1H), 0.99 (s, 9H), 1.26 (td, J=7.8, 4.9 Hz, 1H), 2.24-2.30 (m, 1H), 2.69-2.74 (m, 1H), 2.94-2.95 (m, 2H), 5.02 (d, J=9.5 Hz, 1H), 7.15-7.20 (m, 2H), 7.59 (td, J=7.7, 1.9 Hz, 1H), 7.99 (dd, J=4.2, 1.5 Hz, 1H), 8.18 (d, J=9.5 Hz, 1H), 8.28 (d, J=4.2 Hz, 1H), 8.61-8.63 (m, 1H), 8.92-8.93 (m, 1H).

Example 1.135: Preparation of (1aS,5aS)—(S)-2-Amino-3-methyl-butyric Acid (S)-3,3-Dimethyl-2-{[2-(4-oxy-pyrazin-2-yl)-1a,2,5,5a-tetrahydro-1H-2,3-diaza-cyclopropa[a]pentalene-4-carbonyl]-amino}-butyl Ester (Compound 848)

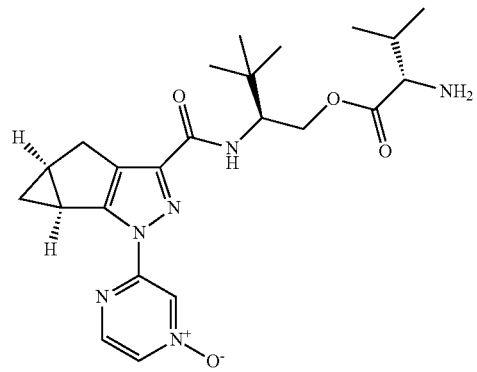 [SMILES: CC(C)[C@H](N)C(=O)OC[C@@H](NC(=O)c1nn(-c2c[n+]([O-])ccn2)c2c1C[C@@H]1C[C@H]21)C(C)(C)C]

Step A: Preparation of (1aS,5aS)-2-Pyrazin-2-yl-1a, 2,5,5a-tetrahydro-1H-2,3-diaza-cyclopropa[a]pentalene-4-carboxylic Acid ((S)-1-Hydroxymethyl-2,2-dimethyl-propyl)-amide To a solution of Intermediate 4 (1.4 g, 5.78 mmol) and triethylamine (1.611 mL, 11.56 mmol) in DMF (15 mL) was added HATU (2.242 g, 5.90 mmol). The reaction was stirred at 23° C. for 5 min, then (S)-2-amino-3,3-dimethylbutan-1-ol (0.711 g, 6.07 mmol) was added. The reaction was stirred at 23° C. for 15 min then concentrated. The residue was purified by silica gel column chromatography to give the title compound (1.97 g) as a white solid. LCMS m/z=342.2 [M+H]$^+$; $^1$H NMR (400 MHz, CDCl$_3$) δ 0.48 (td, J=4.6, 3.4 Hz, 1H), 1.05 (s, 9H), 1.24 (td, J=8.0, 4.7 Hz, 1H), 2.26-2.32 (m, 1H), 2.74-2.78 (m, 1H), 2.94 (d, J=16.8 Hz, 1H), 3.01 (dd, J=16.7, 6.1 Hz, 1H), 3.67-3.72 (m, 1H), 3.93-3.98 (m, 2H), 7.08 (d, J=8.5 Hz, 1H), 8.42 (dd, J=1.4, 0.9 Hz, 1H), 8.51 (d, J=2.7 Hz, 1H), 9.26 (d, J=1.1 Hz, 1H).

Step B: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide To a solution of (1aS,5aS)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (900 mg, 2.64 mmol) in chloroform (10 mL) was added 3-chlorobenzoperoxoic acid (1772 mg, 7.91 mmol). The reaction was stirred at 23° C. for 3 h. Another 1.2 g mCPBA was added and stirring was continued at room temperature for 18 h. The mixture was purified by silica gel column chromatography to give the title compound (550 mg) as a white solid. LCMS m/z=358.3 [M+H]$^+$; $^1$H NMR (400 MHz, CDCl$_3$) δ 0.49 (td, J=4.6, 3.3 Hz, 1H), 1.03 (s, 9H), 1.27 (td, J=8.0, 4.9 Hz, 1H), 2.08 (bs, 1H), 2.27-2.33 (m, 1H), 2.71-2.76 (m, 1H), 2.93 (d, J=16.8 Hz, 1H), 3.00 (dd, J=16.7, 6.1 Hz, 1H), 3.65-3.71 (m, 1H), 3.92-3.97 (m, 2H), 6.97 (d, J=8.5 Hz, 1H), 7.99 (dd, J=4.0, 1.4 Hz, 1H), 8.28 (d, J=4.2 Hz, 1H), 8.78 (dd, J=1.4, 0.8 Hz, 1H).

Step C: Preparation of (S)-2-tert-Butoxycarbonylamino-3-methyl-butyric Acid (S)-3,3-Dimethyl-2-{[(1aS,5aS)-2-(4-oxy-pyrazin-2-yl)-1a,2,5,5a-tetrahydro-1H-2,3-diaza-cyclopropa[a]pentalene-4-carbonyl]-amino}-butyl Ester To a solution of (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (500 mg, 1.399 mmol), (S)-2-(tert-butoxycarbonylamino)-3-methylbutanoic acid (1003 mg, 4.62 mmol), triethylamine (1.170 mL, 8.39 mmol), and DMAP (68.4 mg, 0.560 mmol) in 1,2-dichloroethane (10 mL) was added N1-((ethylimino)methylene)-N3,N3-dimethylpropane-1,3-diamine. The mixture was stirred at 60° C. for 2 h. The mixture was purified by silica gel column chromatography to give the title compound (495 mg) as a white solid. LCMS m/z=557.5.

Step D: Preparation of (1aS,5aS)—(S)-2-Amino-3-methyl-butyric Acid (S)-3,3-Dimethyl-2-{[2-(4-oxy-pyrazin-2-yl)-1a,2,5,5a-tetrahydro-1H-2,3-diaza-cyclopropa[a]pentalene-4-carbonyl]-amino}-butyl Ester To (S)-2-tert-butoxycarbonylamino-3-methyl-butyric acid (S)-3,3-dimethyl-2-{[(1aS,5aS)-2-(4-oxy-pyrazin-2-yl)-1a,2,5,5a-tetrahydro-1H-2,3-diaza-cyclopropa[a]pentalene-4-carbonyl]-amino}-butyl ester (495 mg, 0.889 mmol) was added HCl (4 M in dioxane, 5.56 mL, 22.23 mmol). The reaction was stirred at 23° C. for 1 h then concentrated. The off-white solid was taken up in 2:1 water/acetonitrile (10 mL) then freeze-dried to give the HCl salt of the title compound (437 mg) as a white solid. LCMS m/z=457.3 [M+H]$^+$; $^1$H NMR (400 MHz, DMSO-d$_6$) δ 0.44 (td, J=4.4, 3.4 Hz, 1H), 0.78 (d, J=7.0 Hz, 3H), 0.81 (d, J=7.1 Hz, 3H), 0.97 (s, 9H), 1.27 (td, J=7.8, 4.7 Hz, 1H), 1.98-2.06 (m, 1H), 2.27-2.33 (m, 1H), 2.65-2.69 (m, 1H), 2.73-2.84 (m, 2H), 3.85 (d, J=4.2 Hz, 1H), 4.12 (td, J=10.2, 2.3 Hz, 1H), 4.33 (dd, J=8.2, 2.9 Hz, 1H), 4.47 (t, J=10.9 Hz, 1H), 8.08 (d, J=9.7 Hz, 1H), 8.29 (dd, J=4.2, 1.5 Hz, 1H), 8.33 (s, 3H), 8.48 (d, J=4.2 Hz, 1H), 9.11-9.12 (m, 1H).

Example 1.136: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-3,3,3-Trifluoro-1-hydroxymethyl-propyl)-amide (Compound 914)

Step A: Preparation of (S)-2-Amino-4,4,4-trifluorobutan-1-ol

To an ice-cooled solution of (S)-2-(tert-butoxycarbonylamino)-4,4,4-trifluorobutanoic acid (1.0 g, 3.89 mmol) and N-ethyl-N-isopropylpropan-2-amine (0.813 mL, 4.67 mmol) in THF (15 mL) was added dropwise ethyl chloroformate (0.409 mL, 4.28 mmol). The cooling bath was removed and the mixture was stirred at 23° C. for 2 h. The mixture was filtered to remove the white precipitate, and the filtrate was treated with a 2 M THF solution of lithium borohydride (1.944 mL, 3.89 mmol) resulting in vigorous gas evolution. The mixture was stirred at room temperature for 2 h. Brine (25 mL) was added. The mixture was extracted with ethyl acetate (3×25 mL). The combined organic extracts were dried (MgSO$_4$), filtered, then concentrated under vacuum. The residue was purified by silica gel column chromatography to give (S)-tert-butyl 4,4,4-trifluoro-1-hydroxybutan-2-ylcarbamate (0.80 g) as a white solid. This solid material was treated with 4 M HCl in dioxane (10 mL) for 60 min then concentrated to give the title compound (0.54 g) as a white solid. $^1$H NMR (400 MHz, CD$_3$OD) δ 2.55-2.79 (m, 2H), 3.42 (bs, 1H), 3.54 (dd, J=11.6, 5.6 Hz, 1H), 3.66 (dd, J=11.6, 3.9 Hz, 1H), 3.53 (bs, 1H), 8.27 (bs, 3H).

Step B: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-3,3,3-Trifluoro-1-hydroxymethyl-propyl)-amide To a solution of Intermediate 5 (75 mg, 0.290 mmol), (S)-2-amino-4,4,4-trifluorobutan-1-ol, HCl (52.2 mg, 0.290 mmol), and triethylamine (0.121 mL, 0.871 mmol) in DMF (1 mL) was added HATU (110 mg, 0.290 mmol). The mixture was stirred at 23° C. for 2 h. The mixture was concentrated then purified by silica gel column chromatography to give the title compound (75 mg) as a white solid. LCMS m/z=384.1 [M+H]$^+$; $^1$H NMR (400 MHz, CDCl$_3$) δ 0.48 (td, J=4.7, 3.3 Hz, 1H), 1.28 (td, J=8.0, 4.9 Hz, 1H), 2.28-2.34 (m, 1H), 2.50-2.66 (m, 2H), 2.71-2.76 (m, 1H), 2.92 (d, J=17.1 Hz, 1H), 2.99 (dd, J=16.7, 6.2 Hz, 1H), 3.85-3.86 (m, 2H), 4.34-4.42 (m, 1H), 7.20 (d, J=8.0 Hz, 1H), 7.99 (dd, J=4.2, 1.5 Hz, 1H), 8.28 (dd, J=4.0, 0.5 Hz, 1H), 8.79 (dd, J=1.5, 0.6 Hz, 1H).

Example 1.137: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1,1-bis-Hydroxymethyl-2-methyl-propyl)-amide (Compound 925)

Step A: Preparation of 2-Amino-2-isopropylpropane-1,3-diol

To a solution of 2-amino-2-(hydroxymethyl)-3-methylbutanoic acid (2943 mg, 20 mmol) in THF (60 mL) was added sodium borohydride (2270 mg, 60.0 mmol). The reaction was cooled in an ice bath, and a THF (10 mL) solution of iodine (7614 mg, 30.0 mmol) was added dropwise. The mixture was refluxed (66° C.) for 16 h. The reaction was cooled in an ice bath, and methanol (10 mL) was added (dropwise at first) followed by brine (75 mL). The mixture was extracted with ethyl acetate (2×50 mL). The combined organic extracts were washed with brine, dried (MgSO$_4$), then filtered. 4 M HCl in dioxane (6 mL) was added. The mixture was then concentrated. Ether was added, and the precipitate was collected to give the title compound (300 mg) as a white solid.

Step B: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1,1-bis-Hydroxymethyl-2-methyl-propyl)-amide To a solution of Intermediate 5 (75 mg, 0.290 mmol), 2-amino-2-isopropylpropane-1,3-diol (38.7 mg, 0.290 mmol), and triethylamine (0.121 mL, 0.871 mmol) in DMF (1 mL) was added HATU (110 mg, 0.290 mmol). The mixture was stirred at 23° C. for 20 min then concentrated. The residue was purified by preparative TLC to give the title compound (12 mg) as a white solid. LCMS m/z=374.1 [M+H]$^+$; $^1$H NMR (400 MHz, CDCl$_3$) δ 0.48 (td, J=4.8, 3.3 Hz, 1H), 1.02 (d, J=7.0 Hz, 6H), 1.28 (td, J=8.0, 5.1 Hz, 1H), 2.20-2.34 (m, 2H), 2.72-2.76 (m, 1H), 2.90 (d, J=16.4 Hz, 1H), 2.99 (dd, J=16.6, 6.2 Hz, 1H), 3.76 (d, J=10.7 Hz, 2H), 3.99 (d, J=10.1 Hz, 4H), 7.24 (s, 1H), 8.00 (dd, J=4.0, 1.5 Hz, 1H), 8.29 (dd, J=4.0, 0.5 Hz, 1H), 8.77 (dd, J=1.5, 0.8 Hz, 1H).

Example 1.138: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((R)-1,2-Dimethyl-propyl)-amide (Compound 912)

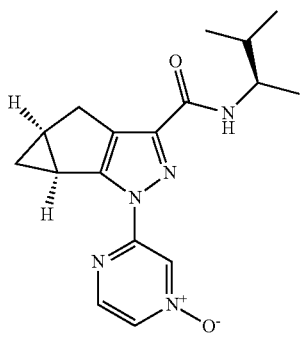 [SMILES: CC(C)[C@@H](C)NC(=O)c1nn(-c2c[n+]([O-])ccn2)c2c1C[C@@H]1C[C@H]21]

The title compound was prepared in a manner similar to that described in Method UU using Intermediate 5 and (R)-3-methylbutan-2-amine. LCMS m/z=328.3 [M+H]$^+$; $^1$H NMR (400 MHz, CDCl$_3$) δ 0.46-0.50 (m, 1H), 0.96 (d, J=6.8 Hz, 3H), 0.97 (d, J=6.7 Hz, 3H), 1.19 (d, J=6.9 Hz, 3H), 1.26 (td, J=8.2, 4.8 Hz, 1H), 1.75-1.87 (m, 1H), 2.26-2.33 (m, 1H), 2.70-2.75 (m, 1H), 2.94 (d, J=16.8 Hz, 1H), 3.01 (dd, J=16.6, 6.0 Hz, 1H), 3.95-4.05 (m, 1H), 6.64 (d, J=9.0 Hz, 1H), 7.98 (dd, J=4.0, 1.4 Hz, 1H), 8.28 (d, J=4.0 Hz, 1H), 8.78-8.80 (m, 1H).

Example 1.139: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((R)-1,2-Dimethyl-propyl)-amide (Compound 828)

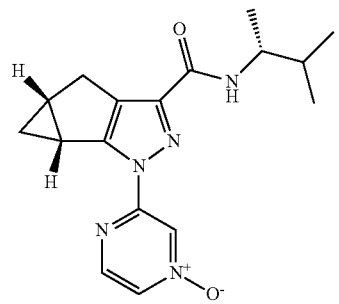 [SMILES: CC(C)[C@@H](C)NC(=O)c1nn(-c2c[n+]([O-])ccn2)c2c1C[C@H]1C[C@@H]21]

The title compound was prepared in a manner similar to that described in Method UU using Intermediate 6 and (R)-3-methylbutan-2-amine. LCMS m/z=328.3 [M+H]$^+$; $^1$H NMR (400 MHz, CDCl$_3$) δ 0.44-0.48 (m, 1H), 0.95 (d, J=6.8 Hz, 3H), 0.97 (d, J=6.9 Hz, 3H), 1.18 (d, J=6.9 Hz, 3H), 1.26 (td, J=8.0, 4.9 Hz, 1H), 1.75-1.88 (m, 1H), 2.26-2.33 (m, 1H), 2.70-2.75 (m, 1H), 2.93 (d, J=17.1 Hz, 1H), 3.02 (dd, J=16.7, 6.2 Hz, 1H), 3.95-4.05 (m, 1H), 6.64 (d, J=8.9 Hz, 1H), 7.98 (dd, J=4.0, 1.4 Hz, 1H), 8.28 (d, J=4.0 Hz, 1H), 8.79-8.80 (m, 1H).

Example 1.140: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (2-Fluoro-1,1-dimethyl-ethyl)-amide (Compound 904)

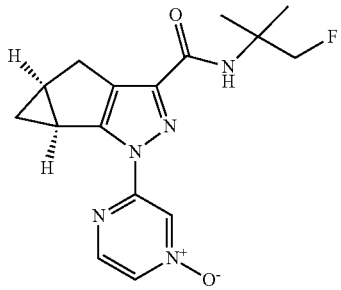 [SMILES: CC(C)(CF)NC(=O)c1nn(-c2c[n+]([O-])ccn2)c2c1C[C@@H]1C[C@H]21]

The title compound was prepared in a manner similar to that described in Method UU using Intermediate 5 and 1-fluoro-2-methylpropan-2-amine. LCMS m/z=332.2

[M+H]+; 1H NMR (400 MHz, CDCl3) δ 0.44-0.48 (m, 1H), 1.27 (td, J=8.0, 5.0 Hz, 1H), 1.46 (s, 3H), 1.47 (s, 3H), 2.26-2.34 (m, 1H), 2.703-2.76 (m, 1H), 2.91 (d, J=16.9 Hz, 1H), 3.00 (dd, J=16.6, 6.2 Hz, 1H), 4.54 (d, J=47.5 Hz, 2H), 6.73 (s, 1H), 7.98 (dd, J=4.0, 1.5 Hz, 1H), 8.28 (d, J=4.2 Hz, 1H), 8.78-8.79 (m, 1H).

Example 1.141: Preparation of (1aS,5aS)-2-(4-Chloro-pyridin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide (Compound 887)

Step A: Preparation of (1aS,5aS)-2-(4-Bromo-pyridin-2-yl)-1a,2,5,5a-tetrahydro-1H-2,3-diaza-cyclopropa[a]pentalene-4-carboxylic Acid Ethyl Ester The title compound was prepared in a manner similar to that described in Method KKK, using (1S,5R)-bicyclo[3.1.0]hexan-2-one and 4-bromo-2-hydrazinylpyridine. LCMS m/z=348.0 [M+H]+.

Step B: Preparation of (1aS,5aS)-2-(4-Chloro-pyridin-2-yl)-1a,2,5,5a-tetrahydro-1H-2,3-diaza-cyclopropa[a]pentalene-4-carboxylic Acid To a solution of (1aS,5aS)-2-(4-bromo-pyridin-2-yl)-1a,2,5,5a-tetrahydro-1H-2,3-diaza-cyclopropa[a]pentalene-4-carboxylic acid ethyl ester (2.1 g, 6.0 mmol) in acetonitrile (30 mL) was added concentrated HCl (1.4 mL, 18.0 mmol). The reaction was stirred for 6 h at 80° C., and then diluted with H2O. The solid was filtered, washed with H2O, and dried to give (1aS,5aS)-2-(4-chloro-pyridin-2-yl)-1a,2,5,5a-tetrahydro-1H-2,3-diaza-cyclopropa[a]pentalene-4-carboxylic acid ethyl ester (1.7 g) which contained ~20% of the hydrolyzed acid. The aforementioned ester was dissolved in dioxane (10 mL). After addition of 1 N LiOH (9.0 mL), the reaction was stirred for 4 h at 40° C. The reaction was cooled down to room temperature, diluted with H2O, and acidified with 4 N HCl to form a precipitate. The solid was filtered, washed with H2O, and dried to give the title compound. LCMS m/z=276.1 [M+H]+.

Step C: Preparation of (1aS,5aS)-2-(4-Chloro-pyridin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide The title compound was prepared in a manner similar to that described in Method UU using (1aS,5aS)-2-(4-chloro-pyridin-2-yl)-1a,2,5,5a-tetrahydro-1H-2,3-diaza-cyclopropa[a]pentalene-4-carboxylic acid and (S)-2-amino-3-methylbutan-1-ol. LCMS m/z=361.2 [M+H]+; 1H NMR (400 MHz, CDCl3) δ 0.43-0.48 (m, 1H), 1.02 (d, J=6.8 Hz, 3H), 1.04 (d, J=6.8 Hz, 3H), 1.20-1.27 (m, 1H), 1.98-1.20 (m, 1H), 2.20-2.27 (m, 1H), 2.74-2.79 (m, 1H), 2.80-2.86 (m, 1H), 2.91 (d, J=16.7 Hz, 1H), 2.99 (dd, J=16.5, 6.2 Hz, 1H), 3.74-3.90 (m, 3H), 7.02 (d, J=8.2 Hz, 1H), 7.20 (dd, J=5.3, 1.9 Hz, 1H), 7.92 (d, J=1.8 Hz, 1H), 8.35 (d, J=5.3 Hz, 1H).

Example 1.142: Preparation of (1aS,5aS)-2-(4-Oxypyrazin-2-yl)-1a,2,5,5a-tetrahydro-1H-2,3-diaza-cyclopropa[a]pentalene-4-carboxylic Acid ((S)-2-Hydroxy-1-phenyl-ethyl)-amide (Compound 913)

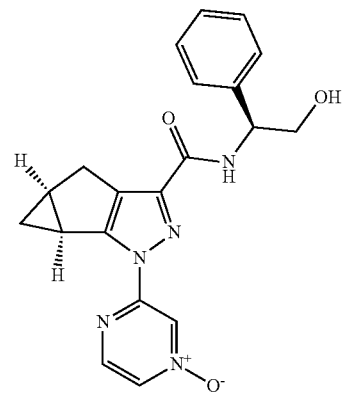 [SMILES: O=C(N[C@H](CO)c1ccccc1)c1nn(-c2c[n+]([O-])ccn2)c2c1C[C@@H]1C[C@H]21]

The title compound was prepared in a manner similar to that described in Method UU using Intermediate 5 and (S)-2-amino-2-phenylethanol. LCMS m/z=378.3 [M+H]+; 1H NMR (400 MHz, CDCl3) δ 0.43-0.47 (m, 1H), 1.26 (td, J=7.8, 4.9 Hz, 1H), 2.26-2.33 (m, 1H), 2.55 (bs, 1H), 2.70-2.76 (m, 1H), 2.90 (d, J=16.9 Hz, 1H), 3.00 (dd, J=16.7, 6.3 Hz, 1H), 3.95-4.04 (m, 2H), 5.18-5.24 (m, 1H), 7.29-7.35 (m, 1H), 7.36-7.41 (m, 4H), 7.44 (d, J=7.4 Hz, 1H), 7.98 (dd, J=4.2, 1.5 Hz, 1H), 8.28 (d, J=4.2 Hz, 1H), 8.80 (d, J=1.1 Hz, 1H).

Example 1.143: Preparation of (1aS,5aS)-2-(4-Chloro-pyridin-2-yl)-1a,2,5,5a-tetrahydro-1H-2,3-diaza-cyclopropa[a]pentalene-4-carboxylic Acid ((S)-2-Fluoro-1-hydroxymethyl-2-methyl-propyl)-amide (Compound 911)

Step A: Preparation of 2-{[(1aS,5aS)-2-(4-Chloro-pyridin-2-yl)-1a,2,5,5a-tetrahydro-1H-2,3-diaza-cyclopropa[a]pentalene-4-carbonyl]-amino}-3-fluoro-3-methyl-butyric Acid Methyl Ester The title compound was prepared by HATU coupling method using (1aS,5aS)-2-(4-chloro-pyridin-2-yl)-1a,2,5,5a-tetrahydro-1H-2,3-diaza-cyclopropa[a]pentalene-4-carboxylic acid and methyl 2-amino-3-fluoro-3-methylbutanoate hydrochloride. LCMS m/z=407.2 [M+H]+; 1H NMR (400 MHz, CDCl3) δ 0.42-0.50 (m, 1H), 1.23-1.30 (m, 1H), 1.49 (d, J=21.6 Hz, 3H), 1.57 (d, J=21.0 Hz, 3H), 2.22-2.30 (m, 1H), 2.79-2.85 (m, 1H), 2.87-3.05 (m, 2H), 3.81 (s, 3H), 4.85-4.94 (m, 1H), 7.22 (dd, J=5.4 and 1.8 Hz, 1H), 7.56 (d, J=9.5 Hz, 1H), 8.01 (d, J=1.8 Hz, 1H), 8.35 (d, J=5.4 Hz, 1H).

Step B: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1-hydroxymethyl-2-methyl-propyl)-amide 2-{[(1aS,5aS)-2-(4-Chloro-pyridin-2-yl)-1a,2,5,5a-tetrahydro-1H-2,3-diaza-cyclopropa[a]pentalene-4-carbonyl]-amino}-3-fluoro-3-methyl-butyric acid methyl ester (171 mg, 0.420 mmol) was dissolved in dioxane (3 mL) and water (2 mL). Sodium borohydride (63.6 mg, 1.681 mmol) was added slowly at 0° C. The reaction mixture was stirred at room temperature overnight, neutralized with 1 N HCl solution, then extracted with ethyl acetate. The combined organics were washed with water, dried over anhydrous $Na_2SO_4$, filtered then concentrated. The residue was purified by column chromatography to give the title compound as a white foam. LCMS m/z=379.4 [M+H]$^+$; $^1$H NMR (400 MHz, CDCl$_3$) δ 0.45-0.50 (m, 1H), 1.23-1.30 (m, 1H), 1.47 (d, J=22.1 Hz, 3H), 1.53 (d, J=21.7 Hz, 3H), 2.22-2.30 (m, 1H), 2.33-2.40 (m, 1H), 2.78-2.85 (m, 1H), 2.88-3.05 (m, 2H), 3.90-4.00 (m, 2H), 4.11-4.25 (m, 1H), 7.22 (dd, J=5.3 and 1.8 Hz, 1H), 7.36 (d, J=9.3 Hz, 1H), 7.97 (d, J=1.4 Hz, 1H), 8.35 (d, J=5.3 Hz, 1H).
Resolution Via Chiral HPLC.
Column: Chiralpak IA: 250×20 mm (L×ID), 5 μM particle size
Eluent: 5% ethanol/hexanes
Gradient: Isocratic
Flow: 10 mL/min
Detector: 280 nm
Retention Times: 1$^{st}$ diastereomer: 25.6 min; 2$^{nd}$ diastereomer: 28.9 min.

Example 1.144: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Fluoromethyl-2,2-dimethyl-propyl)-amide (Compound 916)

Step A: Preparation of (S)-2-(Benzylamino)-3,3-dimethylbutan-1-ol (S)-2-Amino-3,3-dimethylbutan-1-ol (4.01 g, 34.2 mmol) was dissolved in benzene (120 mL). Benzaldehyde (3.65 mL, 35.9 mmol) and p-TsOH monohydrate (1.302 mg, 6.84 μmol) were added. The reaction mixture was heated at reflux for 5 h using Dean-Stark to remove water, the mixture was then concentrated. The residue was dissolved in anhydrous MeOH (100 mL), cooled down in an ice-water bath, and added sodium borohydride (1.942 g, 51.3 mmol) slowly. The reaction mixture was stirred for 30 min, quenched with 1 N NaOH solution, diluted with water, and extracted with ethyl acetate. The combined organics were washed with water, dried over anhydrous $Na_2SO_4$, filtered, then concentrated to give the title compound (5.77 g) as a colorless oil without further purification. LCMS m/z=208.2 [M+H]$^+$; $^1$H NMR (400 MHz, CDCl$_3$) δ 0.88 (s, 9H), 2.33 (dd, J=6.4 and 4.7 Hz, 1H), 3.34 (dd, J=10.6 and 6.4 Hz, 1H), 3.59 (dd, J=10.6 and 4.7 Hz, 1H), 3.76 and 3.85 (dd, J=12.8 Hz, 2H), 7.20-7.27 (m, 5H).

Step B: Preparation of (4S)-4-(tert-Butyl)-3-(phenylmethyl)-1,2,3-oxathiazolidine-2-oxide (S)-2-(Benzylamino)-3,3-dimethylbutan-1-ol (5.77 g, 27.8 mmol) in dry DCM (100 mL) was cooled down to −20° C., DIEA (19.39 ml, 111 mmol) was added, followed by thionyl chloride (2.228 ml, 30.6 mmol) in DCM (10 mL). The reaction mixture was stirred for 1 h at this temperature, then concentrated. The residue was purified by column chromatography to give the title compound (6.26 g) as a diastereomeric mixture. LCMS m/z=254.0 [M+H]$^+$.

Step C: Preparation of (4S)-4-(tert-Butyl)-3-(phenylmethyl)-1,2,3-oxathiazolidine-2,2-dioxide To a solution of (4S)-4-(tert-butyl)-3-(phenylmethyl)-1,2,3-oxathiazolidine-2-oxide (6.26 g, 24.71 mmol) in acetonitrile (30 mL) and water (30 mL) at 0° C. was added ruthenium chloride hydrate (5.13 mg, 0.025 mmol), followed by sodium periodate (7.93 g, 37.1 mmol). The reaction mixture was slowly warmed to room temperature and stirred for 3 h, diluted with water, extracted with ethyl acetate. The combined organics were washed with water, dried over anhydrous $Na_2SO_4$, filtered then concentrated to give the title compound (6.22 g) as an off-white solid. LCMS m/z=270.2 [M+H]$^+$; $^1$H NMR (400 MHz, CDCl$_3$) δ 1.00 (s, 9H), 3.25-3.30 (m, 1H), 4.31-4.40 (m, 2H), 4.47 and 4.55 (dd, J=15.2 Hz, 2H), 7.30-7.48 (m, 5H).

Step D: Preparation of (S)—N-Benzyl-1-fluoro-3,3-dimethylbutan-2-amine

To a solution of (4S)-4-(tert-butyl)-3-(phenylmethyl)-1,2,3-oxathiazolidine-2,2-dioxide (6.22 g, 23.09 mmol) in THF (100 mL) was added a 1 M solution of tetrabutylammonium fluoride in THF (46.2 ml, 46.2 mmol) at 0° C. The reaction mixture was warmed to room temperature and stirred overnight. Solvent was evaporated, and ether (50 mL) and 20% $H_2SO_4$ aqueous solution (20 mL) were added. The reaction mixture was stirred for 2 h at room temperature, diluted with water, neutralized with solid NaHCO$_3$ slowly then extracted with ethyl acetate. The combined organics were dried over anhydrous $Na_2SO_4$, filtered, then concentrated. The residue was purified by column chromatography to give the title compound (4.13 g) as a light yellow oil. LCMS m/z=210.4 [M+H]$^+$; $^1$H NMR (400 MHz, CDCl$_3$) δ 0.96 (s, 9H), 2.41 (dt, J=24.7 and 4.3 Hz, 1H), 3.76 (d, J=13.1 Hz, 1H), 4.01 (d, J=13.1 Hz, 1H), 4.39-4.72 (m, 2H), 7.23-7.38 (m, 5H).

Step E: Preparation of (S)-1-Fluoro-3,3-dimethylbutan-2-amine Hydrochloride

To a solution of (S)—N-benzyl-1-fluoro-3,3-dimethylbutan-2-amine (4.12 g, 19.68 mmol) in methanol (50 mL) was added 10% palladium on carbon (2.095 g, 1.968 mmol). The reaction mixture was shaken under H$_2$ atmosphere (60 Psi) for 24 h, a 1.25 M solution of HCl in ethanol (31.5 mL, 39.4 mmol) was added. The reaction mixture was stirred at room temperature for 1 h. The solid was filtered through Celite, washed with methanol. The filtrate was concentrated to give the title compound (3.1 g). $^1$H NMR (400 MHz, DMSO-d$_6$) δ 0.96 (s, 9H), 3.11-3.20 (m, 1H), 4.55-4.82 (m, 2H), 8.26 (s, 3H).

Step F: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Fluoromethyl-2,2-dimethyl-propyl)-amide The title compound was prepared in a manner similar to that described in Method UU, using Intermediate 5 and (S)-1-fluoro-3,3-dimethylbutan-2-amine hydrochloride. LCMS m/z=360.2 [M+H]$^+$; $^1$H NMR (400 MHz, CDCl$_3$) δ 0.50 (td, J=4.6 and 3.2 Hz, 1H), 1.05 (s, 9H), 1.25-1.30 (m, 1H), 2.27-2.35 (m, 1H), 2.72-2.77 (m, 1H), 2.95 (dt, J=16.8 and 0.7 Hz, 1H), 3.01 (dd, J=16.6 and 5.8 Hz, 1H), 4.03-4.15 (m, 1H), 4.48-4.74 (m, 2H), 7.04 (d, J=10.1 Hz, 1H), 7.99 (dd, J=4.1 and 1.5 Hz, 1H), 8.28 (dd, J=4.1 and 0.6 Hz, 1H), 8.80 (dd, J=1.5 and 0.7 Hz, 1H).

Example 1.145: Preparation of (1aR,5aR)-2-(4-Oxy-pyrazin-2-yl)-1a,2,5,5a-tetrahydro-1H-2,3-di-aza-cyclopropa[a]pentalene-4-carboxylic Acid ((S)-1-Fluoromethyl-2,2-dimethyl-propyl)-amide (Compound 918)

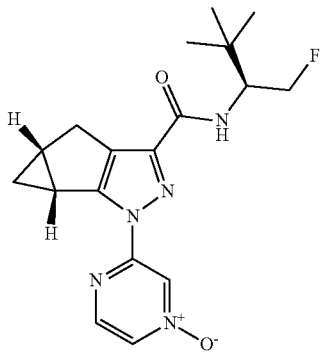 [SMILES: CC(C)(C)[C@@H](CF)NC(=O)c1nn(-c2c[n+]([O-])ccn2)c2c1C[C@H]1C[C@@H]21]

The title compound was prepared in a manner similar to that described in Method UU, using Intermediate 6 and (S)-1-fluoro-3,3-dimethylbutan-2-amine hydrochloride. LCMS m/z=360.2 [M+H]$^+$; $^1$H NMR (400 MHz, CDCl$_3$) δ 0.50 (td, J=4.6 and 3.2 Hz, 1H), 1.05 (s, 9H), 1.25-1.30 (m, 1H), 2.27-2.35 (m, 1H), 2.72-2.77 (m, 1H), 2.93 (d, J=16.9 Hz, 1H), 3.01 (dd, J=16.6 and 6.2 Hz, 1H), 4.03-4.15 (m, 1H), 4.48-4.74 (m, 2H), 7.04 (d, J=10.0 Hz, 1H), 7.99 (dd, J=4.1 and 1.5 Hz, 1H), 8.28 (d, J=4.1 Hz, 1H), 8.81 (d, J=1.5 Hz, 1H).

Example 1.146: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Fluoromethyl-cyclobutyl)-amide (Compound 924)

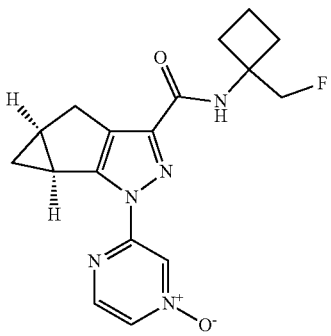 [SMILES: O=C(NC1(CF)CCC1)c1nn(-c2c[n+]([O-])ccn2)c2c1C[C@@H]1C[C@H]21]

The title compound was prepared in a manner similar to that described in Method UU, using Intermediate 5 and 1-(fluoromethyl)cyclobutanamine hydrochloride, which was prepared in a similar manner to that described in Example 1.144, Step A to Step E, using (1-aminocyclobutyl)methanol. LCMS m/z=344.2 [M+H]$^+$; $^1$H NMR (400 MHz, CDCl$_3$) δ 0.48 (td, J=4.6 and 3.2 Hz, 1H), 1.24-1.29 (m, 1H), 1.85-1.95 (m, 1H), 2.00-2.10 (m, 1H), 2.27-2.47 (m, 5H), 2.70-2.75 (m, 1H), 2.91 (d, J=17.3 Hz, 1H), 3.00 (dd, J=16.7 and 6.2 Hz, 1H), 4.68 (d, J=47.8 Hz, 2H), 6.98 (s, 1H), 7.97 (dd, J=4.1 and 1.5 Hz, 1H), 8.28 (dd, J=4.1 and 0.7 Hz, 1H), 8.80 (dd, J=1.5 and 0.7 Hz, 1H).

Example 1.147: Preparation of (1aR,5aR)-2-(4-Oxy-pyrazin-2-yl)-1a,2,5,5a-tetrahydro-1H-2,3-di-aza-cyclopropa[a]pentalene-4-carboxylic Acid [1-(5-Fluoro-pyridin-2-yl)-2,2-dimethyl-propyl]-amide (Compound 832)

Step A: Preparation of 1-(5-Fluoropyridin-2-yl)-2,2-dimethylpropan-1-amine

To an ice-cooled solution of 5-fluoropicolinaldehyde (0.10 g, 0.799 mmol) in THF (5 mL) was added a 1.0 M THF solution of LiHMDS (0.879 mL, 0.879 mmol). The violet solution was stirred at 0° C. for 20 min then cooled to −78° C. A 1.7 M pentane solution of tert-butyllithium (0.470 mL, 0.799 mmol) was added dropwise. Stirring was continued for 1.5 h at −78° C. The reaction was carefully quenched by addition of water (20 mL). The layers were separated, and the aqueous layer was extracted with ethyl acetate. The combined organics were washed with brine, dried over anhydrous MgSO$_4$, filtered, then concentrated to give the title compound (123 mg) as an orange oil. LCMS m/z=183.2 [M+H]$^+$.

Step B: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid [1-(5-Fluoro-pyridin-2-yl)-2,2-dimethyl-propyl]-amide To a solution of Intermediate 6 (175 mg, 0.678 mmol), 1-(5-fluoropyridin-2-yl)-2,2-dimethylpropan-1-amine (123 mg, 0.678 mmol), and triethylamine (0.189 mL, 1.355 mmol) in DMF (5 mL) was added HATU (309 mg, 0.813 mmol). The reaction was stirred at 23° C. for 20 min then purified by preparative HPLC to give the title compound (120 mg) as a mixture of epimers. LCMS m/z=423.3 [M+H]$^+$.

Resolution Via Chiral HPLC.

Column: Chiralpak IA: 250×20 mm (L×ID), 5 μM particle size

Eluent: 35% IPA/hexanes

Gradient: Isocratic

Flow: 8 mL/min

Detector: 280 nm

Retention Times: 1$^{st}$ diastereomer: 15.6 min; 2$^{nd}$ diastereomer: 19.0 min.

1$^{st}$ Diastereomer: 15.6 Min $^1$H NMR (400 MHz, CDCl$_3$) δ 0.51 (td, J=4.5 and 3.4 Hz, 1H), 0.98 (s, 9H), 1.22-1.28 (m, 1H), 2.22-2.30 (m, 1H), 2.70-2.75 (m, 1H), 2.93-2.96 (m, 2H), 5.05 (d, J=9.6 Hz, 1H), 7.20 (dd, J=8.6 and 4.3, 1H), 7.32 (td, J=8.5 and 2.9 Hz, 1H), 8.00 (dd, J=4.0 and 1.4 Hz, 1H), 8.02 (d, J=9.6 Hz, 1H), 8.29 (d, J=4.1 Hz, 1H), 8.48 (d, J=2.8 Hz, 1H), 8.91 (m, 1H).

2$^{nd}$ Diastereomer: 19.0 Min $^1$H NMR (400 MHz, CDCl$_3$) δ 0.51 (td, J=4.5 and 3.4 Hz, 1H), 0.98 (s, 9H), 1.22-1.28 (m, 1H), 2.25-2.32 (m, 1H), 2.70-2.75 (m, 1H), 2.87 (dd, J=16.8 and 1.6 Hz, 1H), 3.03 (dd, J=16.7 and 6.5 Hz, 1H), 5.05 (d, J=9.6 Hz, 1H), 7.20 (dd, J=8.6 and 4.3, 1H), 7.32 (td, J=8.5 and 2.9 Hz, 1H), 8.00 (dd, J=4.0 and 1.4 Hz, 1H), 8.02 (d, J=9.6 Hz, 1H), 8.29 (d, J=4.1 Hz, 1H), 8.48 (d, J=2.8 Hz, 1H), 8.91 (m, 1H).

Example 1.148: Preparation of (1aR,5aR)-2-(4-Fluoro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 931)

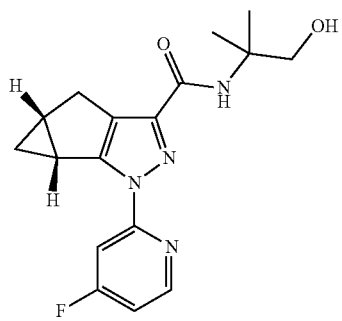 [SMILES: CC(C)(CO)NC(=O)c1nn(-c2cc(F)ccn2)c2c1C[C@H]1C[C@@H]21]

Step A: Preparation of 2-Hydrazinyl-4-iodopyridine

To a solution of 2-fluoro-4-iodopyridine (7.00 g, 31.4 mmol) in ethanol (60 mL) was added hydrazine monohydrate (15.23 mL, 314 mmol). The mixture was stirred at 40° C. for 15 h then concentrated. The resulting residue was triturated with 1:1 hexanes/ether. The remaining solid was further triturated with water then dried under vacuum to give the title compound (6.6 g) as a tan solid. LCMS m/z=235.9 [M+H]+. 1H NMR (400 MHz, DMSO-d6) δ 4.15 (s, 2H), 6.86 (dd, J=5.2, 1.5 Hz, 1H), 7.13 (d, J=1.5 Hz, 1H), 7.56 (s, 1H), 7.67 (d, J=5.3 Hz, 1H).

Step B: Preparation of (1aR,5aR)-2-(4-Iodo-pyridin-2-yl)-1a,2,5,5a-tetrahydro-1H-2,3-diaza-cyclopropa[a]pentalene-4-carboxylic Acid Ethyl Ester To a solution of (1R,5S)-bicyclo[3.1.0]hexan-2-one (2.045 g, 21.27 mmol) and diethyl oxalate (2.91 mL, 21.27 mmol) in absolute ethanol (100 mL) was added a 1.0 M THF solution of potassium 2-methylpropan-2-olate (21.27 mL, 21.27 mmol). The mixture was stirred at 40° C. for 4 h. 2-Hydrazinyl-4-iodopyridine (5.00 g, 21.27 mmol) was added followed by a 3.0 M aqueous solution of hydrogen chloride (21.27 mL, 63.8 mmol). The reaction was stirred at 45° C., for 16 h. Brine (150 mL) was added. The mixture was extracted with dichloromethane (3×50 mL). The combined organic extracts were washed with brine (100 mL), dried (MgSO4), filtered, and then concentrated. The residue was purified by silica gel flash chromatography to give the title compound (5.8 g) as a white solid. LCMS m/z=396.1 [M+H]+; 1H NMR (400 MHz, CDCl3) δ 0.44 (td, J=4.7, 3.5 Hz, 1H), 1.25 (td, J=8.0, 5.1 Hz, 1H), 1.40 (t, J=7.1 Hz, 3H), 2.22-2.29 (m, 1H), 2.80-2.85 (m, 1H), 2.85 (d, J=17.1 Hz, 1H), 2.97 (dd, J=16.9, 6.6 Hz, 1H), 4.39 (q, J=7.1 Hz, 2H), 7.57 (dd, J=5.2, 1.4 Hz, 1H), 8.10 (d, J=5.2 Hz, 1H), 8.48 (s, 1H).

Step C: Preparation of (1aR,5aR)-2-(4-Iodo-pyridin-2-yl)-1a,2,5,5a-tetrahydro-1H-2,3-diaza-cyclopropa[a]pentalene-4-carboxylic Acid To a solution of (1aR,5aR)-2-(4-iodo-pyridin-2-yl)-1a,2,5,5a-tetrahydro-1H-2,3-diaza-cyclopropa[a]pentalene-4-carboxylic acid ethyl ester in MeOH (10.00 mL) and THF (10.00 mL) was added a 2 M aqueous solution of sodium hydroxide (5.20 mL, 10.40 mmol). The mixture was stirred at room temperature for 2 h then concentrated. The remaining solid was dissolved in water (30 mL). The solution was acidified to pH ~2 by addition of 6 M aqueous HCl. The resulting precipitate was collected by filtration, rinsed with water, then dried to give the title compound (190 mg) as a white solid. LCMS m/z=368.1 [M+H]+.

Step D: Preparation of (1aR,5aR)-2-(4-Fluoro-pyridin-2-yl)-1a,2,5,5a-tetrahydro-1H-2,3-diaza-cyclopropa[a]pentalene-4-carboxylic Acid To a solution of (1aR,5aR)-2-(4-iodo-pyridin-2-yl)-1a,2,5,5a-tetrahydro-1H-2,3-diaza-cyclopropa[a]pentalene-4-carboxylic acid (174 mg, 0.47 mmol) in DMSO (2.5 mL) was added cesium fluoride (500 mg, 3.29 mmol). The mixture was heated under microwave irradiation at 200° C. for 60 min. The mixture was purified by preparative HPLC to give the title compound as a white solid (85 mg). LCMS m/z=260.1 [M+H]+.

Step E: Preparation of (1aR,5aR)-2-(4-Fluoro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide To a solution of (1aR,5aR)-2-(4-fluoro-pyridin-2-yl)-1a,2,5,5a-tetrahydro-1H-2,3-diaza-cyclopropa[a]pentalene-4-carboxylic acid (68 mg, 0.262 mmol), 2-amino-2-methyl-propan-1-ol (23.38 mg, 0.262 mmol), and triethylamine (0.073 mL, 0.525 mmol) in DMF (1 mL) was added HATU (105 mg, 0.275 mmol). The reaction was stirred at 23° C. for 20 min then concentrated. The residue was purified by silica gel column chromatography to give the title compound (80 mg) as a white solid. LCMS m/z=331.3 [M+H]+; 1H NMR (400 MHz, CDCl3) δ 0.46 (td, J=4.6, 3.4 Hz, 1H), 1.26 (td, J=7.8, 4.9 Hz, 1H), 1.41 (s, 3H), 1.42 (s, 3H), 2.24-2.30 (m, 1H), 2.79-2.84 (m, 1H), 2.91 (d, J=16.8 Hz, 1H), 3.00 (dd, J=16.6, 6.3 Hz, 1H), 3.70 (d, J=6.4 Hz, 2H), 4.69 (t, J=6.3 Hz, 1H), 6.93-6.98 (m, 2H), 7.63 (dd, J=10.1, 2.4 Hz, 1H), 8.43 (dd, J=8.5, 5.7 Hz, 1H).

Example 1.149: Preparation of 1-(2,4-Difluoro-phenyl)-3b,4,4a,5-tetrahydro-1H-cyclopropa[3,4]cyclopenta[1,2-c]pyrazole-3-carboxylic Acid (2-Hydroxy-1,1-dimethyl-ethyl)-amide (Compound 515)

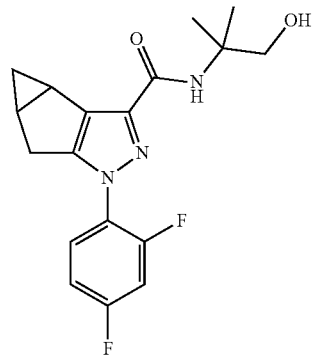 [SMILES: CC(C)(CO)NC(=O)c1nn(-c2ccc(F)cc2F)c2c1C1CC1C2]

The title compound was prepared in a manner similar to that described in Method X using 2-amino-2-methylpropan-1-ol. LCMS m/z=348.2 [M+H]⁺.

Example 1.150: Preparation of (1aR,5aR)-2-(5-Chloro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 151)

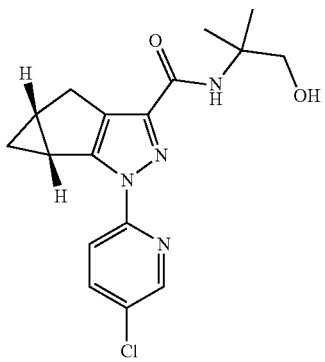 [SMILES: CC(C)(CO)NC(=O)c1nn(-c2ccc(Cl)cn2)c2c1C[C@H]1C[C@@H]21]

The title compound was prepared in a manner similar to that described in Method G using 2-amino-2-methylpropane-1,3-diol and (1aR,5aR)-2-(5-Chloropyridin-2-yl)-1a,2,5,5a-tetrahydro-1H-2,3-diaza-cyclopropa[a]pentalene-4-carboxylic acid. The aforementioned acid was prepared in a similar method as described in Method A and B using (1R,5S)-bicyclo[3,1,0]hexan-2-one and 5-chloro-2-hydrazinylpyridine. LCMS m/z=347.2 [M+H]⁺; ¹H NMR (400 MHz, CDCl₃) δ ppm 0.45 (td, J=4.7, 3.3 Hz, 1H), 1.25 (td, J=8.3, 4.4 Hz, 1H), 1.406 (s, 3H), 1.410 (s, 3H), 2.24-2.30 (m, 1H), 2.75-2.80 (m, 1H), 2.90 (d, J=16.6 Hz, 1H), 3.00 (dd, J=16.6, 6.4 Hz, 1H), 3.70 (s, 2H), 4.63 (bs, 1H), 6.92 (s, 1H), 7.78 (dd, J=8.7, 2.5 Hz, 1H), 7.87 (dd, J=8.8, 0.6 Hz, 1H), 8.41 (dd, J=2.5, 0.6 Hz, 1H).

Example 1.151: Preparation of (1aR,5aR)-2-(2,4-Dichloro-phenyl)-1a,2,5,5a-tetrahydro-1H-2,3-diaza-cyclopropa[a]pentalene-4-carboxylic Acid (1-Hydroxymethyl-cyclopropyl)-amide (Compound 174)

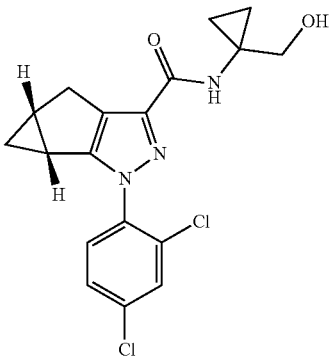 [SMILES: O=C(NC1(CO)CC1)c1nn(-c2ccc(Cl)cc2Cl)c2c1C[C@H]1C[C@@H]21]

The title compound was prepared in a manner similar to that described in Method G using (1aR,5aR)-2-(2,4-dichloro-phenyl)-1a,2,5,5a-tetrahydro-H-2,3-diaza-cyclopropa[a]pentalene-4-carboxylic acid and (1-hydroxymethyl-cyclopropyl)-amine. LCMS m/z=378.2 [M+H]⁺; ¹H NMR (400 MHz, CDCl₃) δ ppm 0.51 (td, J=4.6 and 3.4 Hz, 1H), 0.90-1.03 (m, 4H), 1.14-1.21 (m, 1H), 2.00-2.07 (m, 1H), 2.27-2.37 (m, 1H), 2.97 (d, J=16.6 Hz, 1H), 3.06 (dd, J=16.6 and 6.3 Hz, 1H), 3.71 (s, 2H), 7.28 (bs, 1H), 7.40 (dd, J=8.5 and 2.1 Hz, 1H), 7.44 (d, J=8.5 Hz, 1H), 7.58 (d, J=2.1 Hz, 1H).

Example 1.152: Preparation of (1aR,5aR)-2-Pyrazin-2-yl-1a,2,5,5a-tetrahydro-1H-2,3-diaza-cyclopropa[a]pentalene-4-carboxylic Acid tert-Butyl-amide (Compound 593)

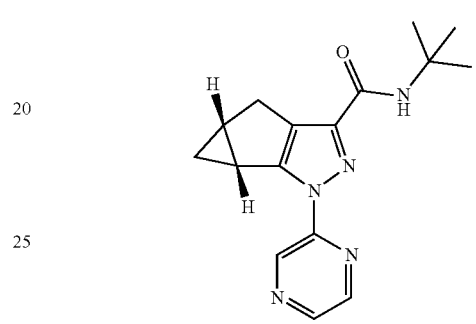

The title compound was prepared in a manner similar to that described in Method G using Intermediate 2 and tert-butyl amine. LCMS m/z=298.3 [M+H]⁺; ¹H NMR (400 MHz, CDCl₃) δ 0.47 (td, J=4.6 and 3.3 Hz, 1H), 1.22-1.27 (m, 1H), 1.48 (s, 9H), 2.25-2.32 (m, 1H), 2.71-2.76 (m, 1H), 2.93 (d, J=16.7 Hz, 1H), 3.02 (dd, J=16.6 and 6.2 Hz, 1H), 6.79 (s, 1H), 8.42 (br, 1H), 8.49 (d, J=2.0 Hz, 1H), 9.25 (s, 1H).

Example 1.153: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 644)

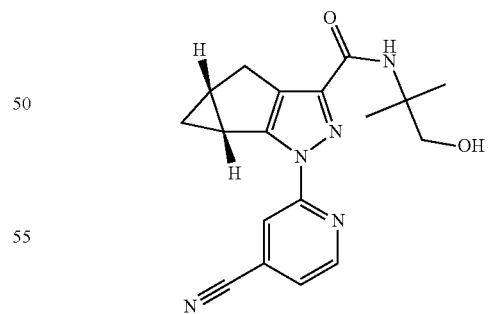

The title compound was prepared in a manner similar to that described in Method T using (1aR,5aR)-2-(5-bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide and dicyanozinc. LCMS m/z=338.3 [M+H]⁺; ¹H NMR (400 MHz, CDCl₃) δ ppm 0.47 (dd, J=4.6 and 3.4 Hz, 1H), 1.25-1.31 (m, 1H), 1.45 (s, 6H), 2.26-2.34 (m, 1H), 2.78-2.84 (m, 1H), 2.93 (d, J=16.1 Hz, 1H), 3.02

(dd, J=16.7 and 6.3 Hz, 1H), 3.73 (s, 2H), 6.93-6.97 (bs, 1H), 7.43 (dd, J=5.0 and 1.2 Hz, 1H), 8.17 (s, 1H), 8.63 (d, J=5.0, 1H).

Example 1.154: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide (Compound 690)

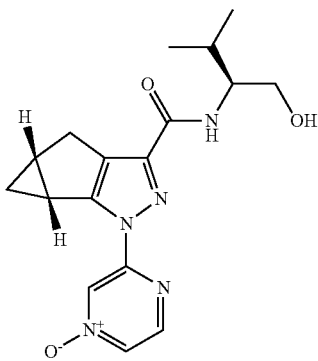 [SMILES: CC(C)[C@@H](CO)NC(=O)c1nn(-c2c[n+]([O-])ccn2)c2c1C[C@H]1C[C@@H]21]

The title compound was prepared in a manner similar to that described in Method CCC. LCMS m/z=344.3 [M+H]$^+$; $^1$H NMR (400 MHz, CDCl$_3$) δ ppm 0.47 (dd, J=8.0 and 4.7 Hz, 1H), 1.02 (t, J=7.2 Hz, 6H), 1.28 (td, J=8.0 and 5.0 Hz, 1H), 2.00-2.05 (m, 1H), 2.28-2.32 (m, 1H), 2.72-2.77 (m, 1H), 2.95 (d, J=17.3 Hz, 1H), 3.02 (dd, J=16.7 and 6.3 Hz, 1H), 3.73-3.89 (m, 3H), 6.98 (d, J=8.3 Hz, NH, 1H), 7.99 (dd, J=4.1 and 1.5 Hz, 1H), 8.28 (d, J=4.1 Hz, 1H), 8.80 (s, 1H).

Example 1.155: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-2,2-Dimethyl-1-methylcarbamoyl-propyl)-amide (Compound 704)

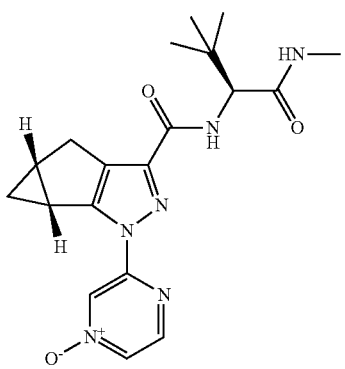 [SMILES: CNC(=O)[C@@H](NC(=O)c1nn(-c2c[n+]([O-])ccn2)c2c1C[C@H]1C[C@@H]21)C(C)(C)C]

The title compound was prepared in a manner similar to that described in Method CCC. LCMS m/z=385.3 [M+H]$^+$; $^1$H NMR (400 MHz, CDCl$_3$) δ ppm 0.44 (dd, J=8.0 and 4.7 Hz, 1H), 1.24-1.29 (m, 1H), 2.26-2.32 (m, 1H), 2.72-2.77 (m, 1H), 2.82 (d, J=4.8 Hz, 3H), 2.88 (d, J=16.7 Hz, 1H), 3.01 (dd, J=16.5 and 6.5 Hz, 1H), 4.30 (d, J=9.5 Hz, 1H), 5.90 (q, J=4.4 Hz, NH, 1H), 7.44 (d, J=9.5 Hz, NH, 1H), 8.00 (dd, J=4.1 and 1.5 Hz, 1H), 8.28 (d, J=4.1 Hz, 1H), 8.84 (s, 1H).

Example 1.156: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-Methylcarbamoyl-phenyl-methyl)-amide (Compound 722)

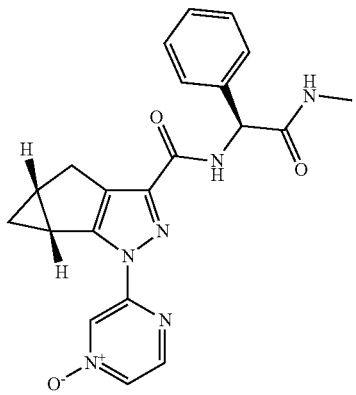 [SMILES: CNC(=O)[C@@H](NC(=O)c1nn(-c2c[n+]([O-])ccn2)c2c1C[C@H]1C[C@@H]21)c1ccccc1]

(S)-2-Amino-N-methyl-2-phenylacetamide was prepared in a manner similar to that described in Method HHH and III using (S)-2-(tert-butoxycarbonylamino)-2-phenylacetic acid and methylamine. The title compound was prepared in a manner similar to that described in Method G using (1aR,5aR)-2-(4-oxy-pyrazin-2-yl)-1a,2,5,5a-tetrahydro-1H-2,3-diaza-cyclopropa[a]pentalene-4-carboxylic acid and (S)-2-amino-N-methyl-2-phenylacetamide. LCMS m/z=405.3 [M+H]$^+$; $^1$H NMR (400 MHz, CDCl$_3$) δ ppm 0.40-0.47 (m, 1H), 1.21-1.29 (m, 1H), 2.23-2.31 (m, 1H), 2.69-2.75 (m, 1H), 2.83 (dd, J=4.9 and 1.9 Hz, 3H), 2.87 (d, J=16.9 Hz, 1H), 2.92-3.00 (m, 1H), 5.50 (d, J=6.8 Hz, 1H), 5.69 (bs, 1H), 7.30-7.41 (m, 3H), 7.43-7.48 (m, 2H), 7.97 (dd, J=4.0 and 1.4 Hz, 1H), 7.98-8.03 (m, 1H), 8.26 (d, J=4.0 Hz, 1H), 8.83-8.85 (m, 1H).

Example 1.157: Preparation of (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric Acid Methyl Ester (Compound 746)

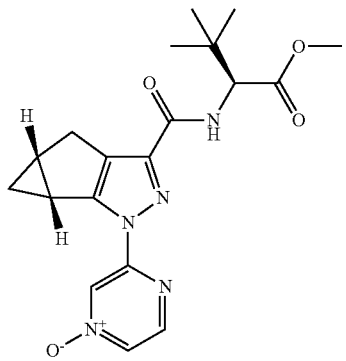 [SMILES: COC(=O)[C@@H](NC(=O)c1nn(-c2c[n+]([O-])ccn2)c2c1C[C@H]1C[C@@H]21)C(C)(C)C]

The title compound was prepared in a manner similar to that described in Method CCC, using (1aR,5aR)-2-(4-oxy-pyrazin-2-yl)-1a,2,5,5a-tetrahydro-1H-2,3-diaza-cyclopropa[a]pentalene-4-carboxylic acid and (S)-methyl 2-amino-3,3-dimethylbutanoate. LCMS m/z=386.2 [M+H]$^+$; $^1$H NMR (400 MHz, CDCl$_3$) δ ppm 0.44 (dd, J=8.0 and 4.7 Hz, 1H), 1.06 (s, 9H), 1.24-1.29 (m, 1H), 2.26-2.32 (m, 1H), 2.72-2.77 (m, 1H), 2.90 (d, J=16.8 Hz, 1H), 3.02 (dd, J=16.7 and 6.4 Hz, 1H), 3.75 (s, 3H), 4.58 (d, J=9.6 Hz, 1H), 7.28 (d, J=9.6 Hz, NH, 1H), 8.00 (dd, J=4.1 and 1.4 Hz, 1H), 8.29 (d, J=4.1 Hz, 1H), 8.83 (d, J=1.3 Hz, 1H).

Example 1.158: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1-fluoromethyl-1-hydroxymethyl-ethyl)-amide (Compound 889)

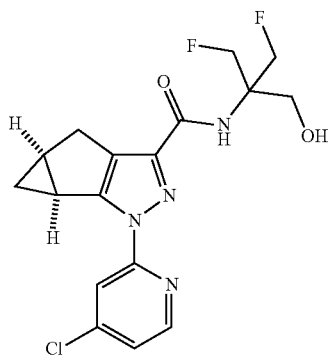 [SMILES: O=C(NC(CO)(CF)CF)c1nn(-c2cc(Cl)ccn2)c2c1C[C@@H]1C[C@H]21]

Step A: Preparation of Methyl 2-Amino-3-fluoro-2-(fluoromethyl)propanoate

The title compound was prepared as described in Synthesis 1994 vol. 7 pp. 701-702.

Step B: Preparation of 2-{[(1aS,5aS)-2-(4-Chloro-pyridin-2-yl)-1a,2,5,5a-tetrahydro-1H-2,3-diaza-cyclopropa[a]pentalene-4-carbonyl]-amino}-3-fluoro-2-fluoromethyl-propionic Acid Methyl Ester To a solution of (1aS,5aS)-2-(4-chloro-pyridin-2-yl)-1a,2,5,5a-tetrahydro-1H-2,3-diaza-cyclopropa[a]pentalene-4-carboxylic acid (100 mg, 0.363 mmol), methyl 2-amino-3-fluoro-2-(fluoromethyl)propanoate hydrochloride (76 mg, 0.399 mmol) and triethylamine (0.101 mL, 0.725 mmol) in DMF (2 mL) was added HATU (138 mg, 0.363 mmol). The reaction was stirred at 50° C. for 2 h, then concentrated. The residue was purified by silica gel flash chromatography to give the title compound as a white solid. LCMS m/z=411.2 [M+H]$^+$; $^1$H NMR (400 MHz, CDCl$_3$) δ 0.46 (td, J=4.7, 3.3 Hz, 1H), 1.25 (td, J=7.8, 4.7 Hz, 1H), 2.24-2.30 (m, 1H), 2.79-2.84 (m, 1H), 2.89 (d, J=16.8 Hz, 1H), 2.99 (dd, J=16.4, 6.2 Hz, 1H), 3.89 (s, 3H), 4.81-5.12 (m, 4H), 7.22 (dd, J=5.3, 1.8 Hz, 1H), 7.51 (s, 1H), 7.98 (d, J=1.8 Hz, 1H), 8.36 (d, J=5.3 Hz, 1H).

Step C: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1-fluoromethyl-1-hydroxymethyl-ethyl)-amide To a solution of 2-{[(1aS,5aS)-2-(4-chloro-pyridin-2-yl)-1a,2,5,5a-tetrahydro-1H-2,3-diaza-cyclopropa[a]pentalene-4-carbonyl]-amino}-3-fluoro-2-fluoromethyl-propionic acid methyl ester (130 mg, 0.316 mmol) in THF (2 mL) and MeOH (0.200 mL) was added sodium borohydride (23.94 mg, 0.633 mmol). The reaction was stirred at 23° C. for 2 h. Saturated aqueous NaHCO$_3$ (15 mL) was added. The mixture was extracted with dichloromethane (3×15 mL). The combined organic extracts were dried (MgSO$_4$), filtered, then concentrated. The residue was purified by silica gel flash chromatography to give the title compound (106 mg) as a white solid. LCMS m/z=383.2 [M+H]$^+$; $^1$H NMR (400 MHz, CDCl$_3$) δ 0.46 (td, J=4.6, 3.5 Hz, 1H), 1.27 (td, J=8.0, 4.9 Hz, 1H), 2.25-2.31 (m, 1H), 2.80-2.85 (m, 1H), 2.89 (d, J=16.9 Hz, 1H), 2.99 (dd, J=16.6, 6.3 Hz, 1H), 3.96 (d, J=5.9 Hz, 2H), 4.25 (t, J=6.8 Hz, 1H), 4.55-4.84 (m, 4H), 7.23 (dd, J=5.3, 1.8 Hz, 1H), 7.27 (s, 1H), 7.92 (d, J=1.6 Hz, 1H), 8.36 (d, J=5.3 Hz, 1H).

Example 1.159: Preparation of (1aS,5aS)-2-(4-Cyano-pyridin-2-yl)-1a,2,5,5a-tetrahydro-1H-2,3-diaza-cyclopropa[a]pentalene-4-carboxylic Acid ((S)-3,3,3-Trifluoro-1-hydroxymethyl-propyl)-amide (Compound 891)

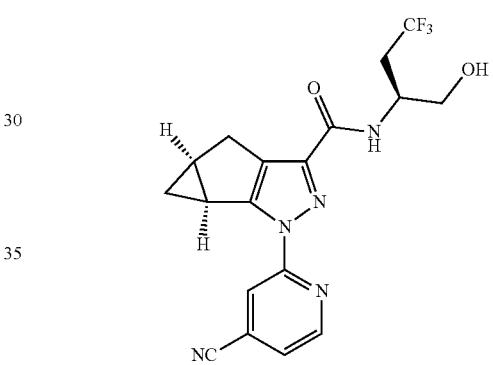

Step A: Preparation of (1aS,5aS)-2-(4-Bromo-pyridin-2-yl)-1a,2,5,5a-tetrahydro-1H-2,3-diaza-cyclopropa[a]pentalene-4-carboxylic Acid To a solution of (1aS,5aS)-2-(4-bromo-pyridin-2-yl)-1a,2,5,5a-tetrahydro-1H-2,3-diaza-cyclopropa[a]pentalene-4-carboxylic acid ethyl ester (1.00 g, 2.87 mmol) in methanol (5 mL) and THF (5.00 mL) was added a 2.0 M aqueous solution of sodium hydroxide (2.87 mL, 5.74 mmol). The reaction was stirred at 23° C. for 2 h. The organic solvents were removed by distillation. The remaining aqueous solution was diluted with water (20 mL) then acidified to pH ~2 by addition of 6 M aq. HCl. The resulting precipitate was collected by filtration, rinsed with water, then dried under vacuum to give the title compound (0.87 g) as a white solid. LCMS m/z=320.0 [M+H]$^+$.

Step B: Preparation of (1aS,5aS)-2-(4-Cyano-pyridin-2-yl)-1a,2,5,5a-tetrahydro-1H-2,3-diaza-cyclopropa[a]pentalene-4-carboxylic Acid (1aS,5aS)-2-(4-Bromo-pyridin-2-yl)-1a,2,5,5a-tetrahydro-1H-2,3-diaza-cyclopropa[a]pentalene-4-carboxylic acid (0.87 g, 2.72 mmol) was dissolved in DMA (10 mL). Sodium hydride (0.109 g, 2.72 mmol) was added, and nitrogen was bubbled through the mixture for 10 min.

Zinc(II) cyanide (0.638 g, 5.44 mmol) and palladium tetrakistriphenylphosphine. (0.157 g, 0.136 mmol) were added. The reaction was stirred under microwave heating in a sealed tube at 120° C. for 2 h. Water (25 mL) and 6 M aqueous HCl (1 mL) were added. The mixture was extracted with 25% iPrOH/dichloromethane (3×25 mL) (The biphasic mixture was filtered after the first extraction to clear up an emulsion). The combined organic extracts were dried (MgSO$_4$), filtered, then concentrated. The residue was purified by flash chromatography to give the title compound (0.68 g) as a tan solid. LCMS m/z=267.0 [M+H]$^+$.

Step C: Preparation of
(S)-2-Amino-4,4,4-trifluorobutan-1-ol

To an ice-cooled solution of (S)-2-(tert-butoxycarbonylamino)-4,4,4-trifluorobutanoic acid (1.0 g, 3.89 mmol) and N-ethyl-N-isopropylpropan-2-amine (0.813 mL, 4.67 mmol) in THF (15 mL) was added dropwise ethyl chloroformate (0.409 mL, 4.28 mmol). The cooling bath was removed and the mixture was stirred at 23° C. for 2 h. The mixture was filtered to remove the white precipitate, and the filtrate was treated with a 2 M THF solution of lithium borohydride (1.944 mL, 3.89 mmol) resulting in vigorous gas evolution. The mixture was stirred at room temperature for 2 h. Brine (25 mL) was added. The mixture was extracted with ethyl acetate (3×25 mL). The combined organic extracts were dried (MgSO$_4$), filtered, then concentrated under vacuum. The residue was purified by silica gel flash chromatography to give (S)-tert-butyl 4,4,4-trifluoro-1-hydroxybutan-2-ylcarbamate (0.80 g) as a white solid. This solid was treated with 4 M HCl in dioxane (10 mL) for 60 min then concentrated to give the HCl salt of the title compound (0.54 g) as a white solid. $^1$H NMR (400 MHz, CD$_3$OD) δ 2.55-2.79 (m, 2H), 3.42 (bs, 1H), 3.54 (dd, J=11.6, 5.6 Hz, 1H), 3.66 (dd, J=11.6, 3.9 Hz, 1H), 3.53 (bs, 1H), 8.27 (bs, 3H).

Step D: Preparation of (1aS,5aS)-2-(4-Cyano-pyridin-2-yl)-1a,2,5,5a-tetrahydro-1H-2,3-diaza-cyclopropa[a]pentalene-4-carboxylic Acid ((S)-3,3,3-Trifluoro-1-hydroxymethyl-propyl)-amide To a solution of (1aS,5aS)-2-(4-cyano-pyridin-2-yl)-1a,2,5,5a-tetrahydro-1H-2,3-diaza-cyclopropa[a]pentalene-4-carboxylic acid (75 mg, 0.282 mmol) and triethylamine (0.118 mL, 0.845 mmol) in DMF (1 mL) was added HATU (118 mg, 0.310 mmol). The reaction was stirred at 23° C., for 5 min, then was added (S)-2-amino-4,4,4-trifluorobutan-1-ol hydrochloride (55.6 mg, 0.310 mmol). The reaction was stirred at 23° C. for 30 min, then concentrated. The residue was purified by silica gel flash chromatography to give the title compound (86 mg) as a white solid. LCMS m/z=392.4 [M+H]$^+$; $^1$H NMR (400 MHz, CDCl$_3$) δ 0.47 (td, J=4.7, 3.2 Hz, 1H), 1.27 (td, J=8.1, 4.8 Hz, 1H), 2.26-2.32 (m, 1H), 2.54-2.69 (m, 3H), 2.77-2.82 (m, 1H), 2.93 (d, J=16.8 Hz, 1H), 3.01 (dd, J=16.6, 6.1 Hz, 1H), 3.88 (d, J=2.9 Hz, 2H), 4.33-4.41 (m, 1H), 7.23 (d, J=8.2 Hz, 1H), 7.41 (dd, J=5.1, 1.4 Hz, 1H), 8.17 (t, J=0.8 Hz, 1H), 8.62 (dd, J=5.1, 0.6 Hz, 1H).

Example 1.160: Analytical Data and Methods of Preparation for Additional Compounds of the Present Invention Certain compounds of the present invention were prepared in a similar manner as described herein. The general synthetic methods and analytical data for these compounds are shown in the table below.

| Cmpd No. | Method(s) | Mass Calc. | Mass Observed | Cmpd No. | Method(s) | Mass Calc. | Mass Observed |
| --- | --- | --- | --- | --- | --- | --- | --- |
| 230 | GG | 382.1238 | 383.4 | 146 | LL | 380.1633 | 381.3 |
| 154 | GG | 387.1753 | 388.1 | 6 | LL | 382.1789 | 383.4 |
| 547 | GG | 386.0744 | 387.2 | 373 | LL | 320.1633 | 321.3 |
| 381 | GG | 345.1285 | 346.3 | 196 | LL | 362.1738 | 363.3 |
| 204 | GG | 382.1238 | 383.3 | 56 | LL | 430.0908 | 431.3 |
| 572 | GG | 413.1103 | 414.5 | 459 | LL | 433.1466 | 434.4 |
| 430 | GG | 393.1648 | 394.3 | 282 | LL | 451.1361 | 452.3 |
| 109 | GG | 411.139 | 412.4 | 105 | OO | 395.1441 | 396.3 |
| 81 | GG | 434.101 | 435.4 | 507 | OO | 395.1441 | 396.2 |
| 533 | GG | 450.1975 | 451.3 | 275 | OO | 450.1225 | 451.0 |
| 248 | GG | 408.0854 | 409.3 | 215 | OO | 381.1398 | 382.4 |
| 73 | GG | 366.1289 | 367.3 | 94 | OO | 366.1289 | 367.4 |
| 303 | GG | 435.0963 | 436.3 | 320 | OO | 391.1492 | 392.3 |
| 127 | GG | 329.1336 | 330.3 | 138 | OO | 395.1441 | 396.1 |
| 529 | GG | 359.1441 | 360.5 | 397 | OO | 395.1441 | 396.4 |
| 354 | GG | 416.1445 | 417.4 | 112 | OO | 441.1296 | 442.5 |
| 51 | GG | 438.1322 | 439.5 | 44 | OO | 411.139 | 412.4 |
| 454 | GG | 436.1706 | 437.4 | 447 | OO | 443.1111 | 444.3 |
| 91 | GG | 345.1285 | 346.3 | 270 | OO | 377.1336 | 378.3 |
| 235 | GG | 386.0744 | 387.4 | 465 | OO | 369.1398 | 370.4 |
| 558 | GG | 359.1441 | 360.5 | 306 | PP | 468.1943 | 469.4 |
| 405 | GG | 359.1441 | 360.5 | 130 | PP | 440.1631 | 441.4 |
| 31 | GG | 333.1285 | 334.5 | 376 | PP | 402.1862 | 403.5 |
| 250 | HH | 333.2046 | 334.5 | 532 | PP | 440.1631 | 441.6 |
| 511 | HH | 330.1488 | 331.3 | 199 | PP | 402.1862 | 403.4 |
| 336 | HH | 333.2046 | 334.6 | 523 | PP | 454.1787 | 455.3 |
| 159 | HH | 351.1941 | 352.2 | 171 | PP | 416.2018 | 417.4 |
| 186 | JJ | 317.1274 | 318.4 | 348 | PP | 454.1787 | 455.3 |
| 562 | JJ | 338.1738 | 339.6 | 555 | PP | 416.2018 | 417.4 |
| 412 | JJ | 308.1633 | 309.5 | 557 | PP | 454.1787 | 455.4 |
| 231 | JJ | 356.1633 | 357.4 | 252 | PP | 416.2018 | 417.4 |
| 357 | PP | 454.1787 | 455.4 | 394 | G | 424.1343 | 425.3 |
| 7 | PP | 416.2018 | 417.4 | 217 | G | 424.1343 | 425.3 |
| 310 | G | 449.1159 | 450.4 | 115 | G | 434.0738 | 435.2 |

-continued

| Cmpd No. | Method(s) | Mass Calc. | Mass Observed | Cmpd No. | Method(s) | Mass Calc. | Mass Observed |
|---|---|---|---|---|---|---|---|
| 140 | G | 395.1441 | 396.3 | 516 | G | 458.0948 | 459.4 |
| 372 | G | 420.1507 | 421.4 | 341 | G | 390.0687 | 391.5 |
| 262 | G | 393.1285 | 394.2 | 160 | G | 441.1926 | 442.5 |
| 86 | G | 464.2018 | 465.5 | 550 | G | 442.2174 | 443.5 |
| 286 | G | 423.0902 | 424.3 | 580 | G | 385.1035 | 386.4 |
| 540 | G | 385.1785 | 386.5 | 501 | G | 406.1601 | 407.1 |
| 64 | G | 391.1492 | 392.4 | 469 | G | 406.1601 | 407.2 |
| 182 | G | 356.1633 | 357.4 | 15 | G | 411.2116 | 412.4 |
| 12 | G | 374.1539 | 375.3 | 442 | G | 366.1289 | 367.4 |
| 484 | G | 382.1238 | 383.3 | 89 | G | 434.1163 | 435.4 |
| 308 | G | 368.1082 | 369.2 | 491 | G | 416.2018 | 417.5 |
| 131 | G | 368.1082 | 369.2 | 241 | G | 395.1242 | 396.3 |
| 313 | G | 420.1757 | 421.3 | 66 | G | 400.09 | 401.2 |
| 240 | G | 435.1753 | 436.2 | 260 | G | 425.1546 | 426.2 |
| 183 | G | 419.1804 | 420.4 | 486 | G | 444.1064 | 445.3 |
| 485 | G | 439.1259 | 440.3 | 437 | G | 413.1347 | 414.2 |
| 234 | G | 359.1441 | 360.2 | 288 | G | 409.1234 | 410.3 |
| 181 | G | 430.0908 | 431.2 | 13 | G | 380.1445 | 381.3 |
| 24 | G | 370.1039 | 371.2 | 211 | G | 421.1597 | 422.2 |
| 331 | G | 366.1289 | 367.4 | 180 | G | 449.1546 | 450.4 |
| 510 | G | 359.1441 | 360.5 | 229 | G | 391.1492 | 392.5 |
| 358 | G | 392.1082 | 393.4 | 564 | G | 430.1811 | 431.1 |
| 327 | G | 451.1815 | 452.3 | 415 | G | 444.1967 | 445.6 |
| 122 | G | 447.0861 | 448.4 | 343 | G | 408.1757 | 409.3 |
| 277 | G | 428.2018 | 429.5 | 166 | G | 408.1757 | 409.5 |
| 503 | G | 370.1039 | 371.2 | 266 | G | 408.1757 | 409.5 |
| 344 | G | 437.1659 | 438.4 | 311 | G | 442.2174 | 443.5 |
| 167 | G | 375.1213 | 376.4 | 134 | G | 440.2381 | 441.4 |
| 35 | G | 393.1285 | 394.4 | 104 | G | 384.1757 | 385.2 |
| 432 | G | 330.1488 | 331.4 | 506 | G | 345.1285 | 346.1 |
| 481 | G | 326.1738 | 327.3 | 330 | G | 359.1441 | 360.0 |
| 573 | G | 330.1488 | 331.4 | 153 | G | 359.1441 | 360.1 |
| 148 | G | 341.1898 | 342.4 | 9 | G | 440.2381 | 441.2 |
| 544 | G | 317.2097 | 318.4 | 380 | G | 421.1597 | 422.2 |
| 375 | G | 355.2616 | 355.4 | 203 | G | 411.139 | 412.3 |
| 198 | G | 381.2046 | 382.4 | 32 | G | 378.1289 | 379.4 |
| 569 | G | 365.2097 | 366.5 | 425 | G | 378.1289 | 379.4 |
| 424 | G | 360.2518 | 361.5 | 247 | G | 408.1394 | 409.2 |
| 246 | G | 355.2054 | 356.3 | 72 | G | 382.1238 | 383.3 |
| 71 | G | 385.1915 | 386.4 | 50 | G | 396.1394 | 397.4 |
| 296 | G | 399.1952 | 400.4 | 208 | G | 380.1445 | 381.3 |
| 120 | G | 335.1992 | 336.4 | 574 | G | 468.0774 | 469.3 |
| 522 | G | 335.1992 | 336.5 | 434 | G | 451.1815 | 452.3 |
| 347 | G | 398.1868 | 399.4 | 257 | G | 435.1866 | 436.3 |
| 175 | G | 384.1757 | 385.3 | 172 | G | 396.1394 | 397.2 |
| 21 | G | 384.1757 | 385.2 | 19 | G | 434.155 | 435.4 |
| 224 | G | 405.1648 | 406.3 | 253 | G | 474.2072 | 475.2 |
| 49 | G | 405.1648 | 406.3 | 42 | G | 399.1503 | 400.4 |
| 452 | G | 406.1601 | 407.4 | 444 | G | 399.1503 | 400.4 |
| 517 | G | 442.2373 | 443.4 | 267 | G | 409.0904 | 410.3 |
| 143 | G | 407.1441 | 408.4 | 145 | G | 416.2018 | 417.5 |
| 361 | G | 386.1913 | 387.3 | 542 | G | 474.2072 | 475.6 |
| 184 | G | 400.2069 | 401.3 | 312 | G | 464.2018 | 465.5 |
| 561 | G | 442.2537 | 443.5 | 537 | G | 402.1862 | 403.3 |
| 410 | G | 428.2381 | 429.3 | 480 | G | 333.1285 | 334.4 |
| 233 | G | 418.1634 | 419.5 | 218 | G | 333.1285 | 334.4 |
| 54 | G | 428.2381 | 429.5 | 107 | G | 363.139 | 364.4 |
| 457 | G | 412.2069 | 413.4 | 508 | G | 363.139 | 364.4 |
| 280 | G | 384.1757 | 385.3 | 333 | G | 363.139 | 364.4 |
| 156 | G | 502.2021 | 503.6 | 338 | G | 369.1398 | 370.3 |
| 548 | G | 361.1234 | 362.3 | 388 | G | 360.1394 | 361.5 |
| 575 | G | 349.1234 | 350.3 | 34 | G | 444.1967 | 445.4 |
| 295 | G | 386.1913 | 387.3 | 429 | G | 444.1967 | 445.7 |
| 119 | G | 386.1913 | 387.3 | 108 | G | 472.2279 | 473.8 |
| 219 | G | 355.164 | 356.2 | 509 | G | 458.2123 | 459.5 |
| 59 | G | 400.2069 | 401.2 | 482 | G | 381.1285 | 382.3 |
| 462 | G | 393.1285 | 394.2 | 367 | G | 444.233 | 445.5 |
| 285 | G | 404.1478 | 405.3 | 162 | G | 396.1394 | 397.3 |
| 80 | G | 311.1629 | 312.3 | 551 | G | 396.1394 | 397.4 |
| 43 | G | 379.0851 | 380.3 | 389 | G | 396.1394 | 397.4 |
| 269 | G | 312.1582 | 313.3 | 28 | G | 410.155 | 411.4 |
| 490 | G | 394.1612 | 395.4 | 416 | G | 423.1866 | 424.2 |
| 379 | G | 388.1298 | 389.4 | 238 | G | 465.1971 | 466.5 |
| 571 | G | 344.1037 | 345.2 | 63 | G | 380.1445 | 381.3 |
| 589 | G | 378.13 | 379.3 | 466 | G | 380.1445 | 381.4 |
| 595 | G | 389.0484 | 390.3 | 545 | G | 380.1445 | 381.4 |

-continued

| Cmpd No. | Method(s) | Mass Calc. | Mass Observed | Cmpd No. | Method(s) | Mass Calc. | Mass Observed |
|---|---|---|---|---|---|---|---|
| 76 | G | 351.2304 | 352.6 | 377 | G | 394.1601 | 395.4 |
| 477 | G | 389.1898 | 390.6 | 200 | G | 394.1601 | 395.4 |
| 370 | G | 366.1289 | 367.4 | 254 | G | 396.1394 | 419.1 |
| 193 | G | 356.1082 | 357.3 | 173 | G | 396.1394 | 397.2 |
| 566 | G | 381.1398 | 382.4 | 556 | G | 396.1394 | 397.2 |
| 133 | G | 431.1253 | 432.3 | 304 | G | 421.1597 | 422.4 |
| 536 | G | 431.1253 | 432.4 | 294 | G | 421.1597 | 422.4 |
| 58 | G | 393.1648 | 394.3 | 268 | G | 421.1597 | 422.2 |
| 461 | G | 381.1285 | 382.3 | 345 | G | 405.1648 | 406.5 |
| 62 | G | 393.1648 | 394.5 | 55 | G | 377.1086 | 378.3 |
| 513 | G | 416.1445 | 417.4 | 458 | G | 380.1445 | 381.3 |
| 284 | G | 357.1035 | 358.3 | 281 | G | 420.1007 | 421.5 |
| 539 | G | 394.1601 | 395.4 | 185 | G | 412.1343 | 413.3 |
| 189 | G | 369.1398 | 370.3 | 335 | G | 386.0744 | 387.2 |
| 158 | G | 402.1289 | 403.3 | 207 | G | 458.2123 | 459.4 |
| 549 | G | 386.0744 | 387.1 | 384 | G | 458.2123 | 459.4 |
| 483 | G | 444.0394 | 445.2 | 436 | G | 407.1111 | 408.4 |
| 307 | G | 400.09 | 401.4 | 259 | G | 393.0955 | 394.2 |
| 177 | G | 413.0984 | 414.4 | 385 | G | 370.1039 | 371.2 |
| 524 | G | 437.1659 | 438.4 | 594 | G | 372.1695 | 373.3 |
| 78 | G | 391.1242 | 392.5 | 421 | G | 359.1441 | 360.4 |
| 349 | G | 444.1064 | 445.5 | 591 | G | 423.1514 | 424.3 |
| 479 | G | 444.1064 | 445.4 | 114 | X | 416.2018 | 417.6 |
| 565 | G | 405.1007 | 406.3 | 163 | X | 373.1597 | 374.2 |
| 239 | G | 387.1941 | 388.5 | 14 | X | 395.1441 | 396.3 |
| 382 | G | 372.1349 | 373.3 | 390 | X | 407.1441 | 408.4 |
| 499 | G | 406.1612 | 407.5 | 213 | X | 391.1492 | 392.5 |
| 111 | G | 380.1456 | 381.3 | 242 | N | 366.1289 | 367.4 |
| 337 | G | 337.1535 | 338.5 | 67 | N | 366.1289 | 367.3 |
| 535 | G | 312.1582 | 313.2 | 453 | N | 382.1238 | 383.3 |
| 360 | G | 346.1193 | 347.2 | 404 | N | 391.1242 | 392.5 |
| 20 | G | 378.13 | 379.4 | 226 | N | 444.0394 | 445.4 |
| 300 | G | 388.0531 | 389.2 | 398 | N | 370.1039 | 371.3 |
| 255 | G | 335.1379 | 336.4 | 514 | N | 353.1086 | 354.3 |
| 298 | G | 366.1289 | 367.2 | 339 | N | 370.1039 | 370.9 |
| 471 | G | 380.1445 | 381.4 | 126 | N | 368.1082 | 369.3 |
| 293 | G | 387.1753 | 388.5 | 392 | N | 352.1133 | 353.3 |
| 117 | G | 387.1753 | 388.3 | 38 | N | 407.1441 | 408.3 |
| 317 | G | 363.139 | 364.4 | 559 | N | 382.1238 | 383.2 |
| 519 | G | 380.1445 | 381.2 | 407 | N | 399.1191 | 400.2 |
| 449 | G | 407.1441 | 408.4 | 334 | N | 352.1133 | 353.2 |
| 272 | G | 407.1441 | 408.4 | 528 | N | 366.1289 | 367.4 |
| 96 | G | 407.1441 | 408.6 | 353 | N | 366.1289 | 367.3 |
| 243 | G | 359.1441 | 360.4 | 176 | N | 366.1289 | 367.4 |
| 8 | G | 373.1234 | 374.4 | 292 | N | 366.1289 | 367.4 |
| 90 | N | 506.2123 | 507.4 | 326 | N | 382.1238 | 383.4 |
| 492 | N | 420.1757 | 421.6 | 302 | N | 353.1086 | 354.3 |
| 194 | N | 383.1191 | 384.3 | 403 | N | 396.1031 | 395.4 |
| 26 | N | 366.1289 | 367.3 | 225 | N | 472.2279 | 473.7 |
| 411 | N | 382.1238 | 383.3 | 3 | N | 472.2279 | 473.5 |
| 474 | N | 353.1086 | 354.3 | 553 | N | 405.1648 | 406.3 |
| 297 | N | 353.1086 | 354.3 | 45 | N | 387.0941 | 388.4 |
| 121 | N | 353.1086 | 354.3 | 475 | N | 367.1242 | 368.2 |
| 276 | N | 372.0854 | 373.2 | 150 | N | 368.1082 | 369.2 |
| 95 | N | 353.1086 | 354.3 | 39 | N | 368.1082 | 369.3 |
| 497 | N | 381.1398 | 382.2 | 165 | N | 352.1133 | 353.0 |
| 321 | N | 382.1238 | 383.3 | 301 | H | 394.1601 | 395.4 |
| 576 | N | 435.1866 | 436.3 | 527 | H | 358.1789 | 359.3 |
| 438 | N | 400.09 | 401.1 | 352 | H | 358.1789 | 359.2 |
| 261 | N | 391.1242 | 392.3 | 356 | S | 390.18 | 391.4 |
| 85 | N | 444.0394 | 445.3 | 23 | S | 402.205 | 403.3 |
| 487 | N | 406.1601 | 407.2 | 406 | S | 402.205 | 403.3 |
| 22 | N | 400.09 | 401.2 | 228 | S | 402.205 | 403.2 |
| 399 | N | 368.1082 | 369.3 | 53 | S | 418.1999 | 419.6 |
| 5 | N | 420.1007 | 421.3 | 456 | S | 424.1706 | 425.2 |
| 216 | N | 370.1039 | 371.1 | 279 | S | 403.2003 | 404.4 |
| 448 | N | 370.1039 | 371.2 | 473 | P | 380.2206 | 381.3 |
| 271 | N | 420.1007 | 421.5 | 17 | P | 395.1412 | 396.2 |
| 578 | N | 380.1445 | 381.3 | 396 | P | 354.205 | 355.4 |
| 443 | N | 381.1398 | 382.3 | 169 | P | 340.1894 | 341.5 |
| 371 | N | 382.1238 | 383.3 | 48 | P | 354.205 | 355.5 |
| 30 | N | 399.1191 | 400.4 | 69 | O | 359.1441 | 360.4 |
| 420 | N | 382.1238 | 383.3 | 577 | O | 387.1753 | 388.4 |
| 113 | N | 380.1445 | 381.4 | 440 | O | 345.1285 | 346.4 |
| 190 | N | 370.1039 | 371.2 | 263 | O | 387.1753 | 388.5 |
| 212 | N | 370.1039 | 371.2 | 87 | O | 359.1441 | 360.5 |

-continued

| Cmpd No. | Method(s) | Mass Calc. | Mass Observed | Cmpd No. | Method(s) | Mass Calc. | Mass Observed |
|---|---|---|---|---|---|---|---|
| 603 | G | 439.1616 | 440.5 | 638 | G | 309.1586 | 310.5 |
| 610 | G | 433.0745 | 434.3 | 671 | G | 309.1586 | 310.5 |
| 560 | G | 390.1244 | 391.4 | 624 | G | 375.1753 | 376.1 |
| 16 | G | 391.1492 | 392.2 | 741 | G | 325.1535 | 326.3 |
| 467 | G | 356.1633 | 357.3 | 740 | G | 325.1898 | 326.3 |
| 534 | G | 409.1398 | 410.3 | 734 | G | 372.1695 | 373.3 |
| 612 | G | 391.064 | 392.3 | 598 | G | 430.1811 | 431.3 |
| 662 | G | 342.1687 | 343.3 | 617 | G | 473.1227 | 474.2 |
| 605 | G | 381.1796 | 382.3 | 640 | G | 398.1118 | 399.2 |
| 613 | G | 419.1509 | 420.2 | 680 | G | 347.1441 | 348.3 |
| 615 | G | 331.1492 | 332.5 | 661 | G | 361.1597 | 362.4 |
| 614 | G | 344.14 | 345.4 | 738 | G | 309.1586 | 310.2 |
| 618 | G | 348.1695 | 349.4 | 602 | G | 439.1616 | 440.4 |
| 619 | G | 405.1909 | 406.5 | 606 | G | 405.1353 | 406.5 |
| 665 | G | 334.1539 | 335.4 | 620 | G | 364.1507 | 365.5 |
| 658 | G | 398.1118 | 399.3 | 622 | G | 390.0687 | 391.3 |
| 633 | G | 351.1304 | 352.3 | 632 | G | 364.1507 | 365.4 |
| 604 | G | 399.2054 | 400.5 | 673 | G | 374.0738 | 375.2 |
| 616 | G | 373.1205 | 374.3 | 648 | G | 449.0847 | 450.0 |
| 627 | G | 308.1383 | 309.2 | 681 | G | 326.1738 | 327.4 |
| 654 | G | 355.1197 | 356.3 | 670 | G | 386.0738 | 387.4 |
| 666 | G | 342.1289 | 343.3 | 645 | G | 384.0582 | 385.3 |
| 641 | G | 385.121 | 386.3 | 733 | G | 359.1441 | 360.4 |
| 623 | G | 375.1304 | 376.3 | 732 | G | 327.1691 | 328.3 |
| 649 | G | 418.1225 | 419.4 | 697 | G | 341.1847 | 342.3 |
| 677 | G | 385.0535 | 386.1 | 686 | G | 311.1742 | 312.5 |
| 655 | G | 428.0456 | 429.1 | 692 | G | 324.1695 | 325.3 |
| 652 | G | 384.1394 | 385.3 | 695 | G | 372.1695 | 373.2 |
| 679 | G | 360.1695 | 361.6 | 634 | G | 402.1862 | 403.5 |
| 659 | G | 358.1539 | 359.4 | 752 | G | 392.2206 | 393.5 |
| 656 | G | 309.1586 | 310.6 | 730 | G | 460.258 | 423.2 |
| 754 | G | 405.1597 | 406.5 | 141 | LL | 337.1455 | 338.3 |
| 688 | CCC | 388.1644 | 389.4 | 400 | LL | 379.156 | 380.4 |
| 702 | CCC | 388.1644 | 389.3 | 359 | G | 392.1445 | 393.3 |
| 706 | CCC | 356.1593 | 357.3 | 328 | G | 392.1445 | 393.3 |
| 689 | CCC | 329.1484 | 330.3 | 427 | G | 409.1398 | 410.3 |
| 691 | CCC | 391.164 | 392.5 | 249 | G | 409.1398 | 410.4 |
| 725 | CCC | 368.1956 | 369.2 | 395 | G | 408.115 | 409.4 |
| 724 | CCC | 340.1644 | 341.1 | 47 | G | 392.1445 | 393.4 |
| 723 | CCC | 326.1488 | 327.2 | 450 | G | 392.1445 | 393.3 |
| 751 | CCC | 410.2061 | 411.4 | 273 | G | 409.1398 | 410.4 |
| 750 | CCC | 398.2061 | 399.3 | 489 | G | 406.1601 | 407.4 |
| 748 | CCC | 400.1854 | 401.2 | 136 | G | 423.1554 | 424.3 |
| 755 | CCC | 400.1854 | 401.2 | 418 | G | 435.1753 | 436.3 |
| 756 | CCC | 414.201 | 415.3 | 25 | G | 423.1554 | 424.2 |
| 731 | CCC | 460.258 | 443.5 | 83 | G | 423.1554 | 424.3 |
| 422 | Z | 474.2072 | 475.5 | 65 | G | 394.1193 | 395.5 |
| 369 | Z | 386.1913 | 387.3 | 587 | G | 422.1561 | 423.3 |
| 60 | GG | 377.1546 | 378.3 | 110 | G | 347.1441 | 348.3 |
| 463 | GG | 331.1492 | 332.5 | 187 | G | 389.1546 | 390.3 |
| 570 | GG | 437.1546 | 438.4 | 387 | G | 313.1535 | 314.3 |
| 426 | GG | 437.1546 | 438.4 | 401 | G | 346.1193 | 347.4 |
| 362 | GG | 373.1597 | 374.4 | 512 | G | 390.0687 | 391.3 |
| 82 | II | 377.2097 | 378.5 | 265 | G | 401.1148 | 402.2 |
| 386 | II | 379.2253 | 380.6 | 315 | G | 391.1492 | 392.5 |
| 79 | II | 317.2097 | 318.3 | 192 | G | 422.155 | 423.3 |
| 209 | II | 393.2409 | 394.5 | 2 | G | 375.1753 | 376.3 |
| 123 | KK | 370.1789 | 371.3 | 364 | G | 375.1753 | 376.3 |
| 525 | KK | 310.1789 | 311.3 | 27 | G | 389.1546 | 390.4 |
| 52 | KK | 352.1894 | 353.4 | 419 | G | 381.1285 | 382.4 |
| 201 | LL | 399.1611 | 400.4 | 237 | G | 397.1398 | 398.4 |
| 318 | LL | 397.1455 | 398.3 | 366 | G | 394.1601 | 395.4 |
| 128 | G | 421.1597 | 422.2 | 409 | RR, C, D | 329.1535 | 330.4 |
| 530 | G | 421.1597 | 422.4 | 232 | RR, C, D | 377.1535 | 378.4 |
| 355 | G | 406.1601 | 407.5 | 383 | RR, C, D | 371.164 | 372.4 |
| 118 | G | 421.1597 | 422.4 | 57 | RR, C, D | 329.1535 | 330.4 |
| 520 | G | 406.1601 | 407.4 | 460 | RR, C, D | 377.1535 | 378.3 |
| 168 | G | 405.1648 | 406.5 | 206 | RR, C, D | 371.164 | 372.3 |
| 554 | G | 405.1648 | 406.4 | 283 | RR, C, D | 326.1738 | 327.4 |
| 92 | G | 401.1546 | 402.5 | 142 | RR, C, D | 408.2518 | 409.6 |
| 494 | G | 415.1702 | 416.4 | 588 | RR | 433.0745 | 434.3 |
| 323 | G | 426.1663 | 427.4 | 600 | RR | 402.1862 | 403.5 |
| 287 | G | 436.0894 | 437.3 | 601 | RR | 402.1862 | 403.5 |
| 4 | G | 434.0738 | 435.4 | 607 | RR | 360.1349 | 361.1 |
| 116 | G | 393.1648 | 394.3 | 608 | RR | 402.1454 | 403.3 |
| 101 | G | 394.1601 | 395.4 | 346 | G, C, D | 311.1629 | 312.5 |

-continued

| Cmpd No. | Method(s) | Mass Calc. | Mass Observed | Cmpd No. | Method(s) | Mass Calc. | Mass Observed |
|---|---|---|---|---|---|---|---|
| 68 | G | 407.1441 | 408.4 | 70 | G, C, D | 390.0687 | 391.2 |
| 439 | G | 416.2018 | 417.6 | 365 | G, C, D | 326.1738 | 327.3 |
| 222 | G | 415.1702 | 416.3 | 188 | G, C, D | 347.1441 | 348.3 |
| 278 | G | 373.1234 | 374.4 | 197 | G, C, D | 329.1535 | 330.4 |
| 504 | G | 401.1546 | 402.5 | 88 | G, C, D | 380.1456 | 381.3 |
| 1 | G | 416.2018 | 417.5 | 164 | G, C, D | 373.1586 | 374.6 |
| 678 | G | 346.1539 | 347.2 | 552 | G, C, D | 388.1695 | 389.4 |
| 650 | G | 388.1706 | 389.5 | 391 | G, C, D | 373.1586 | 374.4 |
| 628 | G | 354.18 | 355.4 | 214 | G, C, D | 388.1695 | 389.5 |
| 220 | OO | 395.1441 | 396.3 | 472 | G, C, D | 357.1586 | 358.3 |
| 496 | OO | 365.1336 | 366.5 | 210 | Q, G, C, D | 348.1394 | 349.2 |
| 541 | OO | 395.1441 | 396.3 | 568 | Q, G, C, D | 327.1691 | 328.4 |
| 316 | OO | 395.1441 | 396.5 | 488 | K | 392.1445 | 393.3 |
| 441 | WW | 355.2003 | 356.5 | 205 | K | 392.1445 | 393.2 |
| 137 | WW | 353.1847 | 354.4 | 708 | HHH, III, G | 380.1593 | 381.3 |
| 581 | WW | 367.2003 | 368.4 | 714 | HHH, III, G | 382.1749 | 383.2 |
| 590 | WW | 395.1952 | 396.2 | 728 | HHH, III, G | 398.2061 | 399.3 |
| 727 | HHH, III, G | 452.1779 | 453.3 | 431 | G, DD | 430.2174 | 431.5 |
| 726 | HHH, III, G | 410.2061 | 411.5 | 37 | U, V | 396.1394 | 397.4 |
| 191 | G, A, B | 425.1058 | 426.3 | 435 | U, V | 396.1394 | 397.4 |
| 417 | G, A, B | 367.189 | 368.4 | 324 | NN | 355.2003 | 356.5 |
| 332 | G, A, B | 392.14 | 393.5 | 502 | QQ | 410.155 | 411.3 |
| 155 | G, A, B | 338.1738 | 339.6 | 563 | VV | 342.18 | 343.3 |
| 10 | G, A, B | 338.1738 | 339.6 | 521 | G, I | 406.18 | 407.5 |
| 97 | G, A, B | 424.1507 | 425.3 | 451 | P | 354.205 | 355.5 |
| 464 | G, A, B | 416.0843 | 417.2 | 289 | SS | 372.1757 | 373.4 |
| 152 | G, A, B | 356.1633 | 357.3 | 41 | OO, U | 394.1601 | 395.4 |
| 546 | G, A, B | 390.1244 | 391.4 | 478 | L, M | 424.1706 | 425.3 |
| 132 | G, A, B | 346.1193 | 347.2 | 322 | Y | 386.0988 | 387.4 |
| 351 | G, A, B | 390.0687 | 391.4 | 202 | J, RR | 313.1535 | 314.3 |
| 106 | RR | 359.1441 | 360.5 | 582 | R | 357.1796 | 358.3 |
| 33 | RR | 349.1234 | 350.3 | 592 | T | 380.1593 | 381.3 |
| 378 | RR | 389.1546 | 390.3 | 585 | T, G, C, D | 337.1535 | 338.5 |
| 455 | RR | 389.1546 | 390.4 | 402 | OO | 345.1648 | 346.3 |
| 102 | RR | 373.1597 | 374.4 | 368 | E, F, G | 463.2065 | 464.3 |
| 178 | RR, A, B | 312.1582 | 313.3 | 433 | DD | 388.1706 | 427.3 |
| 621 | T | 338.1488 | 339.3 | 609 | O | 353.1847 | 354.4 |
| 428 | C, B, G | 347.1441 | 348.1 | 637 | XX | 332.1383 | 333.1 |
| 476 | C, B, G | 325.1785 | 326.4 | 597 | YY, G | 481.1345 | 482.4 |
| 129 | AA | 343.164 | 344.3 | 711 | G | 406.1386 | 407.2 |
| 93 | C, B, G | 347.1146 | 348.1 | 713 | BBB | 405.1546 | 406.4 |
| 223 | C, B, G | 335.1662 | 336.3 | 664 | DDD | 310.1539 | 311.5 |
| 500 | BB | 367.156 | 368.3 | 672 | DDD | 332.1383 | 333.4 |
| 543 | CC | 341.1847 | 342.3 | 676 | DDD | 367.164 | 368.3 |
| 256 | DD | 440.1631 | 441.1 | 736 | EEE | 388.1314 | 389.4 |
| 144 | EE | 368.1082 | 369.3 | 737 | EEE | 410.1158 | 411.3 |
| 221 | FF | 427.1503 | 428.3 | 626 | FFF | 389.1597 | 390.4 |
| 342 | F, G | 418.2163 | 419.5 | 653 | FFF | 367.1753 | 368.3 |
| 749 | J, G | 388.2467 | 389.4 | 757 | AAA | 404.1956 | 405.4 |
| 760 | G, G | 389.1546 | 390.4 | 758 | AAA | 404.1956 | 405.4 |
| 742 | J, G | 403.1702 | 374.2 | 798 | AAA | 388.2007 | 389.4 |
| 745 | J, G | 404.1956 | 405.4 | 797 | AAA | 388.2007 | 389.4 |
| 794 | MMM | 401.1614 | 402.4 | 701 | PPP, G | 384.1905 | 385.3 |
| 850 | MMM | 344.1644 | 345.3 | 890 | UU | 345.1353 | 346.1 |
| 803 | KKK, LLL, NNN | 408.1768 | 409.4 | 817 | UU | 405.1597 | 406.3 |
| 829 | UU | 373.1535 | 374.3 | | | | |
| 813 | KKK, LLL, UU | 340.1894 | 341.4 | | | | |
| 876 | UU | 359.1589 | 360.4 | | | | |
| 928 | UU | 311.1379 | 312.4 | | | | |
| 744 | G | 404.1956 | 405.4 | | | | |
| 717 | GGG | 375.1691 | 376.2 | | | | |
| 716 | GGG | 374.1488 | 375.2 | | | | |
| 715 | GGG | 426.2373 | 427.4 | | | | |
| 639 | DDD | 310.1539 | 311.5 | | | | |
| 125 | H | 394.1601 | 395.4 | | | | |
| 195 | MM | 407.1111 | 408.4 | | | | |
| 84 | G | 425.1546 | * | | | | |
| 161 | G | 382.1601 | ** | | | | |
| 584 | W | 337.1148 | 338.3 | | | | |
| 674 | JJJ | 384.0962 | 385.3 | | | | |
| 712 | ZZ | 426.2373 | 427.4 | | | | |
| 720 | GGG | 431.1702 | 432.2 | | | | |
| 675 | JJJ | 346.1193 | 347.1 | | | | |
| 753 | GGG | 374.1488 | 375.2 | | | | |

-continued

| Cmpd No. | Method(s) | Mass Calc. | Mass Observed | Cmpd No. | Method(s) | Mass Calc. | Mass Observed |
|---|---|---|---|---|---|---|---|
| 777 | OOO, TT | 386.1698 | 387.4 | | | | |
| 135 | RR | 361.1597 | 362.4 | | | | |
| 709 | G | 406.1386 | 407.2 | | | | |

\* Confirmed by NMR: $^1$H NMR: (400 MHz, CD$_3$CN) δ ppm 0.43 (td, J = 4.7 and 3.5 Hz, 1H), 1.14 (td, J = 7.8 and 4.7 Hz, 1H), 2.12-2.18 (m, 1H), 2.23-2.30 (m, 1H), 2.82 (d, J = 16.5 Hz, 1H), 2.94 (dd, J = 16.3 and 6.3 Hz, 1H), 3.76 (s, 3H), 3.82 (s, 3H), 4.38 (d, J = 6.2 Hz, 2H), 6.45 (dd, J = 8.3 and 2.4 Hz, 1H), 6.52 (d, J = 2.4 Hz, 1H), 7.10-7.16 (m, 2H), 7.18-7.24 (m, 1H), 7.35 (s, 1H), 7.68 (td, J = 8.8 and 5.9 Hz, 1H).
\*\* Confirmed by NMR: $^1$H NMR (400 MHz, CDCl$_3$) δ 0.50 (td, J = 4.6 and 3.5 Hz, 1H), 1.16-1.18 (m, 1H), 2.11-2.14 (m, 1H), 2.27 (s, 3H), 2.27-2.31 (m, 1H), 2.95 (d, J = 16.5 Hz, 1H), 3.05 (dd, J = 16.5 and 6.3 Hz, 1H), 3.88 (s, 3H), 4.58 (dd, J = 6.0 and 3.3 Hz, 2H), 6.06 (s, 1H), 7.00-7.07 (m, 3H), 7.56-7.61 (m, 1H).

Example 2: Homogeneous Time-Resolved Fluorescence (HTRF®) Assay for Direct cAMP Measurement A: CB$_2$ Assay Compounds were screened for agonists and inverse agonists of CB$_2$ receptor (e.g., human CB$_2$ receptor) using the HTRF® assay for direct cAMP measurement (Gabriel et al., *ASSAY and Drug Development Technologies*, 1:291-303, 2003) in recombinant CHO-K1 cells stably transfected with the CB$_2$ receptor. CHO-K1 cells were obtained from ATCC® (Manassas, Va.; Catalog #CCL-61). An agonist of the CB$_2$ receptor was detected in the HTRF® assay for direct cAMP measurement as a compound which decreased cAMP concentration. An inverse agonist of the CB$_2$ receptor was detected in the HTRF® assay for direct cAMP measurement as a compound which increased cAMP concentration. The HTRF® assay also was used to determine EC$_{50}$ values for CB$_2$ receptor agonists and inverse agonists.

B: CB$_1$ Assay

Compounds were also screened for agonists and inverse agonists of the CB$_1$ receptor (e.g., human CB$_1$ receptor) using HTRF® assay for direct cAMP measurement (Gabriel et al., *ASSAY and Drug Development Technologies*, 1:291-303, 2003) in recombinant CHO-K1 cells stably transfected with the CB$_1$ receptor. CHO-K1 cells were obtained from ATCC® (Manassas, Va.; Catalog #CCL-61). An agonist of the CB$_1$ receptor was detected in the HTRF® assay for direct cAMP measurement as a compound which decreased cAMP concentration. An inverse agonist of the CB$_1$ receptor was detected in the HTRF® assay for direct cAMP measurement as a compound which increased cAMP concentration. The HTRF® assay also was used to determine EC$_{50}$ values for CB$_1$ receptor agonists and inverse agonists.

Principle of the Assay:

The HTRF® assay kit was purchased from Cisbio-US, Inc. (Bedford, Mass.; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard Curve:

The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the Assay:

HTRF® assay was carried out using a two-step protocol essentially according to the kit manufacturer's instructions, in 20 µL total volume per well in 384-well plate format (ProxiPlates; PerkinElmer, Fremont, Calif.; catalog #6008280). To each of the experimental wells was transferred 1500 recombinant CHO-K1 cells in 5 µL phosphate buffered saline containing calcium chloride and magnesium chloride (PBS+; Invitrogen, Carlsbad, Calif.; catalog #14040) followed by test compound in 5 µL assay buffer (PBS+ supplemented with 0.2% BSA, 4 µM forskolin and 1 mM IBMX (Sigma-Aldrich, St. Louis, Mo.; catalog #s A8806, F6886 and I5879 respectively). The plate was then incubated at room temperature for 1 h. To each well was then added 5 µL cAMP-d2 conjugate in lysis buffer and 5 µL Cryptate conjugate in lysis buffer according to the kit manufacturer's instructions. The plate was then further incubated at room temperature for 1 h, after which the assay plate was read.

Assay Readout:

The HTRF® readout was accomplished using a PHER-Astar (BMG Labtech Inc., Durham, N.C.) or an EnVision™ (Perkin Elmer, Fremont Calif.) microplate reader.

Certain compounds of the present invention and their corresponding EC$_{50}$ values are shown in Table B.

TABLE B

| Compound No. | EC$_{50}$ hCB$_1$ (nM) | EC$_{50}$ hCB$_2$ (nM) |
|---|---|---|
| 269 | NR | 809 |
| 332 | NR | 2.0 |
| 340 | NR | 6.28 |
| 368 | 354.4 | 35.04 |
| 408 | 26,900 | 75.8 |
| 632 | NR | 0.966 |
| 634 | 1.1 | 0.170 |

NR = No Response

Certain other compounds of the invention had hCB$_1$ EC$_{50}$ values ranging from about 279 pM to about 76.47 µM in this assay and hCB$_2$ EC$_{50}$ values ranging from about 170 pM to about 44.72 µM in this assay. Certain other compounds of the invention had hCB$_2$ EC$_{50}$ values ranging from about 94 µM to about 2.7 nM in this assay.

Example 3: PathHunter β-Arrestin Assay

A: CB$_2$ Assay

Compounds were screened for agonists of the human CB$_2$ receptor using the DiscoveRx PathHunter β-arrestin assay which measures the β-arrestin binding to the CB$_2$ receptor upon its activation. CB$_2$ was cloned into the pCMV-PK vector (DiscoveRx, Fremont, Calif.; catalog #93-0167) and transfected into the CHO-K1 EA-Arrestin parental cell line (DiscoveRx, Fremont, Calif.; catalog #93-0164). CHO-K1 positive clones stably expressing the $CB_2$-ProLink fusion protein were identified by their responses to the $CB_2$ agonist CP55,940. Clone #61 was chosen for its big agonist window and homogenous expression as detected by anti-HA flow cytometry Principle of the Assay:

The PathHunter-arrestin assay measures the interaction of β-arrestin with activated GPCRs using Enzyme Fragment Complementation (Yan et al., *J. Biomol. Screen.* 7: 451-459, 2002). A small, 42 amino acid β-galactosidase fragment, Prolink, is fused to the c-terminus of a GPCR, and β-arrestin is fused to the larger β-galactosidase fragment, EA (Enzyme Acceptor). Binding of β-arrestin to the activated GPCR causes the complementation of the two enzyme fragments, forming an active β-galactosidase enzyme which can be measured using the chemiluminiescent PathHunter Flash Detection Kit (DiscoveRx, Fremont, Calif.: catalog #93-0001).

The Assay:

The stable CHO-K1 cells expressing $CB_2$-Prolink fusion protein were plated over night in 384-well plates (Optiplate 384-Plus, PerkinElmer, Fremont Calif.; catalog #6007299) at 5000 cells/5 μL/well in the Opti-MEM medium (Invitrogen, Carlsbad, Calif.; catalog #31985088) with 1% FBS. 5 μL of test compound diluted in Opti-MEM supplemented with 1% BSA was transferred to each well of the Optiplate. The plates were then incubated at 37° C./5% $CO_2$ for two hours. 12 μL of substrate prepared from the PathHunter Flash Detection Kit (DiscoveRx, Fremont, Calif.: catalog #93-0001) was transferred to each well of the Optiplate. The plate was then incubated in the dark at room temperature for 2 h, after which the assay plate was read.

Assay Readout:

β-Arrestin assay readout was accomplished using a PHERAstar (BMG Labtech Inc., Durham, N.C.) or an EnVision™ (PerkinElmer, Fremont Calif.) microplate reader.

B: $CB_1$ Assay

Compounds were screened for agonists of the human $CB_1$ receptor using the DiscoveRx PathHunter β-arrestin assay which measures the β-arrestin binding to the $CB_1$ receptor upon its activation. $CB_1$ was cloned into the pCMV-PK vector (DiscoveRx, Fremont, Calif.; catalog #93-0167) and transfected into the CHO-K1 EA-Arrestin parental cell line (DiscoveRx, Fremont, Calif.; catalog #93-0164). CHO-K1 positive clones stably expressing the $CB_1$-ProLink fusion protein were identified by their responses to the $CB_1$ agonist CP55,940. Clone #3 was chosen for its big agonist window and homogenous expression as detected by anti-HA flow cytometry Principle of the Assay:

The PathHunter β-arrestin assay measures the interaction of β-arrestin with activated GPCRs using Enzyme Fragment Complementation (Yan et al., *J. Biomol. Screen.* 7: 451-459, 2002). A small, 42 amino acid-galactosidase fragment, Prolink, is fused to the c-terminus of a GPCR, and β-arrestin is fused to the larger β-galactosidase fragment, EA (Enzyme Acceptor). Binding of β-arrestin to the activated GPCR causes the complementation of the two enzyme fragments, forming an active β-galactosidase enzyme which can be measured using the chemiluminiescent PathHunter Flash Detection Kit (DiscoveRx, Fremont, Calif.: catalog #93-0001).

The Assay:

The stable CHO-K1 cells expressing $CB_1$-Prolink fusion protein were plated over night in 384-well plates (Optiplate 384-Plus, PerkinElmer, Fremont Calif.; catalog #6007299) at 5000 cells/5 μL/well in the Opti-MEM medium (Invitrogen, Carlsbad, Calif.; catalog #31985088) with 1% FBS. 5 μL of test compound diluted in Opti-MEM supplemented with 1% BSA was transferred to each well of the Optiplate. The plates were then incubated at 37° C./5% $CO_2$ for two h. 12 μL of substrate prepared from the PathHunter Flash Detection Kit (DiscoveRx, Fremont, Calif.: catalog #93-0001) was transferred to each well of the Optiplate. The plate was then incubated in the dark at room temperature for 2 h, after which the assay plate was read.

Assay Readout:

β-Arrestin assay readout was accomplished using a PHERAstar (BMG LABTECH Inc., Durham, N.C.) or EnVision™ (PerkinElmer, Fremont Calif.) microplate reader.

Certain compounds of the present invention and their corresponding $EC_{50}$ values are shown in Table C.

TABLE C

| Compound No. | $EC_{50}$ $hCB_1$ (nM) | $EC_{50}$ $hCB_2$ (nM) |
|---|---|---|
| 631 | NR | 107.7 |
| 633 | NR | 3.20 |
| 673 | 1,009 | 0.6437 |
| 711 | NR | 28.1 |
| 728 | 251.1 | 1.1 |

NR = No Response

Certain other compounds of the invention had $hCB_1$ $EC_{50}$ values ranging from about 2.6 nM to about 89.06 μM in this assay and $hCB_2$ $EC_{50}$ values ranging from about 643 μM to about 7 μM in this assay. Certain other compounds of the invention had $hCB_1$ $EC_{50}$ values ranging from about 10.9 nM to about 100 μM in this assay and $hCB_2$ $EC_{50}$ values ranging from about 384 μM to about 100 μM in this assay.

Example 4: Radioligand Binding Assay

Preparation of Membranes:

HEK293 cells stably expressing human $CB_2$ receptor were collected, washed in ice cold PBS, and centrifuged at 48,000×g for 20 min at 4° C. The cell pellet was then collected, resuspended in wash buffer (20 mM HEPES, pH 7.4 and 1 mM EDTA), homogenized on ice using a Brinkman Polytron, and centrifuged at 48,000×g for 20 min at 4° C. The resultant pellet was resuspended in ice cold 20 mM HEPES, pH 7.4, homogenized again on ice, recentrifuged for 20 min at 4° C., and membrane pellets were then stored at −80° C. until needed.

[$^3$H]CP55,940 and [$^3$H]WIN55,212-2 Radioligand Binding Assays:

Radioligand binding assays for human $CB_2$ receptors were performed using two different agonist radioligands, [$^3$H]CP55,940 and [$^3$H]WIN55,212-2 and similar assay conditions. For both assays, nonspecific binding was determined in the presence of 10 μM unlabeled compound. Competition experiments consisted of addition of 20 μL of assay buffer (50 mM Tris, pH 7.4, 2.5 mM EDTA, 5 mM $MgCl_2$, and 0.5 mg/mL of fatty acid free BSA) containing test compound (concentrations ranging from 1 μM to 100 μM), 25 μL of radioligand (1 nM final assay concentration for [$^3$H]CP55,904 and [$^3$H]WIN55,212-2), and 50 μL of membranes (20 μg/mL final protein for both assays). Incubations were conducted for 1 h at room temperature, assay plates were filtered under reduced pressure over GF/B filters, washed with assay buffer and dried overnight in a 50° C.

oven. Then, 25 μL of BetaScint scintillation cocktail was added to each well, and plates were read in a Packard TopCount scintillation counter.

Certain compounds of the present invention and their corresponding $K_i$ values are shown in Table D.

TABLE D

| Compound No. | $K_i$ hCB$_1$ (nM) | $K_i$ hCB$_2$ (nM) |
|---|---|---|
| 64 | 207 | 97.6 |
| 629 | NR | 97.7 |
| 701 | 105.1 | 1.45 |
| 752 | 568.4 | 58.7 |
| 755 | 1,200 | 3.8 |

NR = No Response

Certain other compounds of the invention had hCB$_1$ $K_i$ values ranging from about 124 nM to about 19.36 μM in this assay and hCB$_2$ $K_i$ values ranging from about 3.22 nM to about 4.69 μM in this assay.

Example 5: Effect of Compounds on Osteoarthritis Pain

Injection of monosodium iodoacetate (MIA) into a joint (Kalbhen, 1987) inhibits the activity of glyceraldehyde-3-phosphate dehydrogenase in chondrocytes, resulting in disruption of glycolysis and eventually in cell death. The progressive loss of chondrocytes results in histological and morphological changes of the articular cartilage, closely resembling those seen in osteoarthritis patients.

The osteoarthritis was induced in 200 g male Sprague Dawley rats. After brief anaesthesia by isoflurane rats received a single intra-articular injection of MIA (2 mg) (Sigma Aldrich, Saint Louis, Mo., USA; Cat #19148) dissolved in 0.9% sterile saline in a 50 μL volume administered through the patella ligament into the joint space of the left knee with a 30 G needle. Following the injection, animals were allowed to recover from anaesthesia before being returned to the main housing vivarium.

Typically during disease progression, there was an inflammation period of 0-7 days post-intra-articular injection followed by progressive degeneration of the cartilage and subchondral bone from days 14-55. Efficacy studies with a compound of the present invention for pain development took place from day 14 onwards and were performed twice a week with at least 3 days' wash-out in between each assay. Three different assays were used to measure pain. Tactile allodynia was measured via von Frey assay, hind limb paw weight distribution was monitored using an incapacitence tester (Columbus Instruments, Columbus, Ohio, USA) and hind limb grip strength was measured using a grip strength meter (Columbus Instruments, Columbus, Ohio, USA). Briefly, the von Frey assay was performed using the standard up down method with von-Frey filaments. Hind paw weight distribution was determined by placing rats in a chamber so that each hind paw rests on a separate force plate of the incapacitence tester. The force exerted by each hind limb (measured in grams) is averaged over a 3 second period. Three measurements were taken for each rat, and the change in hind paw weight distribution calculated. Peak hind limb grip force was conducted by recoding the maximum compressive force exerted on the hind limb mesh gauge set on the grip strength meter. During the testing, each rat was restrained and the paw of the injected knee was allowed to grip the mesh. The animal was then pulled in an upward motion until their grip was broken. Each rat is tested 3 times, with the contralateral paw used as a control.

Figure 2:
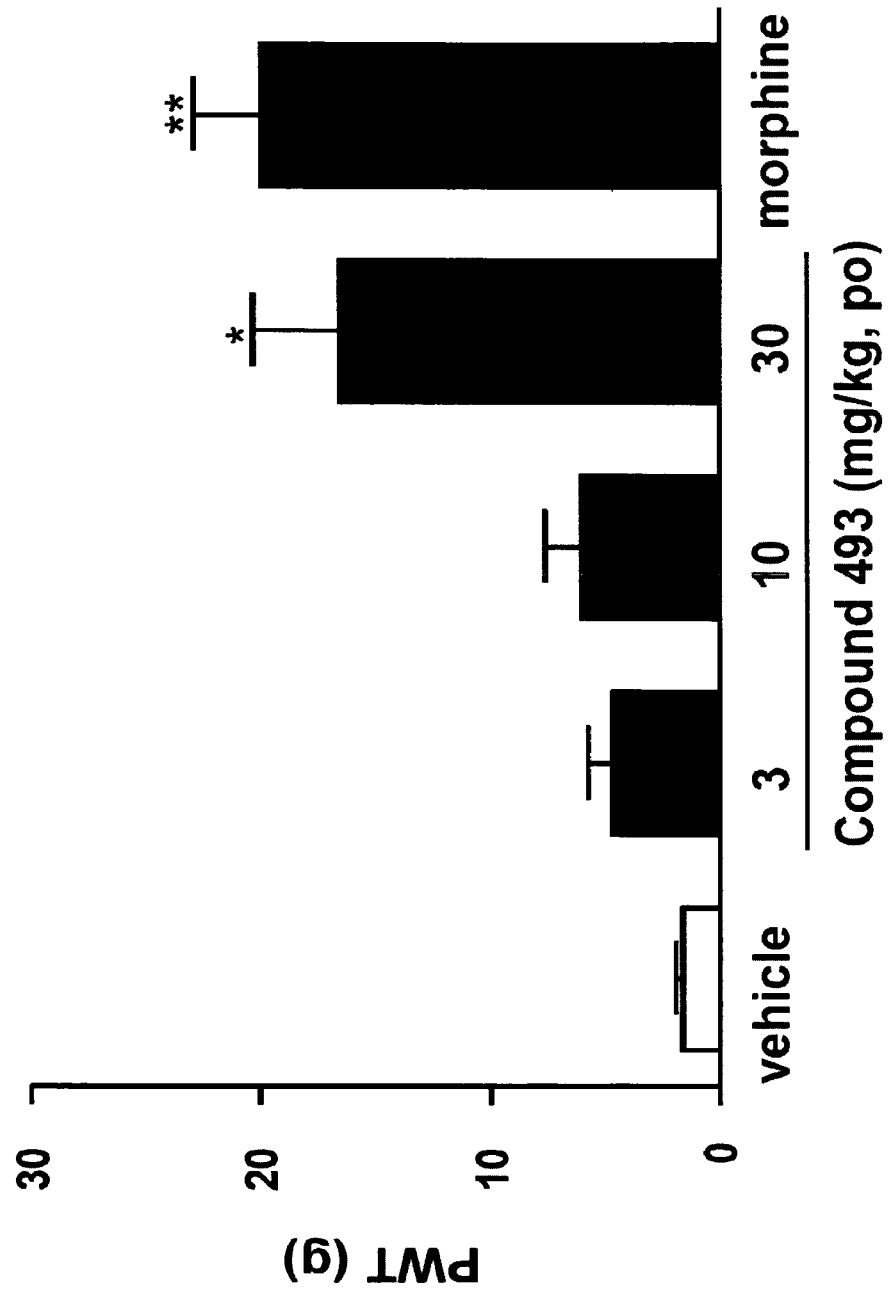
FIG. 2 shows the effect of Compound 493 in the monosodium iodoacetate (MIA) model of osteoarthritis in rats at 1 h post dosing. See Example 5.

Animals were base-lined prior to treatment of the test compound. The MIA treated groups of rats (6 per group) were then dosed with either vehicle (PEG400, orally), Compound 493 (at 3 mg/kg, 10 mg/kg, and 30 mg/kg, orally) or with morphine (3 mg/kg, subcutaneously). Dosing volume was 500 μL. One hour after dosing, von Frey assay, hind limb weight distribution and/or hind limb grip analysis was performed to measure the efficacy of the test compound. Increase in paw withdrawal threshold (PWT) by Compound 493 in comparison with vehicle shown in FIG. 2 was indicative of the test compound exhibiting therapeutic efficacy in the MIA model of osteoarthritis.

Example 6: Effects of Compounds on Skin-Incision Model in Rats

Postoperative pain was produced by a 1 cm incision of the skin and muscle of the plantar surface of the rat hind paw as described (Brennan et al., 1996), with minor modifications. For surgery, rats weighing 200 to 300 g were anesthetized with 2% isoflurane. The plantar surface of the right hind paw was prepared in a sterile manner with a 10% povidone-iodine solution. A 1 cm longitudinal incision was made with a number 11 blade, through skin and fascia of the plantar aspect of the foot, starting in the middle of the paw and extending toward the heel. The plantaris muscle was elevated and incised longitudinally. After hemostasis with gentle pressure, the skin was apposed with 2 mattress sutures of 5-0 nylon. The animals were allowed to recover individually in their cages with clean bedding.

Figure 4:
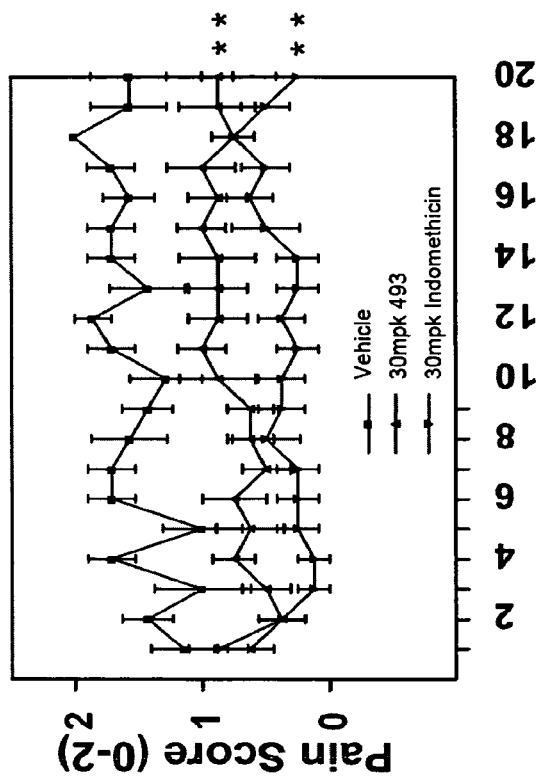
FIG. 4 shows the effect of Compound 493 on the skin incision model of postoperative pain in rats. See Example 6.
Figure 4:
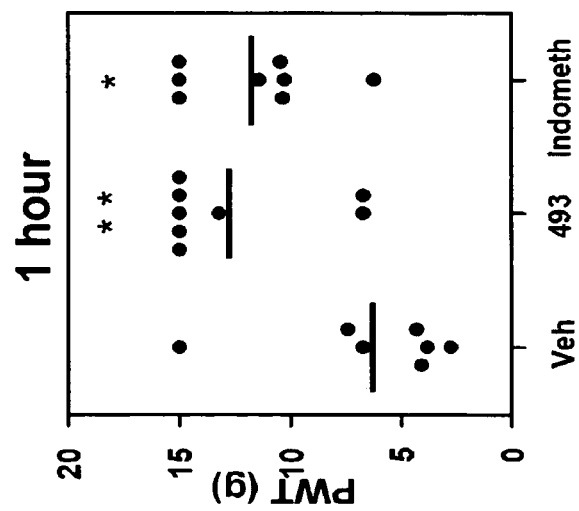

Two to three hours after surgery, animals were treated with the test compound. Compound 493 were dosed orally at 30 mg/kg. Tactile allodynia was assessed with von Frey hair calibrated to bend at specific weights (0.4, 1, 2, 4, 6, 8, 15 g for animal weighing less than 250 g; 1, 2, 4, 6, 8, 15, 26 g for animal weighing 250 g or more in some experiments). Regions adjacent to incision on the mid-plantar surface were first probed to assess the responsive spots with a von Frey force of 8 g. If there was no withdrawal response, the next higher force (15 g) was used until no response at the highest force (26 g for rats weighing 250 g or higher, 15 g for rats weighing less than 250 grams). Once responsive spot was identified, the 50% withdrawal threshold was then determined using the up/down method (Chaplan et al., 1994). Each trial started with a von Frey force of 2 g, if there was no withdrawal response, the next higher force was delivered. If there was a response, the next lower force was delivered. This procedure was performed until no response was made at the highest force (15 g or 26 g depending on animal size) or until four stimuli were delivered following the initial response. The 50% paw withdrawal threshold (PWT) was then calculated as described in Chaplan et al., 1994 (Chaplan S. R., Bach F. W., Pogrel J. W., Chung J. M., Yaksh T. L.: Quantitative assessment of tactile allodynia in the tat paw. J. Neuroscience Methods 1994, 531(1):1022-1027). FIG. 4 shows the pain response of the animals treated with Compound 493 (dosed orally at 30 mg/kg) compared with vehicle and indomethicin (dosed at 30 mg/kg).

Example 7: Effect of Compounds on FCA-Induced Hyperalgesia in Rats

Animal Info:

Male Sprague Dawley rats from Harlan (200-225 g when received) were used. Upon arrival, rats were housed 4 per cage in shoe-box polycarbonate cages with wire tops, wood chip bedding and suspended food and water bottles. Animals were acclimated for 5-7 days prior to being injected with Freund's complete adjuvant (FCA) (Sigma; catalog #5881).

Experimental Procedure:

2 days (48 h) before testing compounds, baseline readings of all rats were taken right before FCA injection. Rats were then injected with 50 µL FCA containing 1 mg/mL Mtb (*Mycobacterium tuberculosis*) in right hind footpad under inhalation anesthesia (isoflurane). 48 hours after FCA injection, readings were taken as pre-dosing baseline and then rats were dosed orally with 0.5 mL of vehicle or compound (0.5 mL per 250 g rat). Readings were taken again at 1 h post dosing. All readings were taken with an Analgesy-Meter (Ugo Basile) which measures mechanical hyperalgesia via paw pressure.

Clinical Scoring:

FCA-induced hyperalgesia was tested with an Analgesy-Meter. Briefly, the Analgesy Meter applied an increasing pressure to the right hind paw. The paw withdrawal threshold was the pressure leading to withdrawal.

Drug Treatment:

48 hours after FCA injection, baseline readings were taken prior to dosing of compounds, and then rats were dosed orally with vehicle (PEG400) or Compound 493 at 0.1, 1, 3, 10 and 30 mg/kg. Meanwhile a group of rats were dosed orally with 50 mg/kg of Diclofenac as a positive control. Readings were taken again at 1 h post dosing. Dosing volume was 500 µL per 250 g rat. As is apparent from FIG. 1, an increase in paw withdrawal threshold (PWT) for Compound 493 in comparison with the vehicle indicates Compound 493 exhibited therapeutic efficacy in the FCA-induced hyperalgesia model of inflammatory pain at 1 h post dosing.

Example 8: Paclitaxel-Induced Allodynia in Sprague Dawley Rats

The mitotic inhibitor, paclitaxel (Taxol®) is one of the most effective and frequently used chemotherapeutic agents for the treatment of solid tumors as well as ovarian and breast cancers. Therapy however is often associated with the unwanted side affects of painful peripheral neuropathy.

Animals:

Male Sprague Dawley rats [200-250 g] (Harlan Laboratories Inc., Livermore, Calif.) were housed three per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Rats were allowed one week of habituation to the animal facility before starting treatment.

Induction of Allodynia:

Rats were treated intraperitoneally, with 2 mg/kg of paclitaxel (Sigma Aldrich, Saint Louis, Mo.) in 10% Cremophor vehicle (500 µL) on days 0, 2, 4, and 6.

Clinical Scoring:

Tactile allodynia was tested using von Frey filaments. Briefly, the von Frey assay was performed using the standardized up down method with von Frey filaments, that determine the tactile sensitivity of the paw. By applying the increasingly or decreasingly thicker filaments to the paw in a logarithmic scale of actual force, a linear scale of perceived intensity is determined.

Figure 3:
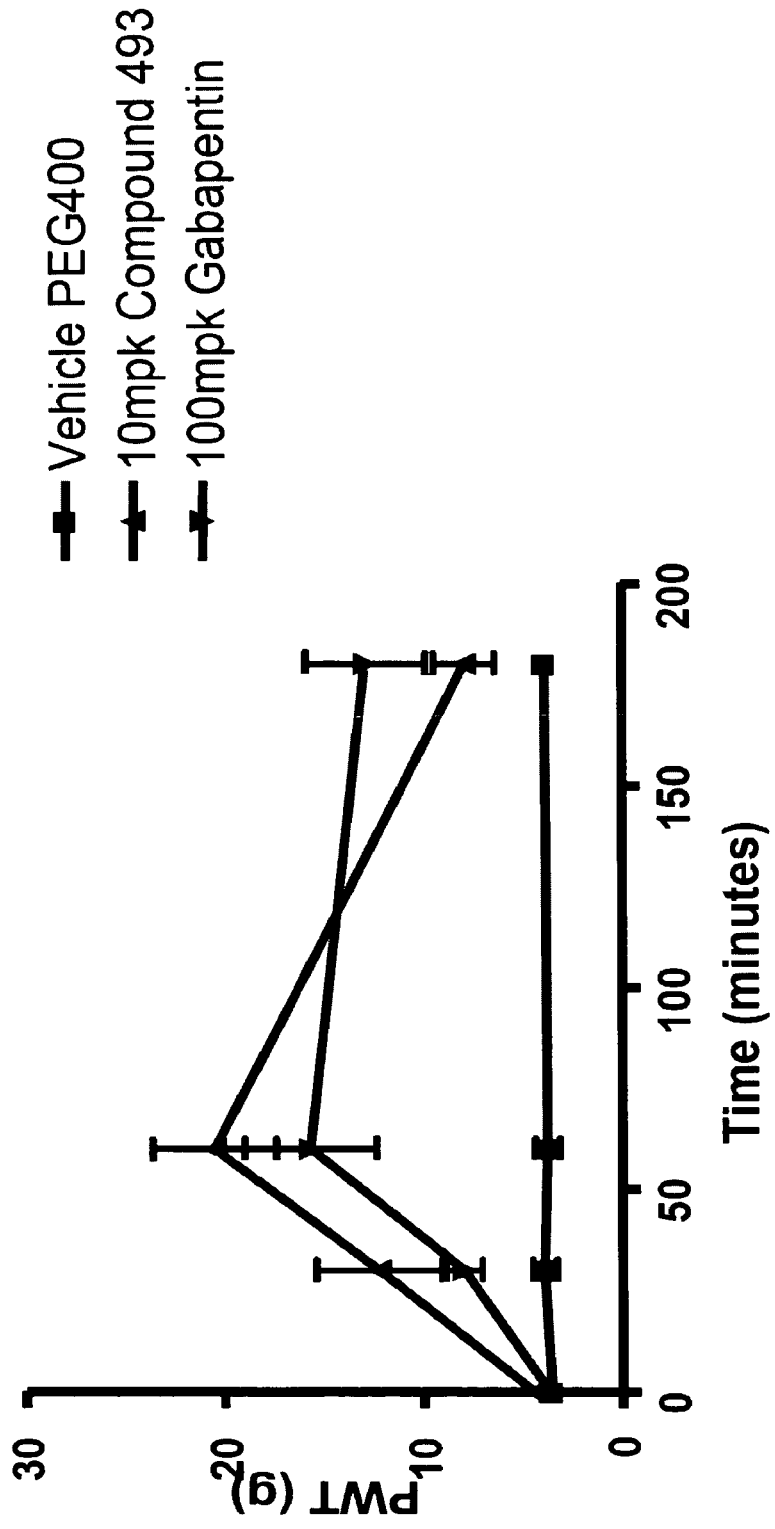
FIG. 3 shows the effect of 10 mg/kg of Compound 493 on paclitaxel-induced allodynia in rats. See Example 8.

Drug Treatment:

Eight days after the start of paclitaxel dosing, a baseline measurement (von Frey assay) was performed prior to dosing of compounds. The paclitaxel treated groups of rats (6 per group) were dosed orally, with vehicle (PEG400) or 10 mg/kg Compound 493. As a positive control, rats were dosed intraperitoneally with 100 mg/kg gabapentin in water. The dosing volume for oral and peritoneal treatment was 500 µL. The von Frey assay was performed to measure the efficacy of the test compound 30, 60 and 180 minutes after dosing. An increase in paw withdrawal threshold (PWT) by treatment with Compound 493 in comparison with vehicle and gabapentin was indicative of the test compound exhibiting therapeutic efficacy in paclitaxel model of cancer pain. The time course shows maximum efficacy at 1 h post-dosing. See FIG. 3.

Example 9: Effects of Compounds on Body Temperature and Locomotor Activity in Rats Animals: Male Sprague-Dawley rats (300-400 g) were housed three per cage and maintained in a humidity-controlled (30-70%) and temperature-controlled (20-22° C.) facility on a 12 h:12 h light/dark cycle (lights on at 7:00 am) with free access to food (Harlan-Teklad, Orange, Calif., Rodent Diet 8604) and water. Rats were allowed one week of habituation to the animal facility before testing.

Measurement of Body Temperature and Locomotor Activity:

Body temperature was measured using a stainless steel rat temperature probe connected to a temperature display device (Physitemp TH-5). The probe was inserted rectally to a depth of 1 inch and the reading was recorded approximately 10 s after insertion, when the reading had stabilized. Body temperature was measured immediately before (time 0) and 60 min post-administration of compounds. Locomotor activity was measured using the Hamilton-Kinder Motor Monitor system, which detected blockage of photocell beams in a standard rat cage and transfers this data to a computer. Motor activity was measured for 30 min starting immediately after the second body temperature measurement, from 60 to 90 min post-administration. Compounds were dosed orally in a volume of 2 to 6 mL/kg, suspended or dissolved in 100% PEG 400.

Figure 5:
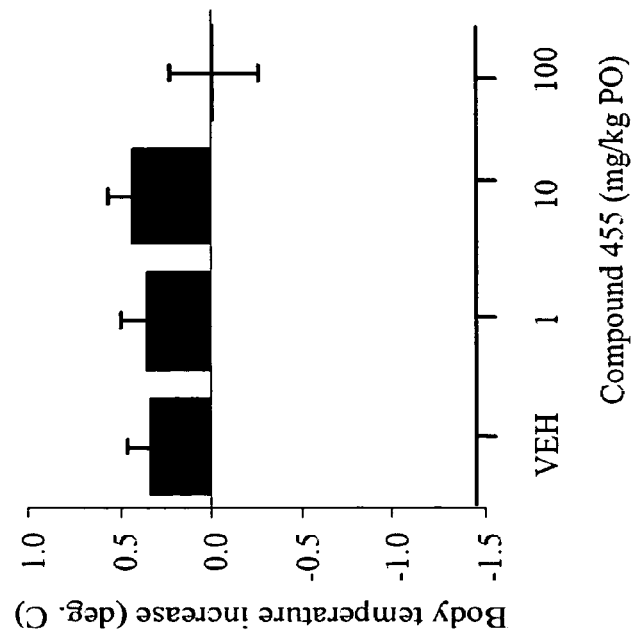
FIG. 5 shows the effect of Compound 455 on body temperature and locomotor activity in rats. See Example 9.
Figure 5:
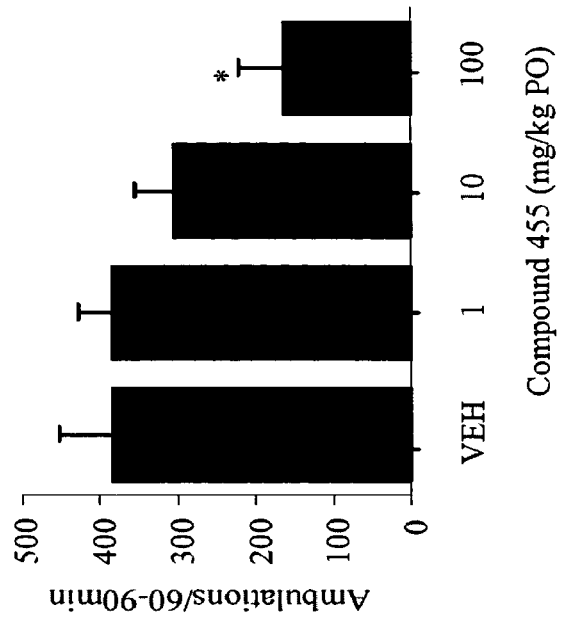
Figure 6:
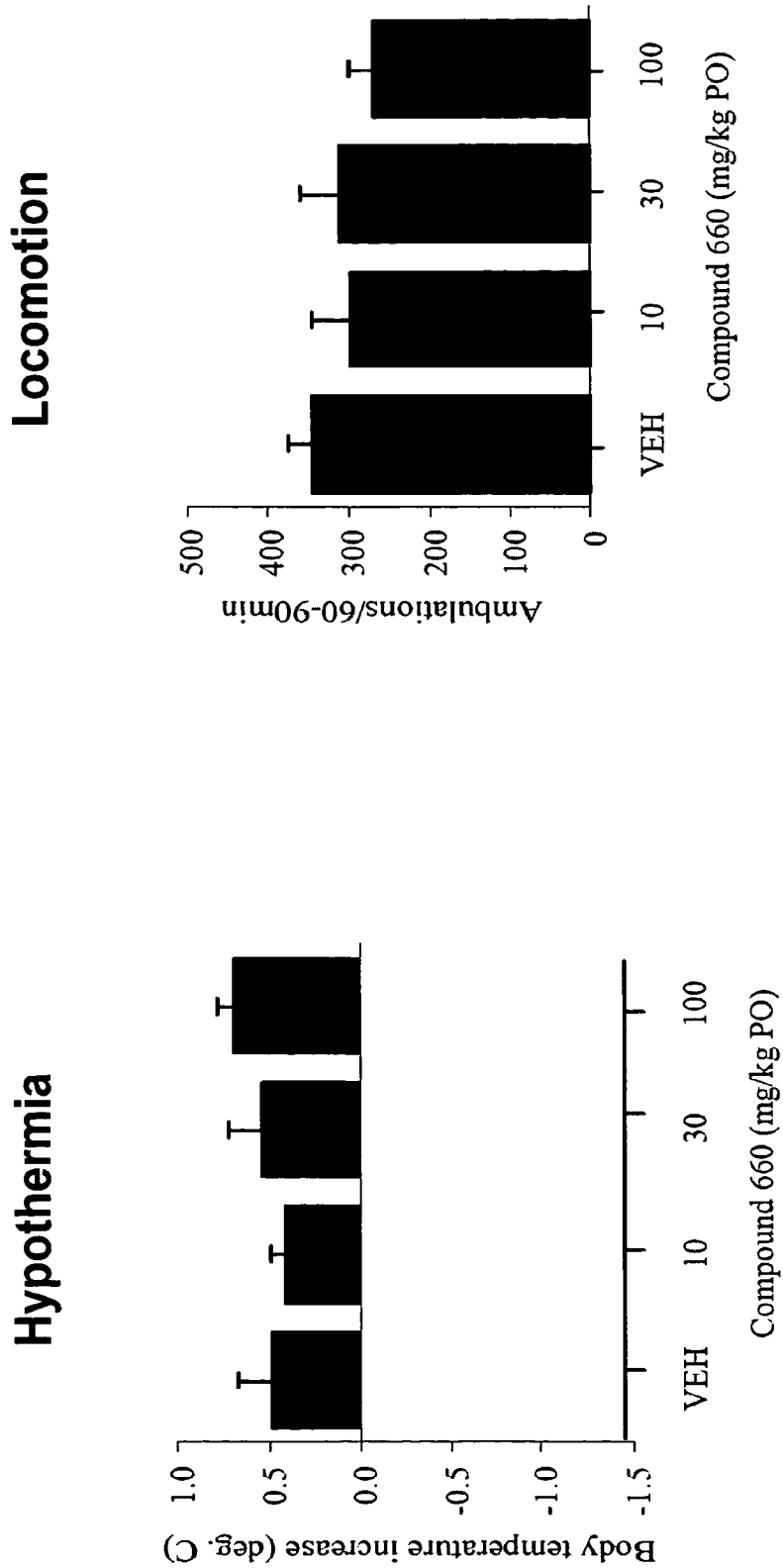
FIG. 6 shows the effect of Compound 660 on body temperature and locomotor activity in rats. See Example 9.
Figure 7:
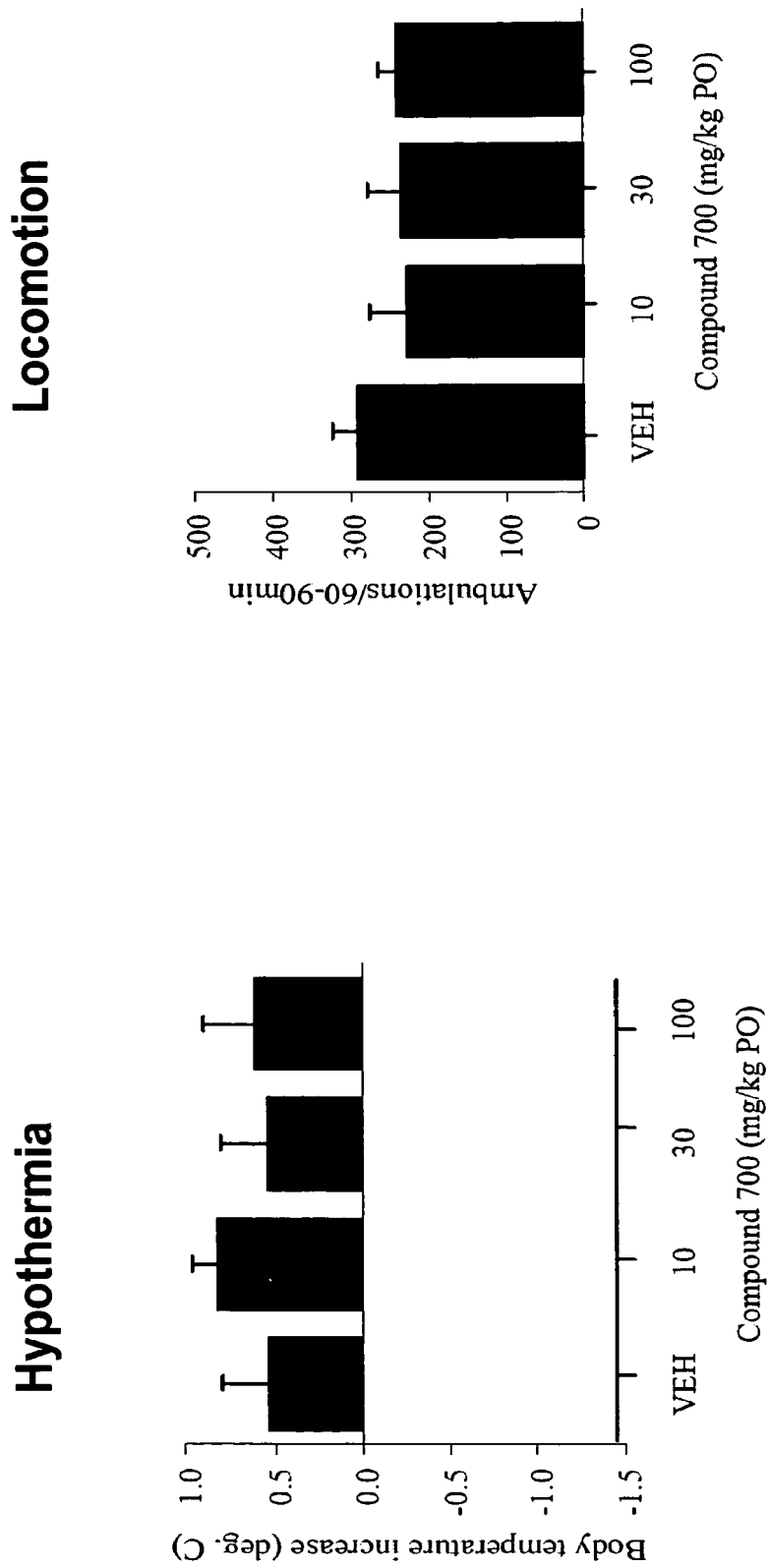
FIG. 7 shows the effect of Compound 700 on body temperature and locomotor activity in rats. See Example 9.
Figure 8:
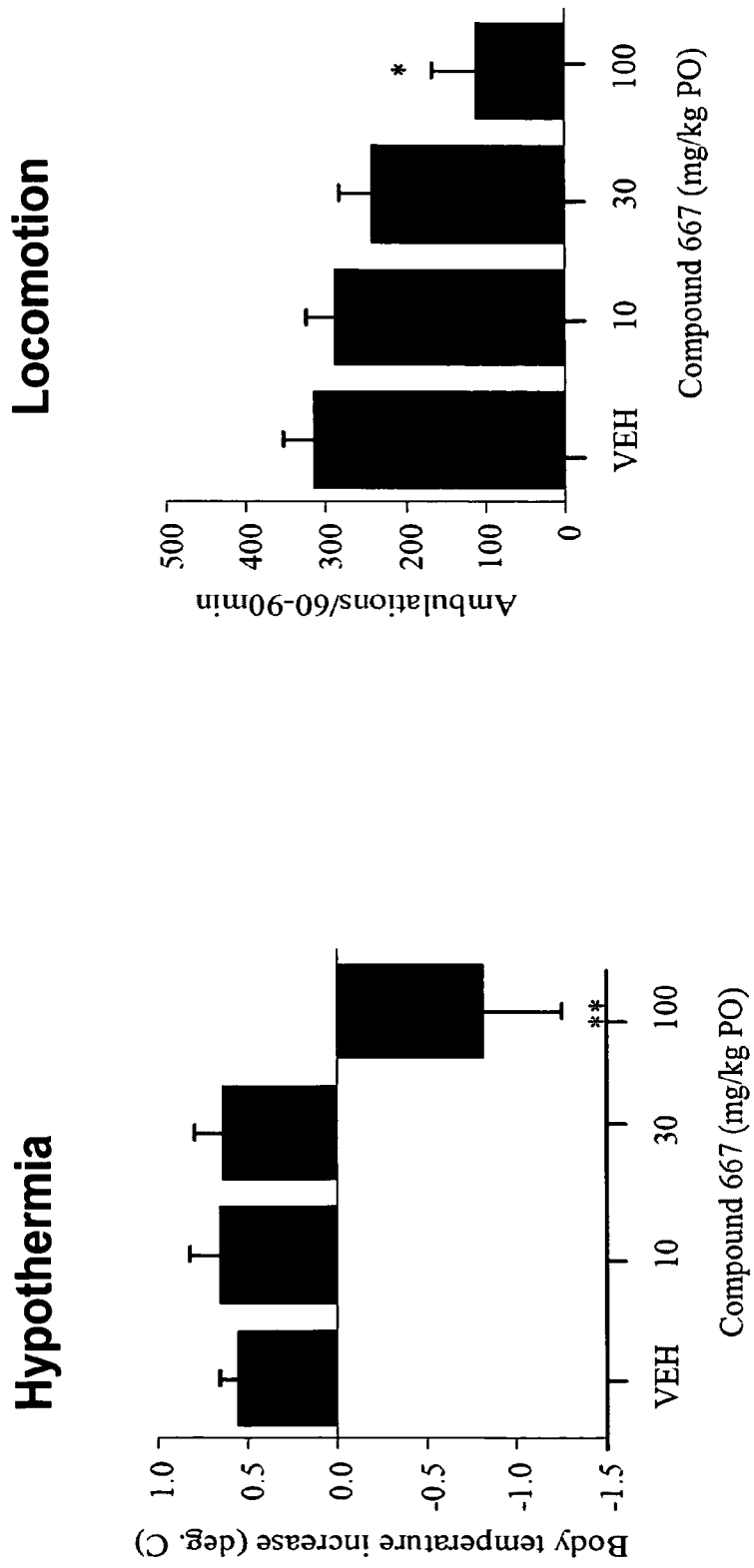
FIG. 8 shows the effect of Compound 667 on body temperature and locomotor activity in rats. See Example 9.
Figure 9:
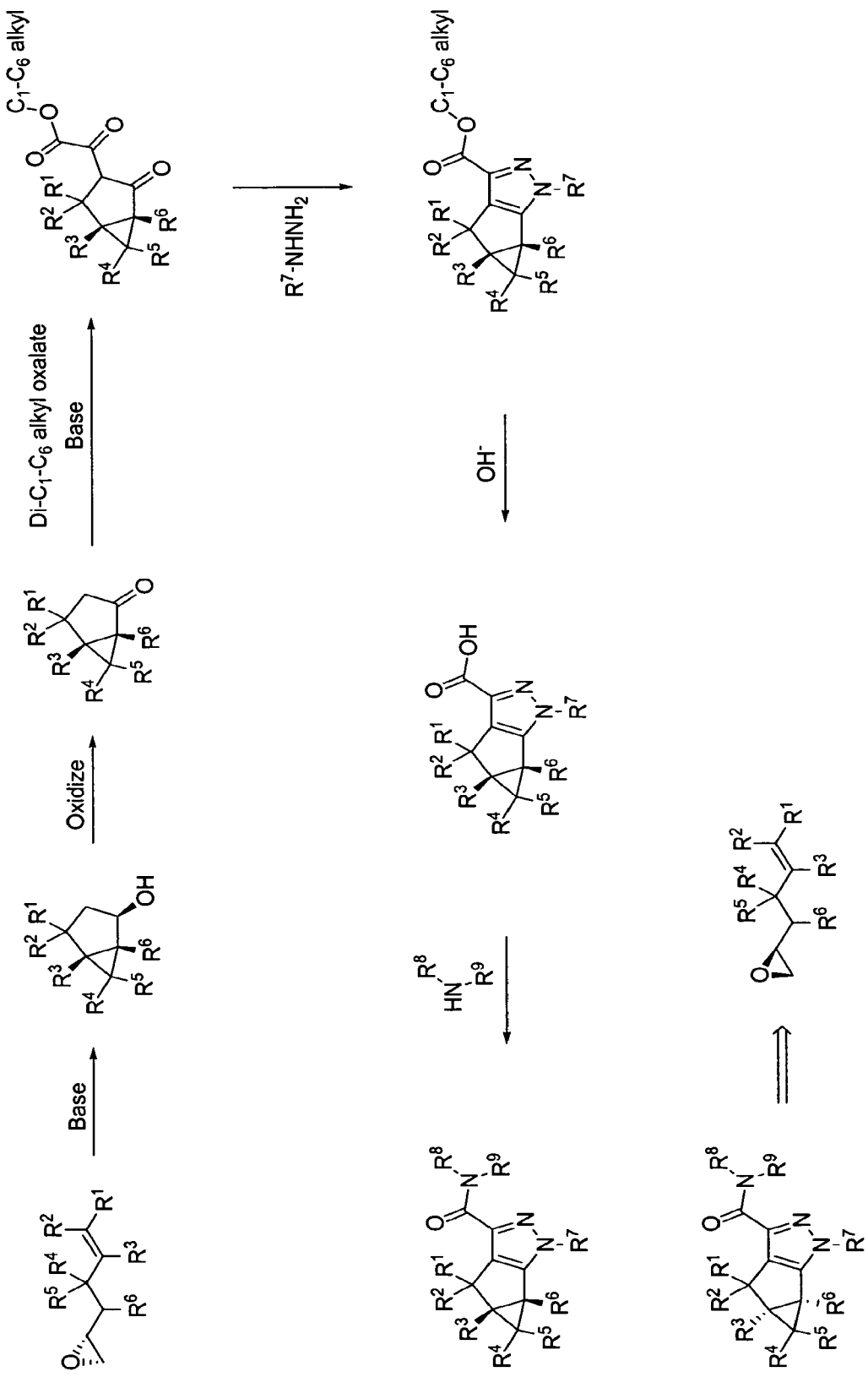
FIG. 9 shows a general synthesis of compounds of the present invention wherein X is CC(O)N($R^8$)$R^9$ and Y is $NR^7$. First, a 2-(but-3-enyl)oxirane derivative is cyclized by treatment with a base. The resulting bicyclic alcohol is oxidized to the ketone and reacted with a dialkyl oxalate derivative in the presence of a base. The pyrazole ring is then formed by reaction with a substituted hydrazine and the resulting ester is hydrolyzed and coupled with an amine to form compounds of the present invention.
Figure 10:
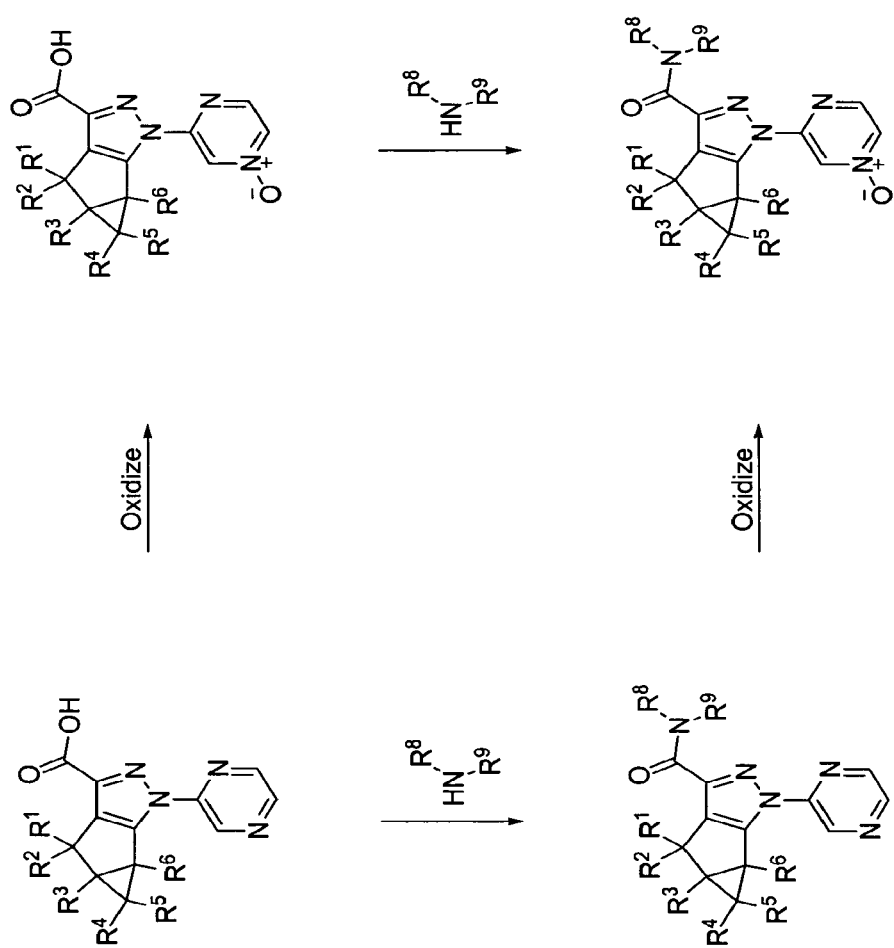
FIG. 10 shows a general synthesis of compounds of the present invention in which $R^7$ is a 4-oxy-pyrazin-2-yl group.
Figure 11:
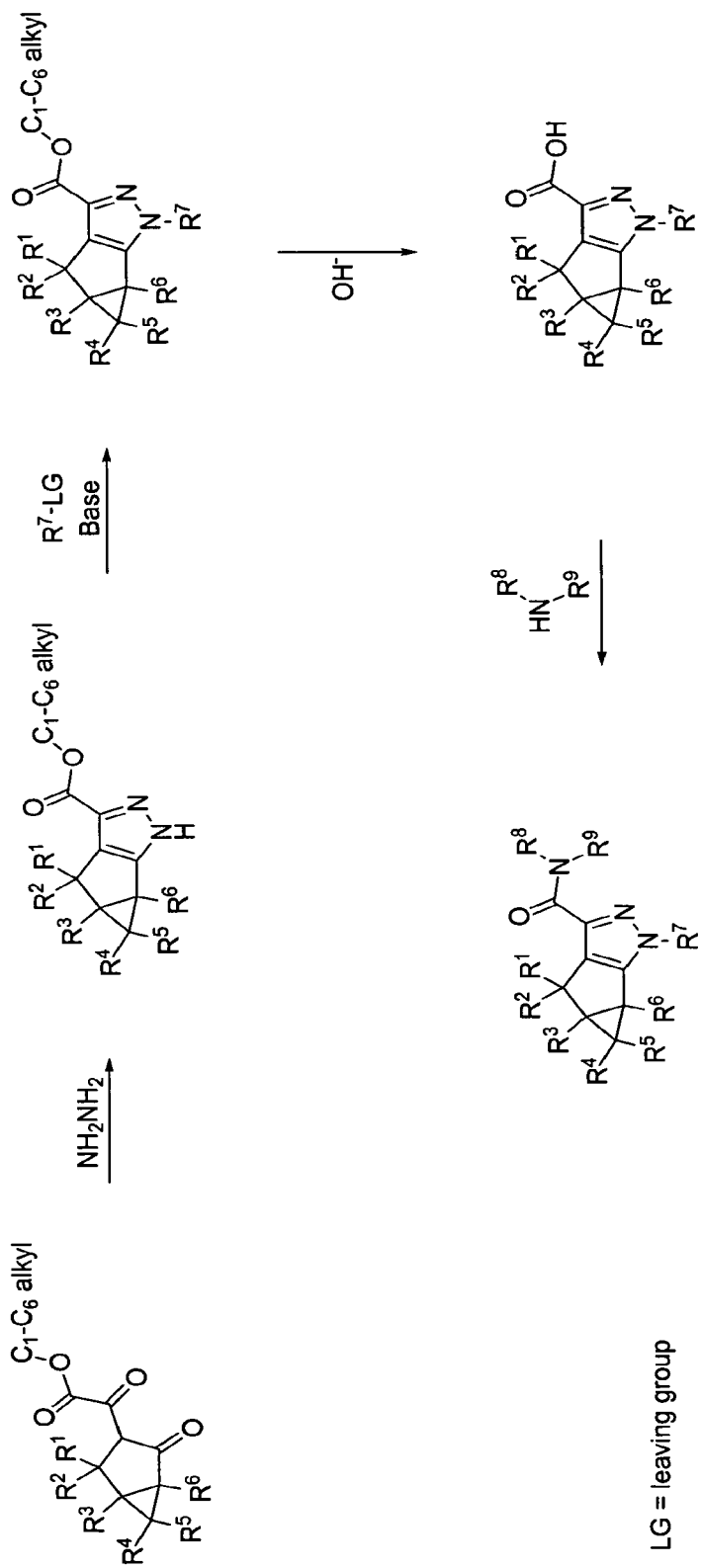
FIG. 11 shows a general synthesis of compounds of the present invention similar to the one shown in FIG. 9 except the group $R^7$ is introduced subsequent to the formation of a tri-substituted pyrazole.
Figure 12:
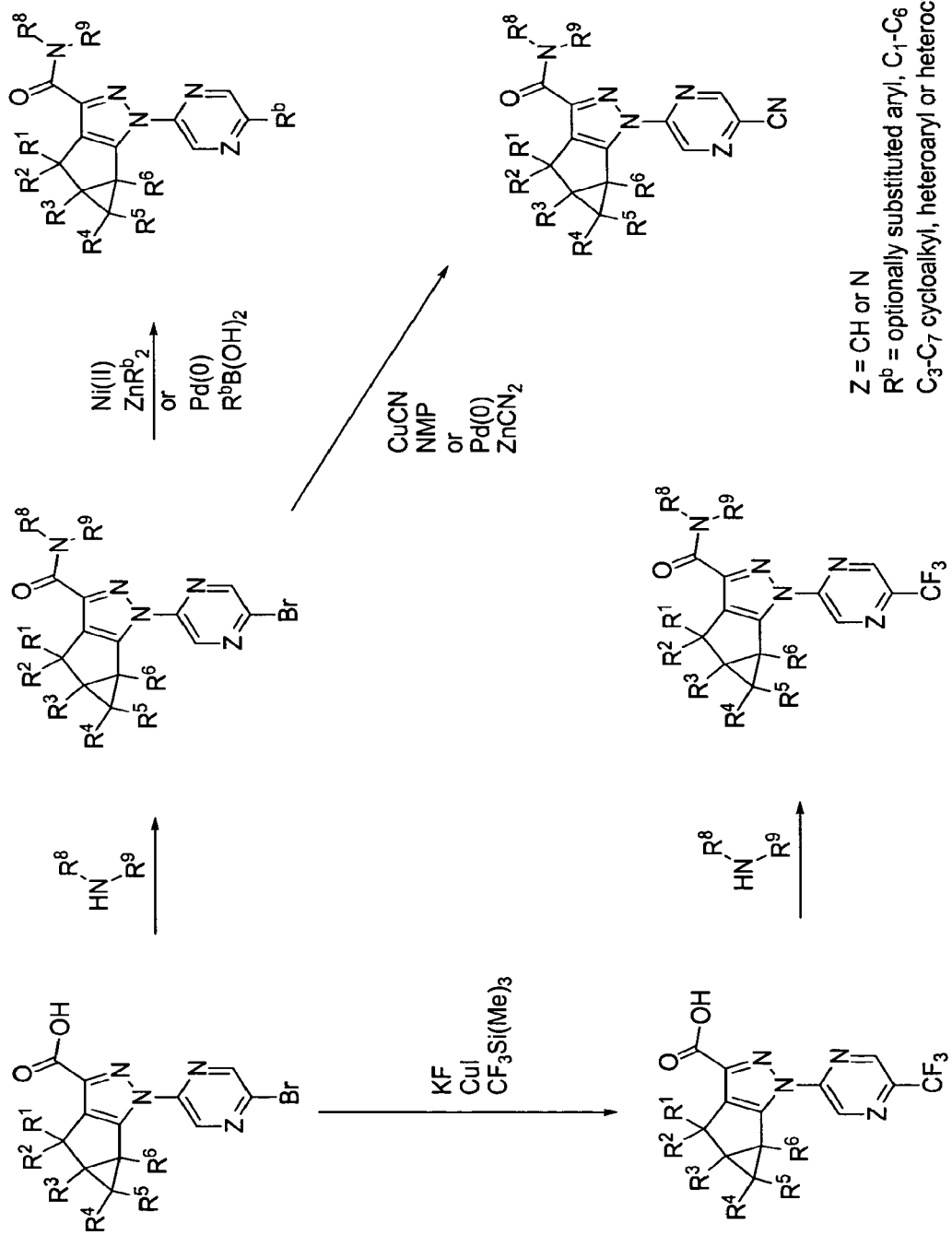
FIG. 12 shows a general synthesis of compounds of the present invention in which $R^7$ is either a 5-substituted-pyridin-2-yl group or a 5-substituted-pyrazin-2-yl group.
Figure 13:
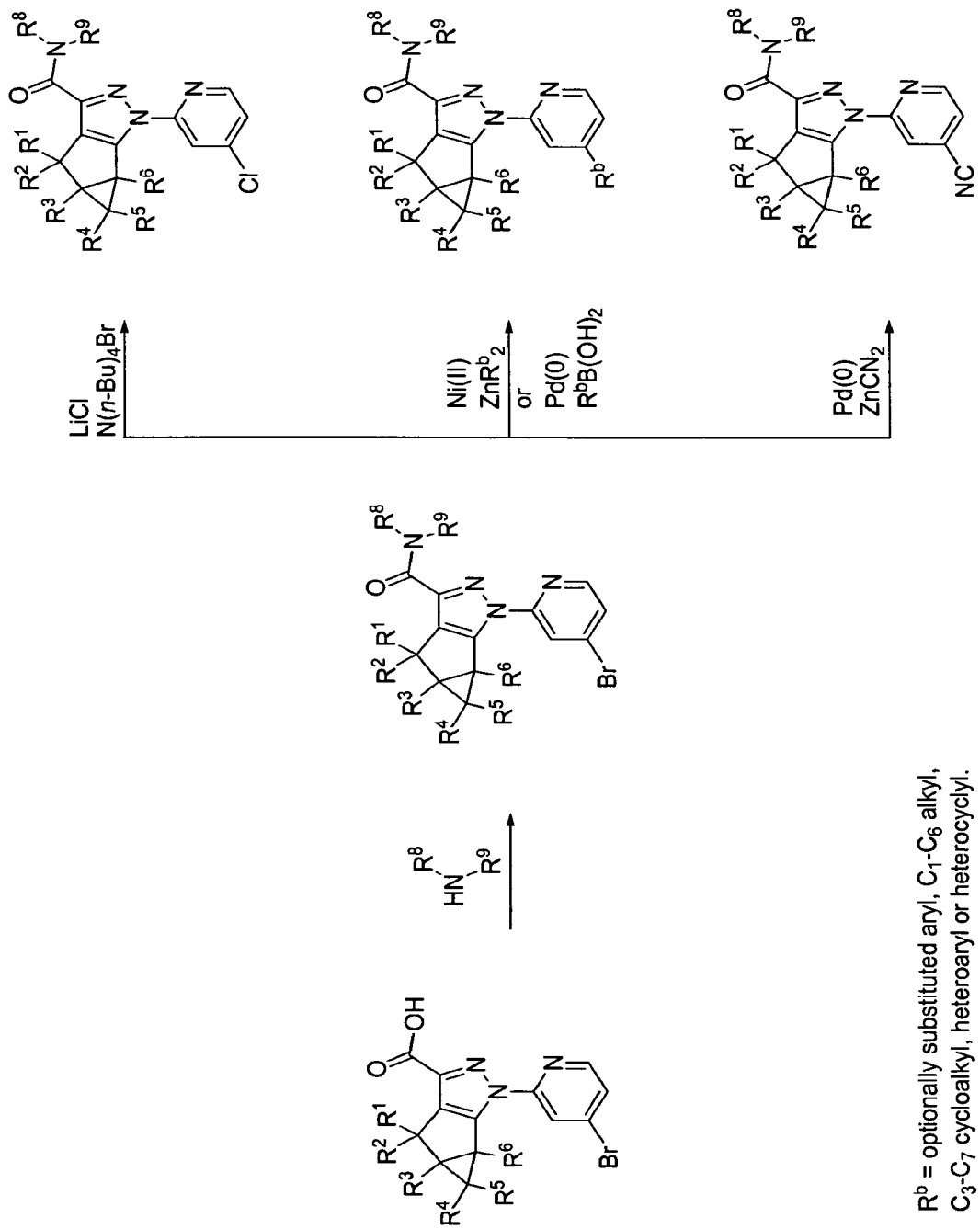
FIG. 13 shows a general synthesis of compounds of the present invention in which $R^7$ is a 4-substituted-pyridin-2-yl group.
Figure 14:
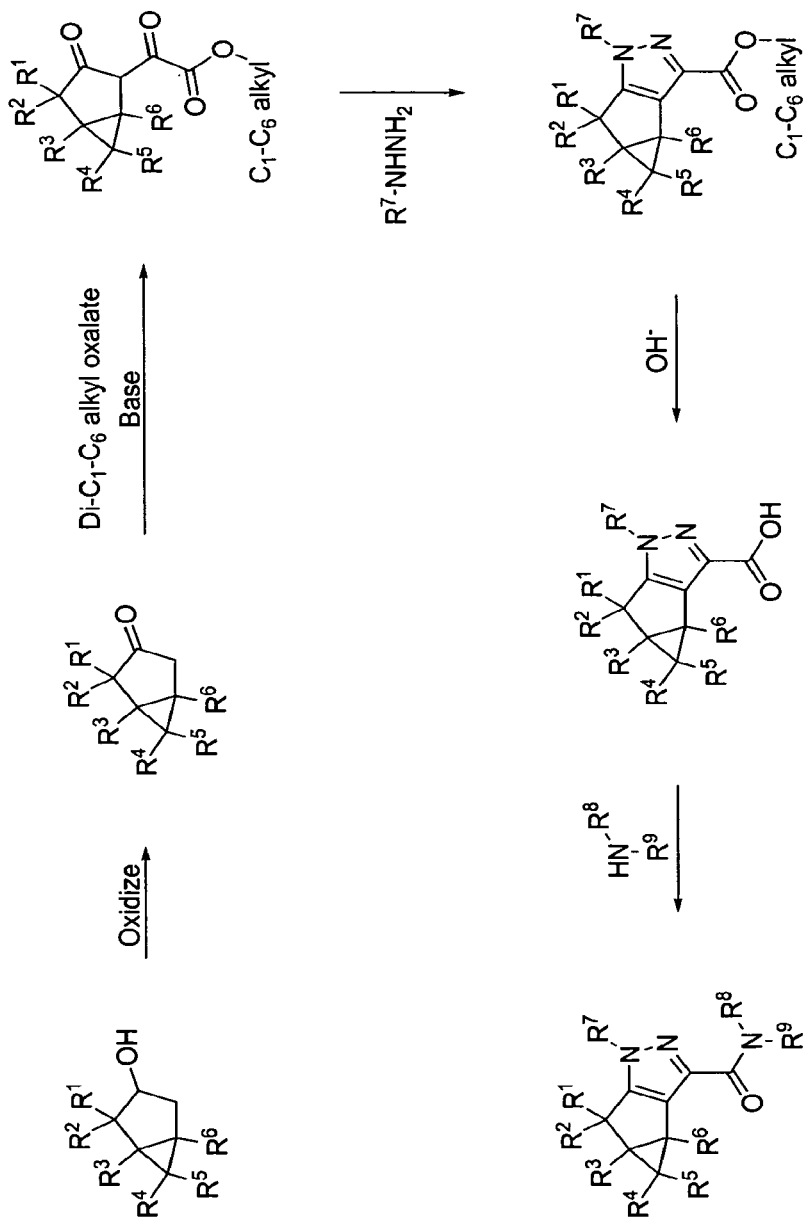
FIG. 14 shows a general synthesis of compounds of the present invention wherein X is $NR^7$ and Y is CC(O)N($R^8$)$R^9$. First, a bicyclo[3.1.0]hexan-3-ol derivative is oxidized and the resulting ketone is reacted with a dialkyl oxalate derivative in the presence of a base. The pyrazole ring is then formed by reaction with a substituted hydrazine and the resulting ester is hydrolyzed and coupled with an amine to form compounds of the present invention.

FIGS. 5 to 8 showed the effects of 4 different compounds on body temperature and locomotor activity in rats. The compounds depicted in FIG. 6 and FIG. 7 were inactive in these tests at doses ranging from 1 to 100 mg/kg PO. In FIG. 5, the compound decreased body temperature at the highest dose tested (100 mg/kg), but this effect was not statistically significant; the compound did, however, significantly reduce motor activity. In FIG. 8, the compound significantly decreased both body temperature and locomotor activity at the highest dose tested (100 mg/kg).

Example 10: Effects of Compounds on Spinal Nerve Ligation Surgery

Rats receive nerve injury by tight ligation of L5 and L6 spinal nerves close to the spine, before they join (along with L4) to form the sciatic nerve. For this surgery, animals are placed under general anesthesia using continuous inhalation of isoflurane. Surgery is performed in a dedicated surgery room, using sterile instruments, surgical gloves, and aseptic procedures to prevent clinical infections. The surgical site is shaved and disinfected with iodine solution and alcohol. Animals are observed continuously for their level of anesthesia, testing for the animal's reflex response to tail or paw pinch. A heating pad is used to maintain body temperature both during the procedure and while the animals are recovering from anesthesia. For this procedure, a skin incision is made over the lower back at the level of L4-L6, and the muscle, ligaments, and facet joints are cut away from the spine. Correct location is confirmed by identifying the pelvis and the L5 transverse process. The L5 transverse is carefully removed to expose the L4 and L5 nerves. L5 is carefully hooked (with a pulled glass hook) without damaging L4 and tightly ligated (6-0 silk suture). L6 is then located just under the pelvic bone, hooked and ligated as well. The wound is debrided and closed with internal sutures and external staples. Animals are administered a post-surgery injection of lactated Ringer's solution and returned to their home cages. They are carefully monitored until completely recovered from anesthesia (defined as the ability to move without significant ataxia), typically less than 10 min. Any animal with loss of motor control of the affected hind paw (L4 motor damage) are euthanized. Neuropathic animals are first tested 7-10 days post surgery for the beginning of tactile allodynia. The allodynia is seen approximately 14 days post surgery and persists for 45-50 days post surgery. During this time analgesic compounds are tested for their ability to reduce or eliminate this chronic pain symptom.

Example 11: Effects of Compounds on Chronic Constriction Injury Surgery

Nerve injury is induced by loose ligature of the sciatic nerve. For this surgery, animals are placed under general anesthesia using continuous inhalation of isoflurane. Surgery is performed in a dedicated surgery room, using sterile instruments, surgical gloves, and aseptic procedures to prevent clinical infections. The surgical site is shaved and disinfected with iodine solution and alcohol. Animals are observed continuously for their level of anesthesia, testing for the animal's reflex response to tail or paw pinch and closely monitoring the animal's breathing. A heating pad is used to maintain body temperature while the animals are recovering from anesthesia. For this procedure, a skin incision is made over the femur and the muscle is bluntly dissected to expose the sciatic nerve. Four loose ligatures (Chromic gut absorbable suture) are placed around the nerve, and the wound is closed with internal sutures and external staples. Animals are administered a post-surgery injection of lactated ringers solution and returned to their home cages. They are carefully monitored until complete recovery from anesthesia (defined as the ability to move without significant ataxia), typically less than 10 min. Neuropathic animals are first tested 7-15 days post surgery for tactile allodynia. During this time period analgesic compounds are tested for their ability to reduce or eliminate these chronic pain symptoms.

Figure 17:
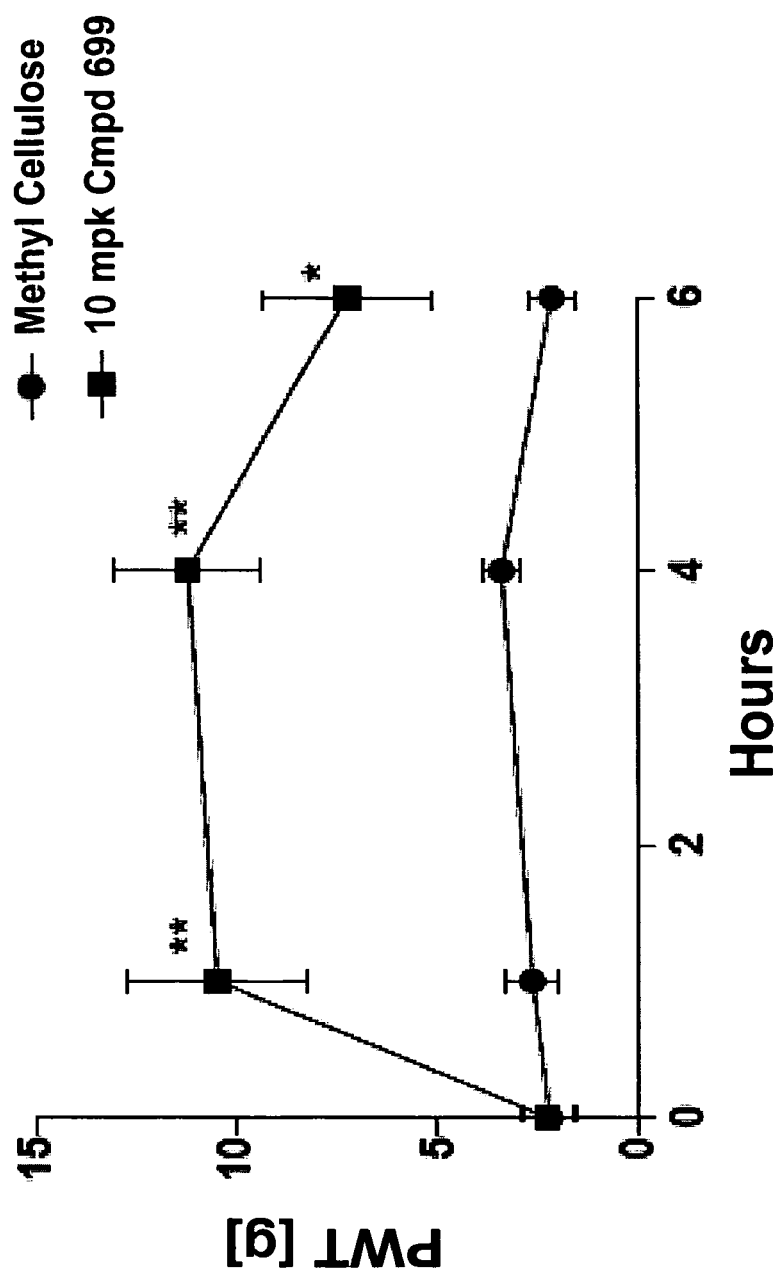
FIG. 17 shows the effect of Compound 699 (10 mpk) compared to vehicle (methyl cellulose) in the STZ-induced PDPN Model. See Example 12.
Figure 18:
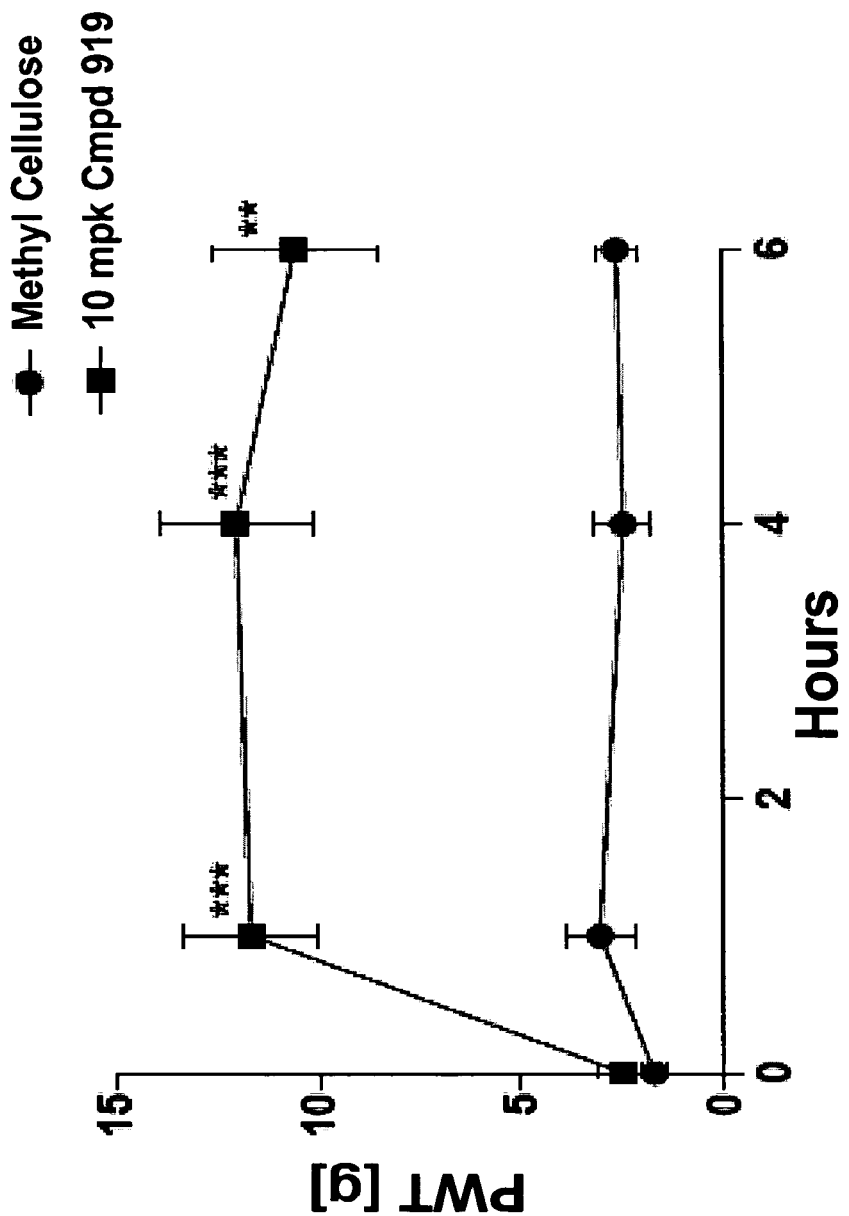
FIG. 18 shows the effect of Compound 919 (10 mpk) compared to vehicle (methyl cellulose) in the STZ-induced PDPN Model. See Example 12.

Example 12: Streptozotocin-Induced Painful Diabetic Peripheral Neuropathy (PDPN) Model Male Sprague-Dawley rats were injected intraperitoneally with 50 mg/kg of streptozotocin (STZ) in sodium citrate buffer. 10% sucrose water was provided ad libitum for the first 48 hours post-STZ followed by regular drinking water. Rats were monitored once weekly for blood glucose levels and body weights. Development of tactile allodynia over time was analyzed using Von Frey filaments and a 50% withdrawal threshold was determined using Dixon's up-down procedure. The effect of CB2 agonists Compound 699 and Compound 919 on pain threshold was evaluated in diabetic and allodynic rats by administering 10 mg/kg dose of either compound orally in 0.5% methylcellulose vehicle. Tactile allodynia was evaluated at 1, 4 and 6 hours post-dosing. As shown in FIG. 17 and FIG. 18, both CB2 agonists Compound 699 and Compound 919 showed robust and sustained analgesic efficacy over 6 hours in this model.

Those skilled in the art will recognize that various modifications, additions, substitutions, and variations to the illustrative examples set forth herein can be made without departing from the spirit of the invention and are, therefore, considered within the scope of the invention.

What is claimed is:
1. A compound selected from (1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide (Compound 919) and pharmaceutically acceptable salts thereof.
2. A compound selected from (1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide (Compound 919) and solvates thereof.
3. The compound (1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide (Compound 919).
4. A pharmaceutically acceptable salt of (1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide.
5. A solvate of (1aS,5aS)-2-(4-Oxy-pyrazin-2-yl)-1a,2,5,5a-tetrahydro-1H-2,3-diaza-cyclopropa[a]pentalene-4-carboxylic acid (2,2,2-trifluoro-1,1-dimethyl-ethyl)-amide.
6. A pharmaceutical composition comprising a compound according to claim 3 and a pharmaceutically acceptable carrier.
7. A pharmaceutical composition comprising the compound according to claim 4 and a pharmaceutically acceptable carrier.
8. A pharmaceutical composition comprising a compound according to claim 5 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 11,214,548 B2 | Page 1 of 1 |
| APPLICATION NO. | : 16/580697 | |
| DATED | : January 4, 2022 | |
| INVENTOR(S) | : Jones et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Seventh Day of February, 2023

Katherine Kelly Vidal
*Director of the United States Patent and Trademark Office*